US010449217B2

(12) United States Patent
Mortenson et al.

(10) Patent No.: US 10,449,217 B2
(45) Date of Patent: *Oct. 22, 2019

(54) GOLD-BASED NANOCRYSTALS FOR MEDICAL TREATMENTS AND ELECTROCHEMICAL MANUFACTURING PROCESSES THEREFOR

(71) Applicants: Mark Gordon Mortenson, North East, MD (US); D. Kyle Pierce, Elkton, MD (US); David A. Bryce, Elkton, MD (US); Reed N. Wilcox, Littleton, CO (US); Anthony Lockett, Leeds (GB); Mikhail Merzliakov, Parkville, MD (US)

(72) Inventors: Mark Gordon Mortenson, North East, MD (US); D. Kyle Pierce, Elkton, MD (US); David A. Bryce, Elkton, MD (US); Reed N. Wilcox, Littleton, CO (US); Anthony Lockett, Leeds (GB); Mikhail Merzliakov, Parkville, MD (US)

(73) Assignee: Clene Nanomedicine, Inc., North East, MD (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/465,092

(22) Filed: Mar. 21, 2017

(65) Prior Publication Data
US 2017/0348350 A1 Dec. 7, 2017

Related U.S. Application Data

(62) Division of application No. 13/382,781, filed as application No. PCT/US2010/041427 on Jul. 8, 2010, now Pat. No. 9,603,870.

(60) Provisional application No. 61/294,690, filed on Jan. 13, 2010, provisional application No. 61/263,648, filed on Nov. 23, 2009, provisional application No. 61/249,804, filed on Oct. 8, 2009, provisional application No. 61/235,574, filed on Aug. 20, 2009, provisional application No. 61/228,250, filed on Jul. 24, 2009, provisional application No. 61/226,153,
(Continued)

(51) Int. Cl.
| | |
|---|---|
| *A61K 33/24* | (2019.01) |
| *B22F 1/00* | (2006.01) |
| *B22F 9/00* | (2006.01) |
| *B82Y 30/00* | (2011.01) |
| *C30B 7/12* | (2006.01) |
| *C30B 29/02* | (2006.01) |
| *C30B 29/60* | (2006.01) |
| *A61K 9/08* | (2006.01) |
| *A61K 47/02* | (2006.01) |
| *A61K 9/00* | (2006.01) |
| *A61K 9/14* | (2006.01) |
| *A61K 9/10* | (2006.01) |

(52) U.S. Cl.
CPC ............ *A61K 33/24* (2013.01); *A61K 9/0095* (2013.01); *A61K 9/08* (2013.01); *A61K 9/10* (2013.01); *A61K 9/14* (2013.01); *A61K 47/02* (2013.01); *B22F 1/0022* (2013.01); *B22F 9/00* (2013.01); *B82Y 30/00* (2013.01); *C30B 7/12* (2013.01); *C30B 29/02* (2013.01); *C30B 29/60* (2013.01); *B22F 2001/0037* (2013.01); *Y02A 50/401* (2018.01); *Y02A 50/411* (2018.01)

(58) Field of Classification Search
None
See application file for complete search history.

(56) References Cited

U.S. PATENT DOCUMENTS

| | | | |
|---|---|---|---|
| 4,093,527 | A | 6/1978 | Tanno et al. |
| 5,478,533 | A | 12/1995 | Inculet |
| 5,876,663 | A | 3/1999 | Laroussi |

(Continued)

FOREIGN PATENT DOCUMENTS

| | | |
|---|---|---|
| EP | 12908 | 5/1910 |
| EP | 0857695 A2 | 8/1998 |

(Continued)

OTHER PUBLICATIONS

Sing, Abhimanyu K., et al., Controlled Synthesis and Optical Properties of Pure Gold Nanoparticles. 2009, Instrumentation Science & Technology, 37: 50-60.
(Continued)

*Primary Examiner* — Melissa L Fisher
(74) *Attorney, Agent, or Firm* — Mark G. Mortenson

(57) ABSTRACT

The present invention relates to novel gold nanocrystals and nanocrystal shape distributions that have surfaces that are substantially free from organic impurities or films. Specifically, the surfaces are "clean" relative to the surfaces of gold nanoparticles made using chemical reduction processes that require organic reductants and/or surfactants to grow gold nanoparticles from gold ions in solution.

The invention includes novel electrochemical manufacturing apparatuses and techniques for making the gold-based nanocrystals. The invention further includes pharmaceutical compositions thereof and the use of the gold nanocrystals or suspensions or colloids thereof for the treatment or prevention of diseases or conditions for which gold therapy is already known and more generally for conditions resulting from pathological cellular activation, such as inflammatory (including chronic inflammatory) conditions, autoimmune conditions, hypersensitivity reactions and/or cancerous diseases or conditions. In one embodiment, the condition is mediated by MIF (macrophage migration inhibiting factor).

36 Claims, 196 Drawing Sheets

Related U.S. Application Data filed on Jul. 16, 2009, provisional application No. 61/223,944, filed on Jul. 8, 2009.

(56) References Cited

U.S. PATENT DOCUMENTS

| | | | |
|---|---|---|---|
| 5,965,994 | A | 10/1999 | Seo |
| 6,214,299 | B1 | 4/2001 | Holladay et al. |
| 6,358,398 | B1 | 3/2002 | Halldorson et al. |
| 6,743,348 | B2 | 6/2004 | Holladay et al. |
| 6,749,759 | B2 | 6/2004 | Denes et al. |
| 6,802,981 | B2 | 10/2004 | Ryazanova et al. |
| 7,033,415 | B2 | 4/2006 | Mirkin et al. |
| 7,118,852 | B2 | 10/2006 | Purdum et al. |
| 7,135,054 | B2 | 11/2006 | Jin et al. |
| 7,135,055 | B2 | 11/2006 | Mirkin et al. |
| 7,135,195 | B2 | 11/2006 | Holladay et al. |
| 7,276,283 | B2 | 10/2007 | Denes et al. |
| 7,438,882 | B2 | 10/2008 | Goodwin et al. |
| 7,452,449 | B2 | 11/2008 | Weinberg et al. |
| 7,486,705 | B2 | 2/2009 | Shah et al. |
| 7,883,606 | B2 | 2/2011 | Parkansky et al. |
| 7,972,390 | B2 | 7/2011 | Blum et al. |
| 8,088,193 | B2 | 1/2012 | Zeng et al. |
| 8,246,714 | B2 | 8/2012 | Liu et al. |
| 8,512,436 | B2 | 8/2013 | Kawasaki et al. |
| 2002/0014400 | A1 | 2/2002 | Zadiraka et al. |
| 2004/0022702 | A1 | 2/2004 | Christensen |
| 2004/0131524 | A1 | 7/2004 | Josephson et al. |
| 2006/0037177 | A1 | 2/2006 | Blum et al. |
| 2006/0068026 | A1 | 3/2006 | Hu et al. |
| 2006/0207388 | A1 | 9/2006 | Mirkin et al. |
| 2006/0249705 | A1 | 11/2006 | Wang et al. |
| 2007/0029185 | A1 | 2/2007 | Tung et al. |
| 2007/0108056 | A1 | 5/2007 | Nyberg et al. |
| 2007/0267289 | A1 | 11/2007 | Jabs et al. |
| 2008/0169182 | A1 | 7/2008 | Denes et al. |
| 2009/0169807 | A1 | 7/2009 | Yang et al. |
| 2009/0178933 | A1 | 7/2009 | Zeng |
| 2011/0192714 | A1 | 8/2011 | Liu et al. |
| 2012/0168669 | A1 | 7/2012 | Che et al. |

FOREIGN PATENT DOCUMENTS

| | | |
|---|---|---|
| EP | 1444903 A | 10/2002 |
| EP | 1449605 A | 10/2002 |
| GB | 432101 | 7/1935 |
| JP | S52-9615 B | 3/1970 |
| JP | 2004-124155 | 10/2005 |
| WO | PCT/AU96/00768 A1 | 6/1997 |
| WO | PCT/US05/47699 | 7/2006 |
| WO | WO2006074117 A2 | 7/2006 |
| WO | PCT/KR2006/003195 | 8/2006 |
| WO | WO 2006/137851 | 12/2006 |
| WO | WO 2010/083040 | 7/2010 |

OTHER PUBLICATIONS

Sobhan, M.A., et al., Formation of Colloidal Gold Nanoparticles by Using Femtosecond Laser Ablation.
Sakamoto, Masanori, et al., Light as Constr.ToolOfMetalNanoparticles:Synthesis&Mechanism. Journal OfPhotochemistryAndPhotobiology C: Photochemistry Reviews. 2009, 33-56.
Wang, Chang-Hai, et al. Structural Properties of Naked Gold Nanoparticles Formed by Synchrotron XRay Irradiation, 2007, Journal of Synchrotron. Radiation, 14, 477-482.
Muto, Hitomi et al., Estimation of Surface Oxide on Surfactant-Free Gold Nanoparticles Laser-Ablated in Water. 2007, J. Phys. Chem., 111, 17221-17226.
Barcikowski Stephan, et al.,Impact & Structure OfLiterature On Nanoparticle Generation ByLaserAblationInLiquids. 2009,SpringerScience&BusinessMedia,JNanopart Res 11:1883-1893.
Menedez-Manjon, Ana, et al., InfluenceOfWaterTemperature On HydrodynamicDiameterOfGoldNanoparticlesFrom LaserAblation. 2010,J.Phys.Chem., 114, 2499-2504.
Yan,K.; Corona Plasma Generation, 2001, Technische Universiteit Eindhoven.
Zsigmondy,R. The Chemistry of Colloids, 1917, p. 11,19,30,68,86-95,114-119,122,123,127,128 John Wiley & Sons, Inc., New York.
Bechhold, H. Colloids in Biology and Medicine, 1919, p. 89-127, D. Van Nostrand Company, New York.
Federal Register/vol. 64, No. 158/Aug. 17, 1999/Rules and Regulations, p. 44653-44658.
Gibbs,R.J. Silver Colloids, Do They Work? 1999, Ronald J. Gibbs, Newark, DE.
Grier, Silver and its Compounds. Disinfection, Sterilization and Preservation, 2001, p. 403-407, Lippincott Williams & Wilkins, Philadelphia.
Pacheco, G. Studies on the Action of Metallic Colloids on Immunisation. Mem.Inst.Oswaldo Cruz, 1925, vol. 18,n.1,pp. 119-149.
De Vries, C.A.M.,et al.;Ionic Species in Negative Corona in Humid Air, 1983, p. 317-321, Eindhoven University of Technology, The.
Tas, M.A., Van Hardeveld, R. et al. Reactions of NO in a Positive Streamer Corona Plasma; Plasma Chem and Plasma Proc; 1997,p. 371-391, vol. 17, No. 4.
Turkevich, et al., A Study of teh Nucleation and Growth Processes in the Synthesis of Colloidal Gold; Discuss, Faraday Soc 55-59, 1951.
Yang, Li; Self-Assembly and Ordering Nanomaterials by Liquid-Phase Pulsed Laser Ablation: Chapter 2, School of Chemistry—University of Bristol, Nov. 2007, pp. 33-51.
Gamaly, E.G., et al., Control Over a Phase State of the Laser Plume Ablated by Femtosecond Laser; Spatial Pulse Shaping: Journal of Applied Physics, 95, 2250 (2004), p. 2250.
Yang, Dongfang, et al., Fabrication of Gold Nanoparticles by Pulsed Laser Ablation in Aqueoue Media; JLMN-Journal of Laser Micro/Nanoengineering vol. 3, No. 3, 2008, p. 147.
Mafune, Fumitaka, et al., Formation and Size Control of Silver Nanoparticles by Laser Ablation in Aqueous Solution; J. Phys. Chem. B 2000, 104, pp. 9111-9117.
Mafune, Fumitaka, et al., Formation of Gold Nanoparticles by Laser Ablation in Aqueous Solution of Surfactant; J. Phys. Chem. B 2001, 105, 5114-5120.
Mafune, Fumitaka, et al., Formation of Stable Platinum Nanoparticles by Laser Ablation in Water; J. Phys. Chem. B 2003, 107, 4218-4223.
Barcikowski, Stephan, et al., Generation of Nanoparticle Colloids by Picosecond and Femtosecond Laser Ablations in Liquid Flow; Appl. Phys. Lett. 91, 083113 (2007).
Nichols, William T., et al. Laser Ablation of a Platinum Target in Water. I. Ablation Mechanisms: Journal of Applied Physics 100, 11491 (2006).
Amendola, Vencenzo, et al., Laser Ablation Syntheses in Solution and Size Manipulation of Noble Metal Nanoparticles; Phys. Chem. Chem. Phys., 2009, 11 3805-3821.
Cheriathundam,E., et al., A Species Differences in the Renal Toxicity of the Antiarthritic Drug, Gold Sodium Thiomalate, 1996, J. Biochem Tox., 11(4), 175-81.
Faraday, M. The Bakerian Lecture. Experimental Relations of Gold (and other metals) to Light. Philosoph. 1857, Trans. R. Soc. London, 147, 145-181.
Walz, D., et al., Biologic Actions and Pharmacokinetic Studies of Auranofin, 1983. Am J Med, 759(6A).
Eisler, Ronald. Biochemica, Health, and Ecotoxicogioal Perspectives on Gold and Gold Mining. 2004, Boca Raton: CRC Press.
Ho, S., et al., Gold Based Metalotherapeutices:UsePotential.InM. Gielen,et al., MetallotherapeuticDrugsandMetalBasedDiagnosticAgents.2005 pp. 507-527),Chictester:JHWileyandSons.
Dabrowiak.J., Gold Compoungs for Treating Arthritis: Cancer and Other Diseases. 2009, In J. Dabrowiak, Metals in Medicine(pp. 191-217), Chichester UK:JohnWileyandSons.
Shaw,C.F.,III. GoldComplexesWithAntiArthriticAntiTumourAndAntiHIVActivityInUsesInorganicChemistryInMedicine,1999a, N.C. Farrell,(Ed.),RoyalSocietyofChemistry,Cambridge,UK,26-57.
Whyman,R., Gold Nanoparticles A Renaissance in Gold Chemistry. 1996, Gold Bulletin, 29(1), 11-15.

(56) References Cited

OTHER PUBLICATIONS

Panyala,N.G.,et al.(2009) Gold and Nano-Gold in Medicine: Overview, Toxicology and Perspectives. Journal of Apppplied Biomedicine, 7,75-91.
Daniel, M.C.,et al.(2004) Gold Nanoparticles: Assembly, Supramolecular Chemistry, Quantum-Size-Related Properties . . . Chem.Rev., 104,293-346.
Lacerda,S.H.D.P., et al.(2010) Interaction of Gold Nanoparticles with Common Human Blood Proteins. American Chemical Society, 4(1),365-379.
Brown, C.L.,et al.(2007) Nanogold-pharmaceutics (i) The use of colloidal gold to treat experimentally-induced arthritis . . . Gold Bulletin, 2007, 40(3),245-250.
Henglein,A., et al.(1998) Radiolytic Control of the Size of Colloidal Gold Nanoparticles. Langmuir, 14, 7392-7396.
Sweeney, S.F., et al.(2006) Rapid Purification and Size Separation of Gold Nanoparticles via Diafiltration. J.Am.Chem.Soc., 128, 3190-3197.
Tao, A.R., et al.(2008) Shape Control of Colloid Metal Nanocrystals. Small, 4(3), 310-325.
Sakai,T.,et al.(2008)Surfactant and Reducer-Free Synthesis of Gold Nanoparticles in Aqueous Solutions,Colloids and Surface A: Physiocochemical and Engineering Aspects,18-26.
Kimling, J.,et al.(2006 Turkevich Method for Gold Nanoparticle Synthesis Revisited. J. Phys. Chem. B, 110, 15700-15707.
Ma, H; Yin, B; Wang, S; Jiao, Y; Pan, W; Huang, S; Chen, S.; Meng, F; Synthesis of Silver and Gold Nanoparticles by a Novel Electrochemical Method, ChemPhysChem, 2004, 5, 68-75.
Powell, J., Our Mightiest Germ Fighter, Science Digest, 1978, p. 57-59.
Svedberg, T. The Formation of Colloids, 1921, p. 22-41, D.Van Nostrand Company, New York.
Liu, Yu-Chuan, et al. Active catalysis of electrochemically prepared gold nanoparticles for the decompsition of aldehyde in alcohol solutions. Electrochemistry Communications (cont'd from above) 2006,1163-1167, 8.
Hickling, A. et al. Contact Glow-Discharge Electrolysis. Trans Faraday Soc., 1964, 783-793, 60.
Toriyabe, Yu, et al. Controlled formation of metallic nanoballs during plasma electrolysis. Applied Physics Letters, 2007, 041501-1-041501-3, 91.
Wuthrich, Rolf, et al. Electrochemical discharges—Discovery and early applications. Electrochimica Acta, 2009, 4031-4035, 54.
Locke. B.R., et al. Electrohydraulic Discharge and Nonthermal Plasma for Water Treatment. Ind. Eng. Chem. Res., 2006, 882-905, 45.
Meiss, Sebastian A., Employing Plasmas a Gaseous Electrodes at the Free Surface of Ionic Liquids: Deposition of Nanocrystalline Silber Particles. ChemPhysChem, 2007, 50-53, 8.
Hickling, A, et al. Glow-Discharge Electrolysis. J. Electroanal. Chem, 1964, 65-81, 8.
Chaffin, John H., et al. Hydrogen Production by Plasma Electrolysis. Journal of Energy Engineering, 2006, 104-108, 132:3.
Staack, David, et al. Nanoscale Corona Discharge in Liquids, Enabling Nanosecond Optical Emission Spectroscopy. Agnew.Chem. Int.Ed., 2008, 8020-8024, 47.
Torimoto, Tsukasa, et al. Sputter deposition onto ionic liquids: Simple and clean synthesis of highly dispersed ultrafine metal nanoperticles. Applied Physics Letters, 2006. (cont'd from above) 243117-1-243117-3, 89.
Nagata, Yoshio, et al. Sonochemical Formation of Gold Particles in Aqueous Solution. Radiation Research, 1996, 333-338, 146.
Saez, Veronica, et al. Sonoelectrochemical Synthesis of Nanoparticles. Molecules, 2009, 4284-4299, 14.
Fujimoto, Taku et al. Sonolytical Preparation of Various Types of Metal Nanoparticles in Aqueous Solution. Scripta mater., 2001, 2183-2186, 44.
Johnston,H.J.,et al., Review of In Vivo and In Vitro Toxicity of Silver and Gold Particulates. Critical Reviews in Toxicology, 40(4), 328-346.

Yuan,H., et al., A Simple Approach to Control the Growth of Non-Spherical Gold Nanoparticles. Chinese Chemical Letters, 14(11),1163-1166.
Abraham, G.E.,et al., P.B. (1997) Management of Rheumatoid Arthritis: Rationale for Use Colloidal Metallic Gold. J.Nutr.Environ. Med.7, 295-305.
Tsai,C., et al.(2007) Amelioration of Collagen-Induced Arthritis in Rats by Nanogold. Arthritis Rheum. 56(2), 544-54.
Wang, C.H., et al.(2007) Aqueous Gold Manosols Stabilized by Electrostatic Protection Generated by X-Ray Irradiation Assisted . . . Materials Chemistry and Physics, 106, 323-329.
Sperling, R.A., et al., W.J.(2008) Biological Applications of Gold Nanoparticles, Chem.Soc.Rev, 37, 1896-1908.
Abraham, G.E. (2008) Clinical Applications of Gold and Silver Nanocolloids. Original Internist, 132-157.
Brown, C.L., et al.(2008) Colloidal Metallic Gold is Not Bio-Inert. Inflammopharmacology, 16, 133-137.
Leonard, T.B., et al.(1986) Effects of Chrysotherapeutic Agents Auranofin and Gold Sodium Thiomalate on Hepatic and Renal Drug . . . Biochemical Pharmacology, 35,(18),3057-3063.
Mucalo.M.R., et al.(2001) Electric arc Generated (Bredig) Palladium Nanoparticles: Surface Analysis by . . . Journal of Materials Science Letters, 20, 1853-1856.
Sanchez-Iglesias, et al., Synthesis and Optical Properties of Gold Nanodecahedra with Size Control; Adv.Mater. 2006, 18, 2529-2534.
Malvery Instruments Technical Note, Zeta Potential; Zetasizer Nano Series Technical Note, MRK654-01.
Kirby, et al., Zeta Potential; Wikipedia.
Salopek, et al., Measurement and Application of Zeta-Potential; Faculty of Mining, Geology & Petroleum Engineering, University of Zagreb, vol. 4, str. 147-151. 1992.
Xia, et al., Shape-Controlled Synthesis of Metal Nanocrystals: Simple Chemistry Meets Physics; Angew. Chem. Int. Ed. 2009, 48, 60-103.
Zhang, et al, Synthesis and Growth Mechanism of Pentagonal Bipyramid-Shaped Gold-Rich Au/AG Alloy Nanparticles; Langmuir 2007, 23, 6372-6376.
Hoben, W.F.L.M.; Pulsed Corona-Induced Degredation of Organic Materials in Water, 2000, Technische Universiteit Eindhoven.
Lofton, C., et al.; Mechanisms Controlling Crystal Habits of Gold and Silver Colloids, Adv. Funct. Mater. 2005, p. 1197-1208, 15.
Martinez, S.S., et al.; Electrolytically Generated Silver and Copper Ions to Treat Cooling Water . . . Intnl. Journal of Hydrogen Energy, 2004, p. 921-932, 29.
Bhattacharyya, S., et al.; Localized Synthesis of Metal Nanoparticles Using Nanoscale Corona Discharge in Aqueous Sols., Adv. Mater.,2009,p. 4039-4022, 21.
Plieth, et al.; Investigations on the Electrochemical Prep. of Gold Nanoparticle Composites, J. Solid State Electrochem., 2004, vol. 8, pp. 209-213.
Yang, G.W., Laser Ablation in Liquids: Applications in the Synthesis of Nanocrystals. 2007, Progress in Materials Science 52, 648-698.
Peng, Zhangquan, et al., Laser Assisted Synthesis of Au—Ag Alloy Nanoparticles in Solution. 2006, J. Phys. Chem., 110, 2549-2554.
Sau, Tapan K., et al., NonsphericalNobleMetalNanoparticles:Colloid-Chemical Synthesis&MorphologyControl. 2010, Material Views,Advanced Materials, 22, 1781-1804.
Barsch, Niko, et al., PureColloidalMetal&CeramicNanoparticlesFromHighPowerPicosecondLaserAblationInWater&Acetone. 2009, Nanotechnology 20, 445603(9pp).
Kabashin, A.V., et al., SynthesisOfColloidalNanoparticlesDuringFemtosecondLaserAblationOfGoldInWater. 2003, Journal of Applied Physics, vol. 94,No. 12,p. 7941-7943.
Tarasenko, N.V., et al., SynthesisOfNanosizedParticlesDuring Laser Ablation of Gold in Water. 2006, Applied Surface Science 252, 4439-4444.
Shen, Qingming, et al., SynthesisOfStabilzerFreeGold Nanoparticles by Pulse Sonoelectrochemical Method. 2011, Ultrasonics Sonochemistry 18, 231-237.
Chen, Yu-Hung, et al., ANewApproachForTheFormationOf Alloy Nanoparticles: LaserSynthesisOfGold-SilverAlloyFromGold-SilverColloidalMixtures. 2001, Chem.Commun., 371-372.

(56) References Cited

OTHER PUBLICATIONS

Simakin, A.V., et al., Nanodisks of Au and Ag Produced by Laser Ablation in Liquid Environment; Ehcmical Physics Letters 348 (2001) 182-186.

Lee, Inhyung, et al., Production of Au—Ag Alloy Nanoparticles by Laser Ablation of Bulk Alloys; Chem. Commun., 2001, 1782-1783.

Barcikowski, S., et al., Properties and Nanoparticles Generated During Femtosecond Laser Machining in Air and Water; Appl. Phys. A 87, 47-55 (2007).

Pyatenko, A., et al., Synthesis of Silver Nanoparticles by Laser Ablation in Pure Water; Appl. Phys. A 79, 803-806 (2004).

Besner, S., et al., Two-Step Femtosecond Laser Ablation-Based Method for the Synthesis of Stable and Ultra-Pure Gold Nanoparticles in Water; Appl. Phys. A 88 269-272 (2007).

Li, Bing, et al., Ultrafast Sources: Ultrafast Lasers Produce Nanoparticles; Laser Focus World, vol. 43, Issue 9, Sep. 24, 2013.

Weibo, et al., Applications of Gold Nanoparticles in Cancer Nanotechnology. 2008, Nanotechnology Science and Applications I, 17-32.

Burda, et al., Chemistry and Properties of Nanocrystals of Different Shapes. 2005, American Chemical Society, vol. 105, pp. 1025-1102.

Liu, Yu-Chuan, et al. New pathway for the synthesis of ultrafine silver nanoparticles from bulk silver substrates in aqueous solutions by sonoeleotrochemical methods. (cont'd from above) Electrochemistry Communications, 2004, 1163-1168, 6.

Bruggeman, Peter, et al. Non-thermal plasmas in and in contact with liquids. J.Phys.D:Appl.Phys, 2009, 053001-053029, 42.

Kravchenko, A.V., e al. On the Change in Properties of Water Subjected to Low-Temperature Plasma Electrolysis. High Energy Chemistry, 2004, 333-337, 38-5.

Koo, Il Gyo, et al. Platinum nanoparticles prepared by a plasma-chemical reduction method. J.Mater.Chem. 2005, 4125-4128, 15.

Aqil, A., et al. Preparation of stable suspensions of gold nanoparticles in water by sonoelectrochemistry. Ultrasonics Sonochemistry, 2008, 1055-1061. 15.

Liu, Yu-Chen, et al. Size-Controlled Synthesis of Gold Nanoparticles from Bulk Gold Substrates by Sonoeleotrochemical Methods. J.Phys. Chem.B, 2004, 19237-19240, 108.

Kean, W., et al., Long Term Chrysotherapy; Incidence of Toxicity and Efficacy During Sequential Time Periods. 1979, Arthritis Rheum, 22(5), 495-501.

Kean, W., et al., The Clinical Pharmacology of Gold. 2008, Immunopharmacology, 16(3), 112-25.

Sylvestre, et al., Surface Chem. of Gold Nanoparticies Produced By Laser Ablation In Aqueous Media, 2004, J. Phys. Chem. B 2004, 108, 16864-16869.

Szabo, K., et al., The Effects of Gold-Containing Compounds on Pregnant Rabbits and Their Fetuses, 1978, Vet Path, Suppl 5, 95-105.

Szabo, K., et al., The Effects of Gold-Containing Compounds on Pregnant Rats and Their Fetuses., 1978, Vet Path, 5, 89-86.

Teixido, M., et al., The Role of Peptides in Blood-Brain Barrier Nanotechnology., 2008, J. Pept. Sic., 14, 163-173.

Payne, B., et al., The Subacute and Chronic Toxicity of SK&F 36914 and SK&F D-39162 in Dogs., 1978, Vet Path, Suppl 5, 9-12.

Payne, B., et al., The Subacute and Chronic Toxicity of SK&F 36914, SK&F D-39162 and Gold Sodium Thiomalate in Rats., 1978, Vet Path Suppl., 15(5), 13-22.

USFDA. Guidance For Industry Estimating the Maximum Safe Starting Dose Initial Clinical Trials for Therapeutics in Adult Health Volunteers., 2005, Pharmacology and Toxicology.

Wu, C.; Zeng, T., Size-Tunable Synthesis of Metallic Nanoparticles in a Continuous and Steady-Flow Reactor, Chem. Mater. 2007, 123-125, vol. 19, No. 2.

Ultra Professional Instructions for making Premium AC Colloidal Silver with your HVAC Ultra Professional System.

HVAC ARC Silver Solutions, System Tech Engineering, http://web.archive.org/web/20021125133241/http://www.hvacsilver.com; Nov. 12, 2008.

Plasma (physics); Wikipedia; http://en.wikipedia.org/wiki/plasma_(physics); 2010.

Taylor cone; Wikipedia; http://en.wikipedia.org/wiki/Taylor_cone; 2010.

Manolache, S; Shamamian, V.; Denes F. Dense Medium Plasma-Plasma-Enhanced Decontamination of Water of Aromatic Compounds, J. of Environ Eng. Jan. 17-25, 2004.

Riegel, E.R.; Osthoff, R.C.; Flach, D.O. Bredig Sols: A Lecture Demonstration, J. Chem. Educ, 1949, p. 519, vol. 26, No. 10.

Weiser, Harry Boyer. Inorganic Colloid Chemistry, 1933, p. 1, 8-17, 45-46, 116-117, 124-125, 132-135, John Wiley & Sons, Inc., New York.

Kraemer, E.O., Svedberg, T. Formation of Colloid Solutions by Electrical Pulverization in the High-Frequency Alternating Current Arc, J. Am. Chem Soc. 1924, 46 (9) p. 1980-1991.

Rodriguez-Sanchez, L., Blanco, M.C., Lopez-Quintela, M.A., Electrochemical Synthesis of Silver Nanoparticles, J. Phys. Chem. B., 2000, 104, p. 9683-9688.

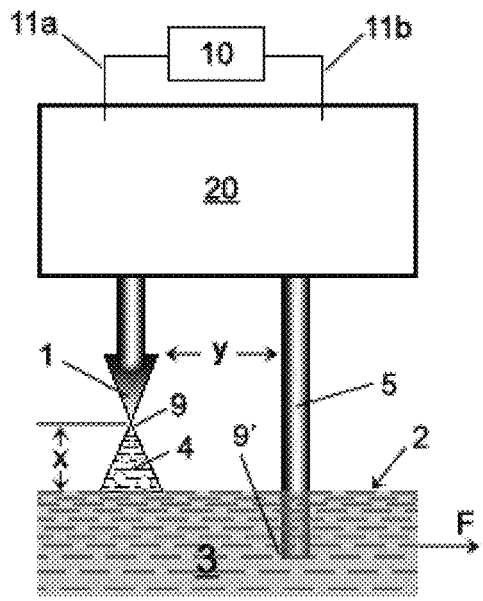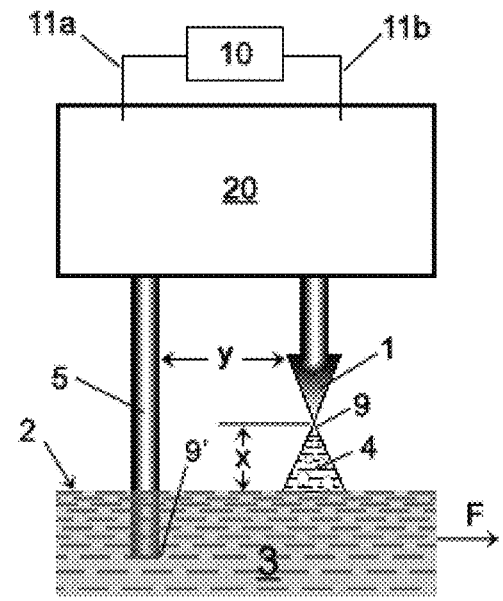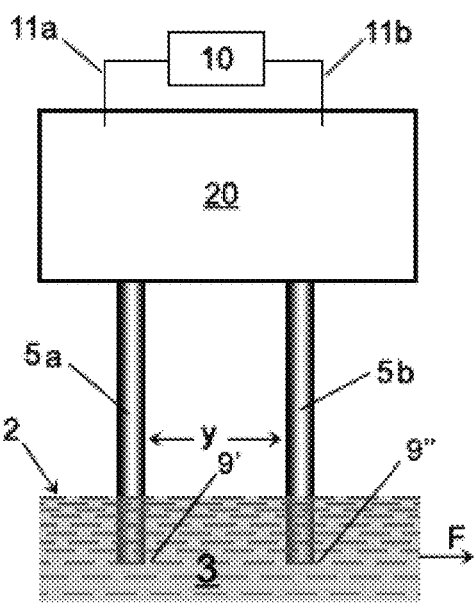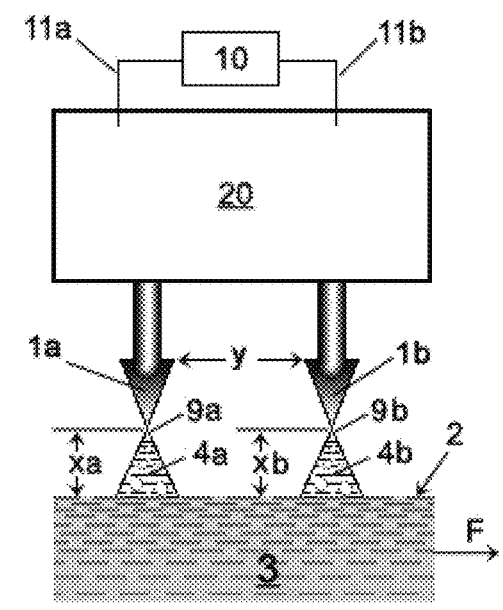

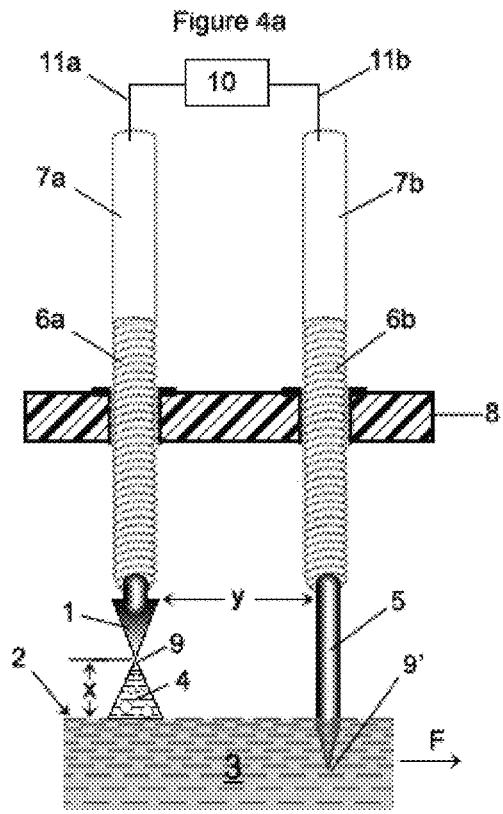
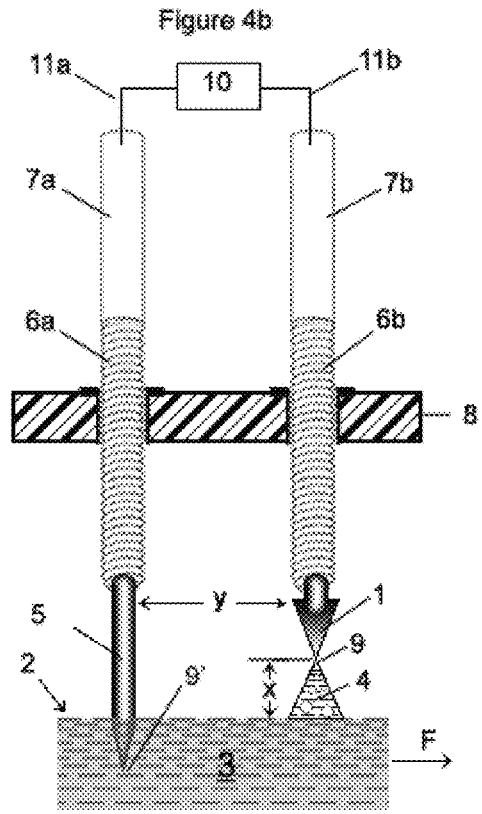
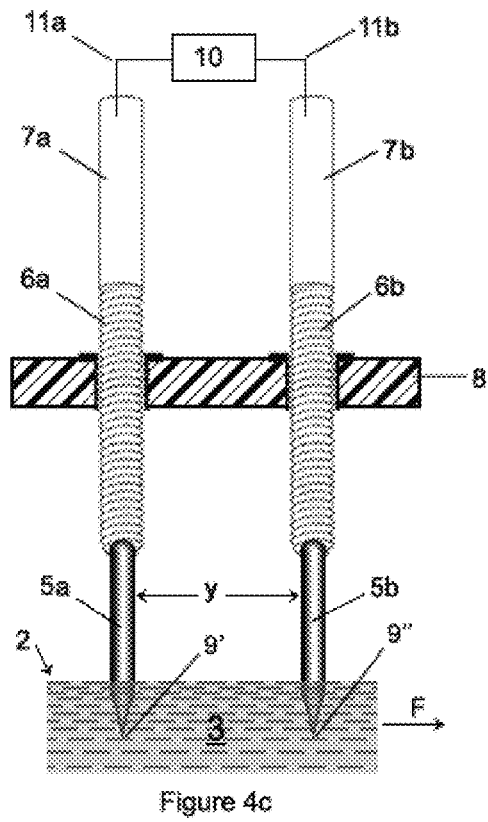
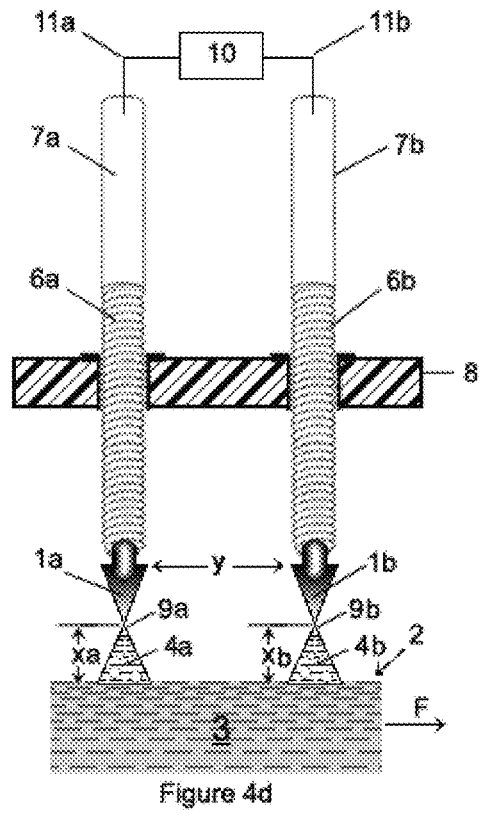

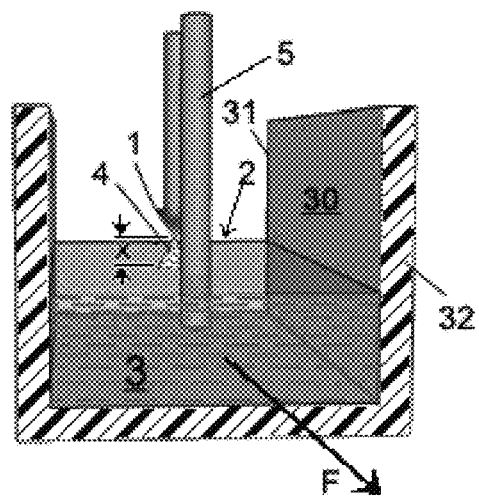
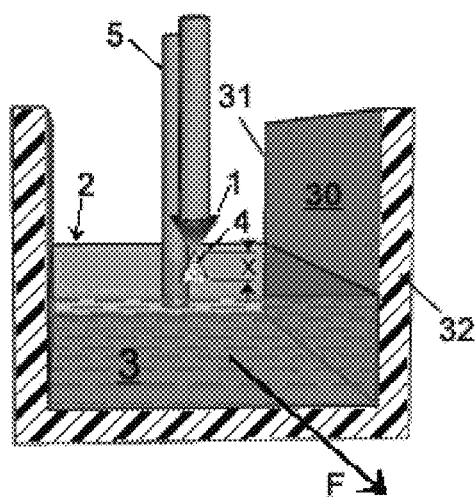
Figure 8a
Figure 8b
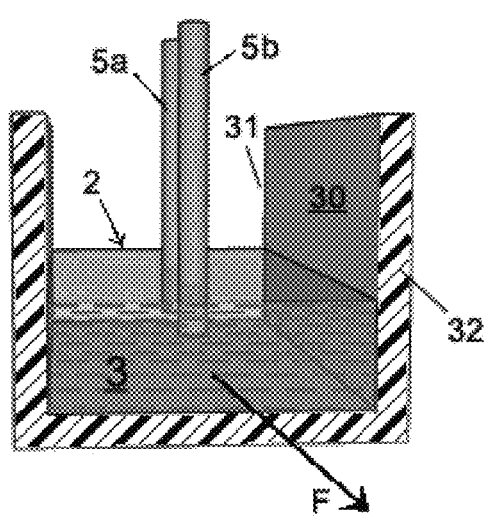
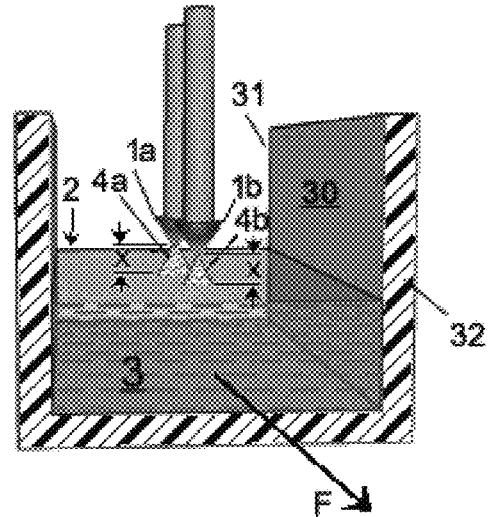
Figure 8c
Figure 8d

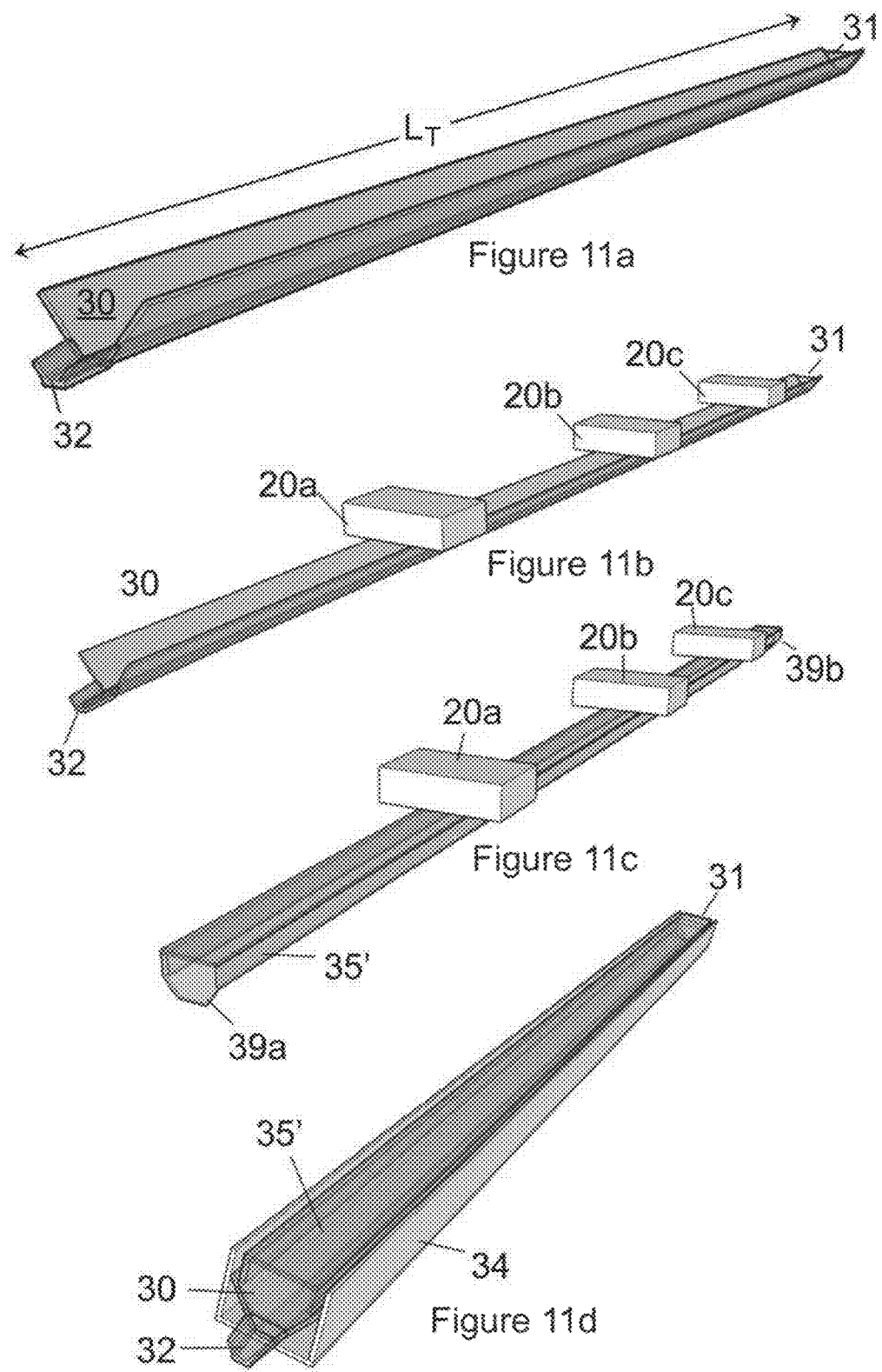

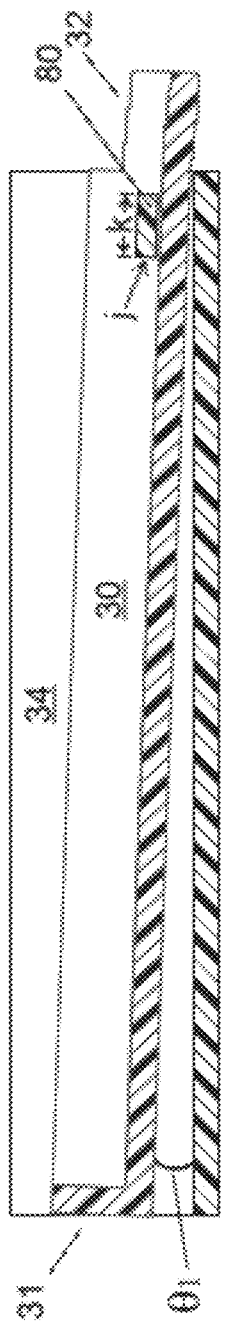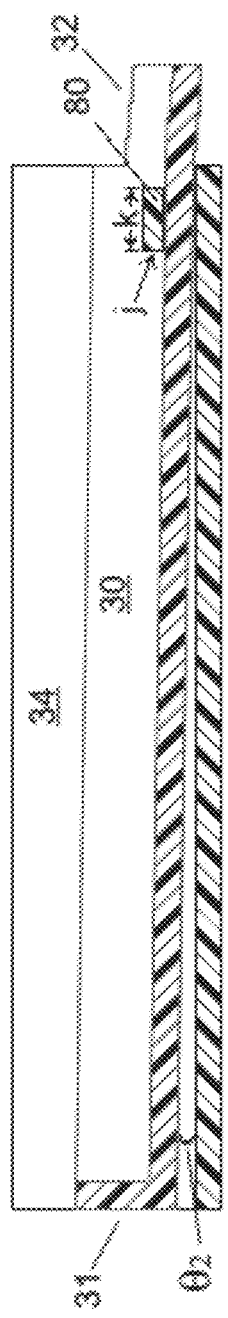

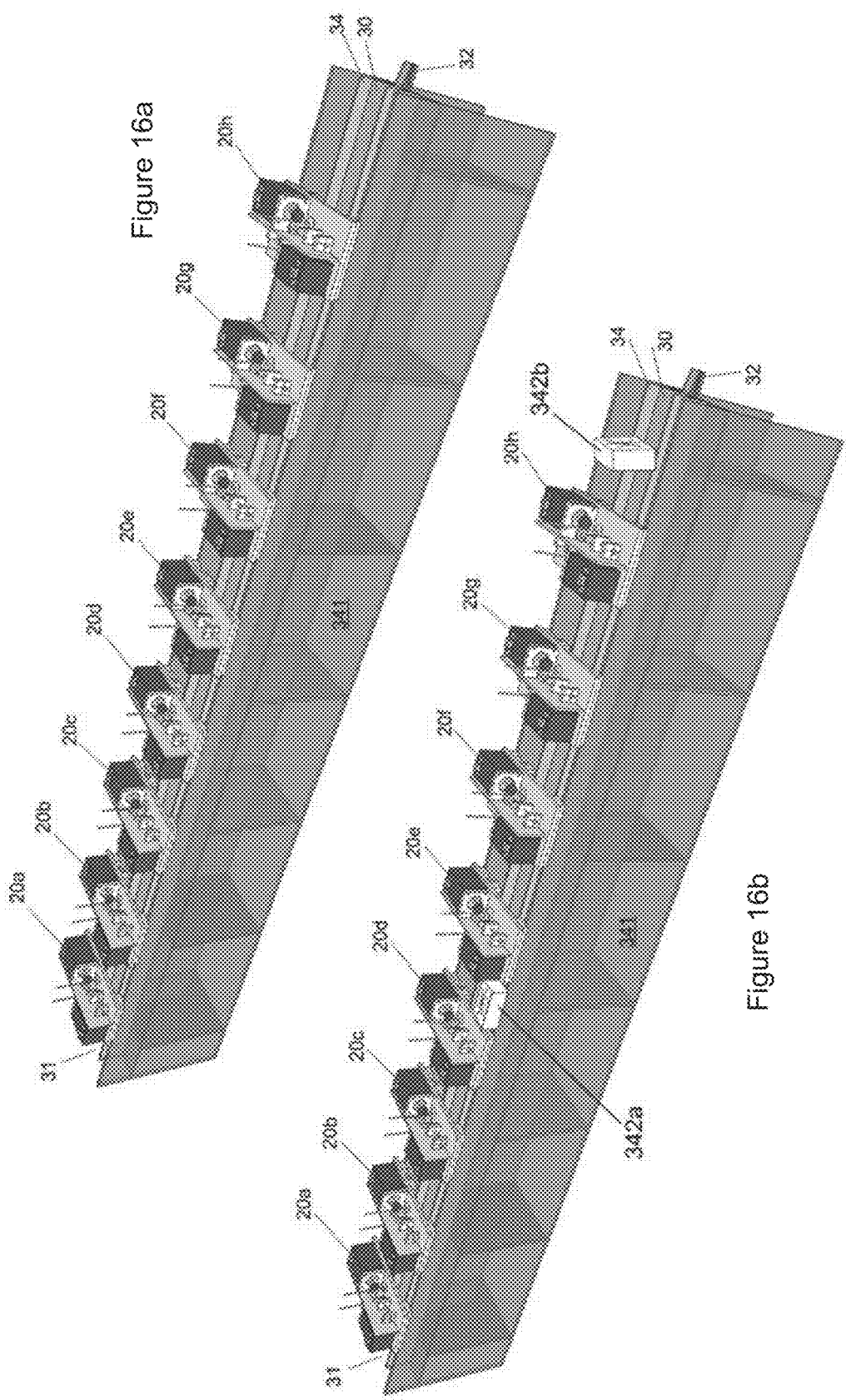

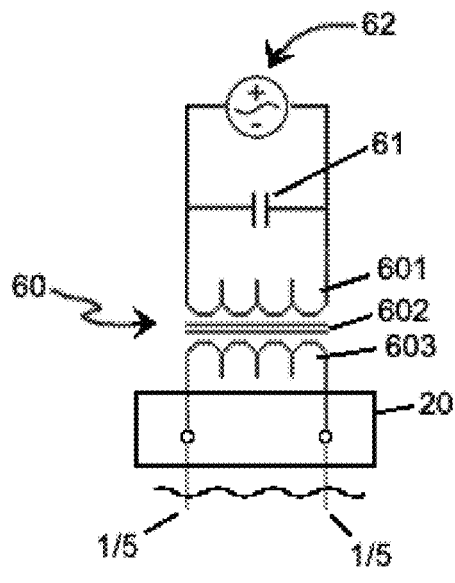
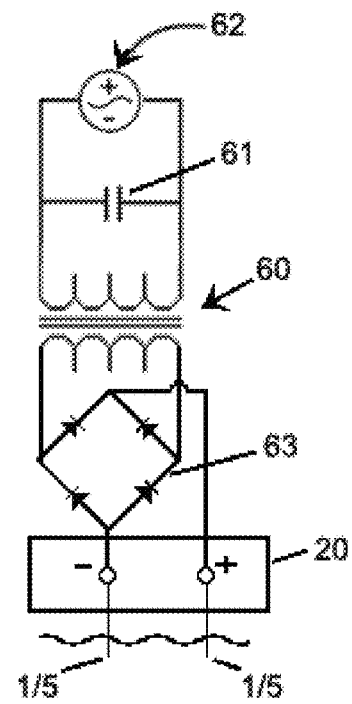
Figure 16d    Figure 16e
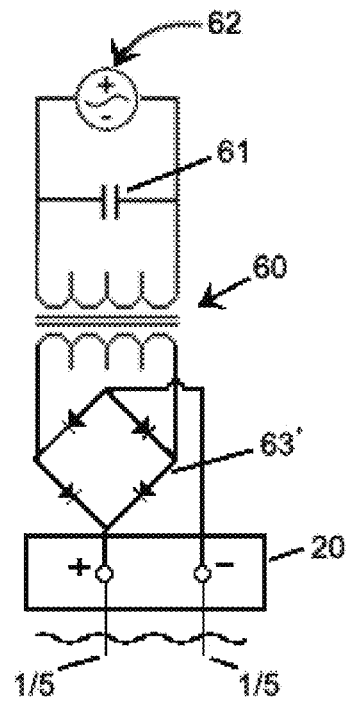
Figure 16f

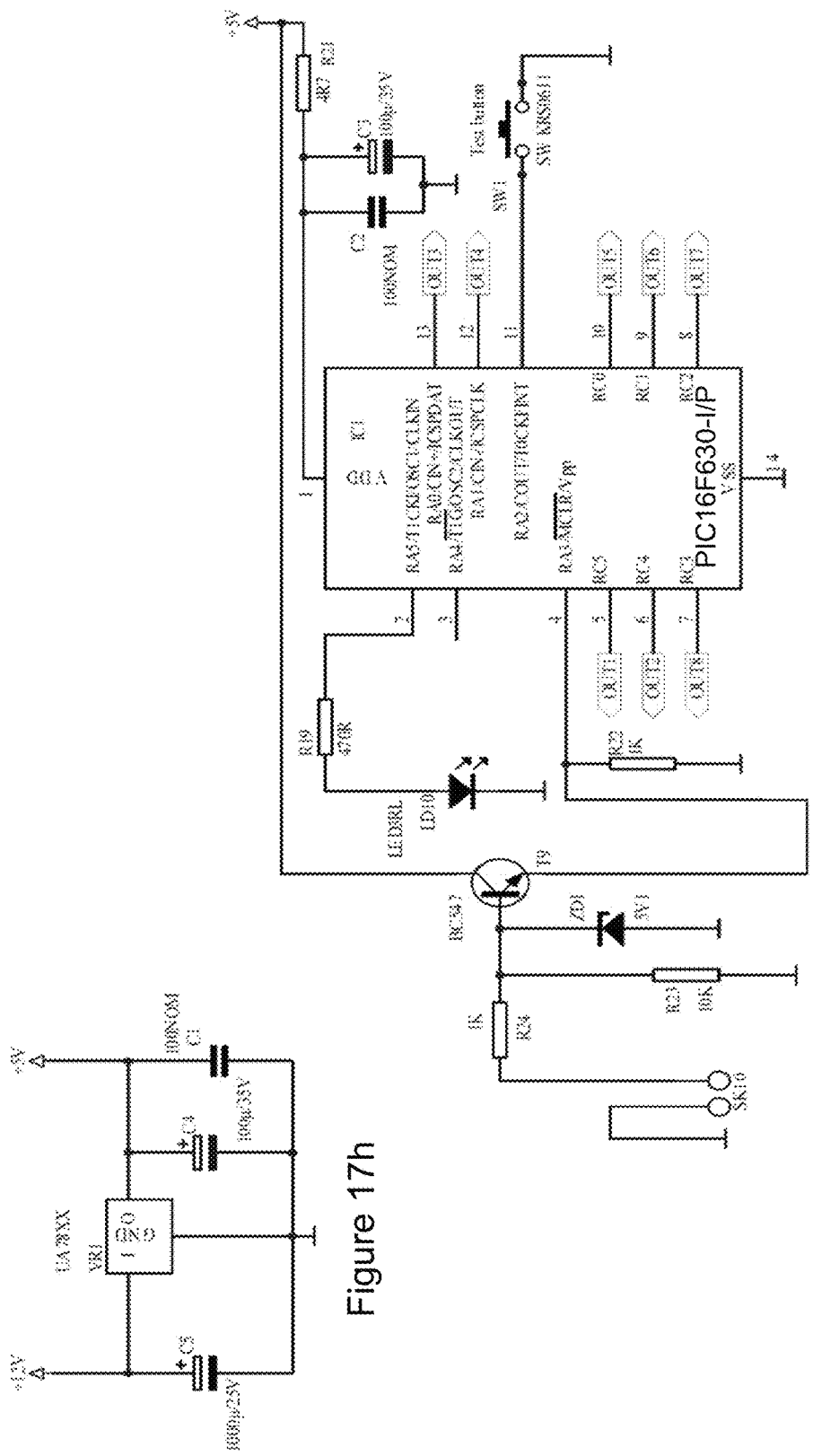

$$V_{out} = \frac{V_1(R_2 \| R_L)}{(R_1 + R_2 \| R_L)}$$

$R_L$ = 10M Ohm input impedance of Multimeter

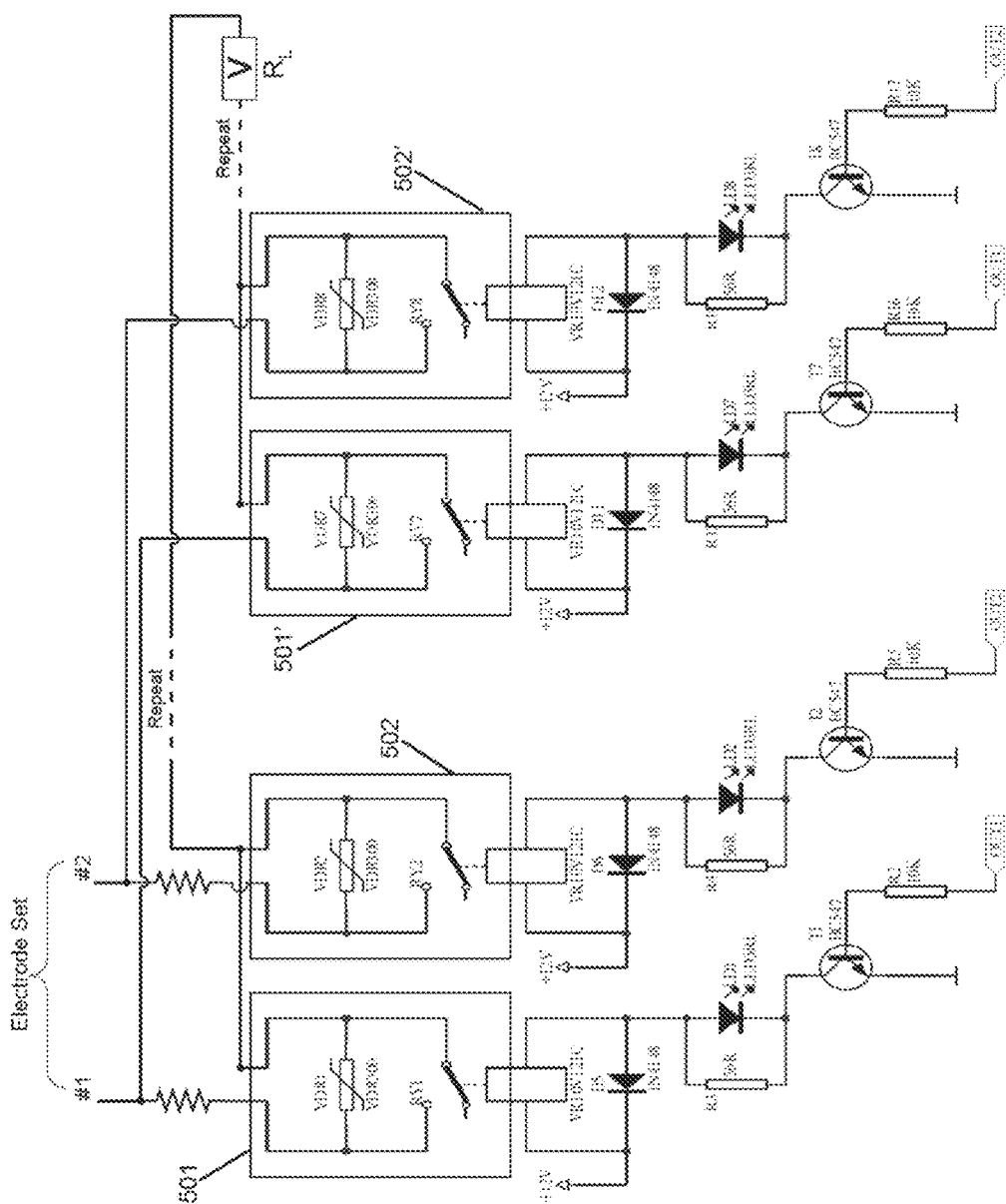

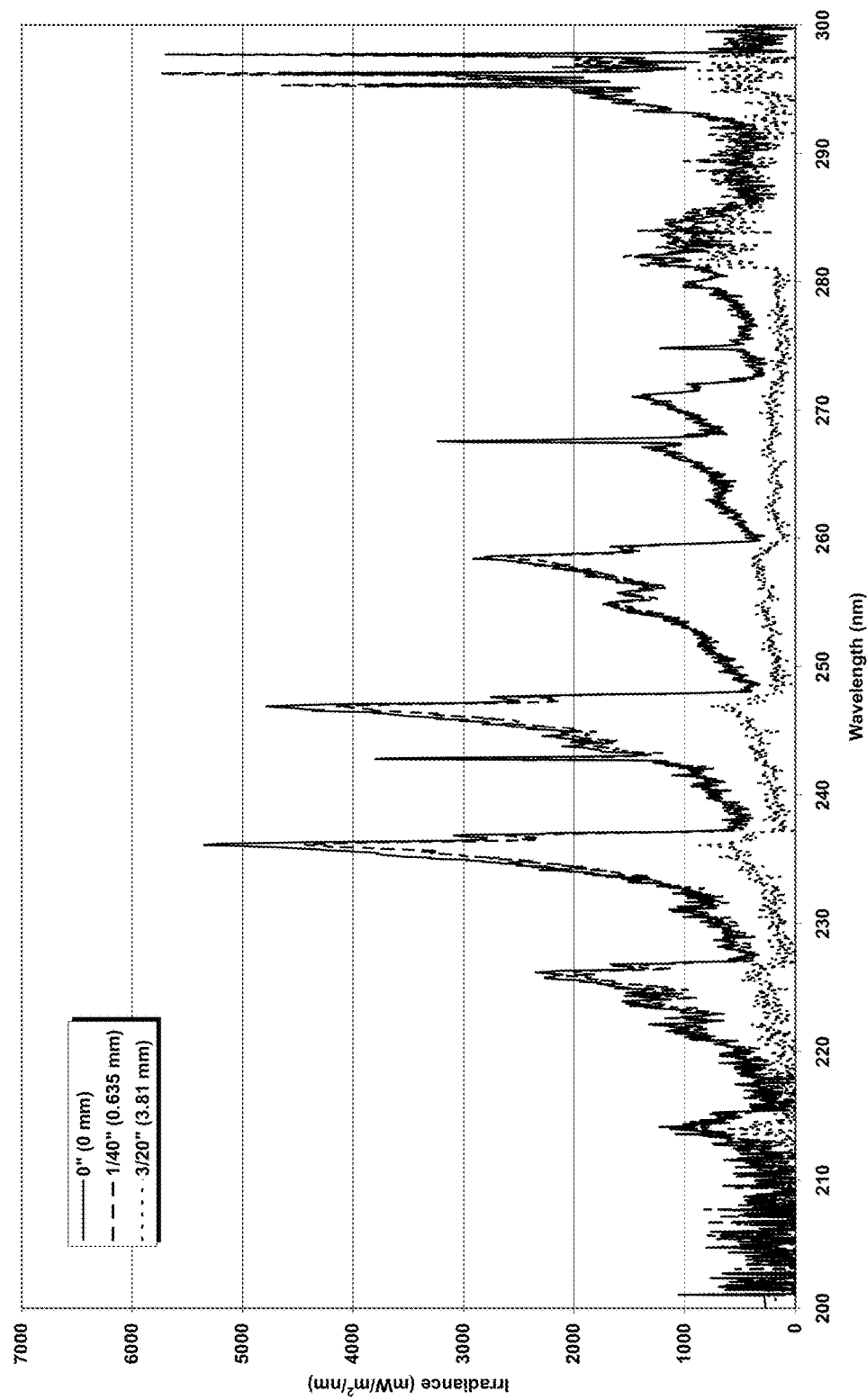

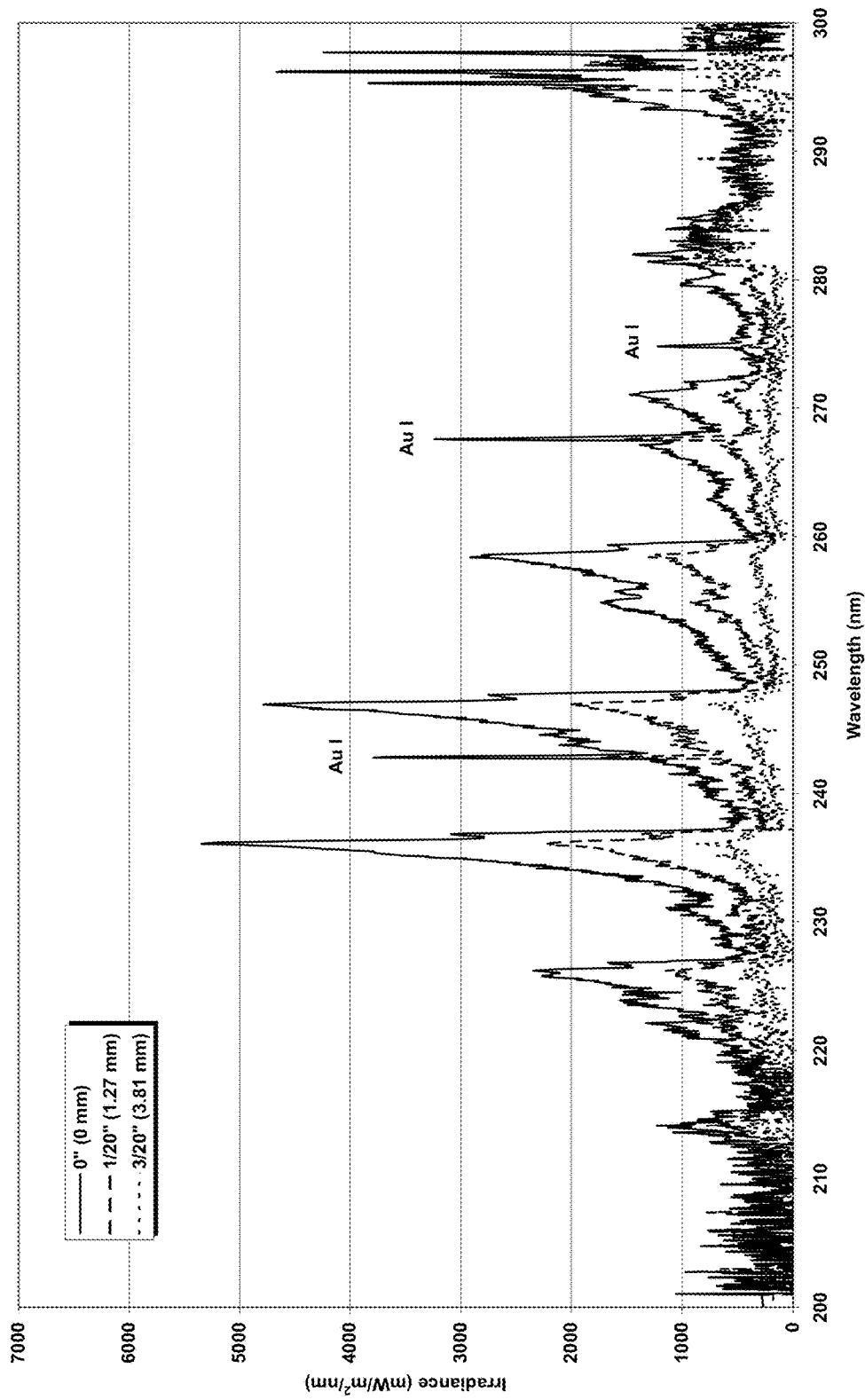

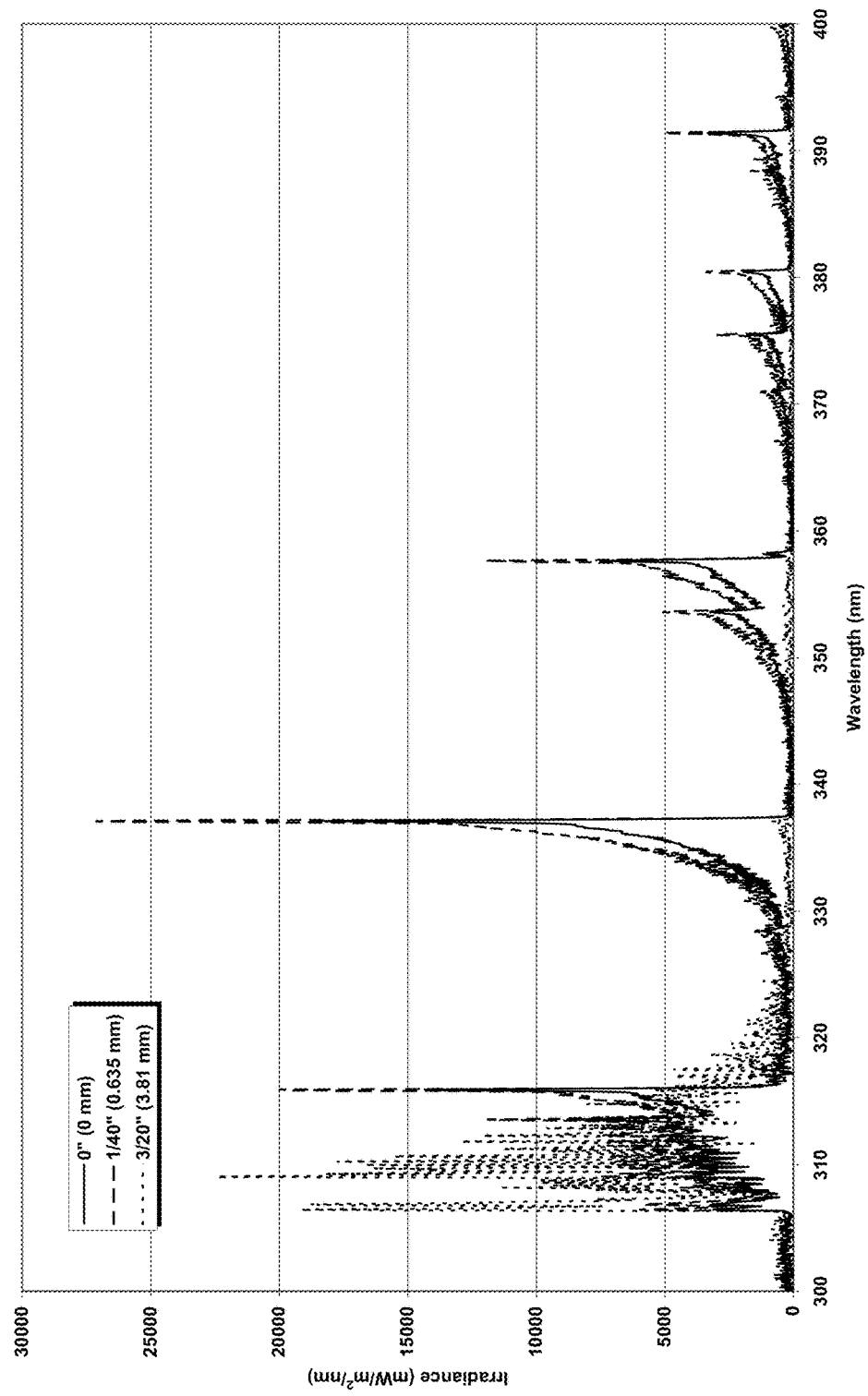

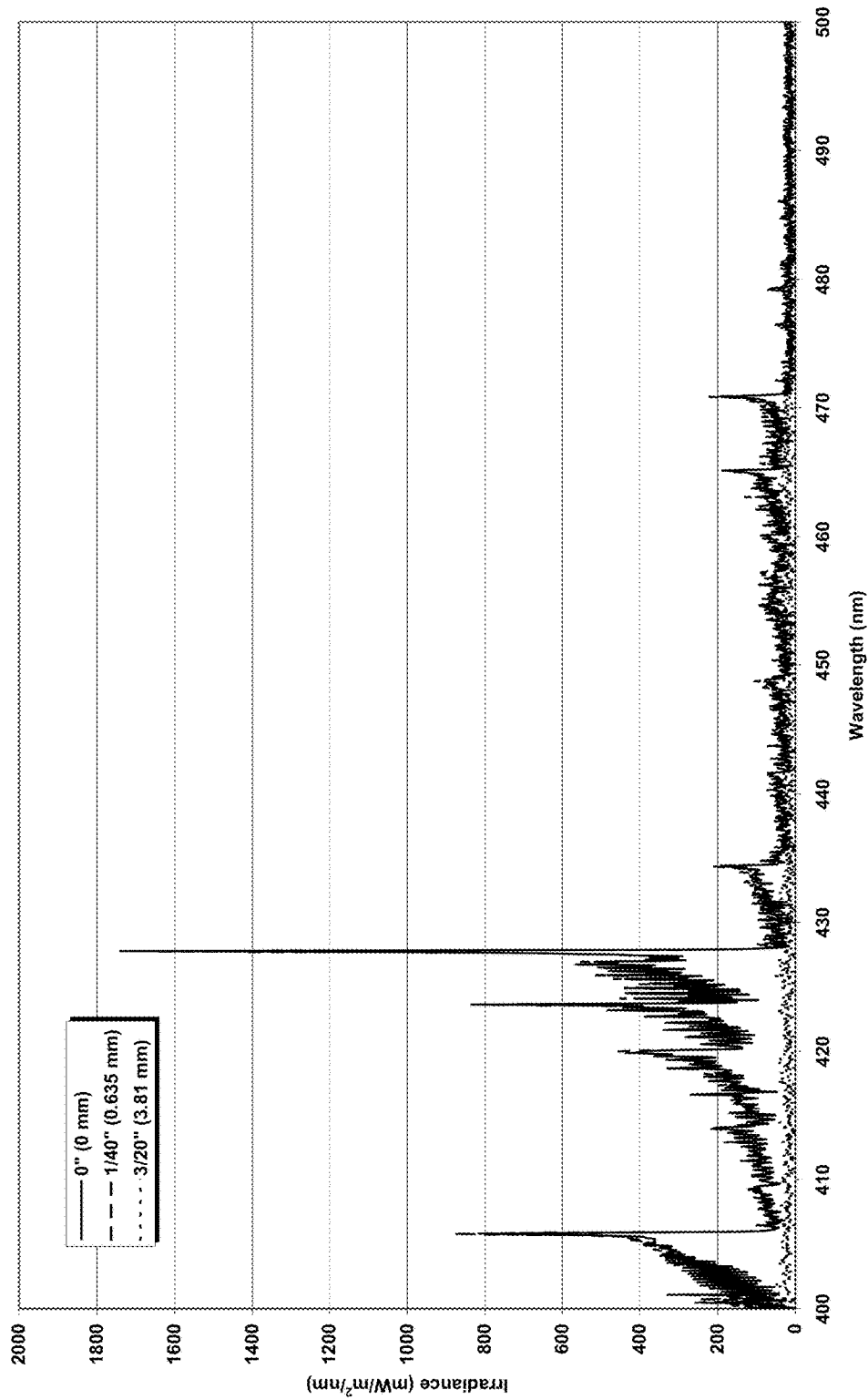

Gold GD-016
5.46% transmission

GB-019
0.81% transmission

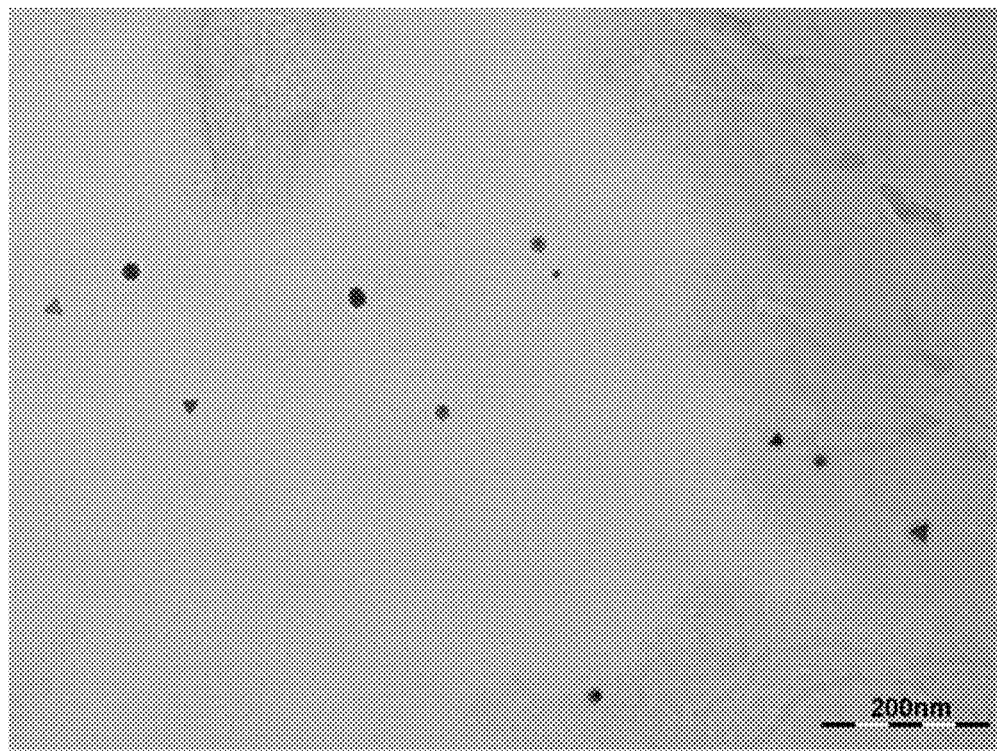
Figure 48 a1
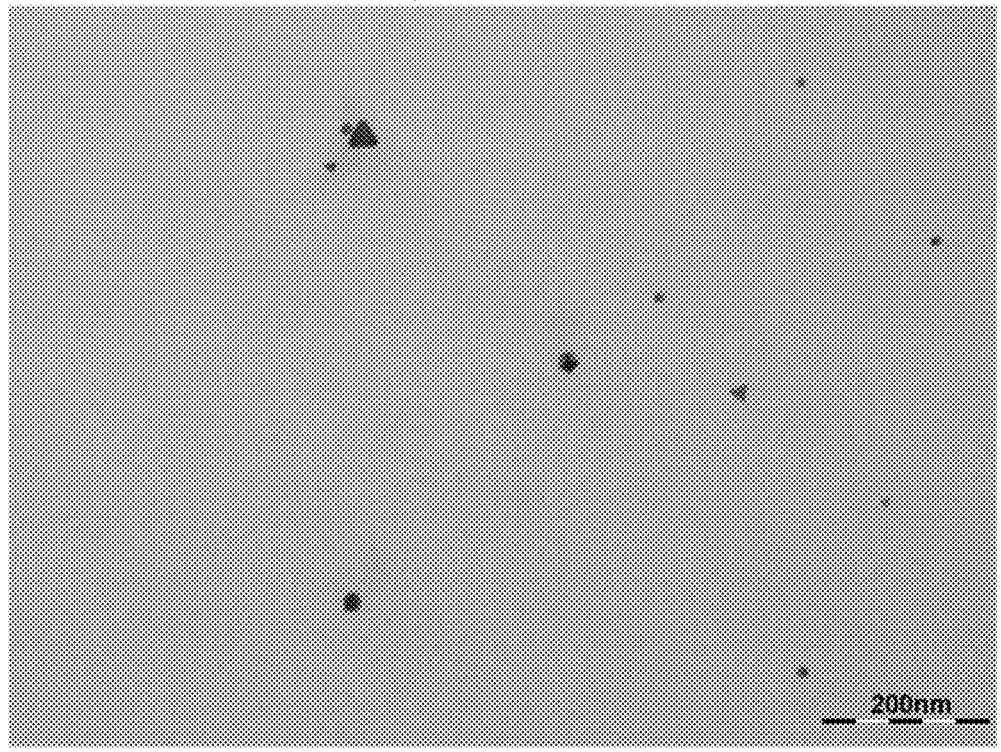
Figure 48 a2
GB-134

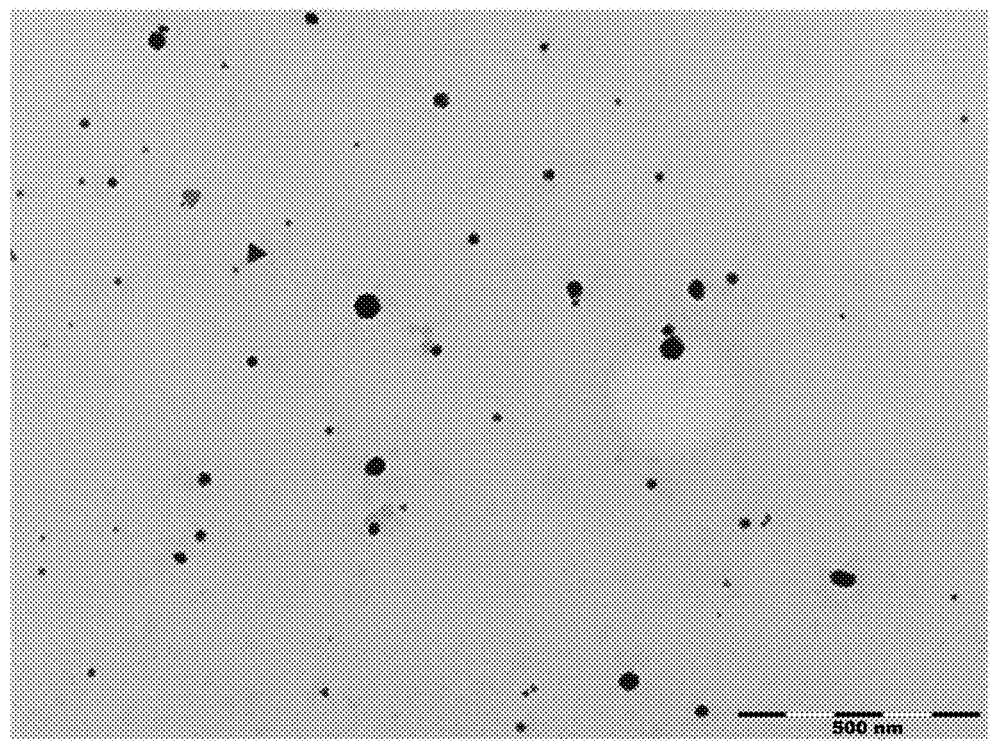
Figure 49 a1
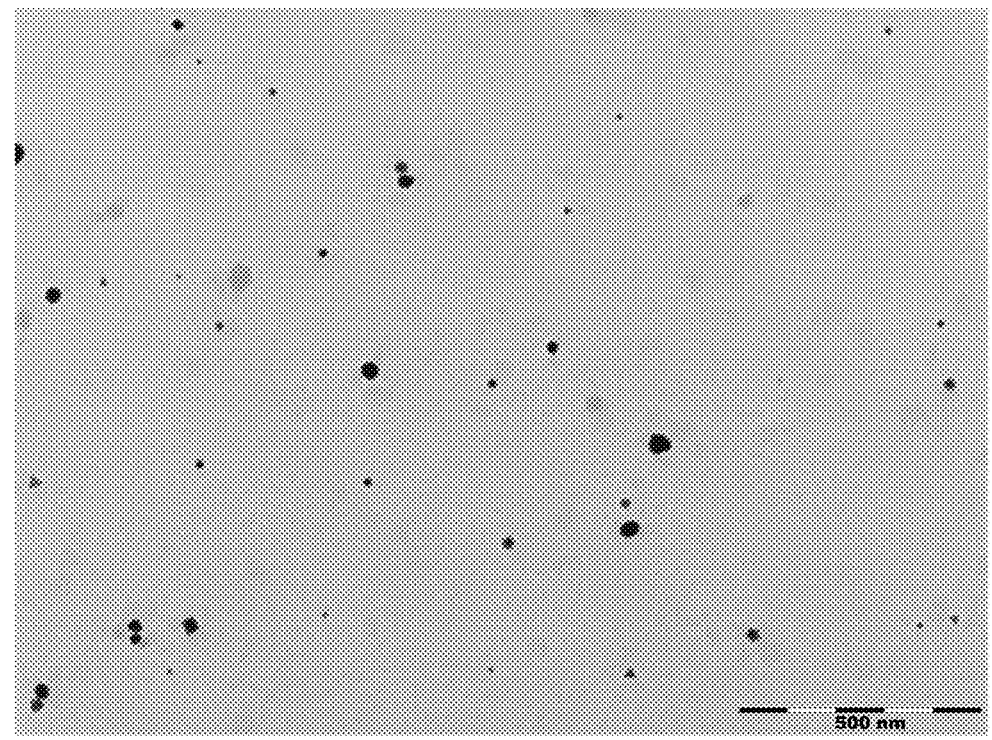
Figure 49 a2
GB-098

Gold GB-098
1.69% transmission

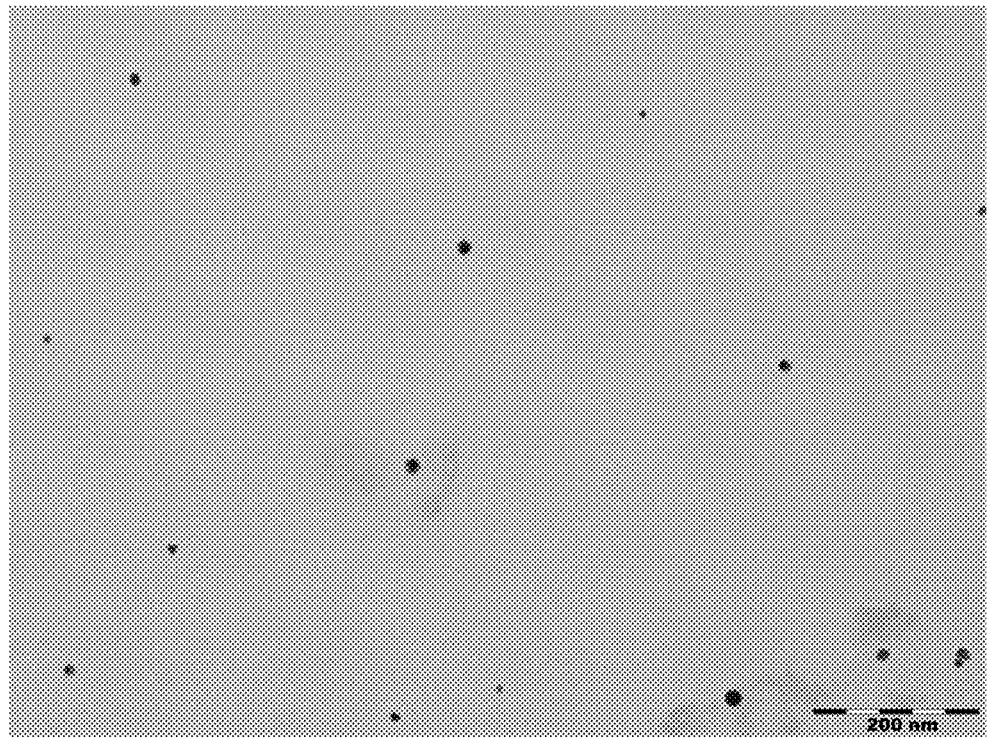
Figure 50 a1
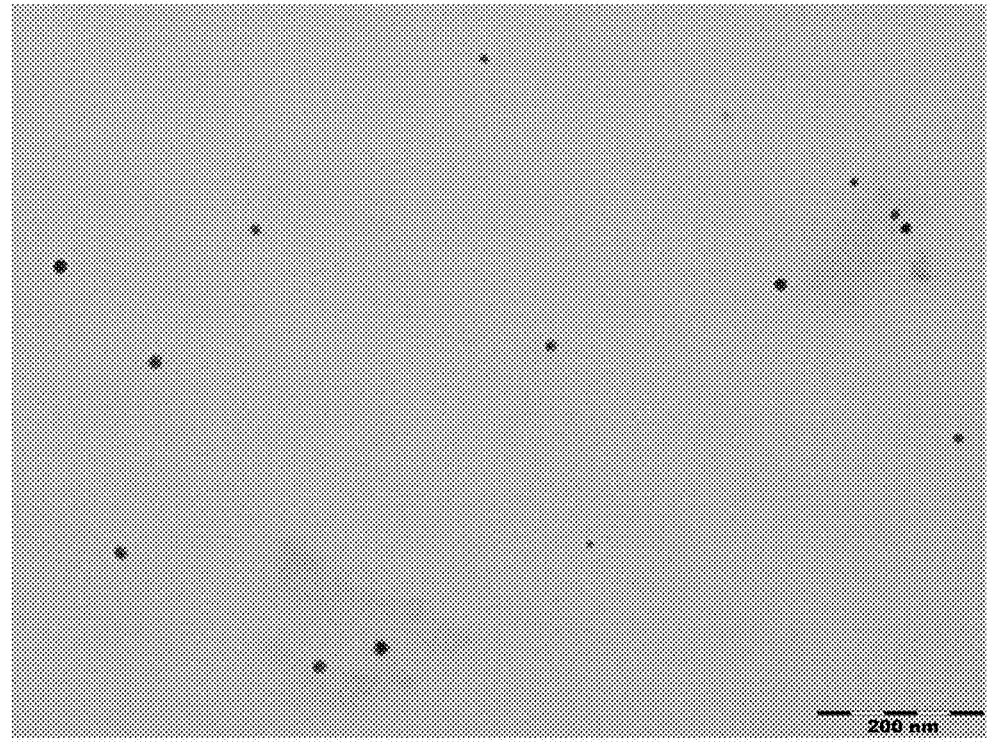
Figure 50 a2
GB-113

Gold GB-113
14.10% transmission

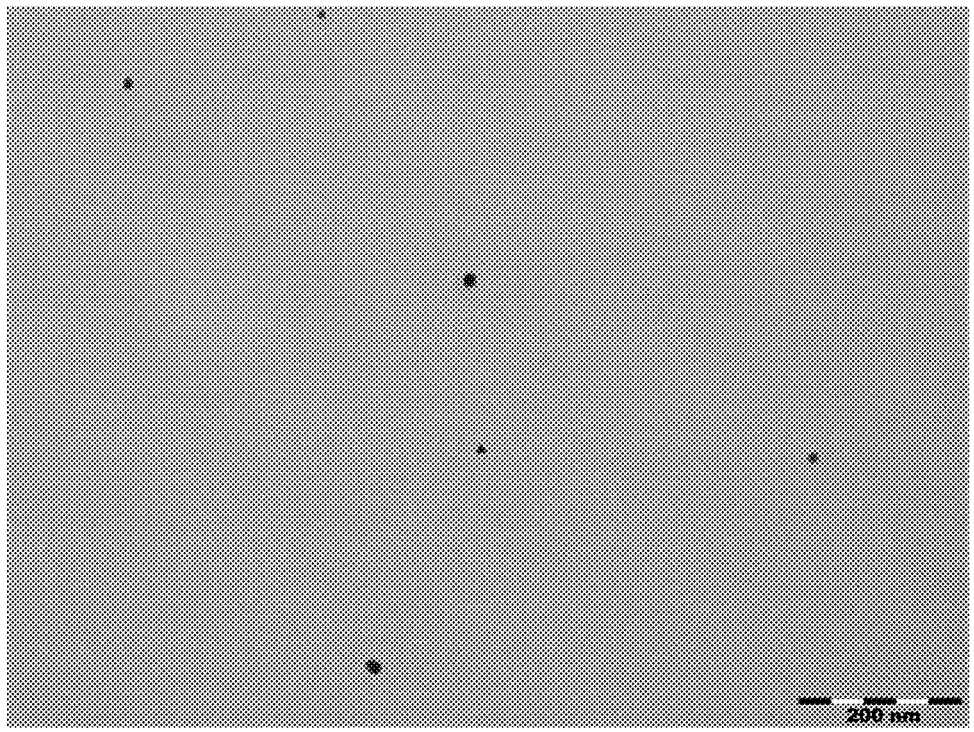
Figure 51 a1
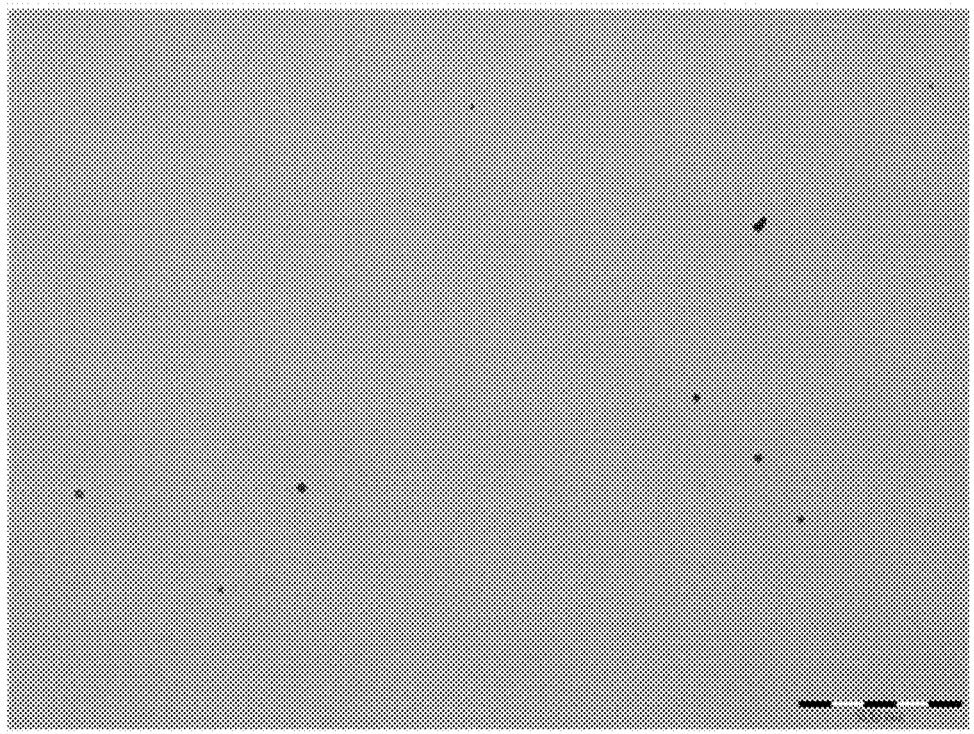
Figure 51 a2
GB-118

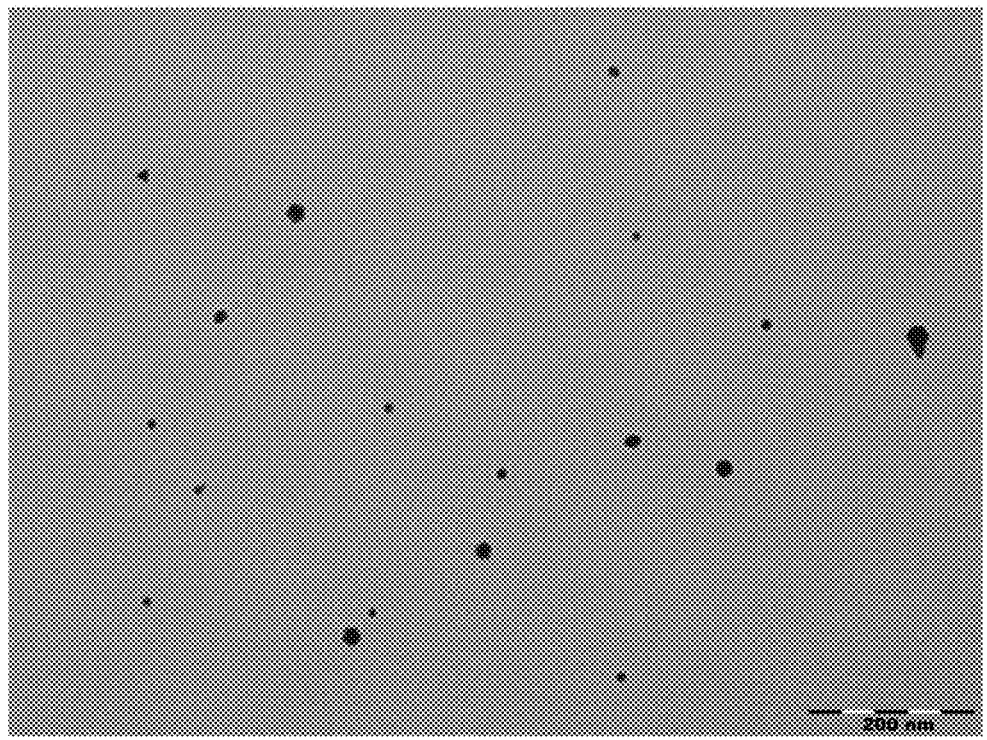
Figure 52 a1
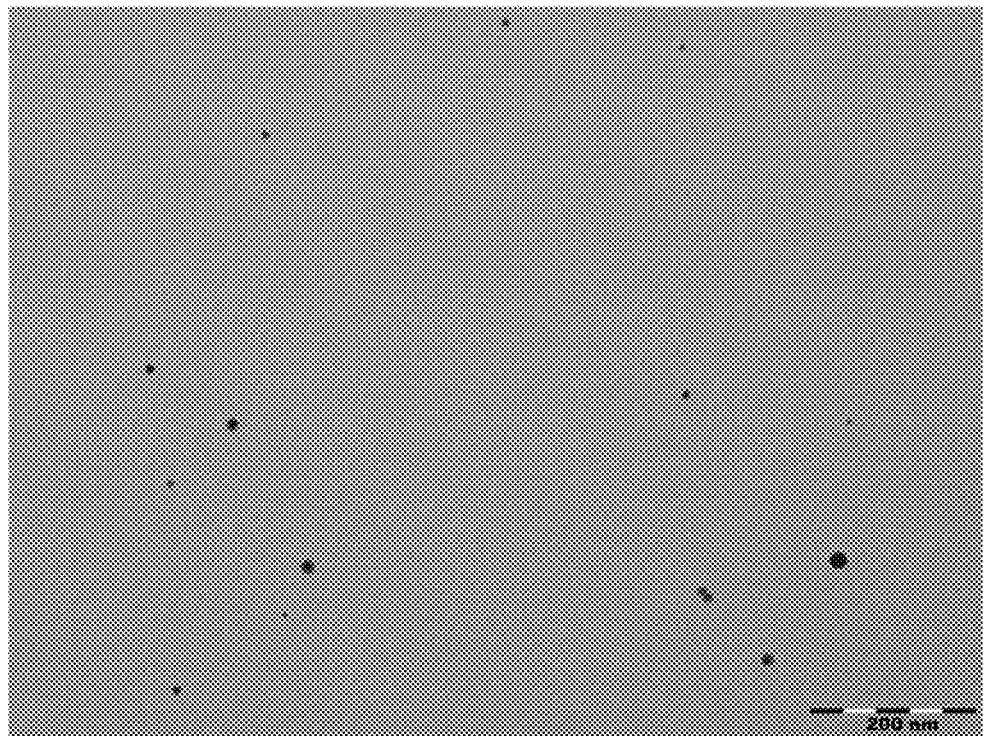
Figure 52 a2
GB-120

Gold GB-120
17.36% transmission

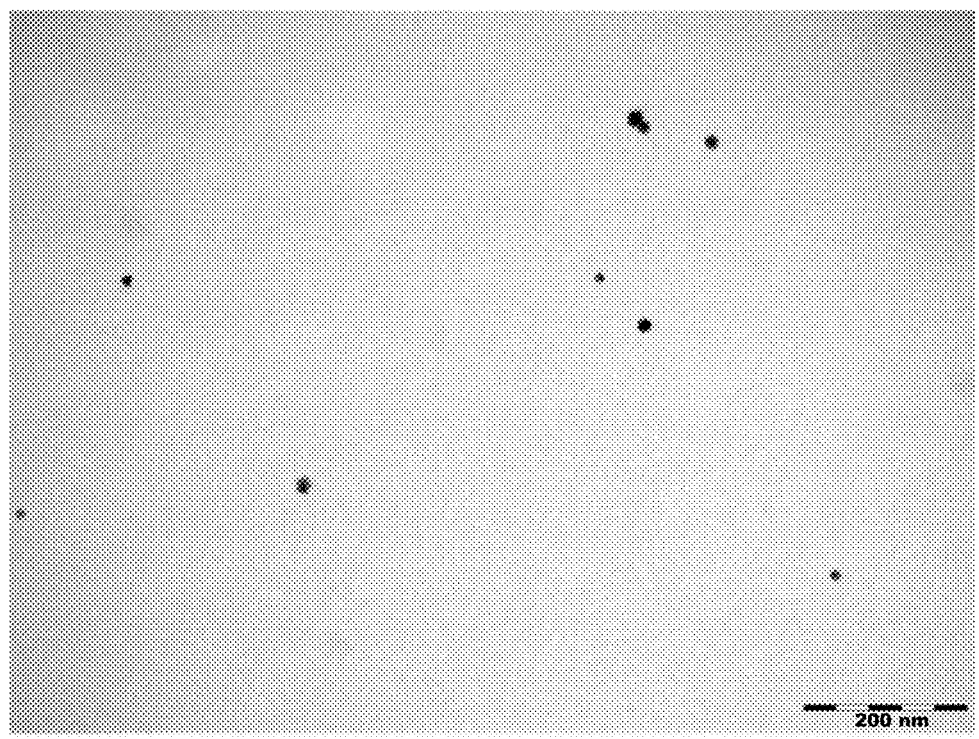
Figure 53 a1
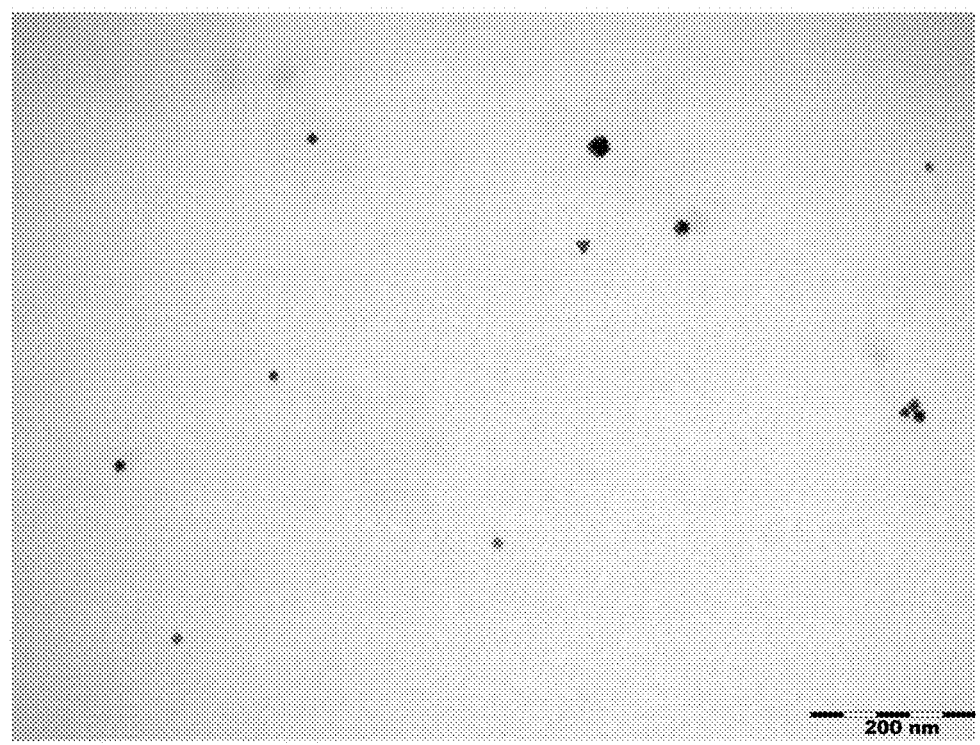
Figure 53 a2
GB-123

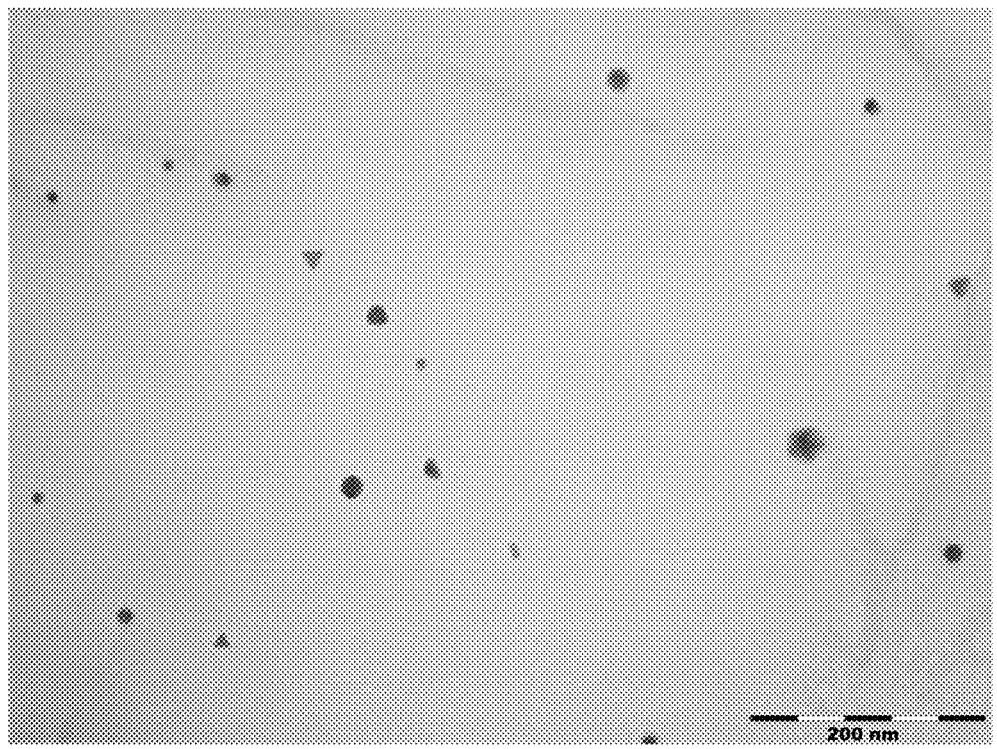
Figure 54 a1
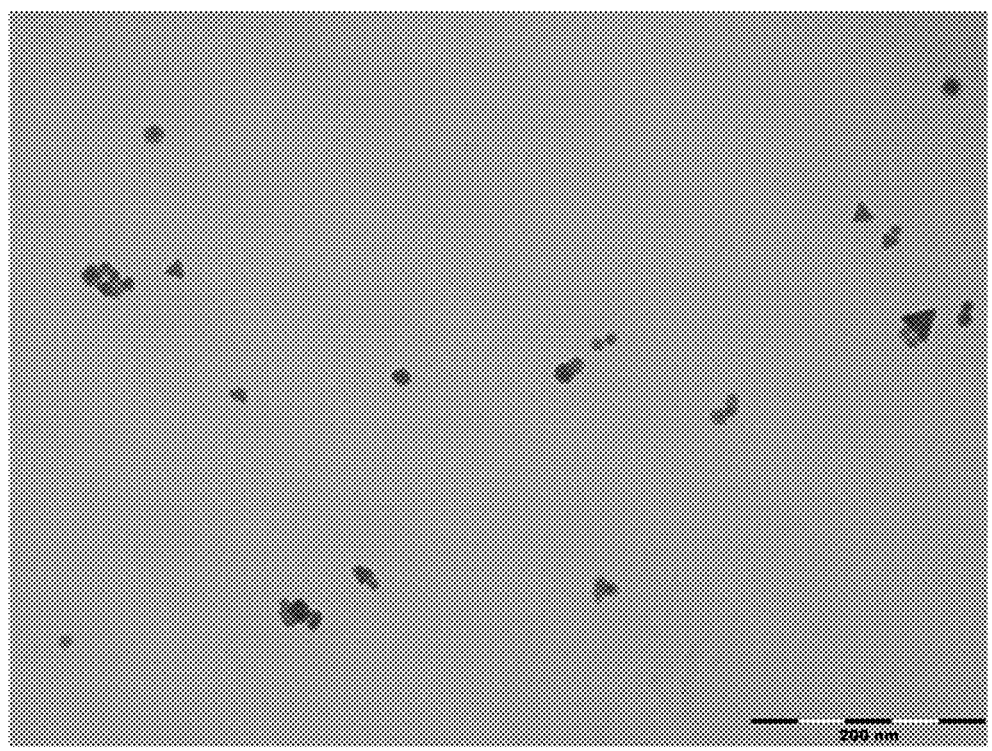
Figure 54 a2
GB-139

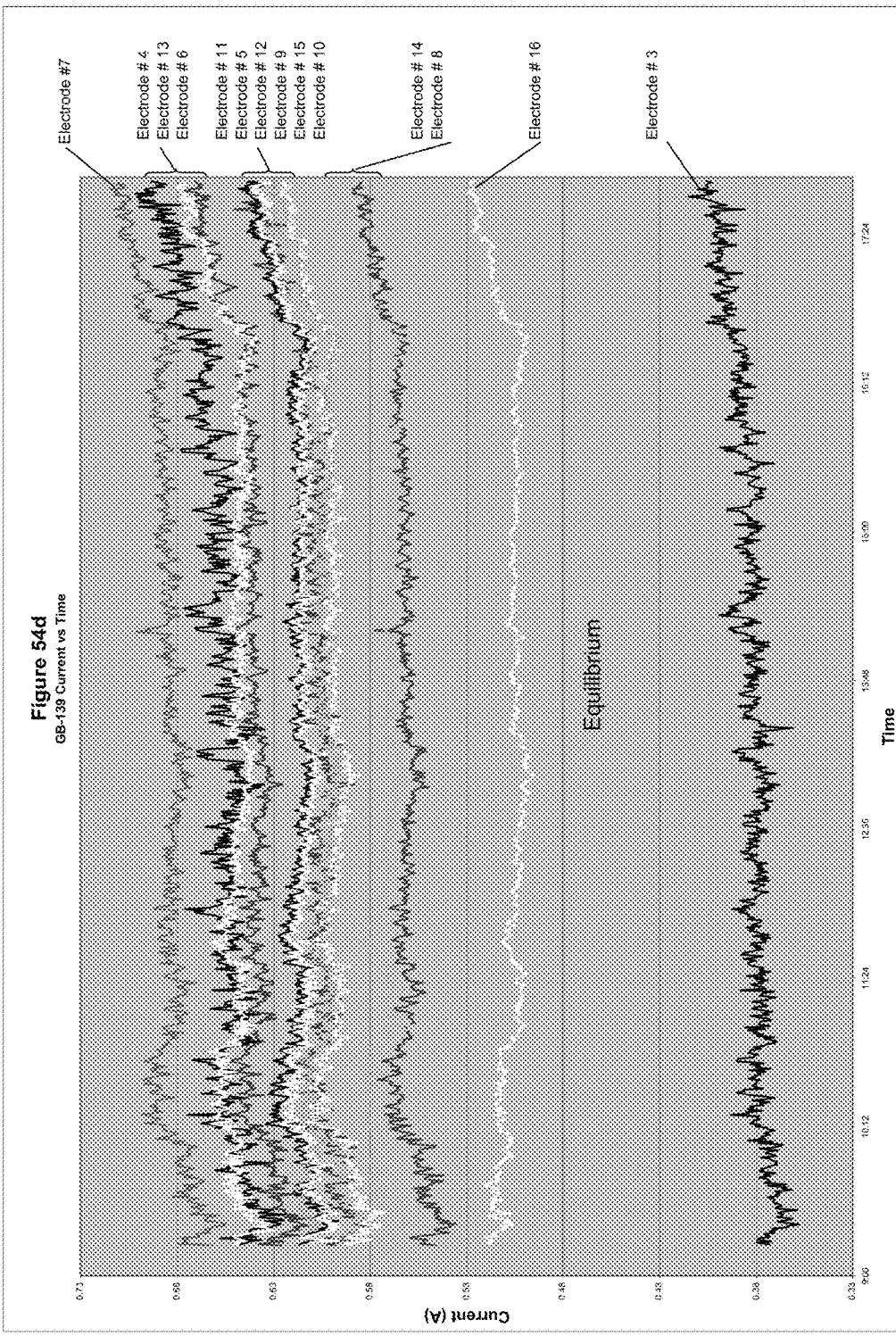

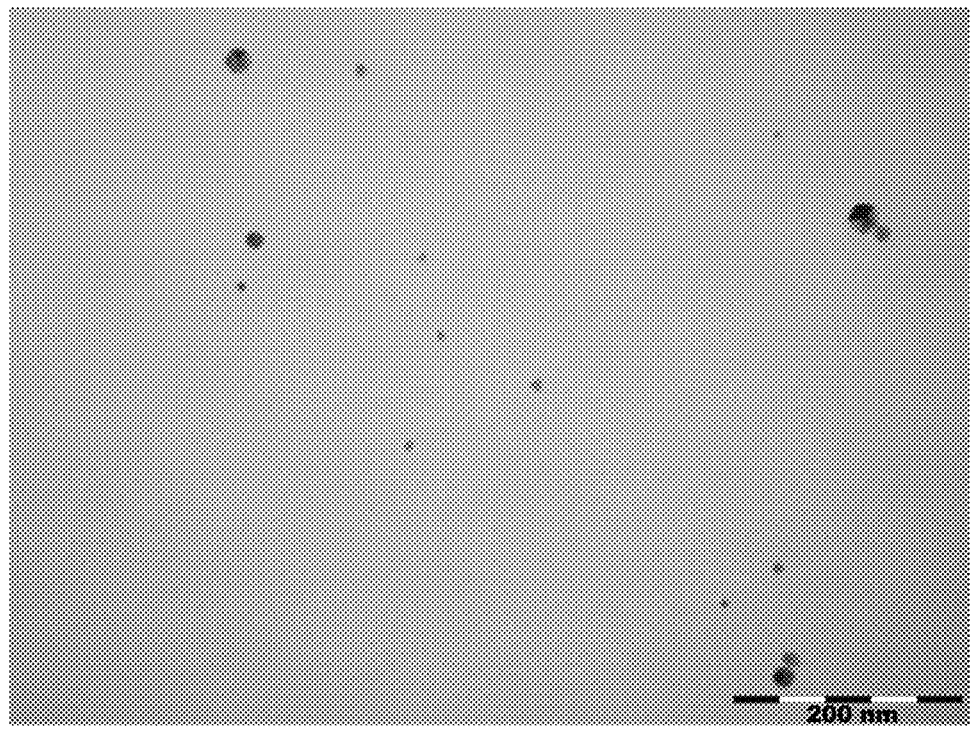
Figure 55 a1
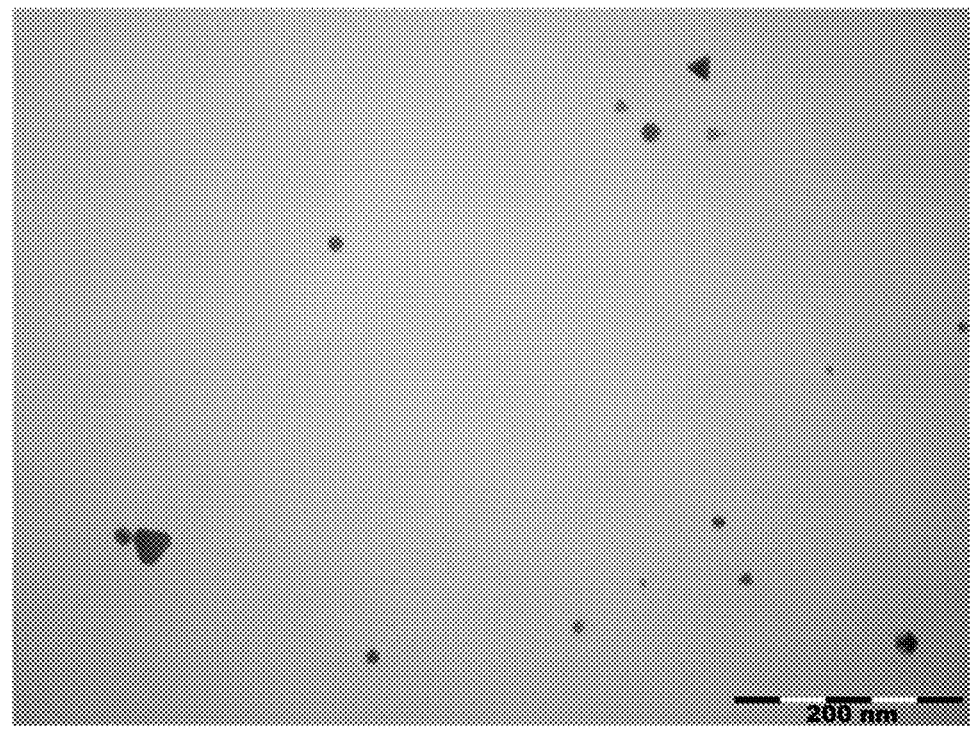
Figure 55 a2
GB-141

Gold GB-141
5.42% transmission

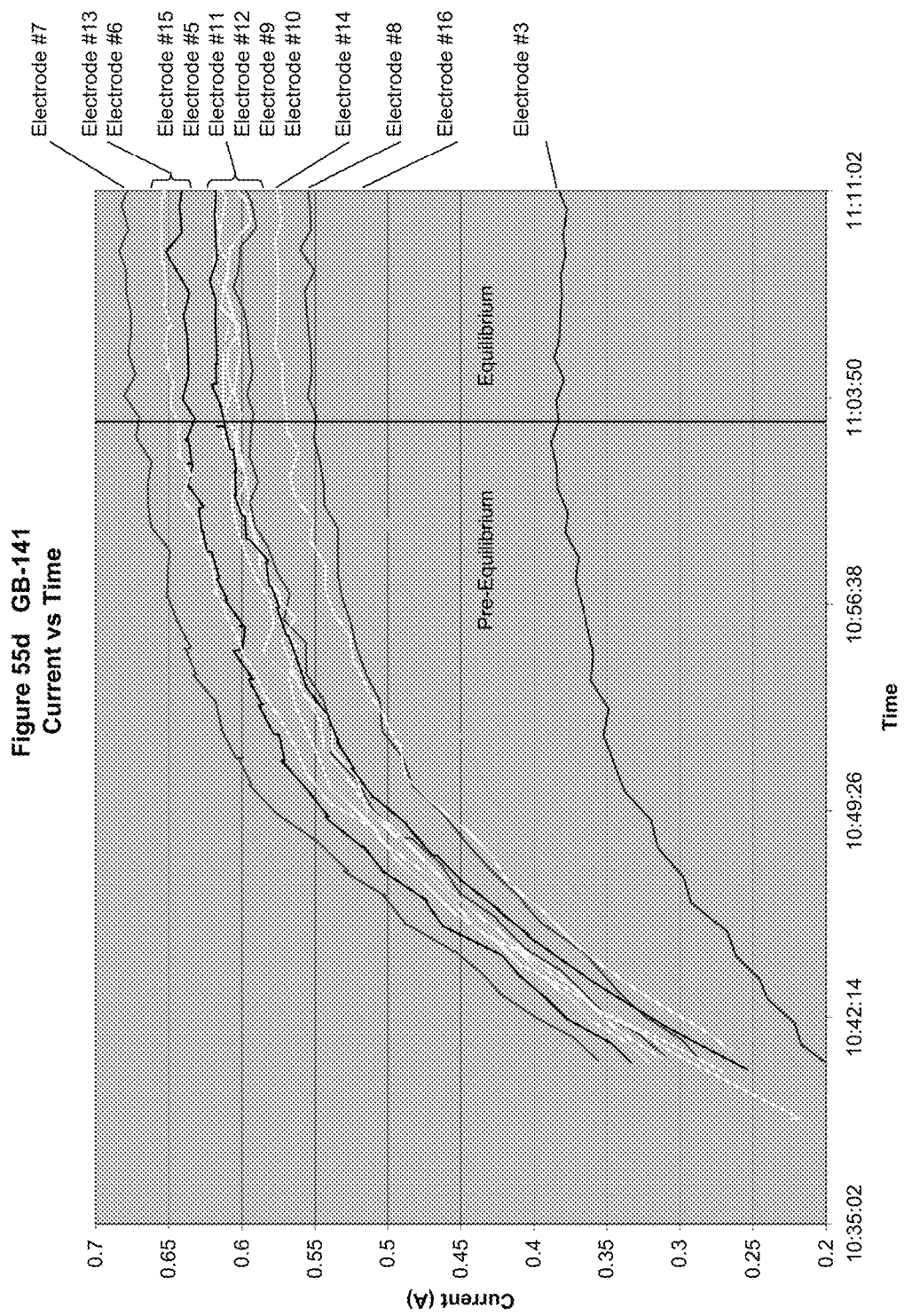

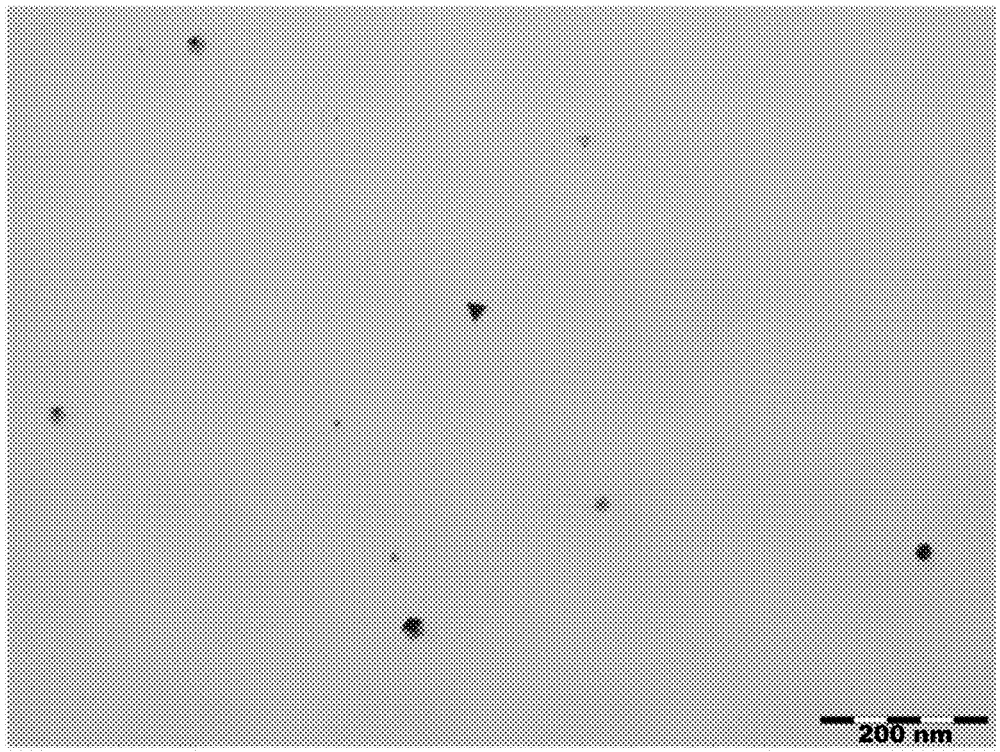
Figure 56 a1
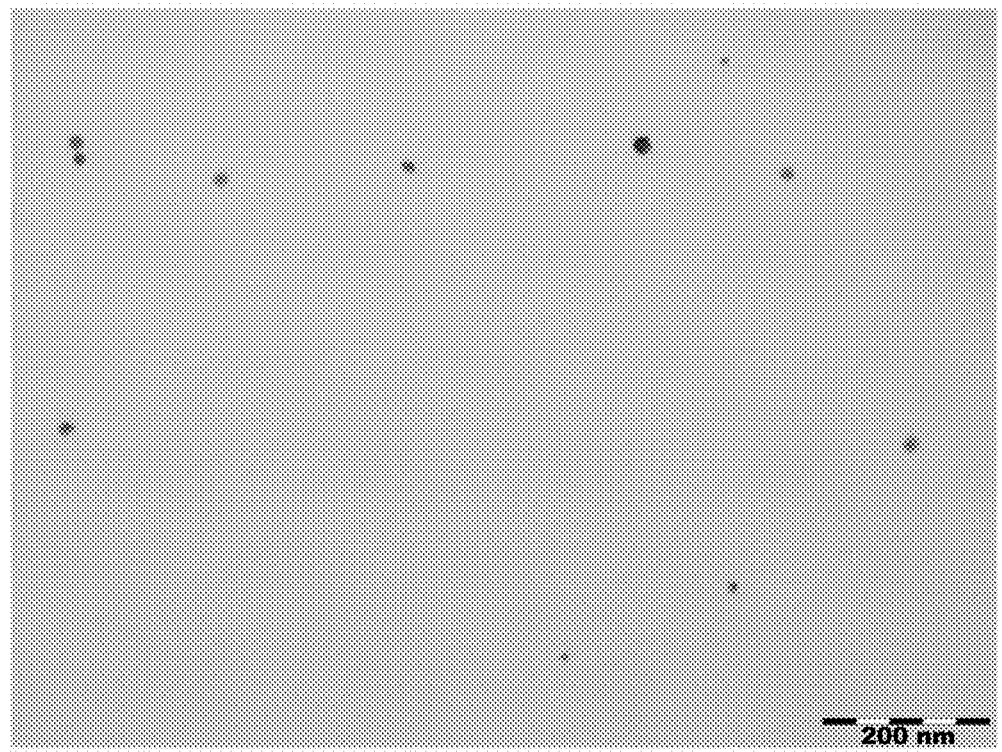
Figure 56 a2
GB-144

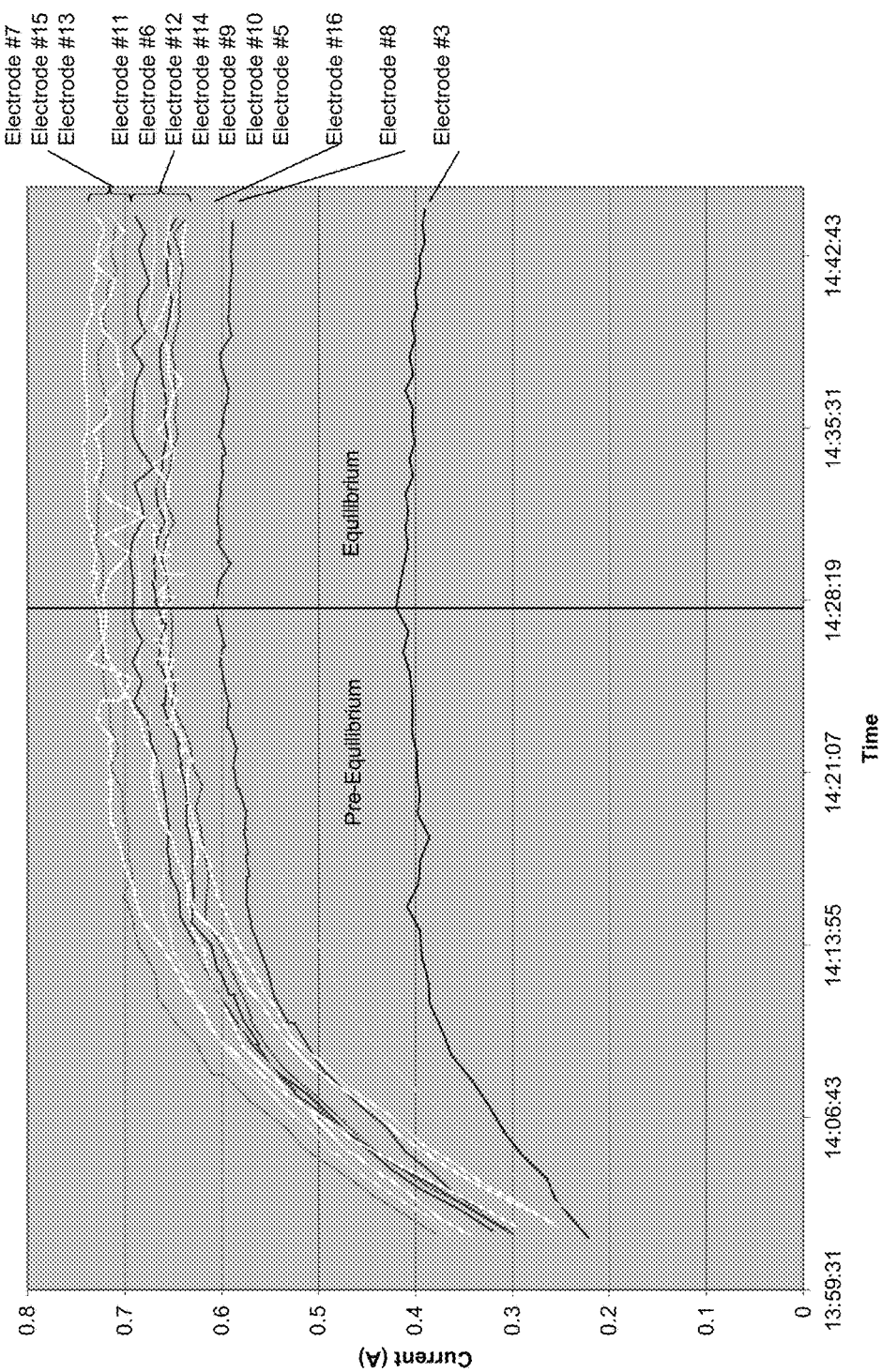

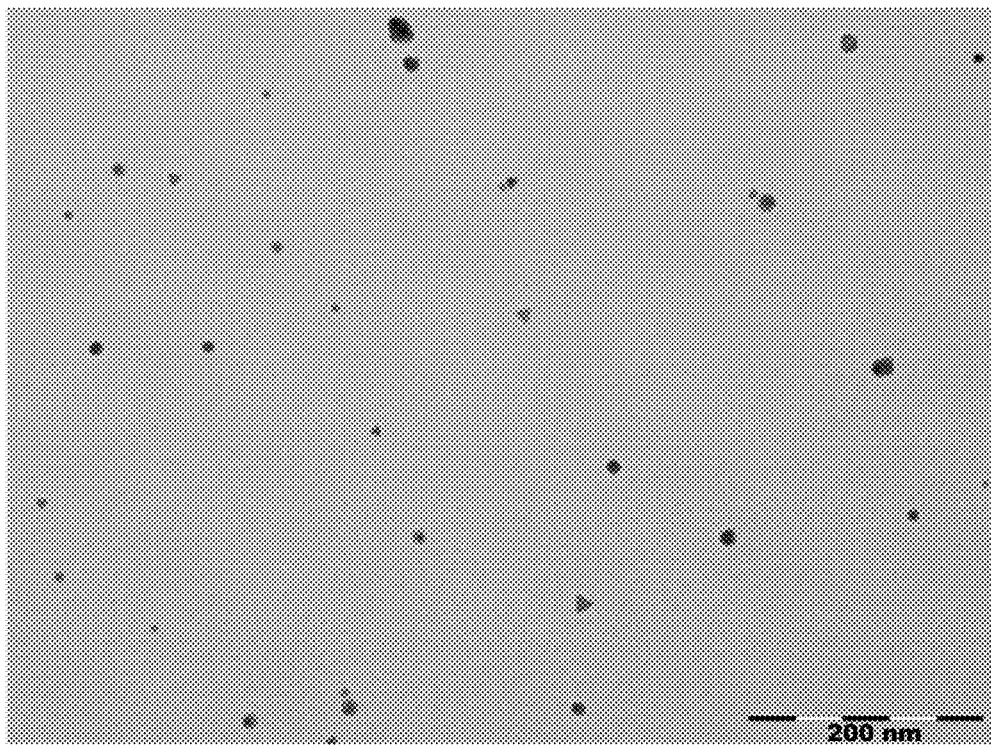
Figure 57 a1
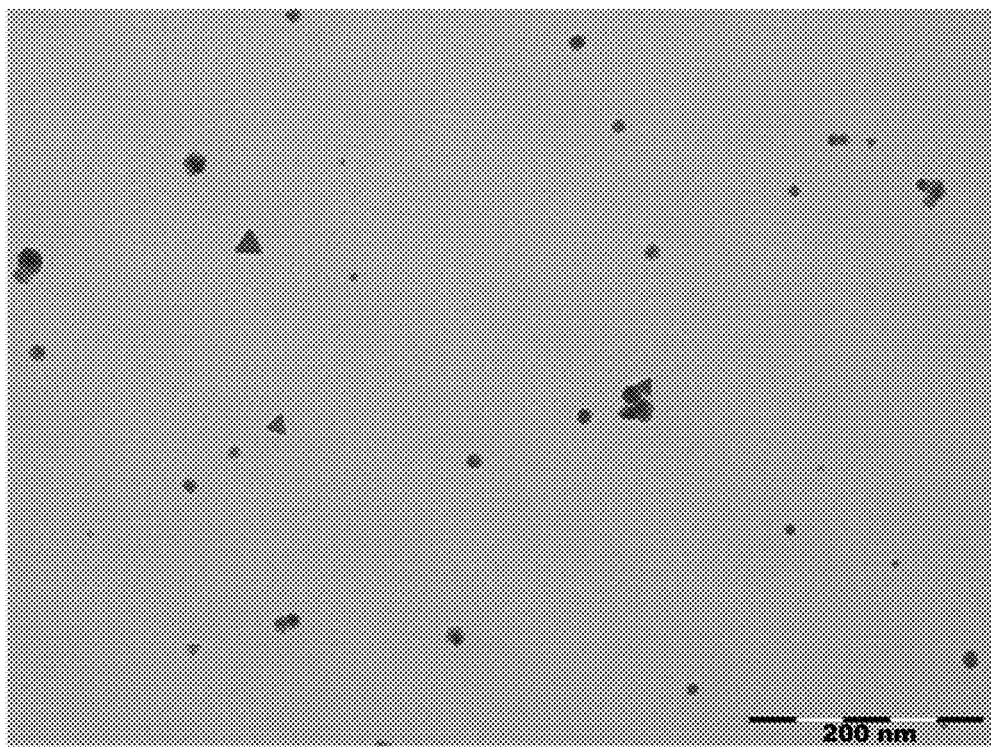
Figure 57 a2
GB-079

Gold GB-079
6.64% transmission

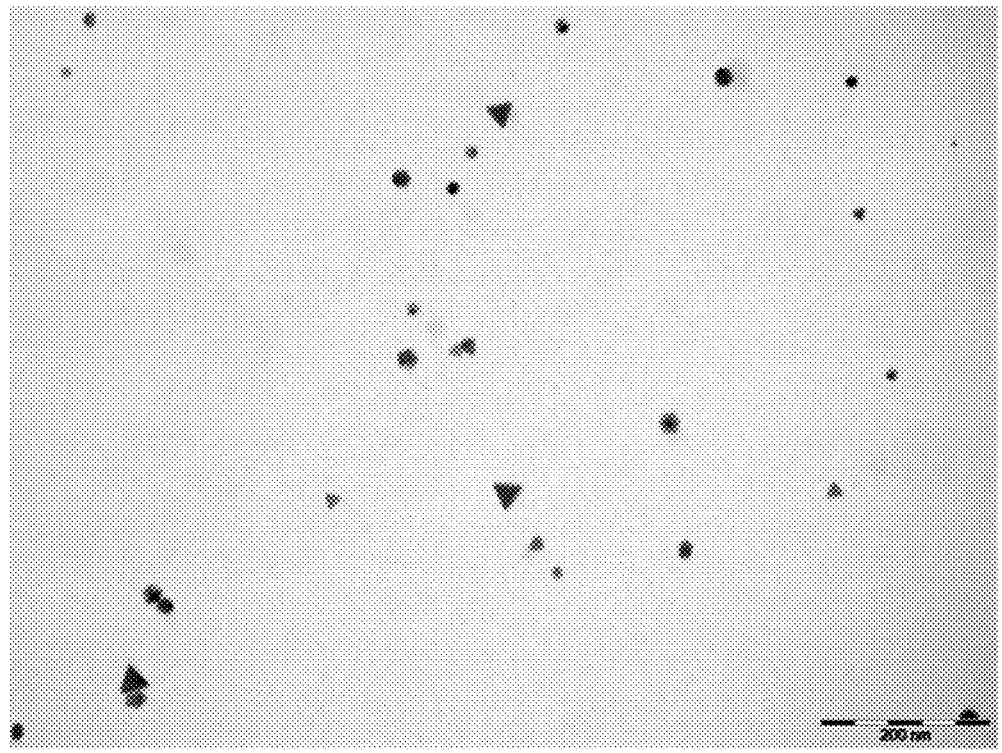
Figure 58 a1
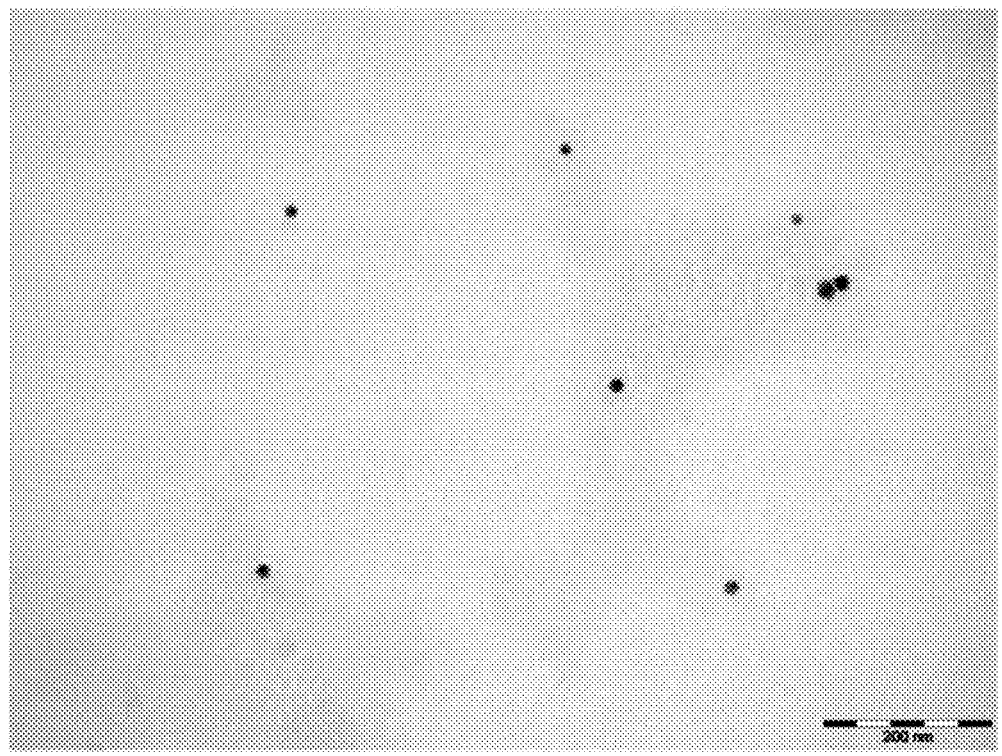
Figure 58 a2
GB-089

Gold GB-089
5.70% transmission

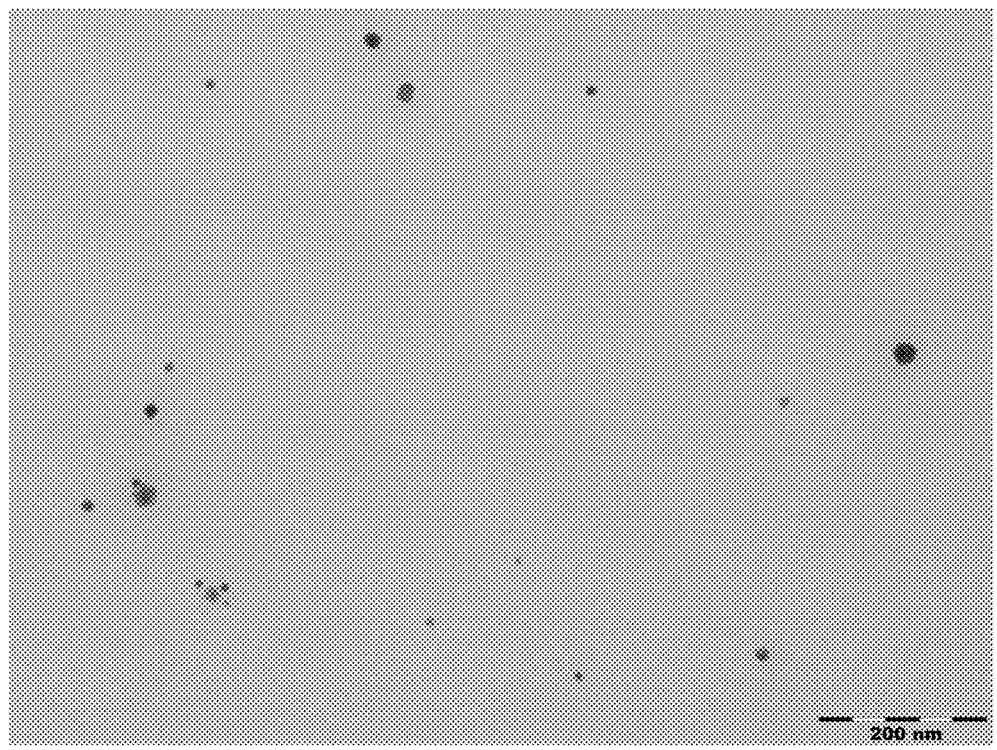
Figure 59 a1
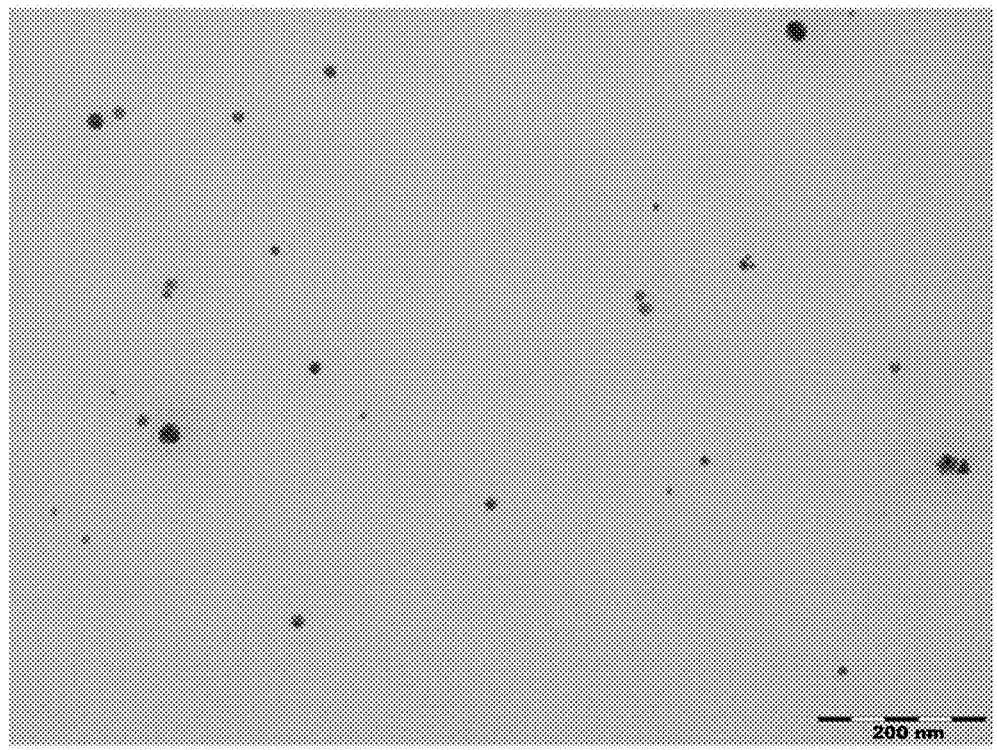
Figure 59 a2
GB-062

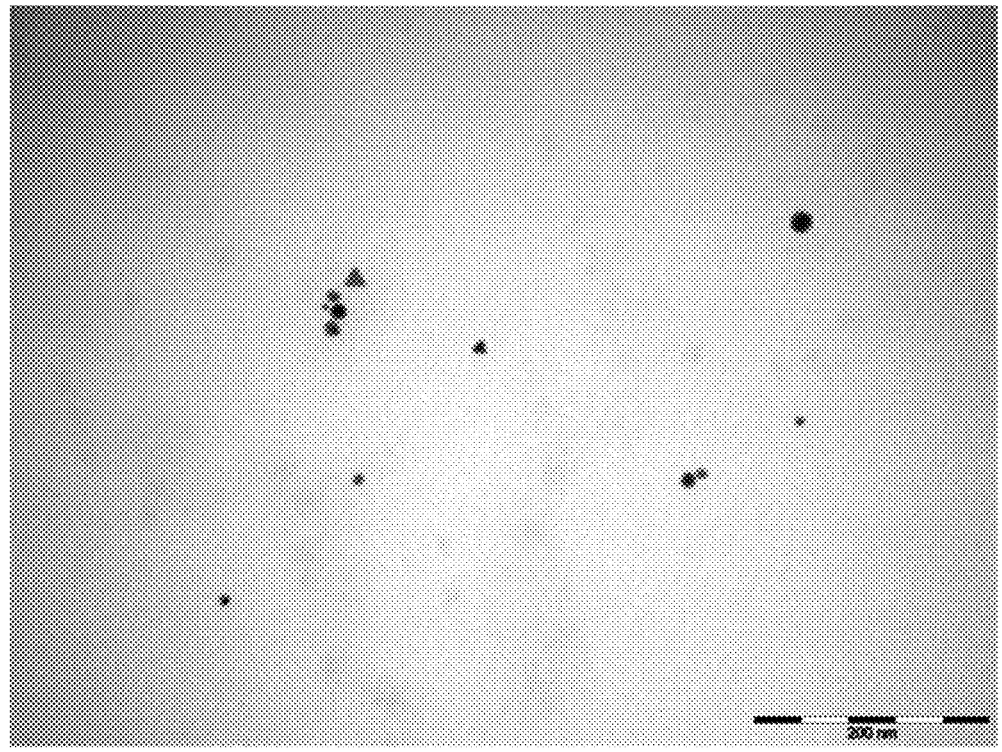
Figure 60 a1
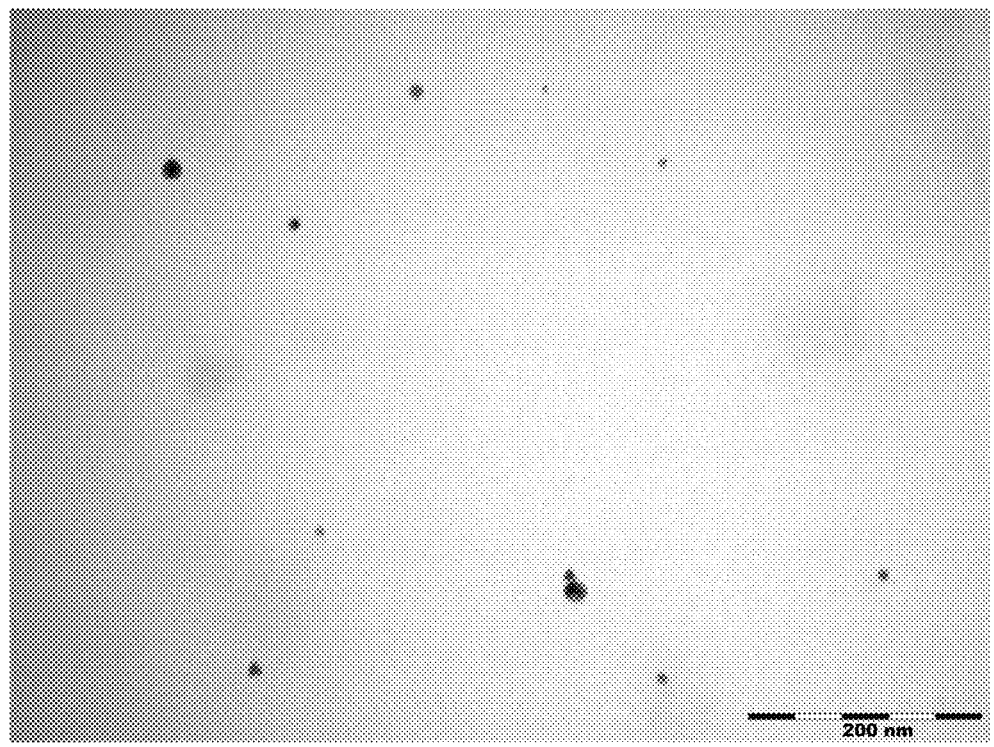
Figure 60 a2
GB-076

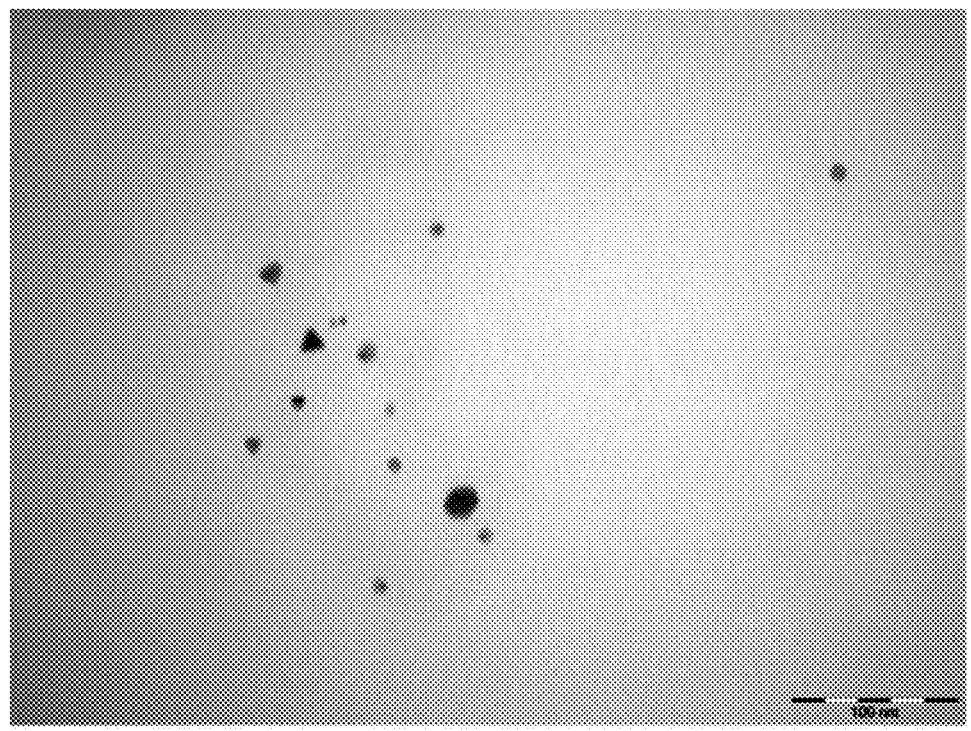
Figure 61 a1
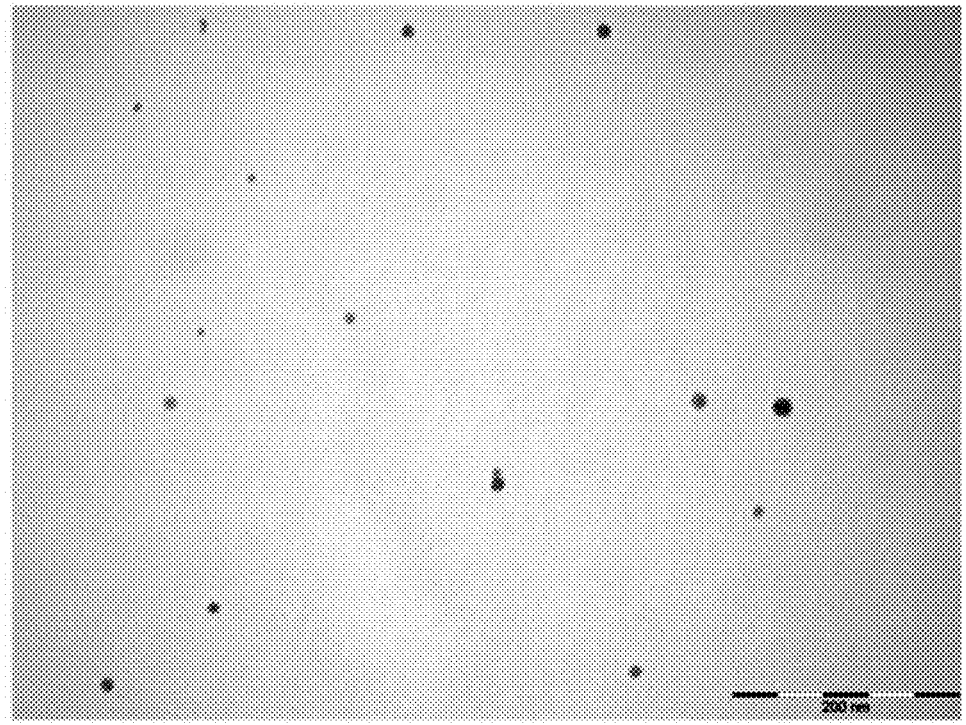
Figure 61 a2
GB-077

GB-151

GB-198

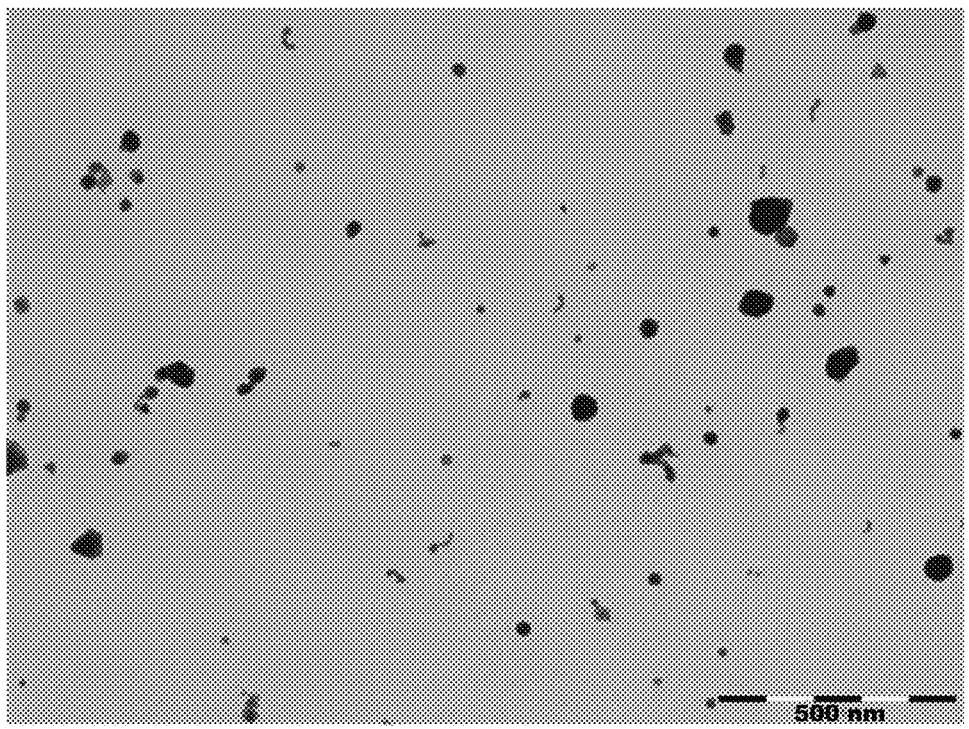
Figure 73 a1
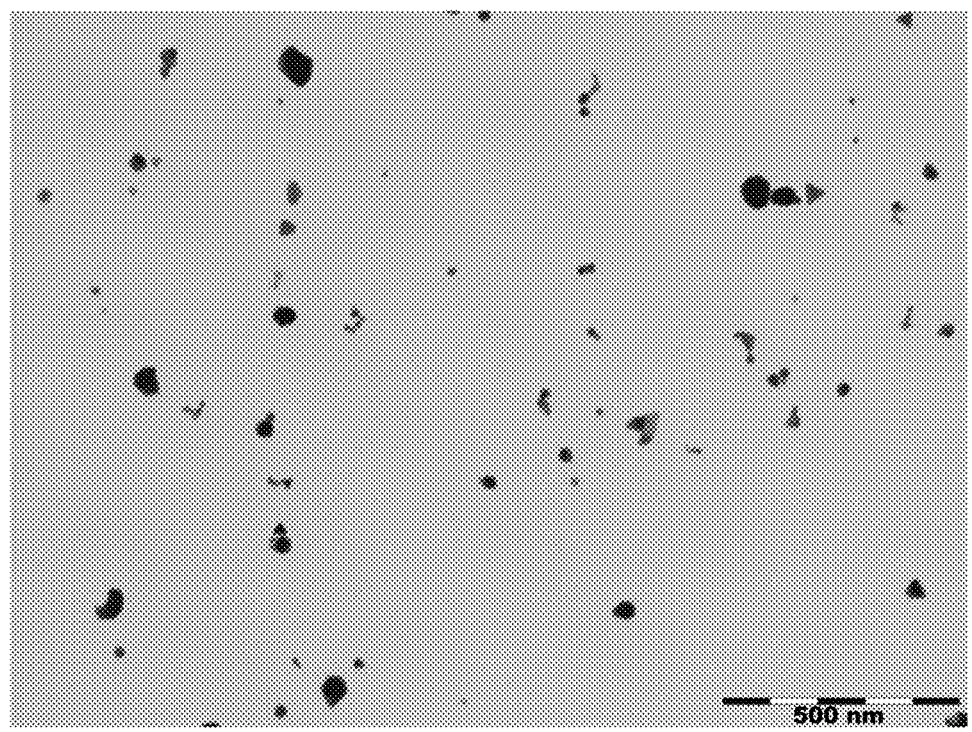
Figure 73 a2
Aurora-020

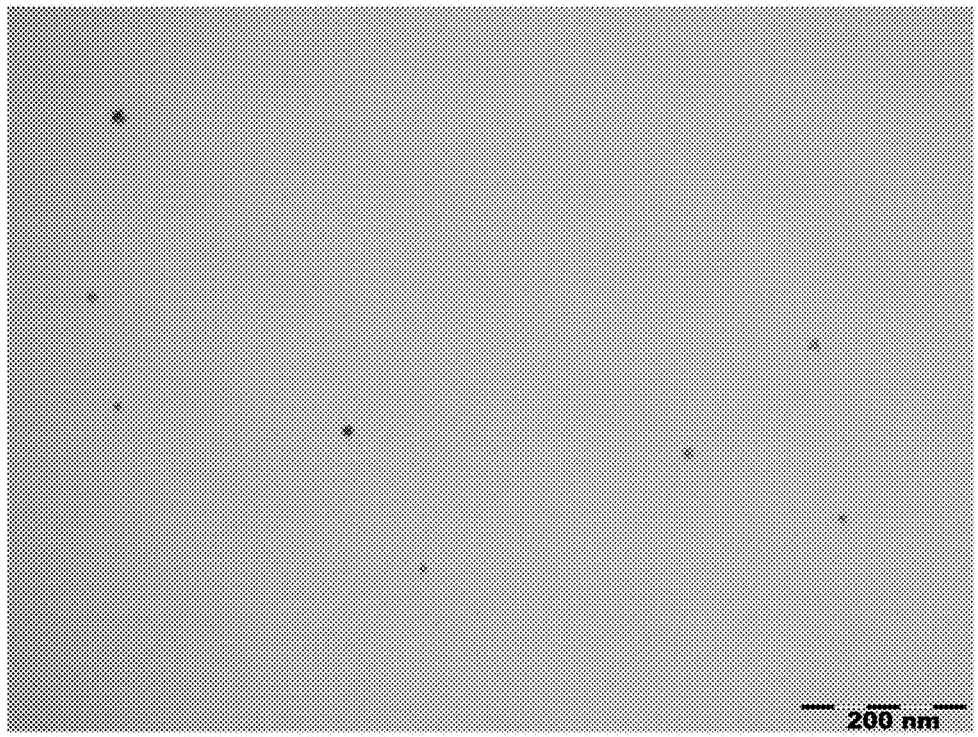
Figure 74 a1
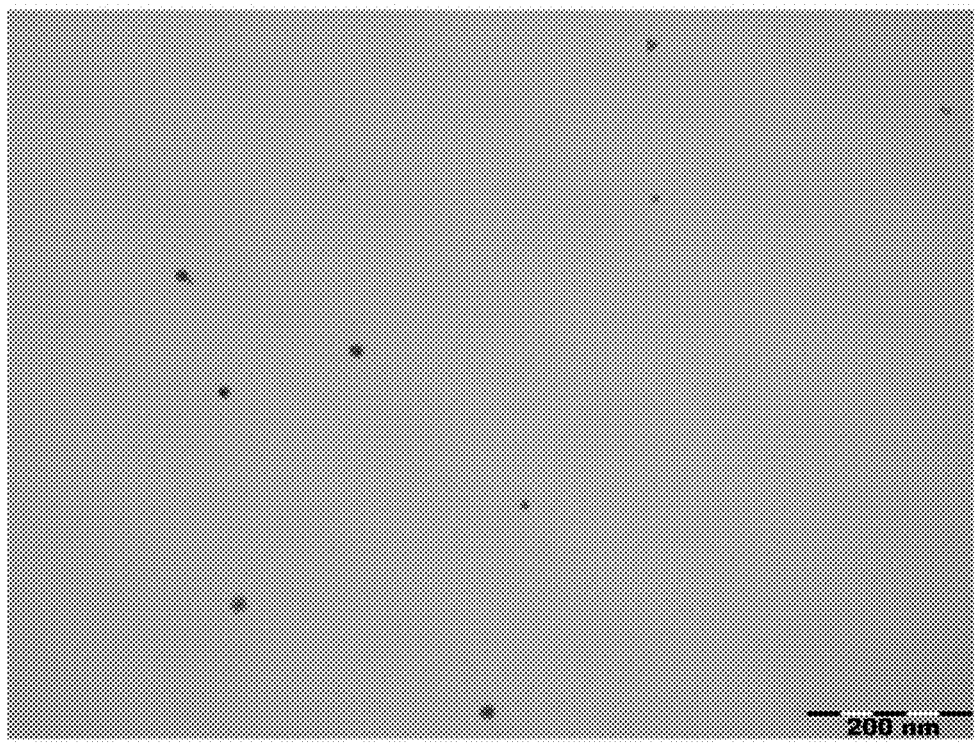
Figure 74 a2
GA-002

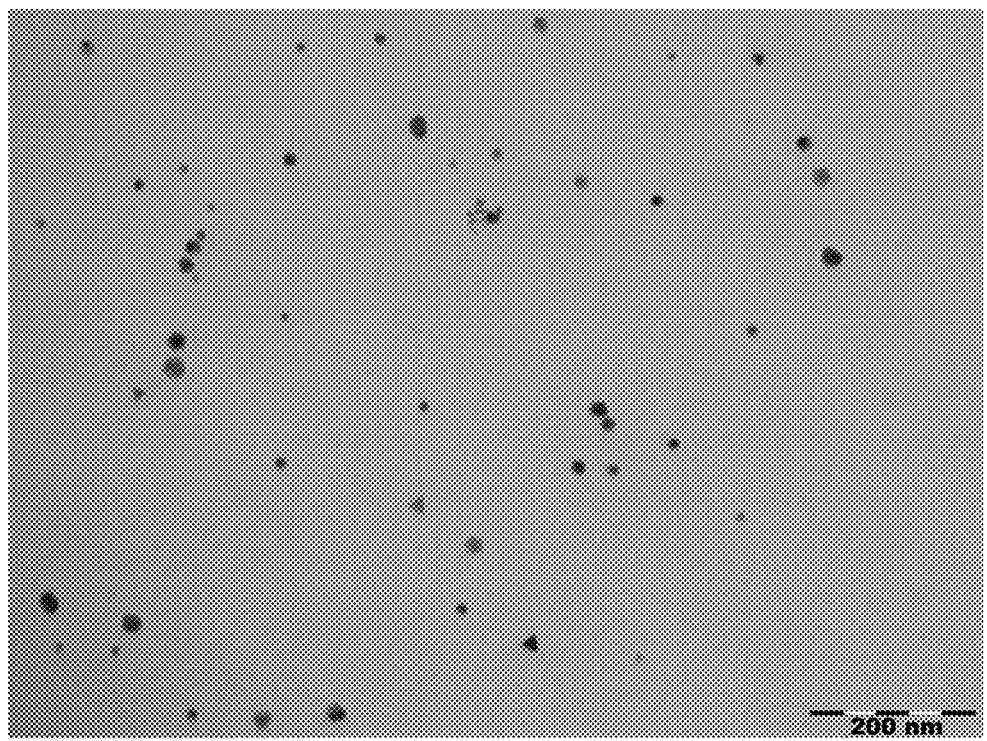
Figure 75 a1
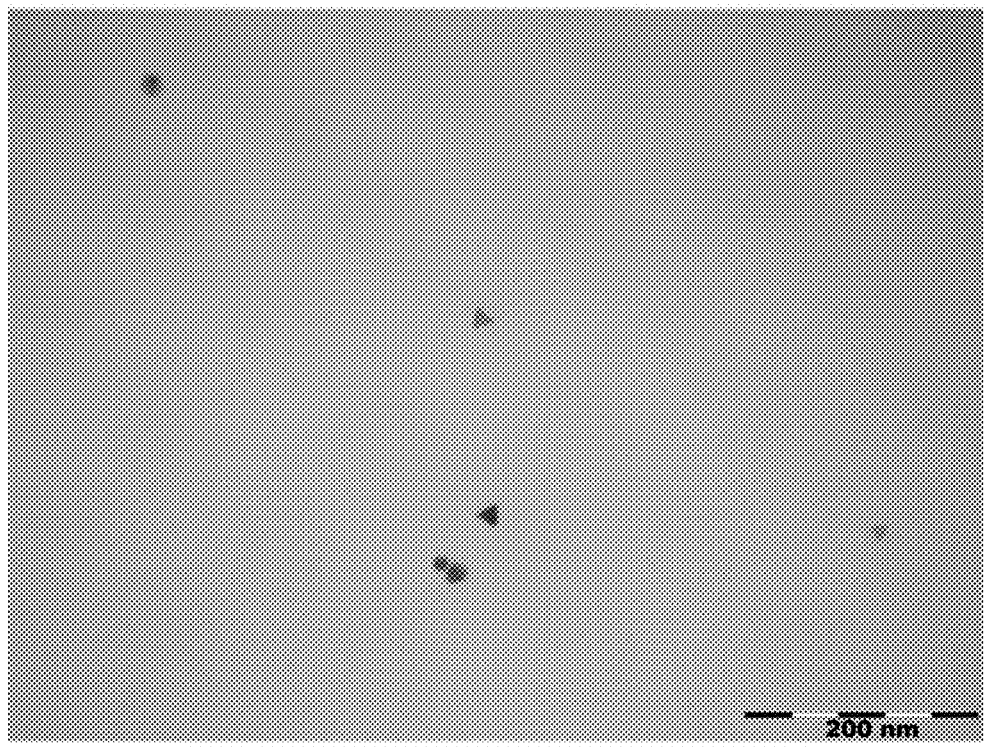
Figure 75 a2
GA-003

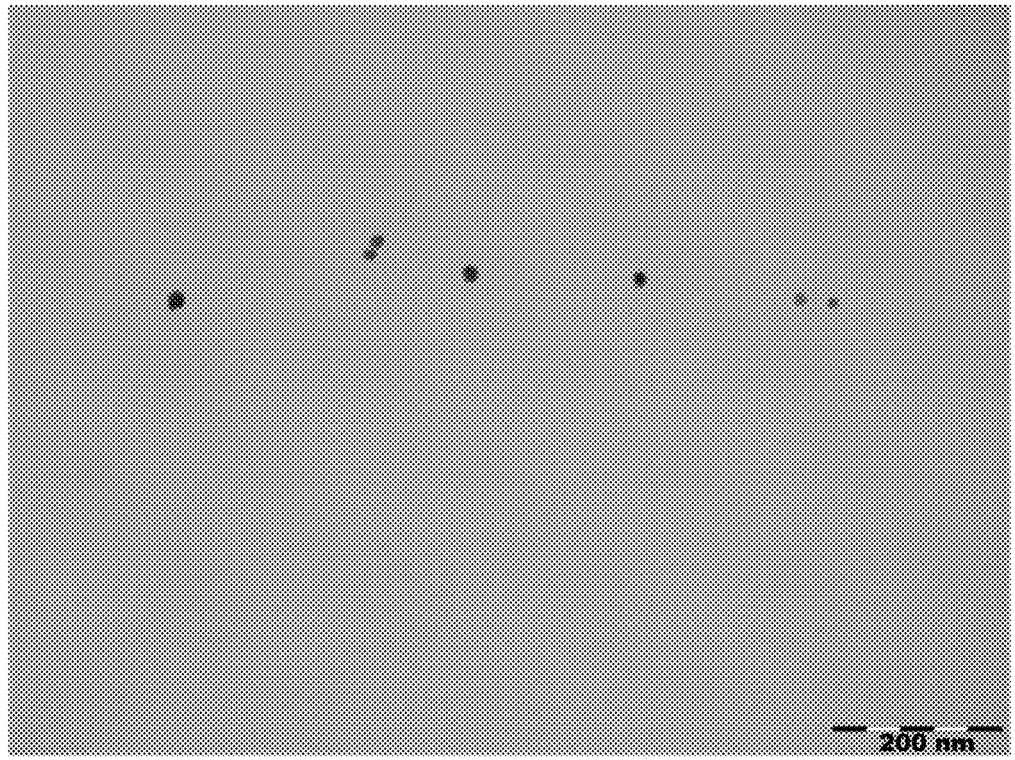
Figure 76 a1
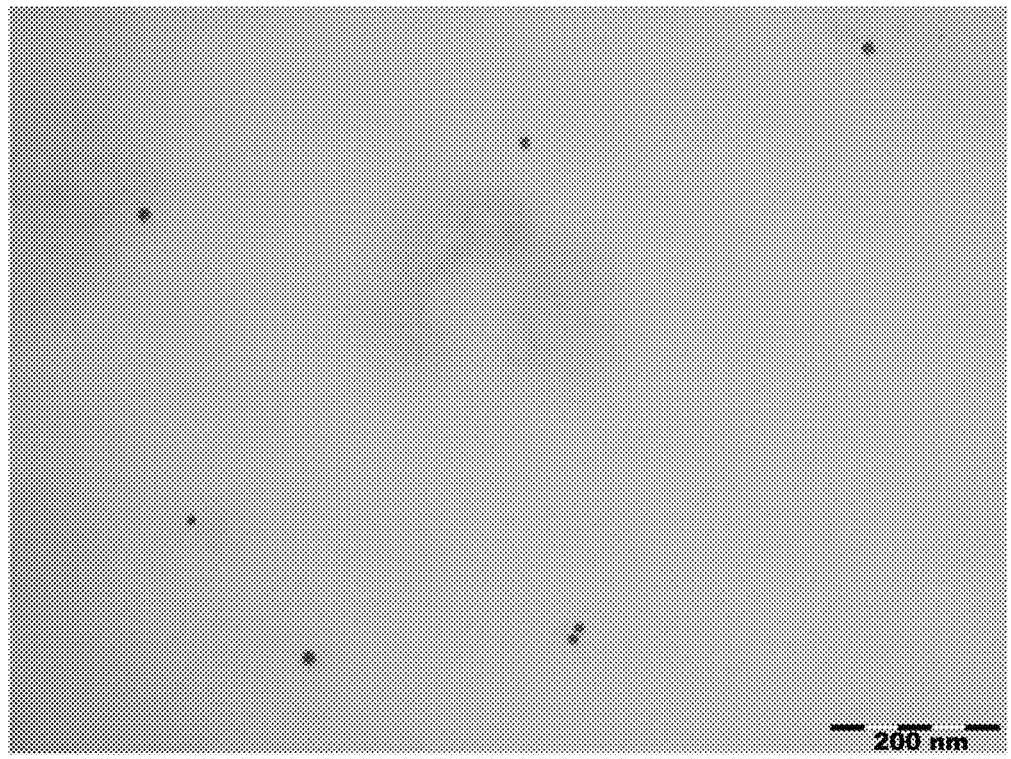
Figure 76 a2
GA-004

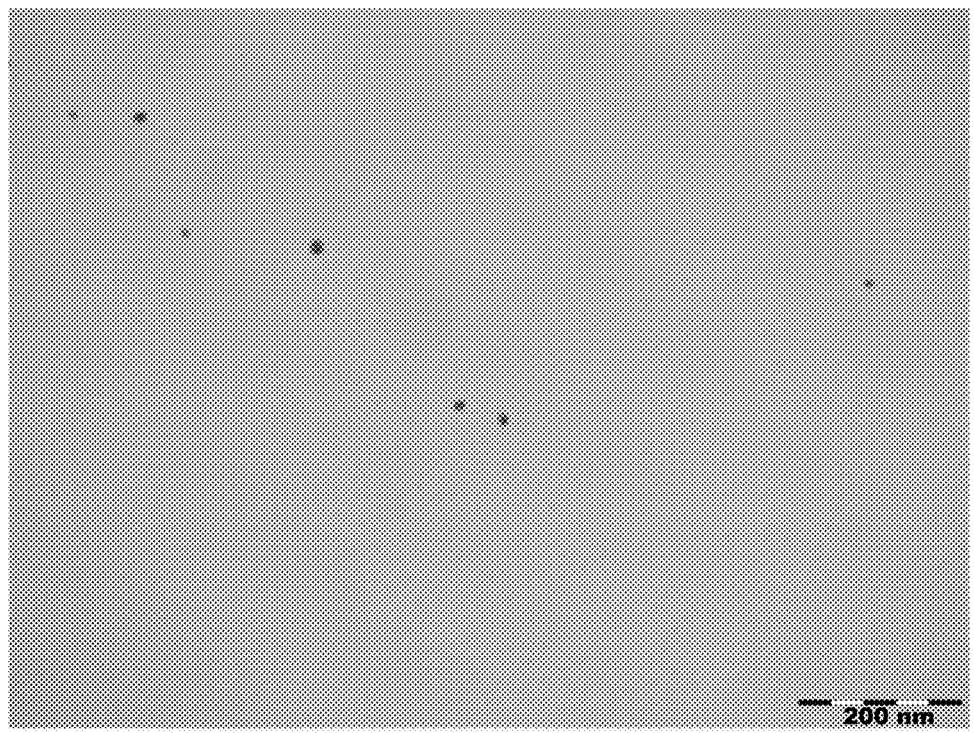
Figure 77 a1
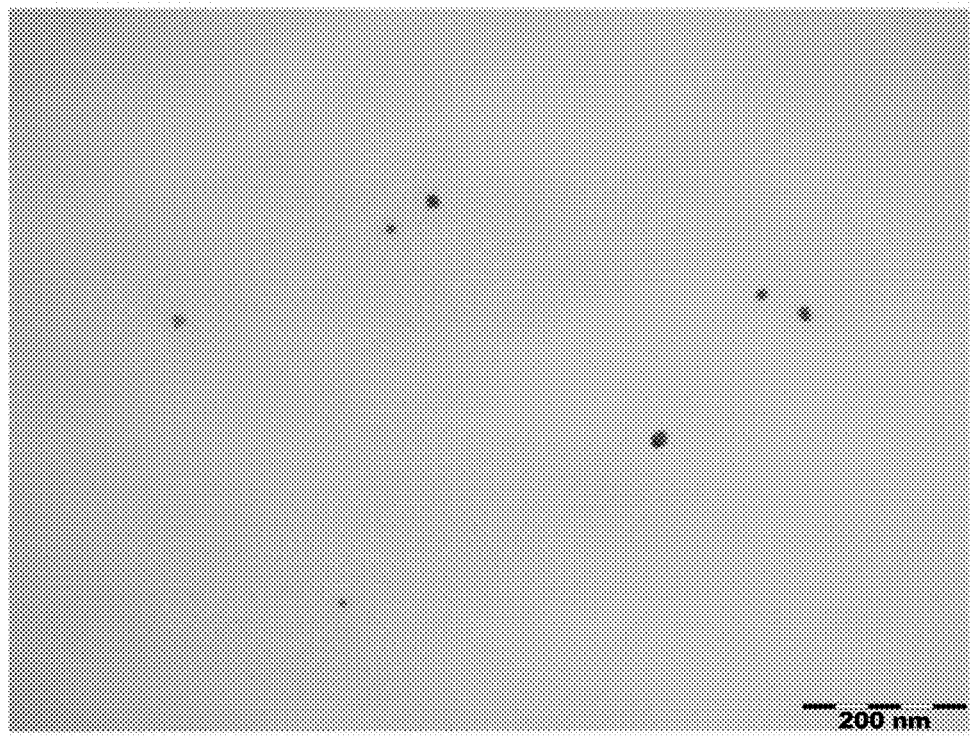
Figure 77 a2
GA-005

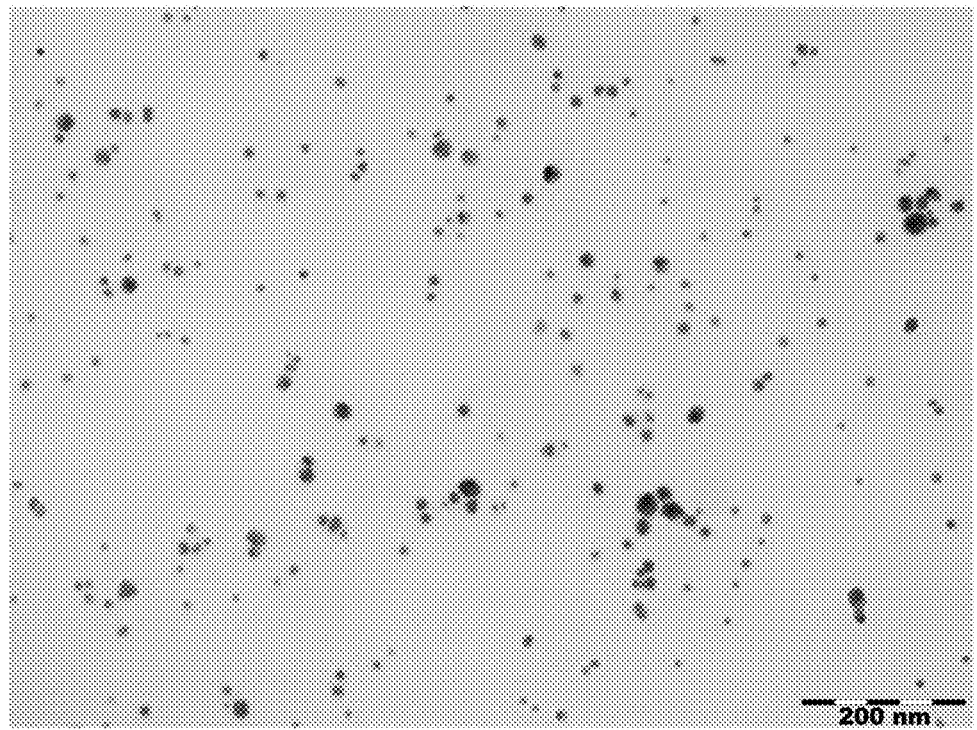
Figure 78 a1
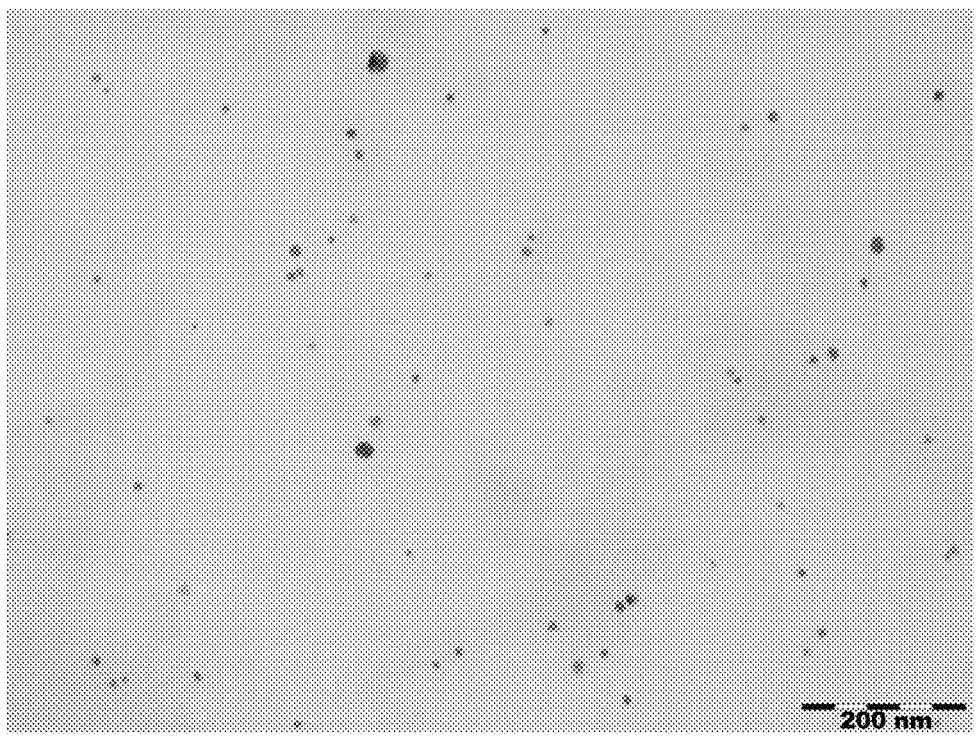
Figure 78 a2
GA-009

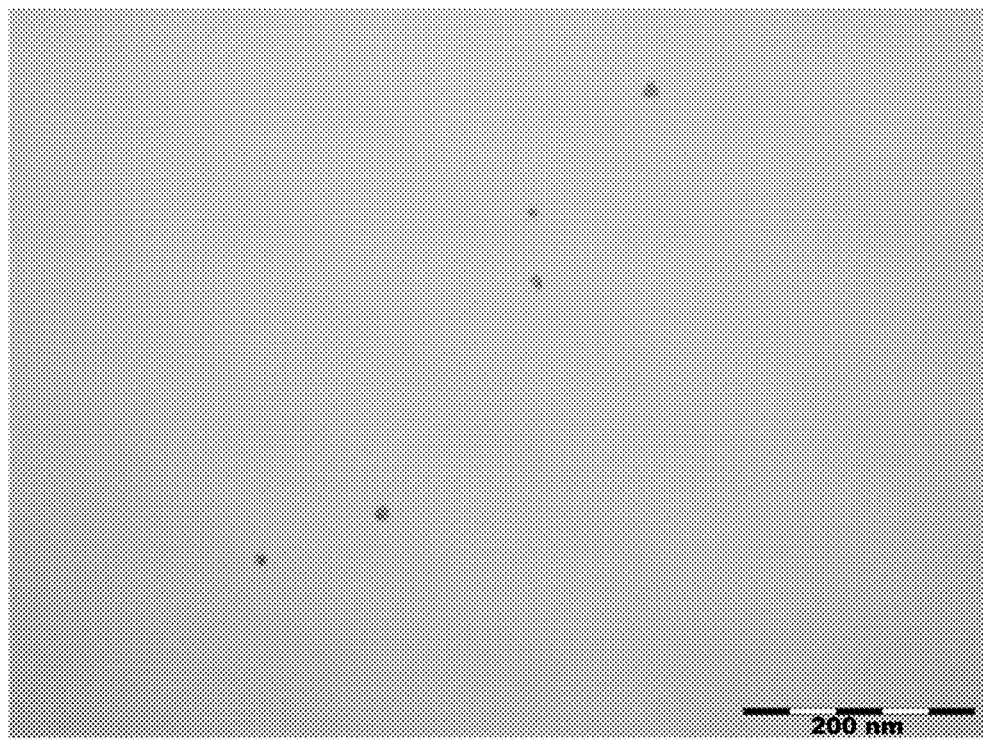
Figure 79 a1
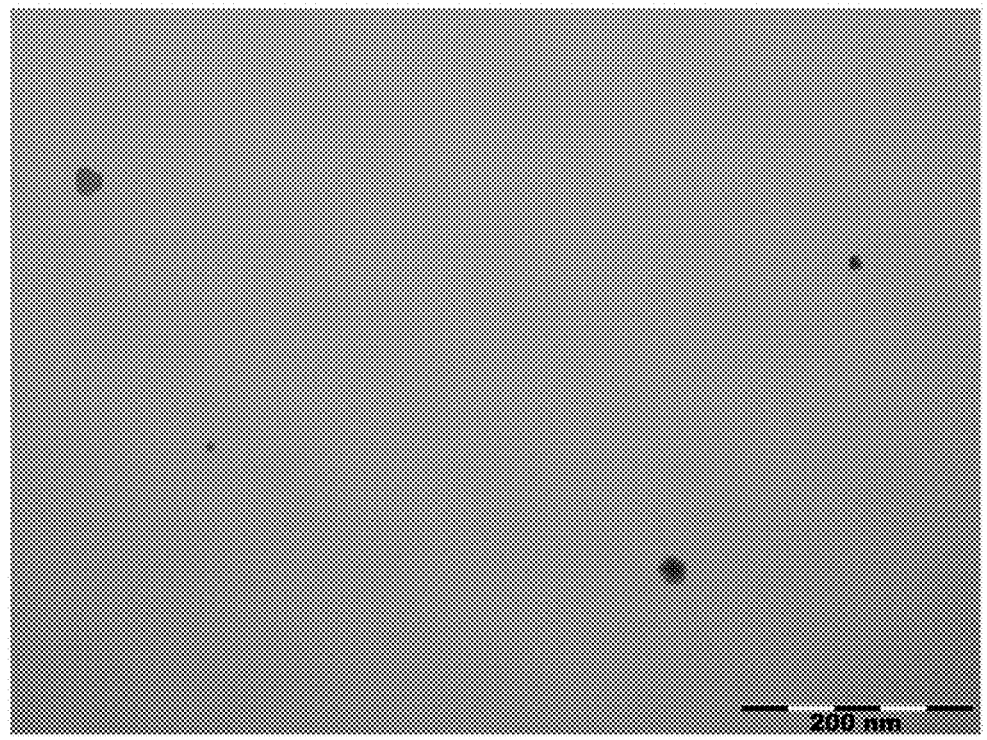
Figure 79 a2
GA-011

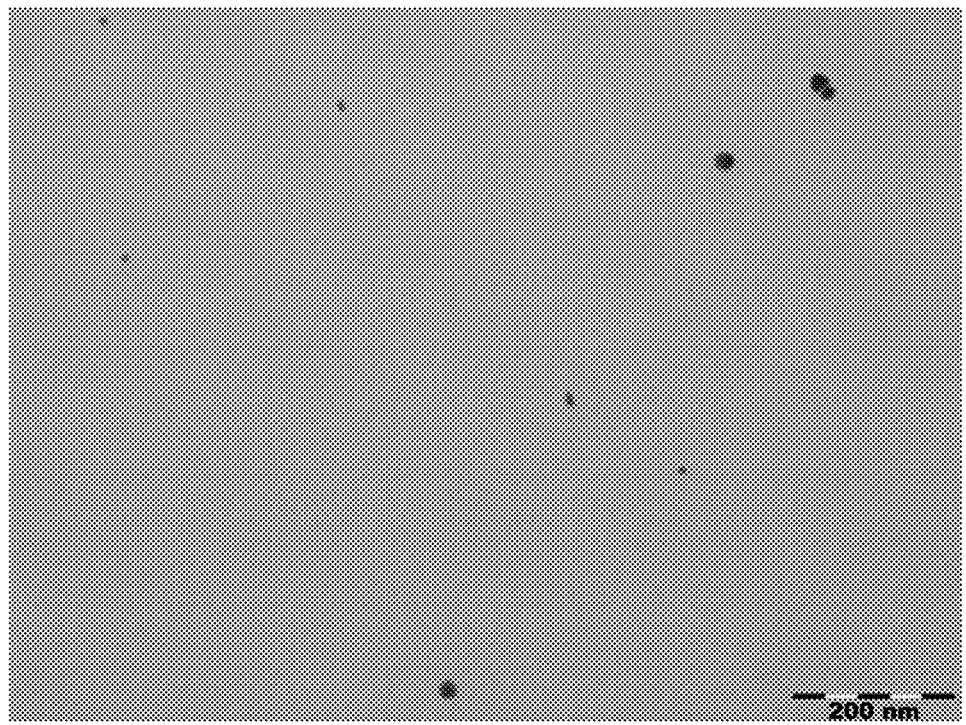
Figure 80 a1
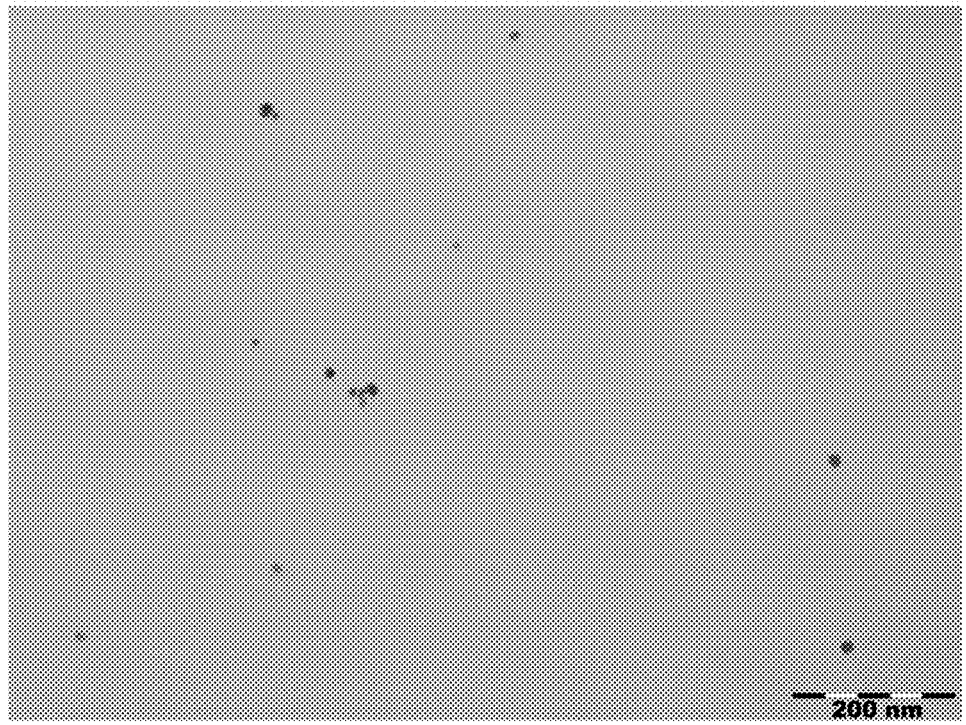
Figure 80 a2
GA-013

Harmonic Gold

GD-006-01
29.00% transmission

Collagen Induced Arthritis in Mice
(Clinical Limb Scores)

(Normal joint)

(Grade 1)

(Grade 2)

(Grade 3)

(Grade 0)

(Grade 1)

(Grade 4)

(Grade 7)

(Grade 9)

GB-056:

GB-056: Day 2 – Day 3

GB-056 DLS Size Distribution: Day 2 – Day 3
5.34% transmission

GB-056: Day 4 – Day 5

GB-056 DLS Size Distribution: Day 4 – Day 5
4.39% transmission

GOLD-BASED NANOCRYSTALS FOR MEDICAL TREATMENTS AND ELECTROCHEMICAL MANUFACTURING PROCESSES THEREFOR

The present application is a division of U.S. application Ser. No. 13/382,781 (filed Dec. 28, 2012, now U.S. Pat. No. 9,603,870 (issued Mar. 28, 2017). U.S. application Ser. No. 13/382,781 is a U.S. national stage entry of International Application No. PCT/US2010/41427, filed Jul. 8, 2010. Said international application claims priority to seven other US patent applications: 1) U.S. Ser. No. 61/223,944 filed on Jul. 8, 2009; 2) U.S. Ser. No. 61/226,153 filed on Jul. 16, 2009; 3) U.S. Ser. No. 61/228,250 filed on Jul. 24, 2009; 4) U.S. Ser. No. 61/235,574 filed on Aug. 20, 2009; 5) U.S. Ser. No. 61/249,804 filed on Oct. 8, 2009; 6) U.S. Ser. No. 61/263,648 filed on Nov. 23, 2009; and 7) U.S. Ser. No. 61/294,690 filed on Jan. 13, 2010.

FIELD OF THE INVENTION

The present invention relates to novel gold nanocrystals and nanocrystal shape distributions that have surfaces that are substantially free from organic or other impurities or films. Specifically, the surfaces are "clean" relative to the surfaces of gold nanoparticles made using chemical reduction processes that require organic reductants and/or surfactants to grow gold nanoparticles from gold ions in solution.

The invention includes novel electrochemical manufacturing apparatuses and techniques for making the gold-based nanocrystals. The invention further includes pharmaceutical compositions thereof and the use of the gold nanocrystals or suspensions or colloids thereof for the treatment or prevention of diseases or conditions for which gold therapy is already known and more generally for conditions resulting from pathological cellular activation, such as inflammatory (including chronic inflammatory) conditions, autoimmune conditions, hypersensitivity reactions and/or cancerous diseases or conditions. In one embodiment, the condition is mediated by MIF (macrophage migration inhibiting factor).

BACKGROUND OF THE INVENTION

Gold Salts

Robert Koch is credited with discovering the bacteriostatic effect of gold cyanide on *Mycobacterium tuberculosis*. It was subsequently observed that patients with tuberculosis often benefited from a reduction in certain inflammatory conditions when given gold salt injections for the disease. This observed reduction in inflammation led to aurothiolates being used by Forestier in 1927 as a treatment for rheumatoid arthritis (Panyala, 2009) (Abraham, 1997). The early gold-based products were typically injected in an intramuscular, or subcutaneous manner (and later in an intraarterial manner) and some are still available today and/or still being used to treat rheumatoid arthritis.

Specifically, it has been known for many years that certain gold compounds possess anti-inflammatory activity. For example, (i) sodium gold thiomalate (also referred to as "gold sodium thiomalate"), marketed as Myocrisin and related chemical versions, marketed as Myochrisine and Myochrisis; (ii) sodium gold thioglucose (also referred to as "gold sodium thioglucose"), marketed as Solganol; (iii) sodium gold thiosulfate, marketed as Sanocrysin and related chemical versions, marketed as Crisalbine, Aurothion and Sanocrysis; and (iv) sodium gold thiopropanolsulfonate, marketed as Allocrysine, have been used in the treatment of rheumatoid arthritis (Sadler, 1976; Shaw, 1999; Eisler, p. 133, 2004). Only monovalent gold salts were believed to exhibit therapeutic effects for the treatment of rheumatoid arthritis. In 1961 the Empire Rheumatism Council affirmed that injectable gold salts showed efficacy and gold salts remain a widely used method of treatment of progressive rheumatoid arthritis (Ueda, 1998).

Treatment with various gold salts has also been suggested, or anecdotally observed, to be effective in a range of other diseases, including asthma, HIV, malaria and cancer. A considerable body of evidence exists in these diseases, in both human and animal models, suggesting that gold may be a viable treatment option for these areas of unmet medical need (Dabrowiak, 2009).

Oral Gold

More recently, an oral gold product, 2,3,4,6-Tetra-o-acetyl I-thio B-D-glucopyranosato-S-(triethyl-phosphine), marketed as Auranofin® or Ridaura® in several parts of the world, has become available (Ho & Tiekink, 2005, Dabrowiak, 2009). Auranofin® was approved by the FDA for human use in the mid-1980's; and Auranofin® had the advantage of being orally absorbed, but was considered to be less effective than the injectable gold thiolates (Sadler, 1976; Shaw 1999).

Toxicology of Gold Salts and Oral Gold

Historically, toxicity has limited the use of all injectable and oral gold-based therapies, with anywhere from 30-50% of patients terminating various gold-based treatments due to undesirable or intolerable side effects. The side effects of many conventional gold therapies include rashes or mucocutaneous effects (e.g., pruritus, dermatitis and stomatitis); hematologic changes (e.g., thrombocytopenia); protein in the urine (proteinuria); inflammation of the mouth; reduction in the number of circulating leukocytes; decreased number of blood platelets; aplastic anemia due to organ damage; lung abnormalities; adverse immune reactions, such as eosinophilia, lymphadenopathy, hypergamma globulinemia; severe hypotension, angina, myocardial infarction, nephrotoxicity and nephrotic syndrome; hepatitis; colitis; and chrysiasis (pigmentation) of the cornea, lens, and skin (Eisler, p. 133-134, 2004). The most common side effect of chrysotherapy was skin toxicity, accounting for up to 60% of all adverse reactions, especially lichenoid eruptions and non-specific dermatitis (Eisler, p. 133-134, 2004). These side effects are believed to be related to the formulations used (e.g., carrier molecule, oxidation state of the gold in the compound, etc.), rather than the gold itself (Ho & Tiekink, 2005).

Payne and Arena in 1978 reported the subacute and chronic toxicity of several oral gold compounds, including Auranofin®, in rats, compared to an injected gold control. Sprague Dawley rats were dosed for periods of 6 weeks, 6 months and one year. In a follow-up study, the 1-year investigation was repeated with sequential kills and a modified dosing regimen.

The target organs identified by this study were the stomach and kidney. Gastric changes consisted of superficial erosions of the mucosa extending up to ⅓ of the thickness of the mucosa and covering up to 5% of its surface area. This change was dose-related and was associated with loss of body weight. Healing lesions were also evident. In the kidney of rats given SK&F 36914 for six months there was enlargement of cortical tubular epithelial cells (cytomegaly). In addition, there was a dose-related enlargement of the nucleus (karyomegaly), with evidence of pleomorphic and multinucleate cells. In the 1-year study similar changes were seen, but in addition renal cortical cell adenomas were seen in a dose-related incidence (0/38, 3/39, 6/37 and 8/37 for control, low, intermediate and high dose respectively). In a repeated 1-year study an unexpectedly high incidence of mortality occurred. This was attributed to ileocaecal lesions that progressed to ulceration that appeared to perforate the gut wall in a number of cases. Presumably death resulted from acute infectious peritonitis. In the injected controls, gold sodium thiomalate was administered by intra-muscular injection once weekly for a year and, in a second study, once weekly for 46 weeks and then daily for 330 days. In the 1-year study, renal tubular cell karyomegaly was observed and renal cell adenoma was seen in 1/16 females but not in males. In the 21 month study all surviving rats showed karyomegaly of the renal cortical tubular epithelium and cystic tubules were frequently observed. Renal adenomas, occasionally multiple, were seen in 8/8 females and 3/7 males surviving to 21 months (Payne & Arena, 1978). Similar results were seen in dogs (Payne & Arena, The subacute and chronic toxicity of SK&F 36914 and SK&F D-39162 in dogs, 1978).

Szabo et al 1978a reported the effects of gold-containing compounds, including Auranofin® on pregnant rats and fetuses. The effects of gold sodium thiomalate and the oral gold compound Auranofin® on maternal and fetal toxicity and teratogenicity were investigated. Oral gold was administered by intubation on days 6-15 of pregnancy, while gold sodium thiomalate was administered on days 6-15 by subcutaneous injection. This was a standard exposure period in such studies and this exposure is considered to be equivalent to the first trimester of a human pregnancy. Standard procedures were used to examine fetuses and group sizes were adequate for the purpose of the study. Maternal and fetal toxicity was evident and fetuses of gold sodium thiomalate-dosed animals showed a pattern of dose-related malformations. The doses used led to death of a proportion of the dams and showed marked effects on body weight (including actual weight loss at the start of dosing) and reduced food consumption. The malformations included skeletal anomalies, external malformations and degrees of hydrocephalus and ocular defects. SK&F D-39162 did not affect food intake or weight gain, but was also associated with reductions in fetal weight compared to controls. The only major defect found with SK&F D-39162 treatment was edema. There was no evidence of an effect of gold sodium thiomalate on implantation, resorption, fetal number or fetal weight in the gold sodium thiomalate-treated animals. These authors concluded that the effects on the fetus were indirect and were attributable to accumulation of gold in the lysosomes of the visceral yolk sac epithelium, with consequent inhibition of vital enzymes involved in fetal nutrition. This hypothesis was advanced to explain the teratogenicity of other chemicals and could be plausible (Szabo, Guerriero, & Kang, The effects of gold containing compounds on pregnant rats and their fetuses, 1978).

Szabo et al 1978b reported the effects of gold-containing compounds on pregnant rabbits and fetuses. In this study pregnant rabbits were dosed from days 6-18 of pregnancy. Gold sodium thiomalate was administered by sub-cutaneous injection and oral compounds were given by intubation. Both routes of administration led to maternal deaths and abortions were also observed in surviving animals. Dose-related decreases in maternal food consumption, leading to actual body weight losses, were observed at the higher doses of both injected and oral gold. Effects were also evident on litter sizes, numbers of resorptions and mean fetal weights. Fetal anomalies and malformations were also observed, primarily in the abdomen (gastroschisis and umbilical hernia), with a lower incidence of anomalies affecting the brain, heart lungs and skeleton. The authors concluded that the incidence of abdominal anomalies, exceeding all of their historical control data, indicated a specific sensitivity in the rabbit to such an effect of gold (Szabo, DiFebbo, & Phelan, 1978).

Based on these studies, oral administration of relatively high doses of gold-containing compounds was associated with a dose-related incidence of erosions of the gastric mucosa and, in a longer duration study, of significant ileocaecal lesions (including ulceration) that caused the deaths of a number of animals. Examination of the data presented suggested that the gastric lesions were typical of a marked direct local effect on the mucosa. The renal cortical tubular epithelium was another target tissue, perhaps through the development of high local concentrations during the concentration of the urine. The cortical tubular epithelium lesions progressed from karyomegaly to adenoma formation in a significant number of animals. Although this is a benign tumor it cannot be ignored in terms of risk assessment. However, it is also notable that lesions of the rodent kidney are relatively common, particularly in males, but these appeared to affect females relatively more than males in these studies.

The gastric lesions occurred after administration of relatively large amounts of gold solutions. There was also a suggestion in these studies that the important toxic agent is ionic gold (e.g., Au (III) or $Au^{3+}$). Lesions of this type are also produced by many NSAID agents used in the treatment of various forms of arthritis and are generally considered to be a manageable, albeit undesirable, side effect. Accordingly, the absence of such negative effects would constitute an advantage over existing gold-based therapies.

Cheriathundam and Alvares in 1996 evaluated the effects of sodium gold thiolate and Auranofin® on liver and kidney markers and metallothionein levels in the Sprague Dawley rat and three strains of mouse (Swiss-Webster, C3H/Hej and DBA/2J). In the rat, gold sodium thiolate led to a 7-fold increase in liver metallothionein levels, whereas in the mouse strains metallothionein levels increased 2-fold in the Swiss-Webster and about 5-fold in the inbred strains. Gold sodium thiolate led to only minimal changes in renal metallothionein levels in the mouse strains. The liver marker serum ALAT was not altered by gold sodium thiolate in any of the species or strains tested. BUN, an indicator of kidney function, was elevated 3-fold in rats but not in any of the mouse strains. These data are consistent with the observation that gold sodium thiolate is nephrotoxic in rats and humans, but it is interesting to note the lack of evidence of nephrotoxicity in the mouse (Cheriathundam & Alvares, 1996).

The observation of embryonic toxicity and fetal defects after treatment of pregnant animals of two species suggests the possibility that gold in many, if not all previously used forms, represents a developmental risk. This has parallels with many other current RA therapies, in which methotrexate, for example, is subject to label warnings regarding potential harmful effects on the fetus.

Several possible pharmacological actions contributing to both clinical efficacy and adverse reactions have been identified for oral gold. For example, Walz and his colleagues showed that Auranofin® inhibited carrageenan-induced edema in rats in a dose-related fashion in concentrations of 40, 20 and 10 mg/kg with maximum inhibition of 86% at the highest dose, and a serum gold level of approximately 10 µg/mL. The two basic ligands of Auranofin®, namely triethylphosphine oxide and 2,3,4,6-tetra-o-acetyl-1-thio-β-D glucopyranose did not show any significant biological activity, and gold sodium thiomalate, gold thioglucose and thiomalic acid did not significantly affect rat paw edema. Auranofin® was shown to significantly suppress adjuvant arthritis, whereas the ligands were without any effect. Auranofin® inhibited antibody dependant complement lysis. Auranofin® has been shown to inhibit the release of lysosomal enzymes such as β-glucuronidase and lysozyme from stimulated polymorphs. Auranofin® is a potent inhibitor of antibody dependent cellular cytotoxicity exhibited by polymorphs from adjuvant arthritic rats. Auranofin® is a much more potent inhibitor of superoxide production than gold sodium thiomalate. In an immune phagocytosis assay, gold sodium thiomalate showed no inhibitory activity at a concentration of 40 times that of Auranofin®, causing marked inhibition (Walz, DiMartino, Intocca, & Flanagan, 1983).

Walz and his colleagues also stated that Auranofin® was more potent than gold sodium thiomalate as an inhibitor of cutaneous migration, chemotaxis and phagocystosis by peripheral blood monocytes. Lipsky and his colleagues showed that Auranofin®, like gold sodium thiomalate, inhibited lymphoblastogenesis in vitro by directly inhibiting of mononuclear phagocytes. However, Auranofin® also had an inhibitory effect on lymphocyte function, not observed with gold sodium thiomalate. Inhibition of monocytes was achieved with concentrations of Auranofin® which were 10 to 20 fold lower than those of the gold sodium thiomalate (Walz, DiMartino, Intocca, & Flanagan, 1983).

In general, patients with active rheumatoid disease have a decreased capacity for either mitogen-stimulated lymphoblastogenesis or for lymphoblastogenesis induced by the mixed lymphocyte reaction. Although patients initially treated with gold sodium thiomalate first showed some suppression of mitogen-stimulated lymphoblastogenesis, those who eventually responded to the drug showed normal lymphocyte responsiveness in vitro. In contrast, within a few weeks of patients receiving Auranofin®, lymphocyte responsiveness was markedly inhibited. Thus, Auranofin® exhibits a powerful immunosuppressant effect in vitro at an order of magnitude less than the injectable gold compounds, most likely due to the major differences in the pharmacological properties of the oral compounds versus the injectable gold-thiol compounds (Dabrowiak, 2009).

Adverse reactions were the major limiting factor to the use of oral gold compounds such as Auranofin®, in that approximately 30-50% of treated patients developed some form of toxicity (Dabrowiak, 2009) (Kean & Anastassiades, 1979) (Kean & Kean, The clinical Pharmacology of Gold, 2008).

Skin rash was the most common negative side effect and some form of rash occurred in approximately 30% of patients. Most lesions occurred on the hands, forearm, trunk and shins, but occasionally occurred on the face and were slightly erythematosus with scaly patches, 1-10 cm in size, resembling a seborrheic rash. Severe problems of skin rash in the form of nummular eczema, total exfoliation and intense pruritus have been recorded as rare.

Oral ulcers (painful and pain free) resembling the aphthous ulcer, occurred in approximately 20% of patients who received injectable gold therapy. The development of a mouth ulcer was a definite contraindication to continuation of gold therapy since it was known that oral ulceration could herald pemphigold-like bullous skin lesions.

The frequency of proteinurea varied widely (0-40%) in the studies reported by Kean and Anastassiades, most likely reflecting different definitions as to what constitutes proteinurea. In these studies there are no well documented cases of any long term serious or permanent renal damage due to gold therapy; however microscopic haematuria was a cause for discontinuing oral gold treatment (Kean & Anastassiades, 1979).

Thrombocytopenia due to gold compounds occurred as two distinct types: the more usual was associated with platelet surface IgG antibody and the other less common was secondary to bone marrow suppression. The genetic marker HLA DR3 may indicate an increased risk of a patient developing thrombocytopenia associated with platelet surface antibodies.

Idiopathic toxicities in the form of cholestatic jaundice or acute enterocolitis have also been associated with the injectable gold compounds, particularly gold sodium thiomalate, but have not been reported with oral gold.

The deposition of elemental gold in the lens of the eye and the cornea has been reported, but this did not seem to result in any specific damage to visual acuity.

Specific to oral gold therapy was the development of loose soft stools, usually in the first month of therapy. The lower incidence of altered stools in later treatment months may be related to an earlier drop-out of those patients susceptible to the diarrhea. The development of frank watery diarrhea occurred in 2-5% of patients and appeared to be dose-related.

In general the adverse event incidence is lower with oral gold than injectable gold, but can still be substantial.

A second major drawback to the use of available gold-based treatments is the very slow onset of efficacy. Patients often must continue treatment with, for example, gold salts for three to six months before experiencing any significant benefit. This long wait for any observed benefit is a major impediment to patient compliance and therefore adversely affects efficacy in use.

The knowledge of the pharmacokinetic profiles of gold is largely centered on the measurement of the element Au, but not much is known of the gold structure (e.g., its chemical or physical or crystalline structure) when the gold is present in various tissues or organs.

After oral ingestion, oral gold complexes are rapidly, but incompletely, absorbed. The gold moiety of the injectable gold complex seems to be rapidly absorbed into the circulation after intramuscular injection. In blood circulation, Auranofin® (or ligands thereof) seem to be bound predominately to albumin. Specifically, after oral administration of radiolabeled Auranofin® to human volunteers, approximately 25% of the administered dose was detected in the blood plasma, with peak concentrations of 6-9 μg/100 mL being reached within 1-2 hours. The plasma half life was on the order of 15-25 days with almost total body elimination after 55-80 days. Only about 1% of radiolabeled Au was detectable after 180 days, whereas up to 30% of gold from gold sodium thiomalate was detected at this time. The gold was widely distributed throughout the reticulo-endothelial system, particularly in the phagocytic cells of the liver, bone marrow, lymph nodes, spleen, and also in the synovium. Deposition in the skin occurred and it has been observed that there may be a quantitative correlation between the amount of gold in the dermis and the total dose of gold given. Electron dense deposits of gold were also observed in the tubular cells of the kidney, another site rich in sulphydryl-containing enzymes, but the presence of gold associated with the glomerulus does not appear to be common (Walz, DiMartino, Intocca, & Flanagan, 1983) (Dabrowiak, 2009).

Gold Nanoparticles

Other formulations of gold have been and continue to be developed, most of which utilize gold nanoparticles made by a variety of chemical reduction techniques; and some of which utilize an underwater plasma arcing technique; and most of which result in various stable or partially stable gold colloids or gold nanoparticles suspensions.

Colloidal Gold Nanoparticles by Chemical Reduction

Michael Faraday made the first colloidal gold suspension by chemical reduction methods around the 1850's (Faraday, 1857). Faraday used reduction chemistry techniques to reduce chemically an aqueous gold salt, chloroaurate (i.e., a gold (III) salt), utilizing either phosphorous dispersed into ether (e.g., $CH_3$—$CH_2$—O—$CH_2$—$CH_3$), or carbon disulfide (i.e., $C_2$), as the reductant.

Today, most colloidal gold preparations are made by a reduction of chloric acid (hydrogen tetrachloroaurate) with a reductant like sodium citrate to result in "Tyndall's purple." There are now a variety of "typical" reduction chemistry methods used to form colloidal gold. Specifically, several classes of synthesis routes exist, each of which displays different characteristics in the final products (e.g., colloidal gold nanoparticles) produced thereby. It has been noted that in addition to the strength, amount and type of the reductant utilized, the action of a stabilizer (i.e., the chemical utilized in the solution phase synthesis process) is critical (Kimling, 2006).

While Faraday introduced colloidal gold solutions, the homogenous crystallization methods of Turkevich and Frens (and variations thereof) are most commonly used today and typically result in mostly spherical-shaped particles over a range of particle sizes (Kimling, 2006). Specifically, most current methods start with a gold (III) complex such as hydrogen tetrachloroaurate (or chloric acid) and reduce the gold in the gold complex to gold metal (i.e., gold (0) or metallic gold) by using added chemical species reductants, such as Na thiocyanate, White P, $Na_3$ citrate & tannic acid, $NaBH_4$, Citric Acid, Ethanol, Na ascorbate, $Na_3$ citrate, Hexadecylaniline and others (Brown, 2008). However, another chemical reduction technique uses sodium borohydride as a chemical species reductant for AuP ($Ph_3$) (Brown, 2008). Depending on the particular processing conditions utilized in these chemical reduction processes, the sizes of these mostly spherical nanoparticles formed range from about 1 nm to about 64 nm in diameter (Brown, 2008). Additionally, specific thermal citrate reduction methods utilized by Kimling resulted in a small fraction of triangular-shaped particles, in addition to spherical-shaped particles, with the triangular-shaped species at most being about 5% (Kimling 2006).

Additional work has focused on controlling shapes of colloidal metal nanoparticles. Biologists and biochemists have long understood that "structure dictates function" with regard to protein functioning. Gold nanoparticles of different shapes also possess different properties (e.g., optical, catalytic, biologic, etc.). Controlling nanoparticle shape provides an elegant approach to, for example, tune nanoparticles optically. While all gold nanoparticles contain a lattice that is face-centered cubic, if permitted or caused by certain processing conditions, gold nanoparticles can adopt a variety of crystalline shapes ranging from irregular ellipsoids with defect loaded surfaces (e.g., steps) to polyhedra with comparatively limited surface defects. Different crystalline morphologies are associated with different crystal planes (or sets of crystal planes). However, some of the most common gold nanoparticle morphologies are not composed of single domains, but rather are made of twinned planes (Tao, 2008).

Yuan, et al. recognized that non-spherical-shaped gold nanoparticles could be most readily achieved by providing seed crystals from a borohydride reduction of a gold salt (i.e., $HAuCl_4$ or auric acid). The seed crystals were then placed into contact with the same gold salt in solution with the chemical species $NH_2OH$, CTAB and sodium citrate being added as reductants and/or surfactants (e.g., capping agents). Several different crystalline shapes were formed by this approach including triangular, truncated triangular, hexagonal layers and pseudo-pentagonal. Yuan concluded that variations in processing by using different chemical reduction techniques can influence the physical and chemical properties of the resulting particles. The researchers noted that the choice of a capping agent was a key factor in controlling the growth (and shape) of the nanoparticles (Yuan, 2003).

The process described and used by Yuan is known as "heterogeneous nucleation" where seed particles are produced in a separate synthetic step. Thus, this type of shape control can be considered an overgrowth process (Tao, 2008). Many chemical reduction techniques utilize this more complex two-step heterogeneous nucleation and growth process. However, others use a single step homogenous nucleation whereby seed crystals are first nucleated and nanoparticles are then formed from the nucleated seed crystals. Typically, a series of chemical reactions occur simultaneously in homogeneous nucleation. A main goal in homogenous nucleation is to balance the rate of nucleation against the rate of crystal growth and to control particle size because both nucleation and growth proceed by the same chemical process(es) (Tao, 2008).

Metal nanoparticle synthesis in solution(s) commonly requires the use of surface-active agents (surfactants) and/or amphiphilic polymers as stabilizing agents and/or capping agents. It is well known that surfactants and/or amphiphilic polymers serve critical roles for controlling the size, shape and stability of dispersed particles (Sakai, 2008).

Some of the most common crystal morphologies observed in crystalline gold nanoparticles (for example in heterogeneous nucleation processes) do not consist of single crystals or single domains, but rather particles containing multiple crystal domains, often bounded by twin planes. A regular decahedron (also referred to as a pentagonal bi-pyramid) is an equilibrium shape bound completely by triangular (III) facets and can be thought of as five tetrahedral sharing a common edge along a fivefold axis. These structures are commonly observed for nano-crystalline particles synthesized by metal evaporation onto solid substrates and seeded heterogeneous nucleation reduction chemistry approaches (Tao, 2008). However, for nanoparticles synthesized by the methods of Turkevich and Frens, decahedra are difficult to observe because they function as favorable seeds for the growth of nanowires and nanorods (Tao, 2008). Thus, a variety of shapes can be achieved by controlling processing conditions, along with the amounts and types of surfactants and capping agents added and used during the reduction chemistry approaches attributed to Turkevich and Frens.

In each of the colloidal gold compositions produced by reduction chemistry approaches, it is apparent that a surface coating comprising one or more elements of the reductant and/or the surfactant or capping agent will be present on (or in) at least a portion of the suspended gold nanoparticles. The use of a reductant (i.e., a reducing agent) typically assists in suspending the nanoparticles in the liquid (e.g., water). However, the reducing agent coating or surface impurity is sometimes added to or even replaced by surfactant coatings or capping agents. Such reductant/surfactant coatings or films can be viewed as impurities located on and/or in the metal-based nanoparticles and may result in such colloids or sols actually possessing more of the properties of the protective coating or film than the gold nanoparticle per se (Weiser, p. 42, 1933).

For example, surfactants and amphiphilic polymers become heavily involved not only in the formation of nanoparticles (thus affecting size and shape), but also in the nanoparticles per se. Surface properties of the nanoparticles are modified by reductant coatings and/or surfactant molecule coatings (Sperling, 2008).

Absorption of a hydrophobic tail, a hydrophilic head group and certain counter ions (at least in the case of the use of ionic surfactants) on the surface of nucleated particles, as well as complexation of metal ions with surfactants and/or amphiphilic polymers with the formed particles, all can influence the shape of the nanoparticles, the surface of the nanoparticles and/or alter the functioning of the nanoparticles (Sakai, 2008).

Different surface chemistries or surface films (e.g., the presence of reductant by-product compositions and/or thicknesses (e.g., films) of reductant by-products) can result in different interactions of the gold nanoparticles with, for example, a variety of proteins in an organism. Biophysical binding forces (e.g., electrostatic, hydrophobic, hydrogen binding, van der Waals) of nanoparticles to proteins are a function not only of the size, shape and composition of the nanoparticles, but also the type of and/or thickness of the surface impurities or coating(s) on the nanoparticles. The Turkevich and Frens methods (and variations thereof) for making gold nanoparticles are the most widely understood and utilized chemical reduction processes. The use of a citric acid or sodium citrate reductant results in citrate-based chemistries (e.g., a citrate-based coating) on the surface of the gold nanoparticle (i.e., also referred to as citrate-stabilized) (Lacerda, 2010).

Further, Daniel et al. reviewed the major gold nanoparticle formation techniques, including the chemical synthesis and assembly processes including: (1) citrate reduction, which results in "a rather loose shell of [citrate-based] ligands" attached to the gold nanoparticles; (2) a variation of the citrate reduction method which uses a citrate salt and an amphiphile surfactant (for size control); (3) the "Brust-Schiffrin" methods which result in thiol or thiolate ligands "that strongly bind gold"; (4) methods that result in sulfur-containing ligands including xanthates, disulfides, dithiols, trithiols and resorcinarene tetrathiols; and (5) other ligands that relate to phosphine, phosphine oxide, amines, carboxylates, aryl isocyanides, and iodides (which can replace citrate coatings). The authors reiterated statements attributed to Brust regarding formed gold nanoparticles: "The resulting physical properties are neither those of the bulk metal nor those of the molecular compounds, but they strongly depend on the particle size, interparticle distance, nature of the protecting organic shell, and shape of the nanoparticles." (Daniel, 2004)

While the organic ligands present on the gold nanoparticles (e.g., citrate-based ligands or coatings or films) helps to stabilize the gold nanoparticles in the liquid to prevent the nanoparticle from, for example, being attached to other nanoparticles and agglomerating and/or settling out of suspension due to, for example, gravity, these organic-based ligands (e.g., organic shells) are impurities (i.e., relative to the underlying gold nanoparticle) and contribute to the gold nanoparticle's interaction with proteins in a living system. Such coating(s) or film(s) can have strong biological influences (Lacerda, 2010).

Further, Wang et al concluded that the commonly used citrate-reduced gold nanoparticles interfere with the uptake of gold nanoparticles relative to reductant and stabilizer-free colloidal solutions (Wang, 2007).

Likewise, Lacerda, et al. stated that a better understanding of the biological effects of nanoparticles requires an understanding of the binding properties of the in-vivo proteins that associate themselves with the nanoparticles. Protein absorption (or a protein corona) on nanoparticles can change as a function of nanoparticle size and surface layer composition and thickness. Lacerda concluded that the protein layers that "dress" the nanoparticle control the propensity of the nanoparticles to aggregate and strongly influence their interaction with biological materials (Lacerda, 2010).

Cleaning Colloidal Gold Nanoparticles Made by Chemical Reduction Techniques

In some cases, the reductant surface coating or film is permitted to remain as an impurity on the surface of the nanoparticles, but in other cases, it is attempted to be removed by a variety of somewhat complex and costly techniques. When removed, the coating typically is replaced by an alternative composition or coating to permit the nanoparticles to stay in suspension when hydrated. The influence of purity on the chemistry and properties of nanoparticles is often overlooked; however, results now indicate that the extent of purification can have a significant impact (Sweeney, 2006). These researchers noted that sufficient purification of nanoparticles can be more challenging that the preparation itself, usually involving tedious, time-consuming and wasteful procedures such as extensive solvent washes and fractional crystallization. Absent such purification, the variables of surface chemistry-related contaminants on the surface of chemically reduced nanoparticles affects the ability to understand/control basic structure-function relationships (Sweeney, 2006).

Subsequent processing techniques may also require a set of washing steps, certain concentrating or centrifuging steps, and/or subsequent chemical reaction coating steps, all of which are required to achieve desirable results and certain performance characteristics (e.g., stabilization due to ligand exchange, efficacy, etc.) for the nanoparticles and nanoparticle suspensions (Sperling, 2008). In other cases, harsh stripping methods are used to ensure very clean nanoparticle surfaces (Panyala, 2009).

Thus, others have concluded that the development of gold nanoparticles in the management, treatment and/or prevention of diseases is hampered by the fact that current manufacturing methods for gold nanoparticles are by-and-large based on chemical reduction processes. Specifically, Robyn Whyman, in 1996, recognized that one of the main hindrances in the progress of colloidal golds manufactured by a variety of reduction chemistry techniques was the lack of any "relatively simple, reproducible and generally applicable synthetic procedures" (Whyman 1996). There are many variations of the original reduction chemistry techniques taught by Faraday each of which can produce colloidal gold having a variety of different physical properties (e.g., alone or in suspension) and reductant coatings, all of which can result in different efficacy/toxicity profiles when used in or with living cells. None of these techniques meet Whyman's criteria. Accordingly, a relatively simple, reproducible and generally applicable manufacturing approach for making gold nanocrystals would be welcomed. Further, the ability of such a manufacturing approach to be compliant with FDA cGMP requirements would be even more valuable.

Others have begun to recognize the inability to extricate completely adverse physical/biological performance of the formed nanoparticles from the chemical formation (i.e., chemical reduction) processes used to make them. In this regard, even though somewhat complex, expensive and non-environmentally friendly, washing or cleaning processes can be utilized to alter or clean the surface of nanoparticles produced by reduction chemistry, elements of the chemical process may remain and affect the surface of nanoparticles (and thus their functioning). Moreover, the presence of certain chemicals during the nanoparticle formation process affects the morphology (i.e., size and/or shape) of the forming nanoparticles. Certain possible desirable morphologies (shapes) known to exist in gold-based crystalline systems are not readily observed in many products produced by these reduction chemistry techniques.

Other Techniques for Making Colloidal Gold

Obtaining a surfactant and reducer-free (e.g., no stabilizing, capping or reducing agents added to achieve reduction of gold ionic species) has become a goal of certain researchers who apparently understand some adverse consequences of reductant/surfactant coatings being present from reduction chemistry approaches. For example, ultrasound techniques have been used whereby a 950 kHz frequency is applied to an aqueous hydrogen tetrachloroaurate solution. Spherical gold nanoparticles in the range of 20-60 nm were prepared at temperatures above 50° C., while relatively larger triangular plates and some hexagonal spheres coexisted when the mixture was processed below 50° C. (Sakai, 2008).

X-ray irradiation of $HAuCl_4$ has been developed to obtain reductant and stabilizer-free gold nanoparticles so as not to "jeopardize" biocompatibility issues in biomedical applications. The authors speculated that they generated the required electrons for chemical reduction of $Au^+$ by using "intense" X-ray beams to create a hydrogen-free radical electron donor (Wang, 2007).

Another older and more complex technique for minimizing or eliminating the need for reducing agents and/or minimizing undesirable oxidation products of the reductant utilizes γ-irradiation from a $^{60}Co$ source at a dose rate of $1.8 \times 10^4$ rad/h. In this instance, Au $(CN)_2$ was reduced by first creating hydrated electrons from the radiolysis of water and utilizing the hydrated electrons to reduce the gold ions, namely:

$$e_{aq}^- + Au(CN)_2 \rightarrow Au^0 + 2CN^-$$ (Henglein, 1998).

It is known that the surface of the gold nanoparticle may be further processed by adding chemical species, such as polyehteylene glycol (PEG), or other specific ligands. In this regard, extensive work has occurred in therapies for cancer where PEG-coated gold nanoparticles are induced by a variety of techniques to migrate to a cancer or tumor site and are thereafter irradiated with, for example, infrared or radiowaves to heat and destroy cancer cells (Panyala, 2009). Surface PEGylation is also known to increase the blood half-life of nanoparticles; and polysorbate-80 can improve the blood-brain-barrier transport of nanoparticles (Teixido & Giralt, 2008).

Colloidal Gold by Underwater Arcing

Also known in the art are methods for making gold nanoparticles by an underwater arcing method. This method was first pioneered by Bredig in the late 1800's. Bredig used a direct current to create an underwater arc between two wires. Bredig used a current of 5-10 amps and a voltage of 30-110 volts. In some cases, Bredig also used 0.001N sodium hydroxide instead of pure water. Bredig thought of his process as pulverizing the metallic electrodes. Bredig obtained hydrosols of gold in this manner (Weiser, pp. 9-17, 45-46, 1933).

Svedberg later improved on Bredig's process by utilizing a high frequency arc instead of the direct current arc of Bredig. Svedberg pointed out that the arc permits the formation of a metal gas which subsequently condenses into particles of colloidal dimensions. Much debate surrounded the exact mechanisms of the process, however vaporization of the metal was viewed as being important (Weiser, pp. 9-17, 45-46, 1933).

The parameters of greatest interest to Svedberg in controlling the electric pulverization process to form colloid solutions were, a) the rate of pulverization, b) the ratio of sediment to total metal dispersed, c) the extent of decomposition of the medium, and d) the dependence of (a)-(c) on the current characteristics. The amount of sediment achieved by the Bredig and Svedberg processes ranged from about 30% to about 50%, under a variety of processing conditions (Kraemer, 1924).

More recent work with the Bredig process on palladium was performed by Mucalo, et al. These investigators tested the theory of whether the metallic particles in Bredig sols were "impure" due to impurities from the concurrent electrolyte decomposition of the electrolyte and oxidized material thought to form during arcing (Mucalo, 2001). These investigators utilized modern surface analytical techniques (i.e., XPS, or "x-ray photoelectron spectroscopy") to determine differences in surface speciation as a function of pH. At lower pH's a grey-black unstable material was produced. At higher pH's, the sol was more stable, but still completely aggregated within 1-2 weeks. Nanoparticles produced consisted of irregularly-shaped spheres. While materials produced at both higher and lower pH's were mostly metallic in character, the surface characteristics of these unstable colloids were different. The higher pH Bredig sols resulted in a thicker outer oxide layer on the unstable nanoparticles (Mucalo, 2001).

The methods of Bredig and Svedberg were subsequently improved on by others to result in a variety of underwater arc-based methods. However, common to each of these underwater arcing methods is the result of somewhat irregularly-shaped metallic-based spheres. In this regard, the nanoparticles produced by the Bredig or Svedberg processes are non-specific, spherical-like shapes, indicative of a metal-based vaporization followed by rapid quench methods, the nanoparticles being coated with (and/or containing) varying amounts of different oxide-based materials.

Toxicology of Colloidal Gold Nanoparticles

A review on the toxicology of gold nanoparticles was performed by Johnston, et al. and reported in 2010. There were four intravenous exposure routes summarized for both mice and rats and an intratracheal approach for rats. Regarding the four intravenous studies summarized, Johnston, et al. reported that tissue sites of accumulation, in order of quantity were liver-spleen in 3 of 4 tests and liver-lung in 1 of 4 tests (i.e., highest gold nanoparticle accumulation was in the liver). Specifically, the four intravenous tests reported by Johnston et al. are summarized below (Johnston, 2010).

The tissue distribution of metal particles, following exposure via a variety of routes (Johnston, et al., 2010).

| Paper | NP | Size (nm) | Exposure Route | Tissue sites of accumulation (in order of quantity) | Conclusion |
|---|---|---|---|---|---|
| Cho, et al., 2009 | Gold (PEG coated) | 13 | Intravenous (mice) | Liver, spleen, kidney, lung, brain | The primary sites of accumulation are the liver and spleen, NP's accumulate within macrophages |
| De Jong, et al., 2008 | Gold | 10, 50, 100, 250 | Intravenous (rats) | Liver, spleen, lungs, kidneys, heart, brain, thymus, testis | Wider organ distribution of smaller particles, whereas larger particles were restricted to the liver and spleen |
| Semmler-Behnke, et al., 2008 | Gold | 4 and 18 | Intravenous (rats) | Liver, spleen, kidneys, skin, GIT, heart | Small particles demonstrate a more widespread accumulation/distribution |
| Sonavane, et al., 2008b | Gold | 15, 50, 100, 200 | Intravenous (mice) | Liver, lung, kidneys, spleen, brain | Wider tissue distribution for smaller particles- 15- and 50-nm NP's accumulated within the |

Johnston, et al. were critical of a variety of uncertainties introduced into a number of the reviewed toxicology studies including that certain conclusions (made by others) regarding toxicity as a function of only particle size were not accurate. Specifically, Johnston, et al. reported that Pan et al (in 2007) concluded that 1.4 nm gold nanoparticles were the most toxic gold nanoparticles tested out of a range of nanoparticle sizes, including 1.2 nm diameter gold nanoparticles. While Pan, et al. believed there to be a difference in toxicity profile as a function of size, Johnston, et al. noted that the 1.4 nm particles were made by the investigators themselves and the 1.2 nm particles were obtained from an outside company (thus suggesting that there were different surface characteristics of both nanoparticles). Johnston, et al. concluded that "agglomerations states or surface chemistry" were the reason(s) for differential performance with both being "known to alter particle behaviour and toxicity" (Johnston, 2010).

Johnston, et al. also concluded that experimental setup influences toxicity results; and that the tissue distribution of gold nanoparticles in an organism is a function of the exposure route, as well as size, shape and surface chemistry of nanoparticles. Additionally, they observed that the liver appears to be the primary site of accumulation and speculated that result is due to the presence of macrophages in the liver. They also noted that nanoparticle uptake is probably a result of the type and extent of protein binding occurring on the surface of the nanoparticles (e.g., a protein corona) which is a function of the size, shape and surface coating on the nanoparticles. In particular, they noted that the ability of a variety of cell types to internalize nanoparticles by, for example, endocytosis. This endocytosis mechanism which appeared to be a function of particle shape, as well as particle surface characteristics, such as protein absorption on the surface thereof. In other words, biological uptake is a function of shape, size and charge; and is also very serum-dependent (Johnston, 2010).

Efficacy of Colloidal Gold

Work by Abraham and Himmel (reported in 1997) disclosed the use of colloidal gold in the treatment of 10 patients who previously did not respond to a variety of other gold-based treatments. The colloidal gold used in the study was made by a variation of the standard "citrate method" of Maclagan and Frens with "several proprietary modifications." Maltodextrins (Food Grade) were used at a concentration of 2.5% to prevent autoaggregation of the gold particles (Abraham, 2008). The sizes of the colloid particles produced were reported as being less than 20 nm, as confirmed by a process of passing the colloidal suspension through a 20 nm filter (i.e., produced by Whatman Anotop). Subsequent TEM work caused Abraham to conclude that 99% of the particles produced were less than 10 nm. Sodium benxoate was also added (Abraham, 2008).

The colloidal gold suspension resulted in a 1,000 mg/L (i.e., 1,000 pm) concentration. The dosage level provided to each patient varied between 30 mg/day and 60 mg/day, with most dosages being 30 mg/day, for a 24 week period. These dosages were taken orally. Table 1 therein lists the patient's sex, age and previous conditions and/or treatments. The article concludes that 9 of the 10 patients "improved markedly by 24 weeks of intervention" (Abraham & Himmel, 1997). Abraham also reported a lowering of certain cytokine concentrations including IL-6 and TNF (Abraham, 2008).

Work on collagen-induced arthritis in rats by Tsai concluded that nanogold particles bound to the protein VEGF and that such binding was the reason for an improved clinical performance of rats that were intra-articularly injected with colloidal gold. In this case, the injected colloidal gold was prepared by the standard chemical reduction method of utilizing a gold chloroaurate reduced with sodium citrate. Tsai, et al. reported that the gold nanoparticles were spherical having an approximate diameter of 13 nm, as measured by transmission electron microscopy. The concentration of the intra-articular solution was 180 µg/ml (i.e., 180 ppm). The intra-articular injection was made one time, either on day 7 or day 10 after induction of CIA (Tsai, 2007).

Brown, et al. disclosed in 2007 that a standard colloidal gold preparation (referred to as Tyndall's purple) was prepared by standard chemical reduction methods, namely, the reduction of chlorauric acid with sodium citrate. The average particle size of the gold nanoparticles produced was 27+/−3 nm. This colloidal gold was dispersed in isotonic sorbitol and injected by a parenteral and subcutaneous approach into rats that experienced experimentally induced arthritis. The dose injected was at a concentration of 3.3 µg/kg. Brown, et al. also disclosed that colloidal gold, when administered subcutaneously, was approximately 1,000 times more effective than the comparative sodium aurothiomalate. Brown, et al. also disclosed that the colloidal gold was ineffective when given orally and concluded that the ineffectiveness was due to coagulation of the gold nanoparticles in the presence of gastric juice and sodium chloride (Brown, 2007).

Brown, et al. reviewed alternative preparation methods for colloidal gold having a variety of sizes and shapes (Brown, 2008). Brown, et al. disclosed in Table 2 a variety of properties associated with "nano-gold hydrosol." The authors concluded that the studies conducted by them (and reviewed by them) "suggest that gold nanoparticle (Au0)-based drugs may play a role in future clinical therapies targeted to regulating macrophages" (Brown, 2008).

The references cited throughout the "Background of the Invention" are listed below in detail.

Abraham, G. E. & Himmel, P. B. (1997). Management of rheumatoid arthritis: rationale for the use of colloidal metallic gold. *J. Nutr. Environ Med.* 7, 295-305.

Abraham, G. E. (2008). Clinical Applications of Gold and Silver Nanocolloids. *Original Internist*, 132-157.

Agata, N., et al. (2000). Suppression of type II collagen-induced arthritis by a new Isocoumarin, NM-3. *Res Commun Mol Pathol Pharmacol.*, 108 (5-6), 297-309.

Brown, C. L., Whitehouse, M. W., Tiekink, E. R. T., & Bushell G. R. (2008). Colloidal metallic gold is not bio-inert. *Inflammopharmacology*, 16, 133-137.

Brown, C. L., et al. (2007). Nanogold-pharmaceutics (i) The use of colloidal gold to treat experimentally-induced arthritis in rat models; (ii) Characterization of the gold in Swarna bhasma, a microparticulate used in traditional Indian medicine. *Gold Bulletin*, 2007, 40 (3), 245-250.

Cheriathundam, E., & Alvares, A. (1996). Species differences in the renal toxicity of the antiarthritic drug, gold sodium thiomalate. *J Biochem Tox*, 11(4), 175-81.

Dabrowiak, J. (2009). Gold Complexes for Treating Arthritis Cancer and Other Diseases. In J. Dabrowiak, *Metals in Medicine* (pp. 191-217). Chichester UK: John Wiley and Sons.

Daniel, M. C. & Astruc, D. (2004). Gold Nanoparticles: Assembly, Supramolecular Chemistry, Quantum-Size-Related Properties, and Applications toward Biology, Catalysis, and Nanotechnology. *Chem. Rev.*, 104, 293-346.

Eisler, Ronald. *Biochemical, Health, and Ecotoxicological Perspectives on Gold and Gold Mining*. Boca Raton: CRC Press, 2004.

Faraday, M. (1857). The Bakerian lecture: Experimental relations of gold (and other metals) to light. *Philosoph. Trans. R. Soc. London*, 147, 145-181.

Henglein, A. & Meisel, D. (1998). Radiolytic Control of the Size of Colloidal Gold Nanoparticles. *Langmuir*, 14, 7392-7396.

Ho, S., & Tiekink, E. (2005). Gold beased metalotherapeutics; Use and Potential. In M. Gielen, & E. Tiekink, *Metallotherapeutic Drugs and Metal-Based Diagnostic Agents* (pp. 507-527). Chictester: JH Wiley and Sons.

Johnston, H. J., Hutchinson, G., Christensen, F. M., Peters, S., Hankin, S. & Stone, V. (2010). A review of the in vivo and in vitro toxicity of silver and gold particulates: Particle attributes and biological mechanisms responsible for the observed toxicity. *Critical Reviews in Toxicology*, 40 (4), 328-346.

Kean, W., & Anastassiades, T. (1979). Long term chrysotherapy; incidence of toxicity and efficacy during sequential time periods. *Arthritis Rheum*, 22(5), 495-501.

Kean, W., & Kean, I. (2008). The clinical Pharmacology of Gold. *Immunopharmacology*, 16(3), 112-25.

Kimling, J., Maier, M., Okenve, B., Kotaidis, V., Ballot, H. & Plech, A. (2006). Turkevich Method for Gold Nanoparticle Synthesis Revisited. *J. Phys. Chem. B*, 110, 15700-15707.

Kraemer, E. O. & Svedberg, T. (1924). Formation of Colloid Solutions by Electrical Pulverization in the High-Frequency Alternating Current Arc. *Journal of the American Chemical Society*, 46 (9), 1980-1991.

Leonard, T. B., Graichen, M. E., Dahm, L. J., & Dent, J. G. (1986). Effects of the Chryosotherapeutic Agents Auranofin and Gold Sodium Thiomalate on Hepatic and Renal Drug Metabolism and Heme Metabolism. *Biochemical Pharmacology*, 35, (18), 3057-3063.

Mucalo, M. R. & Bullen, C. R. (2001). Electric arc generated (Bredig) palladium nanoparticles: Surface analysis by X-ray photoelectron spectroscopy for samples prepared at different pH. *Journal of Materials Science Letters*, 20, 1853-1856.

Panyala, N. G., Pena-Mendez, E. M., & Havel, J. (2009). Gold and nano-gold in medicine: overview, toxicology and perspectives. *Journal of Applied Biomedicine*, 7, 75-91.

Payne, B., & Arena, E. (1978). The subacute and chronic toxicity of SK&F 36914 and SK&F D-39162 in dogs. *Vet Path, Suppl* 5, 9-12.

Payne, B., & Arena, E. (1978). The subacute and chronic toxicity of SK&F 36914, SK&F D-39162 and gold sodium thiomalate in rats. *Vet Path Suppl*, 15(5), 13-22.

Sadler, P. J. (1976). The biological chemistry of gold: a metallo-drug and heavy-atom label with variable valency, *Structure Bonding*, 29, 171-215.

Shaw, C. F., III. (1999a). Gold complexes with anti-arthritic, anti-tumour and anti-HIV activity, in *Uses of Inorganic Chemistry in Medicine*, N. C. Farrell, (Ed.), Royal Society of Chemistry, Cambridge, UK, 26-57.

Shaw, C. F., III. (1999b). The biochemistry of gold, in *Gold: Progress in Chemistry, Biochemistry and Technology*, H. Schmidbaur, (Ed.), John Wiley & Sons, New York, 260-308.

Sakai, T., Enomoto, H., Torigoe, K., Kakai, H. & Abe, M. (2008). Surfactant- and reducer-free synthesis of gold nanoparticles in aqueous solutions. *Colloids and Surface A: Physiocochemical and Engineering Aspects*, 18-26.

Sperling, R. A., Gil, P. R., Zhang, F., Zanella, M., & Parak, W. J. (2008). Biological applications of gold nanoparticles. *Chem. Soc. Rev*, 37, 1896-1908.

Sweeney, S. F., Woehrle, G. H. & Hutchison, J. E. (2006). Rapid Purification and Size Separation of Gold Nanoparticles via Diafiltration. *J. Am. Chem. Soc.*, 128, 3190-3197.

Szabo, K., DiFebbo, M., & Phelan, D. (1978). The effects of gold-containing compounds on pregnant rabbits and their fetuses. *Vet Path, Suppl* 5, 95-105.

Szabo, K., Guerriero, F., & Kang, Y. (1978). The effects of gold containing compounds on pregnant rats and their fetuses. *Vet Path*, 5, 89-86.

Tao, A. R., Habas, S. & Yang Peidong. (2008). Shape Control of Colloid Metal Nanocrystals. *Small*, 4 (3), 310-325.

Teixido, M. & Giralt, E. (2008). The role of peptides in blood-brain barrier nanotechnology. *J. Pept. Sci.*, 14, 163-173.

Tsai, C., Shiau, A., Chen, S., Chen, Y., Cheng, P., Chang, M., et al. (2007). Amelioration of collagen-induced arthritis in rats by nanogold. *Arthritis Rheum*, 56(2), 544-54.

Ueda, S. (1998). Nephrotoxicity of gold salts, D-penicillamine, and allopurinol, in *Clinical Nephrotoxins: Renal*

*Injury from Drugs and Chemicals*, M. E. De Broe, G. A. Porter, W. M. Bennett, and G. A. Verpooten, (eds.), Kluwer Dordrecht, 223-238.

USFDA (2005). Guidance for Industry Estimating the Maximum Safe Starting Dose in Initial Clinical Trials for Therapeutics in Adult Healthy Volunteers. *Pharmacology and Toxicology*.

Walz, D., DiMartino, M., Intocca, A., & Flanagan, T. (1983). Biologic actions and pharmacokinetic studies of Auranofin®. *Am J Med*, 759(6A).

Wang, C. H., et al. (2007). Aqueous gold nanosols stabilized by electrostatic protection generated by X-ray irradiation assisted radical reduction. *Materials Chemistry and Physics*, 106, 323-329.

Weiser, H. B. *Inorganic Colloid Chemistry-Volume I: The Colloidal Elements*. New York: John Wiley & Sons, Inc., 1933.

Whyman, R. (1996). Gold Nanoparticles A Renaissance in Gold Chemistry. *Gold Bulletin*, 29(1), 11-15.

Yuan, H., Cai, R. X. & Pang, D. W. (2003). A Simple Approach to Control the Growth of Non-spherical Gold Nanoparticles. *Chinese Chemical Letters*, 14 (11), 1163-1166.

SUMMARY OF THE INVENTION

New gold nanocrystals are provided that have nanocrystalline surfaces that are substantially free (as defined herein) from organic or other impurities or films. Specifically, the surfaces are "clean" relative to those made using chemical reduction processes that require chemical reductants and/or surfactants to grow gold nanoparticles from gold ions in solution. The majority of the grown gold nanocrystals have unique and identifiable surface characteristics such as spatially extended low index, crystal planes {111}, {110} and/or {100} and groups of such planes (and their equivalents). Resulting gold nanocrystalline suspensions or colloids have desirable pH ranges such as 4.0-9.5, but more typically 5.0-9.5 and zeta potential values of at least –20 mV, and more typically at least –40 mV and even more typically at least –50 mV for the pH ranges of interest.

The shapes and shape distributions of these gold nanocrystals prepared according to the manufacturing process described below include, but are not limited to, triangles (e.g., tetrahedrons), pentagons (e.g., pentagonal bipyramids or decahedrons), hexagons (e.g., hexagonal bipyramids, icosahedrons, octahedrons), diamond (e.g., octahedrons, various elongated bipyramids, fused tetrahedrons, side views of bipyramids) and "others". The shape distribution(s) of nanocrystals (i.e., grown by various embodiments set forth herein) containing the aforementioned spatially extended low index crystal planes (which form the aforementioned shapes) and having "clean" surfaces is unique. Furthermore, the percent of tetrahedrons and/or pentagonal bipyramids formed in the nanocrystalline suspensions is/are also unique.

Any desired average size of gold nanocrystals below 100 nm can be provided. The most desirable crystalline size ranges include those having an average crystal size or "mode" (as measured and determined by specific techniques disclosed in detail herein and reported as "TEM average diameter") that is predominantly less than 100 nm, and more typically less than 50 nm, even more typically less than 30 nm, and in many of the preferred embodiments disclosed herein, the mode for the nanocrystal size distribution is less than 21 nm and within an even more preferable range of 8-18 nm.

Any concentration of gold nanoparticle can be provided according to the invention. For example, concentrations of these gold nanocrystals can be a few parts per million (i.e., µg/ml or mg/l) up to a few hundred ppm, but are typically in the range of 2-200 ppm (i.e., 2 µg/ml-200 µg/ml) and more often in the range of 2-50 ppm (i.e., 2 µg/ml-50 µg/ml) and even more typically 5-20 ppm (i.e., 5 µg/ml-20 µg/ml).

A novel process is provided to produce these unique gold nanocrystals. The process involves the creation of the gold nanocrystals in water. In a preferred embodiment, the water contains an added "process enhancer" which does not significantly bind to the formed nanocrystals, but rather facilitates nucleation/crystal growth during the electrochemical-stimulated growth process. The process enhancer serves important roles in the process including providing charged ions in the electrochemical solution to permit the crystals to be grown. These novel electrochemical processes can occur in either a batch, semi-continuous or continuous process. These processes result in controlled gold nanocrystalline concentrations, controlled nanocrystal sizes and controlled nanocrystal size ranges; as well as controlled nanocrystal shapes and controlled nanocrystal shape distributions. Novel manufacturing assemblies are provided to produce these gold nanocrystals.

Pharmaceutical compositions which include an effective amount of these gold nanocrystals to treat medical conditions are also provided. The pharmaceutical composition can provide any desired systemic dosage, as a non-limiting example, 0.1 mg/kg/day or less, or 0.05 mg/kg/day or less, or even more typically 0.025 mg/kg/day or less, or most typically 0.001 mg/kg/day or less.

Since these gold nanocrystals have substantially cleaner surfaces than the prior available gold nanoparticles, and can desirably contain spatially extended low index crystallographic planes forming novel crystal shapes and/or crystal shape distributions, the nanocrystals appear to be more biologically active (and may be less toxic) than spherical-shaped nanoparticles, as well as nanoparticles (or nanocrystals) containing surface contaminants such as chemical reductants and/or surfactants that result from traditional chemical reduction processes. Therefore, medical treatments may be effected at lower dosages of gold.

Pharmaceutical compositions are provided that are appropriate for systemic or topical use, including oral, intravenous, subcutaneous, intraarterial, buccal, inhalation, aerosol, propellant or other appropriate liquid, etc, as provided further in the Detailed Description of the Invention.

These substantially surface-clean or surface-pure gold crystals can be used to treat any disorder for which gold therapy is known, which includes a broad range of inflammatory and autoimmune disorders as well as certain infectious diseases (e.g., HIV, aids malaria, and Chagas disease) and cancer. Descriptions of many of these uses are provided in the Background of the Invention, above.

It has now been surprisingly discovered as part of this invention that the gold nanocrystals inhibit macrophage migration inhibitory factor ("MIF"). It is believed that this is the first disclosure of such activity of gold nanocrystals (or nanoparticles), and may provide a scientific basis to understand the range of medical uses for gold nanocrystals to date. It also provides a scientific basis to conclude that the gold nanocrystals will be effective against other diseases which are mediated by macrophage migration inhibitory factor. In addition, it has been identified that these gold nanocrystals inhibit IL-6 but not IL-10. For example, because MIF and/or IL-6 is/are indicated in a large variety of conditions and/or biological signaling pathways, such finding confirms that the novel gold nanocrystals will be effective for the treatment or prevention of diseases or conditions resulting from pathological cellular activation, such as inflammatory (including chronic inflammatory) conditions, autoimmune conditions, hypersensitivity reactions and/or cancerous diseases or conditions.

Further, by following the inventive electrochemical manufacturing processes of the invention, these gold-based metallic nanocrystals can be alloyed or combined with other metals in liquids such that gold "coatings" may occur on other metals (or other non-metal species such as $SiO_2$, for example) or alternatively, gold-based nanocrystals may be coated by other metals. In such cases, gold-based composites or alloys may result within a colloid or suspension. Further, certain composites which include both gold and other metals can also be formed.

Still further, gold-based metallic nanocrystals suspensions or colloids of the present invention can be mixed or combined with other metallic-based solutions or colloids to form novel solution or colloid mixtures (e.g., in this instance, distinct metal species can still be discerned).

BRIEF DESCRIPTION OF THE FIGURES

FIGS. 3a-3d show four alternative electrode control configurations for the electrodes 1 and 5 controlled by an automatic device 20.

FIGS. 4a-4d show four alternative electrode configurations for the electrodes 1 and 5 which are manually controlled.

FIGS. 8a-8d show schematic perspective views of four different electrode assemblies arranged with planes parallel to flow direction F.

FIGS. 11a-11h show perspective views of various trough members 30, with FIGS. 11c and 11d showing an atmosphere control device 35' and FIG. 11d showing a support device 34.

FIGS. 15a and 15b show schematic cross-sectional views of various angles $\theta_1$ and $\theta_2$ for the trough members 30.

FIGS. 16a, 16b and 16c show perspective views of various control devices 20 containing electrode assemblies 1 and/or 5 thereon located on top of a trough member 30.

FIGS. 16d, 16e and 16f show AC transformer electrical wiring diagrams for use with different embodiments of the invention.

FIGS. 16j, 16k and 16l each show schematic views of eight electrical wiring diagrams for use with 8 sets of electrodes.

FIGS. 17g, 17h, 17i and 7k show wiring diagrams used to control the devices 20 used in Examples 1-4 and 16.

FIGS. 17j and 17l show wiring diagrams used to power devices 20.

FIG. 25g shows the Au electrode plasma irradiance from 200-300 nm generated by the apparatus shown in FIG. 25f.

FIG. 25h shows the Au1 electrode plasma irradiance from 200-300 nm generated by the apparatus shown in FIG. 25f.

FIG. 25i shows the Au electrode plasma irradiance from 300-400 nm generated by the apparatus shown in FIG. 25f.

FIG. 25j shows the Au electrode plasma irradiance from 400-500 nm generated by the apparatus shown in FIG. 25f.

FIG. 48*a*1 is a representative TEM photomicrograph of gold nanocrystals from dried suspension GB-134 made according to Example 16.

FIG. 48*a*2 is a representative TEM photomicrograph of gold nanocrystals from dried suspension GB-134 made according to Example 16.

FIGS. 49*a*1, *a*2-FIGS. 61*a*1, *a*2 show two representative TEM photomicrographs for dried samples GB-098, GB-113, GB-118, GB-120, GB-123, GB-139, GB-141, GB-144, GB-079, GB-089, GB-062, GB-076 and GB-077, respectively, made according to Example 16.

FIGS. 49*b*-61*b* show the particle size distribution histogram from TEM measurements for the nanocrystals corresponding to dried samples GB-098, GB-113, GB-118, GB-120, GB-123, GB-139, GB-141, GB-144, GB-079, GB-089, GB-062, GB-076 and GB-077, respectively, made according to Example 16.

FIGS. 49*c*-61*c* show dynamic light scattering data (i.e., hydrodynamic radii) for gold nanocrystals corresponding to samples GB-098, GB-113, GB-118, GB-120, GB-123, GB-139, GB-141, GB-144, GB-079, GB-089, GB-062, GB-076 and GB-077, respectively, made according to Example 16; and FIG. 54*d* shows current as a function of time for GB-139 made in accordance with Example 16.

FIGS. 54*d*, 55*d* and 56*d* show measured current (in amps) as a function of process time for the samples GB-139, GB-141 and GB-144 made according to Example 16.

Figure 71A:
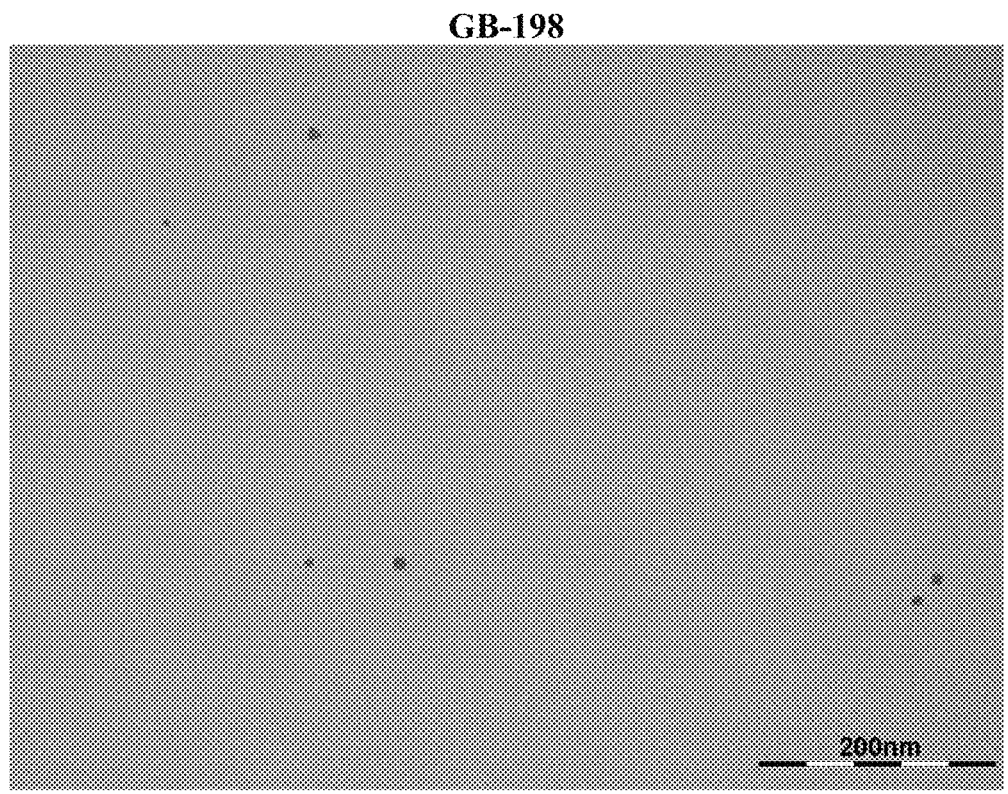

FIG. 71*a* is a representative TEM photomicrograph of gold nanocrystals from dried solution GB-198 made according to Example 18.

Figure 71B:
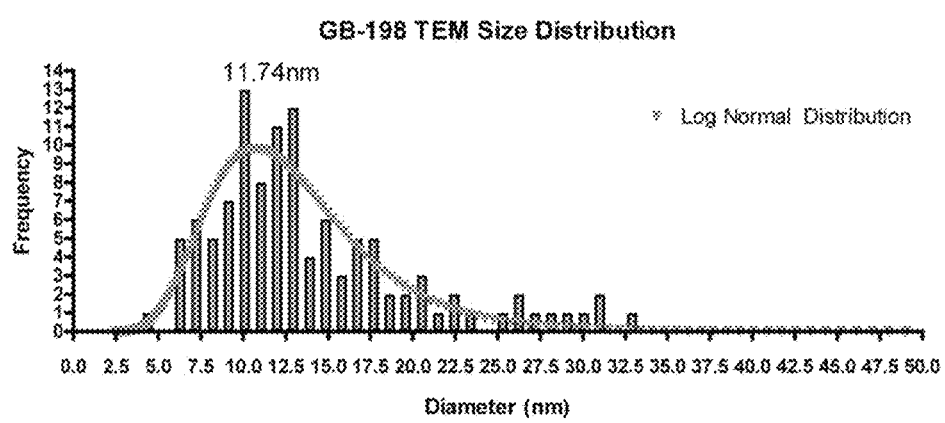

FIG. 71*b* shows a particle size distribution histogram from TEM measurements for the nanocrystals made according to GB-198.

Figure 72A:
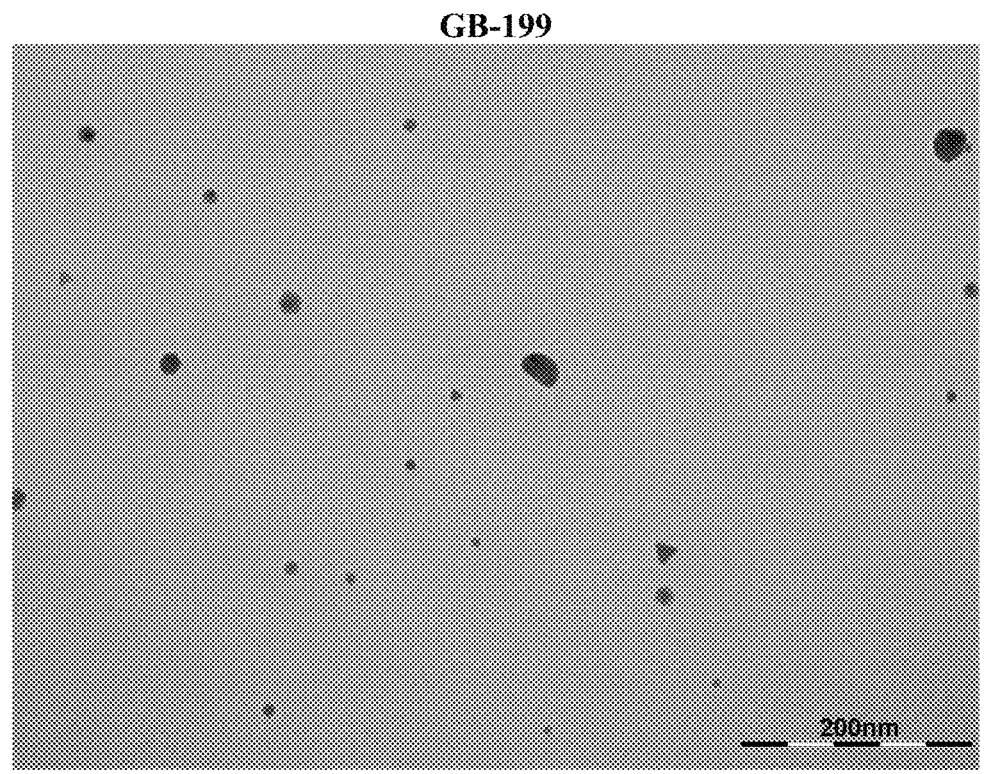

FIG. 72*a* is a representative TEM photomicrograph of gold nanocrystals from dried solution GB-199 made according to Example 18.

Figure 72B:
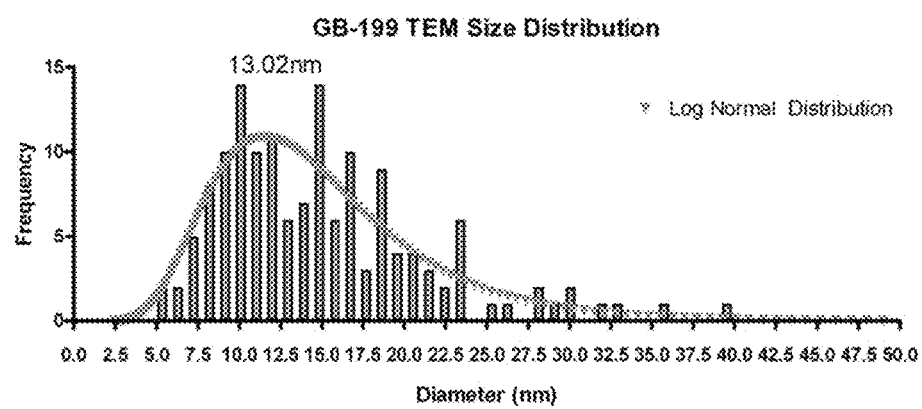

FIG. 72b shows a particle size distribution histogram from TEM measurements for the nanocrystals made according to GB-199.

Figure 72C:
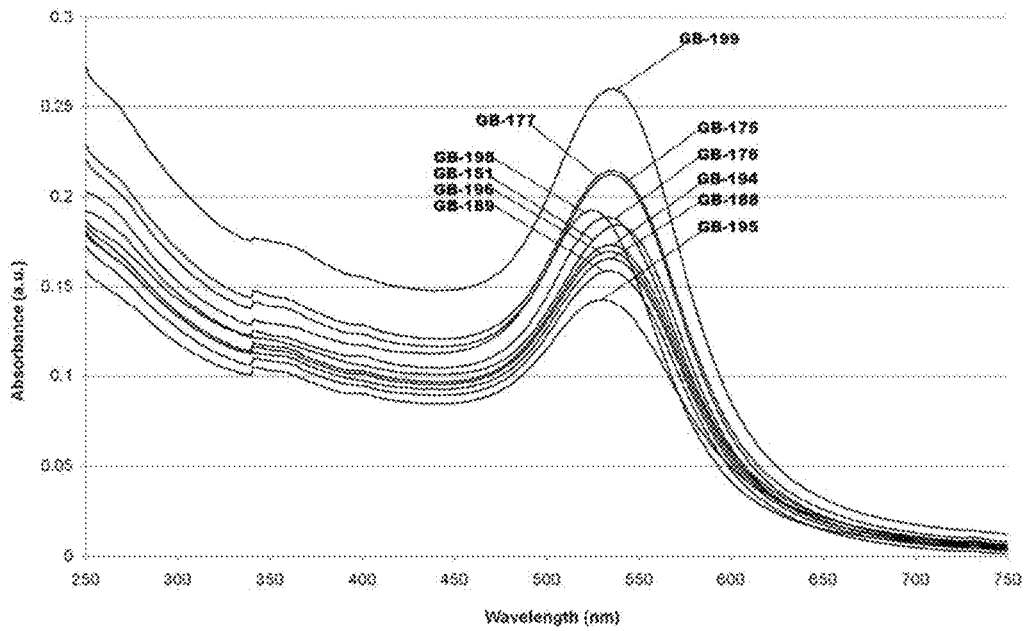

FIG. 72c shows the UV-Vis spectral patterns of each of the 11 suspensions/colloids made according to Example 18 (i.e., GB-151, GB-188, GB-175, GB-177, GB-176, GB-189, GB-194, GB-195, GB-196, GB-198 and GB-199) over an interrogating wavelength range of about 250 nm-750 nm.

Figure 72D:
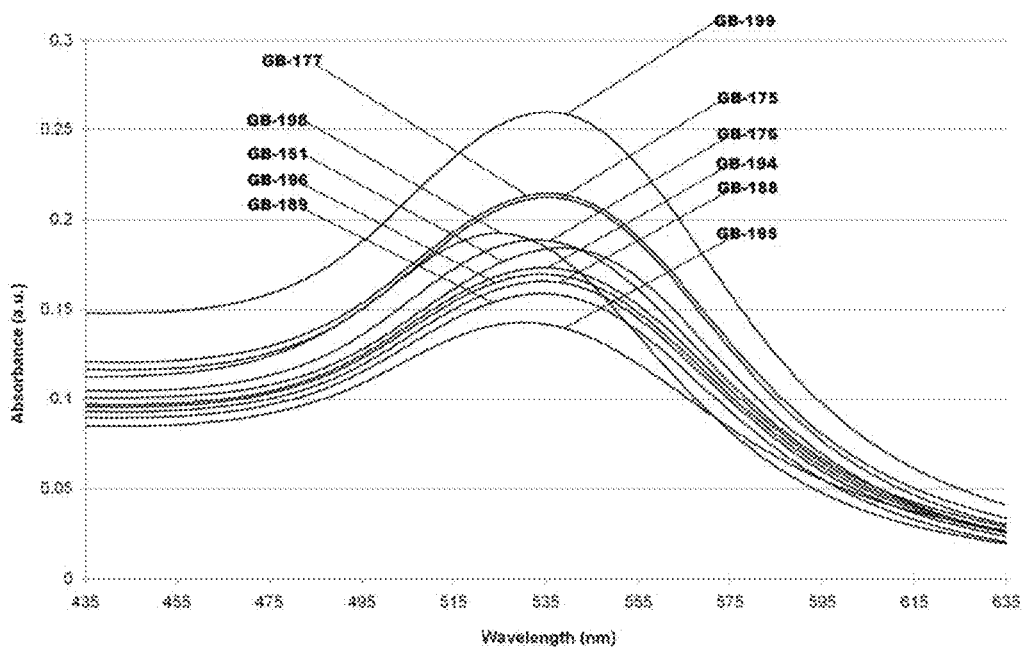

FIG. 72d shows the UV-Vis spectral patterns for each of the 11 suspensions over an interrogating wavelength range of about 435 nm-635 nm.

FIG. 73a1 and FIG. 73a2 show two representative TEM photomicrographs for sample Aurora-020.

Figure 73B:
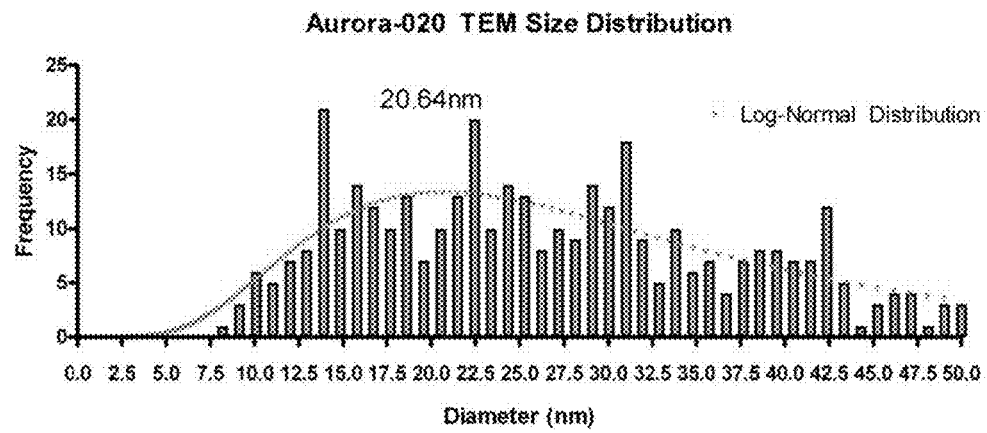

FIG. 73b shows the particle size distribution histogram from TEM measurements for the nanoparticles corresponding to dried sample Aurora-020.

Figure 73C:
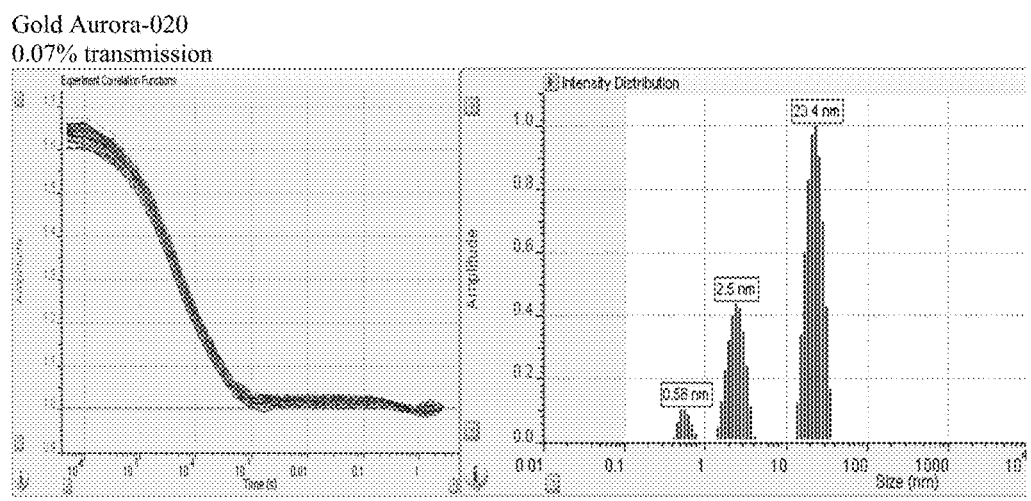

FIG. 73c shows dynamic light scattering data (i.e., hydrodynamic radii) for gold nanoparticles corresponding to sample Aurora-020.

Figure 74B:
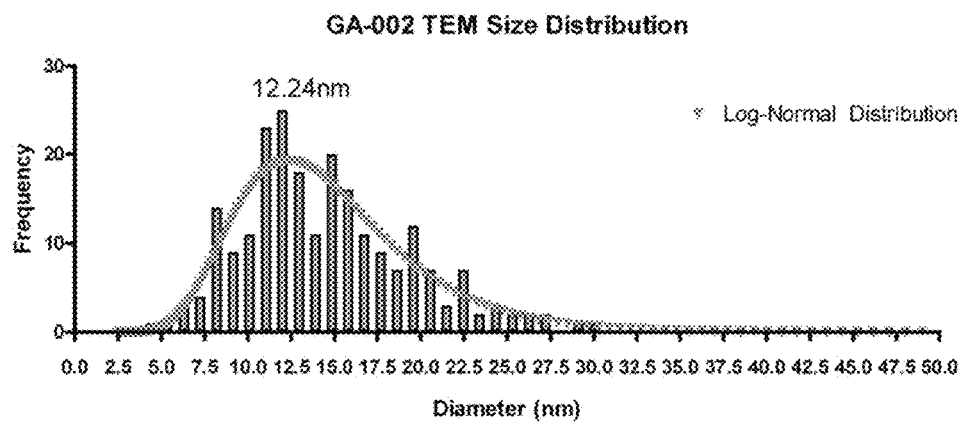
Figure 74C:
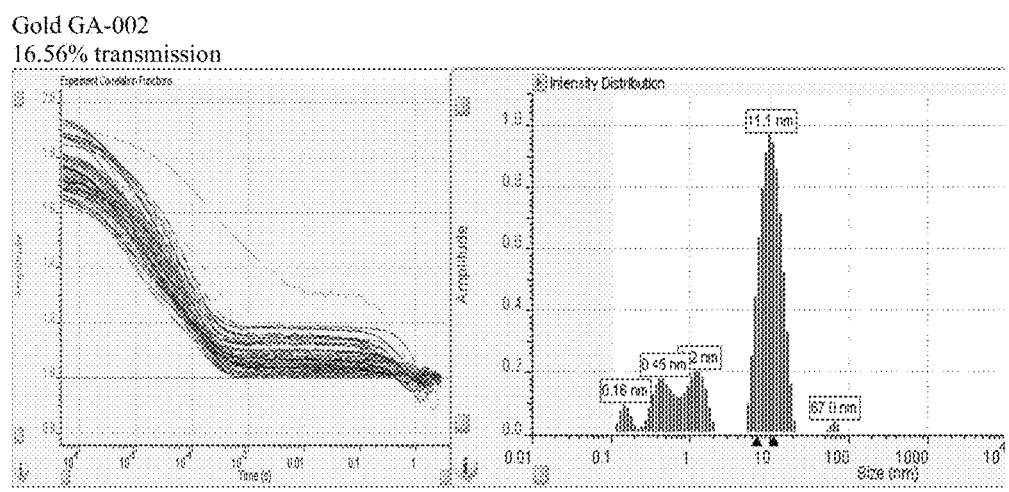
Figure 75B:
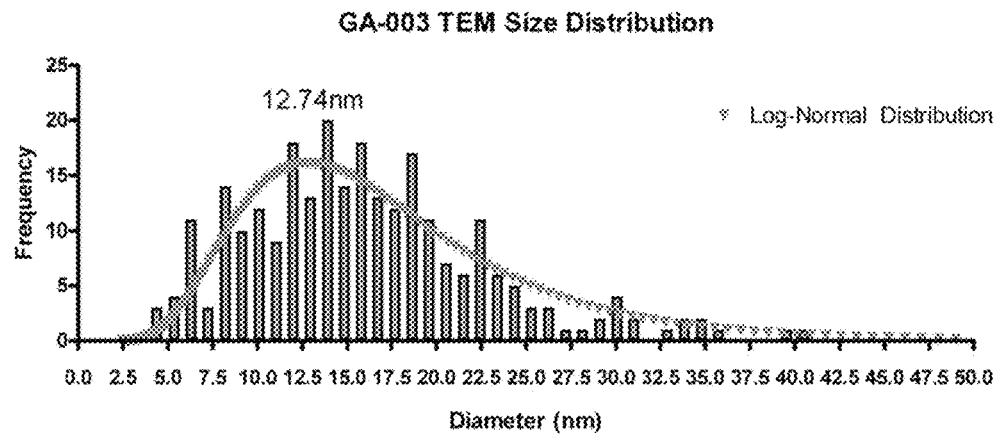
Figure 75C:
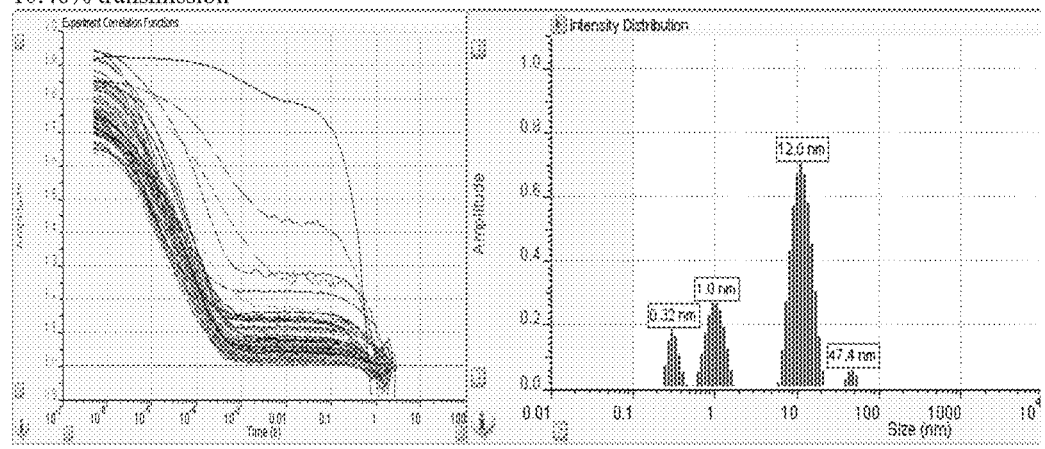
Figure 76B:
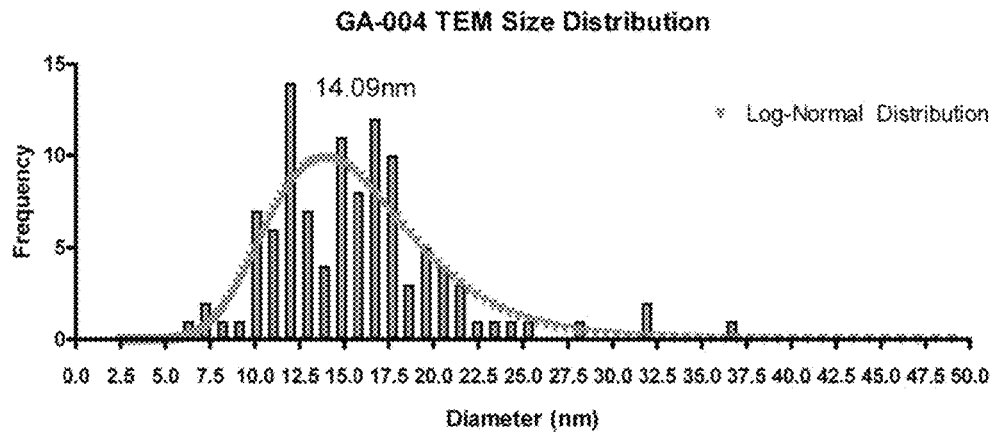
Figure 76C:
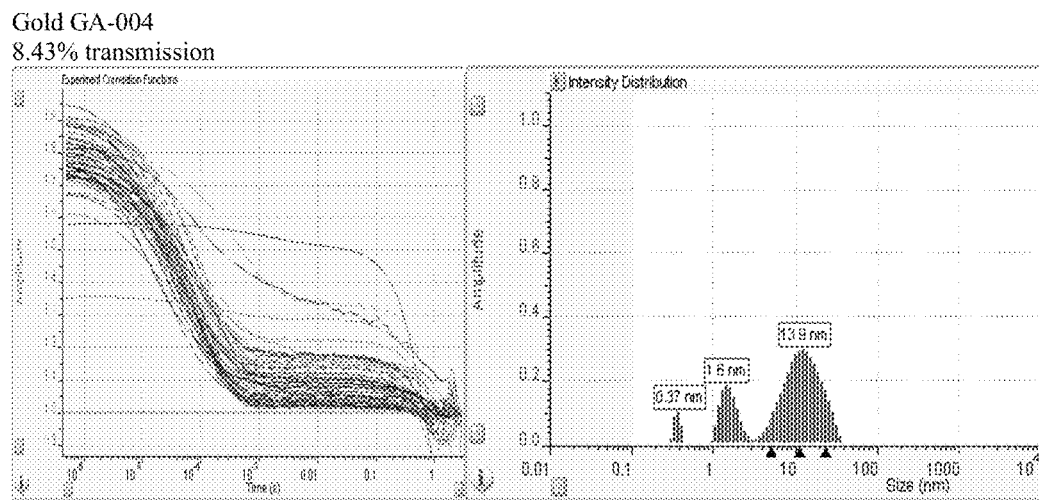
Figure 77B:
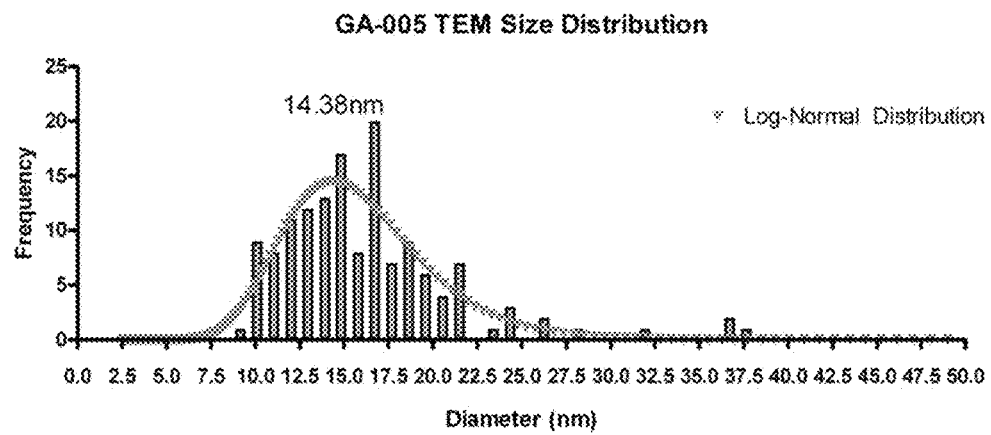
Figure 77C:
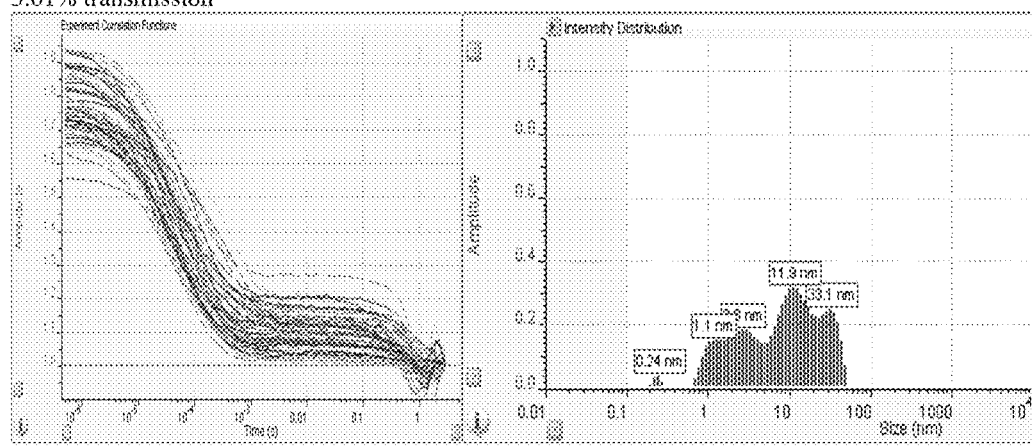
Figure 78B:
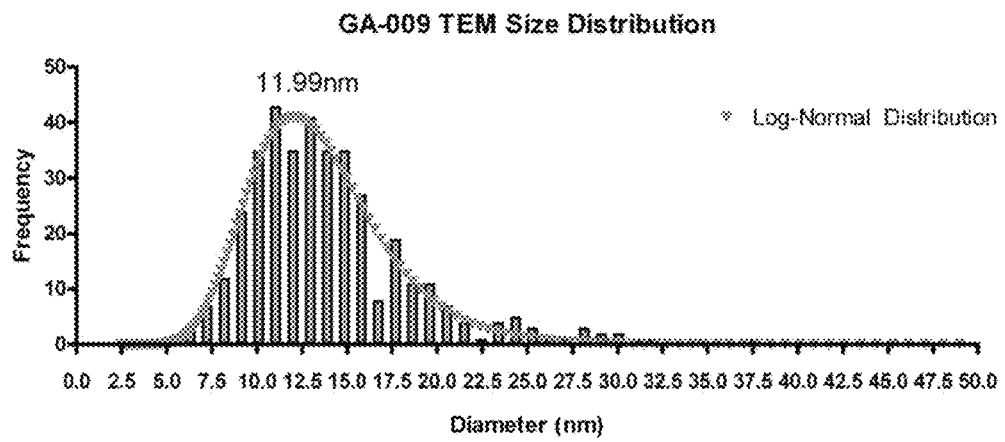
Figure 78C:
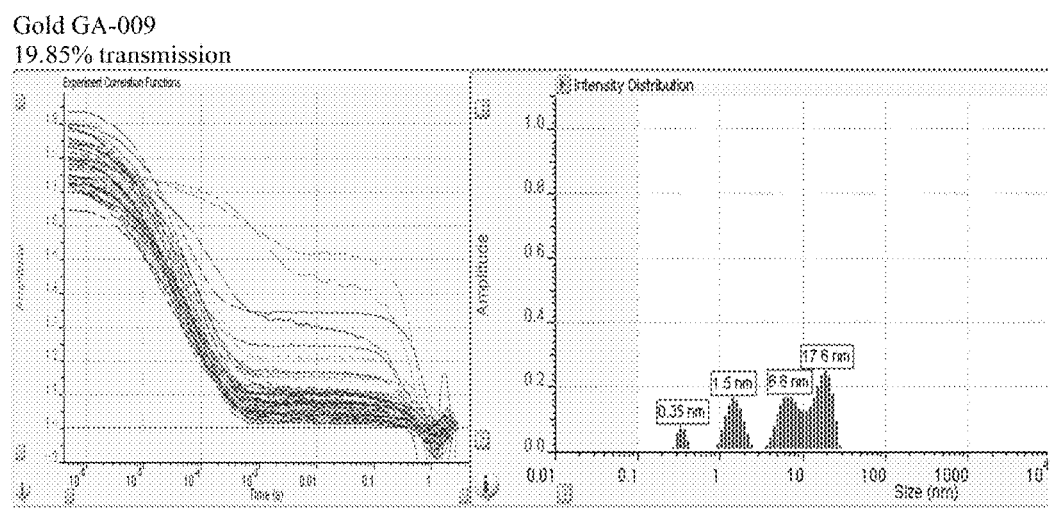
Figure 79B:
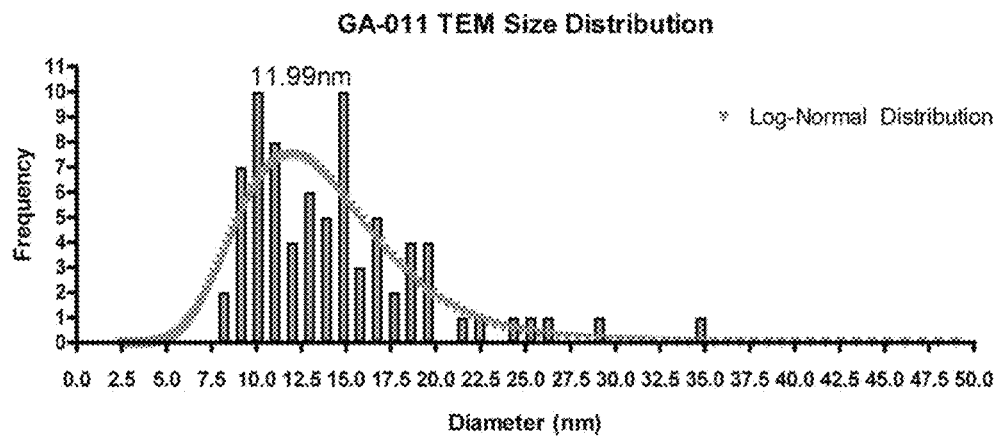
Figure 79C:
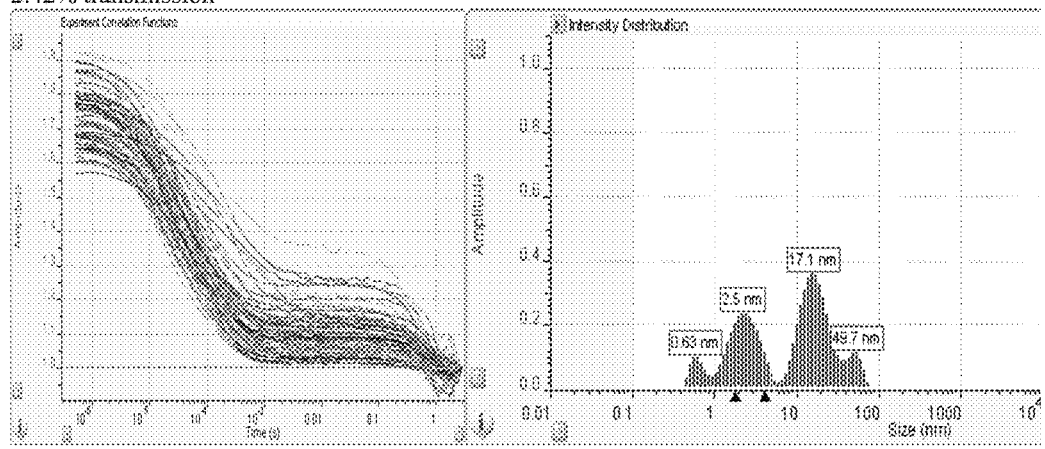
Figure 80B:
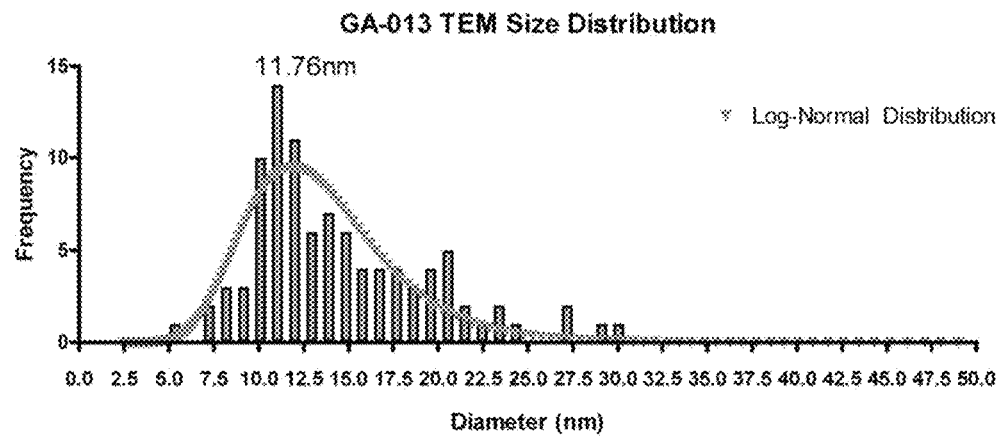
Figure 80C:
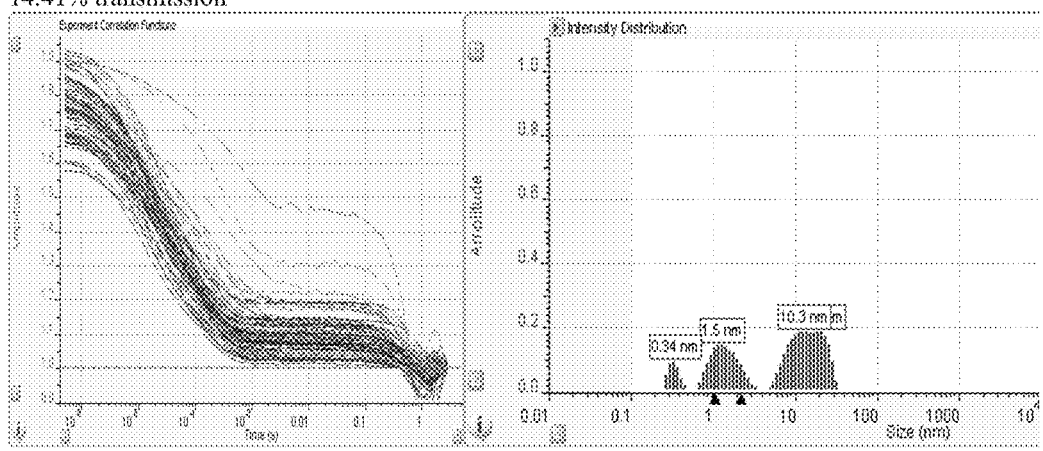

FIGS. 74a1, a2-FIGS. 80a1, a2 show two representative TEM photomicrographs for dried samples GA-002, GA-003, GA-004, GA-005, GA-009, GA-011 and GA-013, respectively.

FIGS. 74b-80b show the particle size distribution histogram from TEM measurements for the nanocrystals corresponding to dried samples GA-002, GA-003, GA-004, GA-005, GA-009, GA-011 and GA-013, respectively.

FIGS. 74c-80c show dynamic light scattering data (i.e., hydrodynamic radii) for gold nanocrystals corresponding to samples GA-002, GA-003, GA-004, GA-005, GA-009, GA-011 and GA-013, respectively.

Figure 81A:
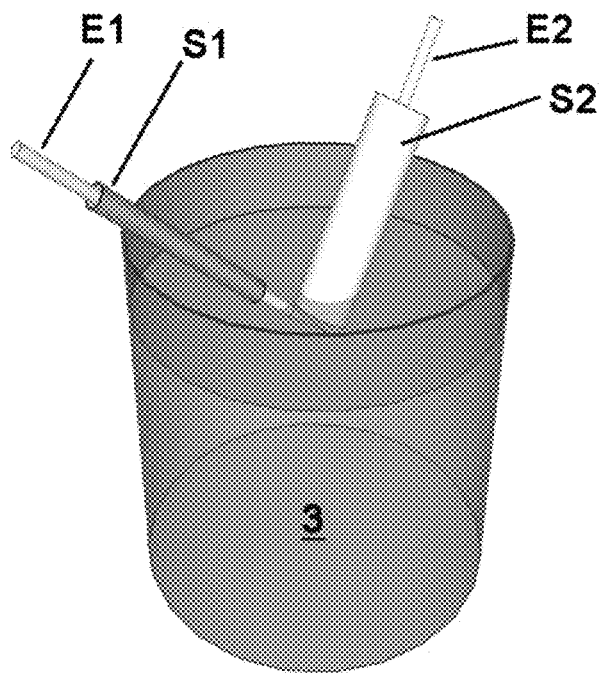

FIG. 81a is a perspective view of a comparative Bredig-arc apparatus utilized to make representative/comparative gold nanoparticles.

Figure 81B:
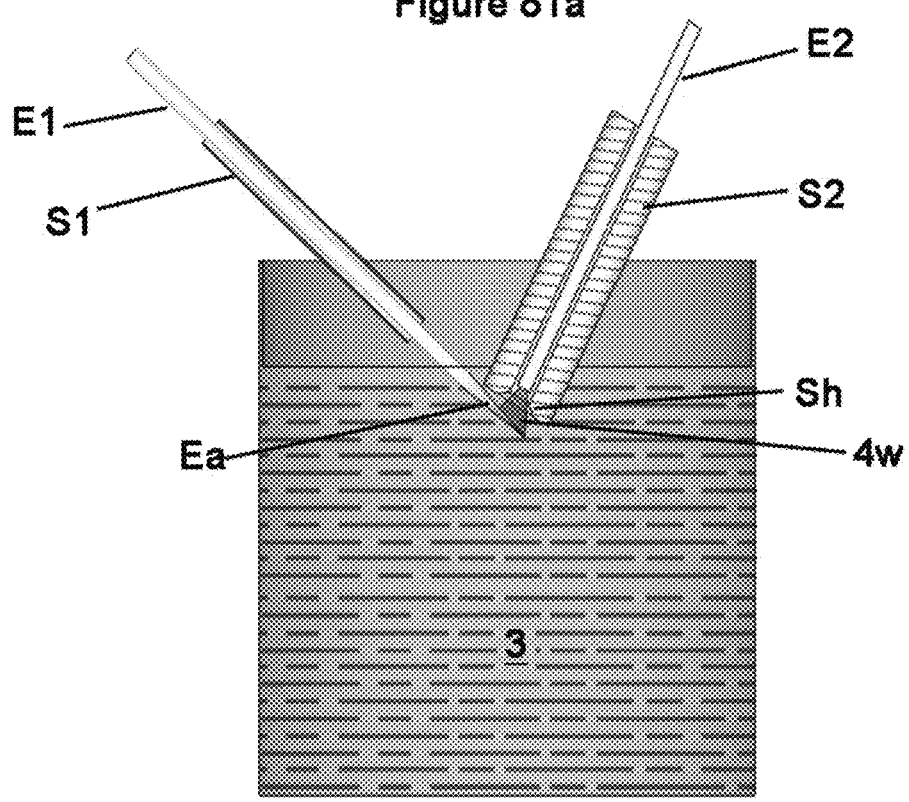

FIG. 81b is a cross-sectional view of a comparative Bredig-arc apparatus utilized to make representative/comparative gold nanoparticles.

Figure 82A:
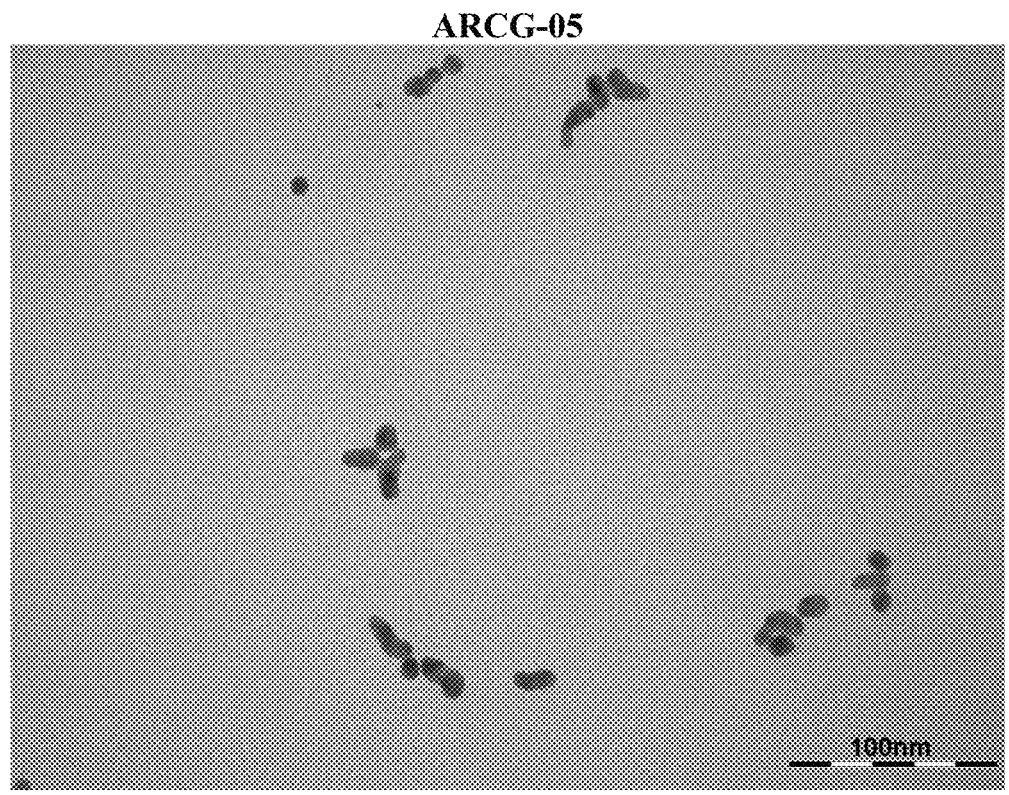

FIG. 82a is a representative TEM photomicrograph of gold nanoparticles from dried solution ARCG-05 made according to Example 21.

Figure 82B:
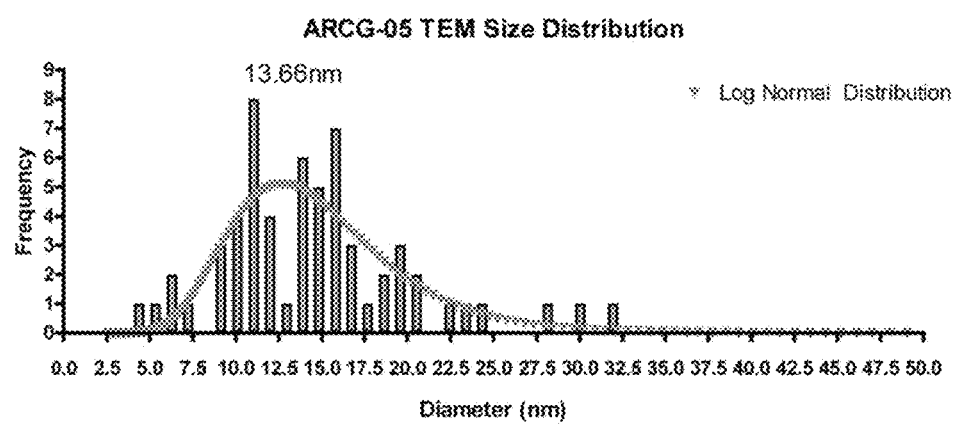
Figure 83A:
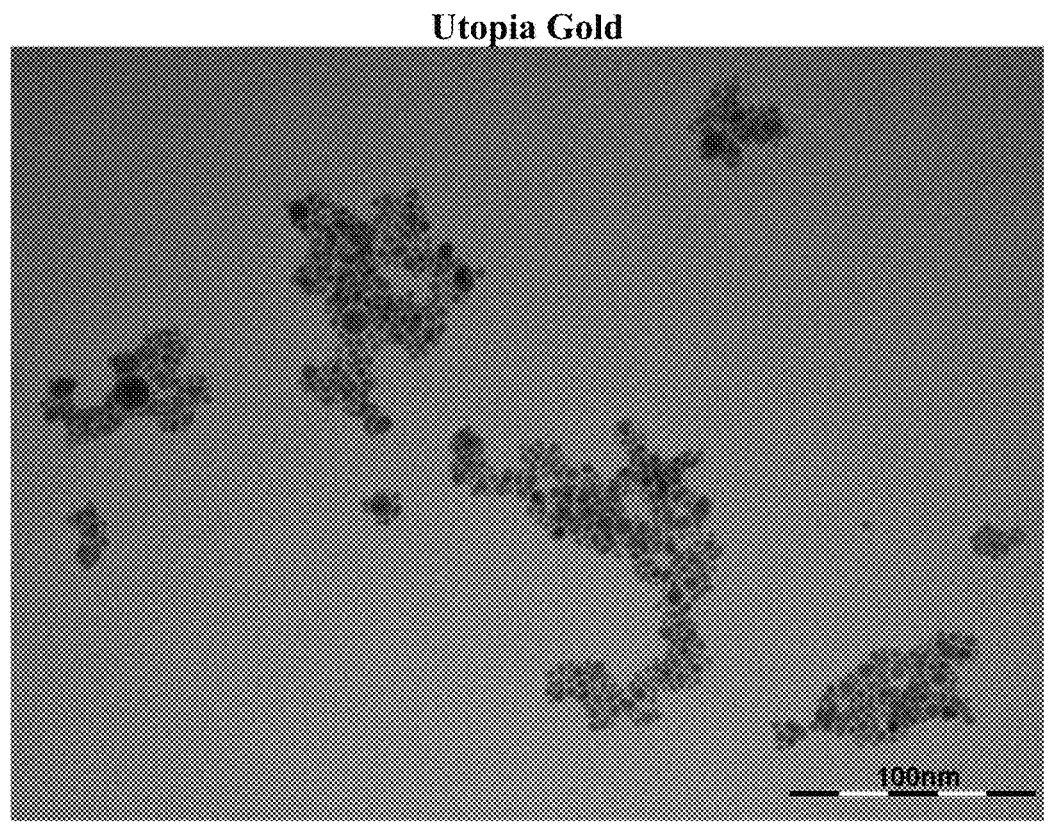
Figure 83B:
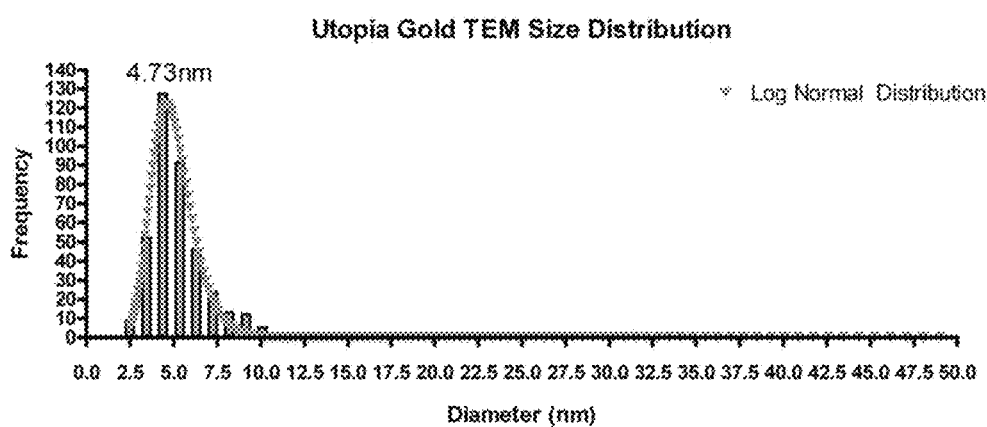
Figure 84A:
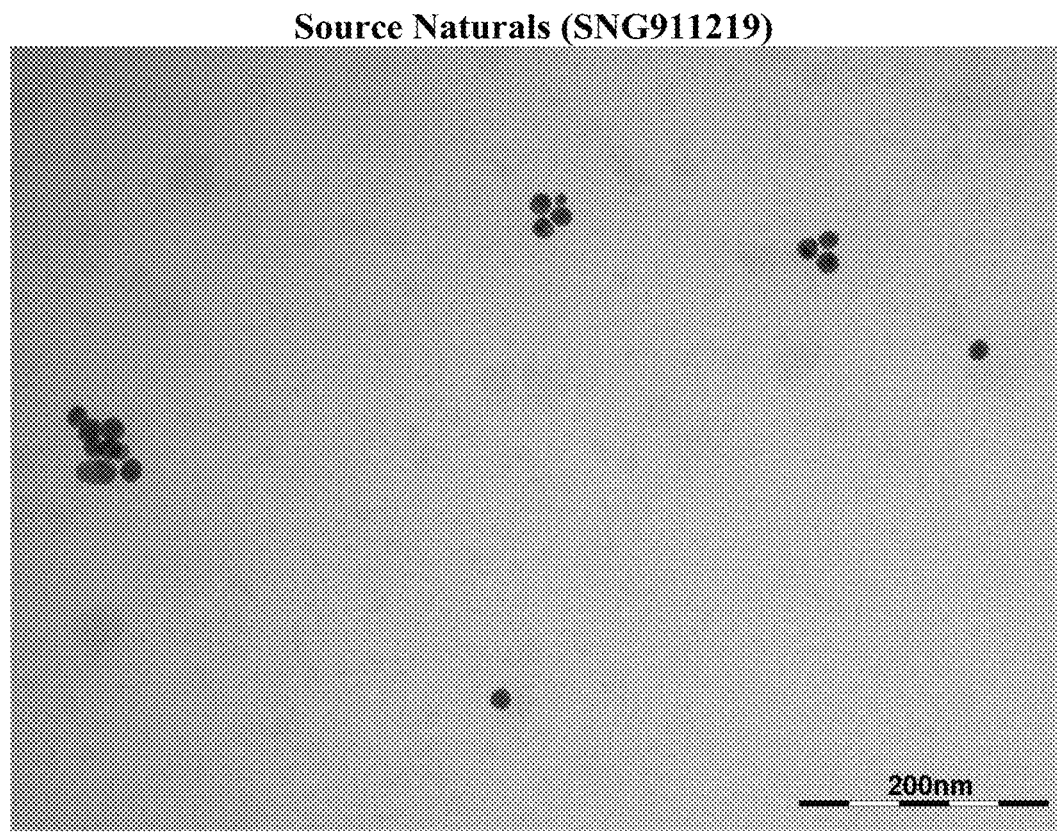
Figure 84B:
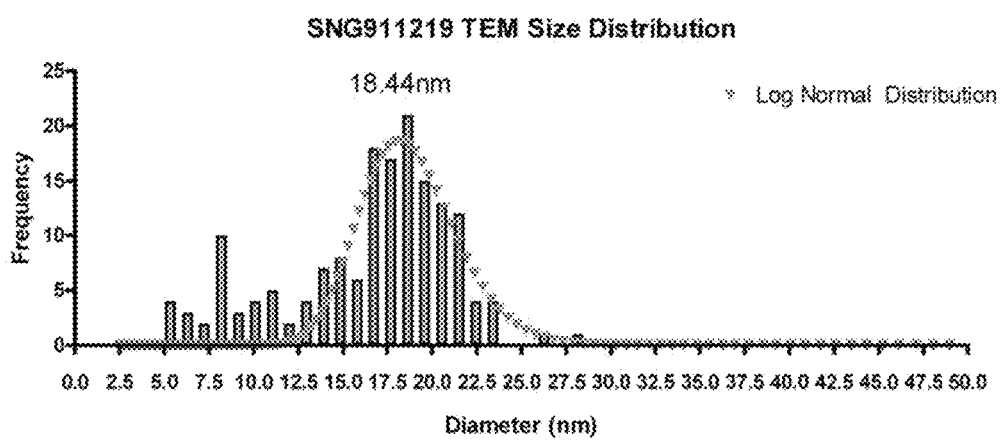
Figure 85A:
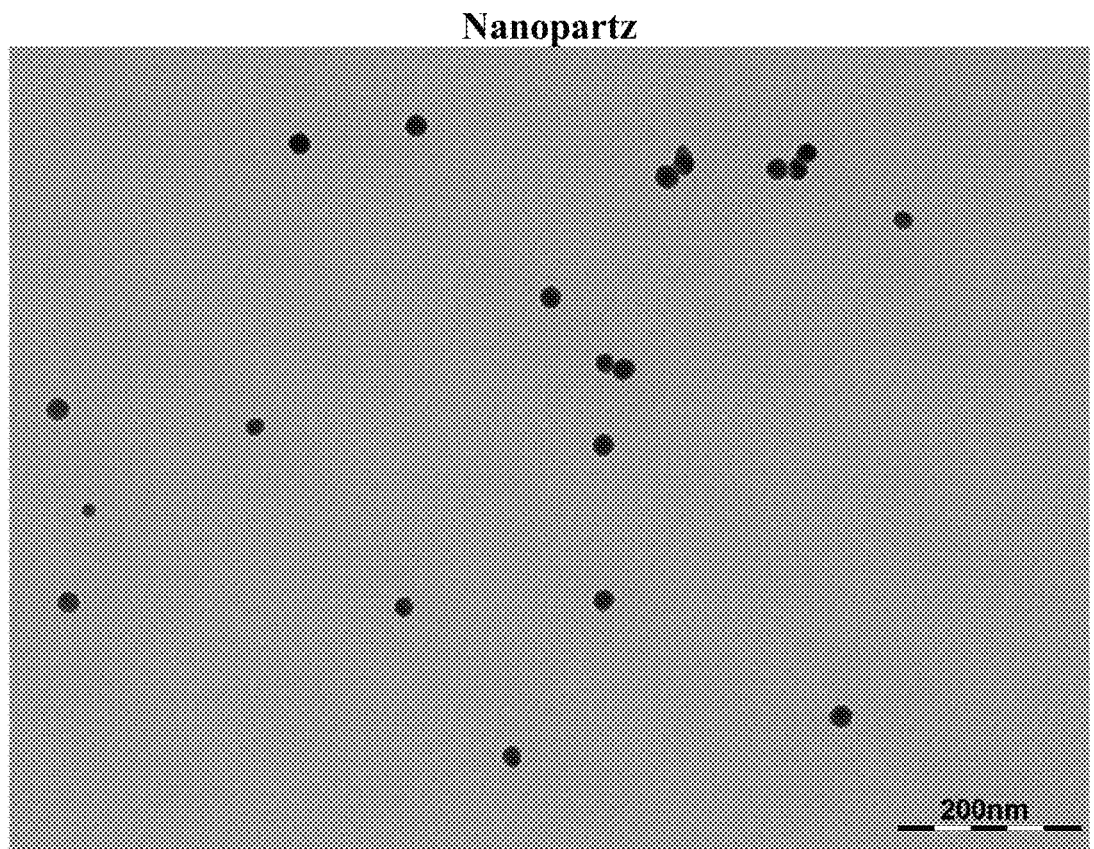
Figure 85B:
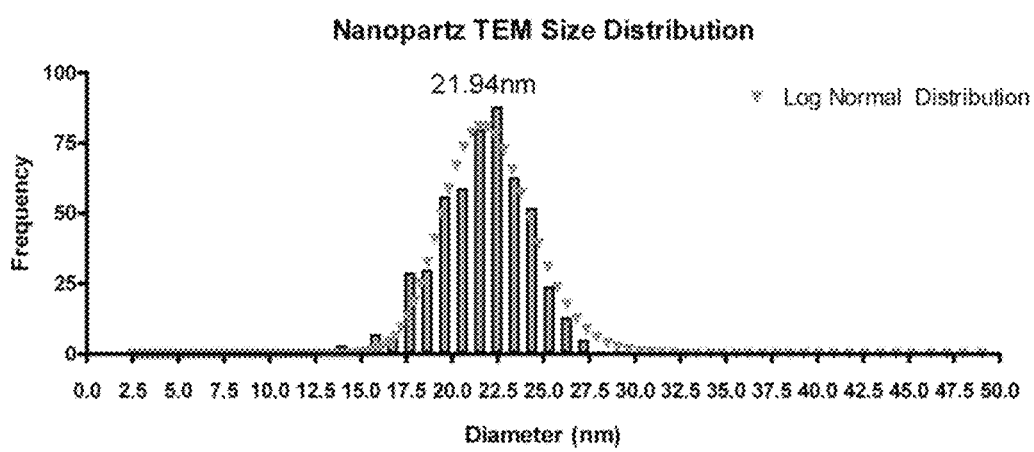
Figure 86A:
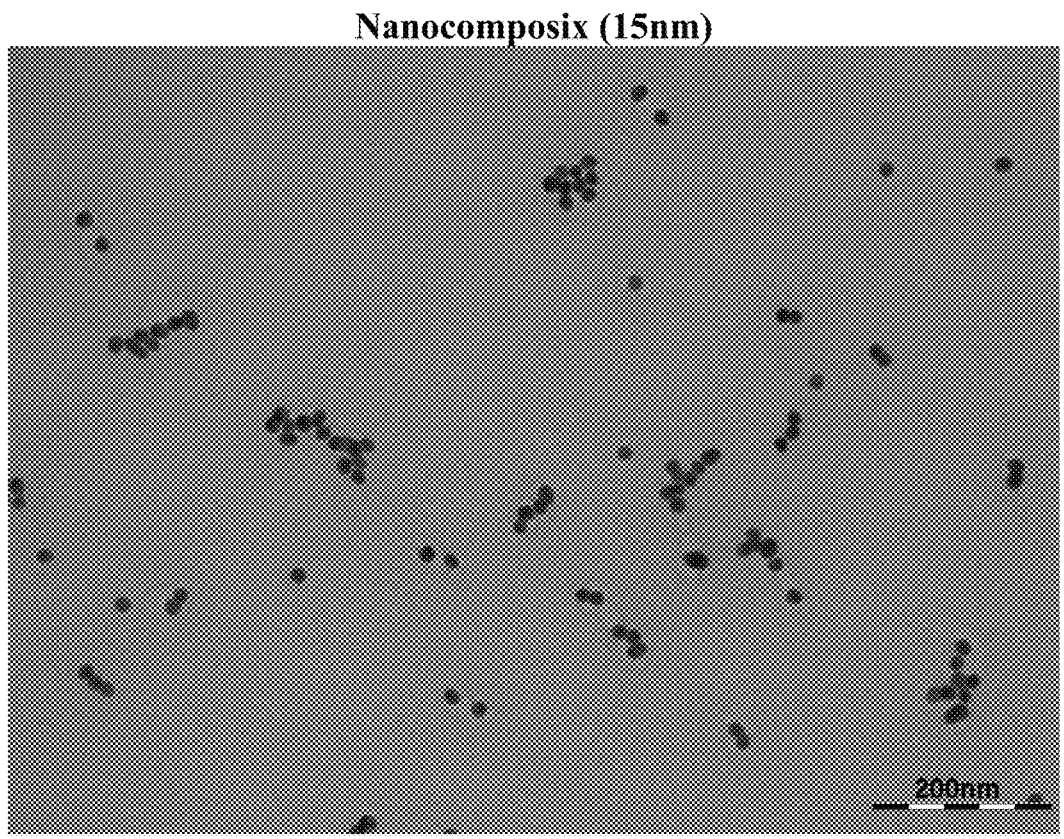
Figure 86B:
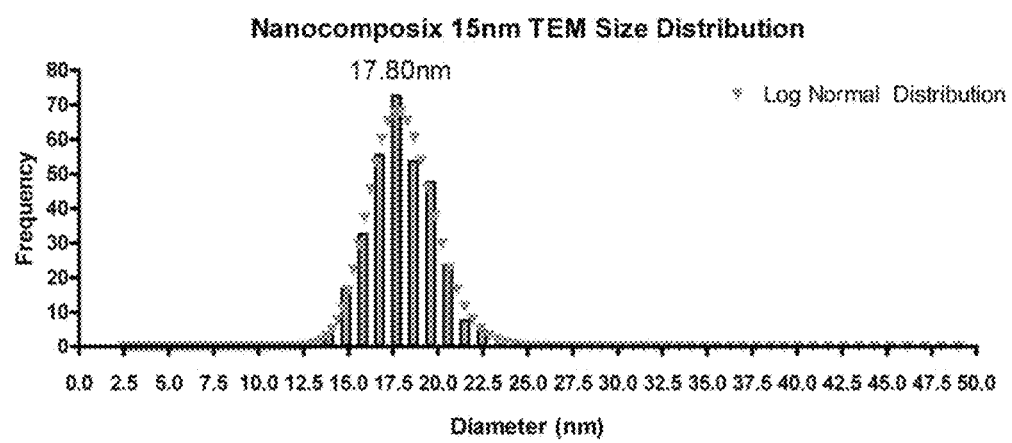
Figure 87A:
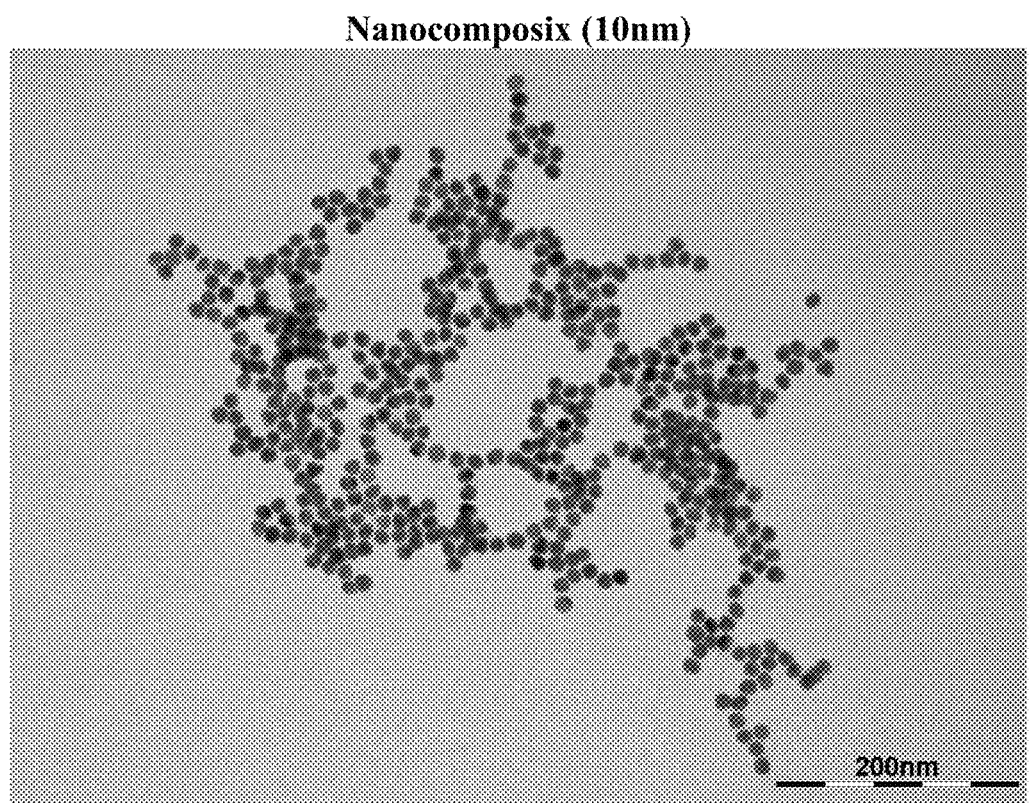
Figure 87B:
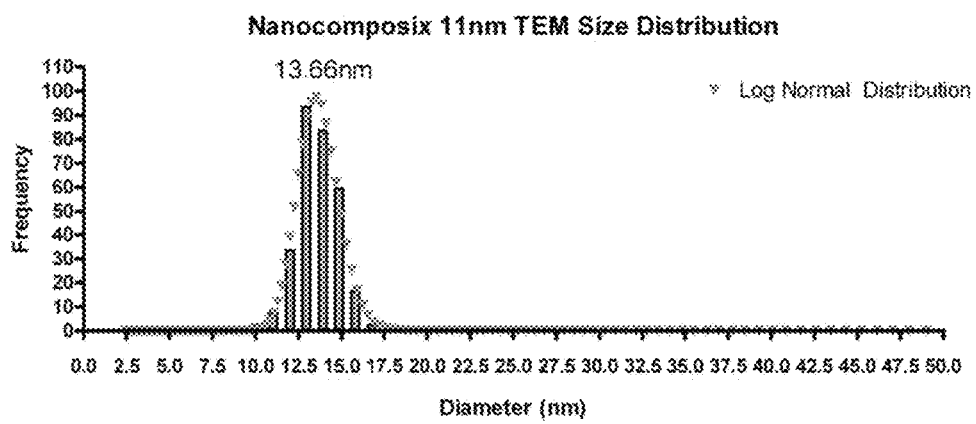
Figure 88A:
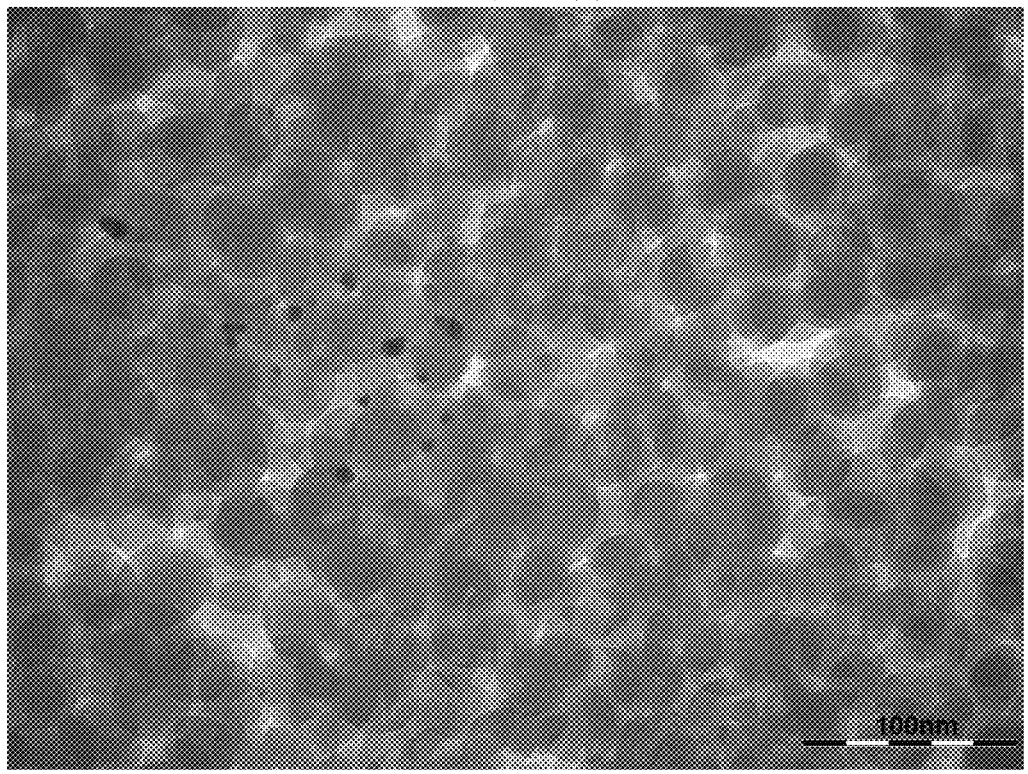
Figure 88B:
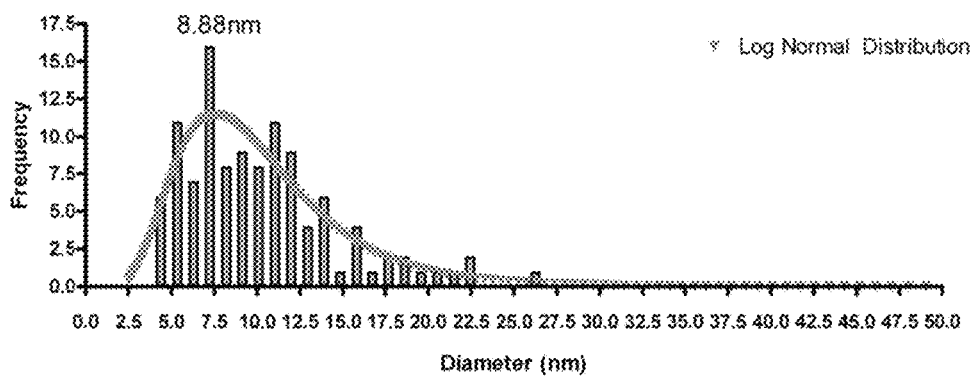
Figure 89A:
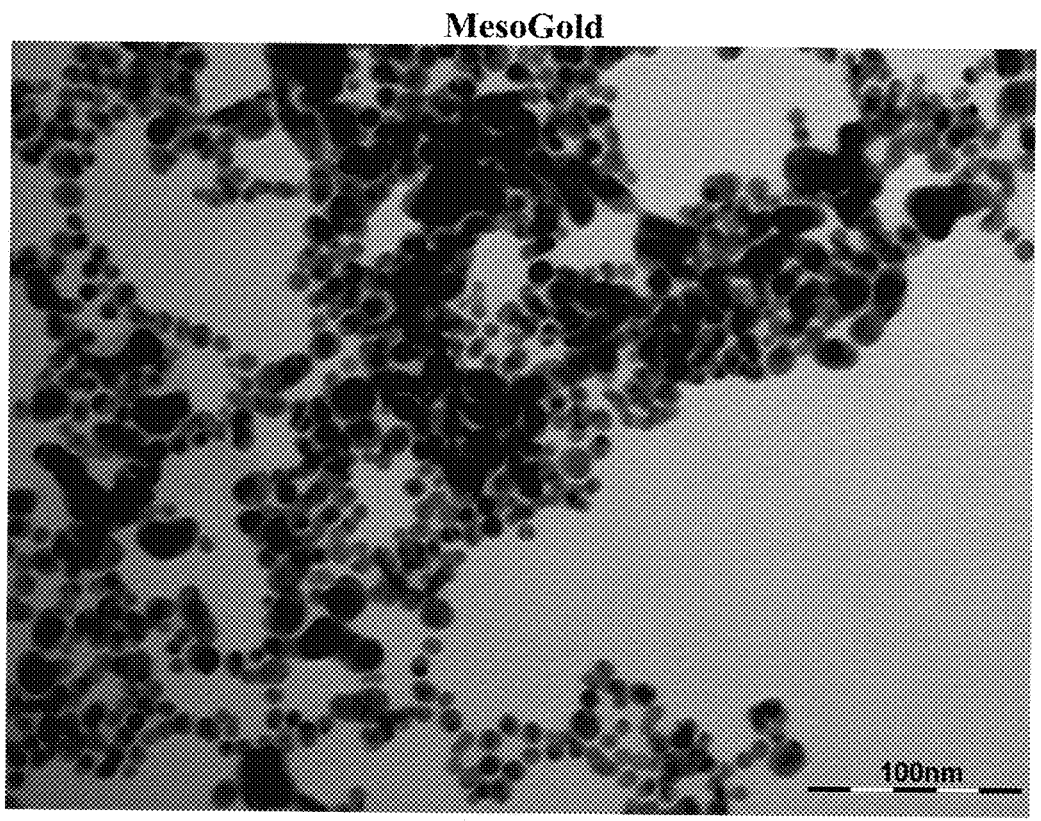
Figure 89B:
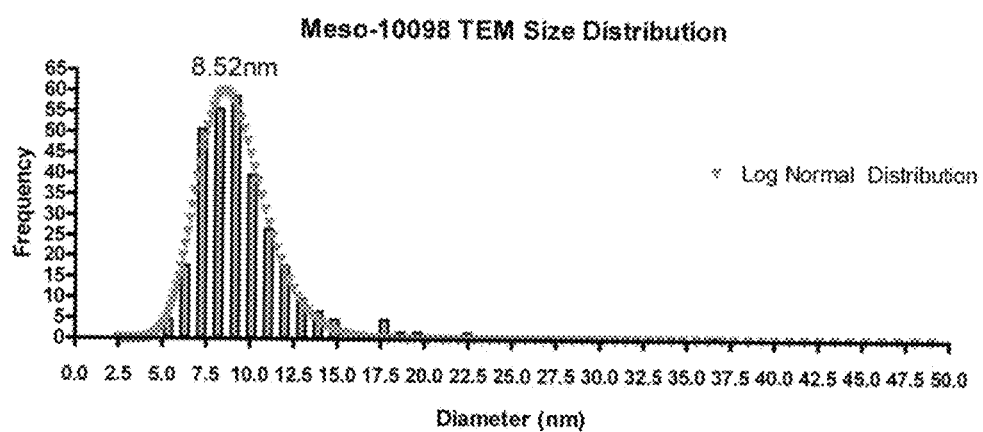

FIG. 82b is a particle size distribution histogram from TEM measurements for the nanoparticles made according to ARCG-05.

FIGS. 83a-90a show representative TEM photomicrographs for eight comparative commercially available colloidal gold products discussed in Example 22.

FIGS. 83b-90b shows the particle size distribution histograms from TEM measurements for the nanoparticles corresponding to the eight comparative commercially available colloidal gold products discussed in Example 22.

Figure 22A:
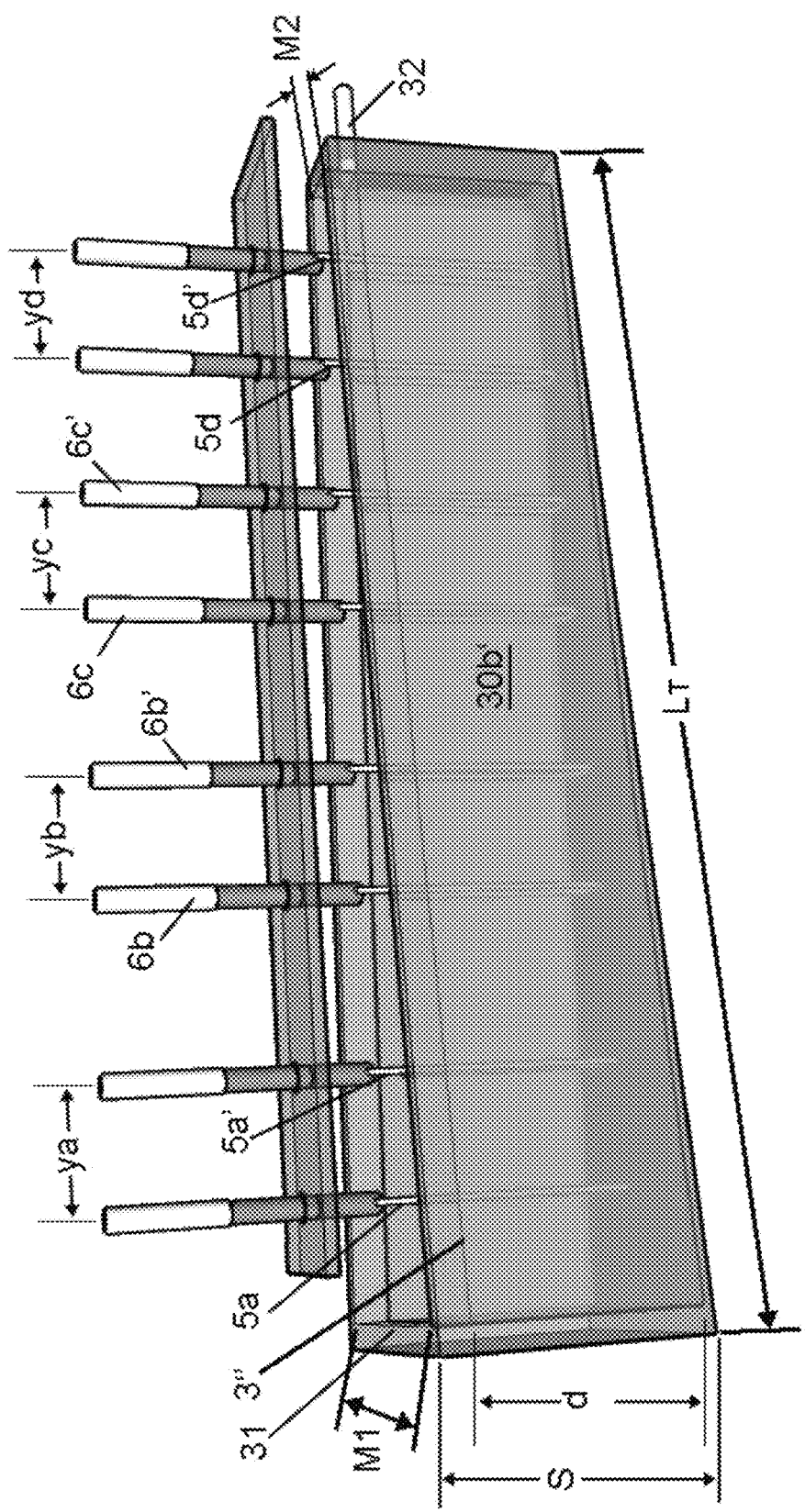
FIGS. 22a and 22b show trough members 30b in connection with FIGS. 19a, 19b and 20 and various Examples herein.
Figure 22B:
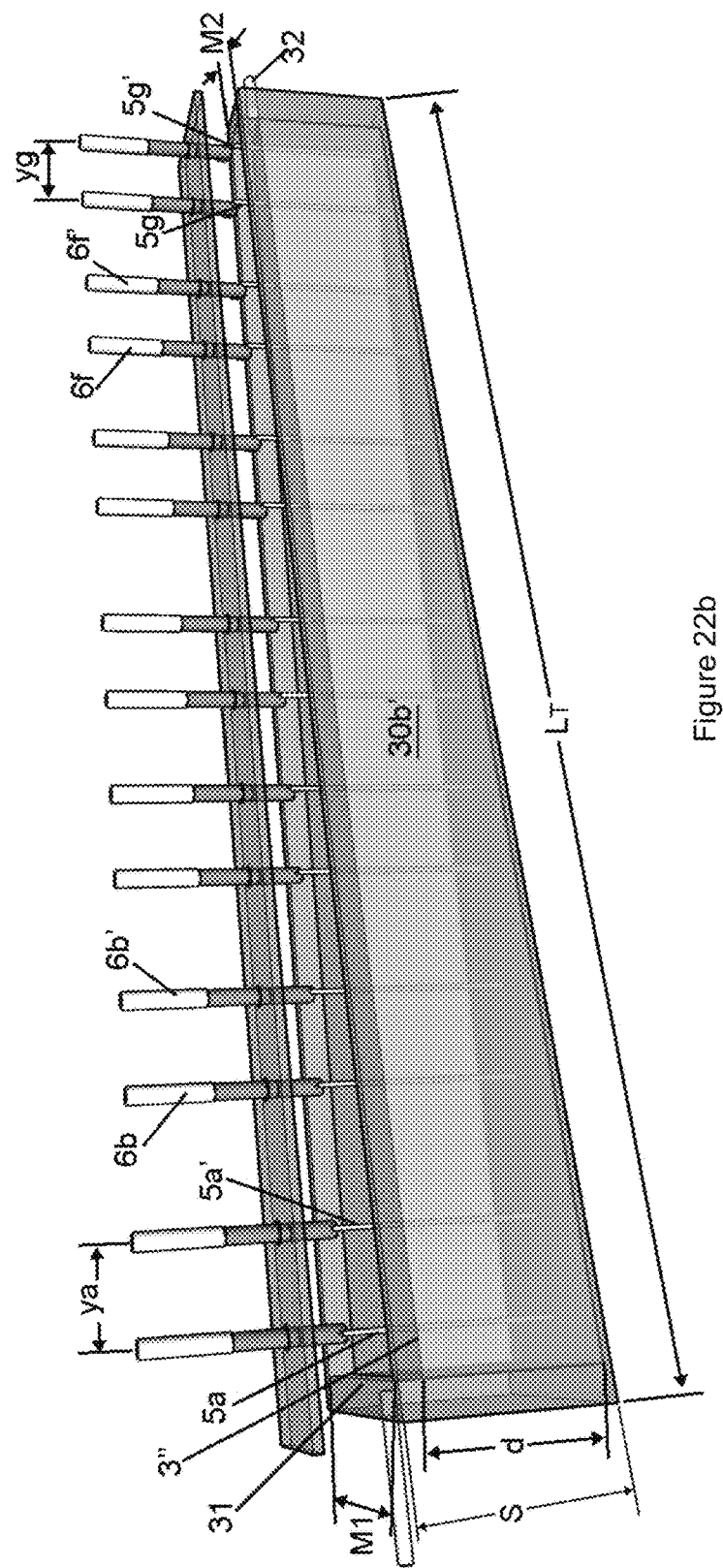
Figure 90A:
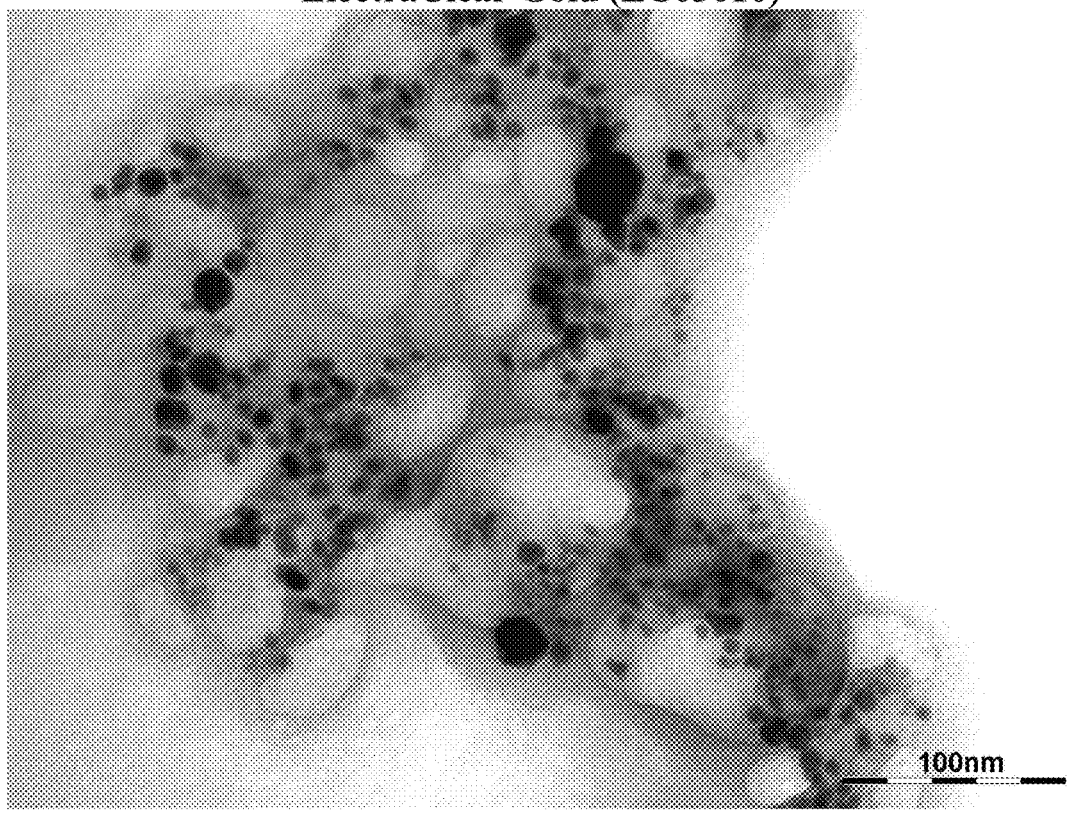
Figure 90B:
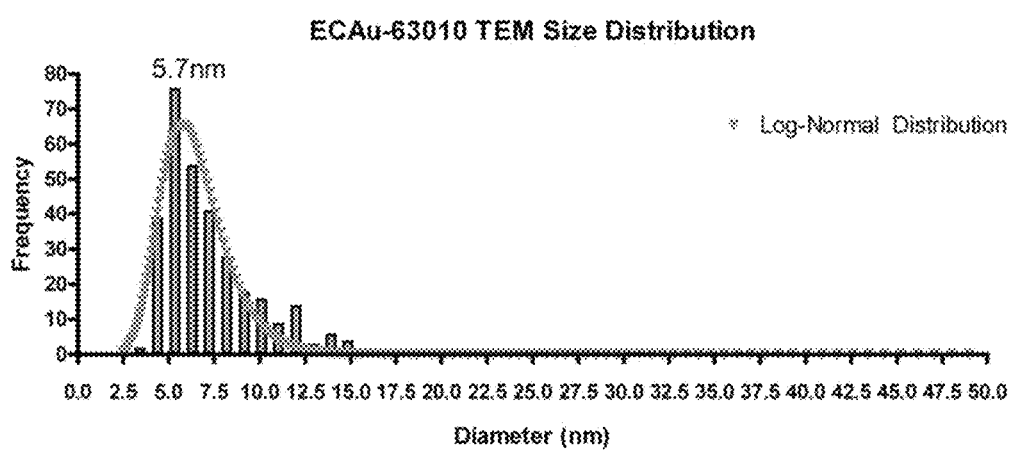
Figure 90C:
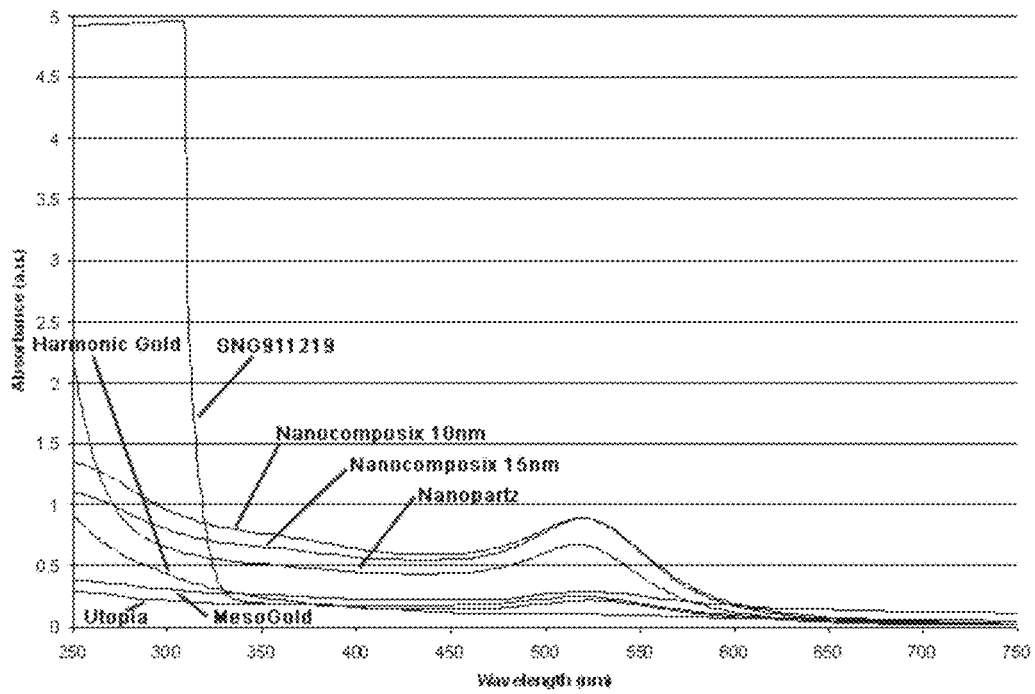

FIG. 90c shows the UV-Vis spectral patterns of each of the 7 of the 8 commercially available gold nanoparticle suspensions discussed in FIG. 22a (Utopia Gold, SNG911219, Nanopartz, Nanocomposix 15 nm, Nanocomposix 10 nm, Harmonic Gold and MesoGold) over an interrogating wavelength range of about 250 nm-750 nm.

Figure 90D:
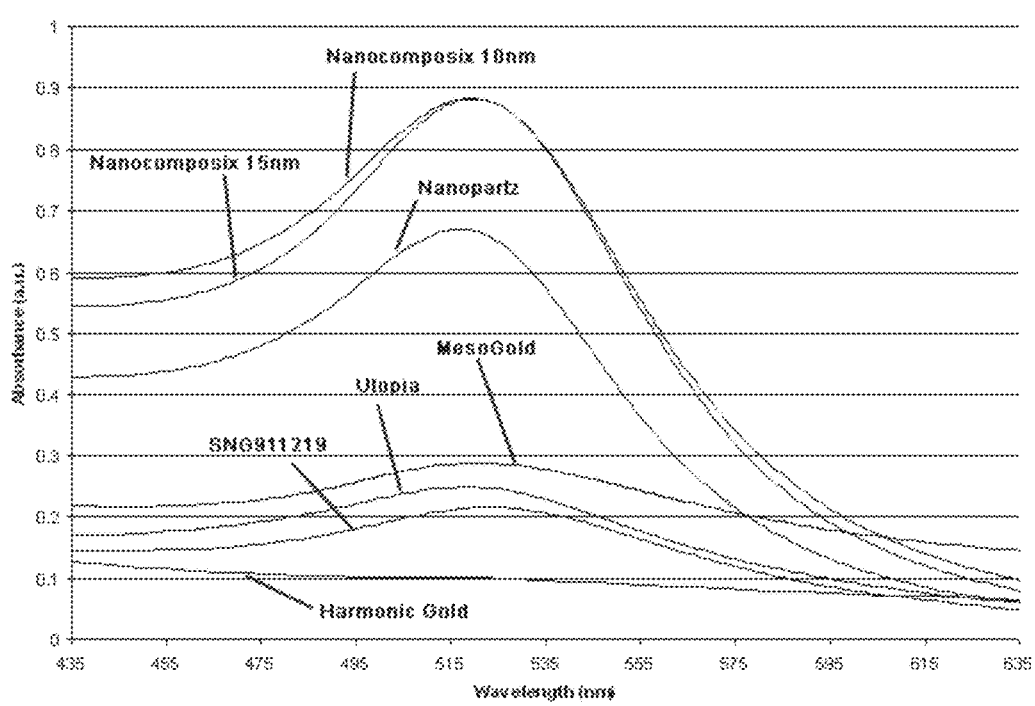

FIG. 90d shows the UV-Vis spectral patterns for 7 of the 8 commercially available gold nanoparticle suspensions discussed in FIG. 22a (Utopia Gold, SNG911219, Nanopartz, Nanocomposix 15 nm, Nanocomposix 10 nm, Harmonic Gold and MesoGold) over an interrogating wavelength range of about 435 nm-635 nm.

Figure 91:
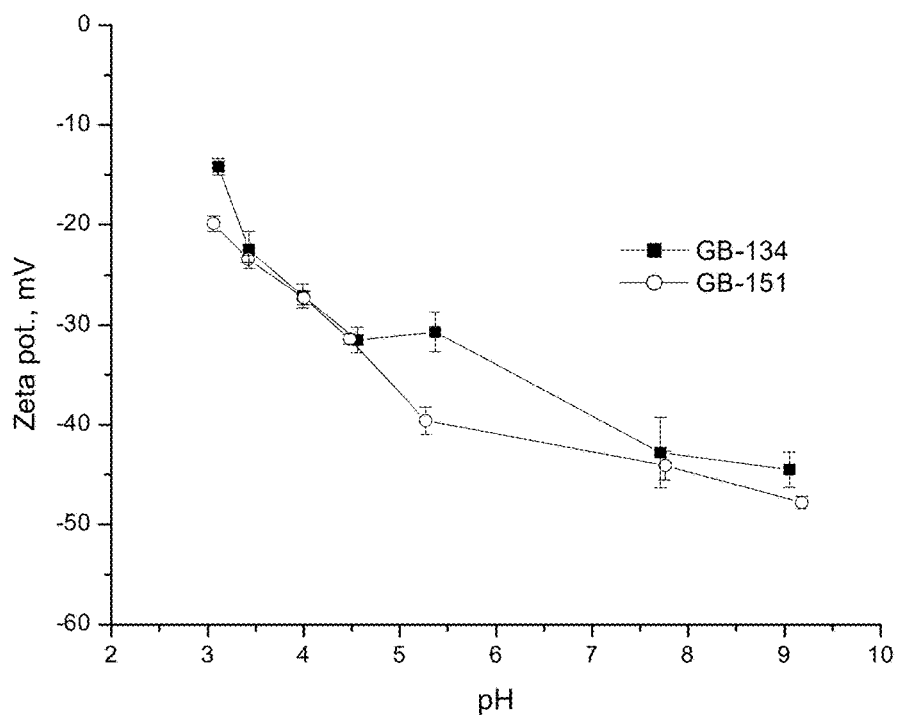

FIG. 91 is a graph showing Zeta Potentials.

Figure 92:
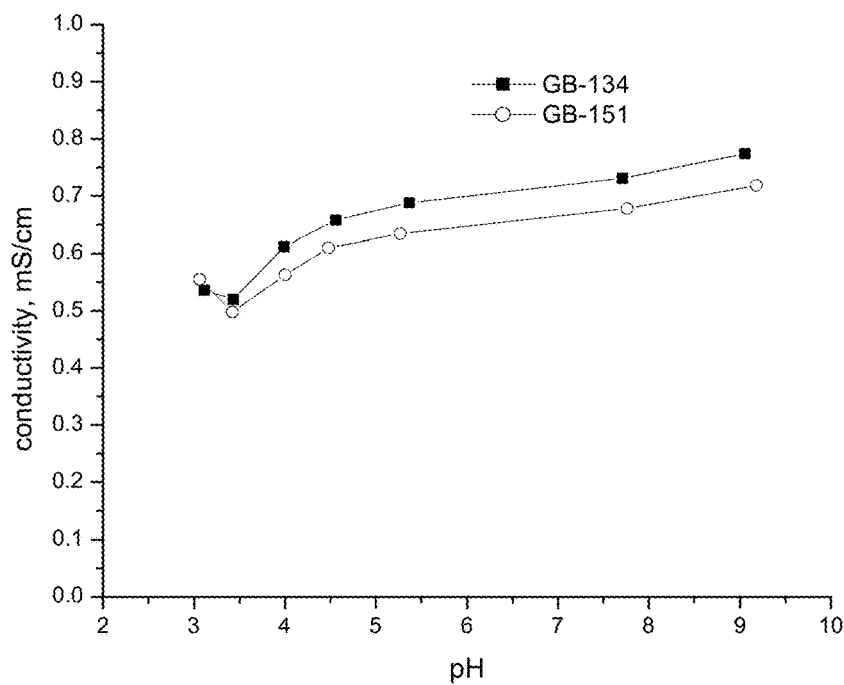

FIG. 92 is a graph showing conductivity.

Figure 93:
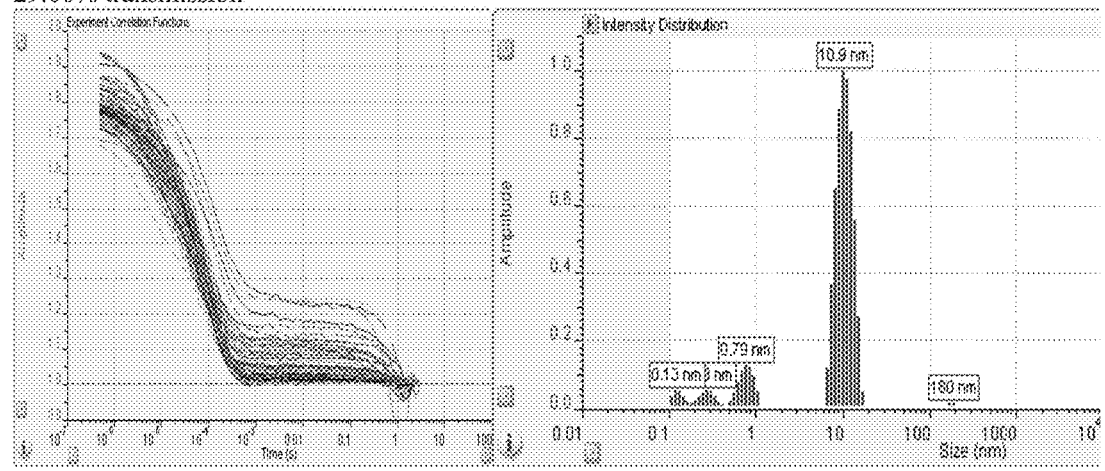

FIG. 93 shows dynamic light scattering data (i.e., hydrodynamic radii) for the nanocrystal suspension GD-006 made according to Example 23a.

FIGS. 94a-94d show graphically amounts of four different cytokines produced by human PBMCs when antagonized by LPS in the presence of different amounts of GB-079.

Figure 95:
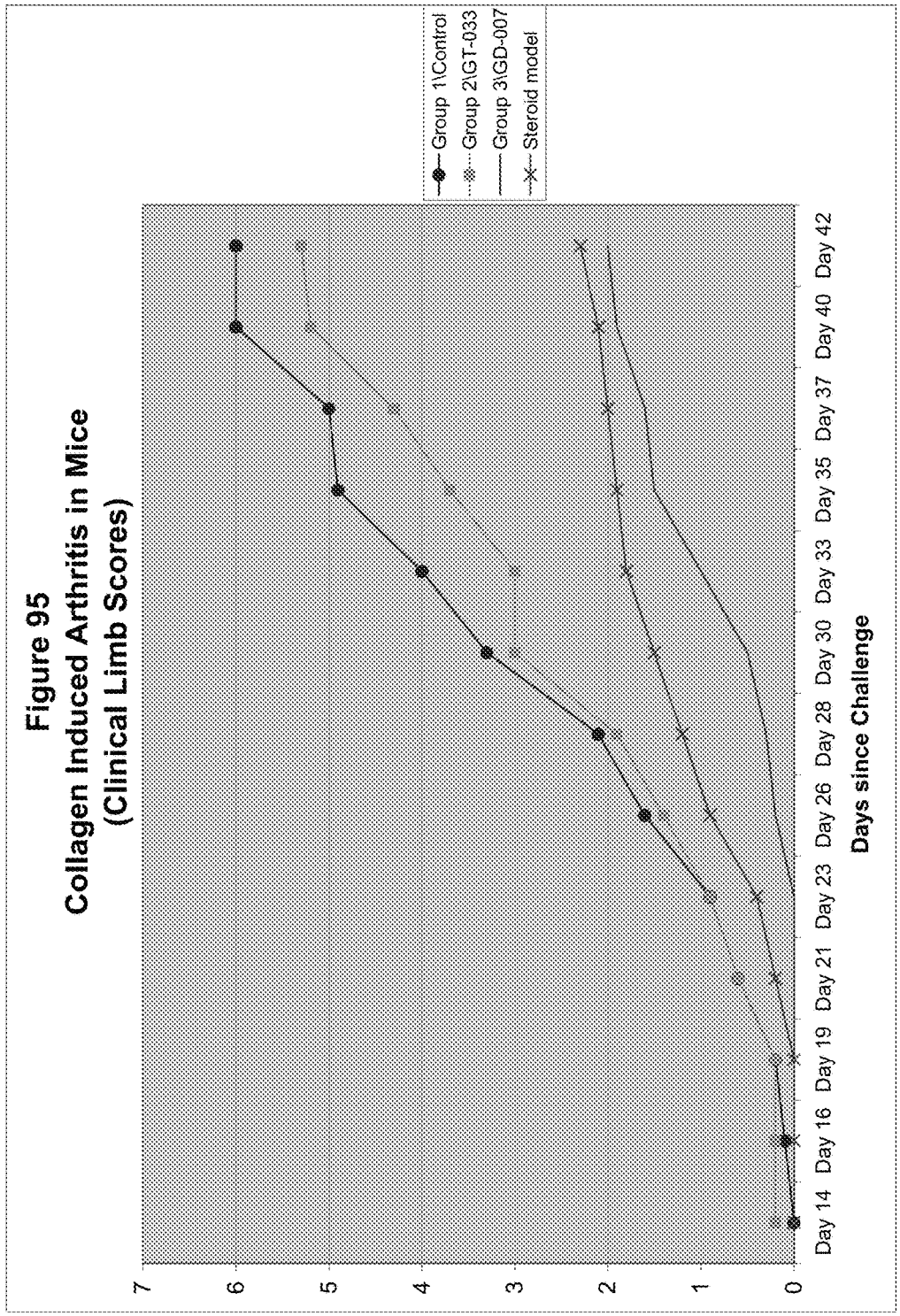
Figure 96A:
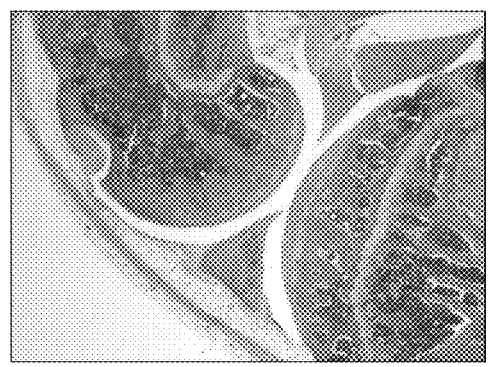
Figure 96B:
Figure 96C:
Figure 96D:

FIG. 95 is a graph showing the results from a collagen-induced arthritis ("CIA") model in mice showing control water, two experimental mixtures (i.e., GT-033 and GD-007) and contrasting the measured experimental results with results from a typical steroid model (i.e., not measured in this model).

FIGS. 96a-96d show representative photomicrographs of cross sections of mouse paw joints at various stages of arthritis.

FIGS. 97a-97e show representative photomicrographs of cross sections of mouse paw joints at various stages of arthritis.

Figure 98:
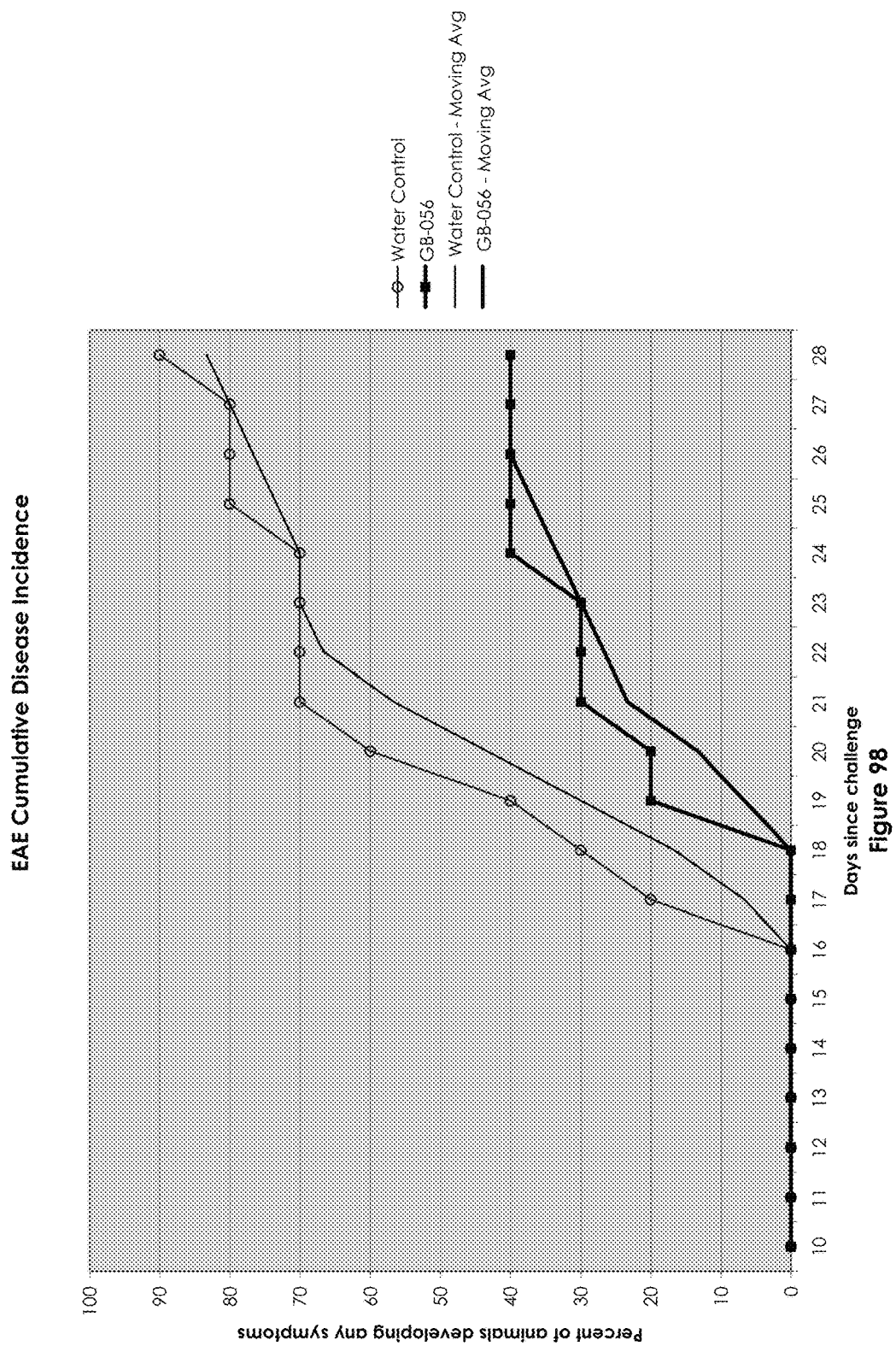

FIG. 98 is a graph showing results from an Experimental Auto-Immune Encephalitis ("EAE") model in Biozzi mice showing the percent of animals developing symptoms in the water Control Group 1 versus the GB-056 Treatment Group 2.

Figure 99:
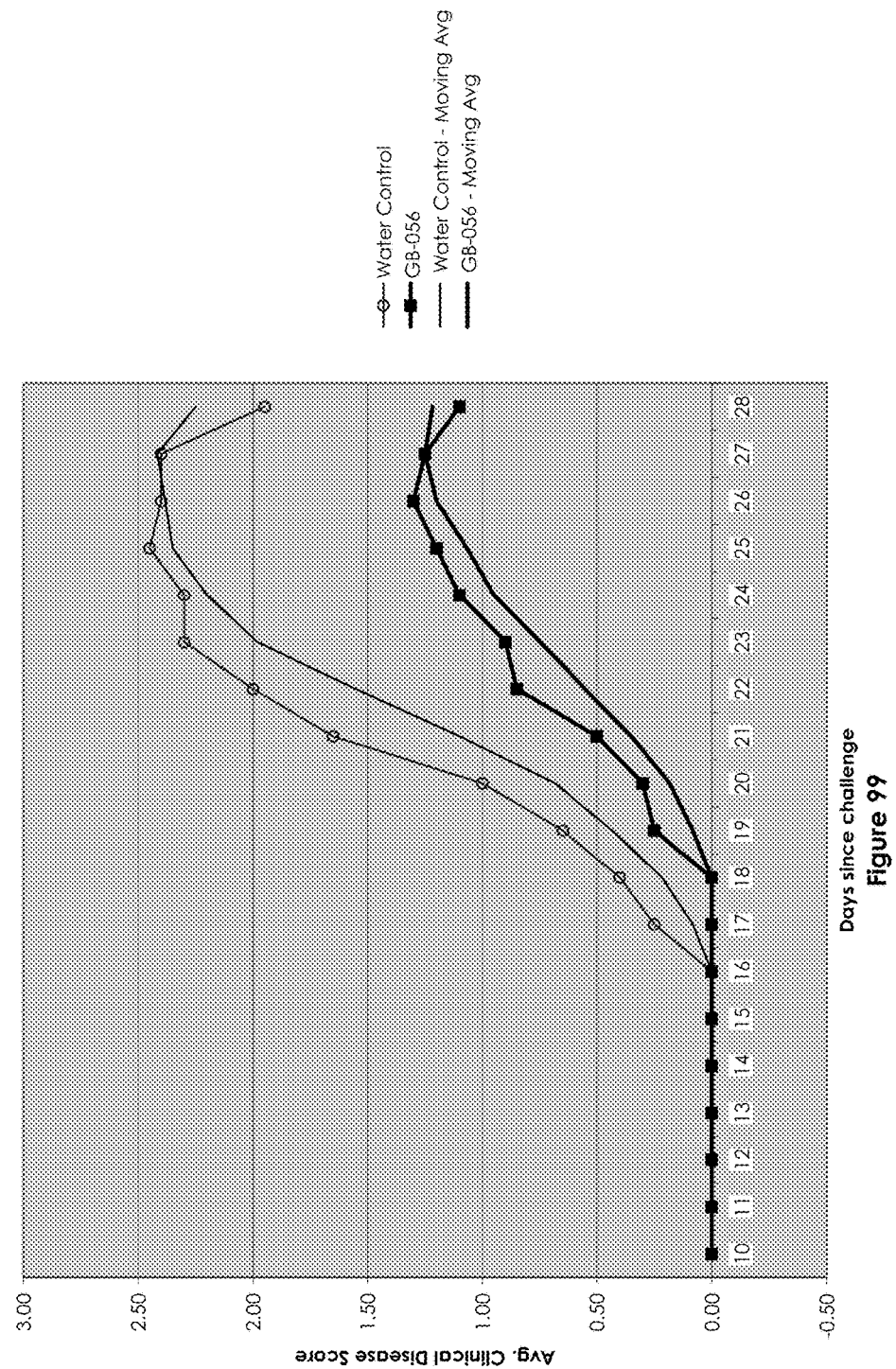
Figure 100A:
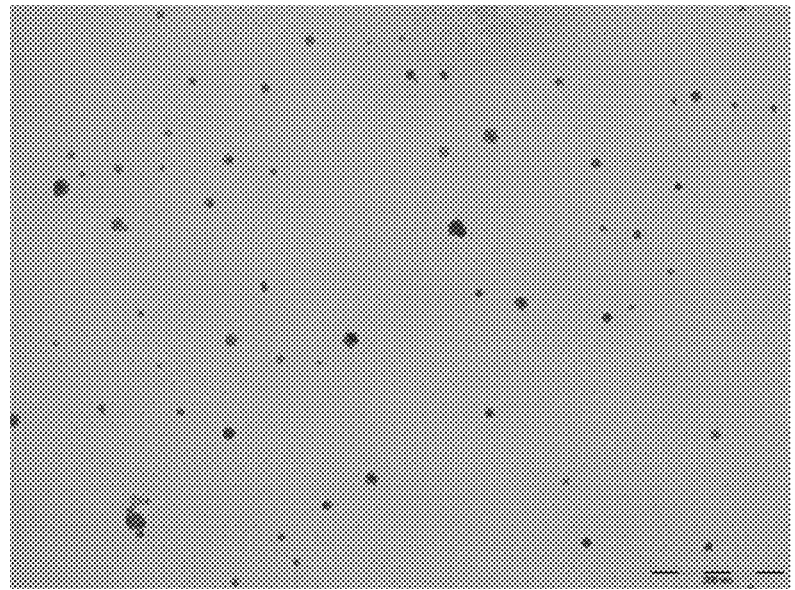
Figure 100B:
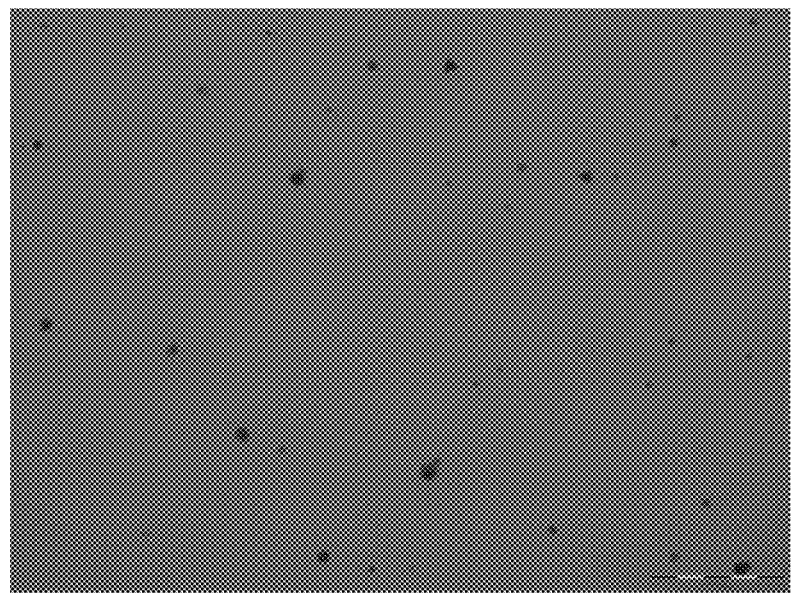
Figure 100C:
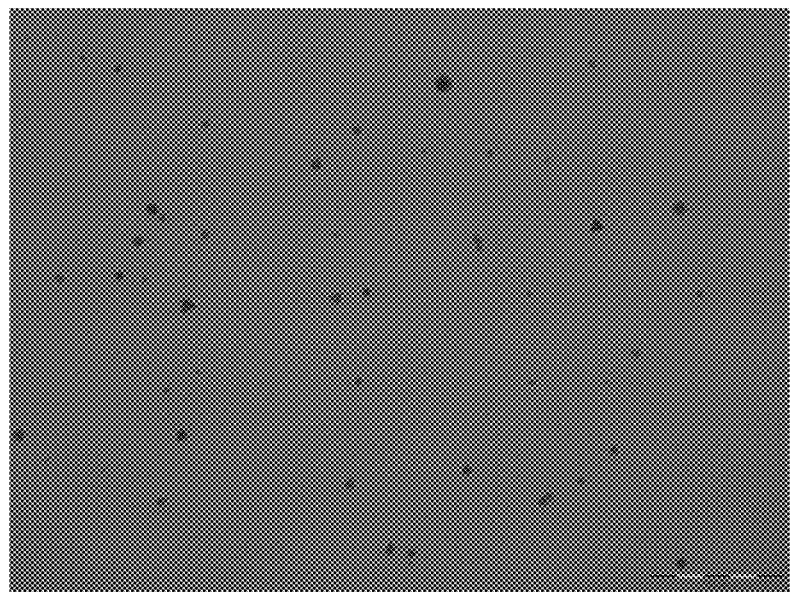
Figure 100D:
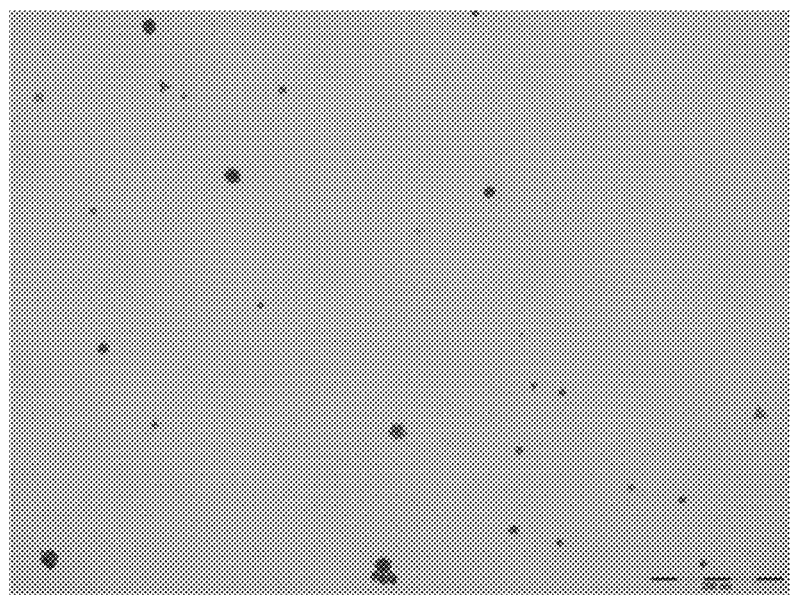
Figure 100E:
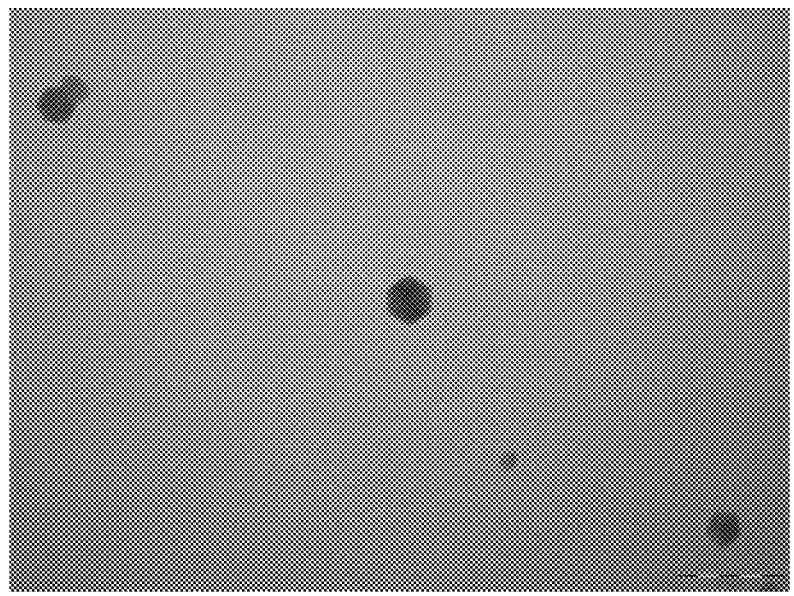

FIG. 99 is a graph showing results from an Experimental Auto-Immune Encephalitis ("EAE") model in Biozzi mice showing the average clinical disease score for the water Control Group 1 versus the GB-056 Treatment Group 2.

FIGS. 100a-e are representative TEM photomicrographs of gold nanocrystals from dried solution GB-056 made in accordance with Example 17.

Figure 101A:
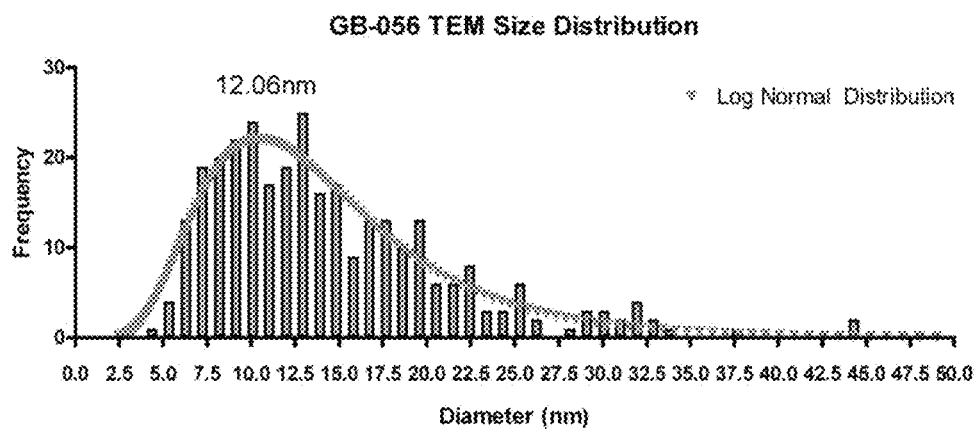

FIG. 101a shows the particle size distribution histogram from TEM measurements for the gold nanocrystals made according to Example 17.

Figure 101B:
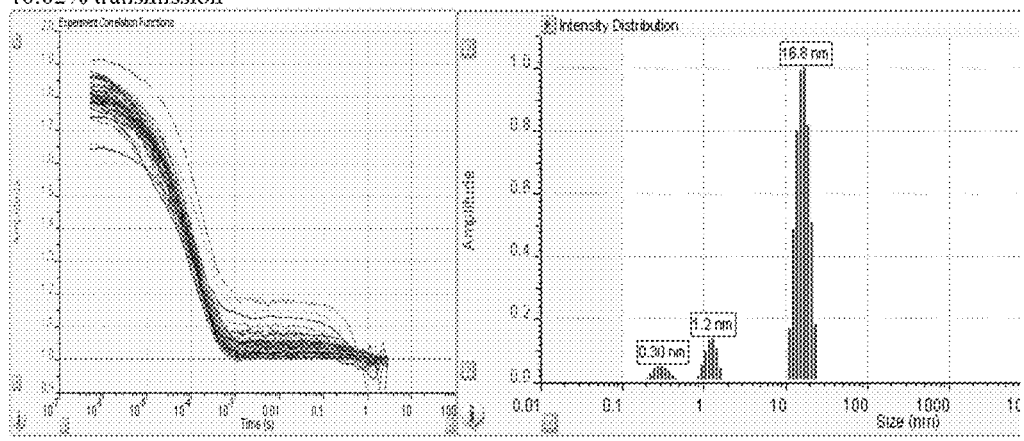
Figure 102A:
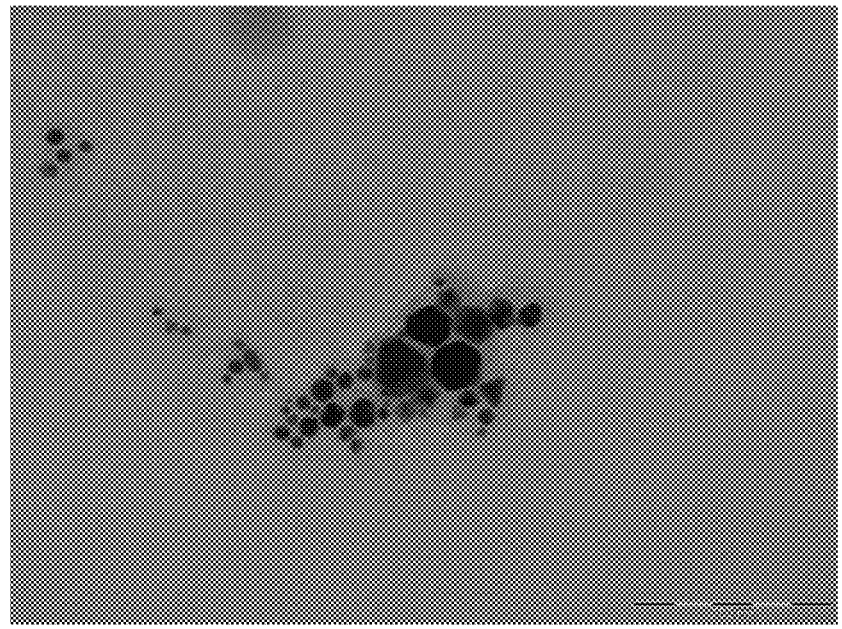
Figure 102B:
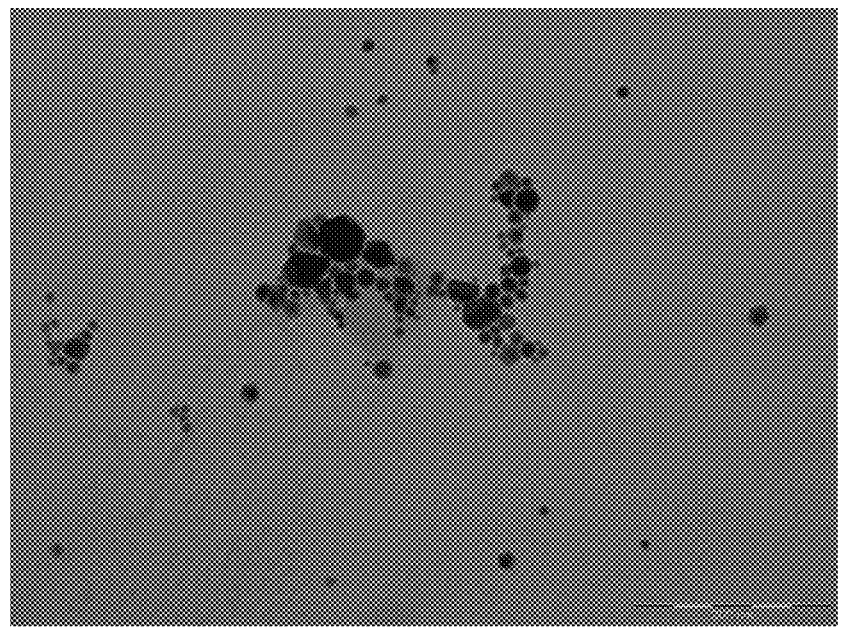
Figure 102C:
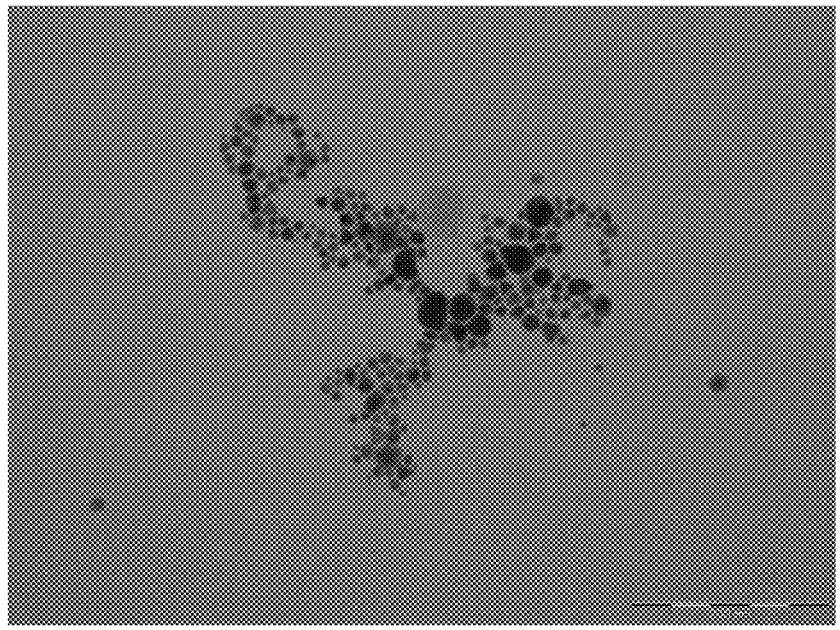
Figure 102D:
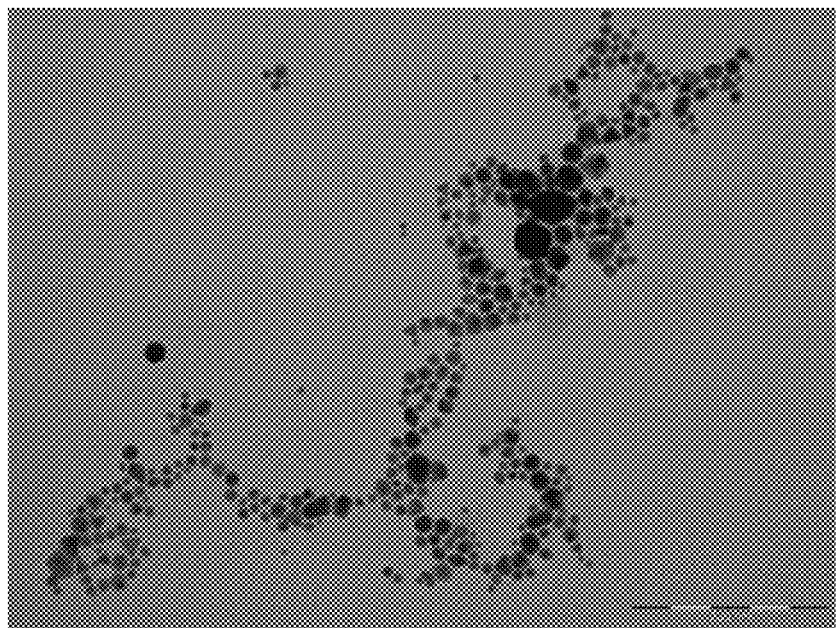

FIG. 101b shows dynamic light scattering data (i.e., hydrodynamic radii) for gold nanocrystals made according to Example 17.

FIGS. 102a-d are representative TEM photomicrographs of the same gold nanocrystals from dried solution GB-056 made in accordance with Example 17 after serving as the test compound for 24 hours in the EAE test of Example 26.

Figure 103A:
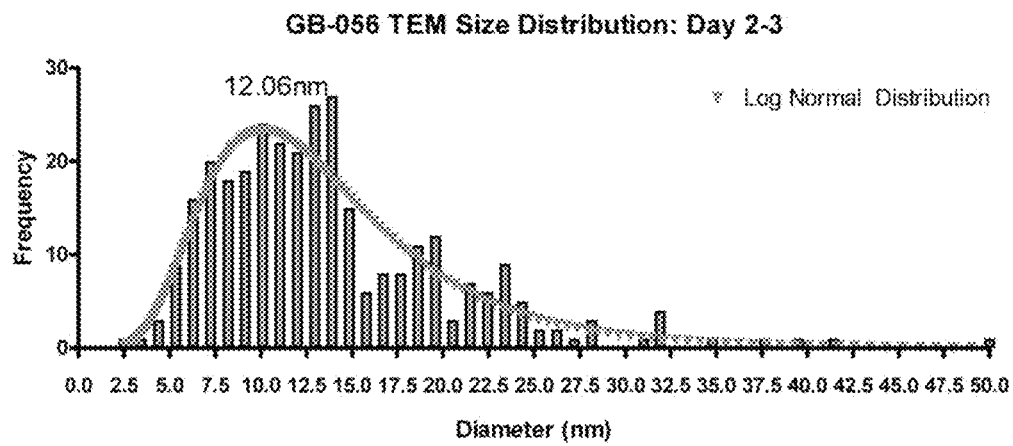

FIG. 103a shows the particle size distribution histogram from TEM measurements for the gold nanocrystals made according to Example 17 after serving as the test compound for 24 hours in the EAE test of Example 26.

Figure 103B:
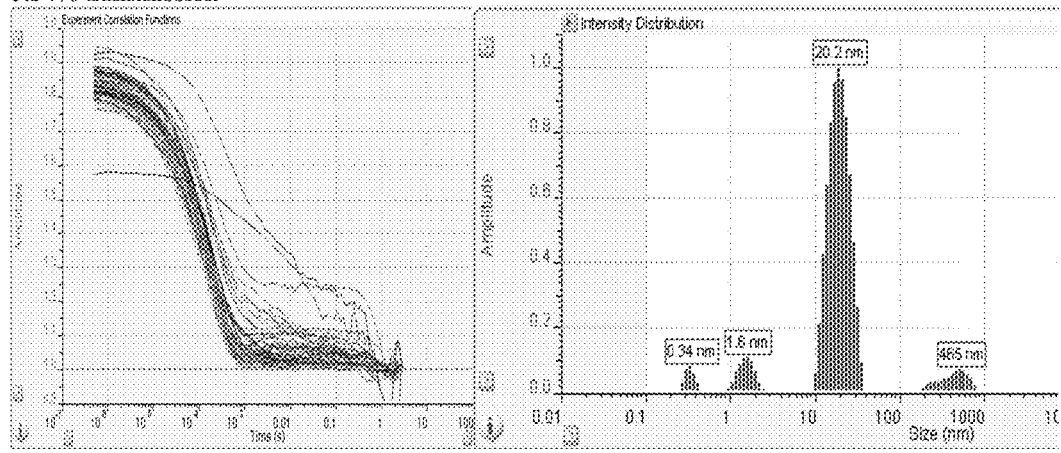

FIG. 103b shows dynamic light scattering data (i.e., hydrodynamic radii) for gold nanocrystals made according to Example 17 after serving as the test compound for 24 hours in the EAE test of Example 26.

Figure 104A:
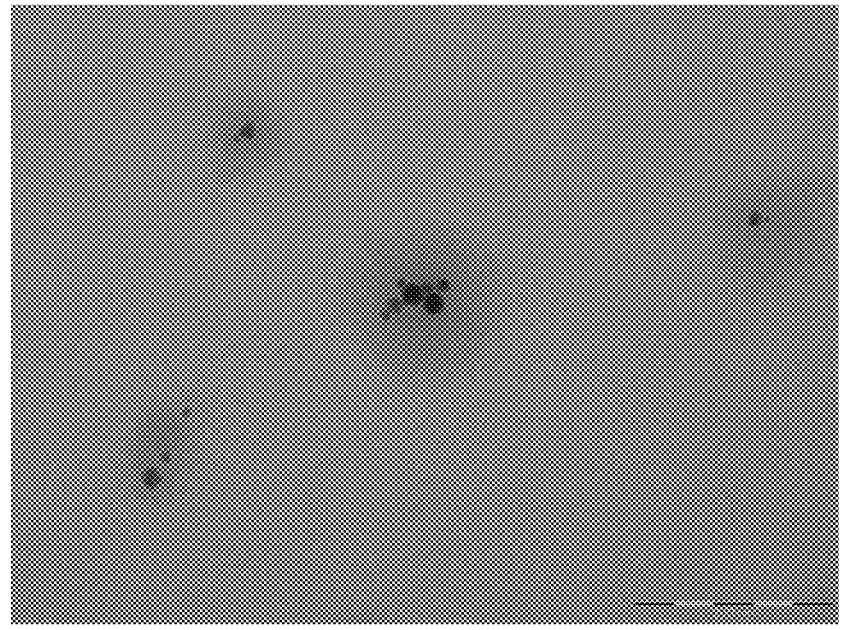
Figure 104B:
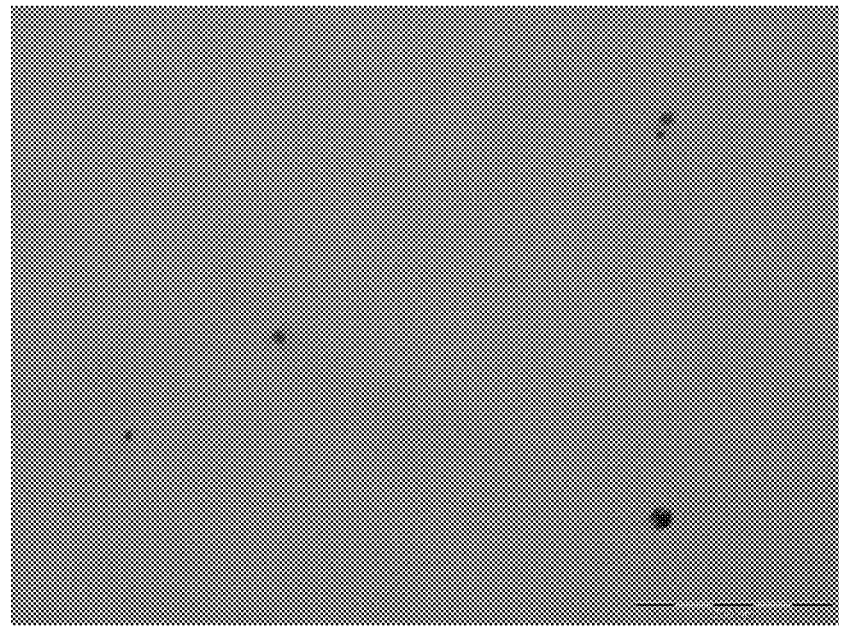
Figure 104C:
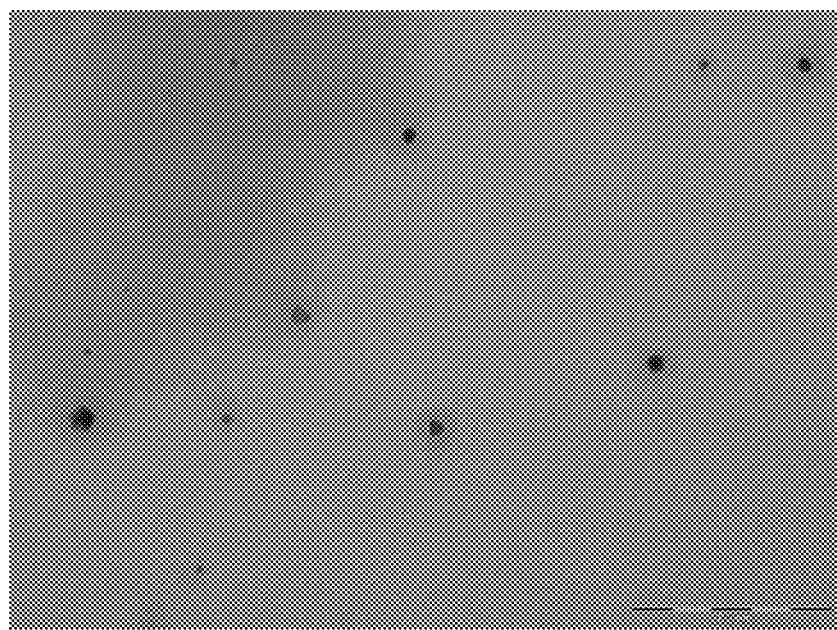

FIGS. 104a-c are representative TEM photomicrographs of the same gold nanoparticles from dried solution GB-056 made in accordance with Example 17 after serving as the test compound for 24 hours in the EAE test of Example 26.

Figure 105A:
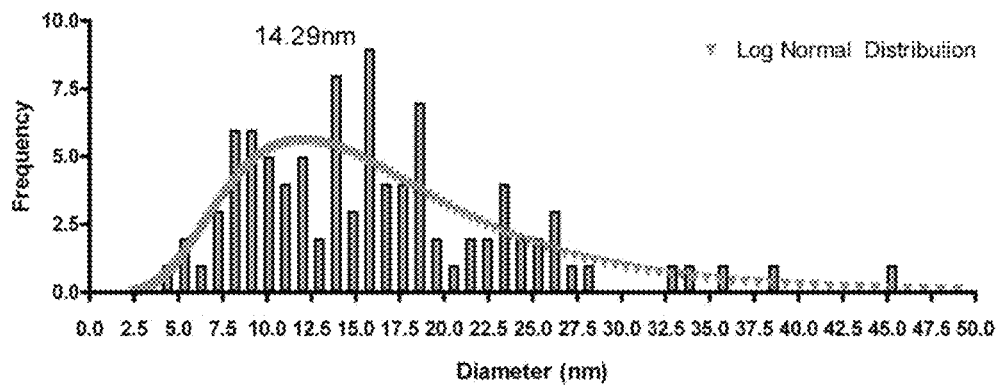

FIG. 105a shows the particle size distribution histogram from TEM measurements for the nanocrystals made according to Example 17 after serving as the test compound for 24 hours in the EAE test of Example 26.

Figure 105B:
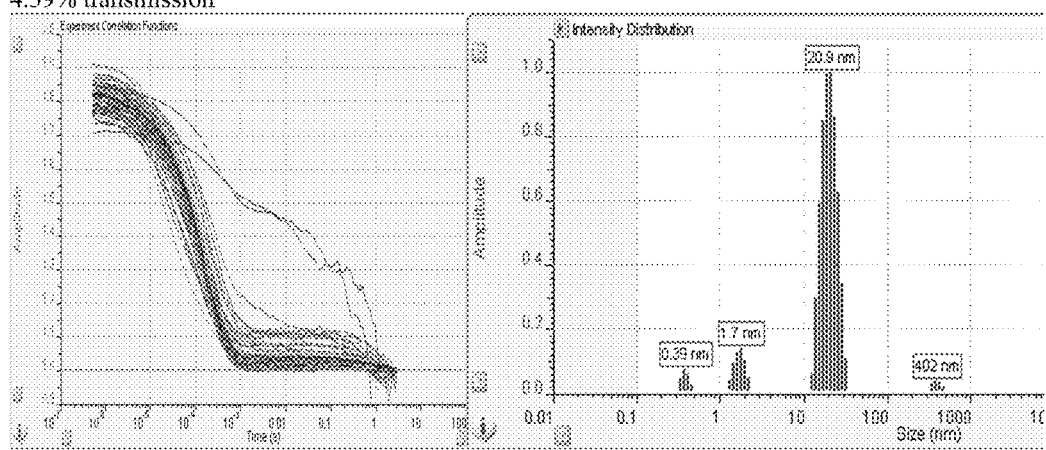

FIG. 105b shows dynamic light scattering data for the nanocrystals made according to Example 17 from Day 4-Day 5.

Figure 106:
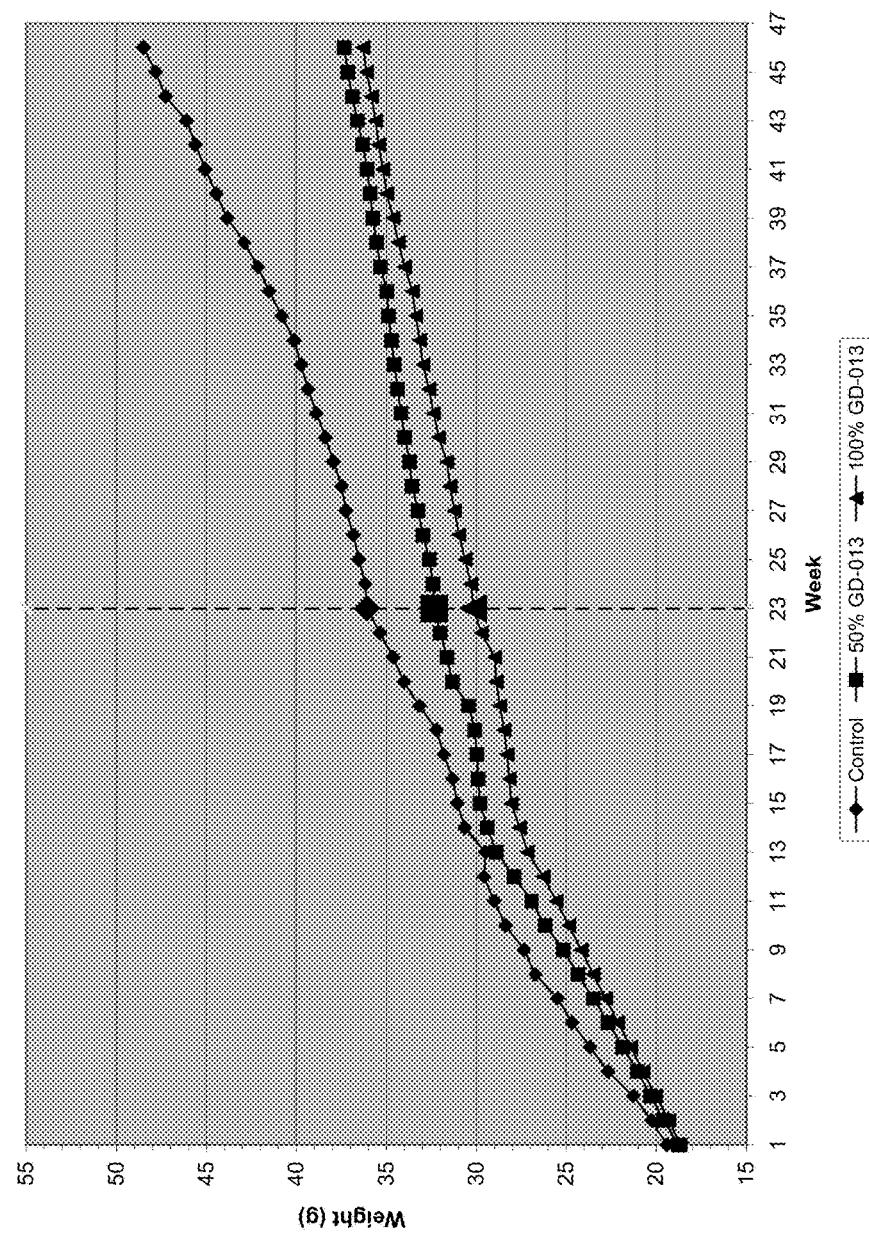

FIG. 106 shows the average weight gain of all mice over a long term study according to Example 27.

Figure 107:
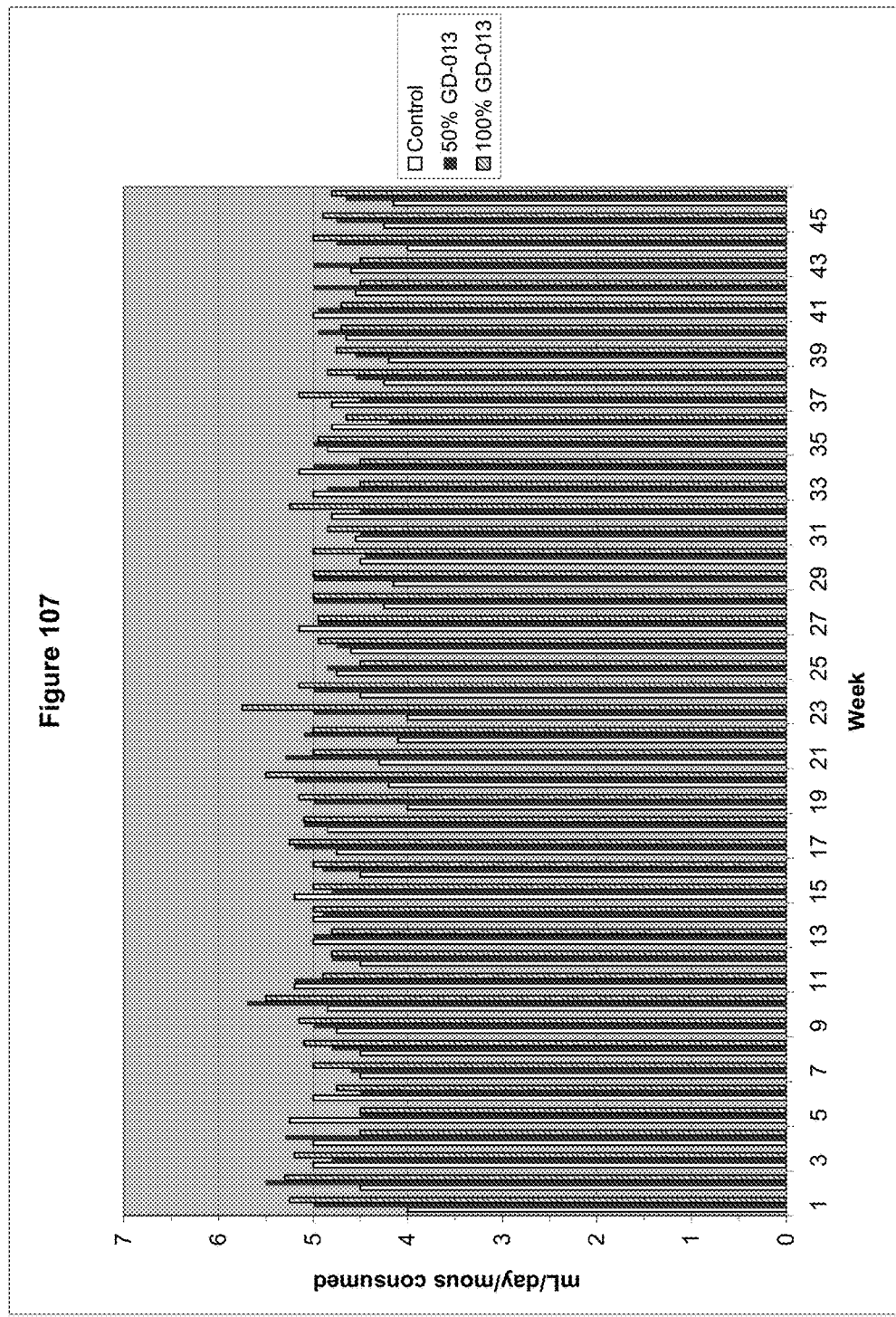

FIG. 107 shows the average amount of treatment and control liquids consumed for all mice over a long term study according to Example 27.

Figure 108:
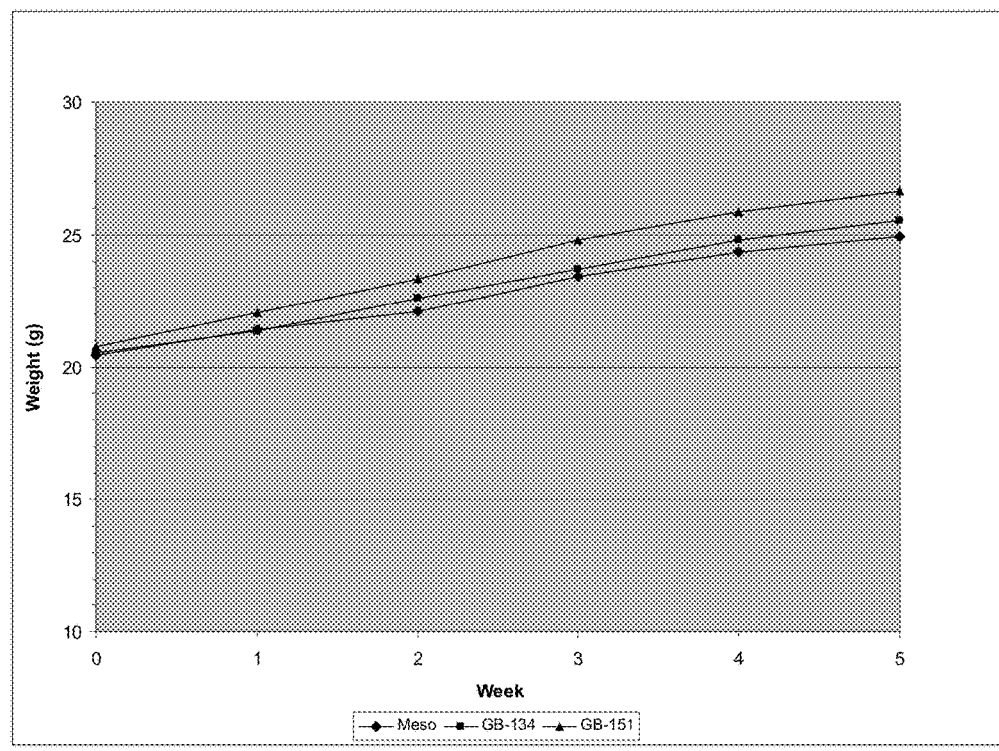

FIG. 108 shows the average weight gain of all mice over a 35 day study according to Example 28.

Figure 109:
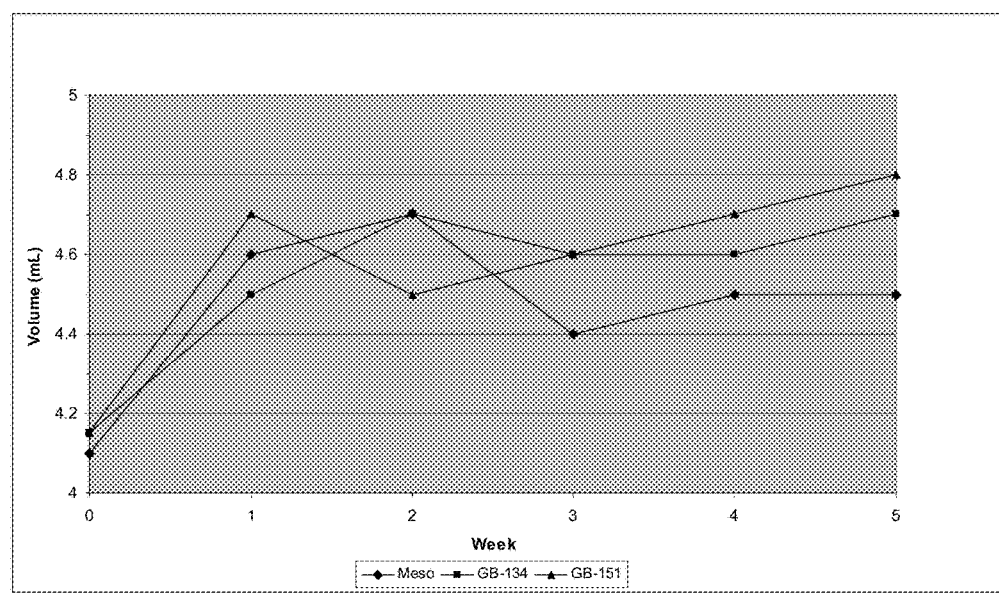

FIG. 109 shows the average amount of treatment and control liquids consumed for all mice over a 35 day study according to Example 28.

Figure 110:
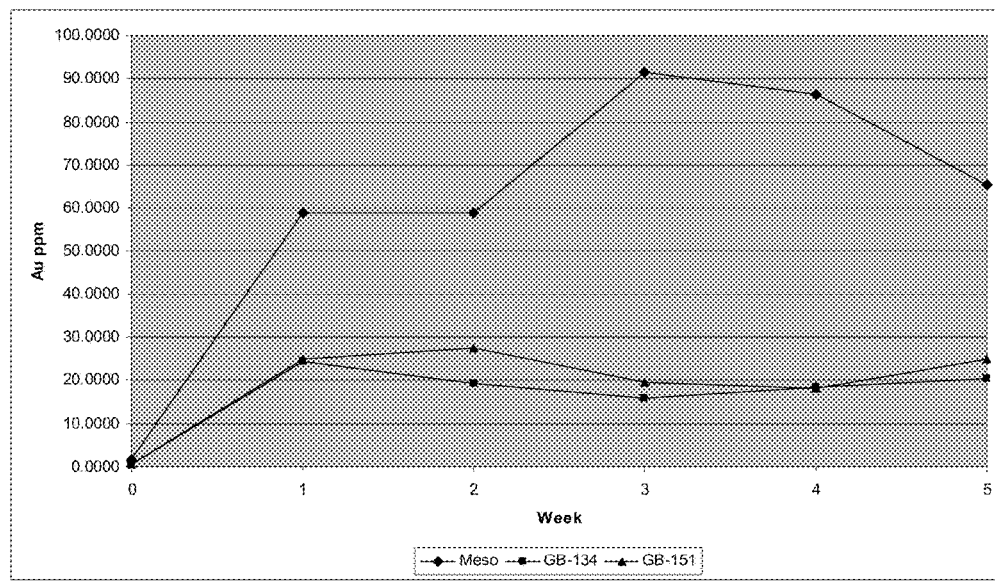

FIG. 110 shows the amount of gold found in the feces of mice according to Example 28.

Figure 111:
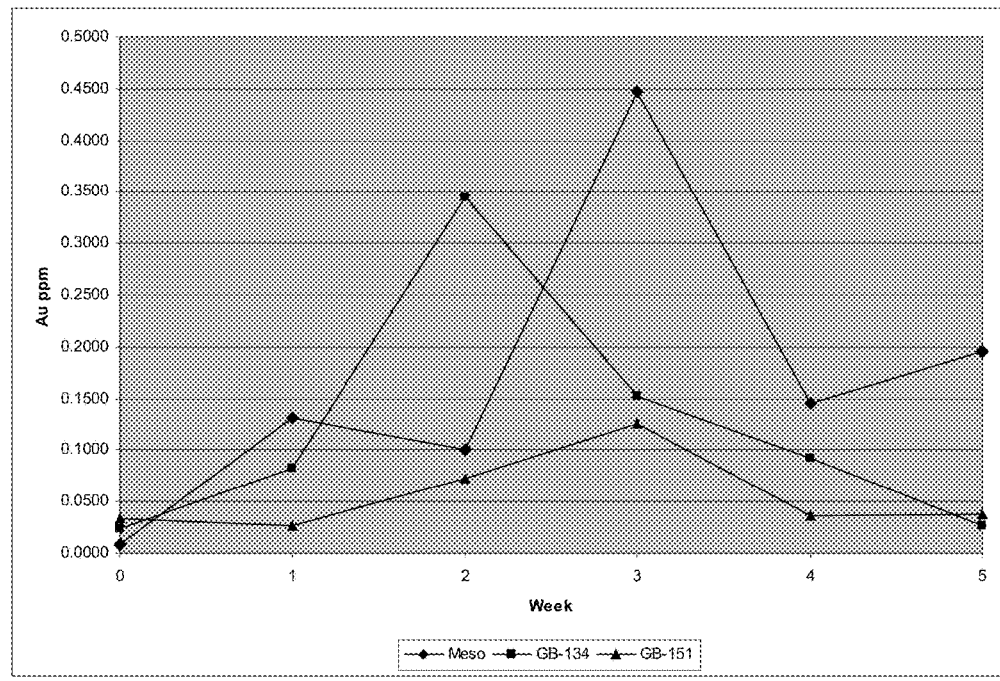

FIG. 111 shows the amount of gold found in the urine of mice according to Example 28.

Figure 112:
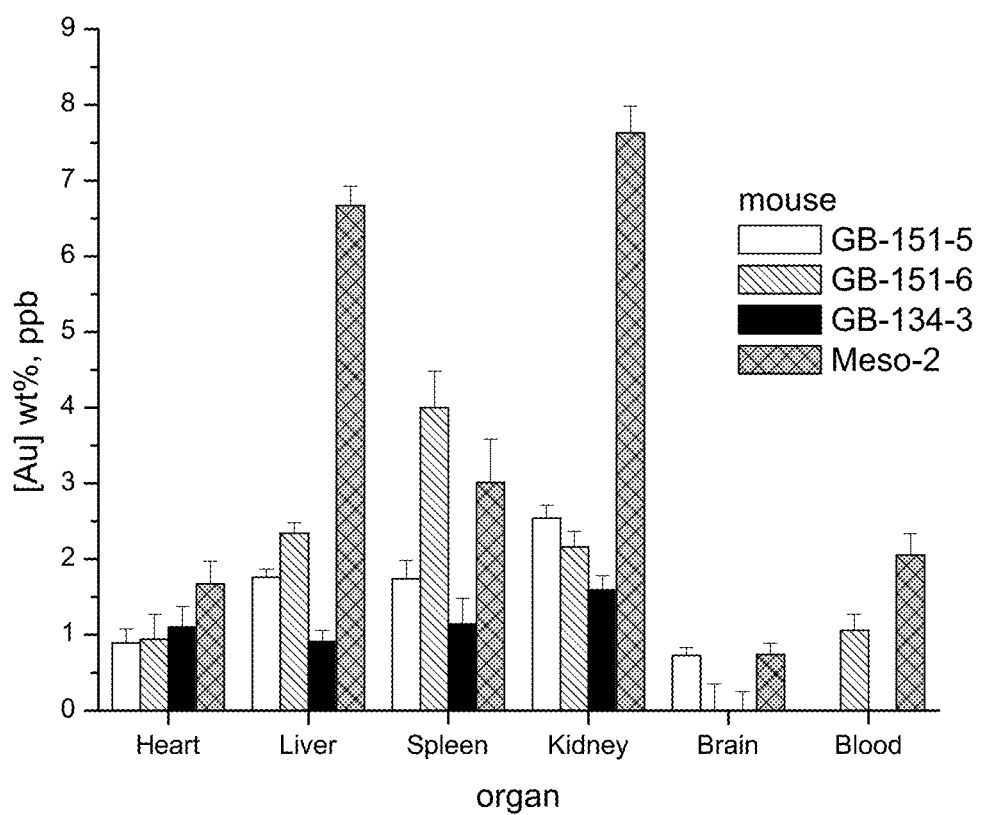

FIG. 112 shows the amount of gold found in the organs and blood of mice according to Example 28.

DETAILED DESCRIPTION OF THE PREFERRED EMBODIMENTS

I. Novel Gold Nanocrystals

New gold nanocrystals are provided that have nanocrystalline surfaces that are substantially free from organic or other impurities or films. Specifically, the surfaces are "clean" relative to those made using chemical reduction processes that require chemical reductants and/or surfactants to form gold nanoparticles from gold ions in solution. The new gold nanocrystals are produced via novel manufacturing procedures, described in detail herein. The new manufacturing procedures avoid the prior use of added chemical reductants and/or surfactants (e.g., organic compounds) or other agents which are typically carried along in, or on, the particles or are coated on the surface of the chemically reduced particles; or the reductants are subsequently stripped or removed using undesirable processes which themselves affect the particle.

In a preferred embodiment, the process involves the nucleation and growth of the gold nanocrystals in water which contains a "process enhancer" or "processing enhancer" (typically an inorganic material or carbonate or such) which does not significantly bind to the formed nanocrystals, but rather facilitates nucleation/growth during electrochemical-stimulated growth process. The process enhancer serves important roles in the process including providing charged ions in the electrochemical solution to permit the crystals to be grown. The process enhancer is critically a compound(s) which remains in solution, and/or does not form a coating (e.g., an organic coating), and/or does not adversely affect the formed nanocrystals or the formed suspension(s), and/or is destroyed, evaporated, or is otherwise lost during the electrochemical process. A preferred process enhancer is sodium bicarbonate. Examples of other process enhancers are sodium carbonate, potassium bicarbonate, potassium carbonate, trisodium phosphate, disodium phosphate, monosodium phosphate, potassium phosphates or other salts of carbonic acid or the like. Further process enhancers may be salts, including sodium or potassium, of bisulfate or sulfite. Still other process enhancers to make gold nanocrystals for medical applications under certain conditions may be other salts, including sodium or potassium, or any material that assists in the electrochemical growth processes described herein; which is not substantially incorporated into or onto the surface of the gold nanocrystals; and does not impart toxicity to the nanocrystals or to the suspension containing the nanocrystals.

Desirable concentration ranges for the processing enhancer include typically 0.01-20 grams/gallon (0.0026-2.1730 mg/ml), more typically, 0.1-7.5 grams/gallon (0.0264-1.9813 mg/ml) and most typically, 0.5-2.0 grams/gallon (0.13210-0.5283 mg/ml).

Because the grown gold nanocrystals have "bare" or "clean" surfaces of gold metal (e.g., in the zero oxidation state) the surfaces are highly reactive or are highly biocatalytic (as well as highly bioavailable). The nanocrystals are essentially surrounded by a water jacket. These features provide increased efficacy in vivo relative to nanoparticle surfaces that contain, for example, organic material present from reduction chemistry processes. The "clean" surfaces may also reduce the toxicity of the nanocrystals, over those nanoparticles that contain coated or "dressed" surfaces. The increased efficacy of these "clean" gold nanocrystals may provide an increased therapeutic index via a lower dose needed to achieve a therapeutic effect. A comparative mouse model example herein (Example 25) compares an inventive gold nanocrystal suspension to Auranofin, a commercially available and FDA-approved gold drug, This Example shows that these novel gold nanocrystals, in mice, are at least 5 times more active than Auranofin in the well-accepted collagen induced arthritis model of inflammation in rheumatoid arthritis.

Specifically, the comparative mouse model (Example 25) compares the dose levels demonstrating efficacy using an inventive crystal suspension to the dose levels demonstrating efficacy using Auranofin, a commercially available and FDA-approved gold-based drug, Example 25 shows that these novel gold nanocrystals, in mice, achieve efficacy at a dose level at least 17 times lower than the effective dose level of Auranofin in the well accepted collagen induced arthritis model of inflammation in the mouse, and 5 times lower than the gold content contained in the effective dose level of Auranofin. Thus, comparing relative efficacy levels of the novel gold nanocrystal to those of the gold-based drug Auranofin, and to only the gold content of those of the Auranofin, the relative potency of the novel gold nanocrystals is 17 times greater than Auranofin and 5 times greater than the gold contained in the Auranofin.

This potency advantage means that treatment efficacy can be achieved at a much lower dose level (17× lower dose than Auranofin, 5× lower dose than the gold contained in Auranofin), or alternatively, that potentially much greater efficacy can be achieved at equivalent dose levels.

There are other important advantages of the novel nanocrystals in two other dimensions: relative toxicity, and relative speed of onset of benefits. With respect to both observed relative toxicity, and observed relative speed of onset of benefits, in an animal model, the novel gold nanocrystals are significantly different and significantly outperform Auranofin, the only orally administrated, FDA-approved gold-based pharmaceutical product in the prior art.

In a preferred embodiment, the nanocrystals are not dried before use but instead used in the liquid they were formed in (i.e., forming a suspension) or a concentrate or a reconstituted concentrate thereof. It appears that completely removing these crystals from their suspension (e.g., completely drying) may, in certain cases, affect the surface properties of the crystals, (e.g., partial oxidation may occur) and/or may affect the ability to rehydrate the crystals by, for example, altering the initially formed water jacket. This suggests that it may be optimal to use sterile pharmaceutical grade water (i.e., USP) and the aforementioned process enhancers in the manufacturing processes.

The gold nanocrystals made according to this invention can also be used for industrial applications where gold reactivity is important (e.g., catalytic and/or electrochemical processes) but pharmaceutical grade products are not required. When prepared for non-pharmaceutical uses, the gold nanocrystals can be made in a wider variety of solvents and with a wider variety of process enhancers, depending on the application.

According to the processes herein, the gold nanocrystals can be grown in a manner that provides unique and identifiable surface characteristics such as spatially extended low index, crystal planes {111}, {110} and/or {100} and groups of such planes (and their equivalents). The shapes of the gold nanocrystals prepared according to the processes described herein include, but are not limited to, triangles (e.g., tetrahedrons), pentagons (e.g., pentagonal bipyramids or decahedrons), hexagons (e.g., hexagonal bipyramids, icosahedrons, octahedrons), diamond (e.g., octahedrons, various eleongated bipyramids, fused tetrahedrons, side views of bipyramids) and "others". The percent of nanocrystals (i.e., grown by various embodiments set forth herein) containing the aforementioned spatially extended low index crystal planes and having "clean" surfaces is another novel feature of the invention. Furthermore, the percent of tetrahedrons and/or pentagonal bipyramids formed or present in the nanocrystalline suspensions is/are also unique.

In a preferred embodiment the percent of pentagonal bipyramids is at least about 5%, or is in a range of about 5%-35%, and more typically at least about 10%, or is in a range of about 10%-35%, and even more typically, at least about 15%, or is in a range of about 15%-35%, and still more typically, at least about 25%, and in some cases at least about 30%. In another preferred embodiment the percent of tetrahedrons is at least 5%, or is in a range of about 5%-35%, and more typically at least about 10%, or is in a range of about 10%-35%, and even more typically, at least about 15%, or is in a range of about 15%-35%, and still more typically, at least about 25%, and in some cases at least about 30%.

Still further, the combination of pentagonal bipyramids and tetrahedrons is at least about 15%, or is in a range of about 15%-50%, and more typically at least about 20%, or is in a range of about 20%-50%, and even more typically, at least about 30%, or is in a range of about 30%-50%, and still more typically, at least about 35%, and in some cases at least about 45%.

Still further, the combination of pentagonal bipyramids, tetrahedrons, octahedrons and hexagonal is at least about 50%, or is in a range of about 50%-85%, and more typically at least about 60%, or is in a range of about 60%-85%, and even more typically, at least about 70%, or is in a range of about 70%-85%, and still more typically, at least about 70%, and in some cases at least about 80%.

Any desired average size of gold nanocrystals below 100 nm can be provided. The most desirable crystalline size ranges include those having an average crystal size or "mode" (as measured and determined by specific techniques disclosed in detail herein and reported as "TEM average diameter") that is predominantly less than 100 nm, and more typically less than 50 nm, even more typically less than 30 nm, and in many of the preferred embodiments disclosed herein, the mode for the nanocrystal size distribution is less than 21 nm and within an even more preferable range of 8-18 nm.

Resulting gold nanocrystalline suspensions or colloids can be provided that have or are adjusted to have target pH ranges. When prepared with, for example, a sodium bicarbonate process enhancer, in the amounts disclosed in detail herein, the pH range is typically 8-9, which can be adjusted as desired.

The nature and/or amount of the surface change (i.e., positive or negative) on formed nanoparticles or nanocrystals can have a large influence on the behavior and/or effects of the nanoparticle/suspension or colloid. For example, protein coronas such as albumin coronas formed in vivo can be influenced by surface charge or surface characteristics of a nanoparticle. Such surface charges are commonly referred to as "zeta potential". It is known that the larger the zeta potential (either positive or negative), the greater the stability of the nanoparticles in the solution (i.e., the suspension is more stable). By controlling the nature and/or amount of the surface charges of formed nanoparticles or nanocrystals, the performance of such nanoparticle suspensions can be controlled.

Zeta potential is known as a measure of the electro-kinetic potential in colloidal systems and is also referred to as surface charge on particles. Zeta potential is the potential difference that exists between the stationary layer of fluid and the fluid within which the particle is dispersed. A zeta potential is often measured in millivolts (i.e., mV). The zeta potential value of approximately 20-25 mV is an arbitrary value that has been chosen to determine whether or not a dispersed particle is stable in a dispersion medium. Thus, when reference is made herein to "zeta potential", it should be understood that the zeta potential referred to is a description or quantification of the magnitude of the electrical charge present at the double layer.

The zeta potential is calculated from the electrophoretic mobility by the Henry equation:

$$U_E = \frac{2\varepsilon z f(ka)}{3\eta}$$

where z is the zeta potential, $U_E$ is the electrophoretic mobility, $\varepsilon$ is a dielectric constant, $\eta$ is a viscosity, $f(ka)$ is Henry's function. For Smoluchowski approximation $f(ka)$= 1.5.

Zeta potentials ("ZP") for the gold nanocrystals prepared according the methods herein typically have a ZP of at least −20 mV, more typically at least about −30 mV, even more typically, at least about −40 mV and even more typically at least about −50 mV.

II. Use of Novel Gold Nanocrystals

The gold nanocrystals of the present invention can be used to treat any disorder for which gold therapy is known to be effective, which includes a broad range of inflammatory and autoimmune disorders as well as certain infectious diseases and cancer. Descriptions of many of these uses are provided in the Background of the Invention, above, or otherwise, in more detail below.

The subject to be treated may be human or other animal such as a mammal. Non-human subjects include, but are not limited to primates, livestock animals (e.g., sheep, cows, horses, pigs, goats), domestic animals (e.g., dogs, cats), birds and other animals (e.g., mice, rats, guinea pigs, rabbits).

Importantly, it has now been surprisingly discovered as part of this invention that the gold nanoparticles (and in particular the gold nanocrystals described in detail herein) inhibit macrophage Migration Inhibitory Factor ("MIF"). It is believed that this is the first disclosure of such activity of gold nanoparticles, and may provide a scientific basis to understand the range of medical uses for gold compositions to date. It also provides a scientific basis to conclude that the gold nanoparticles will be effective against other diseases which are mediated by macrophage migration inhibitory factor. In addition, it has been identified that these gold nanocrystals inhibit IL-6 but not IL-10. Because MIF and/or IL-6 is/are indicated in a large variety of conditions and/or biological signaling pathways, such finding confirms that the novel gold nanocrystals will be effective for the treatment or prevention of diseases or conditions resulting from pathological cellular activation, such as inflammatory (including chronic inflammatory) conditions, autoimmune conditions, certain infections, hypersensitivity reactions and/or cancerous diseases or conditions.

MIF is a macrophage derived multifunctional cytokine important in a number of pro-inflammatory events. MIF was originally described as a product of activated T-lymphocytes that inhibits the random migration of macrophages. While MIF was initially found to activate macrophages at inflammatory sites, MIF has now been shown to mediate a range of signaling agents in the immune system. MIF has been shown to be expressed in human and animal diseases or conditions which include infection, inflammation, injury, ischaemia and/or malignancy. MIF appears to have a key role in cell proliferation, cell differentiation, angiogenesis and wound healing. MIF also seems to mediate glucocorticoid (steroids) activity by counteracting at least some of their anti-inflammatory effects.

As shown in Examples 25 and 26, the nanocrystalline compositions of the present invention are very effective in the animal models for CIA and EAE. A connection between these two animal models (as well as human disease state) is the presence of MIF.

Recent studies have indicated that monoclonal antibody antagonism of MIF may be useful in the treatment of sepsis, certain types of cancers and delayed type hypersensitivity. It appears that sepsis is triggered by an over-reaction of the inflammation and immune systems. In certain infections, upon attack by microorganisms, the innate immune system reacts first, whereby neutrophils, macrophages and natural killer cells ("NK cells") are mobilized. Cytokines (and MIF) thus play an important role as mediators, which regulate activation and differentiation of these cells. Finally, the innate immune system interacts with the adaptive immune system via these and other stimulating molecules, upon which the adaptive immune system has the ability of constructing an immunological memory in addition to providing pathogen specific protection.

MIF is seen as a major mediator in sepsis, as MIF incites the production of TNF, other pro-inflammatory cytokines and eicosanoids, induces the expression of TLR-4, which recognizes LPS, and appears to resist in activating the innate immune response. MIF and glucocorticoids act as antagonists and are at least partially responsible for regulating the inflammatory reaction. MIF has an inhibiting effect on glucocorticoids, which typically inhibit inflammation.

Therapeutic antagonism of MIF can provide "steroid-sparing" effects or can even be therapeutic in "steroid-resistant" diseases. Unlike other pro-inflammatory molecules, such as certain cytokines, the expression and/or release of MIF is coupled to (e.g., can be induced by) glucocorticoids. MIF seems to be able to antagonize the effects of glucocorticoids. MIF has a major role in regulating pro-inflammatory cytokines. This has been shown to be the case for macrophages secreting TNF, IL-1.beta., IL-6 and IL-8. MIF also regulates IL-2 release. MIF also has a role in regulating T cell proliferation. In vivo, MIF exerts a powerful glucocorticoid-antagonist effect in models including endotoxic shock and experimental arthritis (e.g., collagen-induced arthritis or "CIA" models, such as the one utilized in a later example herein and models of other inflammatory conditions and immune diseases including colitis, multiple sclerosis (i.e., the EAE model discussed in greater detail in Example 26), atherosclerosis, glomerulonephritis, uveitis and certain cancers).

Further, MIF has recently been shown to be important in the control of leukocyte-endothelial interactions. Leukocytes interact with vascular endothelial cells in order to gain egress from the vasculature into tissues. The role of MIF in these processes has been demonstrated to affect leukocyte-endothelial adhesion and migration. These processes seem to be an essential part of nearly all inflammatory diseases, and also for diseases less well-identified as inflammatory including, for example, atherosclerosis.

MIF is also expressed in plants (thus "MIF" may also refer to plant MIF) and where appropriate, the inventive gold nanocrystal suspensions (e.g., comprising aqueous gold-based metal nanocrystals and/or mixtures of gold nanocrystals and other metal(s) and/or alloys of gold nanocrystals with other metal(s) and/or a combination therapy approach) may be used in botanical/agricultural applications such as crop control.

MIF is a key cytokine in switching the nature of the immune response. The immune response has two effector mechanisms. The Th1 immune response generates cytotoxic T cells that kill pathogens and damaged/defunct cells. The Th2 response generates antibodies that facilitate phagocytosis and activate complement. The role of MIF in determining the polarization of the immune system is dependent on other cytokines such as IL-10. IL-10 is a potent anti-inflammatory cytokine that blocks the action of MIF on Th1 cells and leads to the generation of a Th2 response. In the absence of IL-10 MIF will stimulate Th1 cells to produce a cytotoxic response. IL10 is produced by Monocytes and B cells in response to stimulation, whereas MIF is, for example, independently produced and stored in the pituitary and T cells. MIF therefore plays an important role in both T Cytotoxic cell mediated diseases—such as rheumatoid arthritis and Crohns, and antibody mediated diseases such as idiopathic thrombocytopenia.

Without wishing to be bound by any particular theory or explanation, when reference is made herein to "one or more signaling pathway(s)" it should be understood as meaning that MIF, or at least one protein associated with MIF (e.g., including receptor sites such as CD74 receptor sites) is/are implicated in the innate immune system (e.g., NK and phagocyte cells, complement proteins (e.g., C5a) and/or inflammatory pathways) and the adaptive immune systems (e.g., the T cell dependent cytotoxicity (Th1) and antibody (Th2) pathways). For example, when MIF is involved in the Th1 signaling pathway generating T Cytotoxic cells other proteins such as, for example, IL6, TNF, and other cytokines are also involved.

When the Th1 signaling pathway is overactive, a variety of diseases can result, such as rheumatic diseases, connective tissue diseases, vasculitides, inflammatory conditions, vascular diseases, ocular diseases, pulmonary diseases, cancers, renal diseases, nervous system disorders, complications of infective disorders, allergic diseases, bone diseases, skin diseases, Type 1 Diabetes, Crohn's Disease, MS and gastrointestinal diseases, etc. Accordingly, by reducing the amount of MIF function associated with this particular Th1 signaling pathway, chronic disease conditions can be mitigated.

In contrast, again without wishing to be bound by any particular theory or explanation, when the Th2 signaling pathway is over-active, the production of various antibodies occurs leading to diseases such as, for example and including, hemolytic anemia, ITP (Idiopathic Thrombocytopenic Purpura), Hemolytic Disease of the newborn, etc. Furthermore, over-activity of this Th2 signaling pathway can result in an under-activity of the Th1 pathway, thus permitting various parasites or cancers to thrive. For example, in the case of malaria where over production of one or more homologues of MIF leads to the generation of an ineffective antibody response that is ineffective against the parasite (e.g., it is plausible that a variety of crystal forms or homologues of MIF (or equivalents thereto) are made or presented by a variety of bacteria, parasites, virus, fungi, etc., each of which may have different reactivity relative to, for example, "ordinary" human MIF, and which may alter host immune response so as to create at least local environments of "immune privilege"). Accordingly, by reducing the amount of MIF function associated with this particular Th2 signaling pathway, other disease conditions can be mitigated.

Still further, without wishing to be bound by any particular theory or explanation, MIF also has a role in driving the signaling pathway associated with innate immunity. This pathway involves the activation of natural killer ("NK") cells, phagocytes and other non-specific pathogen cell types and certain proteins such as complement proteins (e.g., C5a). Excess MIF (and/or MIF homologues), or similar effects of the same, can result in undesirable over-expression or over-reaction in this particular signaling pathway as seen in multiple organ failure as a result of sepsis. Examples include the Systemic Inflammatory Response Syndrome (SIRS). Accordingly, by reducing the amount of MIF activity associated with this particular signaling pathway many inflammatory diseases can be mitigated.

Accordingly when endogenous MIF is present (e.g., in excess under local environmental conditions), as measured by, for example, known body fluid measuring techniques such as ELISA, spectroscopy, etc., it is possible that one or more innate or adaptive immune system signaling pathways may over-express, over activate or over-produce inflammatory/immunological components. If for example, one or more forms of MIF present causes the production of an excessive T Cytotoxic response, or an excessive antibody response or an exaggerated NK/phagocyte cell response, human disease can result. When, for example, too many T Cytotoxic cells are expressed, a variety of chronic inflammatory conditions can result. Similarly when excessive Th2 or innate responses are facilitated by MIF, other diseases are produced.

Still further, it is also known that malaria parasites, and other parasites such as nematodes and filarial worms, and some cancers produce certain types of exogenous or non-regulated MIF or MIF homologues. Again, without wishing to be bound by any particular theory or explanation, it appears that exogenous expression of MIF, or its homologues, leads to stimulation of the Th2 signaling pathway, and may be an attempt by the parasite, or the tumor, (i.e., "the invader") to create a state where the immune response is activated by MIF or its homologues such that that the activated particular signaling pathway is not detrimental to the tumor or the parasite, etc.

With regard to, for example, a malaria parasite, the parasite may stimulate the Th2 signaling pathway by providing excess exogenous MIF resulting in the production of antibodies rather than T Cytotoxic cells. However, such antibodies do not typically harm the parasite. Therefore, the parasite appears to create at least a local area of immune privilege. In this regard if an alternative pathway such as, for example, the Th1 pathway, or the natural killer (NK) cell pathway, can be re-activated, damage could then occur to the parasite (e.g., the immune system could remove the parasite). However, if excess antibodies or other immune/inflammatory products are created, for example, as a result of the preferential activation of the Th2 pathway, it is possible that the excess antibodies will end up cross-linking to various cell sites or activating other immunological molecules. When such cross-linking or activation occurs, a very large inflammatory response could result. Without wishing to be bound by any particular theory or explanation, it is possible that this inflammatory response is precisely the response that occurs in women who are pregnant and are infected with malaria making them vulnerable to severe malaria, and the anemia of malaria. It is believed that pregnant women are particularly susceptible to this effect, due to the immunological effects of the placenta in promoting a Th2 response and sequestering parasites in this immune-privileged zone.

Again, without wishing to be bound by any particular theory or explanation, cancer cells also express MIF apparently in an attempt to at least partially control immune response thereto and/or promote their own growth. In this regard, it appears that cancer cells are also attempting to manipulate the immune system to follow the Th2 signaling pathway, in contrast to the Th1 signaling pathway which could damage or kill the cancer cells. For example, by causing local immune privilege to be created, there is no (or little) particular risk to cancer cells. In contrast, if MIF was to stimulate the Th1 signaling pathway, then a cytokine cell/inflammatory response may result, causing damage or death to the cancer cells (e.g., the tumor could be naturally eliminated by the immune system).

Again, without wishing to be bound by any particular theory or explanation, children possess an immature immune system, particularly the innate and Th1 pathways. This immaturity in some children results in altered MIF metabolism. It thus appears that the modulation of MIF in children could result in the prevention or improvement of infectious or inflammatory diseases.

Accordingly, without wishing to be bound by any particular theory or explanation, the inventive gold nanocrystal suspensions of the present invention can be used to modify one or more signaling pathways (e.g., Th1 signaling pathway, Th2 signaling pathway and/or innate immunity pathway) either alone or in conjunction with other therapies that modulate signaling pathways. Thus, by interacting with or controlling the MIF (or MIF homologue) associated with one or more signaling pathway(s), various immunological responses can be turned on and/or can be turned off. Accordingly, the response along the Th1 and Th2 signaling pathways for the creation of T Cytotoxic cells or antibodies can be turned on, or can be turned off (e.g., the Th1-Th2 switch can be controlled to direct more or less of either immune pathway being invoked). Similarly, the innate immune system and resultant inflammation can be turned on or can be turned off.

With the knowledge that one or more signaling pathways can be turned on/off, very important therapeutic treatments can thus occur. For example, a variety of surrogate endpoints can be monitored or examined for a variety of different diseases, including, for example, many cancers. For example, the antigen, "carcino-embryonic antigen" or "CEA" is a known surrogate endpoint marker for the amount of tumor or the amount of tumor burden present in a variety of different cancers. For example, it is known that the higher the CEA amount, the more tumors there are associated with ovarian cancer, breast cancer, colon cancer, rectal cancer, pancreatic cancer, lung cancer, etc. In this regard, the amount of carcino-embryonic antigen can be measured by, for example, drawing blood and testing for the presence of CEA by known techniques including, for example, ELISA and certain spectroscopy techniques. In this regard, once blood is drawn and a measurement is made to determine the amount of CEA, the extent of treatment required (e.g., the dose, duration and/or the amount) can be driven by monitoring the change in the amount of CEA measured. For example, if 15-45 ml of 10 ppm product is taken 2-3 times per day, monitoring of the amount of CEA could cause an increase in dosage, or a decrease in dosage, depending on the desired outcome.

Likewise, prostate cancer has a known surrogate endpoint of "prostate-specific antigen" or "PSA". This surrogate endpoint can also be monitored by drawing blood and searching for the same by ELISA techniques.

Still further, various cancers, like melanoma (e.g., ocular, etc.) also express antigens for example "GP100" and/or "Melan-A". These surrogate endpoints can also be determined by drawing blood from a patient and then measuring by similar ELISA or spectrographic techniques for the amount of antigen present. In all such cases, the presence of antigen can cause an increase/decrease in the amount of therapeutic treatment provided.

The following "Table A" sets forth a number of known "Tumor Markers" and associated cancers, as well as where biological samples are drawn to measure such markers.

TABLE A

Common Tumor Markers Currently in Use

| Tumor Markers | Cancers | Usual sample |
| --- | --- | --- |
| AFP (Alpha-feto protein) | Liver, germ cell cancer of ovaries or testes | Blood |
| B2M (Beta-2 microglobulin) | Multiple myeloma and lymphomas | Blood |
| CA 15-3 (Cancer antigen 15-3) | Breast cancer and others, including lung, ovarian | Blood |
| CA 19-9 (Cancer antigen 19-9) | Pancreatic, sometimes colorectal and bile ducts | Blood |
| CA-125 (Cancer antigen 125) | Ovarian | Blood |
| Calcitonin | Thyroid medullary carcinoma | Blood |
| CEA (Carcino-embryonic antigen) | Colorectal, lung, breast, thyroid, pancreatic, liver, cervix, and bladder | Blood |
| Chromogranin A (CgA) | Neuroendocrine tumors (carcinoid tumors, neuroblastoma) | Blood |
| Estrogen receptors | Breast | Tissue |
| hCG (Human chorionic gonadotropin) | Testicular and trophoblastic disease | Blood, urine |
| Her-2/neu | Breast | Tissue |
| Monoclonal immunoglobulins | Multiple myeloma and Waldenstrom's macroglobulinemia | Blood, urine |
| Progesterone receptors | Breast | Tissue |
| PSA (Prostate specific antigen), total and free | Prostate | Blood |
| Thyroglobulin | Thyroid | Blood |
| Other Tumor Markers Less Widely Used | | |
| BTA (Bladder tumor antigen) | Bladder | Urine |
| CA 72-4 (Cancer antigen 72-4) | Ovarian | Blood |
| Des-gamma-carboxy prothrombin (DCP) | Hepatocellular carcinoma (HCC) | Blood |
| EGFR (Her-1) | Solid tumors, such as of the lung (non small cell), head and neck, colon, pancreas, or breast | Tissue |
| NSE (Neuron-specific enolase) | Neuroblastoma, small cell lung cancer | Blood |
| NMP22 | Bladder | Urine |
| Prostatic acid phosphatase (PAP) | Metastatic prostate cancer, myeloma, lung cancer | Blood |
| Soluble Mesothelin-Related Peptides (SMRP) | Mesothelioma | Blood |

Still further, various diseases of immune and inflammation dysfunction, like rheumatoid arthritis and Crohn's can be assessed using inflammatory markers such as C Reactive Protein (CRP) or erythrocyte sedimentation rate (ESR). These surrogate endpoints can also be determined by drawing blood from a patient and then measuring by visual ELISA or spectrographic techniques for the amount of marker present. In all such cases, the change in an inflammatory/immune marker can cause an increase/decrease in the amount of therapeutic treatment provided.

Still further, various antibody-based diseases, like hemolytic anemia or Rhesus disease, can be monitored by the concentration of specific antibodies present. These surrogate endpoints can also be determined by drawing blood from a patient and then measuring, by similar ELISA or spectrographic techniques, for the amount of antibody present. In all such cases, the presence of antibody can cause an increase/decrease in the amount of therapeutic treatment provided.

Inhibitors or modifiers of MIF and/or one or more of MIF's signaling pathway(s) may also be used in implantable devices such as stents. Accordingly, in a further aspect the present invention provides an implantable device, preferably a stent, comprising:

(i) a reservoir containing at least one compound of metallic-based compound comprising gold solutions or colloids and mixtures and alloys thereof; and (ii) means to release or elute the inhibitor or modifier from the reservoir.

According to the invention therefore, there are a variety of indications that the nanocrystalline gold-based therapies of the present invention will have desirable efficacy against including various autoimmune diseases, tumors, or chronic or acute inflammatory conditions or diseases, disorders, syndromes, states, tendencies or predispositions, etc., selected from the group comprising:

rheumatic diseases (including but not limited to rheumatoid arthritis, osteoarthritis, psoriatic arthritis, Still's disease) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;

connective tissue diseases (including but not limited to systemic lupus erythematosus, systemic sclerosis, scleroderma, polymyositis, dermatomyositis, Sjogren's syndrome);

vasculitides (including but not limited to polyarteritis nodosa, Wegener's granulomatosis, Churg-Strauss syndrome);

inflammatory conditions or tendencies including consequences of trauma or ischaemia;

sarcoidosis;

vascular diseases including atherosclerotic vascular disease and infarction, atherosclerosis, and vascular occlusive disease (including but not limited to atherosclerosis, ischaemic heart disease, myocardial infarction, stroke, peripheral vascular disease), and vascular stent restenosis;

ocular diseases including uveitis, corneal disease, iritis, iridocyclitis, and cataracts;

autoimmune diseases (including but not limited to diabetes mellitus, thyroiditis, myasthenia gravis, sclerosing cholangitis, primary biliary cirrhosis);

pulmonary diseases (including but not limited to diffuse interstitial lung diseases, pneumoconiosis, fibrosing alveolitis, asthma, bronchitis, bronchiectasis, chronic obstructive pulmonary disease, adult respiratory distress syndrome);

cancers whether primary or metastatic (including but not limited to prostate cancer, colon cancer, bladder cancer, kidney cancer, lymphoma, lung cancer, melanoma, multiple myeloma, breast cancer, stomach cancer, leukaemia, cervical cancer and metastatic cancer);

renal diseases including glomerulonephritis, interstitial nephritis;

disorders of the hypothalamic-pituitary-adrenal axis;

nervous system disorders including multiple sclerosis, Alzheimer's disease, Parkinson's Disease, Huntington's disease;

diseases characterized by modified angiogenesis (e.g., diabetic retinopathy, rheumatoid arthritis, cancer) and endometriosis;

infectious diseases, including but not limited to bacterial, parasites or viral, including HIV, HBV, HCV, tuberculosis, malaria, and worms (including the current FDA designated neglected diseases of the developing world);

complications of infective disorders including endotoxic (septic) shock, exotoxic (septic) shock, infective (true septic) shock, complications of malaria (e.g., cerebral malaria and anemia), other complications of infection, and pelvic inflammatory disease;

transplant rejection, graft-versus-host disease;

allergic diseases including allergies, atopic diseases, allergic rhinitis;

bone diseases (e.g., osteoporosis, Paget's disease);

skin diseases including psoriasis, eczema, atopic dermatitis, UV(B)-induced dermal cell activation (e.g., sunburn, skin cancer);

diabetes mellitus and its complications;

pain, testicular dysfunctions and wound healing;

gastrointestinal diseases including inflammatory bowel disease (including but not limited to ulcerative colitis, Crohn's disease), peptic ulceration, gastritis, oesophagitis, liver disease (including but not limited to cirrhosis and hepatitis).

In one embodiment, the disease or condition is selected from the group consisting of rheumatoid arthritis, osteo arthritis, systemic lupus erythematosus, ulcerative colitis, Crohn's disease, multiple sclerosis, psoriasis, eczema, uveitis, diabetes mellitus, glomerulonephritis, atherosclerotic vascular disease and infarction, asthma, chronic obstructive pulmonary disease, HIV, HBV, HCV, tuberculosis, malaria, worms, and cancer(s).

III. Pharmaceutical Compositions

Pharmaceutical compositions which include an effective amount of the gold nanocrystals to treat any of the medical conditions described in this application are also provided. In a preferred embodiment, the gold nanocrystals are administered in an orally delivered liquid, wherein the gold nanocrystals remain in the water of manufacture which may be concentrated or reconstituted, but preferable not dried to the point that the surfaces of the gold nanocrystals become completely dry or have their surfaces otherwise altered from their pristine state of manufacture.

Based on experiments, it appears that the present gold nanocrystals are a more potent form of gold than prior art gold-based materials, including both FDA-approved gold-based pharmaceutical products, and non-FDA-approved gold colloids, due to the substantially clean very active crystalline surfaces. Because of this, it is expected that significantly lower doses of the present nanocrystals can be used, than dose levels required by prior art compositions, including the oral gold product Auranofin.

For example, in the widely accepted collagen induced arthritis mouse model, a standard dose is 40 mg/kg/day of Auranofin, which is approximately 1 mg/mouse/day of Auranofin and 0.30 mg gold/day of gold contained in Auranofin. This standard Auranofin dose level appears to give an equivalent response to that resulting from a dose of about 0.06 mg/day of the gold nanocrystals of the present invention (Example 25). Thus, in such experiment, the present nanocrystals were calculated to be 17 times more potent than was the Auranofin, and 5 times more potent than the gold species contained in the Auranofin.

The standard FDA-approved dose level for Auranofin in humans is 6 mg/day, or 0.9 mg/kg/day. The gold contained in that human dose levels of Auranofin is 1.74 mg, or 0.025 mg/kg. Given the relative potency of the novel gold nanocrystals compared to that of Auranofin, as demonstrated in the live animal model, an approximate human dose level for the novel gold nanocrystal can be calculated by dividing the human dose level for Auranofin by the relative potency factor of 17×, or by dividing the human dose level of the gold contained in the Auranofin by the relative potency factor of 5×. This results in an approximate human dose level for the novel gold nanocrystals of 0.35 mg/day, versus the 6 mg/day required for Auranofin, and 1.74 mg/day required for gold contained in Auranofin. 0.35 mg/day, for a 70 kg human being, is a dose of 0.005 mg/kg/day.

It is normal in developing dosing levels to establish a range of one order of magnitude or more surrounding an estimated mg/kg dose. In this case, if the approximate suggested base dose is 1/17 that of the base dose of Auranofin, or 0.348 mg/day, which is 0.005 mg/kg/day, this suggests that an effective dosing range for Auranofin-like efficacy with the novel nanocrystals can be achieved at dosing levels of 0.005 mg/kg/day, and even greater efficacy at levels in the range of 0.01 mg/kg/day or 0.25 mg/kg/day.

It is important to recognize that in pharmaceutical products the objective is to establish the minimum dose necessary to achieve efficacy, thus minimizing potential for toxicity or complications. A new orally administered product with significantly greater potency can achieve efficacy at dose levels below those of prior art products, and/or can achieve substantially greater efficacy at equivalent dose levels.

Moreover, it is observed in animal trials that toxicity levels of the novel nanocrystals are low, even at maximum dose levels, which means that even at higher dose levels there is less toxicity than with current products such as Auranofin.

It has also been observed in mice that a therapeutic effect is seen faster than with Auranofin, which has a typical onset of action of weeks, compared to days for the present nanocrystals (See Example 25). This is a major advantage in use, since it means patients enjoy relief sooner, and are much more likely to continue to comply with the regimen and thus continue to benefit from the product.

It has further been observed that the present gold nanocrystals have a better therapeutic index than Auranofin due to the lower dose required to achieve efficacy and a the associated lower toxicity.

It is also important to recognize that to have real value as a pharmaceutical treatment, a product must be manufacturable under high pharmaceutical-grade manufacturing, sourcing, and quality control standards, as defined by the FDA as Good Manufacturing Practice (GMP). Conventional gold nanoparticles are made by a variety of methods, most of which involve chemical reduction processes. There appear to be no current chemical reduction or other conventional processes for production of gold nanoparticles which comply with GMP, and given the nature of these processes, it appears that GMP compliance, if possible, will be extremely challenging and will require substantial time, money, and inventive engineering to achieve. The process by which the present novel gold nanocrystals are produced is designed to be GMP compliant, establishing another major difference and advantage of the present gold nanocrystals.

While clinical trials are required to confirm the therapeutically efficacious dose, it is reasonable to conclude that doses ranging from 0.05 mgs or more (or 0.1, 0.5, 1.0, 2.0 mg or more) to 10 mg or more per dosage (once, twice or multiple times per day) are effective in a human to treat any of the conditions described herein. Given the low toxicity of these gold nanocrystals, for more problematic disorders it is appropriate to use at higher dose levels, including but not limited dosages of 10 mgs or more, such as 20 mg or more per dosage.

Any concentration of gold nanocrystals can be provided according to the invention. For example, concentrations of these gold nanocrystals can be a few parts per million (i.e., µg/ml or mg/l) up to a few hundred ppm, but are typically in the range of 2-200 ppm (i.e., 2 µg/ml-200 µg/ml) and more often in the range of 2-50 ppm (i.e., 2 µg/ml-50 µg/ml). A typical convenient concentration may be around 5-20 µg/ml, and more typically about 8-15 µg/ml.

Pharmaceutical compositions are provided that are appropriate for systemic or topical use, including oral, intravenous, subcutaneous, intra-arterial, buccal, inhalation, aerosol, propellant or other appropriate liquid, etc, as described further herein, including specific gels or creams discussed in Example 23.

Alternatively, suitable dosages of active ingredient may lie within the range of about 0.1 ng per kg of body weight to about 1 g per kg of body weight per dosage. The dosage is typically in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts and dosing regimens can be determined by the attending physician or veterinarian and may depend on the desired level of inhibiting and/or modifying activity, the particular condition being treated, the severity of the condition, whether the dosage is preventative or therapeutic, as well as the general age, health and weight of the subject.

The gold nanocrystals contained in, for example, an aqueous medium, colloid, suspension, foam, gel, paste, liquid, cream or the like, may be administered in a single dose or a series of doses. While it is possible for the aqueous medium containing the metallic-based nanocrystals to be administered alone in, for example, colloid form, it may be acceptable to include the active ingredient mixture with other compositions and or therapies. Further, various pharmaceutical compositions can be added to the active ingredient(s)/suspension(s)/colloid(s).

Accordingly, typically, the inventive gold nanocrystal suspensions or colloids (e.g., comprising aqueous gold-based metal and/or mixtures of gold and other metal(s) and/or alloys of gold with other metal(s) and/or a combination therapy approach) are administered in conjunction with a second therapeutic agent. More typically, the second therapeutic agent comprises a glucocorticoid.

In a further aspect of the invention, there is provided a pharmaceutical composition comprising the inventive gold nanocrystal suspensions or colloids (e.g., comprising aqueous gold-based metal and/or mixtures of gold and other metal(s) and/or alloys of gold with other metal(s) and/or a combination therapy approach) together with a pharmaceutically acceptable carrier, diluent or excipient. The formulation of such compositions is well known to those skilled in the art. The composition may contain pharmaceutically acceptable additives such as carriers, diluents or excipients. These include, where appropriate, all conventional solvents, dispersion agents, fillers, solid earners, coating agents, antifungal and/or antibacterial agents, dermal penetration agents, ibuprofen, ketoprofen, surfactants, isotonic and absorption agents and the like. It will be understood that the compositions of the invention may also include other supplementary physiologically active agents. Still further, a large variety of dietary supplements and homeopathic carriers can also be utilized. Specifically, choices of such ingredients can be based in part on known functionality or use of these ingredients such that when combined with active ingredients of the invention, additive or synergistic affects can be achieved.

The carrier should be pharmaceutically acceptable in the sense of being compatible with the other ingredients in the inventive gold nanocrystal suspensions and not injurious (e.g., toxic at therapeutically active amounts) to the subject. Compositions include those suitable for oral, rectal, inhalational, nasal, transdermal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy, homeopathy and/or dietary supplements. Such methods include the step of bringing into association the inventive metallic-based nanocrystals or suspensions with the carrier which constitutes one or more accessory ingredients. In general, the compositions are prepared by uniformly and intimately bringing into association one or more active ingredients in the solution/colloid under appropriate non-reactive conditions which minimize or eliminate, to the extent possible, negative or adverse reactions.

Depending on the disease or condition to be treated, it may or may not be desirable for the inventive gold nanocrystal suspensions or colloids to cross the blood/brain barrier.

Thus, the gold nanocrystal suspensions or colloids of the present invention may be manufactured to be of desirable size, desirable crystal plane(s) and/or desirable shapes or shape distributions, etc (as discussed elsewhere herein) to assist in crossing the blood/brain barrier.

Gold nanocrystal suspensions according to the present invention suitable for oral administration are presented typically as a stable solution, colloid or a partially stable suspension in water. However, such gold nanocrystals may also be included in a non-aqueous liquid, as discrete units such as liquid capsules, sachets or even tablets (e.g., drying-out suspensions or colloids to result in active ingredient gold-based nanocrystals so long as such processing does not adversely affect the functionality of the pristine gold nanocrystal surfaces) each containing a predetermined amount of, for example, the gold nanocrystal active ingredient; as a powder or granules; as a solution, colloid or a suspension in an aqueous or as non-aqueous liquid; or as an oil-in-water liquid emulsion or a water-in-oil liquid emulsion. The gold nanocrystal active ingredient may also be combined into a bolus, electuary or paste.

A tablet made from the inventive gold nanocrystal suspensions or colloids (e.g., comprising aqueous gold-based nanocrystals and/or alloys of gold with other metal(s) and/or a combination therapy approach) and other materials or compounds may be made by, for example, first drying the suspension or colloid, collecting residual dried material and by compression or molding, forcing the powder into a suitable tablet or the like. For example, compressed tablets may be prepared by compressing in a suitable machine the active ingredient nanocrystals, for example, the metallic-based nanocrystals, in a free-flowing form such as a powder or granules, optionally mixed with a binder (e.g., inert diluent, preservative, disintegrant (e.g., sodium starch glycolate, cross-linked polyvinyl pyrrolidone, cross-linked sodium carboxymethyl cellulose)) surface-active or dispersing agent. Molded tablets may be made by, for example, molding or pressing in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide for release in parts of the gut other than the stomach.

Compositions suitable for topical administration in the mouth include lozenges comprising suspensions or colloids containing one or more active ingredient(s) gold nanocrystal in a flavored base, such as sucrose and acacia or tragacanth gum; pastilles comprising the gold nanocrystal active ingredient in an inert base such as a gelatin and a glycerin, or sucrose and acacia gum; and mouthwashes comprising the gold nanocrystal active ingredient in a suitable liquid carrier.

The inventive gold nanocrystal suspensions or colloids (e.g., comprising aqueous gold-based metal and/or mixtures of gold and other metal(s) and/or alloys of gold with other metal(s) and/or a combination therapy approach) may also be administered intranasally or via inhalation, for example by atomiser, aerosol or nebulizer means for causing one or more constituents in the solution or colloid (e.g., the gold nanocrystals) to be, for example, contained within a mist or spray.

Compositions suitable for topical administration to the skin may comprise the gold nanocrystals of the invention suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol, carbopol and water. Transdermal devices, such as patches, may also be used to administer the compounds of the invention.

Compositions for rectal administration may be presented as a suppository with a suitable carrier base comprising, for example, cocoa butter, gelatin, glycerin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection suspensions or colloids which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions, colloids and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the gold nanocrystal active ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants, time delay agents and/or position release agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl mono stearate or glyceryl distearate.

Further, by following the inventive electrochemical manufacturing processes of the invention, these gold-based metallic nanocrystals can be alloyed or combined with other metals in liquids such that gold "coatings" may occur on other metals (or other non-metal species such as $SiO_2$, for example) or alternatively, gold-based nanocrystals may be coated by other metals. In such cases, gold-based composites or alloys may result within a colloid or suspension. Further, certain composites which include both gold and other metals can also be formed.

Still further, gold-based metallic nanocrystals suspensions or colloids of the present invention can be mixed or combined with other metallic-based solutions or colloids to form novel solution or colloid mixtures (e.g., in this instance, distinct metal species can still be discerned).

IV. Method of Manufacturing Gold Nanocrystals

A novel process is provided to produce these unique gold nanocrystals. The process involves the creation of the gold nanocrystals in water. In a preferred embodiment, the water contains an added "process enhancer" which does not significantly bind to the formed nanocrystals, but rather facilitates nucleation/crystal growth during the electrochemical-stimulated growth process. The process enhancer serves important roles in the process including providing charged ions in the electrochemical solution to permit the crystals to be grown. These novel electrochemical processes can occur in either a batch, semi-continuous or continuous process. These processes result in controlled gold nanocrystalline concentrations, controlled nanocrystal sizes and controlled nanocrystal size ranges; as well as controlled nanocrystal shapes and controlled nanocrystal shape distributions. Novel manufacturing assemblies are provided to produce these gold nanocrystals.

In one preferred embodiment, the gold-based nanocrystal suspensions or colloids are made or grown by electrochemical techniques in either a batch, semi-continuous or continuous process, wherein the amount, average particle size, crystal plane(s) and/or particle shape(s) and/or particle shape distributions are controlled and/or optimized to achieve high biological activity and low cellular/biologic toxicity (e.g., a high therapeutic index). Desirable average crystal sizes include a variety of different ranges, but the most desirable ranges include average crystal sizes that are predominantly less than 100 nm and more typically, for many uses, less than 50 nm and even more typically for a variety of, for example, oral uses, less than 30 nm, and in many of the preferred embodiments disclosed herein, the mode for the nanocrystal size distribution is less than 21 nm and within an even more preferable range of 8-18 nm, as measured by drying such solutions and constructing particle size histograms from TEM measurements (as described in more detail herein). Further, the particles desirably contain crystal planes, such desirable crystal planes including crystals having {111}, {110} and/or {100} facets, which can result in desirable crystal shapes and desirable crystal shape distributions and better performance than gold spherical or randomly-shaped particles.

Further, by following the inventive electrochemical manufacturing processes of the invention, these gold-based metallic nanocrystals can be alloyed or combined with other metals in liquids such that gold "coatings" may occur on other metals (or other non-metal species such as $SiO_2$, for example) or alternatively, gold-based nanocrystals may be coated by other metals. In such cases, gold-based composites or alloys may result within a colloid or suspension. Further, certain composites which include both gold and other metals can also be formed.

Still further, gold-based metallic nanocrystals suspensions or colloids of the present invention can be mixed or combined with other metallic-based solutions or colloids to form novel solution or colloid mixtures (e.g., in this instance, distinct metal species can still be discerned).

Methods for making novel metallic-based nanocrystal suspensions or colloids according to the invention relate generally to novel methods and novel devices for the continuous, semi-continuous and batch manufacture of a variety of constituents in a liquid including micron-sized particles, nanocrystals, ionic species and aqueous-based compositions of the same, including, nanocrystal/liquid(s), solution(s), colloid(s) or suspension(s). The constituents and nanocrystals produced can comprise a variety of possible compositions, concentrations, sizes, crystal planes (e.g., spatially extended low index crystal planes) and/or shapes, which together can cause the inventive compositions to exhibit a variety of novel and interesting physical, catalytic, biocatalytic and/or biophysical properties. The liquid(s) used and created/modified during the process can play an important role in the manufacturing of, and/or the functioning of the constituents (e.g., nanocrystals) independently or synergistically with the liquids which contain them. The particles (e.g., nanocrystals) are caused to be present (e.g., created and/or the liquid is predisposed to their presence (e.g., conditioned)) in at least one liquid (e.g., water) by, for example, typically utilizing at least one adjustable plasma (e.g., created by at least one AC and/or DC power source), which adjustable plasma communicates with at least a portion of a surface of the liquid. However, effective constituent (e.g., nanocrystals) suspensions or colloids can be achieved without the use of such plasmas as well.

Metal-based electrodes of various composition(s) and/or unique configurations or arrangements are preferred for use in the formation of the adjustable plasma(s), but non-metallic-based electrodes can also be utilized for at least a portion of the process. Utilization of at least one subsequent and/or substantially simultaneous adjustable electrochemical processing technique is also preferred. Metal-based electrodes of various composition(s) and/or unique configurations are preferred for use in the electrochemical processing technique(s). Electric fields, magnetic fields, electromagnetic fields, electrochemistry, pH, zeta potential, chemical/crystal constituents present, etc., are just some of the variables that can be positively affected by the adjustable plasma(s) and/or adjustable electrochemical processing technique(s) of the invention. Multiple adjustable plasmas and/or adjustable electrochemical techniques are preferred in many embodiments of the invention to achieve many of the processing advantages of the present invention, as well as many of the novel nanocrystals and nanocrystal compositions which result from practicing the teachings of the preferred embodiments to make an almost limitless set of inventive aqueous solutions, suspensions and/or colloids.

In the continuous process embodiments of the invention, at least one liquid, for example water, flows into, through and out of at least one trough member and such liquid is processed, conditioned, modified and/or effected by said at least one adjustable plasma and/or said at least one adjustable electrochemical technique. The results of the continuous processing include new constituents in the liquid, micron-sized particles, ionic constituents, nanocrystals (e.g., metallic-based nanocrystals) of novel and/or controllable size, hydrodynamic radius, concentration, crystal sizes and crystal size ranges, crystal planes, spatially extended low index crystal planes, crystal shapes and distributions of crystal shapes and, composition, zeta potential, pH and/or properties, such nanocrystal/liquid mixture being produced in an efficient and economical manner.

In a preferred embodiment, the process involves the nucleation and growth of the gold nanocrystals in water which contains a "process enhancer" or "processing enhancer" (typically an inorganic material) which does not significantly bind to the formed nanocrystals, but rather facilitates nucleation/growth during electrochemical-stimulated growth process. The process enhancer serves important roles in the process including providing charged ions in the electrochemical solution to permit the crystals to be grown. The process enhancer is critically a compound(s) which remains in solution, and/or does not form a coating (e.g., an organic coating), and/or does not adversely affect the formed nanocrystals or the formed suspension(s), and/or is destroyed, evaporated, or is otherwise lost during the electrochemical process. A preferred process enhancer is sodium bicarbonate. Examples of other process enhancers are sodium carbonate, potassium bicarbonate, potassium carbonate, trisodium phosphate, disodium phosphate, monosodium phosphate, potassium phosphates or other salts of carbonic acid or the like. Further process enhancers may be salts, including sodium or potassium, of bisulfate or sulfite. Still other process enhancers to make gold nanocrystals for medical applications under certain conditions may be other salts, including sodium or potassium, or any material that assists in the electrochemical growth processes described herein; and any material is not substantially incorporated into or onto the surface of the gold nanocryastsl; and does not impart toxicity to the nanocrystals or to the suspension containing the nanocrystals.

Desirable concentration ranges for the processing enhancer include typically 0.01-20 grams/gallon (0.0026-2.1730 mg/ml), more typically, 0.1-7.5 grams/gallon (0.0264-1.9813 mg/ml) and most typically, 0.5-2.0 grams/gallon (0.13210-0.5283 mg/ml).

For example, certain processing enhancers may dissociate into positive ions (cations) and negative ions (anions). The anions and/or cations, depending on a variety of factors including liquid composition, concentration of ions, applied fields, frequency of applied fields, waveform of the applied filed, temperature, pH, zeta potential, etc., will navigate or move toward oppositely charged electrodes. When said ions are located at or near such electrodes, the ions may take part in one or more reactions with the electrode(s) and/or other constituent(s) located at or near such electrode(s). Sometimes ions may react with one or more materials in the electrode (e.g., when NaCl is used as a processing enhancer, various metal chloride ($MCl$, $MCl_2$, etc.) may form). Such reactions may be desirable in some cases or undesirable in others. Further, sometimes ions present in a solution between electrodes may not react to form a product such as $MCl$, $MCl_2$, etc., but rather may influence material in the electrode (or near the electrode) to form metallic nanocrystals that are "grown" from material provided by the electrode. For example, certain metal ions may enter the liquid 3 from the electrode 5 and be caused to come together (e.g., nucleate) to form constituents (e.g., ions, nanocrystals, etc.) within the liquid 3.

Further, it is important to select a process enhancer that will not impart toxicity to the gold nanocrystal or the liquid that the crystal is in to maximize pharmaceutical acceptability. For example, for certain applications, chloride ion may be undesired if it creates gold chloride salts which may have toxicity.

Further, depending upon the specific formed products, drying, concentrating and/or freeze drying can also be utilized to remove at least a portion of, or substantially all of, the suspending liquid, resulting in, for example, partially or substantially completely dehydrated nanocrystals. If solutions, suspensions or colloids are completely dehydrated, the metal-based species should be capable of being rehydrated by the addition of liquid (e.g., of similar or different composition than that which was removed). However, not all compositions/colloids of the present invention can be completely dehydrated without adversely affecting performance of the composition/colloid. For example, many nanocrystals formed in a liquid tend to clump or stick together (or adhere to surfaces) when dried. If such clumping is not reversible during a subsequent rehydration step, dehydration should be avoided.

In general, it is possible to concentrate, several folds, certain solutions, suspensions or colloids of gold made according to the invention, without destabilizing the composition. However, complete evaporation is difficult to achieve due to, for example, agglomeration effects. In many of the embodiments disclosed herein, such agglomeration effects seem to begin at an approximate volume of 30% of the initial or starting reference volume being removed from the suspension or colloid. Additionally, one can evaporate off a certain volume of liquid and subsequently reconstitute or add-back the amount of liquid evaporated to achieve a very similar product, as characterized by, for example, FAAS, DLS, and UV-Vis techniques. For Example, two 500 ml suspensions of nanocrystalline colloidal gold, made by techniques similar to those to manufacture GB-139 (discussed in detail in the Examples section herein) were each placed into a glass beaker and heated on a hot plate until boiling. The suspensions were evaporated to 300 mL and 200 mL, respectively, and later reconstituted with that amount of liquid which was removed (i.e., with water purified by deionization and reverse osmosis ("DI/RO") water in 200 mL and 300 mL quantities, respectively) and subsequently characterized. Additionally, in another instance, two GB-139 suspension were again evaporated to 300 mL and 200 mL and then characterized without rehydration. It was found that these dehydration processes had little to no detrimental effects on the nanocrystal sizes or nanocrystal shapes (i.e., the nanocrystal size range and nanocrystal shape distributions did not change dramatically when the GB-139 colloid was dehydrated; or dehydrated and rehydrated to its initial gold concentration or ppm level).

One important aspect of the invention involves the creation of at least one adjustable plasma, which adjustable plasma is located between at least one electrode positioned adjacent to (e.g., above) at least a portion of the surface of a liquid (e.g., water) and at least a portion of the surface of the liquid itself. The liquid is placed into electrical communication with at least one second electrode (or a plurality of second electrodes) causing the surface of the liquid to function as an electrode, thus taking part in the formation of the adjustable plasma. This configuration has certain characteristics similar to a dielectric barrier discharge configuration, except that the surface of the liquid is an active electrode participant in this configuration.

Each adjustable plasma utilized can be located between the at least one electrode located above a surface of the liquid and a surface of the liquid due to at least one electrically conductive electrode being located somewhere within (e.g., at least partially within) the liquid. At least one power source (in a preferred embodiment, at least one source of volts and amps such as a transformer or power source) is connected electrically between the at least one electrode located above the surface of the liquid and the at least one electrode contacting the surface of the liquid (e.g., located at least partially, or substantially completely, within the liquid).

The electrode(s) may be of any suitable composition and suitable physical configuration (e.g., size and shape) which results in the creation of a desirable plasma between the electrode(s) located above the surface of the liquid and at least a portion of the surface of the liquid itself.

The applied power (e.g., voltage and amperage) between the electrode(s) (e.g., including the surface of the liquid functioning as at least one electrode for forming the plasma) can be generated by any suitable source (e.g., voltage from a transformer) including both AC and DC sources and variants and combinations thereof. Generally, the electrode or electrode combination located within (e.g., at least partially below the surface of the liquid) takes part in the creation of a plasma by providing voltage and current to the liquid or solution. However, the adjustable plasma is actually located between at least a portion of the electrode(s) located above the surface of the liquid (e.g., at a tip or point thereof) and one or more portions or areas of the liquid surface itself. In this regard, the adjustable plasma can be created between the aforementioned electrodes (i.e., those located above at least a portion of the surface of the liquid and a portion of the liquid surface itself) when a breakdown voltage of the gas or vapor around and/or between the electrode(s) and the surface of the liquid is achieved or maintained.

In one embodiment of the invention, the liquid comprises water (or water containing certain processing enhancer(s)), and the gas between the surface of the water and the electrode(s) above the surface of the water (i.e., that gas or atmosphere that takes part in the formation of the adjustable plasma) comprises air. The air can be controlled to contain various different water content(s) or a desired humidity which can result in different compositions, concentrations, crystal size distributions and/or crystal shape distributions of constituents (e.g., nanocrystals) being produced according to the present invention (e.g., different amounts of certain constituents in the adjustable plasma and/or in the solution or suspension can be a function of the water content in the air located above the surface of the liquid) as well as different processing times required to obtain certain concentrations of various constituents in the liquid, etc. Specific aspects of the adjustable plasma 4 are discussed in greater detail in Examples 5-7.

The breakdown electric field at standard pressures and temperatures for dry air is about 3 MV/m or about 30 kV/cm. Thus, when the local electric field around, for example, a metallic point exceeds about 30 kV/cm, a plasma can be generated in dry air. Equation (1) gives the empirical relationship between the breakdown electric field "$E_c$" and the distance "d" (in meters) between two electrodes:

$$E_c = 3000 + \frac{1.35}{d} \text{ kV/m} \qquad \text{Equation 1}$$

Of course, the breakdown electric field "$E_c$" will vary as a function of the properties and composition of the gas or vapor located between electrodes. In this regard, in one preferred embodiment where water (or water containing a processing enhancer) is the liquid, significant amounts of water vapor can be inherently present in the air between the "electrodes" (i.e., between the at least one electrode located above the surface of the water and the water surface itself which is functioning as one electrode for plasma formation) and such water vapor should have an effect on at least the breakdown electric field required to create a plasma therebetween. Further, a higher concentration of water vapor can be caused to be present locally in and around the created plasma due to the interaction of the adjustable plasma with the surface of the water. The amount of "humidity" present in and around the created plasma can be controlled or adjusted by a variety of techniques discussed in greater detail later herein. Likewise, certain components present in any liquid can form at least a portion of the constituents forming the adjustable plasma located between the surface of the liquid and the electrode(s) located adjacent (e.g., along) the surface of the liquid. The constituents in the adjustable plasma, as well as the physical properties of the plasma per se, can have a dramatic influence on the liquid, as well as on certain of the processing techniques (discussed in greater detail later herein).

The electric field strengths created at and near the electrodes are typically at a maximum at a surface of an electrode and typically decrease with increasing distance therefrom. In cases involving the creation of an adjustable plasma between a surface of the liquid and the at least one electrode(s) located adjacent to (e.g., above) the liquid, a portion of the volume of gas between the electrode(s) located above a surface of a liquid and at least a portion of the liquid surface itself can contain a sufficient breakdown electric field to create the adjustable plasma. These created electric fields can influence, for example, behavior of the adjustable plasma, behavior of the liquid (e.g., influence the crystal state of the liquid) behavior of constituents in the liquid, etc.

Figure 1A:
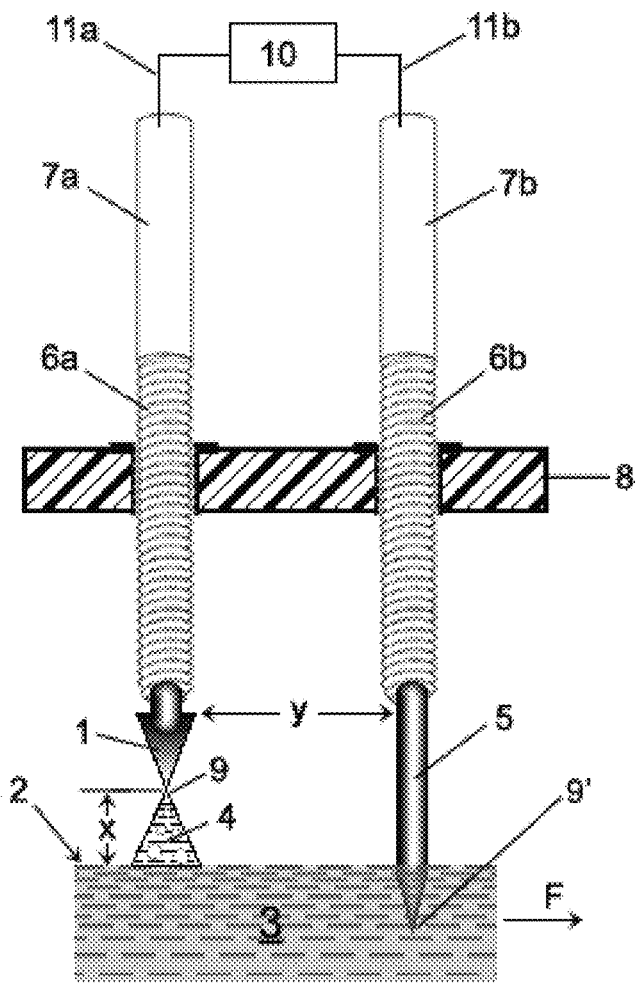
FIGS. 1a, 1b and 1c show schematic cross-sectional views of a manual electrode assembly according to the present invention.
Figure 1B:
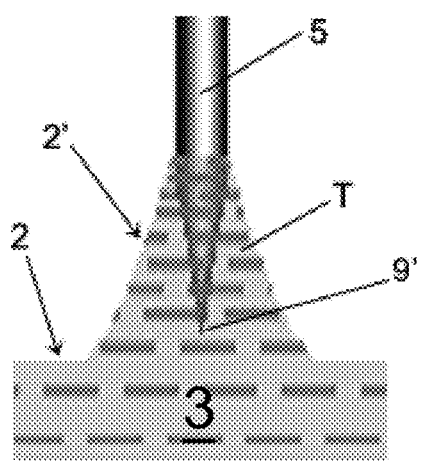

In this regard, FIG. 1a shows one embodiment of a point source electrode 1 having a triangular cross-sectional shape located a distance "x" above the surface 2 of a liquid 3 flowing, for example, in the direction "F". An adjustable plasma 4 can be generated between the tip or point 9 of the electrode 1 and the surface 2 of the liquid 3 when an appropriate power source 10 is connected between the point source electrode 1 and the electrode 5, which electrode 5 communicates with the liquid 3 (e.g., is at least partially below the surface 2 of the liquid 3).

The adjustable plasma region 4, created in the embodiment shown in FIG. 1a can typically have a shape corresponding to a cone-like structure or an ellipsoid-like structure, for at least a portion of the process, and in some embodiments of the invention, can maintain such shape (e.g., cone-like shape) for substantially all of the process. The volume, intensity, constituents (e.g., composition), activity, precise locations, etc., of the adjustable plasma(s) 4 will vary depending on a number of factors including, but not limited to, the distance "x", the physical and/or chemical composition of the electrode 1, the shape of the electrode 1, the power source 10 (e.g., DC, AC, rectified AC, the applied polarity of DC and/or rectified AC, AC or DC waveform, RF, etc.), the power applied by the power source (e.g., the volts applied, which is typically 1000-5000 Volts, and more typically 1000-1500 Volts, the amps applied, electron velocity, etc.) the frequency and/or magnitude of the electric and/or magnetic fields created by the power source applied or ambient, electric, magnetic or electromagnetic fields, acoustic fields, the composition of the naturally occurring or supplied gas or atmosphere (e.g., air, nitrogen, helium, oxygen, ozone, reducing atmospheres, etc.) between and/or around the electrode 1 and the surface 2 of the liquid 3, temperature, pressure, volume, flow rate of the liquid 3 in the direction "F", spectral characteristics, composition of the liquid 3, conductivity of the liquid 3, cross-sectional area (e.g., volume) of the liquid near and around the electrodes 1 and 5, (e.g., the amount of time (i.e., dwell time) the liquid 3 is permitted to interact with the adjustable plasma 4 and the intensity of such interactions), the presence of atmosphere flow (e.g., air flow) at or near the surface 2 of the liquid 3 (e.g., fan(s) or atmospheric movement means provided) etc., (discussed in more detail later herein).

The composition of the electrode(s) 1 involved in the creation of the adjustable plasma(s) 4 of FIG. 1a, in one preferred embodiment of the invention, are metal-based compositions (e.g., metals such as gold and/or alloys or mixtures thereof, etc.), but the electrodes 1 and 5 may be made out of any suitable material compatible with the various aspects (e.g., processing parameters) of the inventions disclosed herein. In this regard, while the creation of a plasma 4 in, for example, air above the surface 2 of a liquid 3 (e.g., water) will, typically, produce at least some ozone, as well as amounts of nitrogen oxide and other components (discussed in greater detail elsewhere herein). These produced components can be controlled and may be helpful or harmful to the formation and/or performance of the resultant constituents in the liquid (e.g., nanocrystals) and/or, nanocrystal suspensions or colloids produced and may need to be controlled by a variety of different techniques, discussed in more detail later herein. Further, the emission spectrum of each plasma 4, as shown for example in Examples 5-7, is also a function of similar factors (discussed in greater detail later herein). As shown in FIG. 1a, the adjustable plasma 4 actually contacts the surface 2 of the liquid 3. In this embodiment of the invention, material (e.g., metal) from the electrode 1 may comprise a portion of the adjustable plasma 4 (e.g., and thus be part of the emission spectrum of the plasma) and may be caused, for example, to be "sputtered" onto and/or into the liquid 3 (e.g., water). Accordingly, when metal(s) are used as the electrode(s) 1, a variety of constituents (such as those shown in Examples 5-7) can be formed in the electrical plasma, resulting in certain constituents becoming part of the processing liquid 3 (e.g., water), including, but not limited to, elementary metal(s), metal ions, Lewis acids, Bronsted-Lowry acids, metal oxides, metal nitrides, metal hydrides, metal hydrates and/or metal carbides, etc., can be found in the liquid 3 (e.g., for at least a portion of the process and may be capable of being involved in simultaneous/subsequent reactions), depending upon the particular set of operating conditions associated with the adjustable plasma 4 and/or subsequent electrochemical processing operations. Such constituents may be transiently present in the processing liquid 3 or may be semi-permanent or permanent. If such constituents are transient or semi-permanent, then the timing of subsequent reactions (e.g., electrochemical reactions) with such formed constituents can influence final products produced. If such constituents are permanent, they should not adversely affect the desired performance of the active ingredient nanocrystals.

Further, depending on, for example, electric, magnetic and/or electromagnetic field strength in and around the liquid 3 and the volume of liquid 3 exposed to such fields (discussed in greater detail elsewhere herein), the physical and chemical construction of the electrode(s) 1 and 5, atmosphere (naturally occurring or supplied), liquid composition, greater or lesser amounts of electrode(s) materials(s) (e.g., metal(s) or derivatives of metals) may be found in the liquid 3. In certain situations, the material(s) (e.g., metal(s) or metal(s) composite(s)) or constituents (e.g., Lewis acids, Bronsted-Lowry acids, etc.) found in the liquid 3 (permanently or transiently), or in the plasma 4, may have very desirable effects, in which case relatively large amounts of such materials will be desirable; whereas in other cases, certain materials found in the liquid 3 (e.g., by-products) may have undesirable effects, and thus minimal amounts of such materials may be desired in the liquid-based final product. Accordingly, electrode composition can play an important role in the materials that are formed according to the embodiments disclosed herein. The interplay between these components of the invention are discussed in greater detail later herein.

Still further, the electrode(s) 1 and 5 may be of similar chemical composition (e.g., have the same chemical element as their primary constituent) and/or mechanical configuration or completely different compositions (e.g., have different chemical elements as their primary constituent) in order to achieve various compositions and/or structures of liquids and/or specific effects discussed later herein.

The distance "y" between the electrode(s) 1 and 5; or 1 and 1 (shown later herein) or 5 and 5 (shown later herein) is one important aspect of the invention. In general, when working with power sources capable of generating a plasma under the operating condition, the location of the smallest distance "y" between the closest portions of the electrode(s) used in the present invention should be greater than the distance "x" in order to prevent an undesirable arc or formation of an unwanted corona or plasma occurring between the electrode (e.g., the electrode(s) 1 and the electrode(s) 5) (unless some type of electrical insulation is provided therebetween). Features of the invention relating to electrode design, electrode location and electrode interactions between a variety of electrodes are discussed in greater detail later herein.

The power applied through the power source 10 may be any suitable power which creates a desirable adjustable plasma 4 under all of the process conditions of the present invention. In one preferred mode of the invention, an alternating current from a step-up transformer is utilized. Preferred transformer(s) 60 (see e.g., FIGS. 16d-16l) for use in various embodiments disclosed herein, have deliberately poor output voltage regulation made possible by the use of magnetic shunts in the transformer 60. These transformers 60 are known as neon sign transformers. This configuration limits current flow into the electrode(s) 1/5. With a large change in output load voltage, the transformer 60 maintains output load current within a relatively narrow range.

The transformer 60 is rated for its secondary open circuit voltage and secondary short circuit current. Open circuit voltage (OCV) appears at the output terminals of the transformer 60 only when no electrical connection is present. Likewise, short circuit current is only drawn from the output terminals if a short is placed across those terminals (in which case the output voltage equals zero). However, when a load is connected across these same terminals, the output voltage of the transformer 60 should fall somewhere between zero and the rated OCV. In fact, if the transformer 60 is loaded properly, that voltage will be about half the rated OCV.

The transformer 60 is known as a Balanced Mid-Point Referenced Design (e.g., also formerly known as balanced midpoint grounded). This is most commonly found in mid to higher voltage rated transformers and most 60 mA transformers. This is the only type transformer acceptable in a "mid-point return wired" system. The "balanced" transformer 60 has one primary coil 601 with two secondary coils 603, one on each side of the primary coil 601 (as shown generally in the schematic view in FIG. 16g). This transformer 60 can in many ways perform like two transformers. Just as the unbalanced midpoint referenced core and coil, one end of each secondary coil 603 is attached to the core 602 and subsequently to the transformer enclosure and the other end of the each secondary coil 603 is attached to an output lead or terminal. Thus, with no connector present, an unloaded 15,000 volt transformer of this type, will measure about 7,500 volts from each secondary terminal to the transformer enclosure but will measure about 15,000 volts between the two output terminals. These exemplary transformers 60 were utilized to form the plasmas 4 disclosed in the Examples herein. However, other suitable transformers (or power sources) should also be understood as falling within the metes and bounds of the invention. Further, these transformers 60 are utilized exclusively in Examples 1-4 herein. However, different AC transformers 50 and 50a (discussed elsewhere herein) are utilized for the electrodes 5/5' in most of the other examples disclosed herein.

In another preferred embodiment, a rectified AC source creates a positively charged electrode 1 and a negatively charged surface 2 of the liquid 3. In another preferred embodiment, a rectified AC source creates a negatively charged electrode 1 and a positively charged surface 2 of the liquid 3. Further, other power sources such as RF power sources and/or microwave power sources can also be used with the present invention. In general, the combination of electrode(s) components 1 and 5, physical size and shape of the electrode(s) 1 and 5, electrode manufacturing process, mass of electrodes 1 and/or 5, the distance "x" between the tip 9 of electrode 1 above the surface 2 of the liquid 3, the composition of the gas between the electrode tip 9 and the surface 2, the flow rate (if any) and/or flow direction "F" of the liquid 3, the amount of liquid 3 provided, type of power source 10, frequency and/or waveform of the power output of the power source 10, all contribute to the design, and thus power requirements (e.g., breakdown electric field) required to obtain a controlled or adjustable plasma 4 between the surface 2 of the liquid 3 and the electrode tip 9.

In further reference to the configurations shown in FIG. 1a, electrode holders 6a and 6b are capable of being lowered and raised by any suitable means (and thus the electrodes are capable of being lowered and raised). For example, the electrode holders 6a and 6b are capable of being lowered and raised in and through an insulating member 8 (shown in cross-section). The mechanical embodiment shown here includes male/female screw threads. The portions 6a and 6b can be covered by, for example, additional electrical insulating portions 7a and 7b. The electrical insulating portions 7a and 7b can be any suitable material (e.g., plastic, polycarbonate, poly (methyl methacrylate), polystyrene, acrylics, polyvinylchloride (PVC), nylon, rubber, fibrous materials, etc.) which prevent undesirable currents, voltage, arcing, etc., that could occur when an individual interfaces with the electrode holders 6a and 6b (e.g., attempts to adjust the height of the electrodes). Likewise, the insulating member 8 can be made of any suitable material which prevents undesirable electrical events (e.g., arcing, melting, etc.) from occurring, as well as any material which is structurally and environmentally suitable for practicing the present invention. Typical materials include structural plastics such as polycarbonates, plexiglass (poly (methyl methacrylate), polystyrene, acrylics, and the like. Additional suitable materials for use with the present invention are discussed in greater detail elsewhere herein.

Figure 1C:
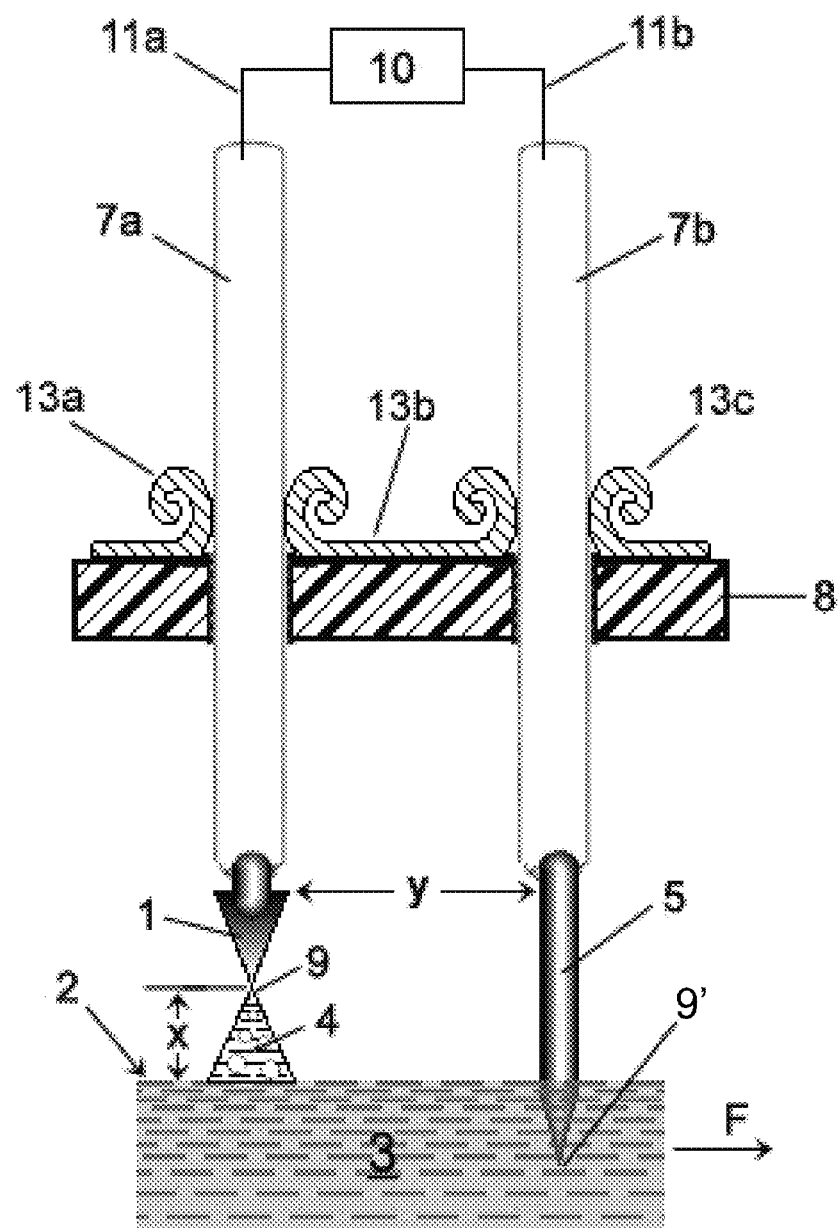

FIG. 1c shows another embodiment for raising and lowering the electrodes 1, 5. In this embodiment, electrical insulating portions 7a and 7b of each electrode are held in place by a pressure fit existing between the friction mechanism 13a, 13b and 13c, and the portions 7a and 7b. The friction mechanism 13a, 13b and 13c could be made of, for example, spring steel, flexible rubber, etc., so long as sufficient contact or friction is maintained therebetween.

Preferred techniques for automatically raising and/or lowering the electrodes 1, 5 are discussed later herein. The power source 10 can be connected in any convenient electrical manner to the electrodes 1 and 5. For example, wires 11a and 11b can be located within at least a portion of the electrode holders 6a, 6b (and/or electrical insulating portions 7a, 7b) with a primary goal being achieving electrical connections between the portions 11a, 11b and thus the electrodes 1, 5.

Figure 2A:
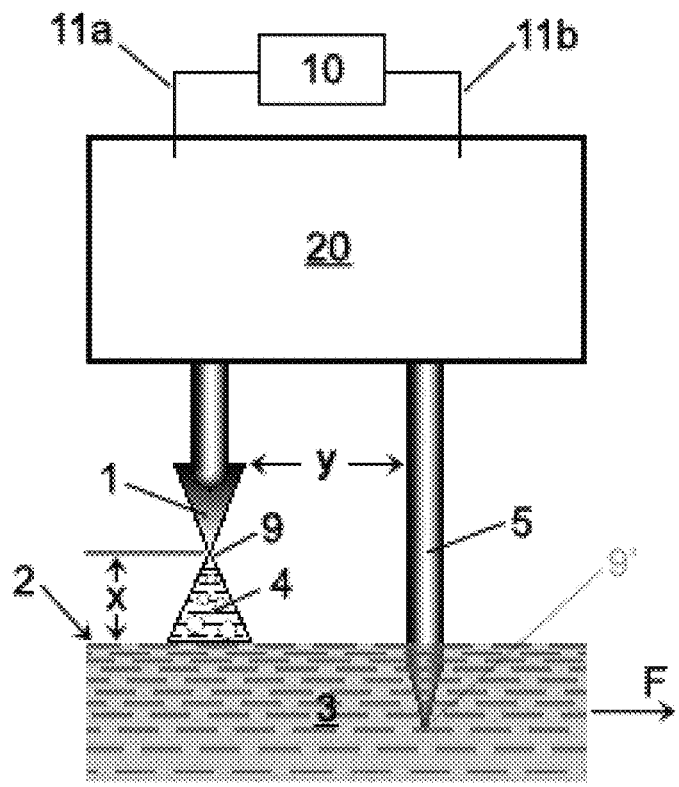
FIGS. 2a and 2b show schematic cross-sectional views of an automatic electrode control assembly according to the present invention.
Figure 2B:
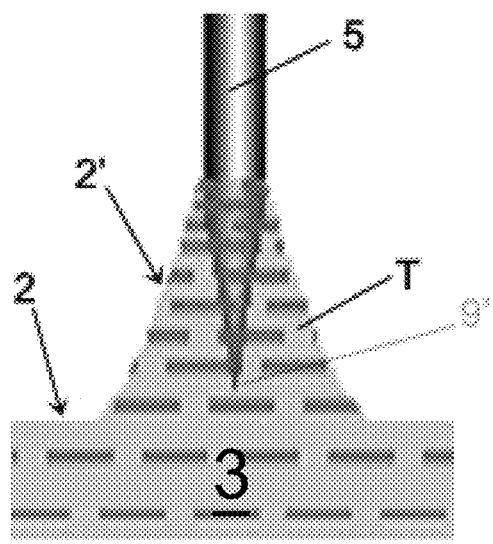

FIG. 2a shows another schematic of a preferred embodiment of the invention, wherein an inventive control device 20 is connected to the electrodes 1 and 5, such that the control device 20 remotely (e.g., upon command from another device or component) raises and/or lowers the electrodes 1, 5 relative to the surface 2 of the liquid 3. The inventive control device 20 is discussed in more detail later herein. In this one preferred aspect of the invention, the electrodes 1 and 5 can be, for example, remotely lowered and controlled, and can also be monitored and controlled by a suitable controller or computer (not shown in FIG. 2a) containing an appropriate software program (discussed in detail later herein). In this regard, FIG. 2b shows an electrode configuration similar to that shown in FIG. 2a, except that a Taylor Cone "T" is utilized for electrical connection between the electrode 5 and the surface 2 (or effective surface 2') of the liquid 3. Accordingly, the embodiments shown in FIGS. 1a, 1b and 1c should be considered to be a manually controlled apparatus for use with the techniques of the present invention, whereas the embodiments shown in FIGS. 2a and 2b should be considered to include an automatic apparatus or assembly 20 which can remotely raise and lower the electrodes 1 and 5 in response to appropriate commands. Further, the FIG. 2a and FIG. 2b preferred embodiments of the invention can also employ computer monitoring and computer control of the distance "x" of the tips 9 of the electrodes 1 (and tips 9' of the electrodes 5) away from the surface 2; or computer monitoring and/or controlling the rate(s) which the electrode 5 is advanced into/through the liquid 3 (discussed in greater detail later herein). Thus, the appropriate commands for raising and/or lowering the electrodes 1 and 5 can come from an individual operator and/or a suitable control device such as a controller or a computer (not shown in FIG. 2a).

FIG. 3a corresponds in large part to FIGS. 2a and 2b, however, FIGS. 3b, 3c and 3d show various alternative electrode configurations that can be utilized in connection with certain preferred embodiments of the invention. FIG. 3b shows essentially a mirror image electrode assembly from that electrode assembly shown in FIG. 3a. In particular, as shown in FIG. 3b, with regard to the direction "F" corresponding to the flow direction of the liquid 3, the electrode 5 is the first electrode which communicates with the fluid 3 when flowing in the longitudinal direction "F" and contact with the plasma 4 created at the electrode 1 follows. FIG. 3c shows two electrodes 5a and 5b located within the fluid 3. This particular electrode configuration corresponds to another preferred embodiment of the invention. In particular, as discussed in greater detail herein, the electrode configuration shown in FIG. 3c can be used alone, or in combination with, for example, the electrode configurations shown in FIGS. 3a and 3b. Similarly, a fourth possible electrode configuration is shown in FIG. 3d. In this FIG. 3d, no electrode(s) 5 are shown, but rather only electrodes 1a and 1b are shown. In this case, two adjustable plasmas 4a and 4b are present between the electrode tips 9a and 9b and the surface 2 of the liquid 3. The distances "xa" and "xb" can be about the same or can be substantially different, as long as each distance "xa" and "xb" does not exceed the maximum distance for which a plasma 4 can be formed between the electrode tips 9a/9b and the surface 2 of the liquid 3. As discussed above, the electrode configuration shown in FIG. 3d can be used alone, or in combination with one or more of the electrode configurations shown in FIGS. 3a, 3b and 3c. The desirability of utilizing particular electrode configurations in combination with each other with regard to the fluid flow direction "F" is discussed in greater detail later herein.

Likewise, a set of manually controllable electrode configurations, corresponding generally to FIG. 1a, are shown in FIGS. 4a, 4b, 4c and 4d, all of which are shown in a partial cross-sectional view. Specifically, FIG. 4a corresponds to FIG. 1a. Moreover, FIG. 4b corresponds in electrode configuration to the electrode configuration shown in FIG. 3b; FIG. 4c corresponds to FIG. 3c and FIG. 4d corresponds to FIG. 3d. In essence, the manual electrode configurations shown in FIGS. 4a-4d can functionally result in similar materials produced according to certain inventive aspects of the invention as those materials produced corresponding to remotely adjustable (e.g., remote-controlled by computer or controller means) electrode configurations shown in FIGS. 3a-3d. The desirability of utilizing various electrode configuration combinations is discussed in greater detail later herein.

FIGS. 5a-5e show perspective views of various desirable electrode configurations for the electrode 1 shown in FIGS. 1-4 (as well as in other Figures and embodiments discussed later herein). The electrode configurations shown in FIGS. 5a-5e are representative of a number of different configurations that are useful in various embodiments of the present invention. Criteria for appropriate electrode selection for the electrode 1 include, but are not limited to the following conditions: the need for a very well defined tip or point 9, composition, mechanical limitations, the ability to make shapes from the material comprising the electrode 1, conditioning (e.g., heat treating or annealing) of the material comprising the electrode 1, convenience, the constituents introduced into the plasma 4, the influence upon the liquid 3, etc. In this regard, a small mass of material comprising the electrodes 1 shown in, for example, FIGS. 1-4 may, upon creation of the adjustable plasmas 4 according to the present invention (discussed in greater detail later herein), rise to operating temperatures where the size and or shape of the electrode(s) 1 can be adversely affected. In this regard, for example, if the electrode 1 was of relatively small mass (e.g., if the electrode(s) 1 was made of gold and weighed about 0.5 gram or less) and included a very fine point as the tip 9, then it is possible that under certain sets of conditions used in various embodiments herein that a fine point (e.g., a thin wire having a diameter of only a few millimeters and exposed to a few hundred to a few thousand volts; or a triangular-shaped piece of metal) would be incapable of functioning as the electrode 1 (e.g., the electrode 1 could deform undesirably or melt), absent some type of additional interactions (e.g., internal cooling means or external cooling means such as a fan, etc.). Accordingly, the composition of (e.g., the material comprising) the electrode(s) 1 may affect possible suitable electrode physical shape due to, for example, melting points, pressure sensitivities, environmental reactions (e.g., the local environment of the adjustable plasma 4 could cause undesirable chemical, mechanical and/or electrochemical erosion of the electrode(s)), etc.

Figure 6:
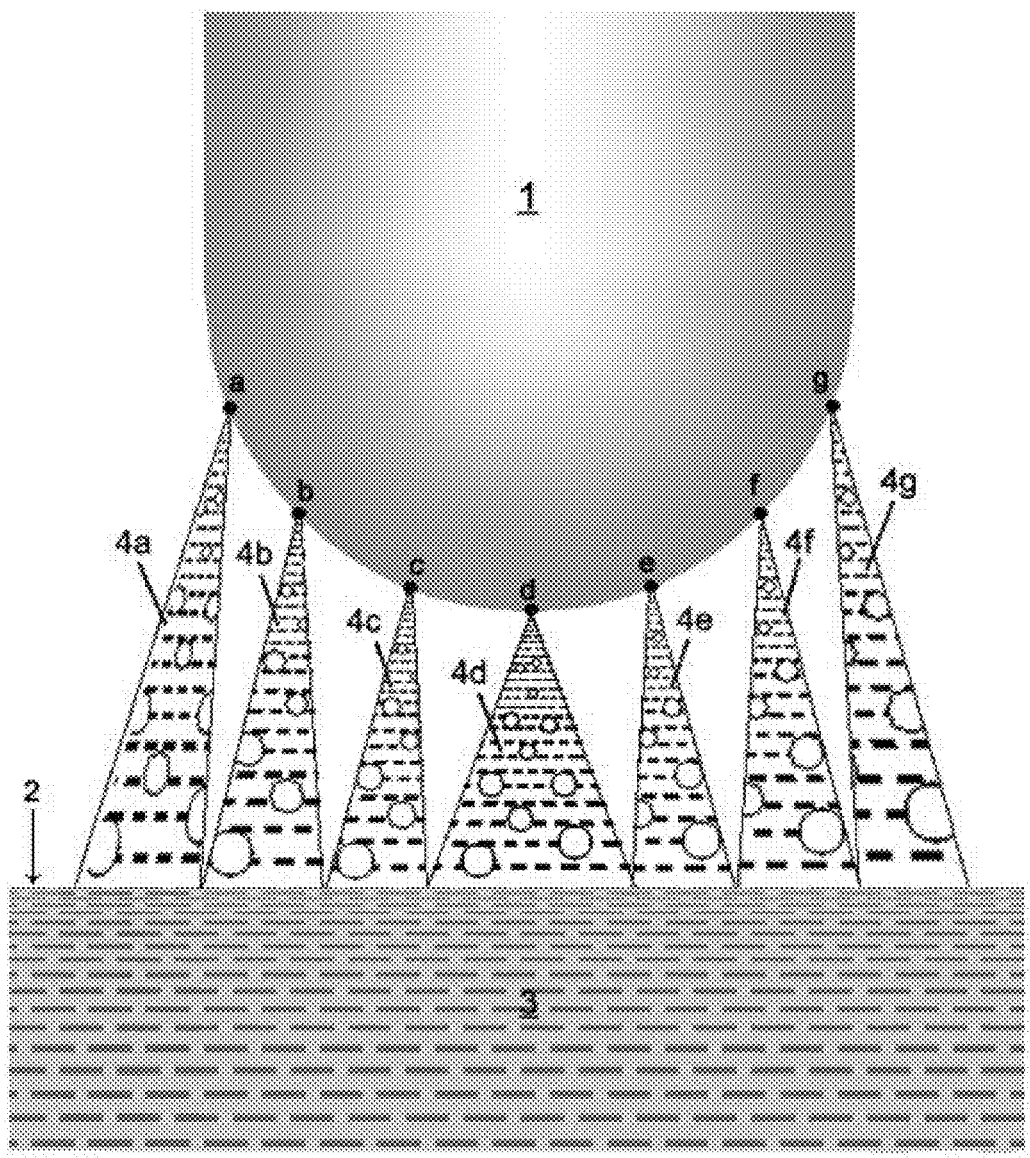
FIG. 6 shows a cross-sectional schematic view of plasmas produced utilizing one specific configuration of the electrode 1 corresponding to FIG. 5e.

Moreover, it should be understood that in alternative preferred embodiments of the invention, well defined sharp points are not always required for the tip 9. In this regard, the electrode 1 shown in FIG. 5e comprises a rounded tip 9. It should be noted that partially rounded or arc-shaped electrodes can also function as the electrode 1 because the adjustable plasma 4, which is created in the inventive embodiments shown herein (see, for example, FIGS. 1-4), can be created from rounded electrodes or electrodes with sharper or more pointed features. During the practice of the inventive techniques of the present invention, such adjustable plasmas can be positioned or can be located along various points of the electrode 1 shown in FIG. 5e. In this regard, FIG. 6 shows a variety of points "a-g" which correspond to initiating points 9 for the plasmas 4a-4g which occur between the electrode 1 and the surface 2 of the liquid 3. Accordingly, it should be understood that a variety of sizes and shapes corresponding to electrode 1 can be utilized in accordance with the teachings of the present invention. Still further, it should be noted that the tips 9, 9' of the electrodes 1 and 5, respectively, shown in various Figures herein, may be shown as a relatively sharp point or a relatively blunt end. Unless specific aspects of these electrode tips 9, 9' are discussed in greater contextual detail, the actual shape of the electrode tip(s) 9, 9' shown in the Figures should not be given great significance.

Figure 7A:
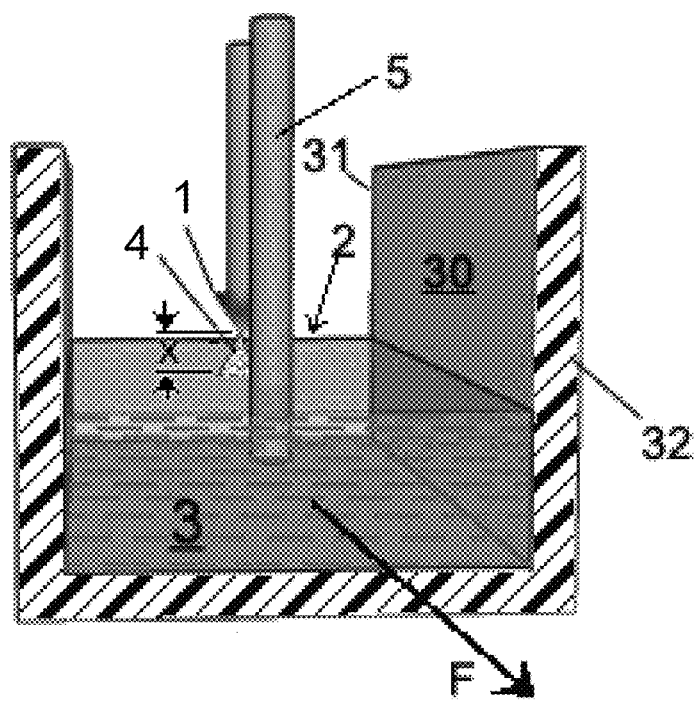
FIGS. 7a and 7b show a cross-sectional perspective view of two electrode assemblies that can be utilized.

FIG. 7a shows a cross-sectional perspective view of the electrode configuration corresponding to that shown in FIG. 2a (and FIG. 3a) contained within a trough member 30. This trough member 30 has a liquid 3 supplied into it from the back side identified as 31 of FIG. 7a and the flow direction "F" is out of the page toward the reader and toward the cross-sectioned area identified as 32. The trough member 30 is shown here as a unitary piece of one material, but could be made from a plurality of materials fitted together and, for example, fixed (e.g., glued, mechanically attached, etc.) by any acceptable means for attaching materials to each other. Further, the trough member 30 shown here is of a rectangular or square cross-sectional shape, but may comprise a variety of different and more desirable cross-sectional shapes (discussed in greater detail later herein). Accordingly, the flow direction of the fluid 3 is out of the page toward the reader and the liquid 3 flows past each of the electrodes 1 and 5, which are, in this embodiment, located substantially in line with each other relative to the longitudinal flow direction "F" of the fluid 3 within the trough member 30. This causes the liquid 3 to first experience an adjustable plasma interaction with the adjustable plasma 4 (e.g., a conditioning reaction) and subsequently then the conditioned fluid 3 is permitted to interact with the electrode(s) 5. Specific desirable aspects of these electrode/liquid interactions and electrode placement(s) or electrode locations within the trough member 30 are discussed in greater detail elsewhere herein.

Figure 7B:
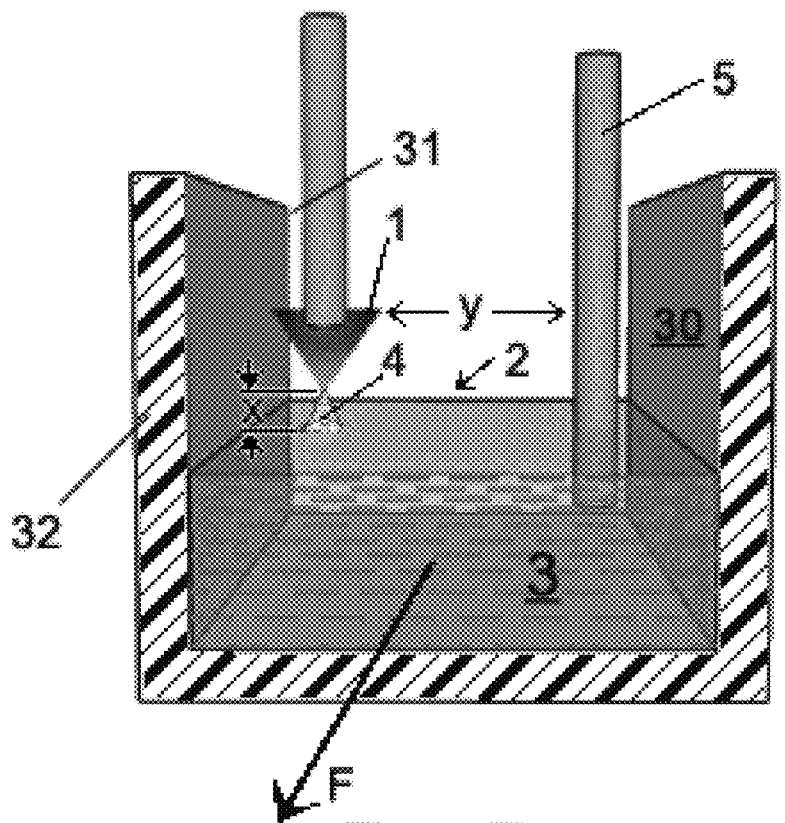

FIG. 7b shows a cross-sectional perspective view of the electrode configuration shown in FIG. 2a (as well as in FIG. 3a), however, these electrodes 1 and 5 are rotated on the page 90 degrees relative to the electrodes 1 and 5 shown in FIGS. 2a and 3a. In this embodiment of the invention, the liquid 3 contacts the adjustable plasma 4 generated between the electrode 1 and the surface 2 of the liquid 3, and the electrode 5 at substantially the same point along the longitudinal flow direction "F" (i.e., out of the page) of the trough member 30. The direction of liquid 3 flow is longitudinally along the trough member 30 and is out of the paper toward the reader, as in FIG. 7a. Various desirable aspects of this electrode configuration are discussed in greater detail later herein.

FIG. 8a shows a cross-sectional perspective view of the same embodiment shown in FIG. 7a. In this embodiment, as in FIG. 7a, the fluid 3 firsts interacts with the adjustable plasma 4 created between the electrode 1 and the surface 2 of the liquid 3. Thereafter the plasma influenced or conditioned fluid 3, having been changed (e.g., conditioned, modified, or prepared) by the adjustable plasma 4, thereafter communicates with the electrode(s) 5 thus permitting various electrochemical reactions to occur, such reactions being influenced by the state (e.g., chemical composition, pH, physical or crystal structure, excited state(s), etc., of the fluid 3 (and constituents, semi-permanent or permanent, within the fluid 3)) discussed in greater detail elsewhere herein. An alternative embodiment is shown in FIG. 8b. This embodiment essentially corresponds in general arrangement to those embodiments shown in FIGS. 3b and 4b. In this embodiment, the fluid 3 first communicates with the electrode 5, and thereafter the fluid 3 communicates with the adjustable plasma 4 created between the electrode 1 and the surface 2 of the liquid 3. In this embodiment, the fluid 3 may have been previously modified prior to interacting with the electrode 5.

FIG. 8c shows a cross-sectional perspective view of two electrodes 5a and 5b (corresponding to the embodiments shown in FIGS. 3c and 4c) wherein the longitudinal flow direction "F" of the fluid 3 contacts the first electrode 5a and thereafter contacts the second electrode 5b in the direction "F" of fluid flow.

Likewise, FIG. 8d is a cross-sectional perspective view and corresponds to the embodiments shown in FIGS. 3d and 4d. In this embodiment, the fluid 3 communicates with a first adjustable plasma 4a created by a first electrode 1a and thereafter communicates with a second adjustable plasma 4b created between a second electrode 1b and the surface 2 of the fluid 3.

Figure 9A:
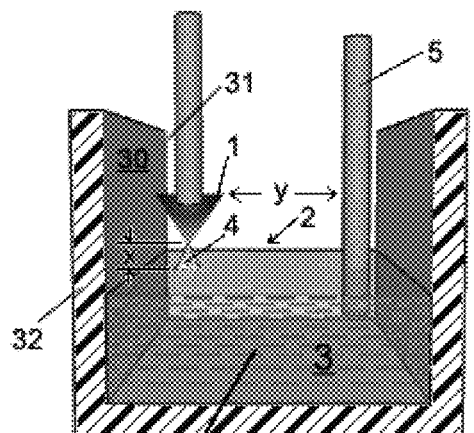
FIGS. 9a-9d show schematic perspective views of four different electrode assemblies arranged with planes perpendicular to flow direction F.

FIG. 9a shows a cross-sectional perspective view and corresponds to the electrode configuration shown in FIG. 7b (and generally to the electrode configuration shown in FIGS. 3a and 4a but is rotated 90 degrees relative thereto). All of the electrode configurations shown in FIGS. 9a-9d are situated such that the electrode pairs shown are located substantially at the same longitudinal point along the trough member 30, as in FIG. 7b.

Figure 9B:
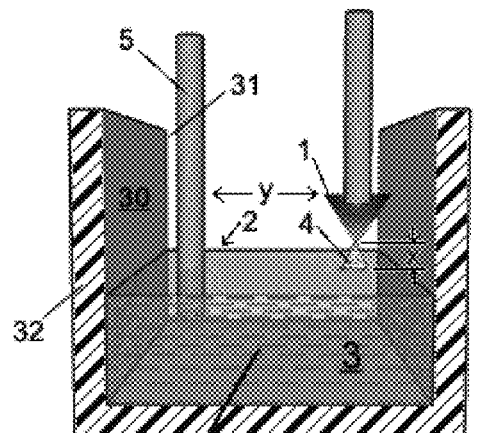

Likewise, FIG. 9b corresponds generally to the electrode configuration shown in FIGS. 3b and 4b, and is rotated 90 degrees relative to the configuration shown in FIG. 8b.

Figure 9C:
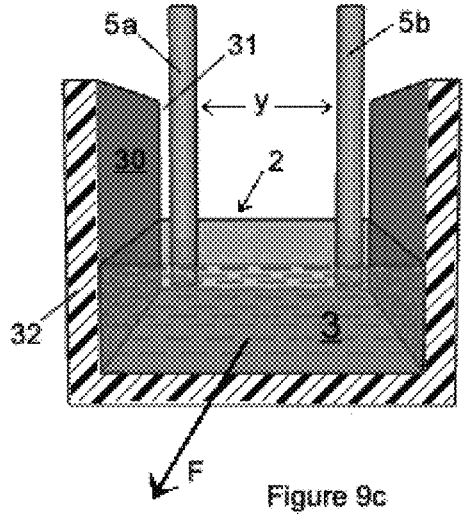

FIG. 9c shows an electrode configuration corresponding generally to FIGS. 3c and 4c, and is rotated 90 degrees relative to the electrode configuration shown in FIG. 8c.

Figure 9D:
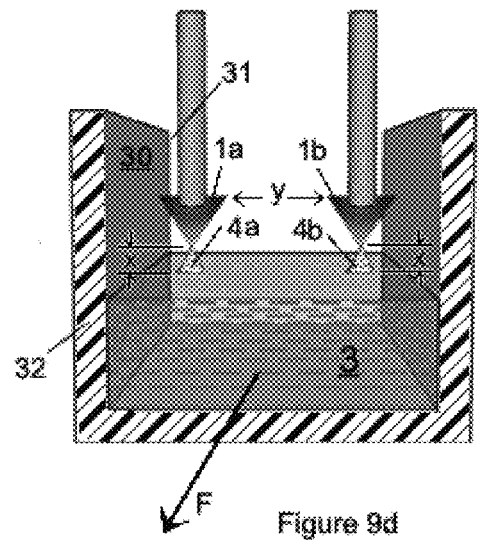

FIG. 9d shows an electrode configuration corresponding generally to FIGS. 3d and 4d and is rotated 90 degrees relative to the electrode configuration shown in FIG. 8d.

The electrode configurations shown generally in FIGS. 7, 8 and 9, all can create different results (e.g., different conditioning effects for the fluid 3, different pH's in the fluid 3, different nanocrystals sizes and size distribution, different nanocrystal shapes and nanocrystal shape distributions, and/or amounts of constituents (e.g., nanocrystal matter) found in the fluid 3, different functioning of the fluid/nanocrystal combinations (e.g., different biologic/biocatalytic effects), different zeta potentials, etc.) as a function of a variety of features including the electrode orientation and position relative to the fluid flow direction "F", cross-sectional shape and size of the trough member 30, and/or amount of the liquid 3 within the trough member 30 and/or rate of flow of the liquid 3 within the trough member 30 and in/around the electrodes 5a/5b, the thickness of the electrodes, the number of electrode pairs provided and their positioning in the trough member 30 relative to each other as well as their depth into the liquid 3 (i.e., amount of contact with the liquid 3), the rate of movement of the electrodes into/through the liquid 3 (which maintains or adjusts the surface profile or shape if the electrodes), the power applied to the electrode pairs, etc. Further, the electrode compositions, size, specific shape(s), number of different types of electrodes provided, voltage applied, amperage applied and/or achieved within the liquid 3, AC source (and AC source frequency and AC waveform shape, duty cycle, etc.), DC source, RF source (and RF source frequency, duty cycle, etc.), electrode polarity, etc., can all influence the properties of the liquid 3 (and/or the nanocrystals formed or contained in the liquid 3) as the liquid 3 contacts, interacts with and/or flows past these electrodes 1, 5 and hence resultant properties of the materials (e.g., the nanocrystals produced and/or the suspension or colloid) produced therefrom. Additionally, the liquid-containing trough member 30, in some preferred embodiments, contains a plurality of the electrode combinations shown in FIGS. 7, 8 and 9. These electrode assemblies may be all the same configuration or may be a combination of various different electrode configurations (discussed in greater detail elsewhere herein). Moreover, the electrode configurations may sequentially communicate with the fluid "F" or may simultaneously, or in parallel communicate with the fluid "F". Different exemplary and preferred electrode configurations are shown in additional figures later herein and are discussed in greater detail later herein in conjunction with different constituents formed (e.g., nanocrystals and solutions or nanocrystal suspensions or colloids produced therefrom).

Figure 10A:
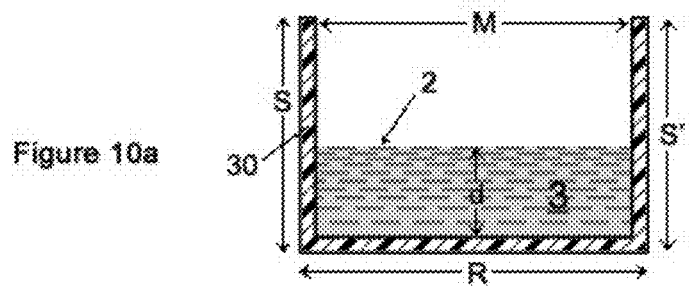
FIGS. 10a-10e show a variety of cross-sectional views of various trough members 30.

FIG. 10a shows a cross-sectional view of the liquid containing trough member 30 shown in FIGS. 7, 8 and 9. This trough member 30 has a cross-section corresponding to that of a rectangle or a square and the electrodes (not shown in FIG. 10a) can be suitably positioned therein.

Likewise, several additional alternative cross-sectional embodiments for the liquid-containing trough member 30 are shown in FIGS. 10b, 10c, 10d and 10e. The distance "S" and "S" for the preferred embodiment shown in each of FIGS. 10a-10e measures, for example, between about 0.25" and about 6" (about 0.6 cm-15 cm). The distance "M" ranges from about 0.25" to about 6" (about 0.6 cm-15 cm). The distance "R" ranges from about ½" to about 7" (about 1.2 cm to about 17.8 cm). All of these embodiments (as well as additional configurations that represent alternative embodiments are within the metes and bounds of this inventive disclosure) can be utilized in combination with the other inventive aspects of the invention. It should be noted that the amount of liquid 3 contained within each of the liquid containing trough members 30 is a function not only of the depth "d", but also a function of the actual cross-section. Briefly, the amount of liquid 3 present in and around the electrode(s) 1 and 5 can influence one or more effects of the adjustable plasma 4 upon the liquid 3 as well as the electrochemical interaction(s) of the electrode 5 with the liquid 3. Further, the flow rate of the liquid 3 in and around the electrode(s) 1 and 5 can also influence many of properties of the nanocrystals formed in the resulting colloids or suspensions. These effects include not only adjustable plasma 4 conditioning effects (e.g., interactions of the plasma electric and magnetic fields, interactions of the electromagnetic radiation of the plasma, creation of various chemical species (e.g., Lewis acids, Bronsted-Lowry acids) within the liquid, pH changes, temperature variations of the liquid (e.g., slower liquid flow can result in higher liquid temperatures and/or longer contact or dwell time with or around the electrodes 1/5 which can also desirably influence final products produced, such as size/shape of the formed nanocrystals, etc.) upon the liquid 3, but also the concentration or interaction of the adjustable plasma 4 with the liquid 3. Similarly, the influence of many aspects of the electrode 5 on the liquid 3 (e.g., electrochemical interactions, temperature, etc.) is also, at least partially, a function of the amount of liquid juxtaposed to the electrode(s) 5. All of these factors can influence a balance which exists between nucleation and growth of the nanocrystals grown in the liquid 3, resulting in, for example, particle size and size range control and/or particle shape and shape range control.

Further, strong electric and magnetic field concentrations will also effect the interaction of the plasma 4 with the liquid 3 as well as effect the interaction of the electrode 5 with the liquid 3. Some important aspects of these important interactions are discussed in greater detail elsewhere herein. Further, a trough member 30 may comprise more than one cross-sectional shape along its entire longitudinal length. The incorporation of multiple cross-sectional shapes along the longitudinal length of a trough member 30 can result in, for example, varying the field or concentration or reaction effects (e.g., crystal growth/nucleation effects) being produced by the inventive embodiments disclosed herein (discussed in greater detail elsewhere herein). Further, a trough member 30 may not be linear or "I-shaped", but rather may be "Y-shaped" or "Ψ-shaped", with each portion of the "Y" (or "Ψ") having a different (or similar) cross-sectional shape and/or set of dimensions and/or set of reaction conditions occurring therein.

Also, the initial temperature of the liquid 3 input into the trough member 30 can also affect a variety of properties of products produced according to the disclosure herein. For example, different temperatures of the liquid 3 can affect nanocrystal size(s) and nanocrystal shape(s), concentration or amounts of various formed constituents (e.g., transient, semi-permanent or permanent constituents), pH, zeta potential, etc. Likewise, temperature controls along at least a portion of, or substantially all of, the trough member 30 can have desirable effects. For example, by providing localized cooling, resultant properties of products formed (e.g., nanocrystal size(s) and/or nanocrystal shape(s)) can be controlled. Preferable liquid 3 temperatures during the processing thereof are between freezing and boiling points, more typically, between room temperature and boiling points, and even more typically, between about 40-98 degrees C., and more typically, between about 50-98 degrees C. Such temperature can be controlled by, for example, conventional means for cooling located at or near various portions of the processing apparatus.

Further, certain processing enhancers may also be added to or mixed with the liquid(s) 3. The processing enhancers include both solids and liquids (and gases in some cases). The processing enhancer(s) may provide certain processing advantages and/or desirable final product characteristics. Some portion of the processing enhancer(s) may function, influence as or become part of, for example, desirable seed crystals (or promote desirable seed crystals, or be involved in the creation of a nucleation site) and/or crystal plane growth promoters/preventers in the electrochemical growth processes of the invention; or may simply function as a current or power regulator in the electrochemical processes of the invention. Such processing enhancers may also desirably affect current and/or voltage conditions between electrodes 1/5 and/or 5/5.

A preferred processing enhancer is sodium bicarbonate. Examples of other process enhancers are sodium carbonate, potassium bicarbonate, potassium carbonate, trisodium phosphate, disodium phosphate, monosodium phosphate, potassium phosphates or other salts of carbonic acid or the like. Further process enhancers may be salts, including sodium or potassium, of bisulfate or sulfite. Still other process enhancers to make gold nanocrystals for medical applications under certain conditions may be other salts, including sodium or potassium, or any material that assists in the electrochemical growth processes described herein; and any material is not substantially incorporated into or onto the surface of the gold nanocrystasl; and does not impart toxicity to the nanocrystals or to the suspension containing the nanocrystals. Processing enhancers may assist in one or more of the electrochemical reactions disclosed herein; and/or may assist in achieving one or more desirable properties in products formed according to the teachings herein.

For example, certain processing enhancers may dissociate into positive ions (cations) and negative ions (anions). The anions and/or cations, depending on a variety of factors including liquid composition, concentration of ions, applied fields, frequency of applied fields, waveform of the applied filed, temperature, pH, zeta potential, etc., will navigate or move toward oppositely charged electrodes. When said ions are located at or near such electrodes, the ions may take part in one or more reactions with the electrode(s) and/or other constituent(s) located at or near such electrode(s). Sometimes ions may react with one or more materials in the electrode (e.g., when NaCl is used as a processing enhancer, various metal chloride (MCl, $MCl_2$, etc.) may form). Such reactions may be desirable in some cases or undesirable in others. Further, sometimes ions present in a solution between electrodes may not react to form a product such as MCl, $MCl_2$, etc., but rather may influence material in the electrode (or near the electrode) to form metallic nanocrystals that are "grown" from material provided by the electrode. For example, certain metal ions may enter the liquid 3 from the electrode 5 and be caused to come together (e.g., nucleate) to form constituents (e.g., ions, nanocrystals, etc.) within the liquid 3.

In the case of gold, a variety of extended surface planes from which crystal growth can occur are available, so long as impurities (such as, for example organic impurities) do not inhibit or prevent such growth. While gold is known to have a face centered cubic (fcc) structure, gold nanocrystals which are grown according to the methods of the present invention, are not single crystals and are typically twinned to result in a variety of desirable and highly reactive nanocrystalline shapes or shape distributions. For example, single crystal surfaces {111}, {100} and {110} are among the most frequently studied and well understood surfaces. The presence of certain species such as ions (e.g., added to or being donated by electrode 5) in an electrochemical crystal nucleation/growth process can influence (e.g., nucleate and/or promote growth of specifically-shaped nanocrystals or nanocrystal shape distributions) the presence or absence of one or more of such extended surfaces. A certain ion (e.g., anion) under certain field conditions may assist in the presence of more {111} extended surfaces or planes relative to other crystal surfaces which can result in the presence of certain nanocrystalline shapes relative to other shapes (e.g., more decahedron shapes relative to other shapes such as tetrahedrons, icosahedrons, octahedrons; or the combination(s) of certain crystalline shapes relative to other crystalline shapes, etc.). By controlling the presence or absence (e.g., relative amounts) of such faces, crystal shapes (e.g., hexagonal plates, octahedrons, tetrahedrons and pentagonal bipyramids (i.e., decahedrons)) and/or crystal sizes or extended crystal planes which contain such faces, nanocrystal shapes, can thus be relatively controlled. Control of the size and shape of nanocrystals (as well as the surface properties of nanocrystals) can control their function(s) in a variety of systems, including biological systems.

Specifically, the presence of certain nanocrystalline shapes (or shape distributions) containing specific spatially extended low index crystal planes can cause different reactions (e.g., different biocatalytic and/or biophysical reactions and/or cause different biological signaling pathways to be active/inactive relative to the absence of such shaped nanoparticles) and/or different reactions selectively to occur under substantially identical conditions. One crystalline shape of a gold nanoparticle (e.g., a pentagonal by-pyramidal structure, or decahedron, or tetrahedron containing $\{111\}$ planes) can result in one set of reactions to occur (e.g., binding to a particular protein or homologue and/or affecting a particular biological signaling pathway of a protein or a cytokine) whereas a different crystal shape (e.g., a octahedron containing the same or different crystal planes such as $\{111\}$ or $\{100\}$) can result in a different reaction endpoint (i.e., a different biocatalytic or signaling pathway effect). More dramatically, the lack of any extended crystal growth plane results in a spherical-shaped nanoparticle (e.g., such as those made by classical homogenous chemical reduction processes) significantly affects the performance of the nanoparticle (e.g., relative to an extended plane nanocrystal). Such differences in performance may be due to differing surface plasmon resonances and/or intensity of such resonances. Thus, by controlling amount (e.g., concentration), nanocrystal sizes, the presence or absence of certain extended growth crystal planes, and/or nanocrystalline shapes or shape distribution(s), certain reactions (e.g., biological reactions and/or biological signaling pathways) can be desirably influenced and/or controlled. Such control can result in the prevention and/or treatment of a variety of different diseases or indications that are a function of certain biologic reactions and/or signaling pathways (discussed later herein).

Further, certain processing enhancers may also include materials that may function as charge carriers, but may themselves not be ions. Specifically, metallic-based particles, either introduced or formed in situ (e.g., heterogeneous or homogenous nucleation/growth) by the electrochemical processing techniques disclosed herein, can also function as charge carriers, crystal nucleators and/or growth promoters, which may result in the formation of a variety of different crystalline shapes (e.g., hexagonal plates, octahedrons, techahedrons, pentagonal bi-pyramids (decahedrons), etc.). Once again, the presence of particular particle crystal sizes, extended crystal planes and/or shapes or shape distributions of such crystals, can desirably influence certain reactions (e.g., binding to a particular protein or protein homologue and/or affecting a particular biological signaling pathway such as an inflammatory pathway or a proteasomal pathway) to occur. Further, since the processing enhancers of the present invention do not contemplate those traditional oraganic-based molecules used in traditional reduction chemistry techniques, the lack of such chemical reductant (or added surfactant) means that the surfaces of the grown nanocrystals on the invention are very "clean" relative to nanoparticles that are formed by traditional reduction chemistry approaches. It should be understood that when the term "clean" is used with regard to nanocrystal surfaces or when the phrase "substantially free from organic impurities or films" (or a similar phrase) is used, what is meant is that the formed nanocrystals do not have chemical constituents adhered or attached to their surfaces which (1) alter the functioning of the nanocrystal and/or (2) form a layer, surface or film which covers a significant portion (e.g., at least 25% of the crystal, or more typically, at least 50% of the crystal). In preferred embodiments, the nanocrystal surfaces are completely free of any organic contaminants which materially change their functionality. It should be further understood that incidental components that are caused to adhere to nanocrystals of the invention and do not adversely or materially affect the functioning of the inventive nanocrystals, should still be considered to be within the metes and bounds of the invention. One example of a nanocrystal surface that is completely free from organic impurities or films is shown in Example 5 herein.

The lack of added chemicals (e.g., organics) permits the growth of the gold atoms into the extended crystal planes resulting in the novel crystalline shape distributions and also affects the performance of the nanocrystals in vivo (e.g., affects the protein corona formed around the nanoparticles/nanocrystals in, for example, serum). For example, but without wishing to be bound by any particular theory or explanation, protein corona formation can control location of a nanoparticle/nanocrystal in vivo, as well as control protein folding of proteins at or near the nanoparticle/nanocrystal surfaces. Such differences in performance may be due to such factors including, but not limited to, surface charge, surface plasmon resonance, epitaxial effectsF, surface double layers, zones of influence, and others.

Still further, once a seed crystal occurs in the process and/or a set of extended crystal planes begins to grow (e.g., homogenous nucleation) or a seed crystal is separately provided (e.g., heterogenous nucleation) the amount of time that a formed particle (e.g., a metal atom) is permitted to dwell at or near one or more electrodes in an electrochemical process can result in the size of such nanocrystals increasing as a function of time (e.g., metal atoms can assemble into metal nanocrystals and, if unimpeded by certain organic constituents in the liquid, they can grow into a variety of shapes and sizes). The amount of time that crystal nucleation/growth conditions are present can control the shape(s) and sizes(s) of grown nanocrystals. Accordingly, dwell time at/around electrodes, liquid flow rate(s), trough cross-sectional shape(s), etc, all contribute to nanocrystal growth conditions, as discussed elsewhere herein.

In a preferred embodiment the percent of pentagonal bipyramids is at least about 5%, or is in a range of about 5%-35%, and more typically at least about 10%, or is in a range of about 10%-35%, and even more typically, at least about 15%, or is in a range of about 15%-35%, and still more typically, at least about 25%, and in some cases at least about 30%.

In another preferred embodiment the percent of tetrahedrons is at least 5%, or is in a range of about 5%-35%, and more typically at least about 10%, or is in a range of about 10%-35%, and even more typically, at least about 15%, or is in a range of about 15%-35%, and still more typically, at least about 25%, and in some cases at least about 30%.

Still further, the combination of pentagonal bipyramids and tetrahedrons is at least about 15%, or is in a range of about 15%-50%, and more typically at least about 20%, or is in a range of about 20%-50%, and even more typically, at least about 30%, or is in a range of about 30%-50%, and still more typically, at least about 35%, and in some cases at least about 45%.

Still further, the combination of pentagonal bipyramids, tetrahedrons, octahedrons and hexagonal is at least about 50%, or is in a range of about 50%-85%, and more typically at least about 60%, or is in a range of about 60%-85%, and even more typically, at least about 70%, or is in a range of about 70%-85%, and still more typically, at least about 70%, and in some cases at least about 80%.

In many of the preferred embodiments herein, one or more AC sources are utilized. The rate of change from "+" polarity on one electrode to "−" polarity on the same electrode is known as Hertz, Hz, frequency, or cycles per second. In the United States, the standard output frequency is 60 Hz, while in Europe it is predominantly 50 Hz. As shown in the Examples herein, the frequency can also influence size and/or shape of nanocrystals formed according to the electrochemical techniques disclosed herein. Preferable frequencies are 5-1000 Hz, more typically, 20-500 Hz, even more typically, 40-200 Hz, and even more typically, 50-100 Hz. For example, and without wishing to be bound by any particular theory or explanation, nucleated or growing crystals can first have attractive forces exerted on them (or on crystal growth constituents, such as ions or atoms, taking part in forming the crystal(s)) due to, for example, unlike charges attracting and then repulsive forces being exerted on such constituents (e.g., due to like charges repelling). These factors also clearly play a large role in nucleation and/or crystal growth of the novel nanocrystals formed by affecting particle size and/or shapes; as well as permitting the crystals to be formed without the need for reductants or surfactants (i.e., that needed to be added to take part in the prior art reduction chemistry techniques) causing the nanocrystal surfaces to be free of such added chemical species. The lack of organic-based coatings on the surface of grown nanocrystals alters (and in some cases controls) their biological function.

Moreover, the particular waveform that is used for a specific frequency also affects nanocrystal growth conditions, and thus effects nanocrystal size(s) and/or shape(s). While the U.S. uses a standard AC frequency of 60 Hz, it also uses a standard waveform of a "sine" wave. As shown in the Examples herein, changing the waveform from a sine wave to a square wave or a triangular wave also affects nanocrystal crystallization conditions and thus affects resultant nanocrystal size(s) and shape(s). Preferred waveforms include sine waves, square waves and triangular waves, however hybrid waveforms should be considered to be within the metes and bounds of the invention.

Still further, the voltage applied in the novel electrochemical techniques disclosed herein can also affect nanocrystalline size(s) and shape(s). A preferred voltage range is 20-2000 Volts, a more preferred voltage range is 50-1000 Volts and an even more preferred voltage range is 100-300 Volts. In addition to voltage, the amperages used with these voltages typically are 0.1-10 Amps, a more preferred amperage range is 0.1-5 Amps and an even more preferred amperage range is 0.4-1 Amps.

Still further, the "duty cycle" used for each waveform applied in the novel electrochemical techniques disclosed herein can also affect nanocrystalline size(s) and shape(s). In this regard, without wishing to be bound by any particular theory or explanation, the amount of time that an electrode is positively biased can result in a first set of reactions, while a different set of reactions can occur when the electrode is negatively biased. By adjusting the amount of time that the electrodes are positively or negatively biased, size(s) and/or shape(s) of grown nanocrystals can be controlled. Further, the rate at which an electrode converts to + or − is also a function of waveform shape and also influences nanocrystal size(s) and/or shape(s).

Temperature can also play an important role. In some of the preferred embodiments disclosed herein, the boiling point temperature of the water is approached in at least a portion of the processing vessel where gold nanocrystals are nucleated and grown. For example, output water temperature in the continuous processing Examples herein ranges from about 60° C.-99° C. However, as discussed elsewhere herein, different temperature ranges are also desirable. Temperature can influence resultant product (e.g., size and/or shape of nanocrystals) as well as the amount of resultant product (i.e., ppm level of nanocrystals in the suspension or colloid). For example, while it is possible to cool the liquid 3 in the trough member 30 by a variety of known techniques (as disclosed in some of the Examples herein), many of the Examples herein do not cool the liquid 3, resulting in evaporation of a portion of the liquid 3 during processing thereof.

Figure 10B:
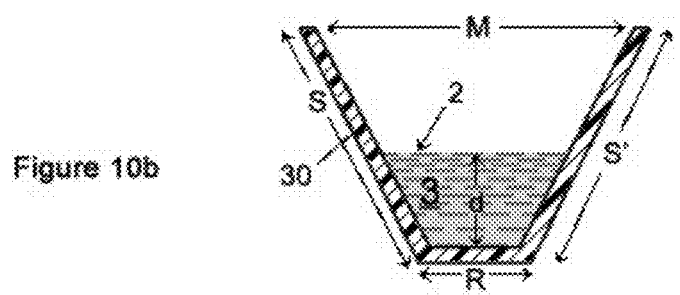
Figure 10C:
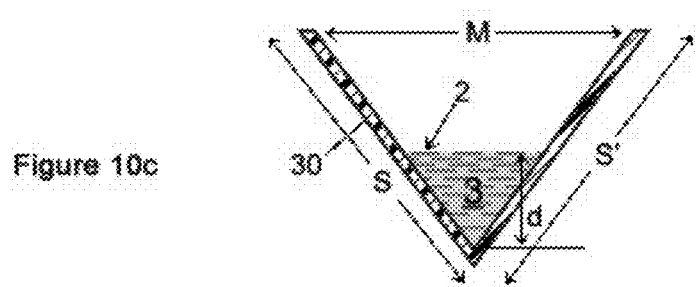
Figure 10D:
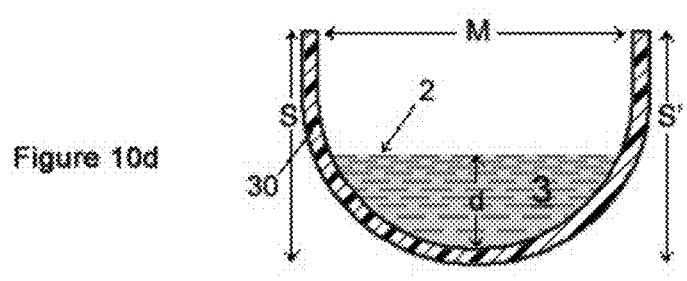
Figure 10E:
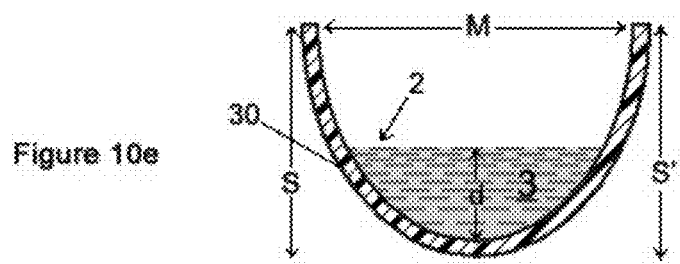

FIG. 11a shows a perspective view of one embodiment of substantially all of one trough member 30 shown in FIG. 10b including an inlet portion or inlet end 31 and an outlet portion or outlet end 32. The flow direction "F" discussed in other figures herein corresponds to a liquid entering at or near the end 31 (e.g., utilizing an appropriate means for delivering fluid into the trough member 30 at or near the inlet portion 31) and exiting the trough member 30 through the end 32. FIG. 11b shows the trough member 30 of FIG. 11a containing three control devices 20a, 20b and 20c removably attached to the trough member 30. The interaction and operations of the control devices 20a, 20b and 20c containing the electrodes 1 and/or 5 are discussed in greater detail later herein. However, in a preferred embodiment of the invention, the control devices 20, can be removably attached to a top portion of the trough member 30 so that the control devices 20 are capable of being positioned at different positions along the trough member 30, thereby affecting certain processing parameters, constituents produced (e.g., sizes and shapes of nanocrystals), reactivity of constituents produced, as well as nanocrystal(s)/fluid(s) produced therefrom.

FIG. 11c shows a perspective view of an atmosphere control device cover 35'. The atmosphere control device or cover 35' has attached thereto a plurality of control devices 20a, 20b and 20c controllably attached to electrode(s) 1 and/or 5. The cover 35' is intended to provide the ability to control the atmosphere within and/or along a substantial portion of (e.g., greater than 50% of) the longitudinal direction of the trough member 30, such that any adjustable plasma(s) 4 created between any electrode(s) 1 and surface 2 of the liquid 3 can be a function of the previously discussed parameters of voltage, current, current density, polarity, etc. (as discussed in more detail elsewhere herein) as well as a controlled atmosphere (also discussed in more detail elsewhere herein).

FIG. 11d shows the apparatus of FIG. 11c including an additional support means 34 for supporting the trough member 30 (e.g., on an exterior portion thereof), as well as supporting (at least partially) the control devices 20 (not shown in FIG. 11d). It should be understood by the reader that various details can be changed regarding, for example, the cross-sectional shapes shown for the trough member 30, atmosphere control(s) (e.g., the cover 35') and external support means (e.g., the support means 34) which are within the metes and bounds of this disclosure, some of which are discussed in greater detail later herein.

Figure 11E:
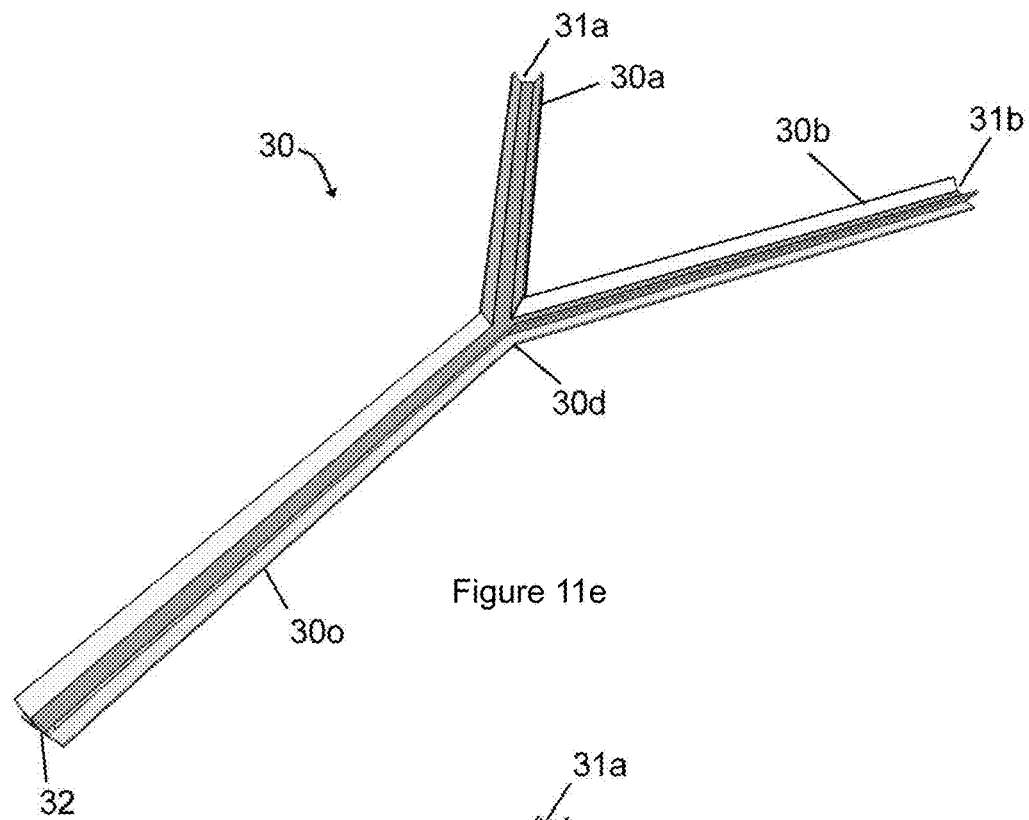

FIG. 11e shows an alternative configuration for the trough member 30. Specifically, the trough member 30 is shown in perspective view and is "Y-shaped". Specifically, the trough member 30 comprises top portions 30a and 30b and a bottom portion 30o. Likewise, inlets 31a and 31b are provided along with an outlet 32. A portion 30d corresponds to the point where 30a and 30b meet 30o.

Figure 11F:
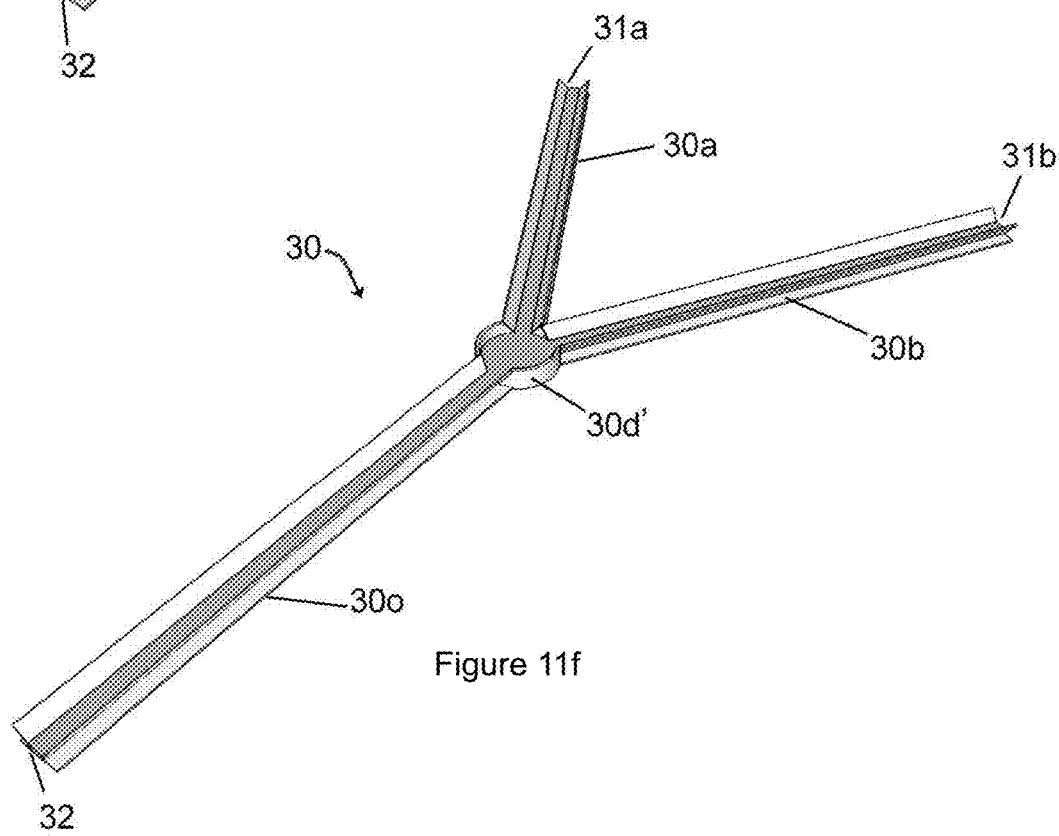

FIG. 11f shows the same "Y-shaped" trough member shown in FIG. 11e, except that the portion 30d of FIG. 11e is now shown as a more definite mixing section 30d'. In this regard, certain constituents manufactured or produced in the liquid 3 in one or all of, for example, the portions 30a, 30b and/or 30c, may be desirable to be mixed together at the point 30d (or 30d'). Such mixing may occur naturally at the intersection 30d shown in FIG. 11e (i.e., no specific or special section 30d' may be needed), or may be more specifically controlled at the portion 30d'. It should be understood that the portion 30d' could be shaped into any effective shape, such as square, circular, rectangular, etc., and be of the same or different depth relative to other portions of the trough member 30. In this regard, the area 30d could be a mixing zone or subsequent reaction zone or a zone where a processing enhancer may be added. More details of the interactions 30d and 30d' are discussed later herein.

Figure 11G:
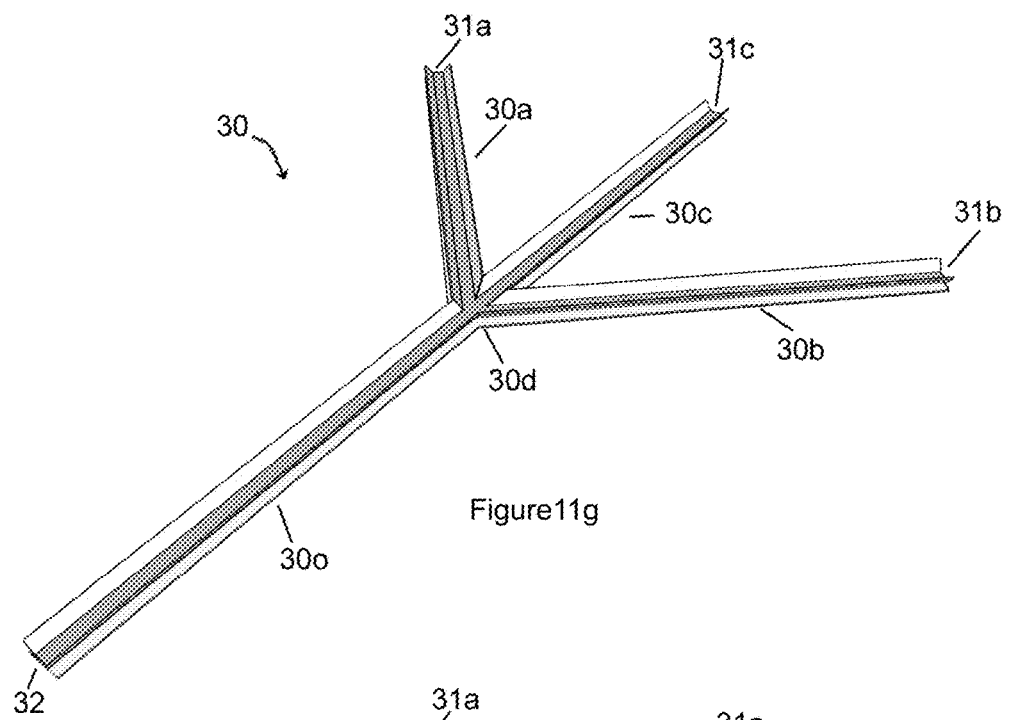
Figure 11H:
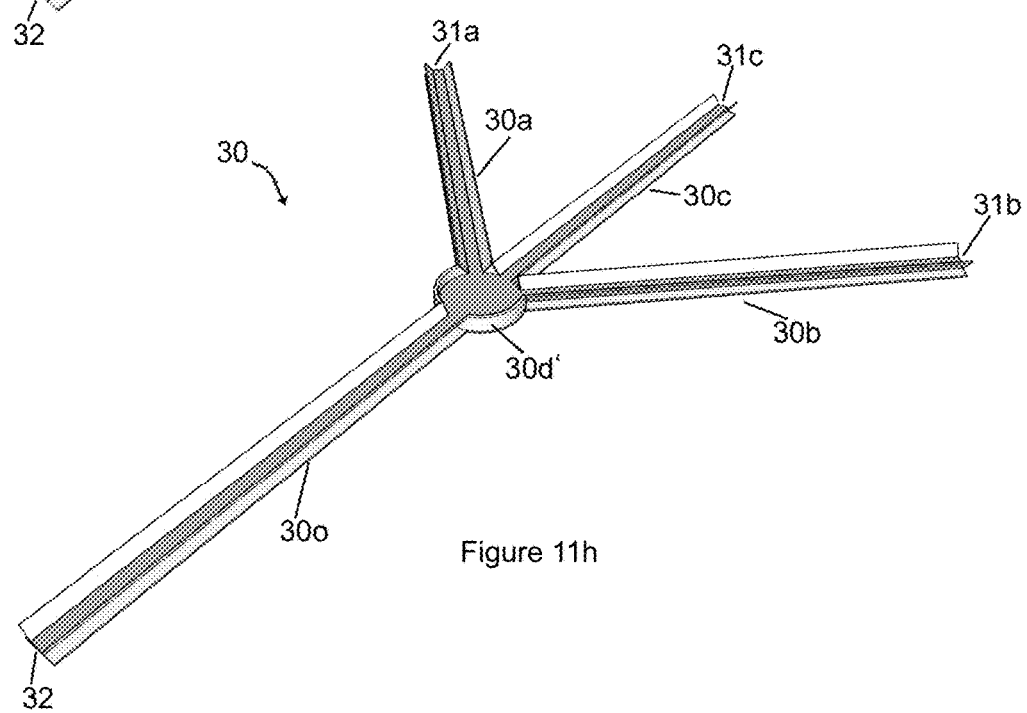

FIGS. 11g and 11h show a "T-shaped" trough member 30. Specifically, a new portion 30c has been added. Other features of FIGS. 11g and 11h are similar to those features shown in 11e and 11f.

It should be understood that a variety of different shapes and/or cross-sections can exist for the trough member 30, any one of which can produce desirable results as a function of a variety of design and production considerations. For example, one or more constituents produced in the portion(s) 30a, 30b and/or 30c could be transient (e.g., a seed crystal or nucleation point) and/or semi permanent (e.g., grown nanocrystals present in a colloid). If such constituent(s) produced, for example, in portion 30a is to be desirably and controllably reacted with one or more constituents produced in, for example, portion 30b, then a final product (e.g., properties of a final product) which results from such mixing could be a function of when constituents formed in the portions 30a and 30b are mixed together. Also, the temperature of liquids entering the section 30d (or 30d') can be monitored/controlled to maximize certain desirable processing conditions and/or desirable properties of final products and/or minimize certain undesirable products. Still further, processing enhancers may be selectively utilized in one or more of the portions 30a, 30b, 30c, 30d (30d') and/or 30o (or at any selected point or portion in the trough member 30).

Figure 12A:
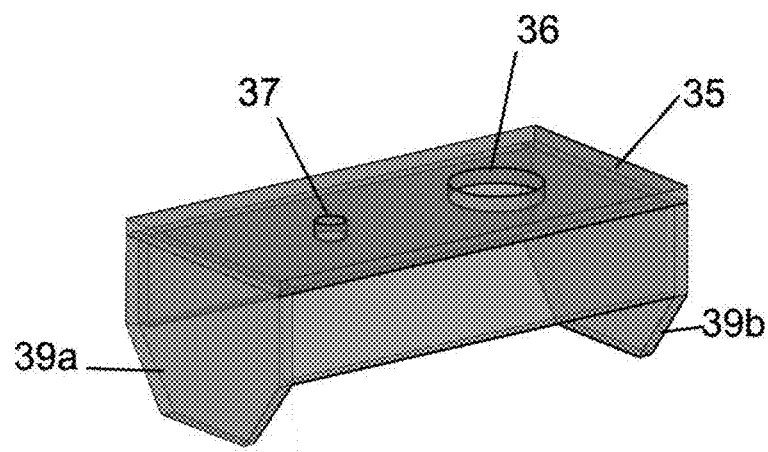
FIGS. 12a and 12b show various atmosphere control devices 35 for locally controlling the atmosphere around electrode set(s) 1 and/or 5.

FIG. 12a shows a perspective view of a local atmosphere control apparatus 35 which functions as a means for controlling a local atmosphere around the electrode sets 1 and/or 5 so that various localized gases can be utilized to, for example, control and/or effect certain components in the adjustable plasma 4 between electrode 1 and surface 2 of the liquid 3, as well as influence adjustable electrochemical reactions at and/or around the electrode(s) 5. The throughholes 36 and 37 shown in the atmosphere control apparatus 35 are provided to permit external communication in and through a portion of the apparatus 35. In particular, the hole or inlet 37 is provided as an inlet connection for any gaseous species to be introduced to the inside of the apparatus 35. The hole 36 is provided as a communication port for the electrodes 1 and/or 5 extending therethrough which electrodes are connected to, for example, the control device 20 located above the apparatus 35. Gasses introduced through the inlet 37 can simply be provided at a positive pressure relative to the local external atmosphere and may be allowed to escape by any suitable means or pathway including, but not limited to, bubbling out around the portions 39a and/or 39b of the apparatus 35, when such portions are caused, for example, to be at least partially submerged beneath the surface 2 of the liquid 3. Alternatively, a second hole or outlet (not shown) can be provided elsewhere in the atmosphere control apparatus 35. Generally, the portions 39a and 39b can break the surface 2 of the liquid 3 effectively causing the surface 2 to act as part of the seal to form a localized atmosphere around electrode sets 1 and/or 5. When a positive pressure of a desired gas enters through the inlet port 37, small bubbles can be caused to bubble past, for example, the portions 39a and/or 39b. Alternatively, gas may exit through an appropriate outlet in the atmosphere control apparatus 35, such as through the hole 36.

Figure 12B:
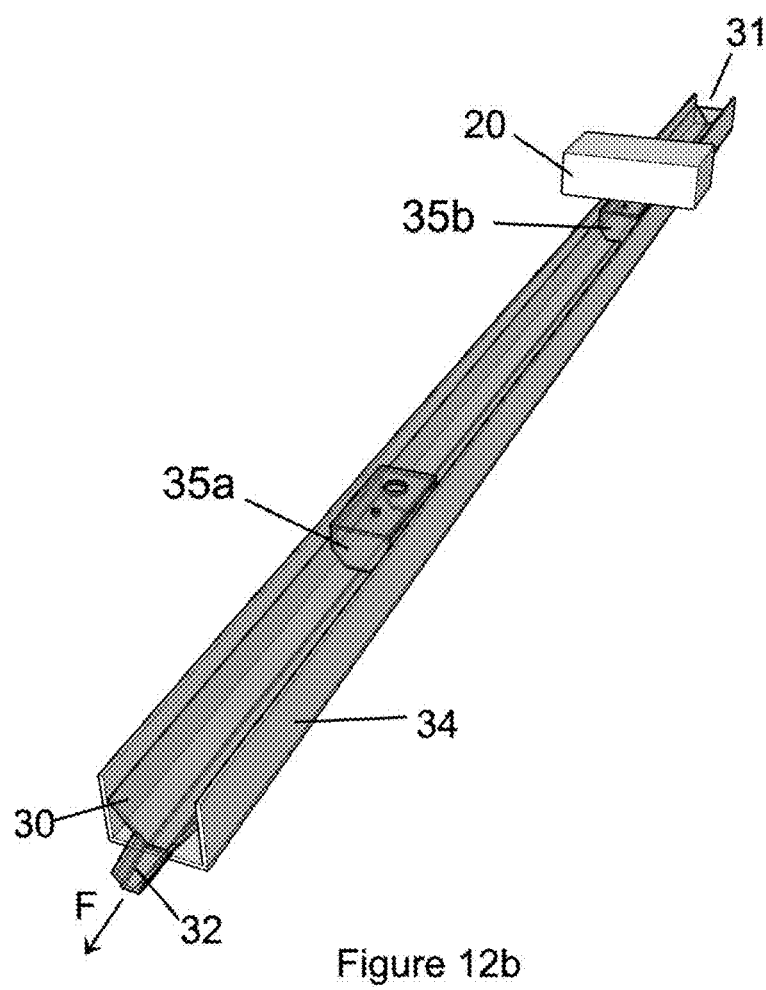

FIG. 12b shows a perspective view of first atmosphere control apparatus 35a in the foreground of the trough member 30 contained within the support housing 34. A second atmosphere control apparatus 35b is included and shows a control device 20 located thereon. "F" denotes the longitudinal direction of flow of liquid through the trough member 30. IF desired, locally controlled atmosphere(s) (e.g., of substantially the same chemical constituents, such as air or nitrogen, or substantially different chemical constituents, such as helium and nitrogen) around different electrode sets 1 and/or 5 can be achieved.

Figure 13:
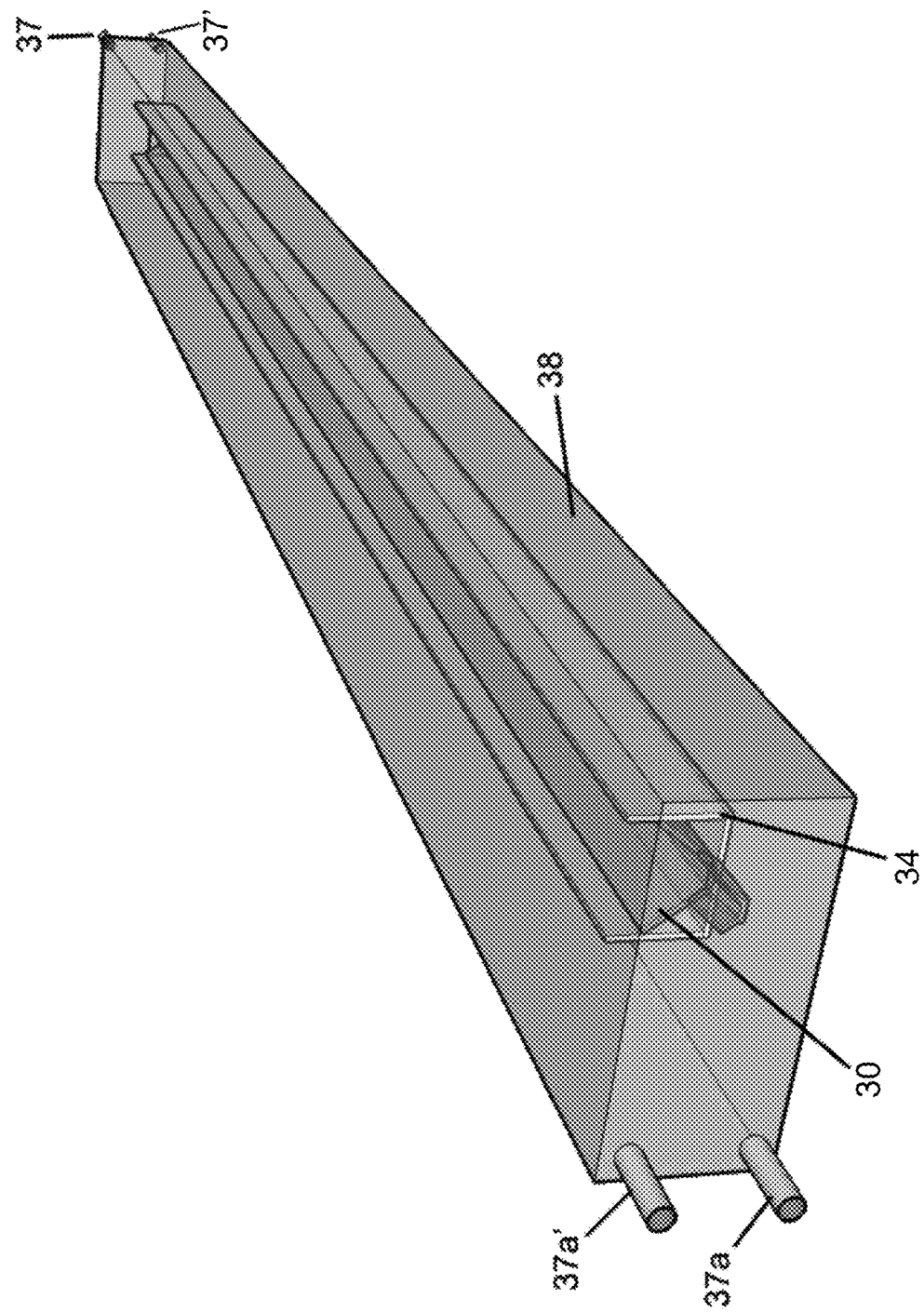
FIG. 13 shows an atmosphere control device 38 for controlling atmosphere around substantially the entire trough member 30.

FIG. 13 shows a perspective view of an alternative atmosphere control apparatus 38 wherein the entire trough member 30 and support means 34 are contained within the atmosphere control apparatus 38. In this case, for example, gas inlet 37 (37') can be provided along with a gas outlet(s) 37a (37a'). The exact positioning of the gas inlet(s) 37 (37') and gas outlet(s) 37a (37a') on the atmosphere control apparatus 38 is a matter of convenience, as well as a matter of the composition of the atmosphere contained therein. In this regard, if the gas is heavier than air or lighter than air, inlet and outlet locations can be adjusted accordingly. Aspects of these factors are discussed in greater detail later herein.

Figure 14:
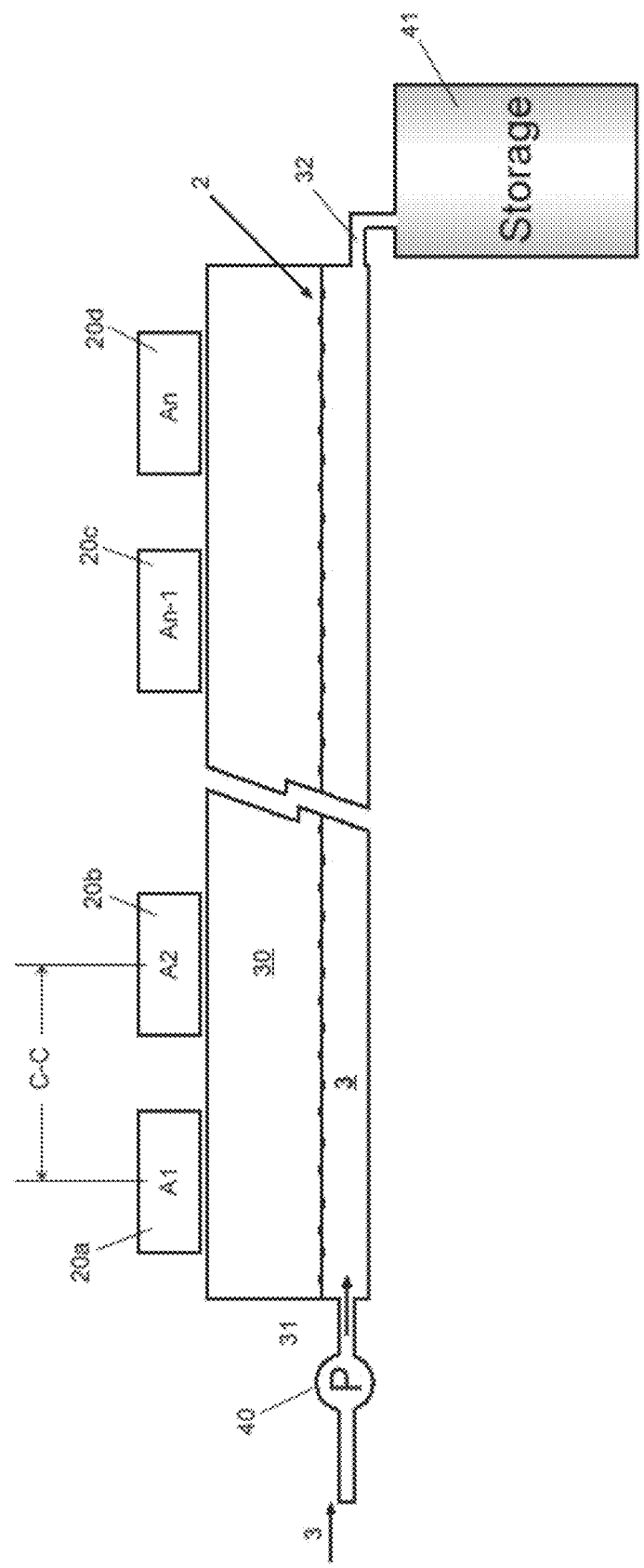
FIG. 14 shows a schematic cross-sectional view of a set of control devices 20 located on a trough member 30 with a liquid 3 flowing therethrough and into a storage container 41.

FIG. 14 shows a schematic view of the general apparatus utilized in accordance with the teachings of some of the preferred embodiments of the present invention. In particular, this FIG. 14 shows a side schematic view of the trough member 30 containing a liquid 3 therein. On the top of the trough member 30 rests a plurality of control devices 20a-20d which are, in this embodiment, removably attached thereto. The control devices 20a-20d may of course be permanently fixed in position when practicing various embodiments of the invention. The precise number of control devices 20 (and corresponding electrode(s) 1 and/or 5 as well as the configuration(s) of such electrodes) and the positioning or location of the control devices 20 (and corresponding electrodes 1 and/or 5) are a function of various preferred embodiments of the invention discussed in greater detail elsewhere herein. However, in general, an input liquid 3 (for example water or purified water) is provided to a liquid transport means 40 (e.g., a liquid pump, gravity or liquid pumping means for pumping the liquid 3) such as a peristaltic pump 40 for pumping the liquid 3 into the trough member 30 at a first-end 31 thereof. Exactly how the liquid 3 is introduced is discussed in greater detail elsewhere herein. The liquid transport means 40 may include any means for moving liquids 3 including, but not limited to a gravity-fed or hydrostatic means, a pumping means, a regulating or valve means, etc. However, the liquid transport means 40 should be capable of reliably and/or controllably introducing known amounts of the liquid 3 into the trough member 30. The amount of time that the liquid 3 is contained within the trough member 30 (e.g., at or around one or more electrode(s) 1/5) also influences the products produced (e.g., the sizes(s) and/or shapes(s) of the grown nanocrystals).

Once the liquid 3 is provided into the trough member 30, means for continually moving the liquid 3 within the trough member 30 may or may not be required. However, a simple means for continually moving the liquid 3 includes the trough member 30 being situated on a slight angle θ (e.g., less than a degree to a few degrees for a low viscosity fluid 3 such as water) relative to the support surface upon which the trough member 30 is located. For example, a difference in vertical height of less than one inch between an inlet portion 31 and an outlet portion 32, spaced apart by about 6 feet (about 1.8 meters) relative to the support surface may be all that is required, so long as the viscosity of the liquid 3 is not too high (e.g., any viscosity around the viscosity of water can be controlled by gravity flow once such fluids are contained or located within the trough member 30). In this regard, FIGS. 15a and 15b show two acceptable angles $\theta_1$ and $\theta_2$, respectively, for trough member 30 that can process various viscosities, including low viscosity fluids such as water. The need for a greater angle θ could be a result of processing a liquid 3 having a viscosity higher than water; the need for the liquid 3 to transit the trough 30 at a faster rate, etc. Further, when viscosities of the liquid 3 increase such that gravity alone is insufficient, other phenomena such as specific uses of hydrostatic head pressure or hydrostatic pressure can also be utilized to achieve desirable fluid flow. Further, additional means for moving the liquid 3 along the trough member 30 could also be provided inside the trough member 30. Such means for moving the fluid include mechanical means such as paddles, fans, propellers, augers, etc., acoustic means such as transducers, thermal means such as heaters and/or chillers (which may have additional processing benefits), etc., are also desirable for use with the present invention.

FIG. 14 also shows a storage tank or storage vessel 41 at the end 32 of the trough member 30. Such storage vessel 41 can be any acceptable vessel and/or pumping means made of one or more materials which, for example, do not negatively interact with the liquid 3 (or constituents contained therein) produced within the trough member 30. Acceptable materials include, but are not limited to plastics such as high density polyethylene (HDPE), glass, metal(s) (such a certain grades of stainless steel), etc. Moreover, while a storage tank 41 is shown in this embodiment, the tank 41 should be understood as including a means for distributing or directly bottling or packaging the fluid 3 processed in the trough member 30.

Figure 16C:
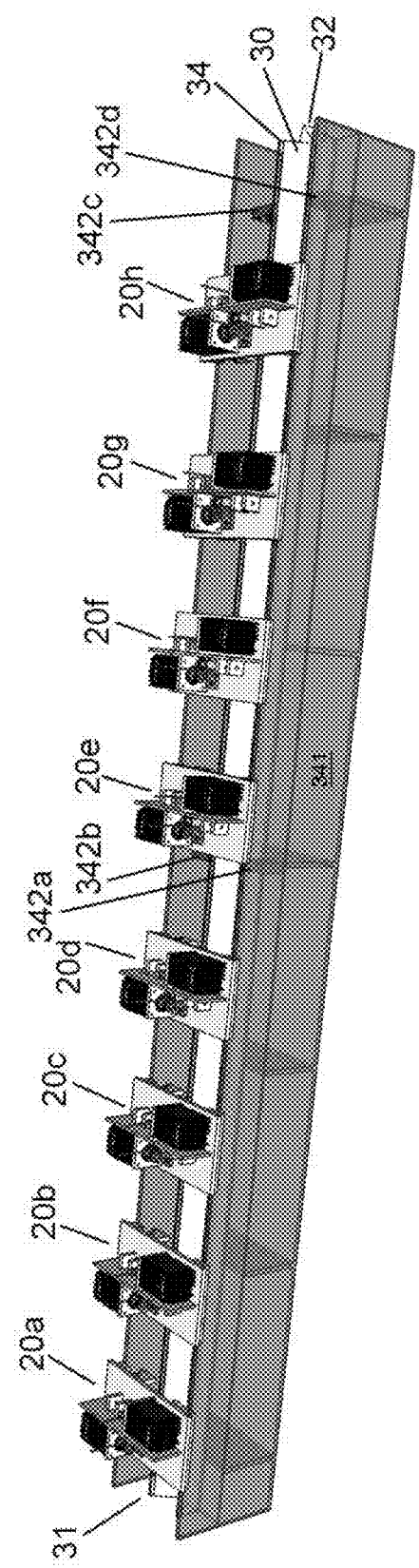

FIGS. 16a, 16b and 16c show a perspective view of one preferred embodiment of the invention. In these FIGS. 16a, 16b and 16c, eight separate control devices 20a-h are shown in more detail. Such control devices 20 can utilize one or more of the electrode configurations shown in, for example, FIGS. 8a, 8b, 8c and 8d. The precise positioning and operation of the control devices 20 (and the corresponding electrodes 1 and/or 5) are discussed in greater detail elsewhere herein. FIG. 16b includes use of two air distributing or air handling devices (e.g., fans 342a and 342b). These air handling devices can assist in removing, for example, humid air produced around the electrodes 1/5. Specifically, in some cases certain amounts of humidity are desirable, but in other cases, excessive localized humidity could be undesirable. Similarly, FIG. 16c includes the use of two alternative air distributing or air handling devices 342c and 342d.

The electrode control devices shown generally in, for example, FIGS. 2, 3, 14 and 16 are shown in greater detail in FIGS. 17d, 17e, 17f, 17m and 17n. In particular, these FIGS. 17d, 17e, 17f, 17m and 17n show a perspective view of various embodiments of the inventive control devices 20.

Figure 17A:
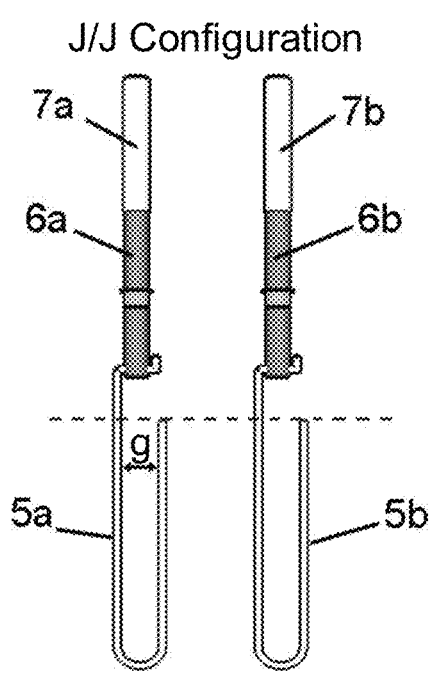
FIG. 17a shows a view of gold wires 5a and 5b used in the trough section 30b of FIG. 22a in connection with Examples 8, 9 and 10.
Figure 17B:
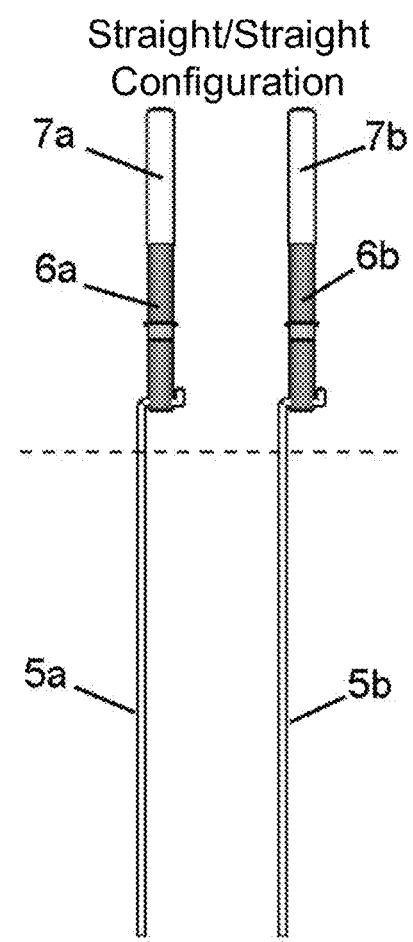
FIG. 17b shows a view of the gold wires 5a and 5b used in the trough section 30b of FIG. 21a in connection with Examples 5, 6 and 7.
Figure 17C:
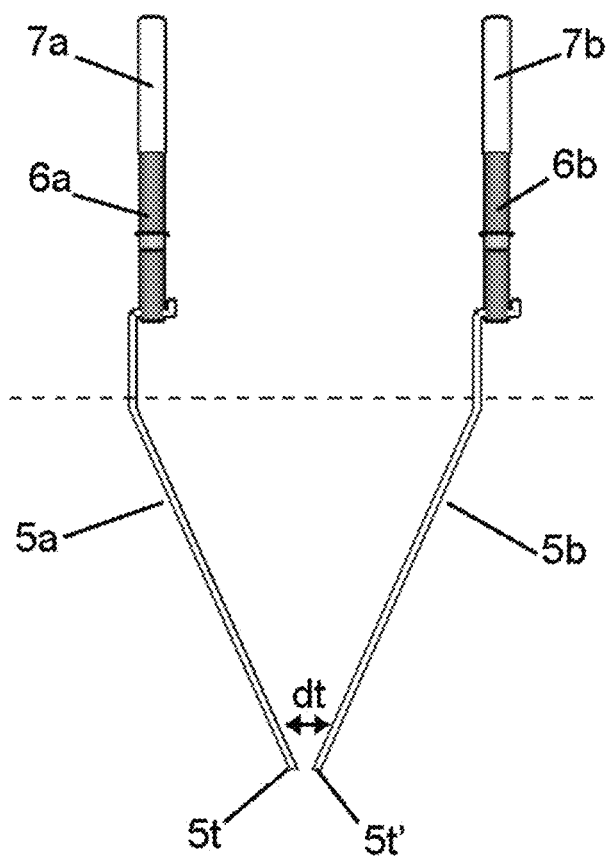
FIG. 17c shows the electrode configuration used to make sample GB-118 in Example 16.
Figure 17D:
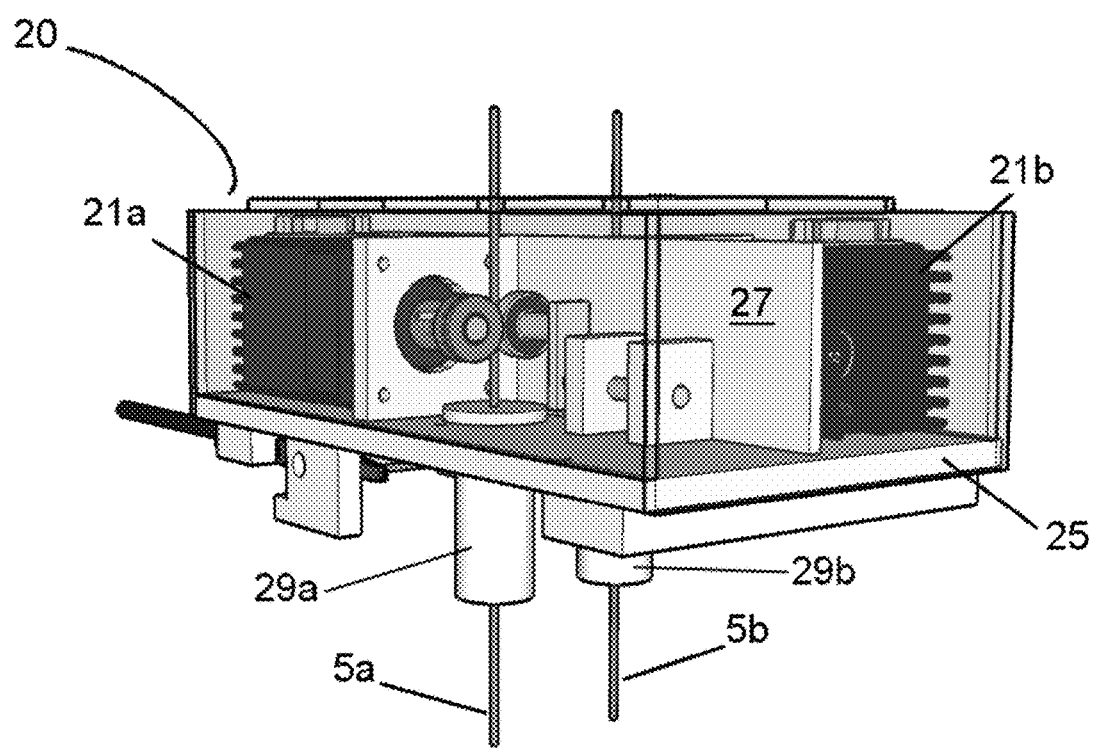
FIGS. 17d-17f show the devices 20 used in Examples 1-4 for suspensions GT032, GT031, GT019 and GT033 and to make Samples GB-139, GB-141 and GB-144 in Example 16.
Figure 17E:
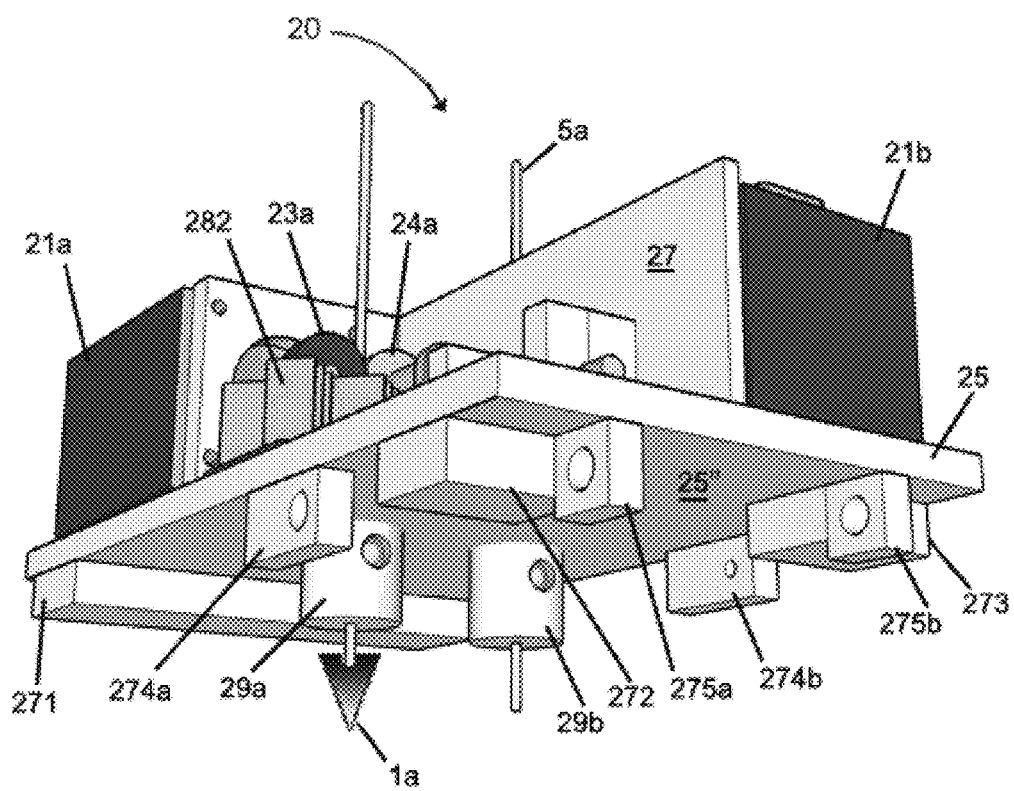
Figure 17F:
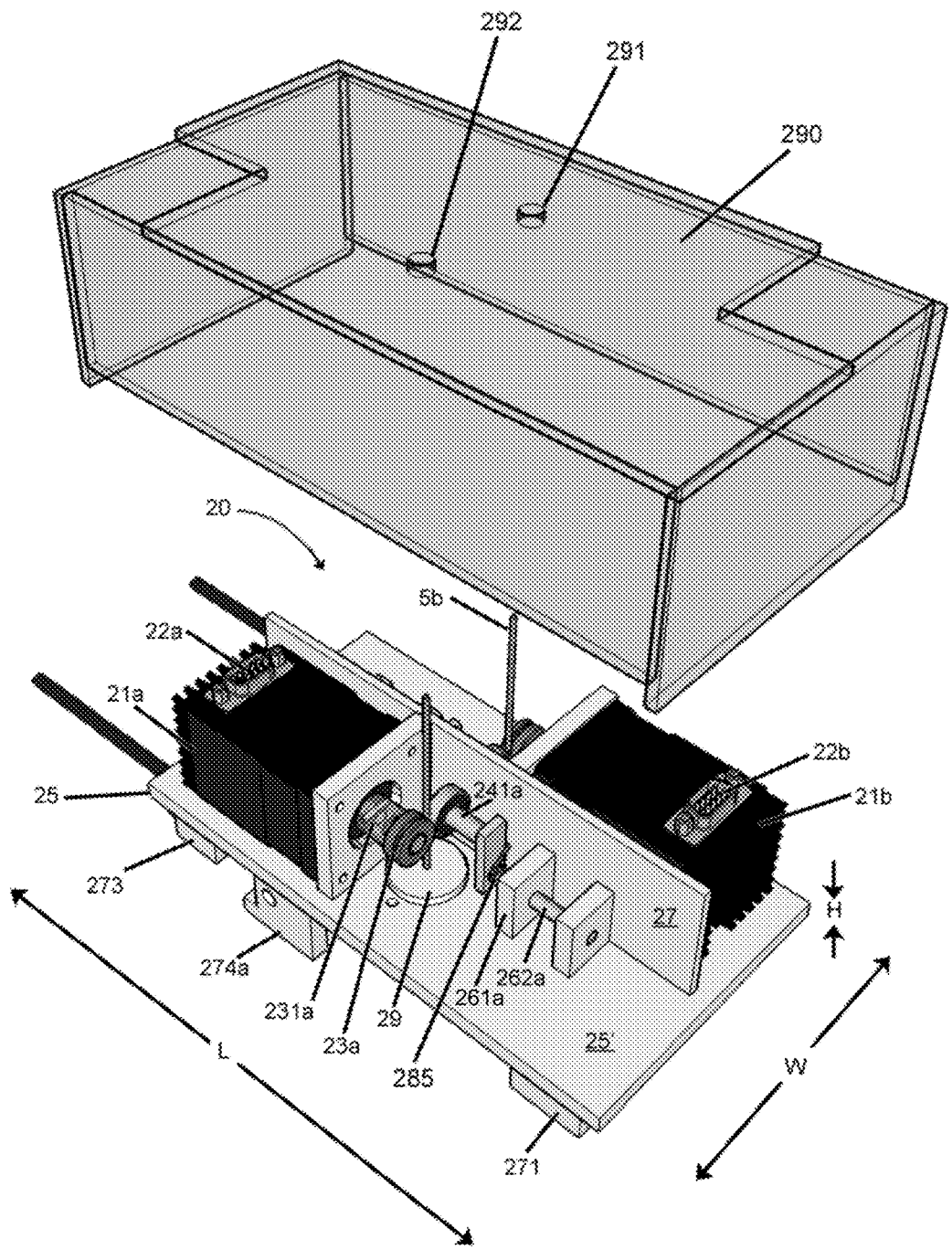
Figure 17G:
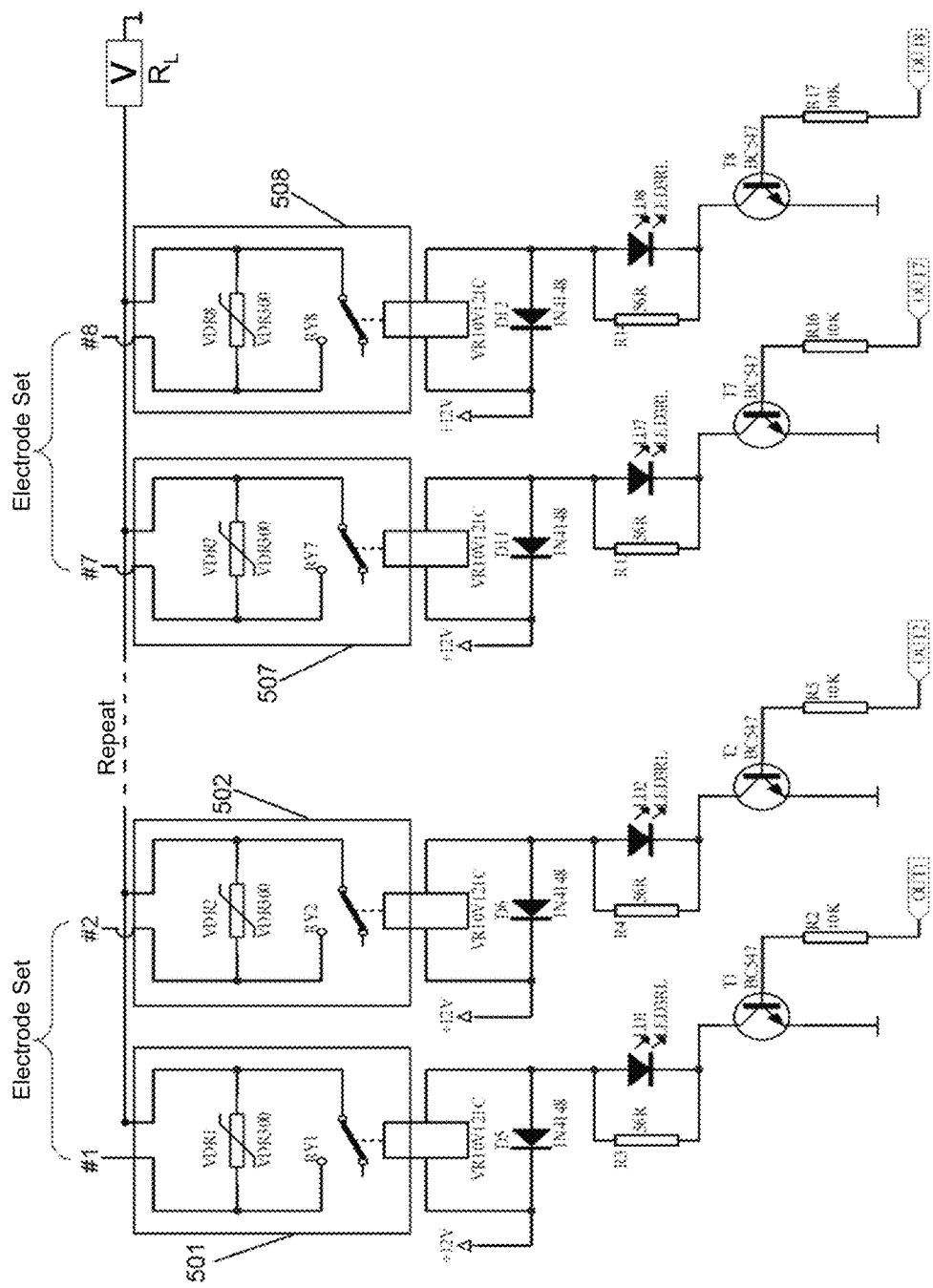

First, specific reference is made to FIGS. 17d, 17e and 17f. In each of these three Figures, a base portion 25 is provided, said base portion having a top portion 25' and a bottom portion 25". The base portion 25 is made of a suitable rigid plastic material including, but not limited to, materials made from structural plastics, resins, polyurethane, polypropylene, nylon, teflon, polyvinyl, etc. A dividing wall 27 is provided between two electrode adjustment assemblies. The dividing wall 27 can be made of similar or different material from that material comprising the base portion 25. Two servo-step motors 21a and 21b are fixed to the surface 25' of the base portion 25. The step motors 21a, 21b could be any step motor capable of slightly moving (e.g., on a 360 degree basis, slightly less than or slightly more than 1 degree) such that a circumferential movement of the step motors 21a/21b results in a vertical raising or lowering of an electrode 1 or 5 communicating therewith. In this regard, a first wheel-shaped component 23a is the drivewheel connected to the output shaft 231a of the drive motor 21a such that when the drive shaft 231a rotates, circumferential movement of the wheel 23a is created. Further, a slave wheel 24a is caused to press against and toward the drivewheel 23a such that frictional contact exists therebetween. The drivewheel 23a and/or slavewheel 24a may include a notch or groove on an outer portion thereof to assist in accommodating the electrodes 1,5. The slavewheel 24a is caused to be pressed toward the drivewheel 23a by a spring 285 located between the portions 241a and 261a attached to the slave wheel 24a. In particular, a coiled spring 285 can be located around the portion of the axis 262a that extends out from the block 261a. Springs should be of sufficient tension so as to result in a reasonable frictional force between the drivewheel 24a and the slavewheel 24a such that when the shaft 231a rotates a determined amount, the electrode assemblies 5a, 5b, 1a, 1b, etc., will move in a vertical direction relative to the base portion 25. Such rotational or circumferential movement of the drivewheel 23a results in a direct transfer of vertical directional changes in the electrodes 1,5 shown herein. At least a portion of the drivewheel 23a should be made from an electrically insulating material; whereas the slavewheel 24a can be made from an electrically conductive material or an electrically insulating material, but typically, an electrically insulating material.

The drive motors 21a/21b can be any suitable drive motor which is capable of small rotations (e.g., slightly below 1°/360° or slightly above 1°/360°) such that small rotational changes in the drive shaft 231a are translated into small vertical changes in the electrode assemblies. A preferred drive motor includes a drive motor manufactured by RMS Technologies model 1MC17-S04 step motor, which is a DC-powered step motor. This step motors 21a/21b include an RS-232 connection 22a/22b, respectively, which permits the step motors to be driven by a remote control apparatus such as a computer or a controller.

The portions 271, 272 and 273 are primarily height adjustments which adjust the height of the base portion 25 relative to the trough member 30. The portions 271, 272 and 273 can be made of same, similar or different materials from the base portion 25. The portions 274a/274b and 275a/275b can also be made of the same, similar or different material from the base portion 25. However, these portions should be electrically insulating in that they house various wire components associated with delivering voltage and current to the electrode assemblies 1a/1b, 5a/5b, etc.

The electrode assembly specifically shown in FIG. 17d comprises electrodes 5a and 5b (corresponding to, for example, the electrode assembly shown in FIG. 3c). However, that electrode assembly could comprise electrode(s) 1 only, electrode(s) 1 and 5, electrode(s) 5 and 1, or electrode(s) 5 only. In this regard, FIG. 17e shows an assembly where two electrodes 1a/5a are provided instead of the two electrode(s) 5a/5b shown in FIG. 17d. All other elements shown in FIG. 17e are similar to those shown in FIG. 17d.

With regard to the size of the control device 20 shown in FIGS. 17d, 17e and 17f, the dimensions "L" and "W" can be any dimension which accommodates the size of the step motors 21a/21b, and the width of the trough member 30. In this regard, the dimension "L" shown in FIG. 17f needs to be sufficient such that the dimension "L" is at least as long as the trough member 30 is wide, and typically slightly longer (e.g., 10-30%). The dimension "W" shown in FIG. 17f needs to be wide enough to house the step motors 21a/21b and not be so wide as to unnecessarily underutilize the longitudinal space along the length of the trough member 30. In one preferred embodiment of the invention, the dimension "L" is about 7 inches (about 19 millimeters) and the dimension "W" is about 4 inches (about 10.5 millimeters). The thickness "H" of the base member 25 is any thickness sufficient which provides structural, electrical and mechanical rigidity for the base member 25 and should be of the order of about ¼"-¾" (about 6 mm-19 mm). While these dimensions are not critical, the dimensions give an understanding of size generally of certain components of one preferred embodiment of the invention.

Further, in each of the embodiments of the invention shown in FIGS. 17d, 17e and 17f, the base member 25 (and the components mounted thereto), can be covered by a suitable cover 290 (shown in FIG. 17o to insulate electrically, as well as creating a local protective environment for all of the components attached to the base member 25. Such cover 290 can be made of any suitable material which provides appropriate safety and operational flexibility. Exemplary materials include plastics similar to that used for other portions of the trough member 30 and/or the control device 20 and is typically transparent. This cover member 290 can also be made of the same type of materials used to make the base portion 25. The cover 290 is also shown as having 2 through-holes 291 and 292 therein. Specifically, these through-holes can, for example, be aligned with excess portions of, for example, electrodes 5, which can be connected to, for example, a spool of electrode wire (not shown in these drawings).

Figure 17J:
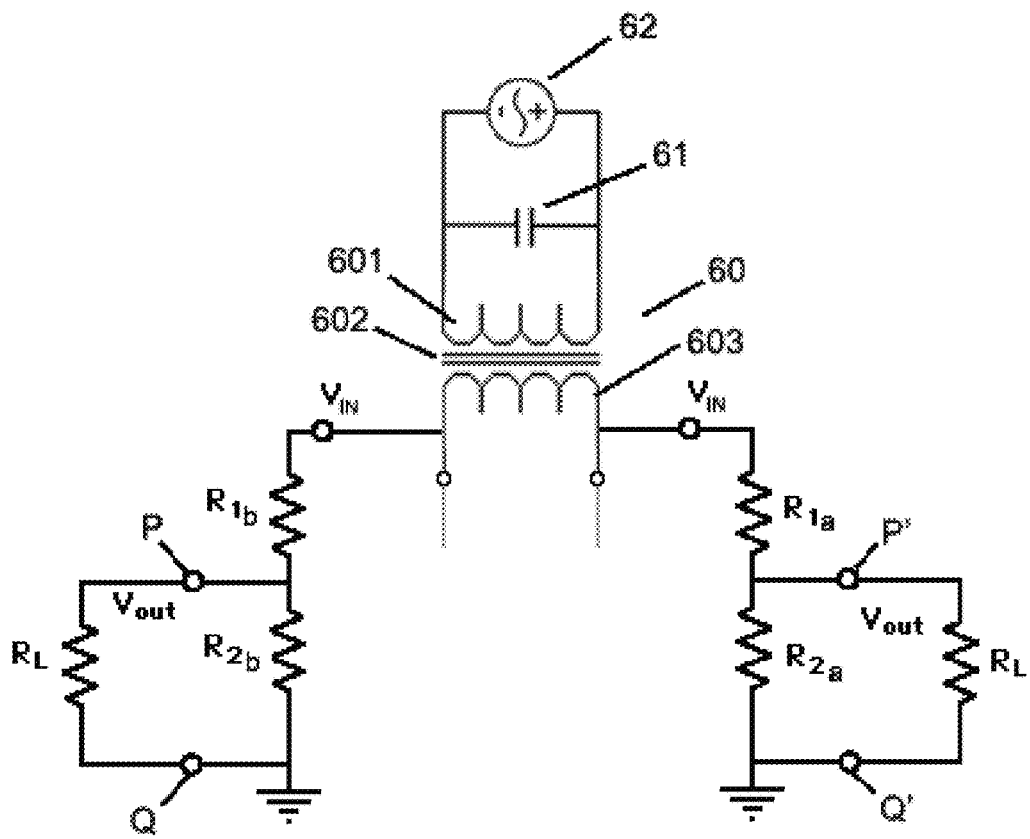
Figure 17I:
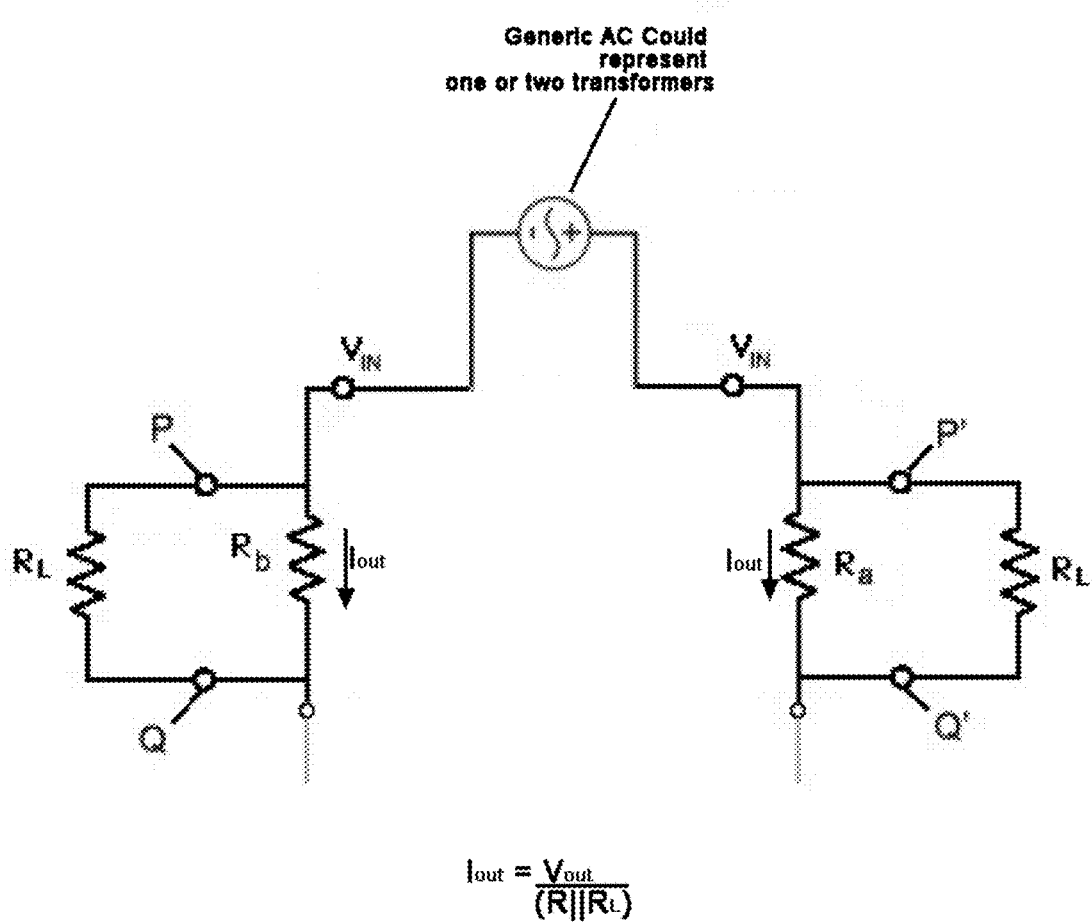
Figure 17M:
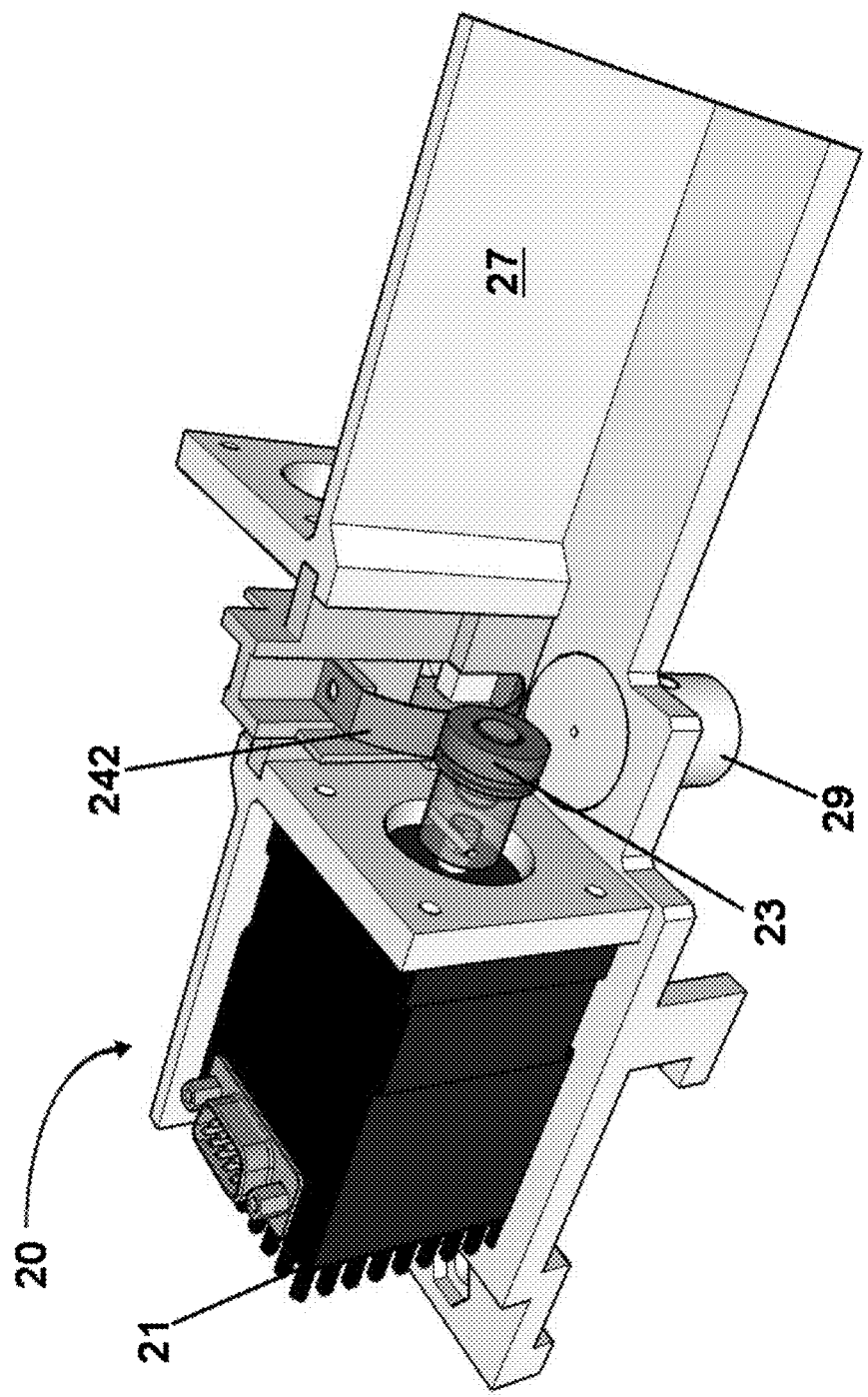
FIGS. 17m-17n show alternative designs for the devices 20. The device 20 in FIG. 17n was used in Example 18.
Figure 17N:
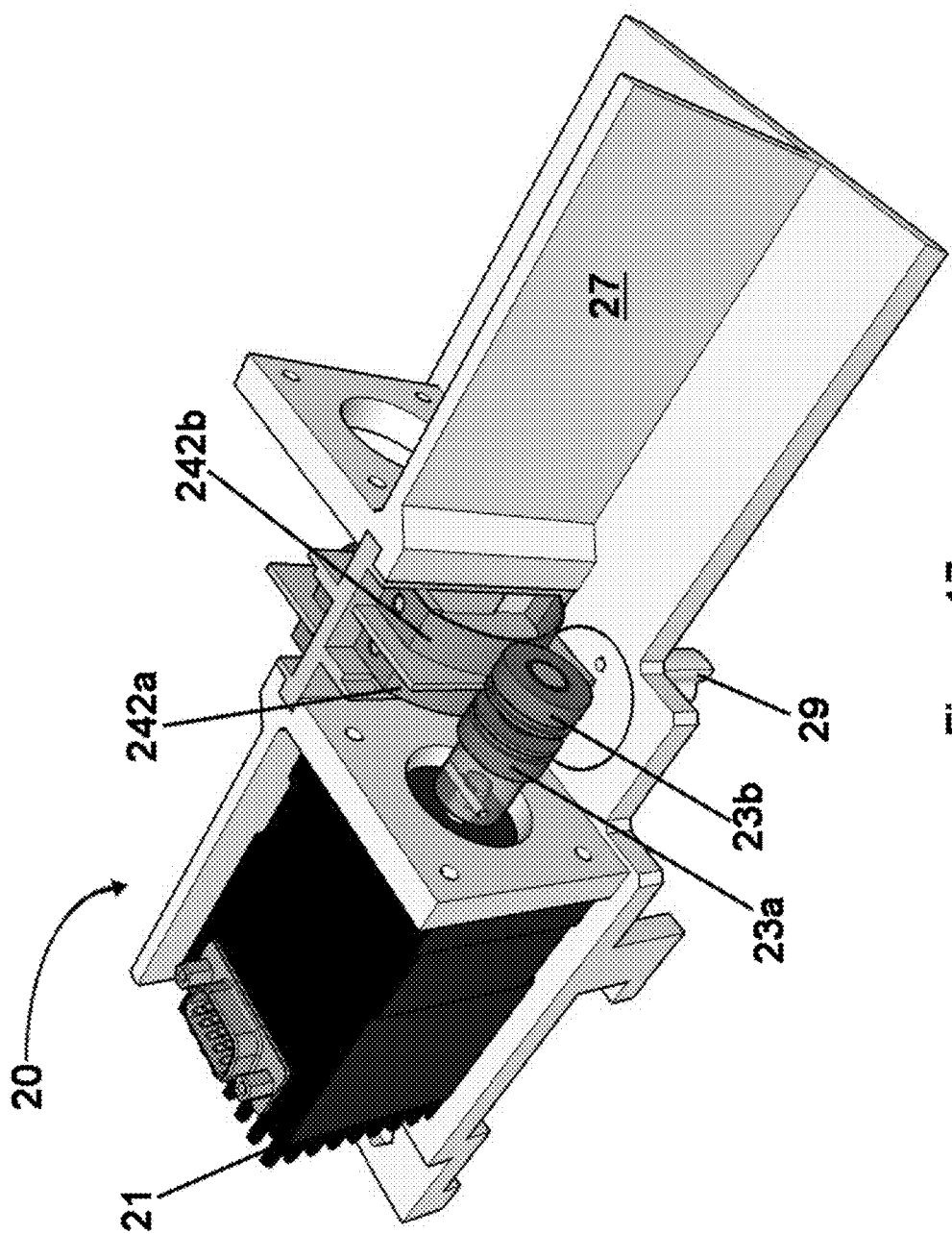

FIGS. 17m and 17n show an alternative configuration for the control device 20. In these devices, similarly numbered components are essentially the same as those components shown in FIGS. 17d, 17e and 17f. The primary differences between the control devices 20 shown in FIGS. 17m and 17n is that while a similar master or drive-pulley 23a is provided, rather than providing a slave wheel 24a or 241 as shown in the embodiments of FIGS. 17d, 17e and 17f, a resilient electrical contact device 242 is provided as shown in FIG. 17m and as 242a/242b in FIG. 17n. In this regard, the portions 242, 242a and 242b provide resilient tension for the wire 5a or 5b to be provided therebetween. Additionally, this control device design causes there to be an electrical connection between the power sources 50/60 and the electrodes 1/5. The servo-motor 21a functions as discussed above, but a single electrode (FIG. 17m) or two electrodes (FIG. 17n) are driven by a single servo drive motor 21a. Accordingly, a single drive motor 21a can replace two drive motors in the case of the embodiment shown in FIG. 17n. Further, by providing the electrical contact between the wires 1/5 and the power sources 50/60, all electrical connections are provided on a top surface of (i.e., the surface further away from the liquid 3, resulting in certain design and production advantages.

FIGS. 17d and 17e show a refractory material component 29. The component 29 is made of, for example, suitable refractory component, including, for example, aluminum oxide or the like. The refractory component 29 may have a transverse through-hole therein which provides for electrical connections to the electrode(s) 1 and/or 5. Further a longitudinal through-hole is present along the length of the refractory component 29 such that electrode assemblies 1/5 can extend therethrough.

FIG. 17e shows a perspective view of the bottom portion of the control device 20. In this FIG. 17e, one electrode(s) 1a is shown as extending through a first refractory portion 29a and one electrode(s) 5a is shown as extending through a second refractory portion 29b. Accordingly, each of the electrode assemblies expressly disclosed herein, as well as those referred to herein, can be utilized in combination with the preferred embodiments of the control device shown herein.

In order for the control devices 20 to be actuated, two general processes need to occur. A first process involves electrically activating the electrode(s) 1 and/or 5 (e.g., applying power thereto from a preferred power source 10), and the second general process occurrence involves determining, for example, how much power is applied to the electrode(s) and appropriately adjusting electrode 1/5 height in response to such determinations (e.g., manually and/or automatically adjusting the height of the electrodes 1/5); or adjusting the electrode height or simply moving the electrode into (e.g., progressively advancing the electrode(s) 5 through the liquid 3) or out of contact with the liquid 3, as a function of time. In the case of utilizing a control device 20, suitable instructions are communicated to the step motor 21 through the RS-232 ports 22a and 22b. Important embodiments of components of the control device 20, as well as the electrode activation process, are discussed herein.

A preferred embodiment of the invention utilizes the automatic control devices 20 shown in various figures herein. The step motors 21a and 21b shown in, for example, FIGS. 17d-17f, and 17m-17n are controlled either by the electrical circuit diagrammed in each of FIGS. 17g-17j (e.g., for electrode sets 1/5 that make a plasma 4 or for electrode sets 5/5); or are controlled by the electrical circuit diagrammed in each of FIGS. 17k and 17l for electrode sets 5/5, in some embodiments herein.

In particular, in this embodiment, the electrical circuit of FIG. 17j is a voltage monitoring circuit. Specifically, voltage output from each of the output legs of the secondary coil 603 in the transformer 60 are monitored over the points "P-Q" and the points "P'-Q'". Specifically, the resistor denoted by "$R_L$" corresponds to the internal resistance of the multimeter measuring device (not shown). The output voltages measured between the points "P-Q" and "P'-Q'" typically, for several preferred embodiments shown in the Examples later herein, range between about 200 volts and about 4,500 volts. However, higher and lower voltages can work with many of the embodiments disclosed herein. In Examples 1-4 later herein, desirable target voltages have been determined for each electrode set 1 and/or 5 at each position along a trough member 30. Such desirable target voltages are achieved as actual applied voltages by, utilizing, for example, the circuit control shown in FIGS. 17g, 17h and 17i. These FIGS. 17g and 17h refer to sets of relays controlled by a Velleman K8056 circuit assembly (having a micro-chip PIC16F630-I/P). In particular, a voltage is detected across either the "P-Q" or the "P'-Q" locations and such voltage is compared to a predetermined reference voltage (actually compared to a target voltage range). If a measured voltage across, for example, the points "P-Q" is approaching a high-end of a pre-determined voltage target range, then, for example, the Velleman K8056 circuit assembly causes a servo-motor 21 (with specific reference to FIG. 17o to rotate in a clockwise direction so as to lower the electrode 5a toward and/or into the fluid 3. In contrast, should a measured voltage across either of the points "P-Q" or "P'-Q" be approaching a lower end of a target voltage, then, for example, again with reference to FIG. 17f, the server motor 21a will cause the drive-wheel 23a to rotate in a counter-clockwise position thereby raising the electrode 5a relative to the fluid 3.

Each set of electrodes in Examples 1-4 of the invention has an established target voltage range. The size or magnitude of acceptable range varies by an amount between about 1% and about 10%-15% of the target voltage. Some embodiments of the invention are more sensitive to voltage changes and these embodiments should have, typically, smaller acceptable voltage ranges; whereas other embodiments of the invention are less sensitive to voltage and should have, typically, larger acceptable ranges. Accordingly, by utilizing the circuit diagram shown in FIG. 17j, actual voltages output from the secondary coil 603 of the transformer 60 are measured at "$R_L$" (across the terminals "P-Q" and "P'-Q"), and are then compared to the predetermined voltage ranges. The servo-motor 21 responds by rotating a predetermined amount in either a clockwise direction or a counter-clockwise direction, as needed. Moreover, with specific reference to FIGS. 17g-17j, it should be noted that an interrogation procedure occurs sequentially by determining the voltage of each electrode, adjusting height (if needed) and then proceeding to the next electrode. In other words, each transformer 60 is connected electrically in a manner shown in FIG. 17j. Each transformer 60 and associated measuring points "P-Q" and "P'-Q" are connected to an individual relay. For example, the points "P-Q" correspond to relay number 501 in FIG. 17g and the points "P'-Q" correspond to the relay 502 in FIG. 17g. Accordingly, two relays are required for each transformer 60. Each relay, 501, 502, etc., sequentially interrogates a first output voltage from a first leg of a secondary coil 603 and then a second output voltage from a second leg of the secondary coil 603; and such interrogation continues onto a first output voltage from a second transformer 60b on a first leg of its secondary coil 603, and then on to a second leg of the secondary coil 603, and so on.

The computer or logic control for the disclosed interrogation voltage adjustment techniques are achieved by any conventional program or controller, including, for example, in a preferred embodiment, standard visual basic programming steps utilized in a PC. Such programming steps include interrogating, reading, comparing, and sending an appropriate actuation symbol to increase or decrease voltage (e.g., raise or lower an electrode relative to the surface 2 of the liquid 3). Such techniques should be understood by an artisan of ordinary skill.

Further, in another preferred embodiment of the invention utilized in Example 16 for the electrode sets 5/5', the automatic control devices 20 are controlled by the electrical circuits of FIGS. 17h, 17i, 17k and 17l. In particular, the electrical circuit of FIG. 17l is a voltage monitoring circuit used to measure current. In this case, voltage and current are the same numerical value due to choice of a resistor (discussed later herein). Specifically, voltage output from each of the transformers 50 are monitored over the points "P-Q" and the points "P'-Q". Specifically, the resistor denoted by "$R_L$" corresponds to the internal resistance of the multi-meter measuring device (not shown). The output voltages measured between the points "P-Q" and "P'-Q" typically, for several preferred embodiments shown in the Examples later herein, range between about 0.05 volts and about 5 volts. However, higher and lower voltages can work with many of the embodiments disclosed herein. Desirable target voltages have been determined for each electrode set 5/5' at each position along a trough member 30b'. Such desirable target voltages are achieved as actual applied voltages by, utilizing, for example, the circuit control shown in FIGS. 17h, 17i, 17k and 17l. These FIG. 17 refer to sets of relays controlled by a Velleman K8056 circuit assembly (having a micro-chip PIC16F630-I/P).

In particular, in the Example 16 embodiments the servo-motor 21 is caused to rotate at a specific predetermined time in order to maintain a desirable electrode 5 profile. The servo-motor 21 responds by rotating a predetermined amount in a clockwise direction. Specifically the servo-motor 21 rotates a sufficient amount such that about 0.009 inches (0.229 mm) of the electrode 5 is advanced toward and into the female receiver portion o5 (shown, for example in some of FIGS. 20 and 21). Thus, the electrode 5 is progressively advanced through the liquid 3. In one preferred embodiment discussed herein, such electrode 5 movement occurs about every 5.8 minutes. Accordingly, the rate of vertical movement of each electrode 5 into the female receiver portion o5 is about ¾ inches (about 1.9 cm) every 8 hours. Accordingly, a substantially constant electrode 5 shape or profile is maintained by its constant or progressive advance into and through the liquid 3. Further, once the advancing end of the electrode 5 reaches the longitudinal end of the female receiver portion o5, the electrode 5 can be removed from the processing apparatus. Alternatively, an electrode collecting means for collecting the "used" portion of the electrode can be provided.

Such means for collecting the electrode(s) 5 include, but are not limited to, a winding or spooling device, and extended portion o5, a wire clipping or cutting device, etc. However, in order to achieve different current/voltage profiles (and thus a variety of different nanocrystal size(s) and/or shapes(s), other rates of electrode movement are also within the metes and bounds of this invention.

Moreover, with specific reference to FIGS. 17h, 17i, 17k and 17l, it should be noted that an interrogation procedure occurs sequentially by determining the voltage of each electrode, which in the embodiments of Example 16, are equivalent to the amps because in FIG. 17l the resistors Ra and Rb are approximately 1 ohm, accordingly, V=I. In other words, each transformer 50 is connected electrically in a manner shown in 17h, 17i, 17k and 17l. Each transformer 50 and associated measuring points "P-Q" and "P'-Q" are connected to two individual relays. For example, the points "P-Q" correspond to relay number 501 and 501' in FIG. 17k and the points "P'-Q" correspond to the relay 502, 502' in FIG. 17k. Accordingly, relays are required for each electrode set 5/5. Each relay, 501/501' and 502/502', etc., sequentially interrogates the output voltage from the transformer 50 and then a second voltage from the same transformer 50, and so on.

The computer or logic control for the disclosed electrode height adjustment techniques are achieved by any conventional program or controller, including, for example, in a preferred embodiment, standard visual basic programming steps utilized in a PC. Such programming steps include reading and sending an appropriate actuation symbol to lower an electrode relative to the surface 2 of the liquid 3. Such techniques should be understood by an artisan of ordinary skill.

Definitions

For purposes of the present invention, the terms and expressions below, appearing in the Specification and Claims, are intended to have the following meanings:

"Carbomer", as used herein in Example 23, means a class of synthetically derived cross-linked polyacrylic acid polymers that provide efficient rheology modification with enhanced self-wetting for ease of use. In general, a carbomer/solvent mixture is neutralized with a base such as triethanolamine or sodium hydroxide to fully open the polymer to achieve the desired thickening, suspending, and emulsion stabilization properties to make creams or gels.

"Substantially clean", as used herein should be understood when used to describe nanocrystal surfaces means that the nanocrystals do not have chemical constituents adhered or attached to their surfaces in such an amount that would materially alter the functioning of the nanocrystal in at least one of its significant properties of the gold nanocrystals set forth in the Examples herein. Alternatively, the gold nanocrystal does not have a layer, surface or film which covers a significant portion (e.g., at least 25% of the crystal, or in another embodiment at least 50% of the crystal). It also can mean that the nanocrystal surfaces are completely free of any organic contaminants which materially change their functionality over bare gold crystal surfaces. It should be understood that incidental components that are caused to adhere to nanocrystals of the invention and do not adversely or materially affect the functioning of the inventive nanocrystals, should still be considered to be within the metes and bounds of the invention. The term should also be understood to be a relative term referencing the lack of traditional organic-based molecules (i.e., those used in traditional reduction chemistry techniques) on the surfaces of the grown nanocrystals of the invention.

A "diagnostic effective amount", as used herein, means an amount sufficient to bind to MIF to enable detection of the MIF-compound complex such that diagnosis of a disease or condition is possible.

An "effective amount", as used herein, means a certain amount of solution or compound which, when administered according to, for example, a desired dosing regimen, provides the desired MIF cytokine inhibiting or treatment or therapeutic activity, or disease/condition prevention or MIF signaling pathway(s). Dosing may occur at intervals of minutes, hours, days, weeks, months or years or continuously over any one of these periods.

As used herein, "immune privilege" refers to an area or site within a living system (e.g., a body) which tolerates the presence of an antigen that would normally elicit a response from the immune system (e.g., an inflammatory immune response).

The term "operably coating" a stent means coating a stent in a way that permits the timely release of the inventive metallic-based nanocrystals (e.g., comprising aqueous gold-based metal and/or mixtures of gold and other metal(s) and/or alloys of gold with other metal(s)) into the surrounding tissue to be treated once the coated stent is administered.

As used herein, the term "processing-enhancer" or "processing-enhanced" or "process enhancer" means at least one material (e.g., solid, liquid and/or gas) and typically means an inorganic material, which material does not significantly bind to the formed nanocrystals, but rather facilitates nucleation/growth during an electrochemical-stimulated growth process. The material serves important roles in the process including providing charged ions in the electrochemical solution to permit the crystals to be grown. The process enhancer is critically a compound(s) which remains in solution, and/or does not form a coating (in one embodiment an organic coating), and/or does not adversely affect the formed nanocrystals or the formed suspension(s), and/or is destroyed, evaporated, or is otherwise lost during the electrochemical crystal growth process.

The term "Steroid-sparing", as used herein, means providing a material other than a steroid in a combination therapy which reduces the amount of steroid required to be effective for treating/preventing an indication.

The phrase "trough member" as used herein should be understood as meaning a large variety of fluid handling devices including, pipes, half pipes, channels or grooves existing in materials or objects, conduits, ducts, tubes, chutes, hoses and/or spouts, so long as such are compatible with the electrochemical processes disclosed herein.

The following Examples serve to illustrate certain embodiments of the invention but should not to be construed as limiting the scope of the disclosure as defined in the appended claims.

Examples 1-4

Manufacturing Gold-Based Nanoparticles/Nanoparticle Solutions GT032, GT031, GT019 and GT033

Figure 16G:
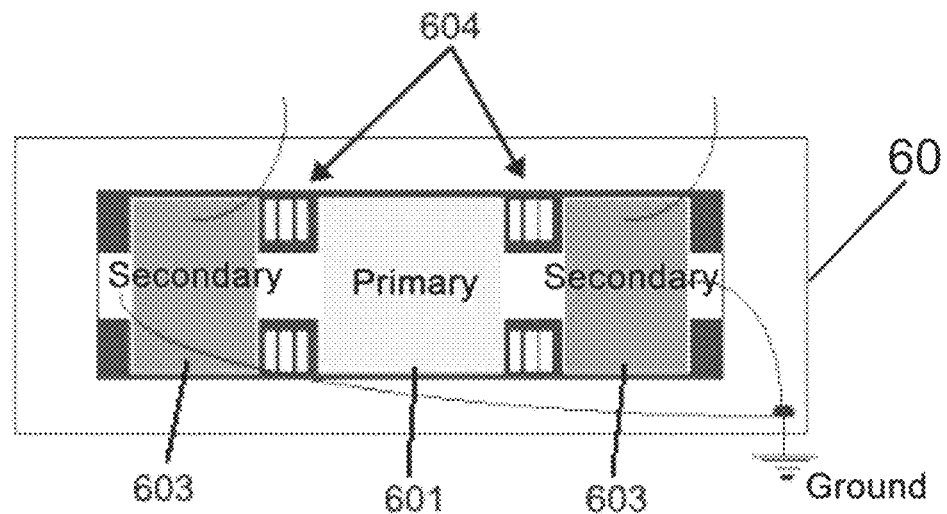
FIG. 16g shows a schematic view of a transformer 60 and FIGS. 16h and 16i show schematic representations of two sine waves in phase and out of phase, respectively.

In general, each of Examples 1-4 utilizes certain embodiments of the invention associated with the apparatuses generally shown in FIGS. 16b, 16c and 16g. Specific differences in processing and apparatus will be apparent in each Example. The trough member 30 was made from plexiglass, all of which had a thickness of about 3 mm-4 mm (about ⅛"). The support structure 34 was also made from plexiglass which was about ¼" thick (about 6-7 mm thick). The cross-sectional shape of the trough member 30 corresponds to that shape shown in FIG. 10b (i.e., a truncated "V"). The base portion "R" of the truncated "V" measured about 0.5" (about 1 cm), and each side portion "S", "S'" measured about 1.5" (about 3.75 cm). The distance "M" separating the side portions "S", "S'" of the V-shaped trough member 30 was about 2¼"-2 5/16" (about 5.9 cm) (measured from inside to inside). The thickness of each portion also measured about ⅛" (about 3 mm) thick. The longitudinal length "$L_T$" (refer to FIG. 11a) of the V-shaped trough member 30 measured about 6 feet (about 2 meters) long from point 31 to point 32. The difference in vertical height from the end 31 of the trough member 30 to the end 32 was about ¼-½" (about 6-12.7 mm) over its 6 feet length (about 2 meters) (i.e., less than 1°).

Purified water (discussed later herein) was used as the input liquid 3 in Example 1. In Examples 2-4, a processing enhancer was added to the liquid 3 being input into the trough member 30. The specific processing enhancer added, as well as the specific amounts of the same, were effective in these examples. However, other processing enhancer(s) and amounts of same, should be viewed as being within the metes and bounds of this disclosure and these specific examples should not be viewed as limiting the scope of the invention. The depth "d" (refer to FIG. 10b) of the water 3 in the V-shaped trough member 30 was about 7/16" to about ½" (about 11 mm to about 13 mm) at various points along the trough member 30. The depth "d" was partially controlled through use of the dam 80 (shown in FIGS. 15a and 15b). Specifically, the dam 80 was provided near the end 32 and assisted in creating the depth "d" (shown in FIG. 10b) to be about 7/16"-½" (about 11-13 mm) in depth. The height "j" of the dam 80 measured about ¼" (about 6 mm) and the longitudinal length "k" measured about ½" (about 13 mm). The width (not shown) was completely across the bottom dimension "R" of the trough member 30. Accordingly, the total volume of water 3 in the V-shaped trough member 30 during operation thereof was about 26 in$^3$ (about 430 ml).

The rate of flow of the water 3 into the trough member 30 was about 90 ml/minute. Due to some evaporation within the trough member 30, the flow out of the trough member 30 was slightly less, about 60-70 ml/minute. Such flow of water 3 into the trough member 30 was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 90 milliliters per minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30 by a flow diffusion means located therein. The flow diffusion means tended to minimize disturbance and bubbles in water 3 introduced into the trough member 30 as well as any pulsing condition generated by the peristaltic pump 40. In this regard, a small reservoir served as the diffusion means and was provided at a point vertically above the end 31 of the trough member 30 such that when the reservoir overflowed, a relatively steady flow of water 3 into the end 31 of the V-shaped trough member 30 occurred.

With regard to FIGS. 16b and 16c, 8 separate electrode sets (Set 1, Set 2, Set 3, -Set 8) were attached to 8 separate control devices 20. Each of Tables 1a-1d refers to each of the 8 electrode sets by "Set #". Further, within any Set #, electrodes 1 and 5, similar to the electrode assemblies shown in FIGS. 3a and 3c were utilized. Each electrode of the 8 electrode sets was set to operate within specific target voltage range. Actual target voltages are listed in each of Tables 1a-1d. The distance "c-c" (with reference to FIG. 14) from the centerline of each electrode set to the adjacent electrode set is also represented. Further, the distance "x" associated with any electrode(s) 1 utilized is also reported. For any electrode 5's, no distance "x" is reported. Other relevant distances are reported, for example, in each of Tables 1a-1d.

The power source for each electrode set was an AC transformer 60. Specifically, FIG. 16d shows a source of AC power 62 connected to a transformer 60. In addition, a capacitor 61 is provided so that, for example, loss factors in the circuit can be adjusted. The output of the transformer 60 is connected to the electrode(s) 1/5 through the control device 20. A preferred transformer for use with the present invention is one that uses alternating current flowing in a primary coil 601 to establish an alternating magnetic flux in a core 602 that easily conducts the flux.

When a secondary coil 603 is positioned near the primary coil 601 and core 602, this flux will link the secondary coil 603 with the primary coil 601. This linking of the secondary coil 603 induces a voltage across the secondary terminals. The magnitude of the voltage at the secondary terminals is related directly to the ratio of the secondary coil turns to the primary coil turns. More turns on the secondary coil 603 than the primary coil 601 results in a step up in voltage, while fewer turns results in a step down in voltage.

Preferred transformer(s) 60 for use in these Examples have deliberately poor output voltage regulation made possible by the use of magnetic shunts in the transformer 60. These transformers 60 are known as neon sign transformers. This configuration limits current flow into the electrode(s) 1/5. With a large change in output load voltage, the transformer 60 maintains output load current within a relatively narrow range.

The transformer 60 is rated for its secondary open circuit voltage and secondary short circuit current. Open circuit voltage (OCV) appears at the output terminals of the transformer 60 only when no electrical connection is present. Likewise, short circuit current is only drawn from the output terminals if a short is placed across those terminals (in which case the output voltage equals zero). However, when a load is connected across these same terminals, the output voltage of the transformer 60 should fall somewhere between zero and the rated OCV. In fact, if the transformer 60 is loaded properly, that voltage will be about half the rated OCV.

The transformer 60 is known as a Balanced Mid-Point Referenced Design (e.g., also formerly known as balanced midpoint grounded). This is most commonly found in mid to higher voltage rated transformers and most 60 mA transformers. This is the only type transformer acceptable in a "mid-point return wired" system. The "balanced" transformer 60 has one primary coil 601 with two secondary coils 603, one on each side of the primary coil 601 (as shown generally in the schematic view in FIG. 16g). This transformer 60 can in many ways perform like two transformers. Just as the unbalanced midpoint referenced core and coil, one end of each secondary coil 603 is attached to the core 602 and subsequently to the transformer enclosure and the other end of the each secondary coil 603 is attached to an output lead or terminal. Thus, with no connector present, an unloaded 15,000 volt transformer of this type, will measure about 7,500 volts from each secondary terminal to the transformer enclosure but will measure about 15,000 volts between the two output terminals.

Figure 16H:
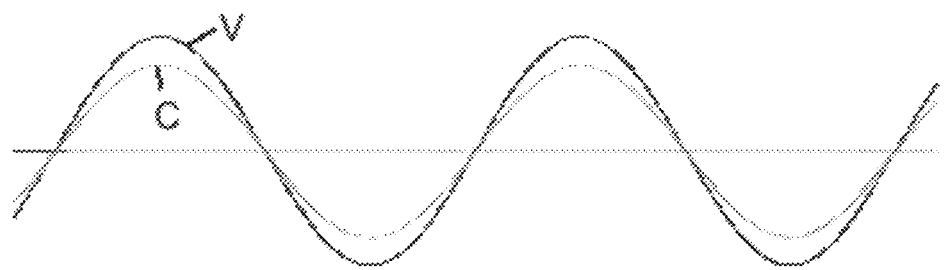
Figure 16I:
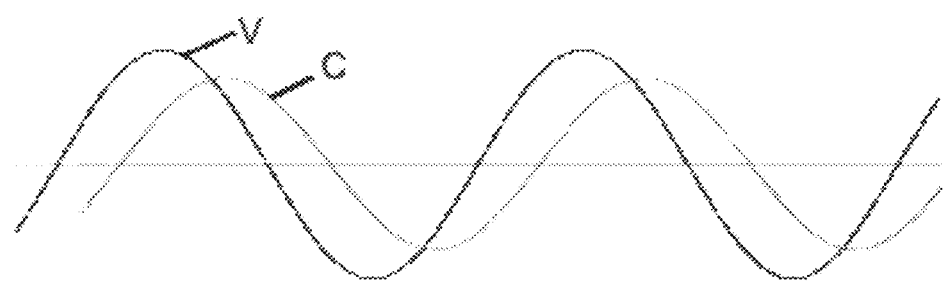

In alternating current (AC) circuits possessing a line power factor or 1 (or 100%), the voltage and current each start at zero, rise to a crest, fall to zero, go to a negative crest and back up to zero. This completes one cycle of a typical sine wave. This happens 60 times per second in a typical US application. Thus, such a voltage or current has a characteristic "frequency" of 60 cycles per second (or 60 Hertz) power. Power factor relates to the position of the voltage waveform relative to the current waveform. When both waveforms pass through zero together and their crests are together, they are in phase and the power factor is 1, or 100%. FIG. 16h shows two waveforms "V" (voltage) and "C" (current) that are in phase with each other and have a power factor of 1 or 100%; whereas FIG. 16i shows two waveforms "V" (voltage) and "C" (current) that are out of phase with each other and have a power factor of about 60%;

both waveforms do not pass through zero at the same time, etc. The waveforms are out of phase and their power factor is less than 100%.

The normal power factor of most such transformers 60 is largely due to the effect of the magnetic shunts 604 and the secondary coil 603, which effectively add an inductor into the output of the transformer's 60 circuit to limit current to the electrodes 1/5. The power factor can be increased to a higher power factor by the use of capacitor(s) 61 placed across the primary coil 601 of the transformer, 60 which brings the input voltage and current waves more into phase.

The unloaded voltage of any transformer 60 to be used in the present invention is important, as well as the internal structure thereof. Desirable unloaded transformers for use in the present invention include those that are around 9,000 volts, 10,000 volts, 12,000 volts and 15,000 volts. However, these particular unloaded volt transformer measurements should not be viewed as limiting the scope acceptable power sources as additional embodiments. A specific desirable transformer for use in these Examples is made by France-former, Catalog No. 9060-P-E which operates at: primarily 120 volts, 60 Hz; and secondary 9,000 volts, 60 mA.

FIGS. 16e and 16f show an alternative embodiment of the invention (i.e., not used in this Example), wherein the output of the transformer 60 that is input into the electrode assemblies 1/5 has been rectified by a diode assembly 63 or 63'. The result, in general, is that an AC wave becomes substantially similar to a DC wave. In other words, an almost flat line DC output results (actually a slight 120 Hz pulse can sometimes be obtained). This particular assembly results in two additional preferred embodiments of the invention (e.g., regarding electrode orientation). In this regard, a substantially positive terminal or output and substantially negative terminal or output is generated from the diode assembly 63. An opposite polarity is achieved by the diode assembly 63'. Such positive and negative outputs can be input into either of the electrode(s) 1 and/or 5. Accordingly, an electrode 1 can be substantially negative or substantially positive; and/or an electrode 5 can be substantially negative and/or substantially positive.

Figure 16J:
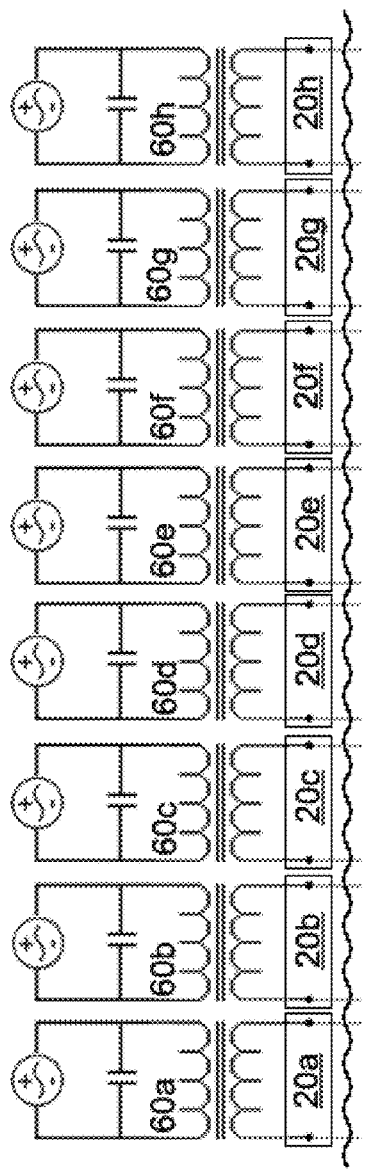

FIG. 16j shows 8 separate transformer assemblies 60a-60h each of which is connected to a corresponding control device 20a-20h, respectively. This set of transformers 60 and control devices 20 are utilized in these Examples 1-4.

Figure 16K:
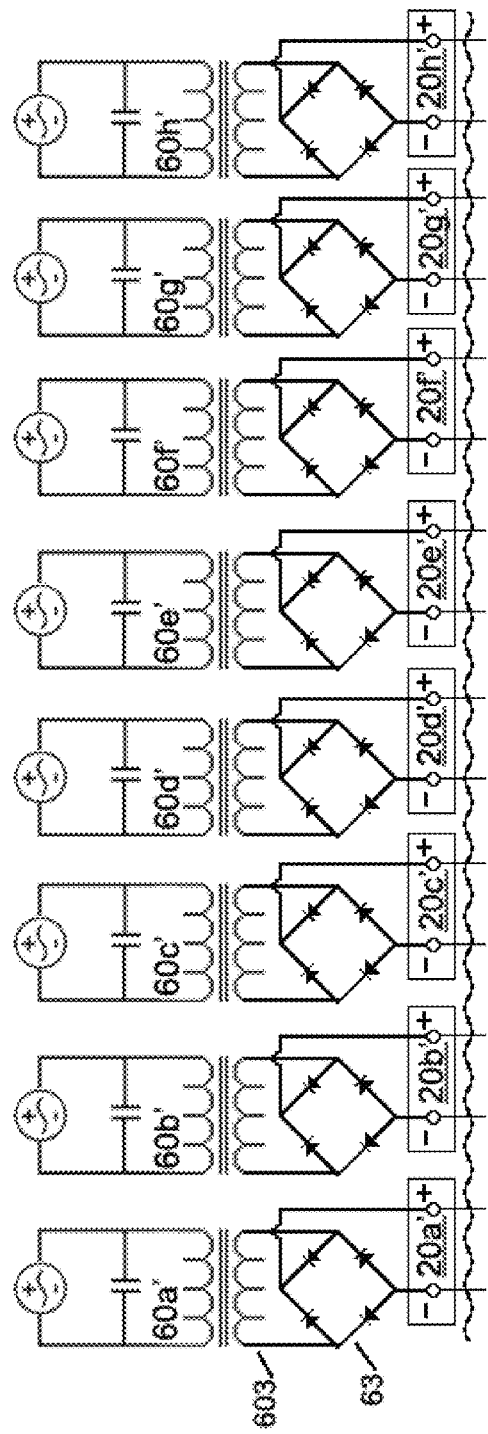
Figure 16I:
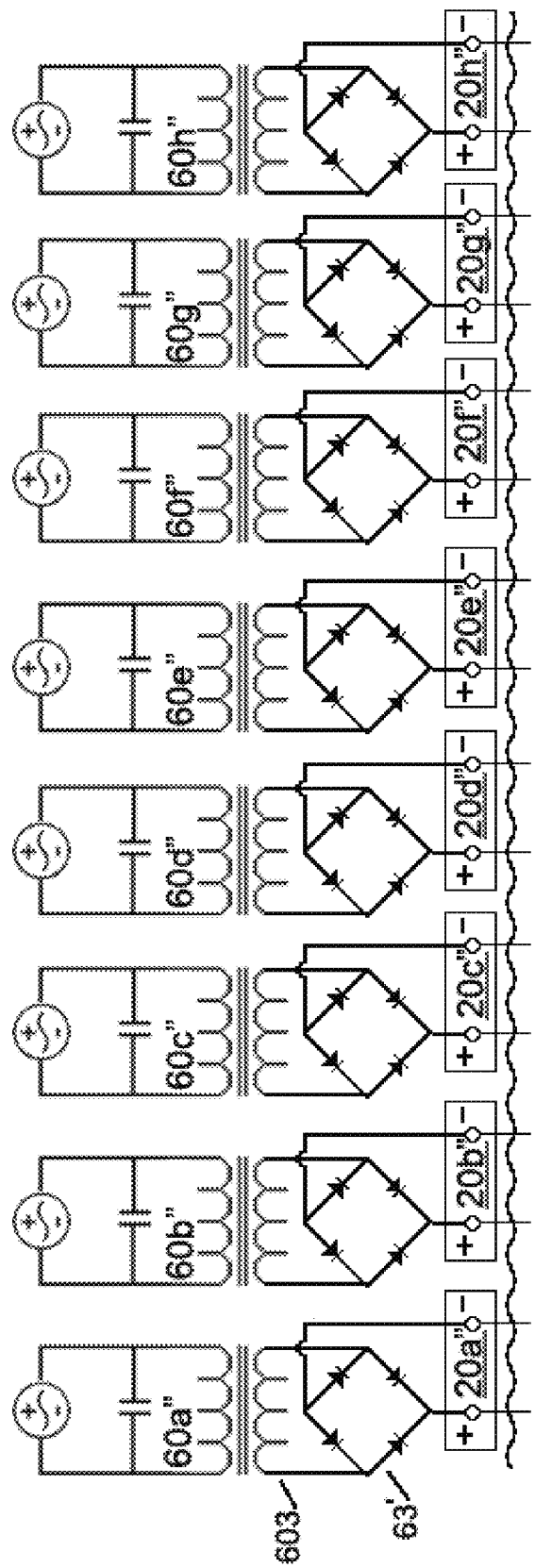

FIG. 16k shows 8 separate transformers 60a'-60h', each of which corresponds to the rectified transformer diagram shown in FIG. 16e. This transformer assembly also communicates with a set of control devices 20a-20h and can be used as a preferred embodiment of the invention, although was not used in these Examples.

FIG. 16l shows 8 separate transformers 60a"-60h", each of which corresponds to the rectified transformer diagram shown in FIG. 16f. This transformer assembly also communicates with a set of control devices 20a-20h and can be used as a preferred embodiment of the invention, although was not used in these Examples.

Accordingly, each transformer assembly 60a-60h (and/or 60a'-60h'; and/or 60a"-60h") can be the same transformer, or can be a combination of different transformers (as well as different polarities). The choice of transformer, power factor, capacitor(s) 61, polarity, electrode designs, electrode location, electrode composition, cross-sectional shape(s) of the trough member 30, local or global electrode composition, atmosphere(s), local or global liquid 3 flow rate(s), liquid 3 local components, volume of liquid 3 locally subjected to various fields in the trough member 30, neighboring (e.g., both upstream and downstream) electrode sets, local field concentrations, the use and/or position and/or composition of any membrane used in the trough member, etc., are all factors which influence processing conditions as well as composition and/or volume of constituents produced in the liquid 3, nanocrystals and nanocrystal/suspensions or colloids made according to the various embodiments disclosed herein. Accordingly, a plethora of embodiments can be practiced according to the detailed disclosure presented herein.

The size and shape of each electrode 1 utilized was about the same. The shape of each electrode 1 was that of a right triangle with measurements of about 14 mm×23 mm×27 mm. The thickness of each electrode 1 was about 1 mm. Each triangular-shaped electrode 1 also had a hole therethrough at a base portion thereof, which permitted the point formed by the 23 mm and 27 mm sides to point toward the surface 2 of the water 3. The material comprising each electrode 1 was 99.95% pure (i.e., 3N5) unless otherwise stated herein. When gold was used for each electrode 1, the weight of each electrode was about 9 grams.

The wires used to attach the triangular-shaped electrode 1 to the transformer 60 were, for Examples 1-3, 99.95% (3N5) platinum wire, having a diameter of about 1 mm.

The wires used for each electrode 5 comprised 99.95% pure (3N5) gold each having a diameter of about 0.5 mm. All materials for the electrodes 1/5 were obtained from ESPI having an address of 1050 Benson Way, Ashland, Oreg. 97520.

The water 3 used in Example 1 as an input into the trough member 30 (and used in Examples 2-4 in combination with a processing enhancer) was produced by a Reverse Osmosis process and deionization process. In essence, Reverse Osmosis (RO) is a pressure driven membrane separation process that separates species that are dissolved and/or suspended substances from the ground water. It is called "reverse" osmosis because pressure is applied to reverse the natural flow of osmosis (which seeks to balance the concentration of materials on both sides of the membrane). The applied pressure forces the water through the membrane leaving the contaminants on one side of the membrane and the purified water on the other. The reverse osmosis membrane utilized several thin layers or sheets of film that are bonded together and rolled in a spiral configuration around a plastic tube. (This is also known as a thin film composite or TFC membrane.) In addition to the removal of dissolved species, the RO membrane also separates out suspended materials including microorganisms that may be present in the water. After RO processing a mixed bed deionization filter was used. The total dissolved solvents ("TDS") after both treatments was about 0.2 ppm, as measured by an Accumet® AR20 pH/conductivity meter.

These examples use gold electrodes for the 8 electrode sets. In this regard, Tables 1a-1d set forth pertinent operating parameters associated with each of the 16 electrodes in the 8 electrode sets utilized to make gold-based nanocrystals/nanocrystal suspensions.

TABLE 1a

| Cold Input Water (Au) | |
|---|---|
| Run ID: | GT032 |
| Flow Rate: | 90 ml/min |
| Wire Dia.: | .5 mm |
| Configuration: | Straight/Straight |
| PPM: | 0.4 |
| Zeta: | n/a |

TABLE 1a-continued

Cold Input Water (Au)

| Set # | Electrode # | Target Voltage (kV) | Distance "c-c" in/mm | Distance "x" in/mm | Average Voltage (kV) |
|---|---|---|---|---|---|
|   |   |   | 7/177.8* |   |   |
| 1 | 1a | 1.6113 |   | 0.22/5.59 | 1.65 |
|   | 5a | 0.8621 |   | N/A | 0.84 |
|   |   |   | 8/203.2 |   |   |
| 2 | 5b | 0.4137 |   | N/A | 0.39 |
|   | 5b' | 0.7679 |   | N/A | 0.76 |
|   |   |   | 8/203.2 |   |   |
| 3 | 5c | 0.491 |   | N/A | 0.49 |
|   | 5c' | 0.4816 |   | N/A | 0.48 |
|   |   |   | 8/203.2 |   |   |
| 4 | 1d | 0.4579 |   | N/A | 0.45 |
|   | 5d | 0.6435 |   | N/A | 0.6 |
|   |   |   | 9/228.6 |   |   |
| 5 | 5e | 0.6893 |   | N/A | 0.67 |
|   | 5e' | 0.2718 |   | N/A | 0.26 |
|   |   |   | 8/203.2 |   |   |
| 6 | 5f | 0.4327 |   | N/A | 0.43 |
|   | 5f' | 0.2993 |   | N/A | 0.3 |
|   |   |   | 8/203.2 |   |   |
| 7 | 5g | 0.4691 |   | N/A | 0.43 |
|   | 5g' | 0.4644 |   | N/A | 0.46 |
|   |   |   | 8/203.2 |   |   |
| 8 | 5h | 0.3494 |   | N/A | 0.33 |
|   | 5h' | 0.6302 |   | N/A | 0.61 |
|   |   |   | 8/203.2** |   |   |
|   | Output Water Temperature |   |   |   | 65 C. |

*Distance from water inlet to center of first electrode set
**Distance from center of last electrode set to water outlet

TABLE 1b

.0383 mg/mL of NaHCO₃ (Au)

| Run ID: | GT031 |
|---|---|
| Flow Rate: | 90 ml/min |
| NaHCO₃: | 0.038 mg/ml |
| Wire Dia.: | .5 mm |
| Configuration: | Straight/Straight |
| PPM: | 1.5 |
| Zeta: | n/a |

| Set # | Electrode # | Target Voltage (kV) | Distance "c-c" in/mm | Distance "x" in/mm | Average Voltage (kV) |
|---|---|---|---|---|---|
|   |   |   | 7/177.8* |   |   |
| 1 | 1a | 1.7053 |   | 0.22/5.59 | 1.69 |
|   | 5a | 1.1484 |   | N/A | 1.13 |
|   |   |   | 8/203.2 |   |   |
| 2 | 5b | 0.6364 |   | N/A | 0.63 |
|   | 5b' | 0.9287 |   | N/A | 0.92 |
|   |   |   | 8/203.2 |   |   |
| 3 | 5c | 0.7018 |   | N/A | 0.71 |
|   | 5c' | 0.6275 |   | N/A | 0.62 |
|   |   |   | 8/203.2 |   |   |
| 4 | 5d | 0.6798 |   | N/A | 0.68 |
|   | 5d' | 0.7497 |   | N/A | 0.75 |
|   |   |   | 9/228.6 |   |   |
| 5 | 5e | 0.8364 |   | N/A | 0.85 |
|   | 5e' | 0.4474 |   | N/A | 0.45 |
|   |   |   | 8/203.2 |   |   |
| 6 | 5f | 0.5823 |   | N/A | 0.59 |
|   | 5f' | 0.4693 |   | N/A | 0.47 |
|   |   |   | 8/203.2 |   |   |
| 7 | 5g | 0.609 |   | N/A | 0.61 |
|   | 5g' | 0.5861 |   | N/A | 0.59 |

TABLE 1b-continued

.0383 mg/mL of NaHCO₃ (Au)

| Set # | Electrode # | Target Voltage (kV) | Distance "c-c" in/mm | Distance "x" in/mm | Average Voltage (kV) |
|---|---|---|---|---|---|
|   |   |   | 8/203.2 |   |   |
| 8 | 5h | 0.4756 |   | N/A | 0.48 |
|   | 5h' | 0.7564 |   | N/A | 0.76 |
|   |   |   | 8/203.2** |   |   |
|   | Output Water Temperature |   |   |   | 64 C. |

*Distance from water inlet to center of first electrode set
**Distance from center of last electrode set to water outlet

TABLE 1c

.045 mg/ml of NaCl (Au)

| Run ID: | GT019 |
|---|---|
| Flow Rate: | 90 ml/min |
| NaCl: | .045 mg/ml |
| Wire Dia.: | .5 mm |
| Configuration: | Straight/Straight |
| PPM: | 6.1 |
| Zeta: | n/a |

| Set # | Electrode # | Target Voltage (kV) | Distance "c-c" in/mm | Distance "x" in/mm | Average Voltage (kV) |
|---|---|---|---|---|---|
|   |   |   | 7/177.8* |   |   |
| 1 | 1a | 1.4105 |   | 0.22/5.59 | 1.41 |
|   | 5a | 0.8372 |   | N/A | 0.87 |
|   |   |   | 8/203.2 |   |   |
| 2 | 5b | 0.3244 |   | N/A | 0.36 |
|   | 5b' | 0.4856 |   | N/A | 0.65 |
|   |   |   | 8/203.2 |   |   |
| 3 | 5c | 0.3504 |   | N/A | 0.37 |
|   | 5c' | 0.3147 |   | N/A | 0.36 |
|   |   |   | 8/203.2 |   |   |
| 4 | 5d | 0.3526 |   | N/A | 0.37 |
|   | 5d' | 0.4539 |   | N/A | 0.5 |
|   |   |   | 9/228.6 |   |   |
| 5 | 5e | 0.5811 |   | N/A | 0.6 |
|   | 5e' | 0.2471 |   | N/A | 0.27 |
|   |   |   | 8/203.2 |   |   |
| 6 | 5f | 0.3624 |   | N/A | 0.38 |
|   | 5f' | 0.2905 |   | N/A | 0.31 |
|   |   |   | 8/203.2 |   |   |
| 7 | 5g | 0.3387 |   | N/A | 0.36 |
|   | 5g' | 0.3015 |   | N/A | 0.33 |
|   |   |   | 8/203.2 |   |   |
| 8 | 5h | 0.2995 |   | N/A | 0.33 |
|   | 5h' | 0.5442 |   | N/A | 0.57 |
|   |   |   | 8/203.2** |   |   |
|   | Output Water Temperature |   |   |   | 77 C. |

*Distance from water inlet to center of first electrode set
**Distance from center of last electrode set to water outlet

TABLE 1d

.038 mg/mL of NaHCO₃ (Au)

| Run ID: | GT033 |
|---|---|
| Flow Rate: | 90 ml/min |
| NaHCO₃: | 0.038 mg/ml |
| Wire Dia.: | .5 mm |
| Configuration: | Straight/Straight |
| PPM: | 2.0 |
| Zeta: | n/a |

TABLE 1d-continued

.038 mg/mL of NaHCO$_3$ (Au)

| Set # | Electrode # | Target Voltage (kV) | Distance "c-c" in/mm | Distance "x" in/mm | Average Voltage (kV) |
|---|---|---|---|---|---|
|   |   | 7/177.8* |   |   |   |
| 1 | 1a | 1.6033 |   | 0.22/5.59 | 1.641826 |
|   | 5a | 1.1759 |   | N/A | 1.190259 |
|   |   | 8/203.2 |   |   |   |
| 2 | 5b | 0.6978 |   | N/A | 0.727213 |
|   | 5b' | 0.8918 |   | N/A | 0.946323 |
|   |   | 8/203.2 |   |   |   |
| 3 | 5c | 0.6329 |   | N/A | 0.795378 |
|   | 5c' | 0.526 |   | N/A | 0.609542 |
|   |   | 8/203.2 |   |   |   |
| 4 | 5d | 0.609 |   | N/A | 0.613669 |
|   | 5d' | 0.6978 |   | N/A | 0.719777 |
|   |   | 9/228.6 |   |   |   |
| 5 | 5e | 0.9551 |   | N/A | 0.920594 |
|   | 5e' | 0.5594 |   | N/A | 0.547233 |
|   |   | 8/203.2 |   |   |   |
| 6 | 5f | 0.6905 |   | N/A | 0.657295 |
|   | 5f' | 0.5516 |   | N/A | 0.521984 |
|   |   | 8/203.2 |   |   |   |
| 7 | 5g | 0.5741 |   | N/A | 0.588502 |
|   | 5g' | 0.5791 |   | N/A | 0.541565 |
|   |   | 8/203.2 |   |   |   |
| 8 | 5h | 0.4661 |   | N/A | 0.46091 |
|   | 5h' | 0.7329 |   | N/A | 0.741009 |
|   |   | 8/203.2** Output Water Temperature |   |   | 83 C. |

*Distance from water inlet to center of first electrode set
**Distance from center of last electrode set to water outlet Table 1a shows that a "1/5" electrode configuration was utilized for Electrode Set #1 and for Electrode Set #4, and all other sets were of the 5/5 configuration; whereas Tables 1b, 1c and 1d show that Electrode Set #1 was the only electrode set utilizing the 1/5 configuration, and all other sets were of the 5/5 configuration.

Additionally, the following differences in manufacturing set-up were also utilized:

Example 1: GT032: The input water 3 into the trough member 30 was chilled in a refrigerator unit until it reached a temperature of about 2° C. and was then pumped into the trough member 30;

Example 2: GT031: A processing enhancer was added to the input water 3 prior to the water 3 being input into the trough member 30. Specifically, about 0.145 grams/gallon (i.e., about 38.3 mg/liter) of sodium hydrogen carbonate ("soda"), having a chemical formula of NaHCO$_3$, was added to and mixed with the water 3. The soda was obtained from Alfa Aesar and the soda had a formula weight of 84.01 and a density of about 2.159 g/cm$^3$ (i.e., stock #14707, lot D15T043).

Example 3: GT019: A processing enhancer was added to the input water 3 prior to the water 3 being input into the trough member 30. Specifically, about 0.17 grams/gallon (i.e., about 45 mg/liter) of sodium chloride ("salt"), having a chemical formula of NaCl, was added to and mixed with the water 3.

Figure 32A:
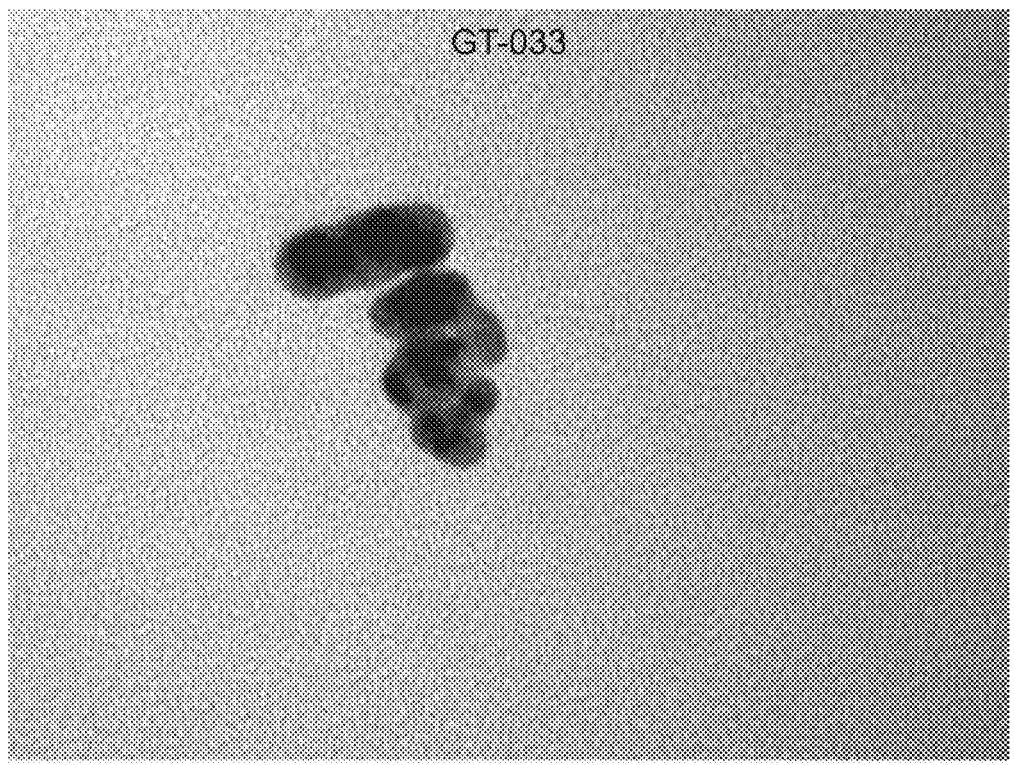
FIG. 32a is a representative TEM photomicrograph of gold nanocrystals from dried solution GT-033 made according to Example 4.
Figure 32B:
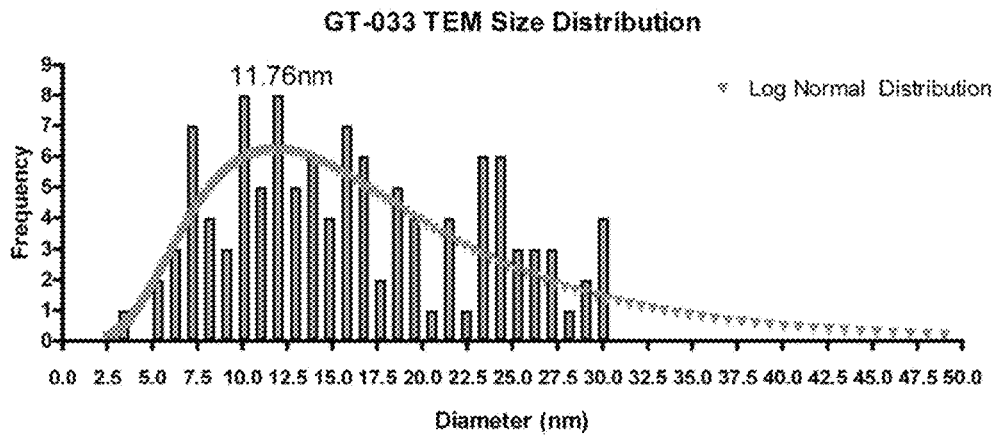
FIG. 32b shows the particle size distribution histogram from TEM measurements for the nanocrystals made according to Example 14.
Figure 32C:
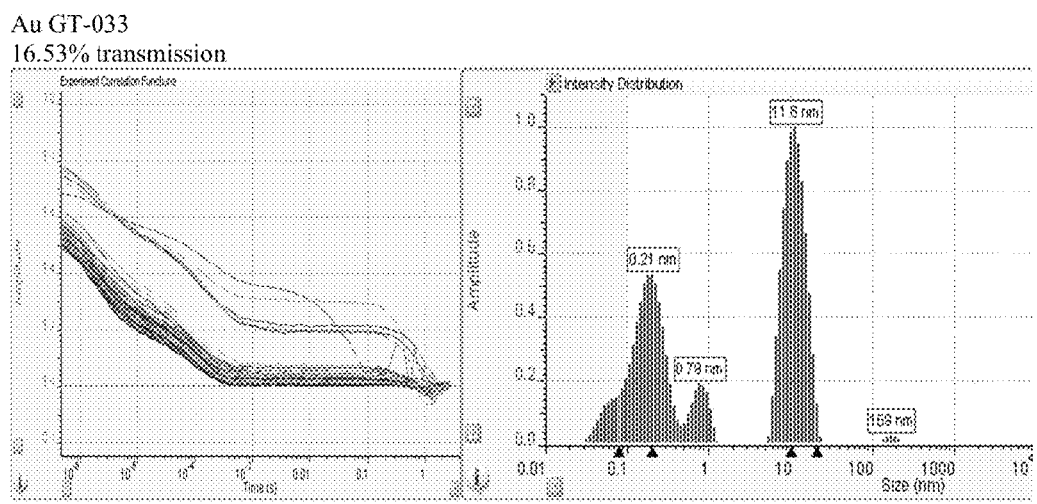
FIG. 32c shows dynamic light scattering data (i.e., hydrodynamic radii) for gold nanocrystals made according to Example 4.

Example 4: GT033: A processing enhancer was added to the input water 3 prior to the water 3 being input into the trough member 30. Specifically, about 0.145 grams/gallon (i.e., about 38.3 mg/liter) of sodium hydrogen carbonate ("soda"), having a chemical formula of NaHCO$_3$, was added to and mixed with the water 3. The soda was obtained from Alfa Aesar and the soda had a formula weight of 84.01 and a density of about 2.159 g/cm$^3$ (i.e., stock #14707, lot D15T043). A representative TEM photomicrograph of dried solution GT033 is shown in FIG. 32a. Also, FIG. 32b shows dynamic light scattering data (i.e., hydrodynamic radii) of suspension GT033.

The salt used in Example 3 was obtained from Fisher Scientific (lot #080787) and the salt had a formula weight of 58.44 and an actual analysis as follows:

| | |
|---|---|
| Assay | 100% |
| Barium (BA) | Pass Test |
| Bromide | <0.010% |
| Calcium | 0.0002% |
| Chlorate & Nitrate | <0.0003% |
| Heavy Metals (AS PB) | <5.0 ppm |
| Identification | Pass Test |
| Insoluble Water | <0.001% |
| Iodide | 0.0020% |
| Iron (FE) | <2.0 ppm |
| Magnesium | <0.0005% |
| Ph 5% Soln @ 25 Deg C. | 5.9 |
| Phosphate (PO4) | <5.0 ppm |
| Potassium (K) | <0.003% |
| Sulfate (SO4) | <0.0040% |

Table 1e summarizes the physical characteristics results for each of the three suspensions GT032, GT031 and GT019. Full characterization of GT019 was not completed, however, it is clear that under the processing conditions discussed herein, both processing enhancers (i.e., soda and salt) increase the measured ppm of gold in the suspensions GT031 and GT019 relative to GT032.

TABLE 1e

|   | PPM | Zeta Potential (Avg) | pH | DLS % Transmission | Predominant DLS Mass Distribution Peak (Radius in nm) | Color of Suspension |
|---|---|---|---|---|---|---|
| GT032 | 0.4 | −19.30 | 3.29 | 11.7% | 3.80 | Clear |
| GT031 | 1.5 | −29.00 | 5.66 | 17.0% | 0.78 | Purple |
| GT019 | 6.1 | ** | ** | ** | ** | Pink |
| GT033 | 2.0 | ** | ** | 30% | ** | Pink |

**Values not measured

Examples 5-7

Manufacturing Gold-Based Nanocrystals/Nanocrystal Suspensions GD-007, GD-016 and GD-015

In general, each of Examples 5-7 utilize certain embodiments of the invention associated with the apparatuses generally shown in FIGS. 17b, 18a, 19a and 21a. Specific differences in processing and apparatus will be apparent in each Example. The trough members 30a and 30b were made from ⅛" (about 3 mm) thick plexiglass, and ¼" (about 6 mm) thick polycarbonate, respectively. The support structure 34 was also made from plexiglass which was about ¼" thick (about 6-7 mm thick). The cross-sectional shape of the trough member 30a shown in FIG. 18a corresponds to that shape shown in FIG. 10b (i.e., a truncated "V"). The base portion "R" of the truncated "V" measured about 0.5" (about 1 cm), and each side portion "S", "S measured about 1.5" (about 3.75 cm). The distance "M" separating the side portions "S", "S'" of the V-shaped trough member 30a was about 2¼"-2⁵⁄₁₆" (about 5.9 cm) (measured from inside to inside). The thickness of each portion also measured about ⅛" (about 3 mm) thick. The longitudinal length "$L_T$" (refer to FIG. 11a) of the V-shaped trough member 30a measured about 3 feet (about 1 meter) long from point 31 to point 32.

Purified water (discussed elsewhere herein) was mixed with about 0.396 g/L of $NaHCO_3$ and was used as the liquid 3 input into trough member 30a. While the amount of $NaHCO_3$ used was effective, this amount should not be viewed as limiting the metes and bounds of the invention, and other amounts are within the metes and bounds of this disclosure. The depth "d" (refer to FIG. 10b) of the water 3 in the V-shaped trough member 30a was about 7/16" to about ½" (about 11 mm to about 13 mm) at various points along the trough member 30a. The depth "d" was partially controlled through use of the dam 80 (shown in FIG. 18a). Specifically, the dam 80 was provided near the end 32 and assisted in creating the depth "d" (shown in FIG. 10b) to be about ⅞"-½" (about 11-13 mm) in depth. The height "j" of the dam 80 measured about ¼" (about 6 mm) and the longitudinal length "k" measured about ½" (about 13 mm). The width (not shown) was completely across the bottom dimension "R" of the trough member 30a. Accordingly, the total volume of water 3 in the V-shaped trough member 30a during operation thereof was about 6.4 in³ (about 105 ml).

The rate of flow of the water 3 into the trough member 30a was about 150 ml/minute (note: there was minimal evaporation in the trough member 30a). Such flow of water 3 into the trough member 30a was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30a by a flow diffusion means located therein. The flow diffusion means tended to minimize disturbance and bubbles in water 3 introduced into the trough member 30a as well as any pulsing condition generated by the peristaltic pump 40. In this regard, a small reservoir served as the diffusion means and was provided at a point vertically above the end 31 of the trough member 30a such that when the reservoir overflowed, a relatively steady flow of water 3 into the end 31 of the V-shaped trough member 30a occurred.

There were 5 electrode sets used in Examples 5-7 and one set was a single electrode set 1a/5a located in trough member 30a. The plasma 4 in trough member 30a from electrode 1a was created with an electrode 1a similar in shape to that shown in FIG. 5e, and weighed about 9.2 grams. This electrode was 99.95% pure gold. The other electrode 5a comprised a right-triangular shaped platinum plate measuring about 14 mm×23 mm×27 mm and about 1 mm thick and having about 9 mm submerged in the liquid 3'. The AC transformer used to create the plasma 4 was that transformer 60 shown in FIG. 16d and discussed elsewhere herein. AC transformers 50 (discussed below) were connected to the other electrode sets 5/5. All other pertinent run conditions are shown in Tables 2a, 2b and 2c.

The output of the processing-enhanced, conditioned water 3' was collected into a reservoir 41 and subsequently pumped by another pump 40' into a second trough member 30b, at substantially the same rate as pump 40 (e.g., minimal evaporation occurred in trough member 30a). The second trough member 30b measured about 30 inches long by 1.5 inches wide by 5.75 inches high and contained about 2500 ml of water 3" therein. Each of four electrode sets 5b, 5b'-5e, 5e' comprised 99.95% pure gold wire measuring about 0.5 mm in diameter and about 5 inches (about 12 cm) in length and was substantially straight. About 4.25 inches (about 11 cm) of wire was submerged in the water 3" which was about 4.5 inches (about 11 cm) deep.

Figure 19A:
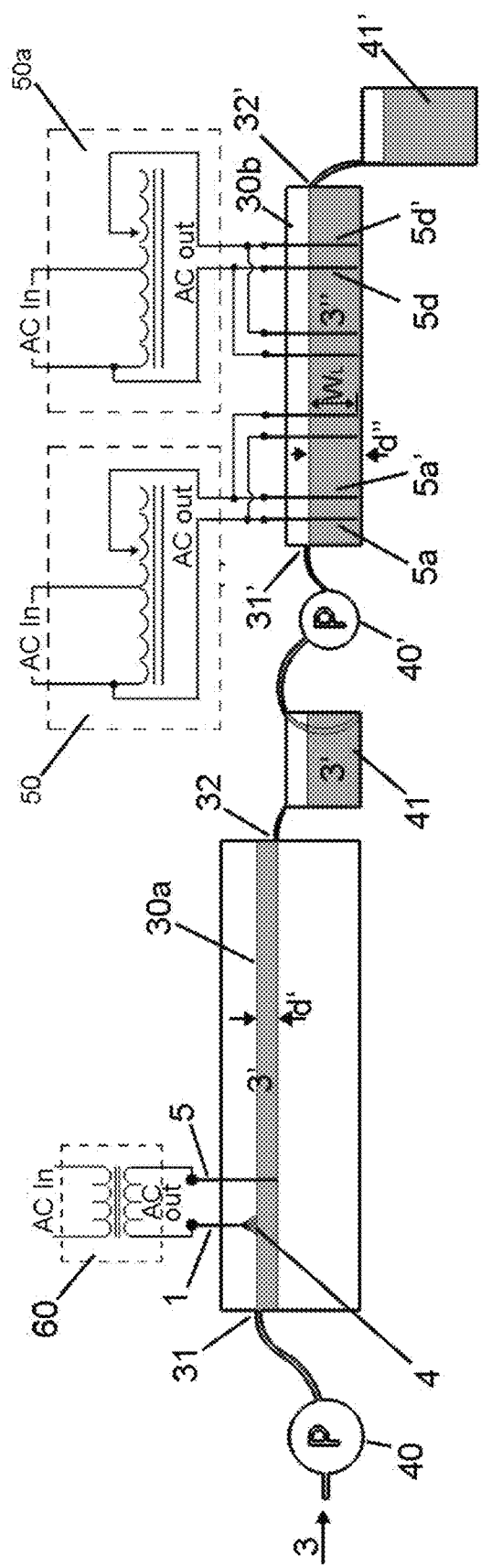
FIGS. 19a and 19b are schematics of two trough members 30a and 30b having two different electrode 5 wiring arrangements utilizing one transformer (Examples 8-10) and utilizing two transformers (Examples 5-7).
Figure 21A:
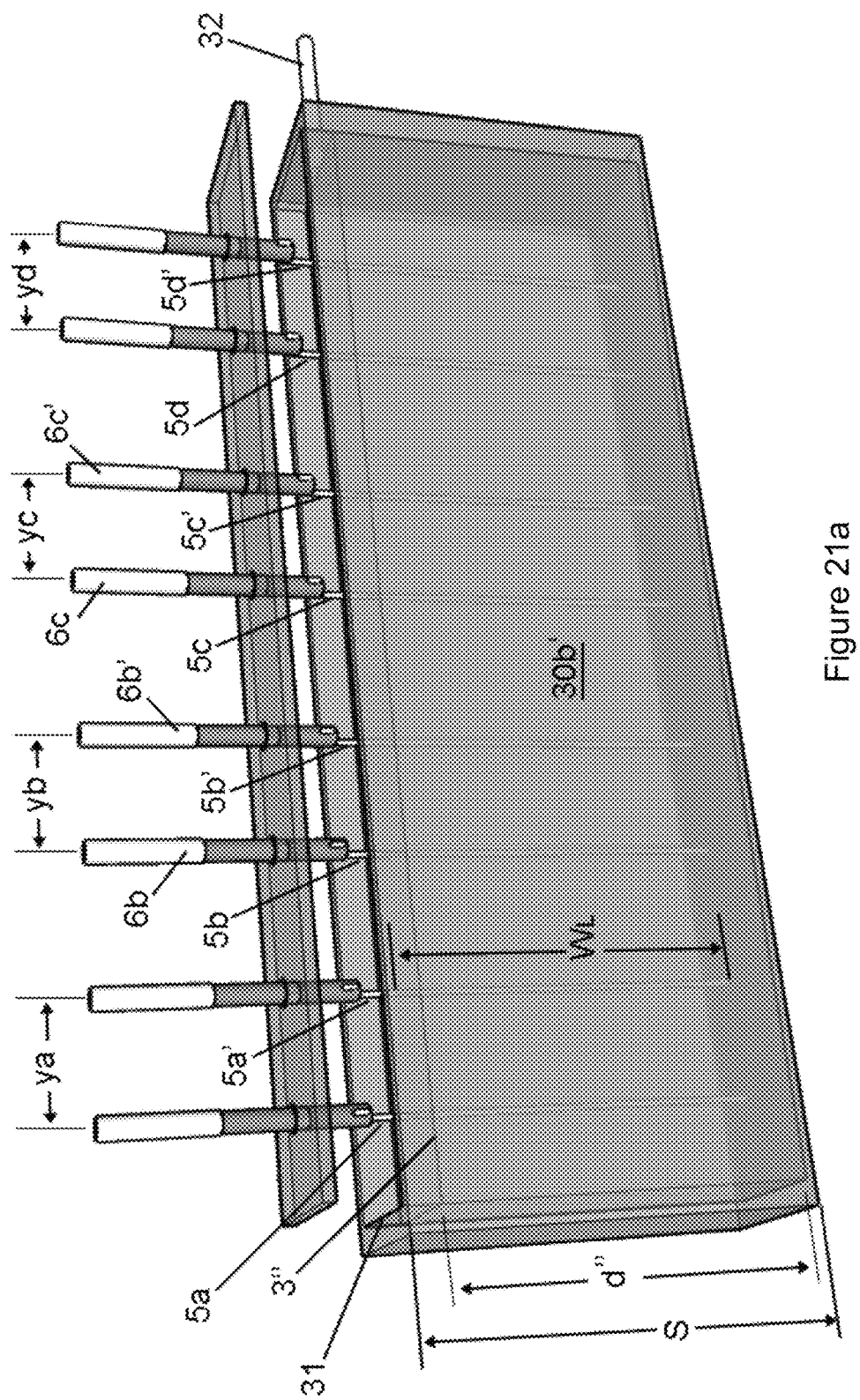
FIGS. 21a-21g show various trough members 30b in connection with FIGS. 20a-h and various Examples herein.
Figure 21B:
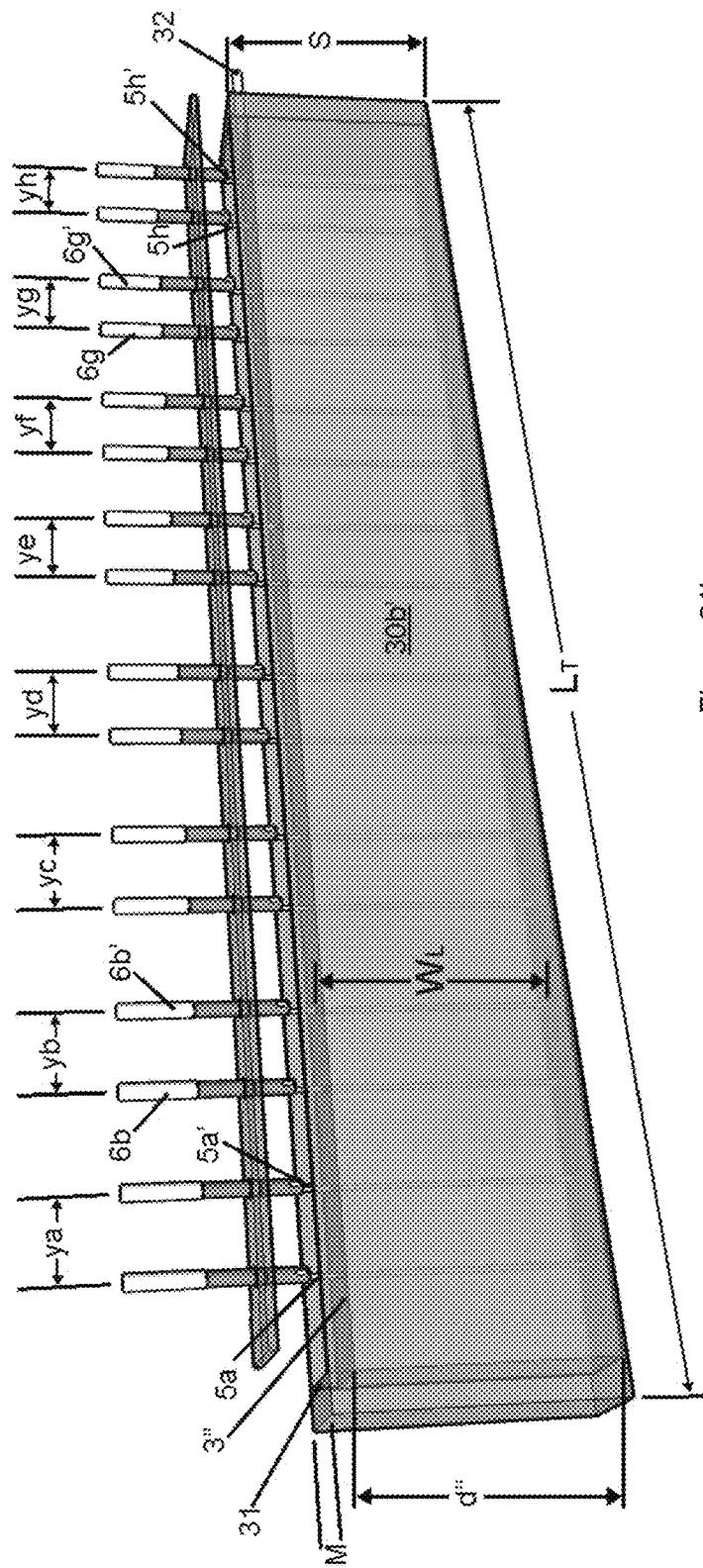
Figure 21C:
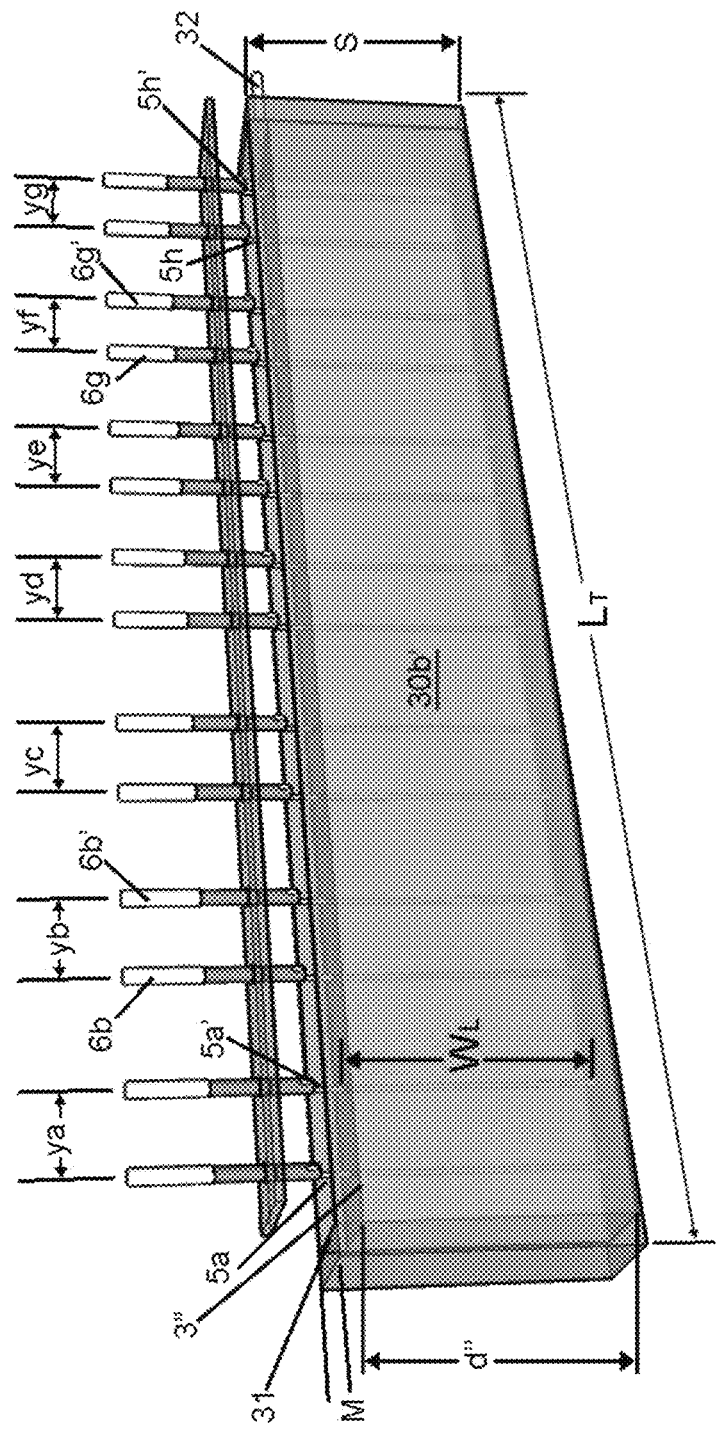

With regard to FIGS. 19a and 21a, 4 separate electrode sets (Set 2, Set 3, Set 4 and Set 5) were attached to 2 separate transformer devices 50 and 50a, as shown in FIG. 19a. Specifically, transformers 50 and 50a were electrically connected to each electrode set, according to the wiring diagram show in FIG. 19a. Each transformer device 50, 50a was connected to a separate AC input line that was 120° out of phase relative to each other. The transformers 50 and 50a were electrically connected in a manner so as not to overload a single electrical circuit and cause, for example, an upstream circuit breaker to disengage (e.g., when utilized under these conditions, a single transformer 50/50a could draw sufficient current to cause upstream electrical problems). Each transformer 50/50a was a variable AC transformer constructed of a single coil/winding of wire. This winding acts as part of both the primary and secondary winding. The input voltage is applied across a fixed portion of the winding. The output voltage is taken between one end of the winding and another connection along the winding. By exposing part of the winding and making the secondary connection using a sliding brush, a continuously variable ratio can be obtained. The ratio of output to input voltages is equal to the ratio of the number of turns of the winding they connect to. Specifically, each transformer was a Mastech TDGC2-5 kVA, 10A Voltage Regulator, Output 0-250V.

Each of Tables 2a-2c contains processing information relating to each of the 4 electrode sets in trough 30b by "Set #". Each electrode of the 4 electrode sets in trough 30b was set to operate at a specific target voltage. Actual operating voltages of about 255 volts, as listed in each of Tables 2a-2c, were applied across the electrode sets. The distance "c-c" (with reference to FIG. 14) from the centerline of each electrode set to the adjacent electrode set is also represented. Further, the distance "x" associated with the electrode 1 utilized in trough 30a is also reported. For the electrode 5's, no distance "x" is reported. Other relevant parameters are also reported in each of Tables 2a-2c.

All materials for the electrodes 1/5 were obtained from ESPI having an address of 1050 Benson Way, Ashland, Oreg. 97520.

The water 3 used in Examples 5-7 was produced by a Reverse Osmosis process and deionization process and was mixed with the $NaHCO_3$ processing-enhancer and together was input into the trough member 30a. In essence, Reverse Osmosis (RO) is a pressure driven membrane separation process that separates species that are dissolved and/or suspended substances from the ground water. It is called "reverse" osmosis because pressure is applied to reverse the natural flow of osmosis (which seeks to balance the concentration of materials on both sides of the membrane). The applied pressure forces the water through the membrane leaving the contaminants on one side of the membrane and the purified water on the other. The reverse osmosis membrane utilized several thin layers or sheets of film that are bonded together and rolled in a spiral configuration around a plastic tube. (This is also known as a thin film composite or TFC membrane.) In addition to the removal of dissolved species, the RO membrane also separates out suspended materials including microorganisms that may be present in the water. After RO processing a mixed bed deionization filter was used. The total dissolved solvents ("TDS") after both treatments was about 0.2 ppm, as measured by an Accumet® AR20 pH/conductivity meter.

TABLE 2a 0.396 mg/ml of NaHCO₃ (Au)

| Run ID: | GD-007 |
|---|---|
| Flow Rate: | 150 ml/min |
| Voltage: | 255 V |
| NaHCO₃: | 0.396 mg/ml |
| Wire Dia.: | .5 mm |
| Configuration: | Straight/Straight |
| PPM: | 14.8 |
| Zeta: | n/a |

| Set# | Electrode # | Distance "c-c" in/mm | Distance "x" in/mm | Voltage | cross section |
|---|---|---|---|---|---|
| 1 | 1a | 4.5/114.3* | 0.25 | 750 | V |
|  | 5a |  | N/A | 750 |  |
|  |  | 23/584.2** |  |  |  |
| 2 | 5b | 2.5/63.5* | N/A | 255 |  |
|  | 5b' |  | N/A |  |  |
|  |  | 8.5/215.9 |  |  |  |
| 3 | 5c |  | N/A | 255 |  |
|  | 5c' |  | N/A |  |  |
|  |  | 8.5/215.9 |  |  | Rectangle 5.25" Deep |
| 4 | 5d |  | N/A | 255 |  |
|  | 5d' |  | N/A |  |  |
|  |  | 8/203.2 |  |  |  |
| 5 | 5e |  | N/A | 255 |  |
|  | 5e' |  | N/A |  |  |
|  |  | 2/50.8** |  |  |  |
|  |  |  |  |  | Output Water Temperature 96 C. |

*Distance from water inlet to center of first electrode set
**Distance from center of last electrode set to water oulet TABLE 2b 0.396 mg/ml of NaHCO₃ (Au)

| Run ID: | GD-016 |
|---|---|
| Flow Rate: | 150 ml/min |
| Voltage: | 255 V |
| NaHCO₃: | 0.396 mg/ml |
| Wire Dia.: | .5 mm |
| Configuration: | Straight/Straight |
| PPM: | 12.5 |
| Zeta: | −56.12 |

| Se# | Electrode # | Distance "c-c" in/mm | Distance "x" in/mm | Voltage | cross section |
|---|---|---|---|---|---|
| 1 | 1a | 4.5/114.3* | 0.25 | 750 | V |
|  | 5a |  | N/A | 750 |  |
|  |  | 23/584.2** |  |  |  |
| 2 | 5b | 2.5/63.5* | N/A | 255 |  |
|  | 5b' | N/A |  |  |  |
|  |  | 8.5/215.9 |  |  |  |
| 3 | 5c |  | N/A | 255 |  |
|  | 5c' |  | N/A |  |  |

TABLE 2b-continued 0.396 mg/ml of NaHCO₃ (Au)

| | | 8.5/215.9 | | | Rectangle 5.25" Deep |
|---|---|---|---|---|---|
| 4 | 5d |  | N/A | 255 |  |
|  | 5d' |  | N/A |  |  |
|  |  | 8/203.2 |  |  |  |
| 5 | 5e |  | N/A | 255 |  |
|  | 5e' |  | N/A |  |  |
|  |  | 2/50.8** |  |  |  |
|  |  |  |  |  | Output Water Temperature 97 C. |

*Distance from water inlet to center of first electrode set
**Distance from center of last electrode set to water oulet TABLE 2c 0.396 mg/ml of NaHCO3 (Au)

| Run ID: | GD-015 |
|---|---|
| Flow Rate: | 150 ml/min |
| Voltage: | 255 V |
| NaHCO₃: | 0.396 mg/ml |
| Wire Dia.: | .5 mm |
| Configuration: | Straight/Straight |
| PPM: | 14.5 |
| Zeta: | −69.1 |

| Set# | Electrode # | Distance "c-c" in/mm | Distance "x" in/mm | Voltage | cross section |
|---|---|---|---|---|---|
| 1 | 1a | 4.5/114.3* | 0.25 | 750 | V |
|  | 5a |  | N/A | 750 |  |
|  |  | 23/584.2** |  |  |  |
| 2 | 5b | 2.5/63.5* | N/A | 255 |  |
|  | 5b' |  | N/A |  |  |
|  |  | 8.5/215.9 |  |  |  |
| 3 | 5c |  | N/A | 255 |  |
|  | 5c' |  | N/A |  |  |
|  |  | 8.5/215.9 |  |  | Rectangle 5.25" Deep |
| 4 | 5d |  | N/A | 255 |  |
|  | 5d' |  | N/A |  |  |
|  |  | 8/203.2 |  |  |  |
| 5 | 5e |  | N/A | 255 |  |
|  | 5e' |  | N/A |  |  |
|  |  | 2/50.8** |  |  |  |
|  |  |  |  |  | Output Water Temperature 96 C. |

*Distance from water inlet to center of first electrode set
**Distance from center of last electrode set to water oulet Representative Transmission Electron Microscopy (TEM) photomicrographs (FIGS. 25a, 26a and 27a) were taken of each dried suspension made according to each of these Examples 5-7.

Transmission Electron Microscopy

Specifically, TEM samples were prepared by utilizing a Formvar coated grid stabilized with carbon having a mesh size of 200. The grids were first pretreated by a plasma treatment under vacuum. The grids were placed on a microscope slide lined with a rectangular piece of filter paper and then placed into a Denton Vacuum apparatus with the necessary plasma generator accessory installed. The vacuum was maintained at 75 mTorr and the plasma was initiated and run for about 30 seconds. Upon completion, the system was vented and the grids removed. The grids were stable up to 7-10 days depending upon humidity conditions, but in all instances were used within 12 hours.

Approximately 1 μL of each inventive nanocrystal suspension was placed onto each grid and was allowed to air dry at room temperature for 20-30 minutes, or until the droplet evaporated. Upon complete evaporation, the grids were placed onto a holder plate until TEM analysis was performed.

A Philips/FEI Tecnai 12 Transmission Electron Microscope was used to interrogate all prepared samples. The instrument was run at an accelerating voltage of 100 keV. After alignment of the beam, the samples were examined at various magnifications up to and including 630,000×. Images were collected via the attached Olympus Megaview III side-mounted camera that transmitted the images directly to a PC equipped with iTEM and Tecnai User Interface software which provided for both control over the camera and the TEM instrument, respectively.

Within the iTEM software, it was possible to randomly move around the grid by adjusting the position of a crosshair on a circular reference plane. By selecting and moving the cross-hairs, one could navigate around the grid. Using this function, the samples were analyzed at four quadrants of the circular reference, allowing for an unbiased representation of the sample. The images were later analyzed with ImageJ 1.42 software. Another similar software program which measured the number of pixels across each particle relative to a known number of pixels in a spacer bar was used to streamline the particle counting process. The particles were measured using the scale bar on the image as a method to calibrate the software prior to measuring each individual particle. Once calibrated, particles were measured based upon the following parameters: Tetrahedral particles were measured from the triangle's apex to the base. Pentagonal by pyramids were measured from either apex to apex of the diamond or apex of the pentagon to the base of the pentagon depending upon the particle orientation on the grid. Icosahedrons were measured using the longest distance between two faces of a hexagonal particle. Spherical or irregular shaped particles were measured along the longest axis. The data collected from each sample set was exported to Excel, and using a simple histogram function with 50 bins with a minimum of 5 nm and maximum of 50 nm, a histogram was generated. Subsequently, the data generated within Excel was exported to Prism (GraphPad™) and fit to one of two models, a normal distribution or log normal distribution, each having a unique probability density function (PDF). Within Prism, it was possible to analyze the histogram data by performing a non-linear fit to the data which generates a distribution known as a normal distribution. Moreover, it was possible to perform a logarithmic transformation on the non-linear data set to generate a data set that is then fit to a non-linear model and then transformed via an exponential transformation to generate a log-normal fit of the data. The two models were then visually compared to the histogram and the model that fit the data to a better degree was chosen. The particle diameter noted above, and reported in the many Histogram Figures and Tables herein, is the mode of the PDF, which is defined as the maximum value of the lognormal or normal PDF curve. This PDF curve is overlaid on all histogram figures wherein the mode value is displayed directly above and is referenced in text as the TEM average diameter.

Figure 25A:
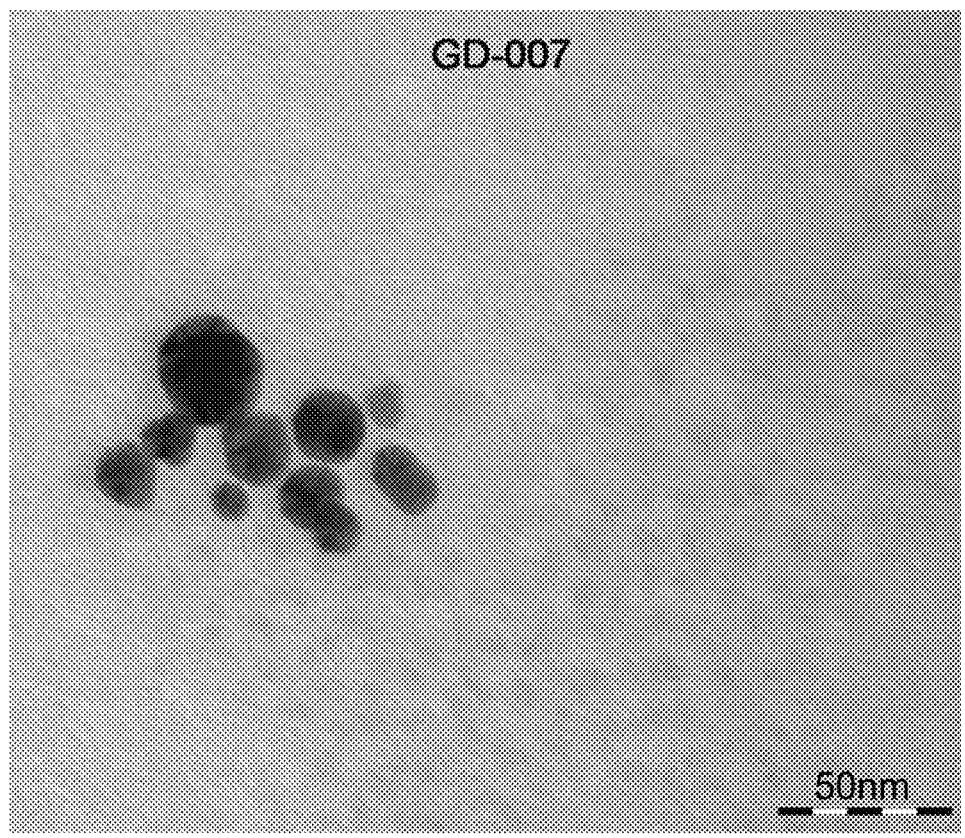
FIG. 25a is a representative TEM photomicrograph of gold nanocrystals from dried suspension GD-007 made according to Example 5.
Figure 25B:
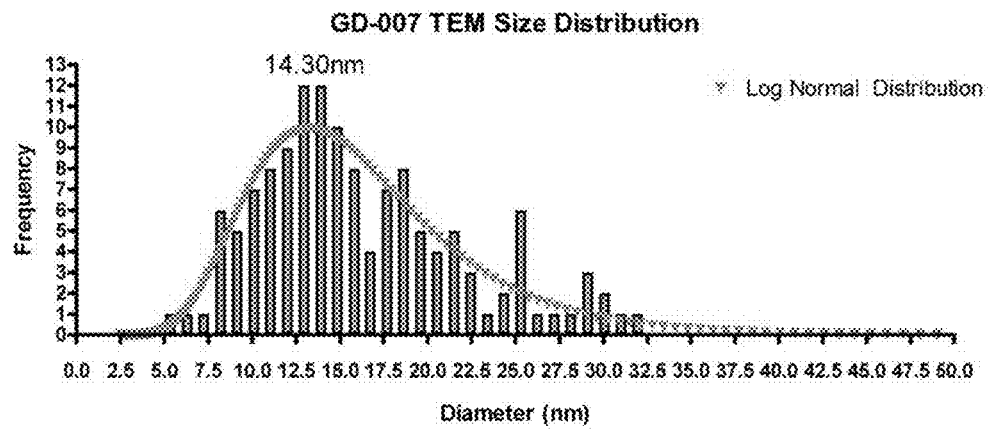
FIG. 25b shows the particle size distribution histogram from TEM measurements for the nanocrystals of suspension GD-007 made according to Example 5.
Figure 26A:
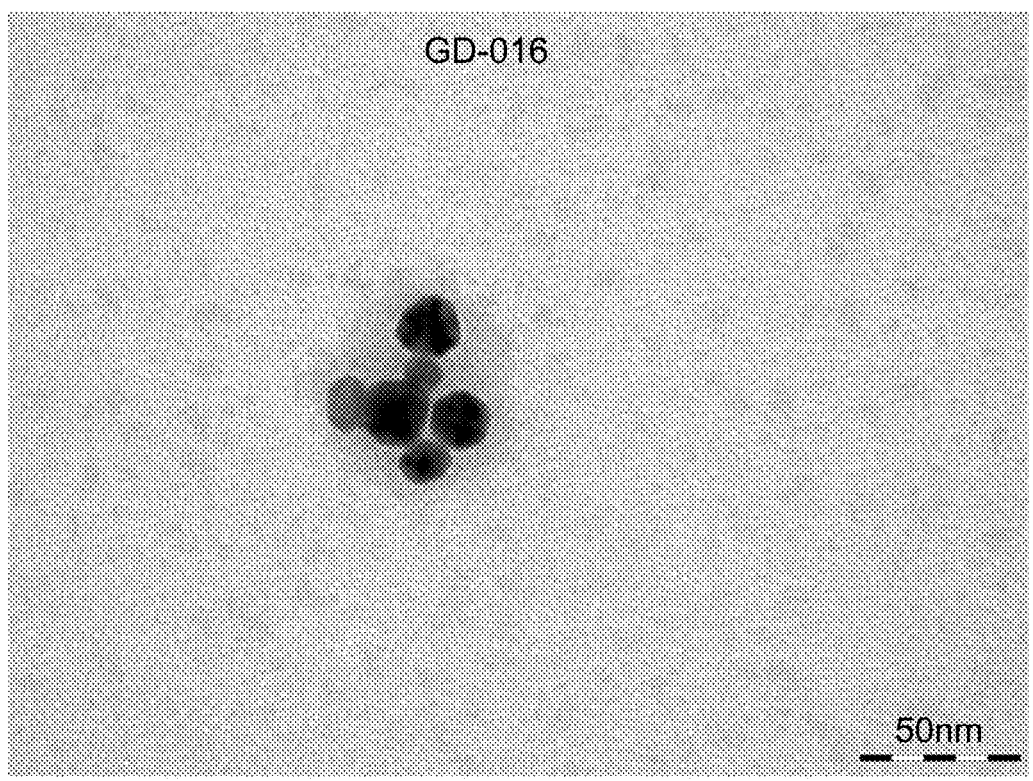
FIG. 26a is a representative TEM photomicrograph of gold nanocrystals from dried solution GD-016 made according to Example 6.
Figure 26B:
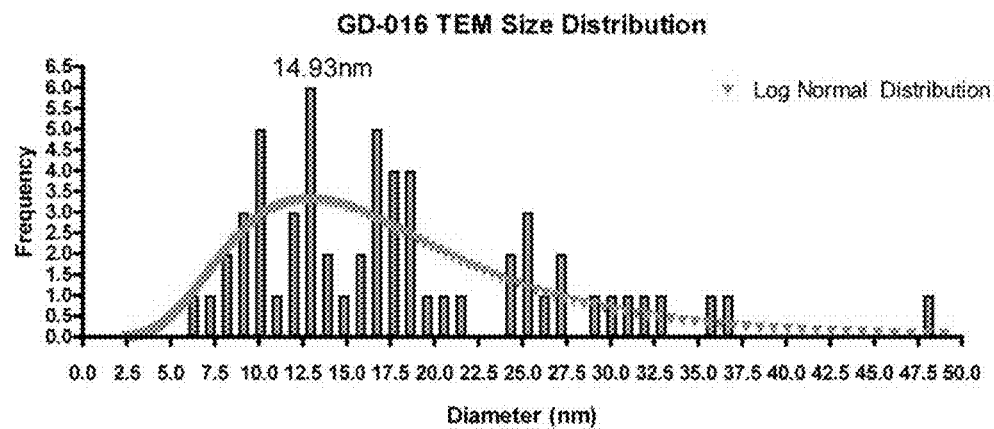
FIG. 26b shows the particle size distribution from TEM measurements for the nanocrystals made according to Example 6.
Figure 27A:
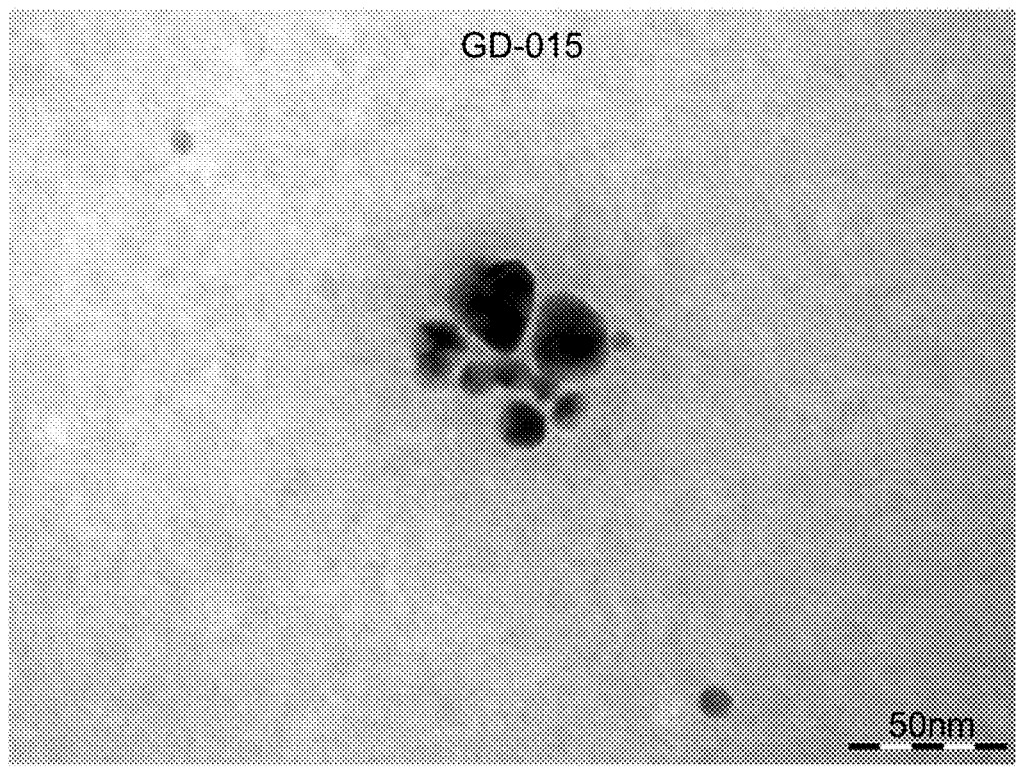
FIG. 27a is a representative TEM photomicrograph of gold nanocrystals from dried solution GD-015 made according to Example 7.
Figure 27B:
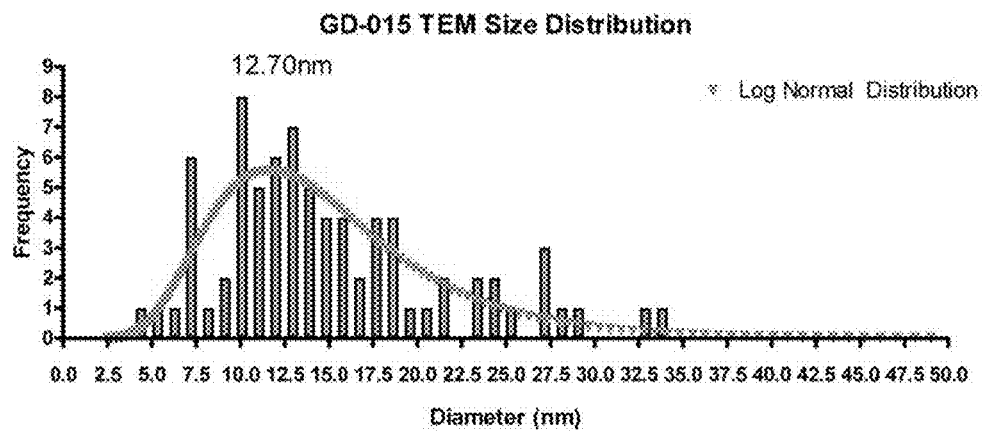
FIG. 27b shows the particle size distribution histogram from TEM measurements for the nanocrystals made according to Example 7.

For example, FIGS. 25b, 26b and 27b are crystal size distribution histograms measured from TEM photomicrographs corresponding to dried solutions GD-007, GD-016 and GD-015 corresponding to Examples 5, 6 and 7, respectively. Each of the numbers reported on these histograms corresponds to the discussion above.

FIGS. 25a, 26a and 27a are representative TEM photomicrographs corresponding to dried solutions GD-007, GD-016 and GD-015 corresponding to Examples 5, 6 and 7, respectively.

Figure 25C:
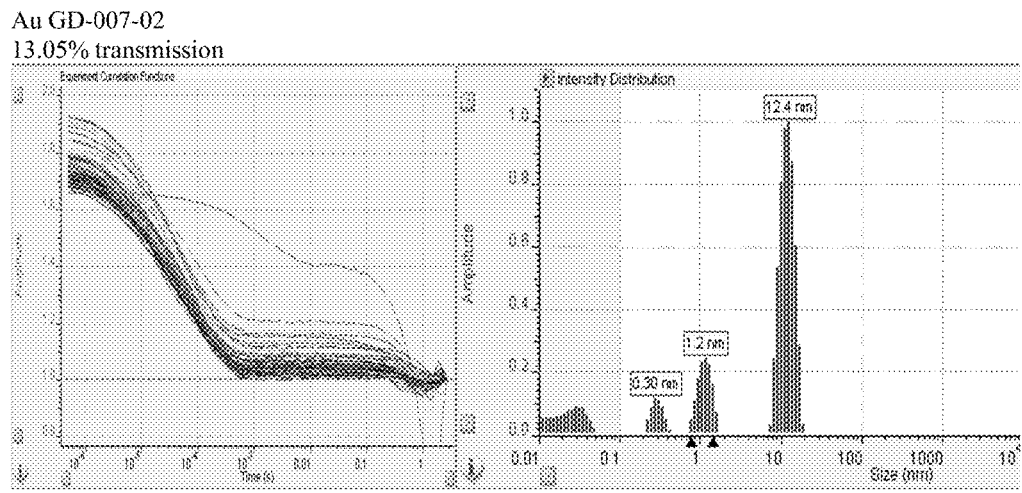
FIG. 25c shows dynamic light scattering data (i.e., hydrodynamic radii) for gold nanocrystals made according to Example 5.
Figure 25D:
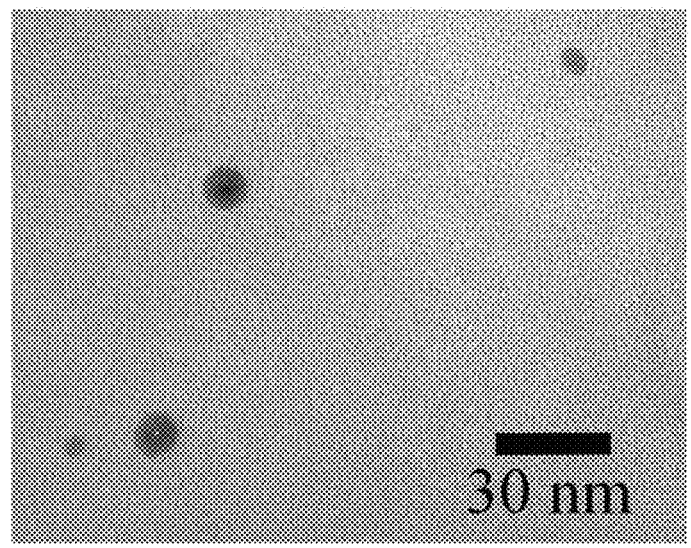
FIG. 25d is a representative TEM photomicrograph of gold nanocrystals from dried suspension GD-007 made according to Example 5.
Figure 25E:
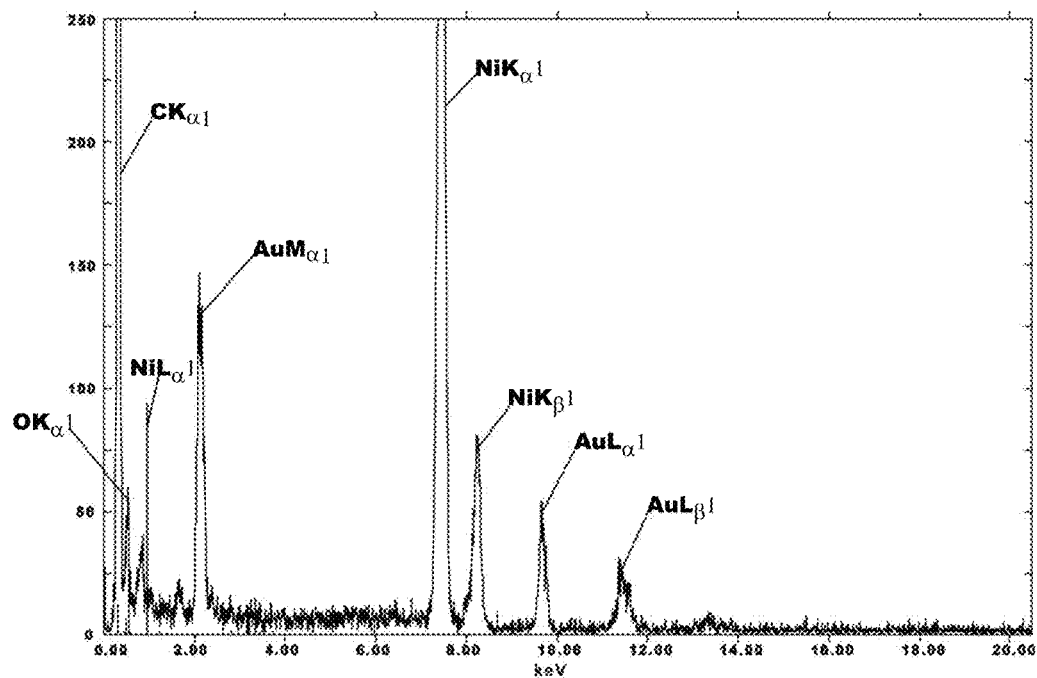
FIG. 25e shows the energy dispersive x-ray pattern of the interrogation beam point of the nanocrystal from suspension GD-007.

The results shown in FIGS. 25d and 25e were obtained using a Philips 420ST transmission electron microscope equipped with an Energy Dispersive X-ray Spectroscopy detector (EDS). The microscope was located in the Electron Microbeam Analytical Facility at Johns Hopkins University and operated under the guidance of a trained operator. Briefly, approximately 1 μL of GD-007 nanocrystalline suspension was placed onto a Formvar carbon-coated 200 square mesh nickel grid and was allowed to air dry at room temperature for about 20-30 minutes, or until the droplet evaporated. Upon complete evaporation, the grids were placed into the TEM sample holder and interrogated at an accelerating voltage of 120 keV. The microscope's EDS system was comprised of the following components: Oxford light electron detector, Oxford XP3 pulse processor, and a 4 pi multi-channel analyzer connected to a Macintosh computer. Particle composition was determined via energy dispersive x-ray spectroscopy wherein a high energy beam of electrons was directed at the surface of the nanocrystal resulting in the ejection of an electron within the inner shell, thereby creating an available site for an outer electron to "fall" into, thus emitting a characteristic x-ray. The x-ray is then detected by the detector having a resolution of 173.00 eV.

FIG. 25d shows one of the gold nanocrystals grown according to Example 5 (i.e., GD-007). The nanocrystal was interrogated with the electron beam as discussed herein.

FIG. 25e shows the energy dispersive x-ray pattern of the interrogation beam point of the nanocrystal from solution GD-007. Because this measuring technique is accurate to about a mono-layer of atoms, the lack of a pattern corresponding to a sodium peak shows that no sodium-based mono-layer was present on the crystal's surface. Likewise, no significant carbon-based peak is observable either, indicative of the lack of any carbon-based monolayer. Note is made of the presence of the oxygen peak, which corresponds to the underlying nickel grid. Accordingly, these FIGS. 25d and 25e show: 1) no organics are present on these molecules and 2) that the nanocrystals contain a relatively clean surface devoid of adverse molecules or coatings.

Figure 26C:
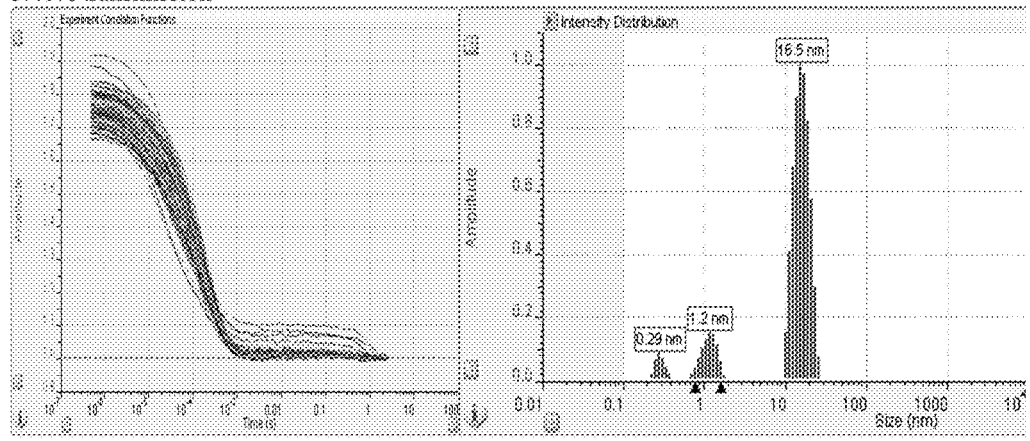
FIG. 26c shows dynamic light scattering data (i.e., hydrodynamic radii) for gold nanocrystals made according to Example 6.
Figure 27C:
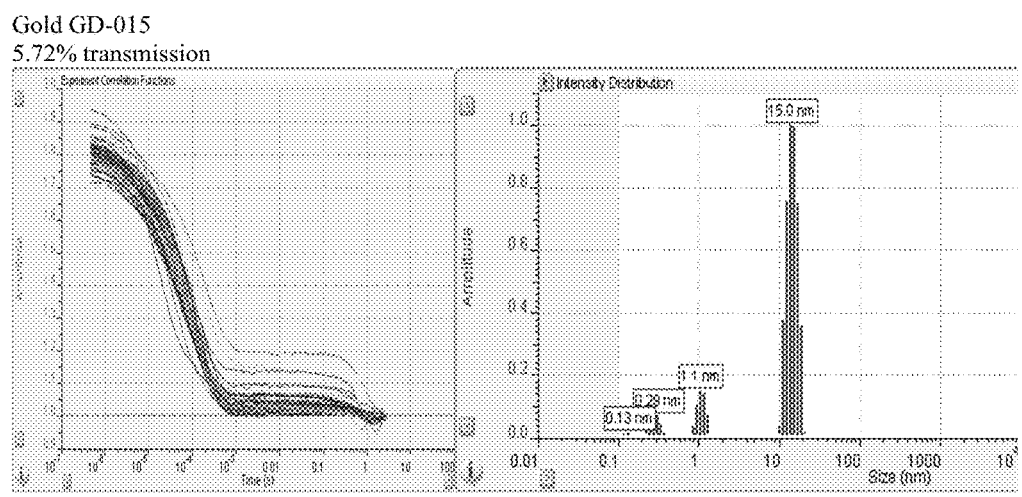
FIG. 27c shows dynamic light scattering data (i.e., hydrodynamic radii) for gold nanocrystals made according to Example 7.

Further, dynamic light scattering techniques were also utilized to obtain an indication of crystal sizes (e.g., hydrodynamic radii) produced according to the Examples herein. FIGS. 25c, 26c and 27c show the graphical result of the separate dynamic light scattering data sets.

Dynamic Light Scattering

Specifically, dynamic light scattering (DLS) measurements were performed on Viscotek 802 DLS instrument. In DLS, as the laser light hits small particles and/or organized water structures around the small particles (smaller than the wavelength), the light scatters in all directions, resulting in a time-dependent fluctuation in the scattering intensity. Intensity fluctuations are due to the Brownian motion of the scattering particles/water structure combination and contain information about the crystal size distribution.

The instrument was allowed to warm up for at least 30 min prior to the experiments. The measurements were made using 12 μl quartz cell. The following procedure was used:
1. First, 1 ml of DI water was added into the cell using 1 ml micropipette, then water was poured out of the cell to a waste beaker and the rest of the water was shaken off the cell measuring cavity. This step was repeated two more times to thoroughly rinse the cell.
2. 100 μl of the sample was added into the cell using 200 μl micropipette. After that all liquid was removed out of the cell with the same pipette using the same pipette tip and expelled into the waste beaker. 100 μl of the sample was added again using the same tip.
3. The cell with the sample was placed into a temperature controlled cell block of the Viscotek instrument with frosted side of the cell facing left. A new experiment in Viscotek OmniSIZE software was opened. The measurement was started 1 min after the temperature equilibrated and the laser power attenuated to the proper value. The results were saved after all runs were over.
4. The cell was taken out of the instrument and the sample was removed out of the cell using the same pipette and the tip used if step 2.
5. Steps 2 to 4 were repeated two more times for each sample.
6. For a new sample, a new pipette tip for 200 μl pipette was taken to avoid contamination with previous sample and steps 1 through 5 were repeated.

Data collection and processing was performed with OmniSIZE software, version 3.0.0.291. The following parameters were used for all the experiments: Run Duration—3 s; Experiments—100; Solvent—water, 0 mmol; Viscosity—1 cP; Refractive Index—1.333; Spike Tolerance—20%; Baseline Drift—15%; Target Attenuation—300 kCounts; block temperature—+40° C. After data for each experiment were saved, the results were viewed on "Results" page of the software. Particle size distribution (i.e., hydrodynamic radii) was analyzed in "Intensity distribution" graph. On that graph any peaks outside of 0.1 nm-10 μm range were regarded as artifacts. Particularly, clean water (no particles) results no peaks within 0.1 nm-10 μm range and a broad peak below 0.1 nm. This peak is taken as a noise peak (noise flow) of the instrument. Samples with very low concentration or very small size of suspended nanocrystals or nanoparticles may exhibit measurable noise peak in "Intensity distribution" graph. If the peaks within 0.1 nm-10 μm range have higher intensity than the noise peak, those peaks considered being real, otherwise the peaks are questionable and may represent artifacts of data processing.

FIG. 25c shows graphical data corresponding to representative Viscotek output data sets for Example 5 (i.e., GD-007); FIG. 26c shows graphical data corresponding to representative Viscotek output data sets for Example 6 (i.e., GD-016); and FIG. 27c shows graphical data corresponding to representative Viscotek output data sets for Example 7 (i.e., GD-015). The numbers reported at the tops of the peaks in each of FIGS. 25c, 26c and 27c correspond to the average hydrodynamic radii of nanocrystals, and light scattered around such nanocrystals, detected in each solution. It should be noted that multiple (e.g., hundreds) of data-points were examined to give the numbers reported in each data set, as represented by the "s-shaped" curves (i.e., each curve represents a series of collected data points). The reported "% transmission" in each data set corresponds to the intensity of the interrogation beam required in order to achieve the dynamic light scattering data. In general, but not always, when the reported "% transmission" is below 50%, very strong particle and/or particle/ordered water structures are present. Also, when the "% transmission" approaches 100%, often ions and/or very small particles (e.g., pico-sized particles) are present and the reported hydrodynamic radii may comprise more ordered or structured water then actual solid particles.

It should be noted that the dynamic light scattering particle size information is different from the TEM measured histograms because dynamic light scattering uses algorithms that assume the nanocrystals are all spheres (which they are not) as well as measures the hydrodynamic radius (e.g., the nanocrystal's influence on the water is also detected and reported in addition to the actual physical radii of the particles). Accordingly, it is not surprising that there is a difference in the reported particle sizes between those reported in the TEM histogram data and those reported in the dynamic light scattering data, just as in the other Examples included herein.

Atomic Absorption Spectroscopy

The AAS values were obtained from a Perkin Elmer AAnalyst 400 Spectrometer system.

I) Principle

The technique of flame atomic absorption spectroscopy requires a liquid sample to be aspirated, aerosolized and mixed with combustible gases, such as acetylene and air. The mixture is ignited in a flame whose temperature ranges from about 2100 to about 2400 degrees C. During combustion, atoms of the element of interest in the sample are reduced to free, unexcited ground state atoms, which absorb light at characteristic wavelengths. The characteristic wavelengths are element specific and are accurate to 0.01-0.1 nm. To provide element specific wavelengths, a light beam from a hollow cathode lamp (HCL), whose cathode is made of the element being determined, is passed through the flame. A photodetector detects the amount of reduction of the light intensity due to absorption by the analyte. A monochromator is used in front of the photodetector to reduce background ambient light and to select the specific wavelength from the HCL required for detection. In addition, a deuterium arc lamp corrects for background absorbance caused by non-atomic species in the atom cloud.

II) Sample Preparation 10 mL of sample, 0.6 mL of 36% v/v hydrochloric acid and 0.15 mL of 50% v/v nitric acid are mixed together in a glass vial and incubated for about 10 minutes in 70 degree C. water bath. If gold concentration in the suspension is expected to be above 10 ppm a sample is diluted with DI water before addition of the acids to bring final gold concentration in the range of 1 to 10 ppm. For example, for a gold concentration around 100 ppm, 0.5 mL of sample is diluted with 9.5 mL of DI water before the addition of acids. Aliquoting is performed with adjustable micropipettes and the exact amount of sample, DI water and acids is measured by an Ohaus PA313 microbalance. The weights of components are used to correct measured concentration for dilution by DI water and acids.

Each sample is prepared in triplicate and after incubation in water bath is allowed to cool down to room temperature before measurements are made.

III) Instrument Setup

The following settings are used for Perkin Elmer AAnalyst 400 Spectrometer system:

a) Burner head: 10 cm single-slot type, aligned in three axes according to the manufacture procedure to obtain maximum absorbance with a 2 ppm Cu standard.
b) Nebulizer: plastic with a spacer in front of the impact bead.
c) Gas flow: oxidant (air) flow rate about 12 L/min, fuel (acetylene) flow rate about 1.9 mL/min.
d) Lamp/monochromator: Au hollow cathode lamp, 10 mA operating current, 1.8/1.35 mm slits, 242.8 nm wavelength, background correction (deuterium lamp) is on.

IV) Analysis Procedure a) Run the Au lamp and the flame for approximately 30 minutes to warm up the system.
b) Calibrate the instrument with 1 ppm, 4 ppm and 10 ppm Au standards in a matrix of 3.7% v/v hydrochloric acid. Use 3.7% v/v hydrochloric acid as a blank.
c) Verify calibration scale by measuring 4 ppm standard as a sample. The measured concentration should be between 3.88 ppm and 4.12 ppm. Repeat step b) if outside that range.
d) Measure three replicas of a sample. If the standard deviation between replicas is higher than 5%, repeat measurement, otherwise proceed to the next sample.
e) Perform verification step c) after measuring six samples or more often. If verification fails, perform steps b) and c) and remeasure all the samples measured after the last successful verification.

V) Data Analysis

Measured concentration value for each replica is corrected for dilution by water and acid to calculate actual sample concentration. The reported Au ppm value is the average of three corrected values for individual replica.

Plasma Irradiance and Characterization

This Example provides a spectrographic analysis of the adjustable plasmas 4, utilizing a gold electrode 1, all of which were utilized in the Examples herein. Three different spectrometers with high sensitivities were used to collect spectral information about the plasmas 4. Specifically, spectrographic analysis was conducted on several gold electrode plasmon. The species in the plasmas 4, as well as different intensities of some of the species, were observed. The presence/absence of such species can affect (e.g., positively and negatively) processing parameters and products made according to the teachings herein.

Figure 25F:
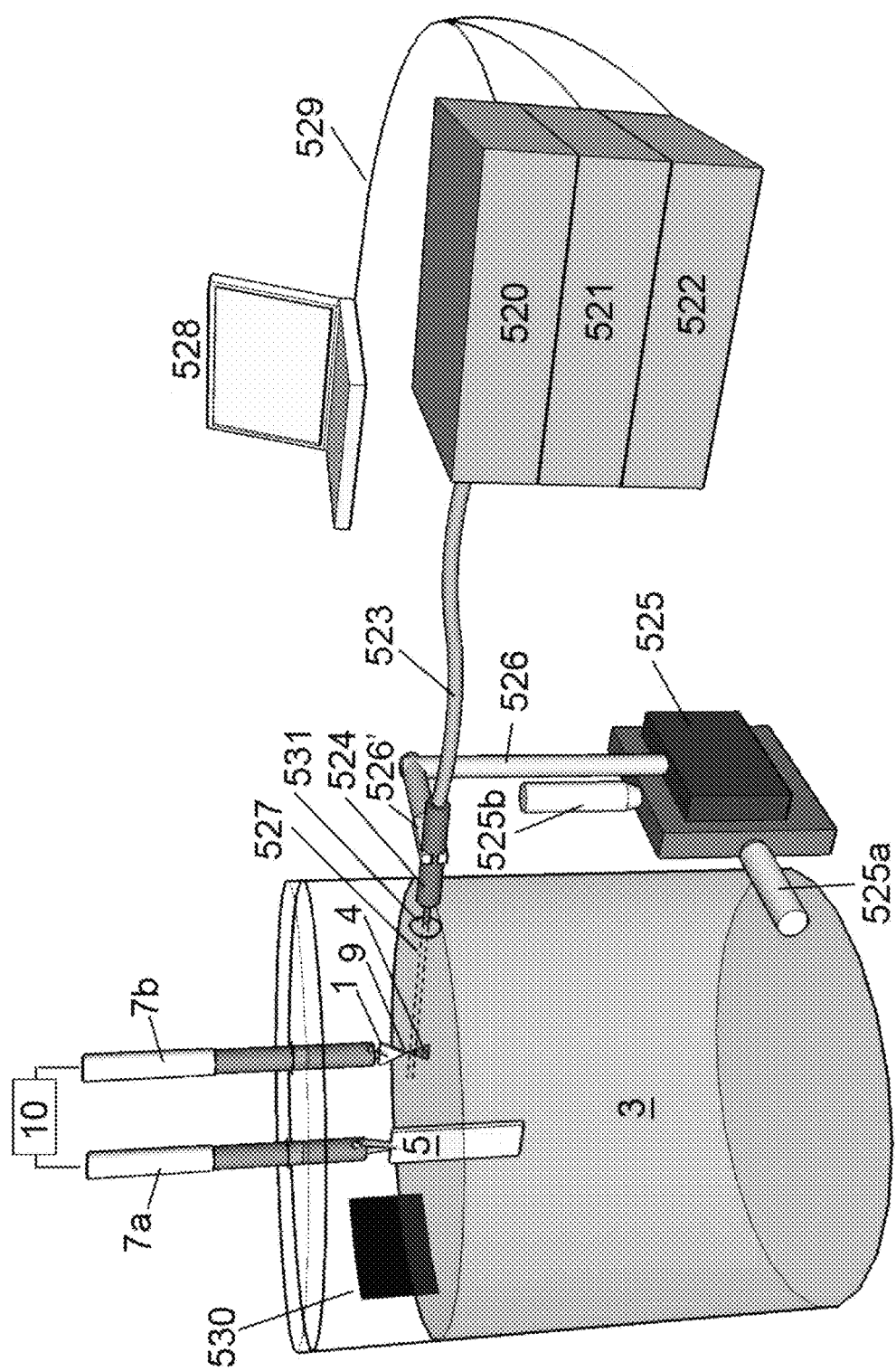
FIG. 25f shows the experimental setup for collecting plasma emission data (e.g., irradiance).

In this regard, FIG. 25f shows a schematic view, in perspective, of the experimental setup used to collect emission spectroscopy information from the adjustable plasmas 4 utilized herein.

Specifically, the experimental setup for collecting plasma emission data (e.g., irradiance) is depicted in FIG. 25f. In general, three spectrometers 520, 521 and 522 receive emission spectroscopy data through a UV optical fiber 523 which transmits collimated spectral emissions collected by the assembly 524, along the path 527. The assembly 524 can be vertically positioned to collect spectral emissions at different vertical locations within the adjustable plasma 4 by moving the assembly 524 with the X-Z stage 525. Accordingly, the presence/absence and intensity of plasma species can be determined as a function of interrogation location within the plasma 4. The output of the spectrometers 520, 521 and 522 was analyzed by appropriate software installed in the computer 528. All irradiance data was collected through the hole 531 which was positioned to be approximately opposite to the non-reflective material 530. The bottom of the hole 531 was located at the top surface of the liquid 3. More details of the apparatus for collecting emission radiance follows below.

The assembly 524 contained one UV collimator (LC-10U) with a refocusing assembly (LF-10U100) for the 170-2400 nm range. The assembly 524 also included an SMA female connector made by Multimode Fiber Optics, Inc. Each LC-10U and LF-10U100 had one UV fused silica lens associated therewith. Adjustable focusing was provided by LF-10U100 at about 100 mm from the vortex of the lens in LF-10U100 also contained in the assembly 524.

The collimator field of view at both ends of the adjustable plasma 4 was about 1.5 mm in diameter as determined by a 455 µm fiber core diameter comprising the solarization resistant UV optical fiber 523 (180-900 nm range and made by Mitsubishi). The UV optical fiber 523 was terminated at each end by an SMA male connector (sold by Ocean Optics; QP450-1-XSR).

The UV collimator-fiber system 523 and 524 provided 180-900 nm range of sensitivity for plasma irradiance coming from the 1.5 mm diameter plasma cylinder horizontally oriented in different locations in the adjustable plasma 4.

The X-Z stage 525 comprised two linear stages (PT1) made by Thorlabs Inc., that hold and control movement of the UV collimator 524 along the X and Z axes. It is thus possible to scan the adjustable plasma 4 horizontally and vertically, respectively.

Emission of plasma radiation collected by UV collimator-fiber system 523, 524 was delivered to either of three fiber coupled spectrometers 520, 521 or 522 made by StellarNet, Inc. (i.e., EPP2000-HR for 180-295 nm, 2400 g/mm grating, EPP2000-HR for 290-400 nm, 1800 g/mm grating, and EPP2000-HR for 395-505 nm, 1200 g/mm grating). Each spectrometer 520, 521 and 522 had a 7 µm entrance slit, 0.1 nm optical resolution and a 2048 pixel CCD detector. Measured instrumental spectral line broadening is 0.13 nm at 313.1 nm.

Spectral data acquisition was controlled by SpectraWiz software for Windows/XP made by StellarNet. All three EPP2000-HR spectrometers 520, 521 and 522 were interfaced with one personal computer 528 equipped with 4 USB ports. The integration times and number of averages for various spectral ranges and plasma discharges were set appropriately to provide unsaturated signal intensities with the best possible signal to noise ratios. Typically, spectral integration time was order of 1 second and number averaged spectra was in range 1 to 10. All recorded spectra were acquired with subtracted optical background. Optical background was acquired before the beginning of the acquisition of a corresponding set of measurements each with identical data acquisition parameters.

Each UV fiber-spectrometer system (i.e., 523/520, 523/521 and 523/522) was calibrated with an AvaLight-DH-CAL Irradiance Calibrated Light Source, made by Avantes (not shown). After the calibration, all acquired spectral intensities were expressed in (absolute) units of spectral irradiance (mW/m$^2$/nm), as well as corrected for the nonlinear response of the UV-fiber-spectrometer. The relative error of the AvaLight-DH-CAL Irradiance Calibrated Light Source in 200-1100 nm range is not higher than 10%.

Alignment of the field of view of the UV collimator assembly 524 relative to the tip 9 of the metal electrode 1 was performed before each set of measurements. The center of the UV collimator assembly 524 field of view was placed at the tip 9 by the alignment of two linear stages and by sending a light through the UV collimator-fiber system 523, 524 to the center of each metal electrode 1.

The X-Z stage 525 was utilized to move the assembly 524 into roughly a horizontal, center portion of the adjustable plasma 4, while being able to move the assembly 524 vertically such that analysis of the spectral emissions occurring at different vertical heights in the adjustable plasma 4 could be made. In this regard, the assembly 524 was positioned at different heights, the first of which was located as close as possible of the tip 9 of the electrode 1, and thereafter moved away from the tip 9 in specific amounts. The emission spectroscopy of the plasma often did change as a function of interrogation position.

For example, FIGS. 25g-25j show the irradiance data associated with a gold (Au) electrode 1 utilized to form the adjustable plasma 4. Each of the aforementioned FIGS. 25g-25j show emission data associated with three different vertical interrogation locations within the adjustable plasma 4. The vertical position "0" (0 nm) corresponds to emission spectroscopy data collected immediately adjacent to the tip 9 of the electrode 1; the vertical position "1/40" (0.635 nm) corresponds to emission spectroscopy data 0.635 mm away from the tip 9 and toward the surface of the water 3; and the vertical position "3/20" (3.81 mm) corresponds to emission spectroscopy data 3.81 mm away from the tip 9 and toward the surface of the water 3.

Table 2d shows specifically each of the spectral lines identified in the adjustable plasma 4 when a gold electrode 1 was utilized to create the plasma 4.

TABLE 2d

| Transition | λ tab. (nm) | λ meas. (nm) | λ meas. − λ tab. (nm) | En (1/cm) | Em (1/cm) | gn | gm | Amn (1/s) |
|---|---|---|---|---|---|---|---|---|
| NO $A^2\Sigma^+$-$X^2\Pi$ γ-system: (1-0) | 214.7 | 214.7000 | 0.0000 | | | | | |
| NO $A^2\Sigma^+$-$X^2\Pi$ γ-system: (0-0) | 226.9 | 226.8300 | −0.0700 | | | | | |
| NO $A^2\Sigma^+$-$X^2\Pi$ γ-system: (0-1) | 236.3 | 236.2100 | −0.0900 | | | | | |
| Au I 5d $^{10}$6s $^2S_{1/2}$-5d $^{10}$6p $^2P^o_{3/2}$ | 242.795 | 242.7900 | −0.0050 | 0 | 41174.613 | 2 | 4 | 1.99E+8 |
| NO $A^2\Sigma^+$-$X^2\Pi$ γ-system: (0-2) | 247.1 | 246.9300 | −0.1700 | | | | | |
| NO $A^2\Sigma^+$-$X^2\Pi$ γ-system: (0-3) | 258.3 | 258.5300 | 0.2300 | | | | | |
| NO $A^2\Sigma^+$-$X^2\Pi$ γ-system: (1-1) | 267.1 | 267.0600 | −0.0400 | | | | | |
| Au I 5d $^{10}$6s $^2S_{1/2}$-5d $^{10}$6p $^2P^o_{1/2}$ | 267.595 | 267.59 | −0.0050 | 0 | 37358.991 | 2 | 2 | 1.64E+8 |
| NO $A^2\Sigma^+$-$X^2\Pi$ γ-system: (0-4) | 271 | 271.1400 | 0.1400 | | | | | |
| Au I $5d^96s^2$ $^2D_{5/2}$-$5d^9(^2D_{5/2})6s6p$ $^24^o_{7/2}$ | 274.825 | 274.82 | −0.0050 | 9161.177 | 45537.195 | 6 | 8 | |
| OH $A^2\Sigma$-$X^2\Pi$ (1-0) | 281.2 | 281.2000 | 0.0000 | | | | | |
| OH $A^2\Sigma$-$X^2\Pi$ (1-0) | 282 | 281.9600 | −0.0400 | | | | | |
| $N_2$ ($C^3\Pi_u$-$B^3\Pi_g$) $2^+$-system (4-2) | 295.32 | 295.3300 | 0.0100 | | | | | |
| $N_2$ ($C^3\Pi_u$-$B^3\Pi_g$) $2^+$-system (3-1) | 296.2 | 296.1900 | −0.0100 | | | | | |
| $N_2$ ($C^3\Pi_u$-$B^3\Pi_g$) $2^+$-system (2-0) | 297.7 | 297.7000 | 0.0000 | | | | | |
| OH $A^2\Sigma$-$X^2\Pi$: (0-0) | 306.537 | 306.4600 | −0.0770 | | | | | |
| OH $A^2\Sigma$-$X^2\Pi$: (0-0) | 306.776 | 306.8400 | 0.0640 | | | | | |
| OH $A^2\Sigma$-$X^2\Pi$: (0-0) | 307.844 | 307.8700 | 0.0260 | | | | | |
| OH $A^2\Sigma$-$X^2\Pi$: (0-0) | 308.986 | 309.0700 | 0.0840 | | | | | |
| $N_2$ ($C^3\Pi_u$-$B^3\Pi_g$) $2^+$-system (2-1) | 313.57 | 313.5800 | 0.0100 | | | | | |
| $N_2$ ($C^3\Pi_u$-$B^3\Pi_g$) $2^+$-system (1-0) | 316 | 315.9200 | −0.0800 | | | | | |
| $O_2$ ($B^3\Sigma^-_u$-$X^3\Sigma^-_g$) (0-14) | 337 | 337.0800 | 0.0800 | | | | | |
| $N_2$ ($C^3\Pi_u$-$B^3\Pi_g$) $2^+$-system (0-0) | 337.1 | 337.1400 | 0.0400 | | | | | |
| $N_2$ ($C^3\Pi_u$-$B^3\Pi_g$) $2^+$-system (2-3) | 350.05 | 349.9700 | −0.0800 | | | | | |
| $N_2$ ($C^3\Pi_u$-$B^3\Pi_g$) $2^+$-system (1-2) | 353.67 | 353.6400 | −0.0300 | | | | | |
| $N_2$ ($C^3\Pi_u$-$B^3\Pi_g$) $2^+$-system (0-1) | 357.69 | 357.6500 | −0.0400 | | | | | |
| $N_2^+$ ($B^2\Sigma^+_u$-$X^2\Sigma^+_g$) $1^-$-system (1-0) | 358.2 | 358.2000 | 0.0000 | | | | | |
| $N_2$ ($C^3\Pi_u$-$B^3\Pi_g$) $2^+$-system (2-4) | 371 | 370.9500 | −0.0500 | | | | | |
| $N_2$ ($C^3\Pi_u$-$B^3\Pi_g$) $2^+$-system (1-3) | 375.54 | 375.4500 | −0.0900 | | | | | |
| $N_2$ ($C^3\Pi_u$-$B^3\Pi_g$) $2^+$-system (0-2) | 380.49 | 380.4000 | −0.0900 | | | | | |
| $N_2^+$ ($B^2\Sigma^+_u$-$X^2\Sigma^+_g$) $1^-$-system (1-1) | 388.4 | 388.4200 | 0.0200 | | | | | |
| $N_2^+$ ($B^2\Sigma^+_u$-$X^2\Sigma^+_g$) $1^-$-system (0-0) | 391.4 | 391.3700 | −0.0300 | | | | | |
| $N_2$ ($C^3\Pi_u$-$B^3\Pi_g$) $2^+$-system (1-4) | 399.8 | 399.7100 | −0.0900 | | | | | |
| $N_2$ ($C^3\Pi_u$-$B^3\Pi_g$) $2^+$-system (0-3) | 405.94 | 405.8100 | −0.1300 | | | | | |
| $N_2$ ($C^3\Pi_u$-$B^3\Pi_g$) $2^+$-system (4-8) | 409.48 | 409.4900 | 0.0100 | | | | | |
| $N_2^+$ ($B^2\Sigma^+_u$-$X^2\Sigma^+_g$) $1^-$-system (2-3) | 419.96 | 420.0000 | 0.0400 | | | | | |
| $N_2^+$ ($B^2\Sigma^+_u$-$X^2\Sigma^+_g$) $1^-$-system (1-2) | 423.65 | 423.6400 | −0.0100 | | | | | |
| $N_2^+$ ($B^2\Sigma^+_u$-$X^2\Sigma^+_g$) $1^-$-system (0-1) | 427.785 | 427.7700 | −0.0150 | | | | | |
| $N_2$ ($C^3\Pi_u$-$B^3\Pi_g$) $2^+$-system (3-8) | 441.67 | 441.6200 | −0.0500 | | | | | |
| Au I $5d^9(^2D_{5/2})6s6p$ $^24^o_{7/2}$ - $5d^9(^2D_{5/2})6s7s$ $10_{7/2}$ | 448.8263 | 448.7500 | −0.0763 | 45537.195 | 67811.329 | 8 | 8 | |
| $N_2^+$ ($B^2\Sigma^+_u$-$X^2\Sigma^+_g$) $1^-$-system (1-3) | 465.1 | 465.1300 | 0.0300 | | | | | |
| $N_2^+$ ($B^2\Sigma^+_u$-$X^2\Sigma^+_g$) $1^-$-system (0-2) | 470.9 | 470.8400 | −0.0600 | | | | | |
| Na I 3s $^2S_{1/2}$-3p $^2P^o_{3/2}$ | 588.99 | 588.995 | 0.0050 | | | | | |
| H I 2p $^2P_{3/2}$-3d $^2D_{5/2}$ | 656.2852 | 655.8447 | −0.4405 | 82259.287 | 97492.357 | 4 | 6 | 6.47E+7 |
| N I 3s $^4P_{5/2}$-3p $^4S_{3/2}$ | 746.8312 | 746.8815 | 0.0503 | 83364.62 | 96750.84 | 6 | 4 | 1.93E+7 |
| $N_2$ ($B^3\Pi_g$-$A^3\Sigma^-_u$) $1^+$-system | 750 | 749.9618 | −0.0382 | | | | | |
| O I 3s $^5S_2$-3p$^5P_3$ | 777.1944 | 776.8659 | −0.3285 | 73768.2 | 86631.454 | 5 | 7 | 3.69E+7 |
| O I 3s $^3S_1$-3p $^3P_2$ | 844.6359 | 844.2905 | −0.3454 | 76794.978 | 88631.146 | 3 | 5 | 3.22E+7 |
| N I 3s $^4P_{5/2}$-3p $^4D_{7/2}$ | 868.0282 | 868.2219 | 0.1937 | 83364.62 | 94881.82 | 6 | 8 | 2.46E+7 |
| O I 3p $^5P_3$-3d $^5D_4$ | 926.6006 | 926.3226 | −0.2780 | 86631.454 | 97420.63 | 7 | 9 | 4.45E+7 |

A variety of species associated with the gold metallic electrode 1 are identified in Table 2d. These species include, for example, gold from the electrodes 1, as well as common species including, NO, OH, $N_2$, etc. It is interesting to note that some species' existence and/or intensity (e.g., amount) is a function of location within the adjustable plasma. Accordingly, this suggests that various species can be caused to occur as a function of a variety of processing conditions (e.g., power, location, composition of electrode 1, etc.) of the invention.

Examples 8-10

Manufacturing Gold-Based Nanocrystals Nanocrystal Suspensions GB-018, GB-019 and GB-020

In general, each of Examples 8-10 utilize certain embodiments of the invention associated with the apparatuses generally shown in FIGS. 17a, 18a, 19b and 22a (e.g., a tapered trough member 30b). Specific differences in processing and apparatus will be apparent in each Example. The trough members 30a and 30b were made from ⅛" (about 3 mm) thick plexiglass, and ¼" (about 6 mm) thick polycarbonate, respectively. The support structure 34 was also made from plexiglass which was about ¼" thick (about 6-7 mm thick). The cross-sectional shape of the trough member 30a shown in FIG. 18a corresponds to that shape shown in FIG. 10b (i.e., a truncated "V"). The base portion "R" of the truncated "V" measured about 0.5" (about 1 cm), and each side portion "S", "S'" measured about 1.5" (about 3.75 cm). The distance "M" separating the side portions "S", "S'" of the V-shaped trough member 30a was about 2¼"-2⁵⁄₁₆" (about 5.9 cm) (measured from inside to inside). The thickness of each portion also measured about ⅛" (about 3 mm) thick. The longitudinal length "$L_T$" (refer to FIG. 11a) of the V-shaped trough member 30a measured about 3 feet (about 1 meter) long from point 31 to point 32.

Purified water (discussed elsewhere herein) was mixed with $NaHCO_3$ in a range of about 0.396 to 0.528 g/L of $NaHCO_3$ and was used as the liquid 3 input into trough member 30a. While this range of $NaHCO_3$ utilized was effective, it should not be viewed as limiting the metes and bounds of the invention. The depth "d" (refer to FIG. 10b) of the water 3 in the V-shaped trough member 30a was about ⁷⁄₁₆" to about ½" (about 11 mm to about 13 mm) at various points along the trough member 30a. The depth "d" was partially controlled through use of the dam 80 (shown in FIG. 18a). Specifically, the dam 80 was provided near the end 32 and assisted in creating the depth "d" (shown in FIG. 10b) to be about ⅞"-½" (about 11-13 mm) in depth. The height "j" of the dam 80 measured about ¼" (about 6 mm) and the longitudinal length "k" measured about ½" (about 13 mm). The width (not shown) was completely across the bottom dimension "R" of the trough member 30a. Accordingly, the total volume of water 3 in the V-shaped trough member 30a during operation thereof was about 6.4 $in^3$ (about 105 ml).

The rate of flow of the water 3 into the trough member 30a ranged from about 150 ml/minute to at least 280 ml/minute. Such flow of water 3 was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30a by a flow diffusion means located therein. The flow diffusion means tended to minimize disturbance and bubbles in water 3 introduced into the trough member 30a as well as any pulsing condition generated by the peristaltic pump 40. In this regard, a small reservoir served as the diffusion means and was provided at a point vertically above the end 31 of the trough member 30a such that when the reservoir overflowed, a relatively steady flow of water 3 into the end 31 of the V-shaped trough member 30a occurred.

There were 5 electrode sets used in Examples 8-10 and one electrode set was a single electrode set 1a/5a located in the trough member 30a. The plasma 4 from electrode 1a in trough member 30a was created with an electrode 1 similar in shape to that shown in FIG. 5e, and weighed about 9.2 grams. This electrode was 99.95% pure gold. The other electrode 5a comprised a right-triangular shaped platinum plate measuring about 14 mm×23 mm×27 mm and about 1 mm thick and having about 9 mm submerged in the liquid 3'. The AC transformer used to create the plasma 4 was that transformer 60 shown in FIG. 16d and discussed elsewhere herein. AC transformers 50 (discussed elsewhere herein) were connected to the other electrode sets 5/5. All other pertinent run conditions are shown in Tables 3a, 3b and 3c.

The output of the processing-enhanced, conditioned water 3' was collected into a reservoir 41 and subsequently pumped by another pump 40' into a second trough member 30b, at substantially the same rate as pump 40 (e.g., there was minimal evaporation in trough member 30a). The second trough member 30b shown in FIG. 22a was tapered and measured about 3.75 inches high, about 3.75 inches wide at the end 32 thereof, and about 1 inch wide at the end 31 thereof, thus forming a tapered shape. This trough member 30b contained about 1450 ml of liquid 3" therein which was about 2.5 inches deep. Each of four electrode sets 5b, 5b'-5e, 5e' comprised 99.95% pure gold wire which measured about 5 inches (about 13 cm) in length, and about 0.5 mm in diameter in Examples 8 and 9, and about 1.0 mm in diameter in Example 10. In each of Examples 8-10, approximately 4.25 inches (about 11 cm) of the wire was submerged within the water 3", which had a depth of about 2.5 inches (about 6 cm). Each electrode set 5a, 5a'-5d, 5d' was shaped like a "J", as shown in FIG. 17a. The distance "g" shown in FIG. 17a measured about 1-8 mm.

Figure 19B:
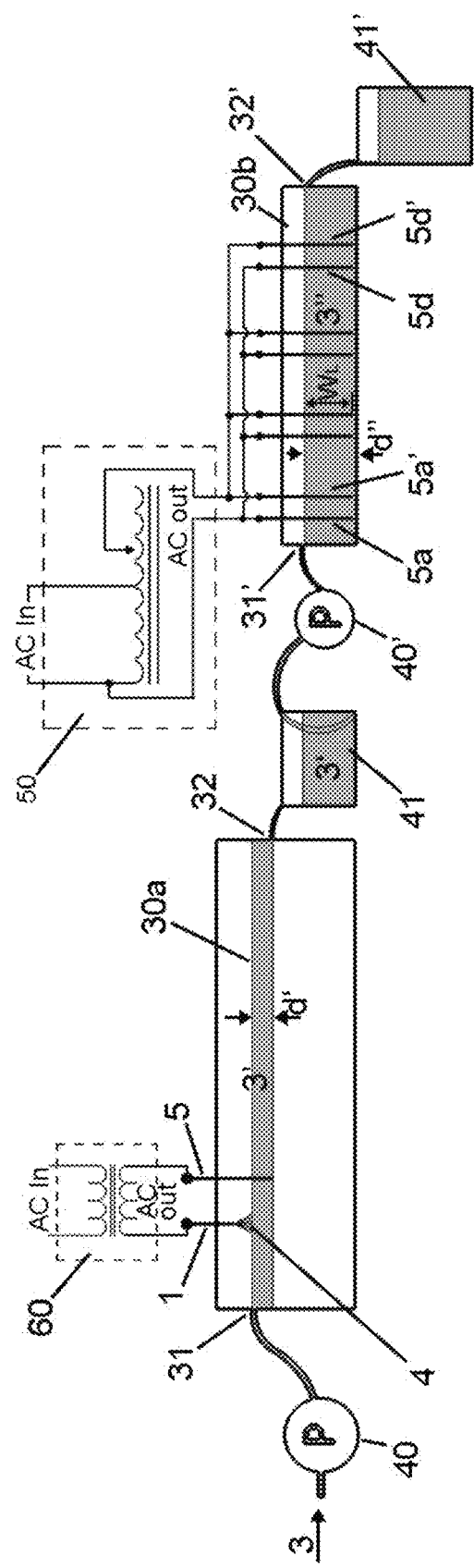

With regard to FIGS. 19b and 22a, 4 separate electrode sets (Set 2, Set 3, Set 4 and Set 5) were attached to a single transformer device 50. Specifically, transformer 50 was the same transformer used in Examples 5-7, but was electrically connected to each electrode set according to the wiring diagram shown in FIG. 19b. In contrast, this wiring configuration was different than that used in Examples 5-7, discussed above, only a single transformer 50 was required due to the lower amperage requirements (e.g., less wire was in contact with the liquid 3) of this inventive trough 30b design.

Each of Tables 3a-3c contains processing information relative to each of the 4 electrode sets by "Set #". Each electrode of the 4 electrode sets in trough 30b was set to operate at a specific target voltage. Actual operating voltages of about 255 volts, as listed in each of Tables 3a-3c, were applied to the four electrode sets. The distance "c-c" (with reference to FIG. 14) from the centerline of each electrode set to the adjacent electrode set is also represented. Further, the distance "x" associated with the electrode 1 utilized in trough 30a is also reported. For the electrode 5's, no distance "x" is reported. Other relevant parameters are reported in each of Tables 3a-3c.

All materials for the electrodes 1/5 were obtained from ESPI having an address of 1050 Benson Way, Ashland, Oreg. 97520.

The water 3 used in Examples 8-10 was produced by a Reverse Osmosis process and deionization process and was mixed with the $NaHCO_3$ processing-enhancer and together was input into the trough member 30a. In essence, Reverse Osmosis (RO) is a pressure driven membrane separation process that separates species that are dissolved and/or suspended substances from the ground water. It is called "reverse" osmosis because pressure is applied to reverse the natural flow of osmosis (which seeks to balance the concentration of materials on both sides of the membrane). The applied pressure forces the water through the membrane leaving the contaminants on one side of the membrane and the purified water on the other. The reverse osmosis membrane utilized several thin layers or sheets of film that are bonded together and rolled in a spiral configuration around a plastic tube. (This is also known as a thin film composite or TFC membrane.) In addition to the removal of dissolved species, the RO membrane also separates out suspended materials including microorganisms that may be present in the water. After RO processing a mixed bed deionization filter was used. The total dissolved solvents ("TDS") after both treatments was about 0.2 ppm, as measured by an Accumet® AR20 pH/conductivity meter.

TABLE 3a 0.528 mg/ml of $NaHCO_3$ (Au)

| Run ID: | GB-018 |
| --- | --- |
| Flow Rate: | 280 ml/min |
| Voltage: | 255 V |
| $NaHCO_3$: | 0.528 mg/ml |
| Wire Dia.: | .5 mm |
| Configuration: | J/J |
| PPM: | 2.9 |
| Zeta: | −98.84 |

| Set# | Electrode# | Distance "c-c" in/mm | Distance "x" in/mm | Voltage | cross section |
| --- | --- | --- | --- | --- | --- |
| 1 | 1a | 4.5/114.3* | 0.25 | 750 | V |
|   | 5a |   | N/A | 750 |   |
|   |   | 23/584.2** |   |   |   |
|   |   | 2.5/63.5* |   |   |   |
| 2 | 5b |   | N/A | 255 |   |
|   | 5b' |   | N/A |   |   |
|   |   | 3.5/88.9 |   |   |   |
| 3 | 5c |   | N/A | 255 |   |
|   | 5c' |   | N/A |   |   |
|   |   | 3.5/88.9 |   |   | Tapered 3" Deep |
| 4 | 5d |   | N/A | 255 |   |
|   | 5d' |   | N/A |   |   |
|   |   | 3.5/88.9 |   |   |   |
| 5 | 5e |   | N/A | 255 |   |
|   | 5e' |   | N/A |   |   |
|   |   | 376.2** |   |   |   |
|   |   |   |   | Output Water Temperature | 80 C. |

*Distance from water inlet to center of first electrode set
**Distance from center of last electrode set to water oulet TABLE 3b 0.396 mg/ml of $NaHCO_3$ (Au)

| Run ID: | GB-019 |
| --- | --- |
| Flow Rate: | 150 ml/min |
| Voltage: | 255 V |
| $NaHCO_3$: | 0.396 mg/ml |
| Wire Dia.: | 1 mm |
| Configuration: | J/J |
| PPM: | 23.6 |
| Zeta: | −56.6 |

| Set# | Electrode # | Distance "c-c" in/mm | Distance "x" in/mm | Voltage | cross section |
| --- | --- | --- | --- | --- | --- |
| 1 | 1a | 4.5/114.3* | 0.25/6.35 | 750 | V |
|   | 5a |   | N/A | 750 |   |
|   |   | 23/584.2** |   |   |   |
|   |   | 2.5/63.5* |   |   |   |
| 2 | 5b |   | N/A | 255 |   |
|   | 5b' |   | N/A |   |   |
|   |   | 3.5/88.9 |   |   |   |
| 3 | 5c |   | N/A | 255 |   |
|   | 5c' |   | N/A |   |   |
|   |   | 3.5/88.9 |   |   | Tapered 3" Deep |
| 4 | 5d |   | N/A | 255 |   |
|   | 5d' |   | N/A |   |   |
|   |   | 3.5/88.9 |   |   |   |
| 5 | 5e |   | N/A | 255 |   |
|   | 5e' |   | N/A |   |   |
|   |   | 376.2** |   |   |   |
|   |   |   |   | Output Water Temperature | 97 C. |

*Distance from water inlet to center of first electrode set
**Distance from center of last electrode set to water oulet TABLE 3c 0.396 mg/ml of $NaHCO_3$ (Au)

| Run ID: | GB-020 |
| --- | --- |
| Flow Rate: | 250 ml/min |
| Voltage: | 255 V |
| $NaHCO_3$: | 0.396 mg/ml |
| Wire Dia.: | 1 mm |
| Configuration: | J/J |
| PPM: | 4.9 |
| Zeta: | −58.01 |

| Set# | Electrode# | Distance "c-c" in/mm | Distance "x" in/mm | Voltage | cross section |
| --- | --- | --- | --- | --- | --- |
| 1 | 1a | 4.5/114.3* | 0.25 | 750 | V |
|   | 5a |   | N/A | 750 |   |
|   |   | 23/584.2** |   |   |   |
|   |   | 2.5/63.5* |   |   |   |
| 2 | 5b |   | N/A | 255 |   |
|   | 5b' |   | N/A |   |   |
|   |   | 3.5/88.9 |   |   |   |
| 3 | 5c |   | N/A | 255 |   |
|   | 5c' |   | N/A |   |   |

TABLE 3c-continued 0.396 mg/ml of NaHCO₃ (Au)

| | | 3.5/88.9 | | | Tapered 3" Deep |
|---|---|---|---|---|---|
| 4 | 5d | | N/A | 255 | |
| | 5d' | | N/A | | |
| | | 3.5/88.9 | | | |
| 5 | 5e | | N/A | 255 | |
| | 5e' | | N/A | | |
| | | 376.2** | | | |
| | | | | Output Water Temperature | 86 C. |

Figure 28A:
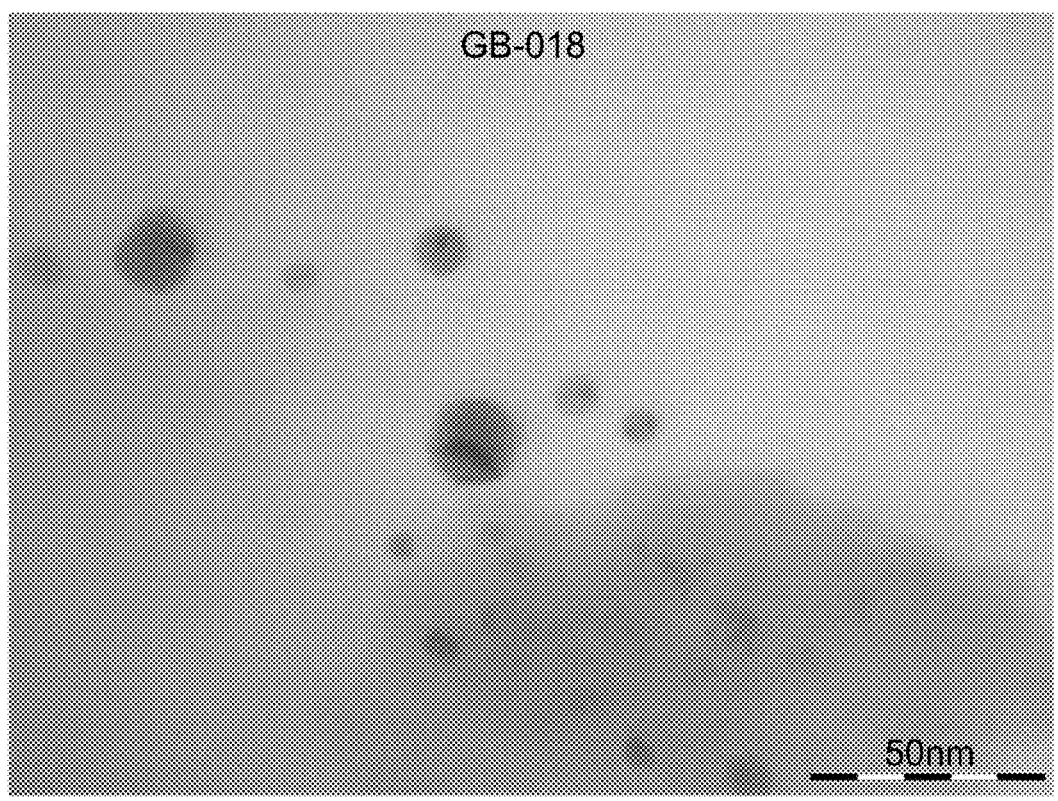
FIG. 28a is a representative TEM photomicrograph of gold nanocrystals from dried solution GB-018 made according to Example 8.
Figure 29A:
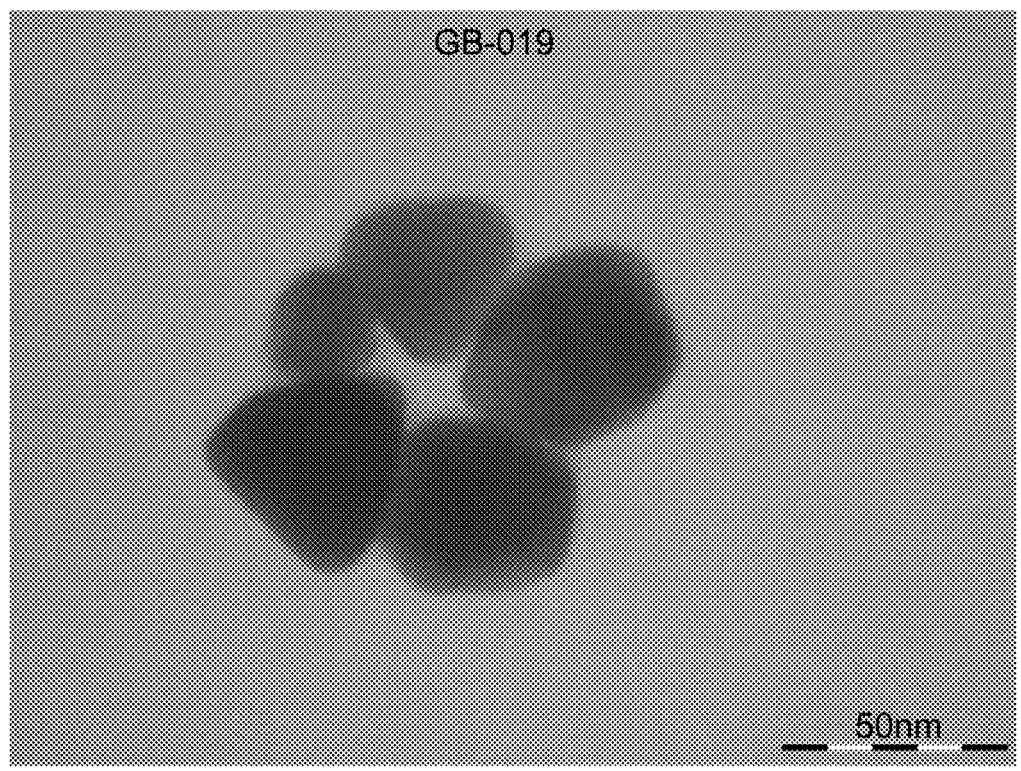
FIG. 29a is a representative TEM photomicrograph of gold nanoparticles from dried solution GB-019 made according to Example 9.
Figure 30A:
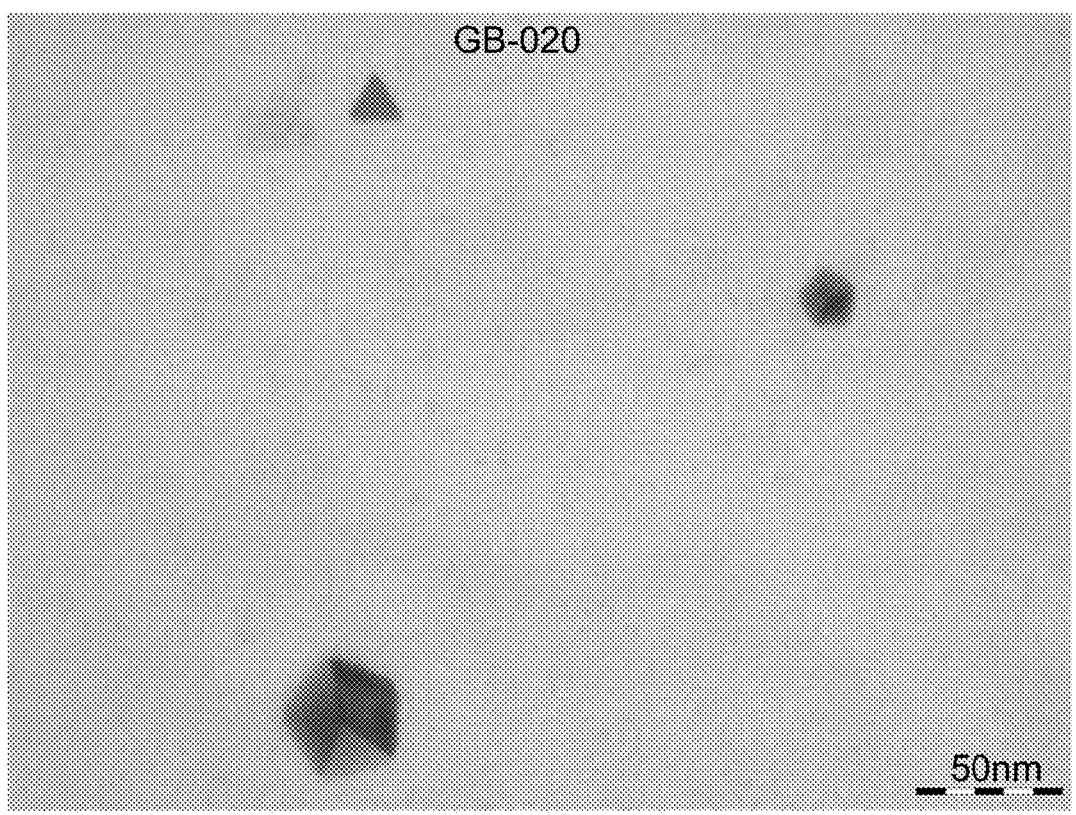
FIG. 30a is a representative TEM photomicrograph of gold nanocrystals from dried solution GB-020 made according to Example 10.

*Distance from water inlet to center of first electrode set
**Distance from center of last electrode set to water oulet FIGS. 28a, 29a and 30a are representative TEM photomicrographs corresponding to dried suspensions GB-018, GB-019 and GB-020, respectively, showing gold crystals grown in each of Examples 8, 9 and 10.

Figure 28B:
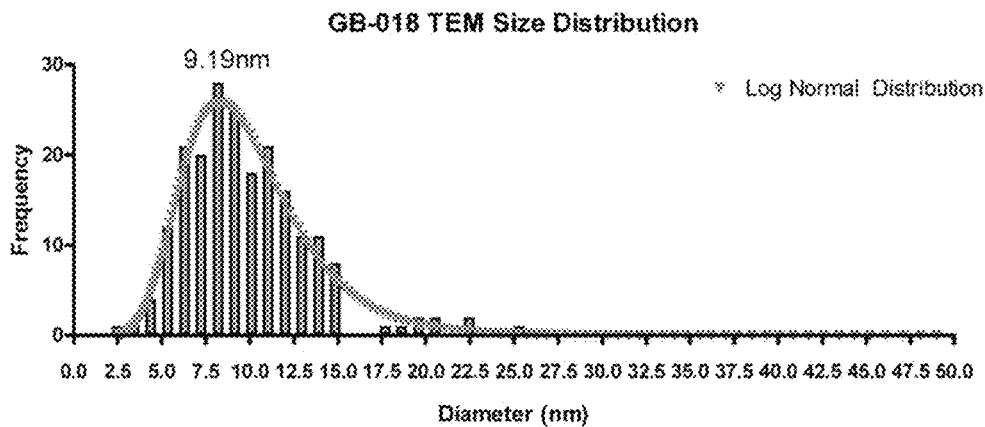
FIG. 28b shows the particle size distribution histogram from TEM measurements for the nanocrystals made according to Example 8.
Figure 29B:
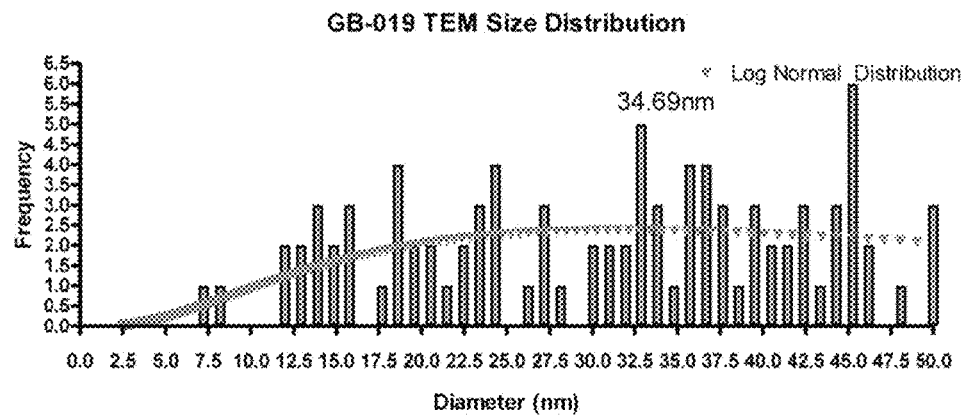
FIG. 29b shows the particle size distribution histogram from TEM measurements for the nanocrystals made according to Example 9.
Figure 30B:
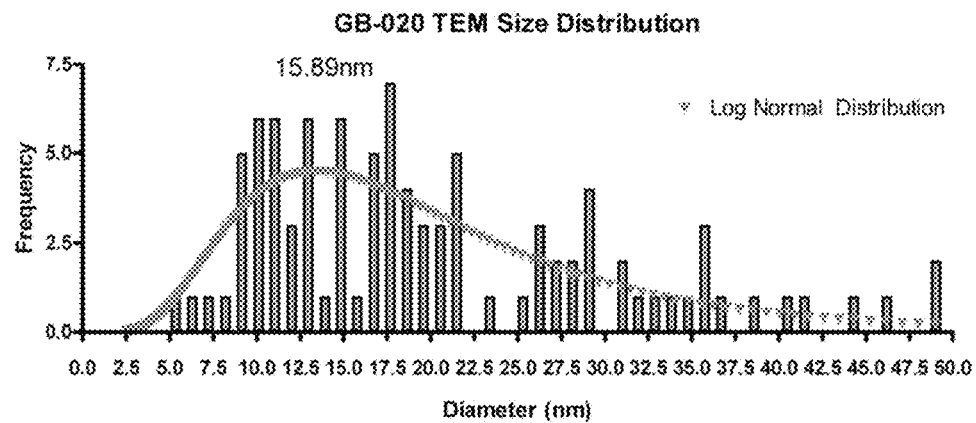
FIG. 30b shows particle size distribution histogram from TEM measurements for the nanocrystals made according to Example 10.

FIGS. 28b, 29b and 30b are particle size distribution histograms measured from the TEM photomicrographs (i.e., using the software described earlier in Examples 5-7) corresponding to dried suspensions taken from Examples 8, 9 and 10, respectively.

Figure 28C:
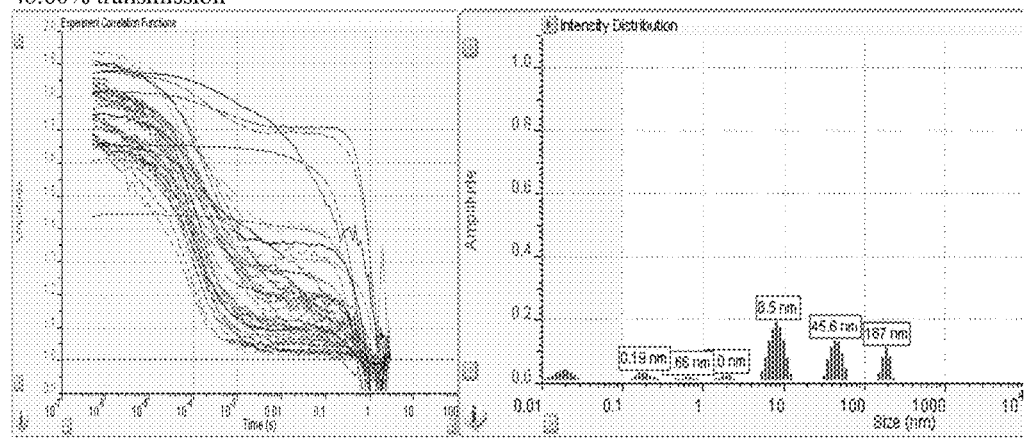
FIG. 28c shows dynamic light scattering data (i.e., hydrodynamic radii) for gold nanocrystals made according to Example 8.
Figure 29C:
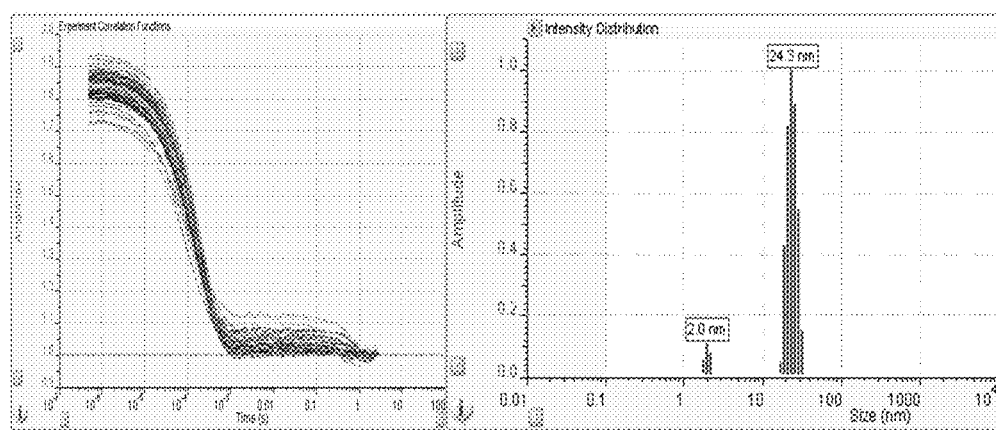
FIG. 29c shows dynamic light scattering data (i.e., hydrodynamic radii) for gold nanocrystals made according to Example 9.
Figure 30C:
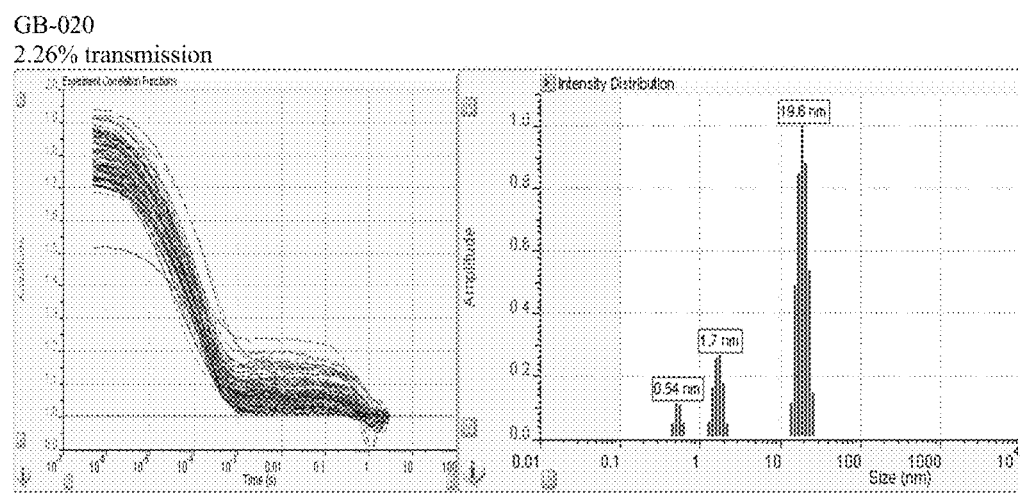
FIG. 30c shows dynamic light scattering data (i.e., hydrodynamic radii) for gold nanocrystals made according to Example 10.

FIGS. 28c, 29c, and 30c show dynamic light scattering data (i.e., hydrodynamic radii) of the gold nanocrystal suspensions made in each of Examples 8, 9 and 10, respectively. Each of these Figures shows the graphical results of dynamic light scattering data sets.

It should be noted that the dynamic light scattering particle size information is different from the TEM measured histograms because dynamic light scattering uses algorithms that assume the crystals are all spheres (which they are not) as well as measures the hydrodynamic radius (e.g., the crystal's influence on the water is also detected and reported in addition to the actual physical radii of the crystals). Accordingly, it is not surprising that there is a difference in the reported crystal sizes between those reported in the TEM histogram data and those reported in the dynamic light scattering data, just as in the other Examples included herein.

Example 11

Figure 24A:
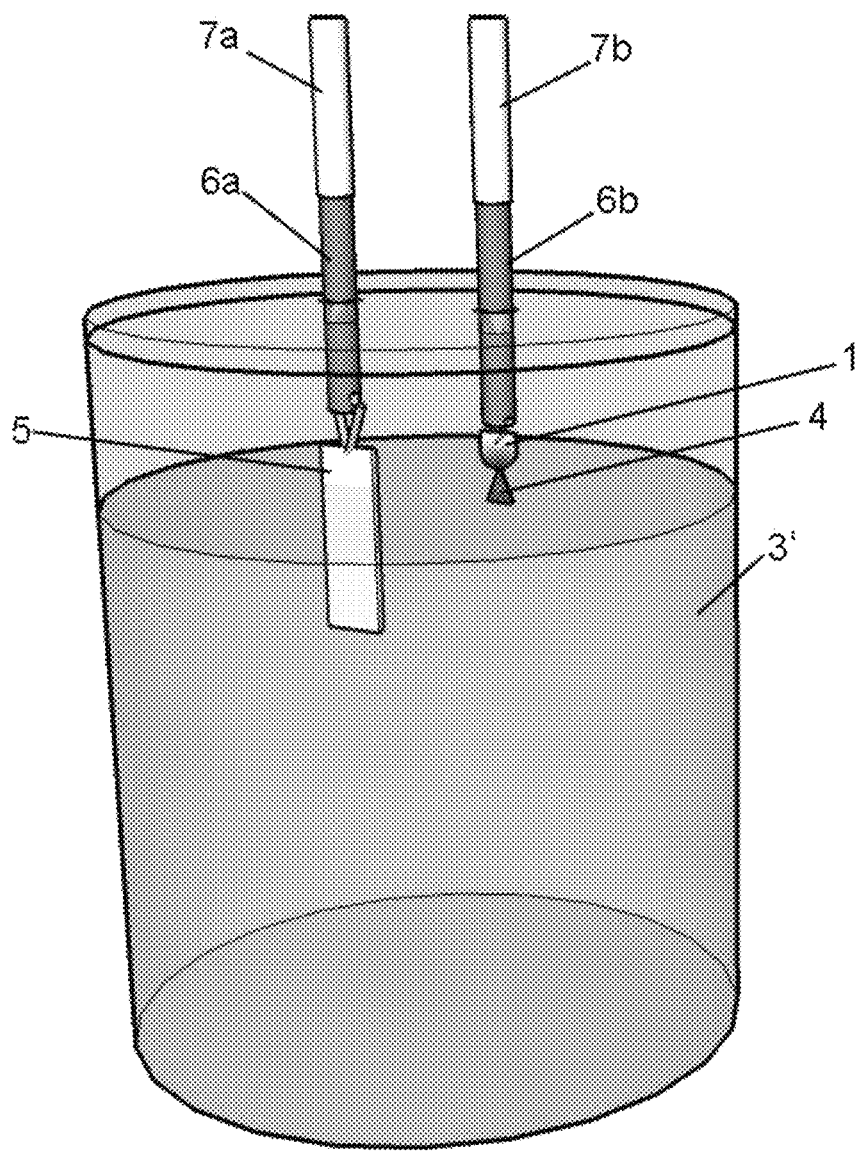
FIG. 24a shows a schematic of an apparatus used in a batch method whereby in a first step, a plasma 4 is created to condition a fluid 3.
Figure 24B:
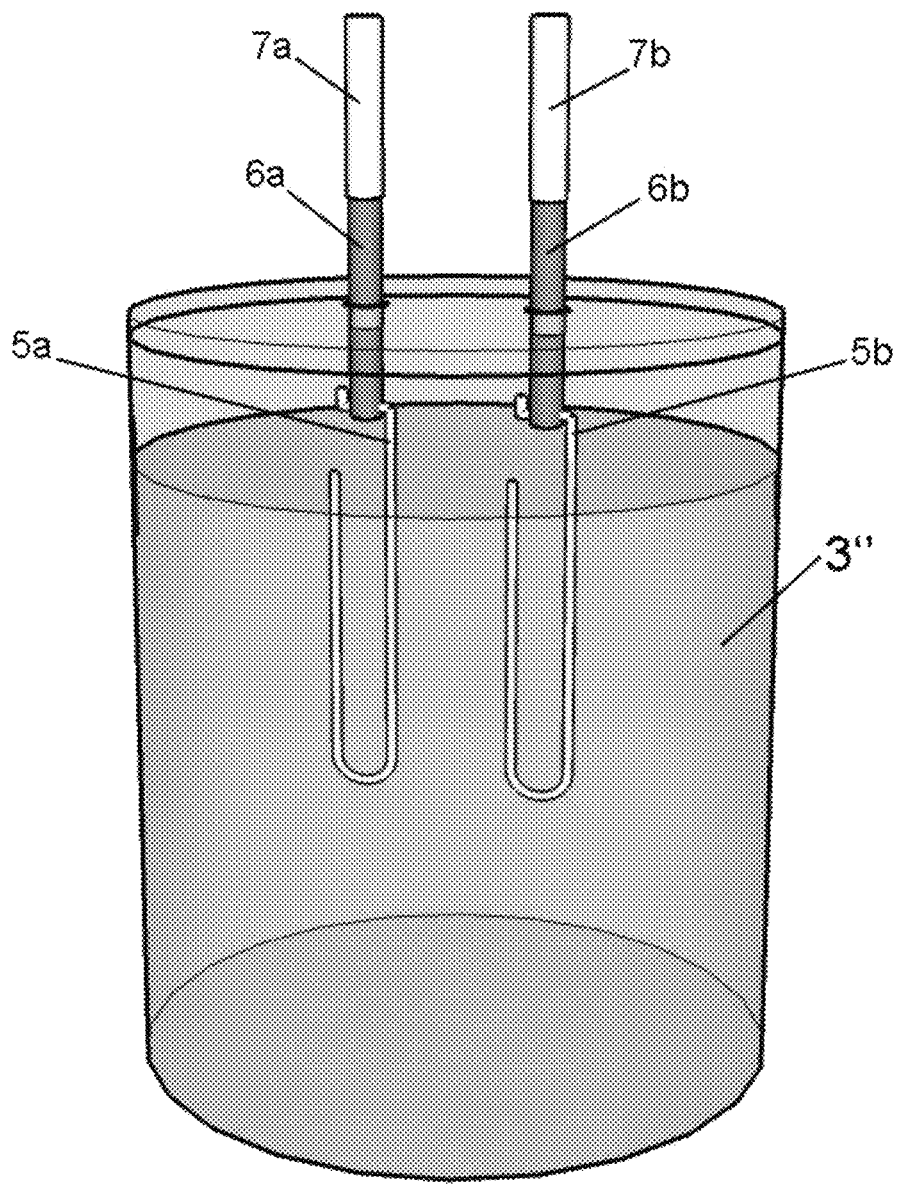
FIGS. 24b and 24c show a schematic of an apparatus used in a batch method utilizing wires 5a and 5b to make nanocrystals in suspension (e.g., a colloid) in association with the apparatus shown in FIG. 24a and as discussed in Examples herein.

Manufacturing Gold-Based Nanoparticles/Nanoparticle Solutions or Colloids IAC-202-7 by a Batch Process This Example utilizes a batch process according to the present invention. FIG. 24a shows the apparatus used to condition the liquid 3. Once conditioned, the liquid 3' was processed in the apparatus shown in FIG. 24b.

Figure 24C:
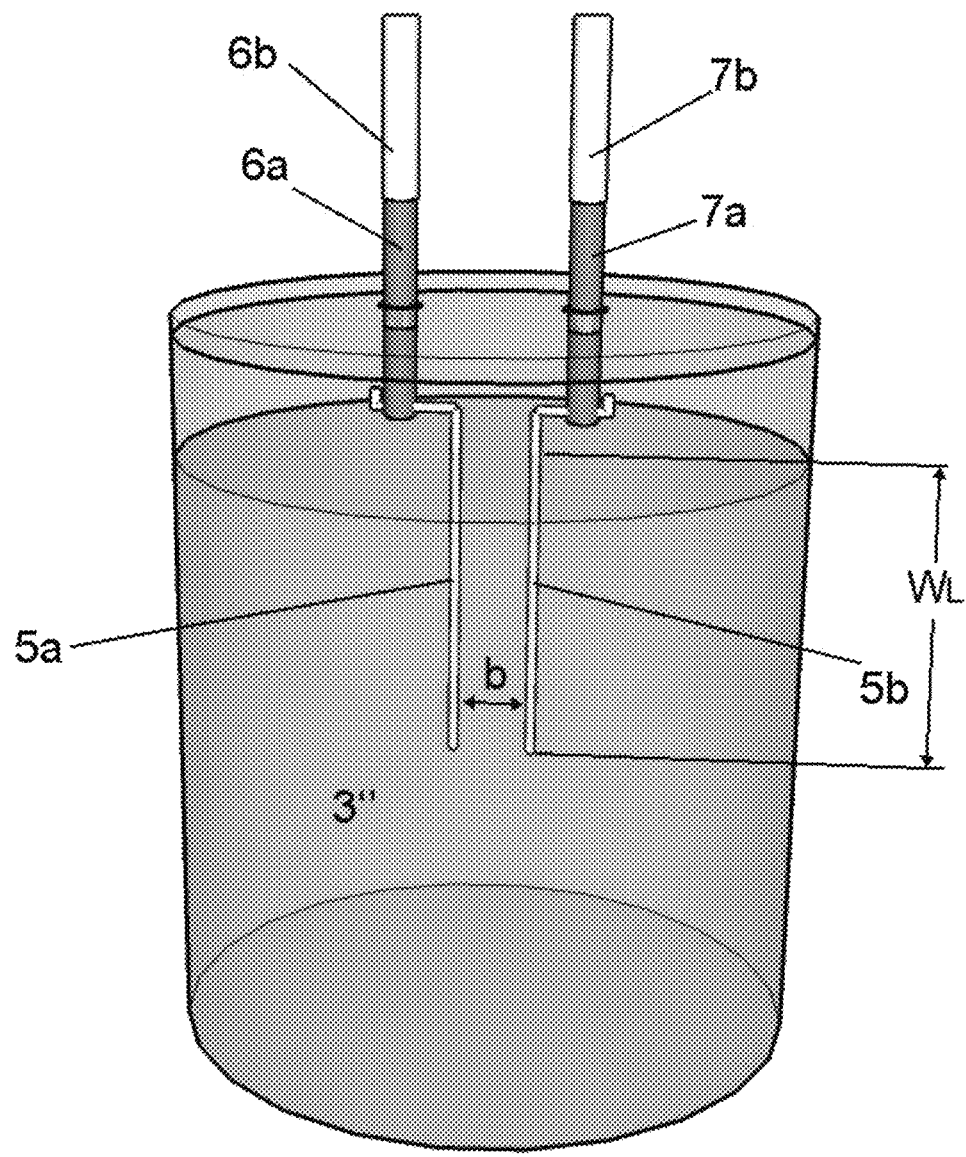

Table 4a shows a matrix where the amount of processing enhancer baking soda (i.e., NaHCO₃) varies from about 1 gram/gallon to about 2 grams/gallon (i.e., about 0.264 g/L to about 0.528 g/L); and the dwell time reflected in Table 4a in the apparatus of FIG. 24a (i.e., the amount of time that the water 3 with processing enhancer was exposed to the plasma 4) was varied from about 20 minutes to about 60 minutes, prior to subsequent processing in the apparatus shown in FIG. 24c. The applied voltage for each plasma 4 made by electrode 1 was about 750 volts. This voltage was achieved by a transformer 60 (i.e., the Balanced Mid-Point Referenced Design) discussed elsewhere herein. A second and different transformer was electrically connected to the electrodes 5a/5b shown in FIG. 24c. This transformer was an by AC power source having a voltage range of 0-300V, a frequency range of 47-400 Hz and a maximum power rating of 1 kVA. The applied voltage for each identified run in Tables 4a and 4b was about 250 volts. The current changed as a function of time with minimum and maximum amps reported in Table 4b. All other process variables remained constant.

Accordingly, Table 4a shows that a number of variables (e.g., processing enhancer and predetermined dwell time) influence both the amount or concentration of gold nanocrystals in water, and the size distribution of the gold nanocrystals. In general, as the concentration of the processing enhancer increases from about 1 g/gallon (0.264 g/L) to about 2 g/gallon (0.528 g/L), the concentration (i.e., "ppm") more or less increases under a given set of processing conditions. However, in some cases the particle size distribution ("psd") unfavorably increases such that the formed nanocrystals were no longer stable and they "settled", as a function of time (e.g., an unstable suspension was made). These settling conditions were not immediate thus suggesting that this suspension of nanocrystals in water could be processed immediately into a useful product, such as, for example, a gel or cream. This Example shows clearly various important effects of multiple processing variables which can be translated, at least directionally, to the inventive continuous processes disclosed elsewhere herein. These data are illustrative and should not be viewed as limiting the metes and bounds of the present invention. Moreover, these illustrative data should provide an artisan of ordinary skill with excellent operational directions to pursue.

As a specific example, Table 4c shows that a first electrode Set #1 (i.e., FIG. 24a) was operating at a voltage of about 750 volts, to form the plasma 4. This is similar to the other plasmas 4 reported elsewhere herein. However, electrode Set #2 (i.e., FIG. 24c) was powered by the hy-AC source discussed above.

TABLE 4a

| | | | Pretreatment Dwell (minutes) | | | | | | | | | | | |
|---|---|---|---|---|---|---|---|---|---|---|---|---|---|---|
| | | | 20 | | | | 40 | | | | 60 | | | |
| | | | 1AC-201 | | 1AC-202 | | 1AC-201 | | 1AC-202 | | 1AC-201 | | 1AC-202 | |
| NaHCO₃ (mg/ml) | .264 | ppm | 1AC- | 11.8 | 1AC- | 11.1 | 1AC- | 13.5 | 1AC- | 11.4 | 1AC- | 14.3 | 1AC- | 12.2 |
| | | psd | 201-9 | 18.4 | 202-1 | 19.1 | 201-8 | 19.5 | 202-2 | 18.4 | 201-7 | 16.8 | 202-3 | 19.6 |
| | .396 | ppm | 1AC- | 20.1 | 1AC- | 16.1 | 1AC- | 21.4 | 1AC- | settled | 1AC- | 23.3 | 1AC- | settled |
| | | psd | 201-6 | 21.4 | 202-7 | 32.3 | 201-5 | 126 | 202-8 | 84.8 | 201-4 | 36.3 | 202-9 | 23.8 |
| | .528 | ppm | 1AC- | 27.4 | 1AC- | 23 | 1AC- | 31.1 | 1AC- | 24.9 | 1AC- | settled | 1AC- | settled |
| | | psd | 201-1 | 17.1 | 202-4 | 43.8 | 201-2 | 21.6 | 202-5 | 21.4 | 201-3 | 190 | 202-6 | settled |

TABLE 4b

| | Current | Pretreatment Dwell (minutes) | | | | | | | | | | | |
|---|---|---|---|---|---|---|---|---|---|---|---|---|---|
| | | 20 | | | | 40 | | | | 60 | | | |
| | Amps | 1AC-201 | | 1AC-202 | | 1AC-201 | | 1AC-202 | | 1AC-201 | | 1AC-202 | |
| NaHCO$_3$ (mg/ml) | .264 min | 1AC-201-9 | 0.405 1.1 | 1AC-202-1 | 0.382 1 | 1AC-201-8 | 0.41 1 | 1AC-202-2 | 0.411 1.06 | 1AC-201-7 | 0.432 1 | 1AC-202-3 | 0.461 1.13 |
| | max | | | | | | | | | | | | |
| | .396 min | 1AC-201-6 | 0.554 1.6 | 1AC-202-7 | 0.548 1.35 | 1AC-201-5 | 0.591 1.6 | 1AC-202-8 | 0.598 1.43 | 1AC-201-4 | 0.617 1.6 | 1AC-202-9 | 0.681 1.43 |
| | max | | | | | | | | | | | | |
| | .528 min | 1AC-201-1 | 0.686 1.82 | 1AC-202-4 | 0.735 1.6 | 1AC-201-2 | 0.843 2.06 | 1AC-202-5 | 0.769 2 | 1AC-201-3 | 0.799 2.01 | 1AC-202-6 | 0.865 2.1 |
| | max | | | | | | | | | | | | |

TABLE 4c 1.5 g/Gal of NaHCO$_3$ (Au)

| Run ID: | 1AC-202-7 |
|---|---|
| Pretreatment: | 20 min GZA in 3600 ml |
| Volume: | 800 ml |
| Run time: | 35 minutes |
| Voltage: | 250 V |
| NaHCO$_3$: | 0.396 mg/ml |
| Wire Dia.: | .5 mm |
| Configuration: | J/J |
| PPM: | 16.1 |
| Zeta: | n/a |

| Set# | Electrode# | Distance "x" in/mm | Voltage |
|---|---|---|---|
| 1 | 1a | 0.25/6.35 | 750 |
| | 5a | N/A | 750 |
| 2 | 5b | N/A | 250 |
| | 5b | N/A | |

Figure 31A:
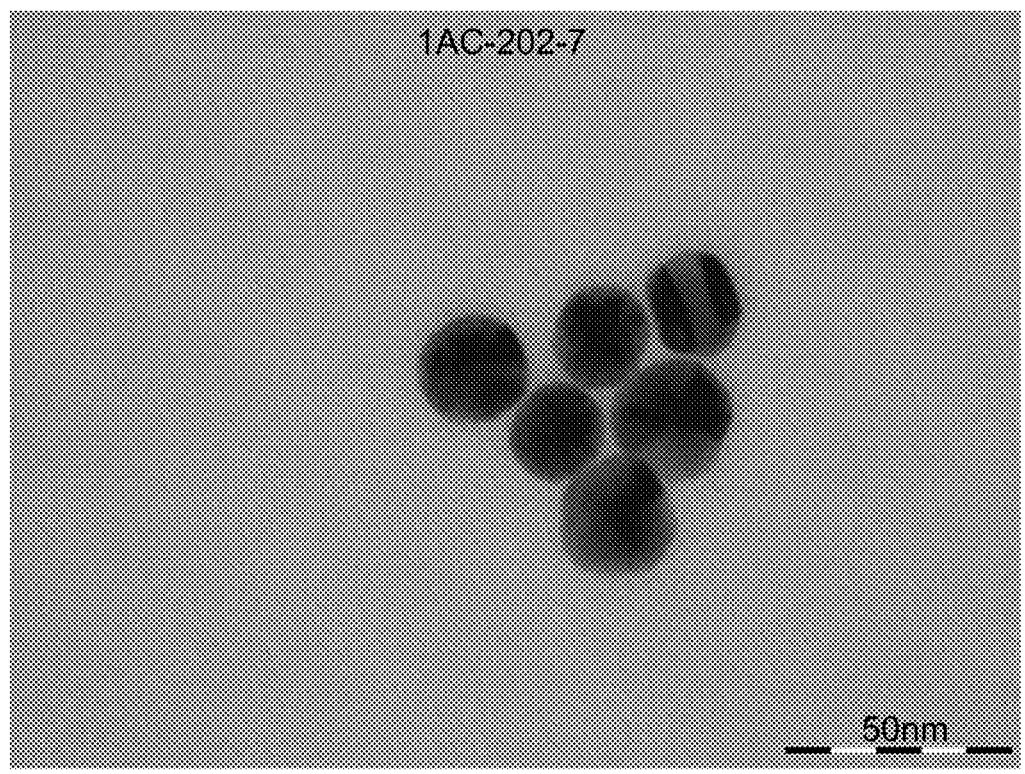
FIG. 31a is a representative TEM photomicrograph of gold nanocrystals from dried solution 1AC-202-7 made according to Example 11.

FIG. 31a shows a representative TEM Photomicrograph of gold crystals, dried from solution, made according to this Example 11.

Figure 31B:
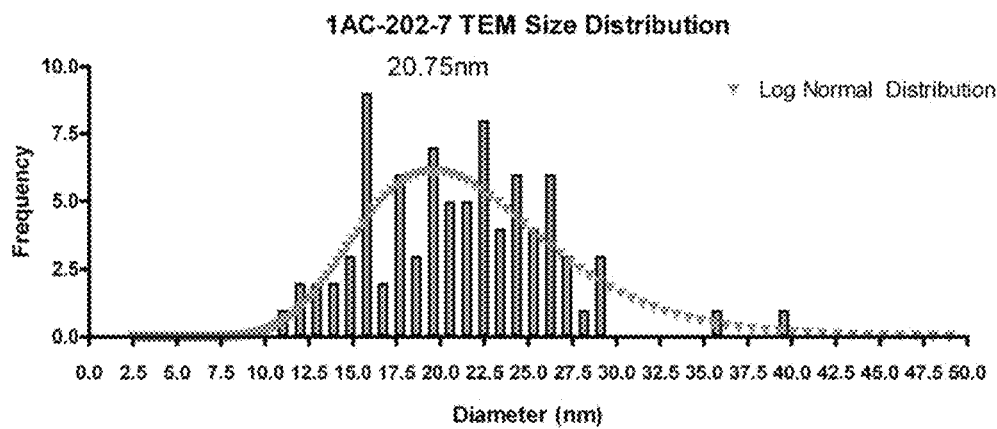
FIG. 31b shows the particle size distribution histogram from TEM measurements for the nanocrystals made according to Example 11.

FIG. 31b shows the particle size distribution histogram based on TEM measurements of the dried gold nanocrystals made according to Example 11.

Figure 31C:
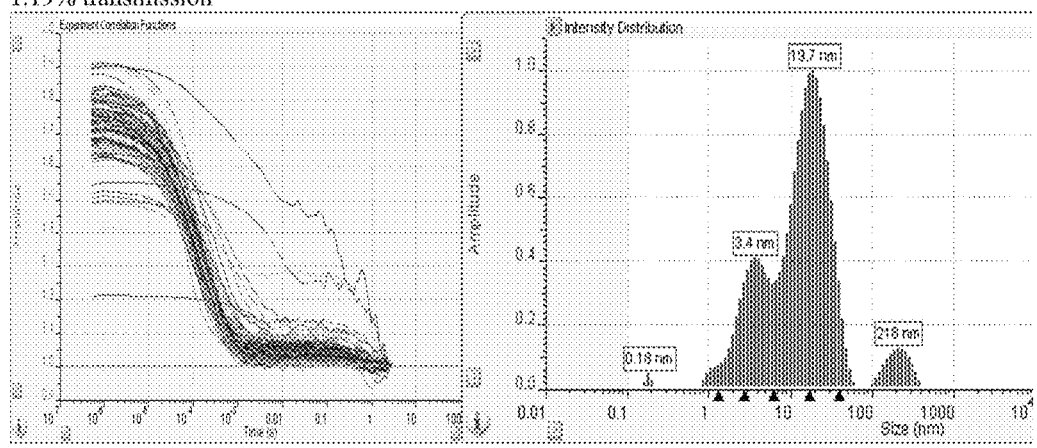
FIG. 31c shows the dynamic light scattering data (i.e., hydrodynamic radii) for gold nanocrystals made according to Example 11.

FIG. 31c shows graphical dynamic light scattering particle size data (i.e., hydrodynamic radii) from this Example 11. Specifically, a representative Viscotek data set is set forth in this Figure, similar to what is reported elsewhere herein.

It should be noted that the dynamic light scattering particle size information is different from the TEM measured histograms because dynamic light scattering uses algorithms that assume the nanocrystals are all spheres (which they are not) as well as measures the hydrodynamic radius (e.g., the nanocrystal's influence on the water is also detected and reported in addition to the actual physical radii of the nanocrystals). Accordingly, it is not surprising that there is a difference in the reported nanocrystals sizes between those reported in the TEM histogram data and those reported in the dynamic light scattering data, just as in the other Examples included herein.

Example 12

Manufacturing Gold-Based Nanoparticles/Nanoparticle Solutions or Colloids IAC-261 by a Batch Process This Example utilizes a batch process according to the present invention. FIG. 24a shows the apparatus used to condition the liquid 3. Once conditioned, the liquid 3' was processed in the apparatus shown in FIG. 24c The amount of processing enhancer baking soda (i.e., NaHCO$_3$) was about 1.5 grams/gallon (i.e., about 0.396 g/L). The amount of time that the water 3 with processing enhancer was exposed to the plasma 4 was about 60 minutes, prior to subsequent processing in the apparatus shown in FIG. 24c.

The applied voltage for each plasma 4 made by electrode 1 was about 750 volts. This voltage was achieved by a transformer 60 (i.e., the Balanced Mid-Point Referenced Design) discussed elsewhere herein.

A second and different transformer was electrically connected to the electrodes 5a/5b shown in FIG. 24c. This transformer was an by AC power source having a voltage range of 0-300V, a frequency range of 47-400 Hz and a maximum power rating of 1 kVA. The applied voltage was about 300 volts. The current changed as a function of time with minimum amps being 0.390 and maximum amps being 0.420 amps over a 60 minute operating time. The diameter of the gold wire electrodes was 1 mm.

Figure 33A:
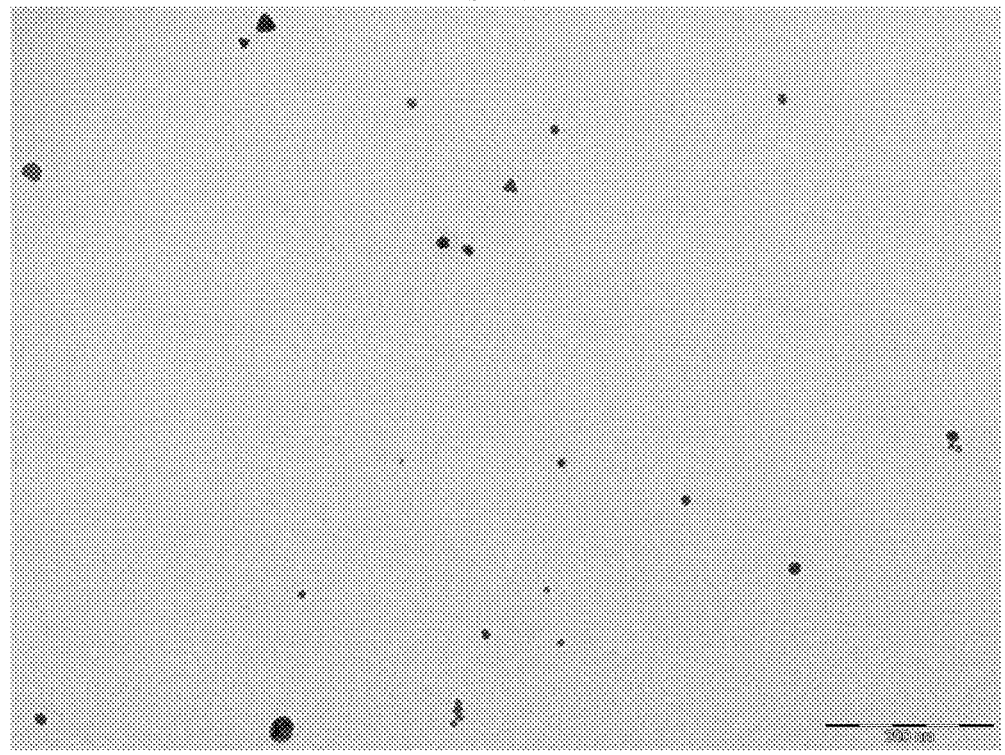
FIG. 33a is a representative TEM photomicrograph of gold nanocrystals from dried solution 1AC-261 made according to Example 12.

The amount of gold nanoparticles produced in the suspension was about 13.7 ppm as measured by the atomic absorption spectroscopy techniques discussed elsewhere herein. The sizes and shapes of the nanoparticles made according to this Example are fully discussed in Table 12 herein FIG. 33a shows a representative TEM Photomicrograph of gold crystals, dried from suspension 1AC-261, made according to this Example 12.

Figure 33B:
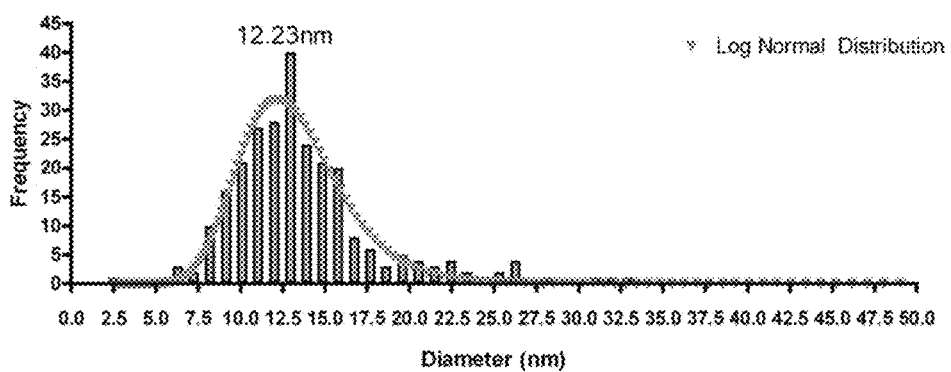
FIG. 33b shows a particle size distribution histogram from TEM measurements for the nanocrystals made according to Example 12.

FIG. 33b shows the particle size distribution histogram based on TEM measurements of the dried gold nanoparticles made according to Example 12.

Example 13

Manufacturing Gold-Based Nanocrystals/Nanocrystal Suspensions GB-154-20 Hz, GB-157-40 Hz, GB-159-60 Hz, GB-161-80 Hz, GB-173-100 Hz and GB-156-300 Hz)

In general, this Example used the same manufacturing set-up used for making GB-134 in Example 16, and for the sake of brevity, the specifics of the trough apparatus used are discussed in detail in that Example. The primary difference in making the suspensions or colloids in this Example is that different sine waveform frequencies from a programmable AC source were used as electrical inputs to the electrodes 5a/5b.

In particular, sine wave AC frequencies as low as 20 Hz and as high as 300 Hz were utilized to make nanocrystal suspensions or colloids, in accordance with the teachings herein. The AC power source 501AC utilized a Chroma 61604 programmable AC source. The applied voltage was 300 volts. The waveform was a sine wave at six different frequencies-20, 40, 60, 80, 100 and 300 Hz. The applied current varied between 4.2 amps and 4.8 amps.

Figure 34A:
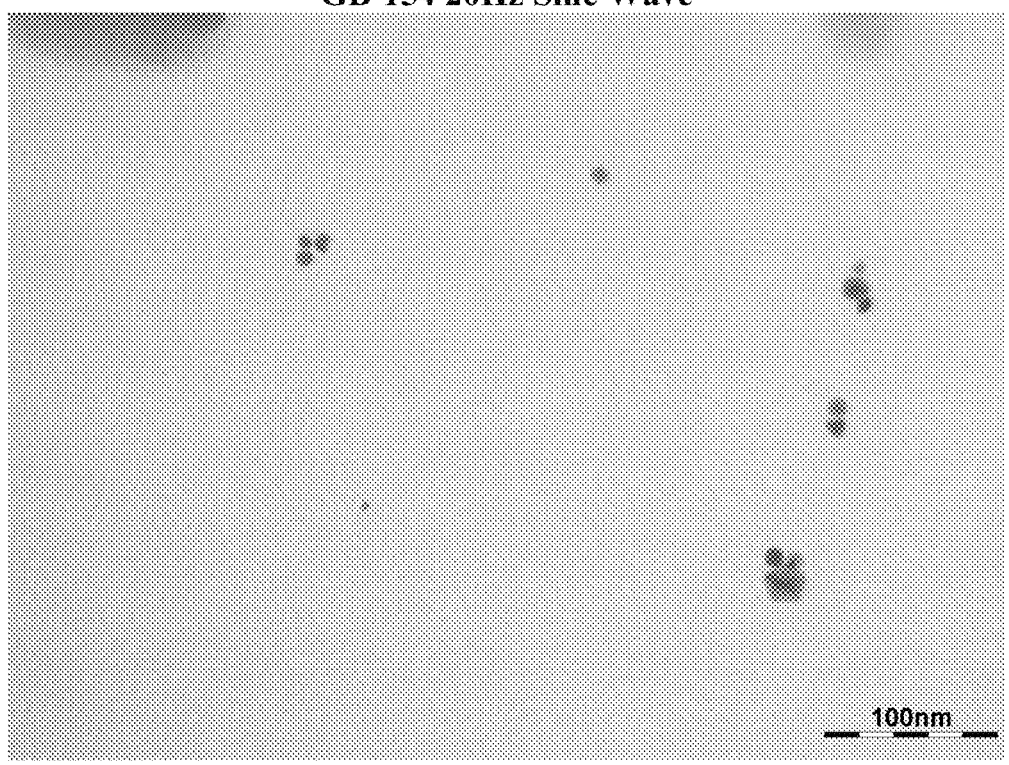
FIG. 34a is a representative TEM photomicrograph of gold nanocrystals from dried solution GB-154 (20 Hz sine wave) made according to Example 13.
Figure 34B:
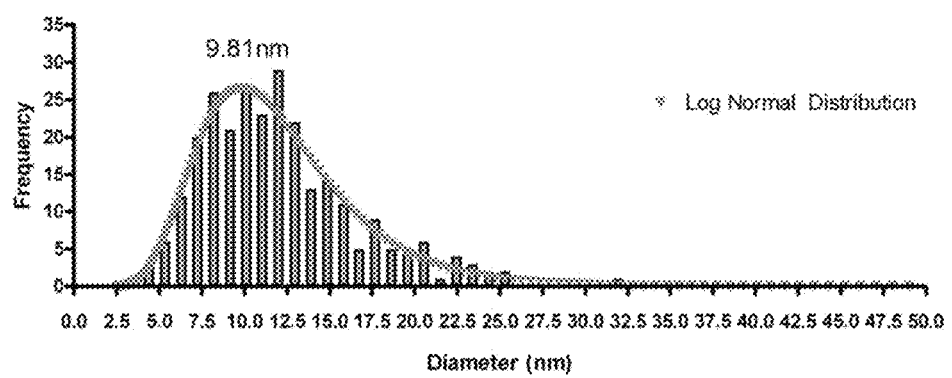
FIG. 34b shows a particle size distribution histogram from TEM measurements for the nanocrystals made according to Example 13.

FIG. 34a shows a representative TEM Photomicrograph of gold nanocrystals, dried from suspension GB-154; and FIG. 34b shows the particle size distribution histogram based on TEM measurements of the dried gold nanocrystals from suspension GB-154.

Figure 35A:
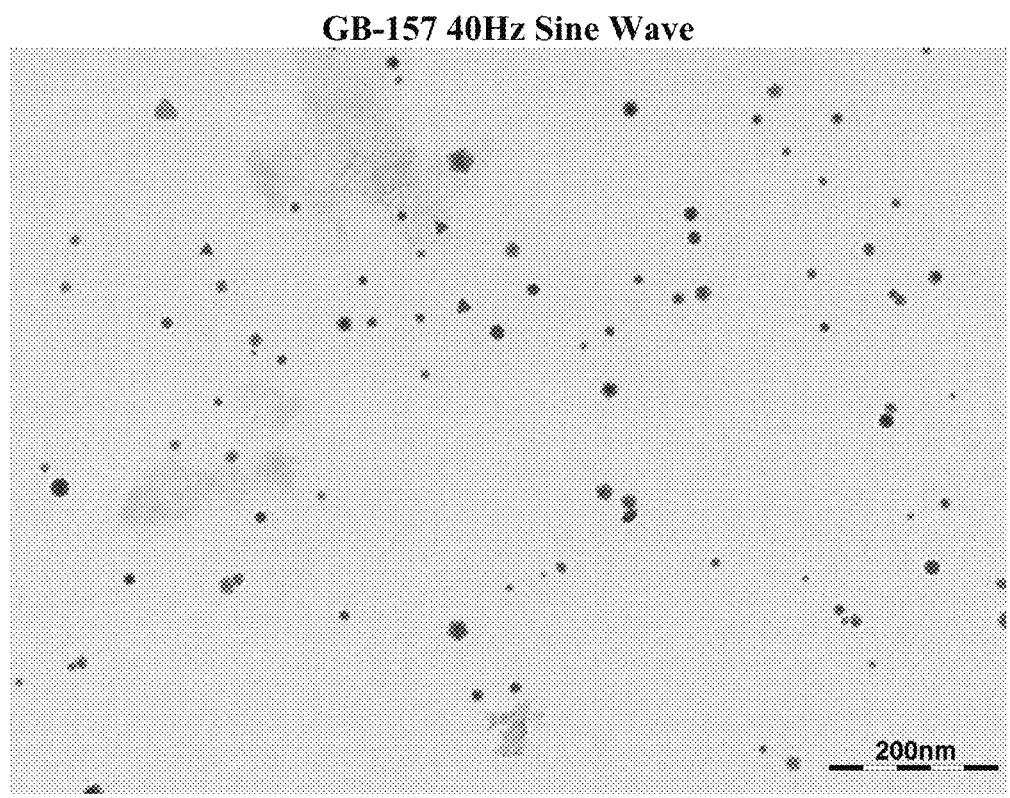
FIG. 35a is a representative TEM photomicrograph of gold nanocrystals from dried solution GB-157 (40 hz sinewave) made according to Example 13.
Figure 35B:
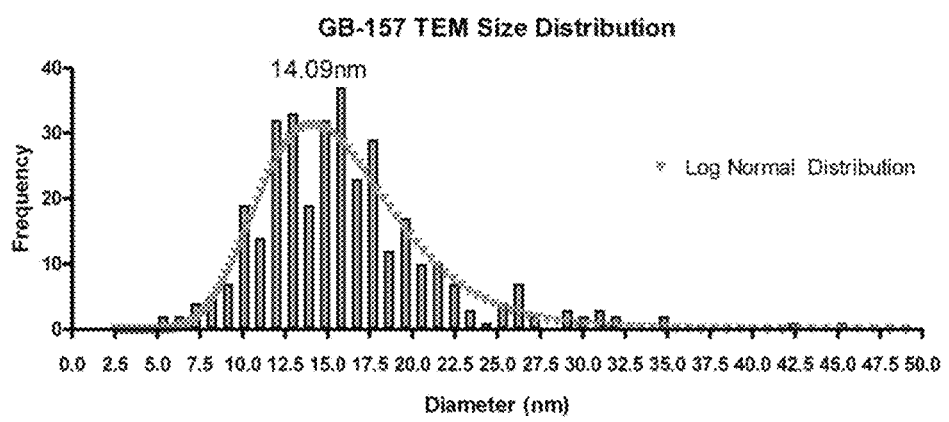
FIG. 35b shows a particle size distribution histogram from TEM measurements for the nanocrystals made according to Example GB-157.

FIG. 35a shows a representative TEM Photomicrograph of gold nanocrystals, dried from suspension GB-157; and FIG. 35b shows the particle size distribution histogram based on TEM measurements of the dried gold nanocrystals from suspension GB-157.

Figure 36A:
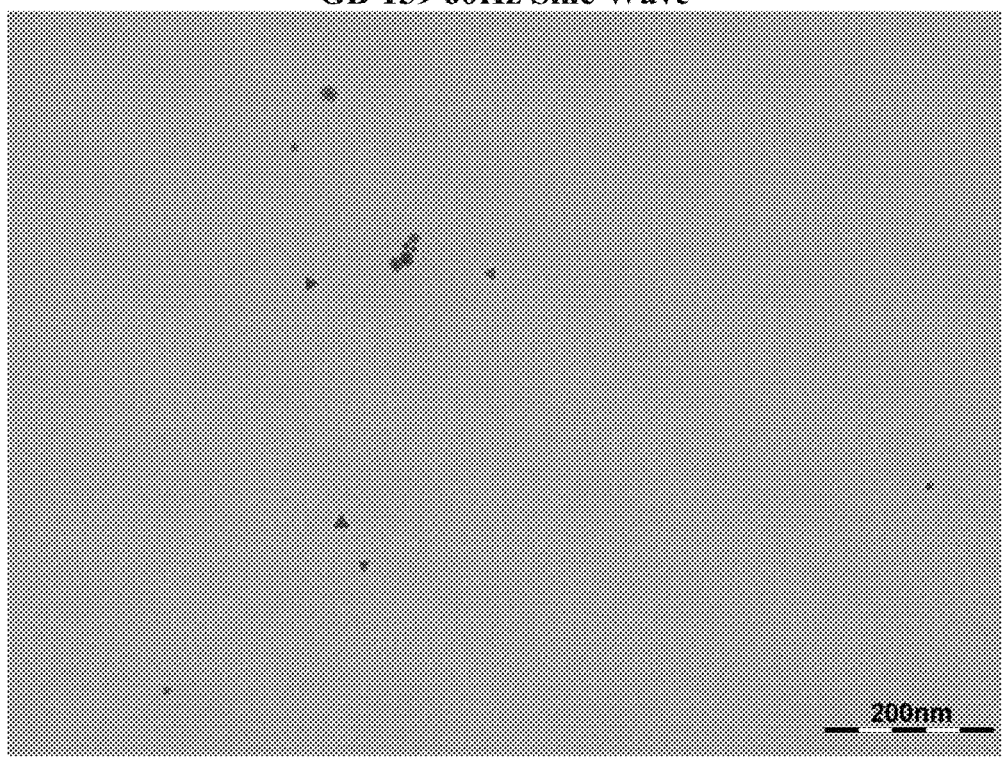
FIG. 36a is a representative TEM photomicrograph of gold nanocrystals from dried solution GB-159 (60 Hz sine wave) made according to Example 13.
Figure 36B:
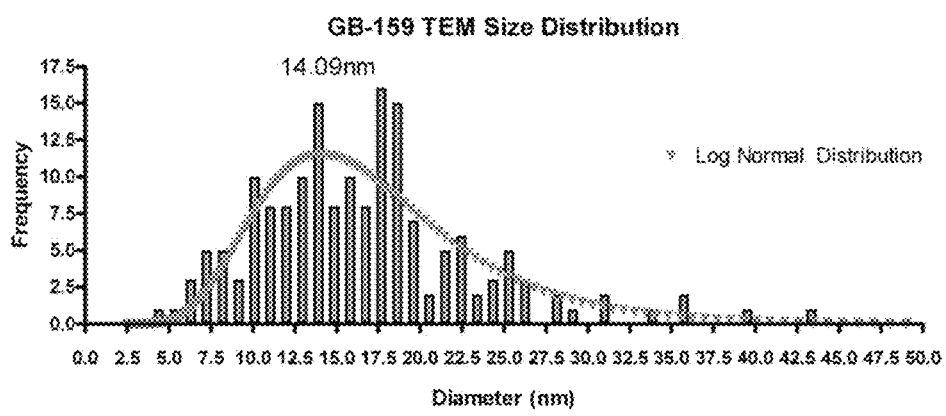
FIG. 36b shows a particle size distribution histogram from TEM measurements for the nanocrystals made according to GB-159.

FIG. 36a shows a representative TEM Photomicrograph of gold nanocrystals, dried from suspension GB-159; and FIG. 36b shows the particle size distribution histogram based on TEM measurements of the dried gold nanocrystals from suspension GB-159.

Figure 37A:
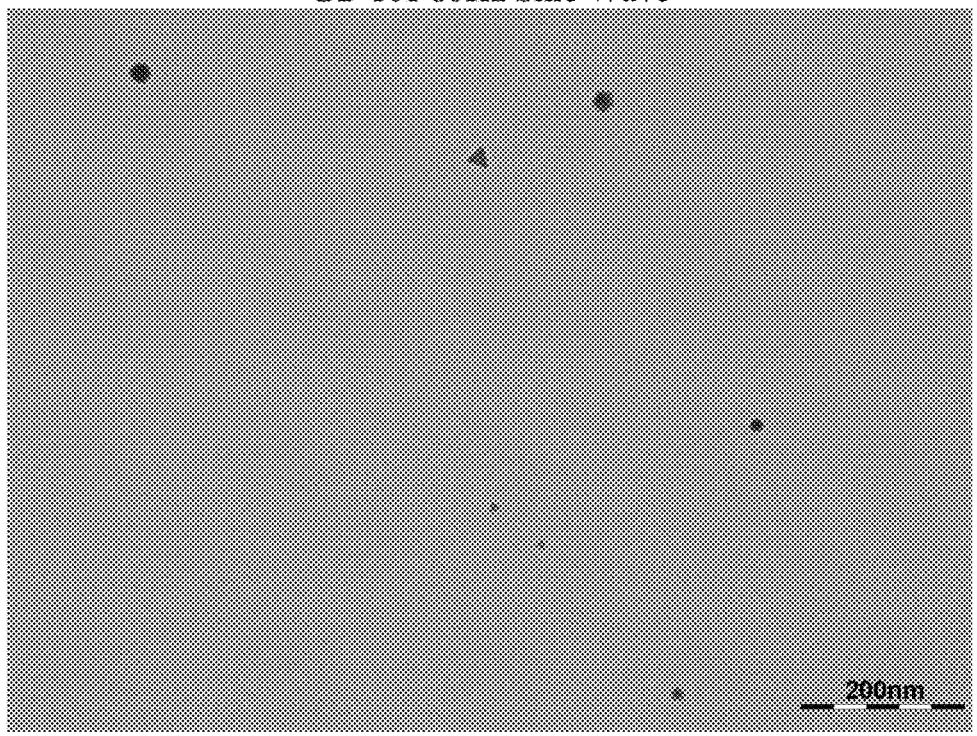
FIG. 37a is a representative TEM photomicrograph of gold nanocrystals from dried solution GB-161 (80 Hz sine wave) made according to Example 13.
Figure 37B:
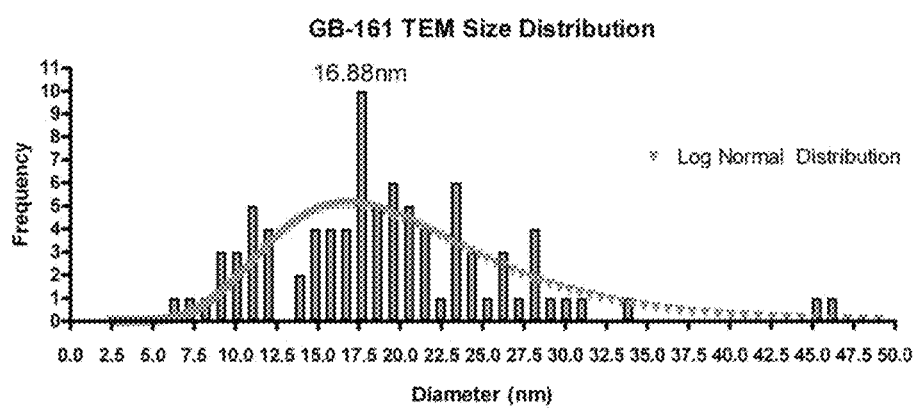
FIG. 37b shows a particle size distribution histogram from TEM measurements for the nanocrystals made according to GB-161.

FIG. 37a shows a representative TEM Photomicrograph of gold nanocrystals, dried from suspension GB-161; and FIG. 37b shows the particle size distribution histogram based on TEM measurements of the dried gold nanocrystals from suspension GB-161.

Figure 38A:
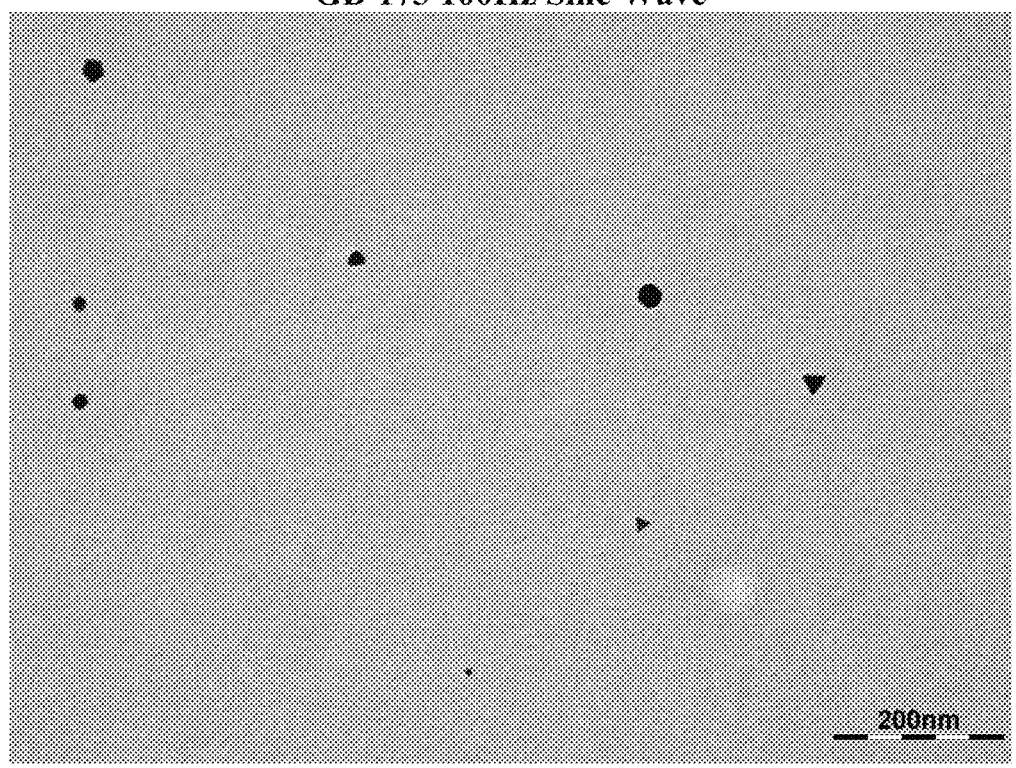
FIG. 38a is a representative TEM photomicrograph of gold nanocrystals from dried solution GB-173 (100 Hz sine wave) made according to Example 13.
Figure 38B:
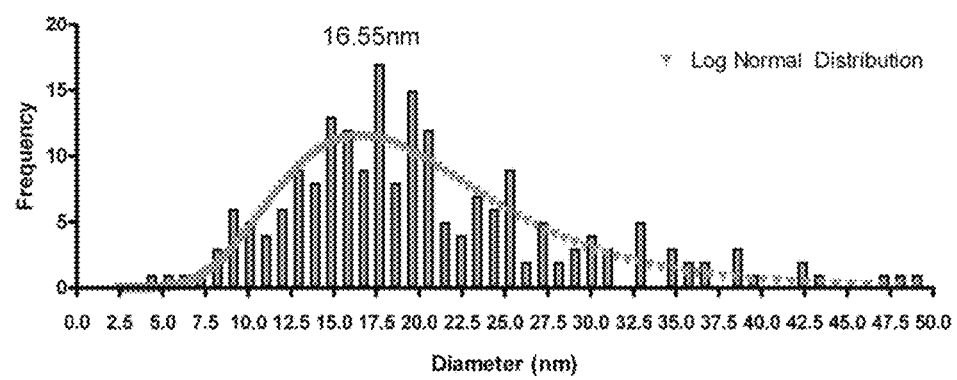
FIG. 38b shows a particle size distribution histogram from TEM measurements for the nanocrystals made according to GB-173.

FIG. 38a shows a representative TEM Photomicrograph of gold nanocrystals, dried from suspension GB-173; and FIG. 38b shows the particle size distribution histogram based on TEM measurements of the dried gold nanocrystals from suspension GB-173.

Figure 39A:
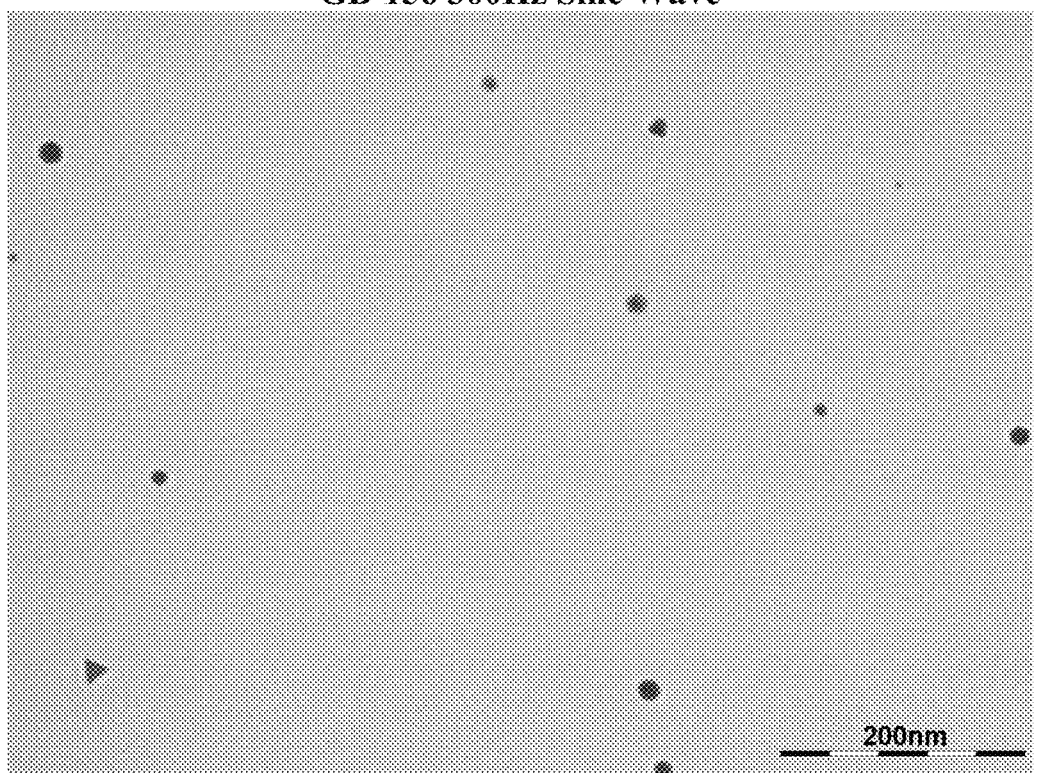
FIG. 39a is a representative TEM photomicrograph of gold nanocrystals from dried solution GB-156 (300 Hz sine wave) made according to Example 13.
Figure 39B:
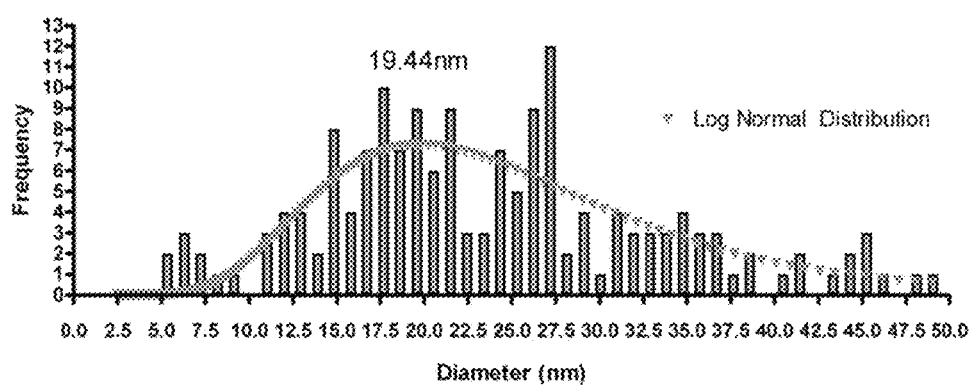
FIG. 39b shows a particle size distribution histogram from TEM measurements for the nanocrystals made according to GB-156.
Figure 40:
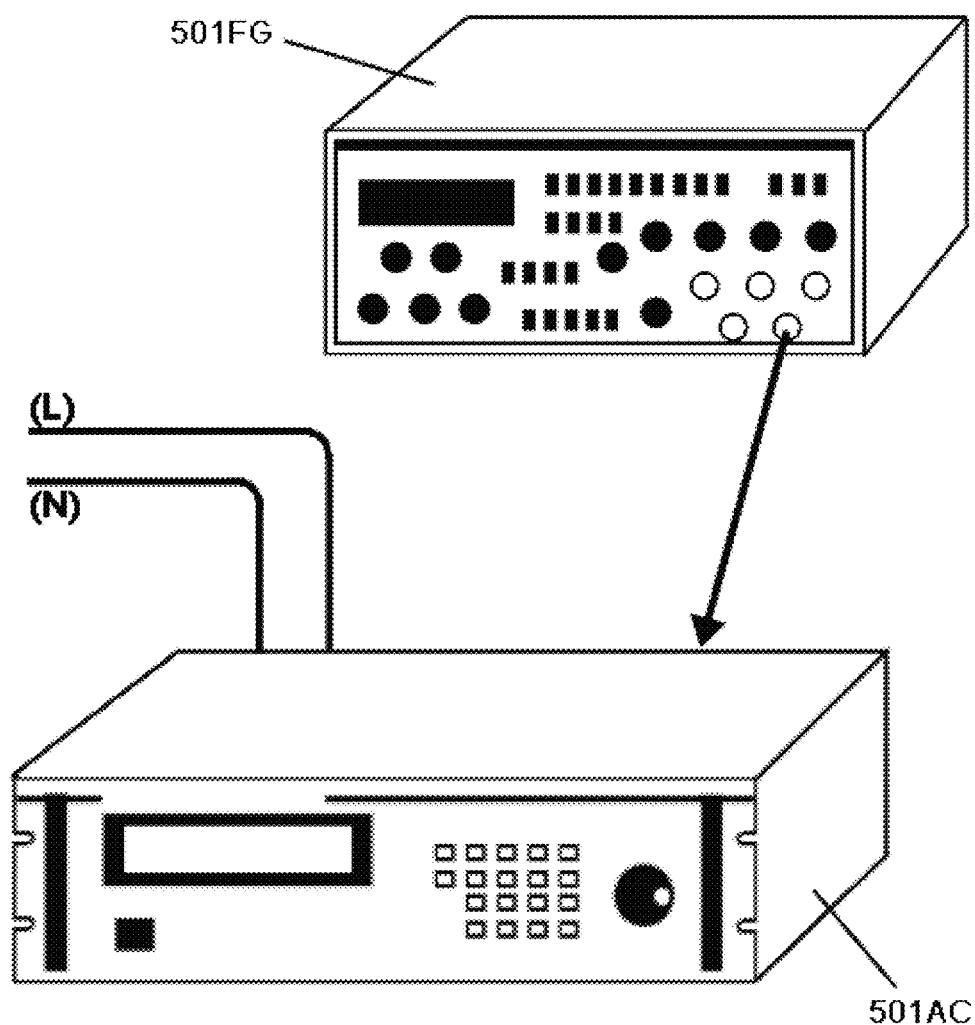
FIG. 40 is a schematic diagram of the electrical setup used to generate the nanocrystals in solutions GB-166, GB-165, GB-162, GB-163 and GB-164.

FIG. 39a shows a representative TEM Photomicrograph of gold nanocrystals, dried from suspension GB-156; and FIG. 39b shows the particle size distribution histogram based on TEM measurements of the dried gold nanocrystals from suspension GB-156.

It is clear form this Example that particle size "mode" and particle size distribution both increased as a function of increasing the frequency AC sine waveform under the conditions of this Example.

Example 14

Manufacturing Gold-Based
Nanocrystals/Nanocrystal Suspensions
(GB-166-Sine, GB-165-Square and
GB-162-Triangle)

Figure 41:
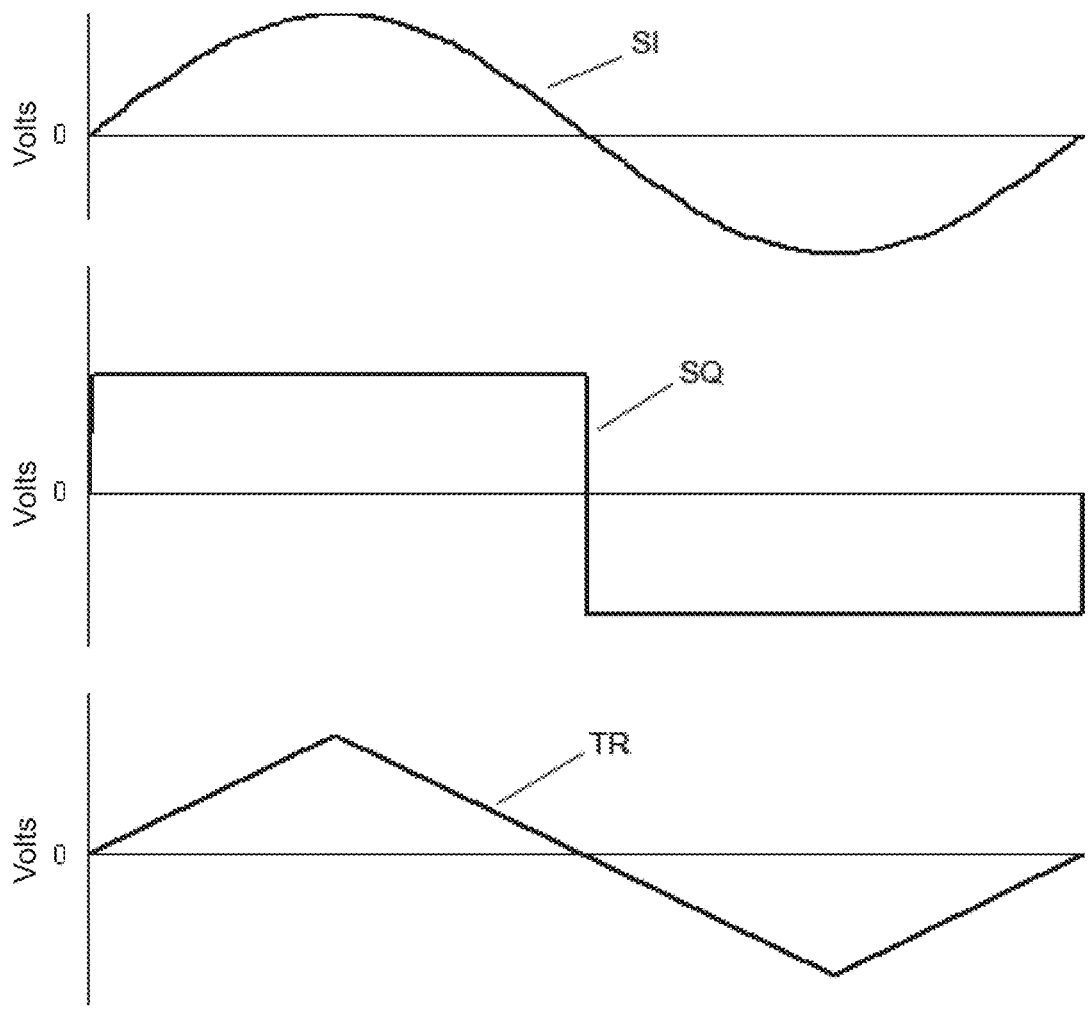
FIG. 41 shows a schematic of the electrical wave forms utilized in solutions GB-166, GB-165 and GB-162.

In general, this Example used the same manufacturing set-up used for making GB-134 in Example 16, and for the sake of brevity, the specifics of the trough apparatus used are discussed in detail in that Example. The primary difference in making the suspensions or colloids in this Example was three different types of waveforms (i.e., sine, square, and triangular waves) were generated by a BK Precision 4040 20 MHz function generator, 501FG. The waveform output was input into a chroma 61604 programmable AC source, 501AC. The applied voltage for the sine waves ("SI") and square waves ("SQ") was 300 volts, while the applied voltage for the triangular-shaped waveforms ("TR") was 250 volts. Each of these waveforms is shown in FIG. 41. Specifically, GB-166 utilized a sine wave; GB-165 utilized a square wave; and GB-162 utilized a triangular wave as electrical inputs to the electrodes 5a/5b.

Figure 42A:
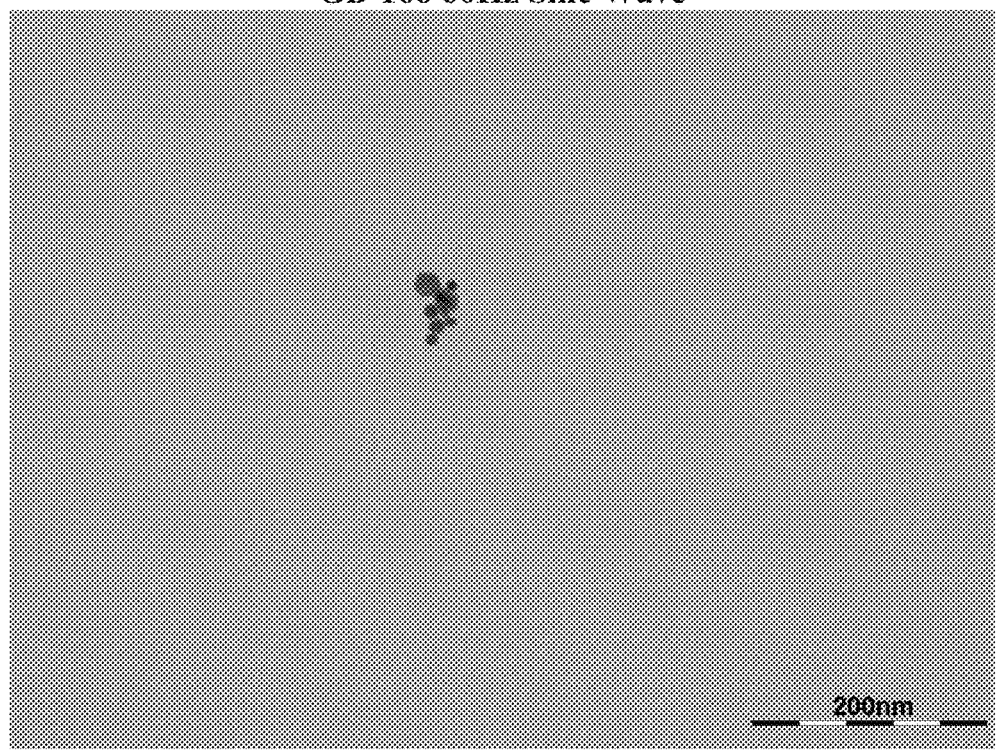
FIG. 42a is a representative TEM photomicrograph of gold nanocrystals from dried solution GB-166 (60 Hz sine wave) made according to Example 14
Figure 42B:
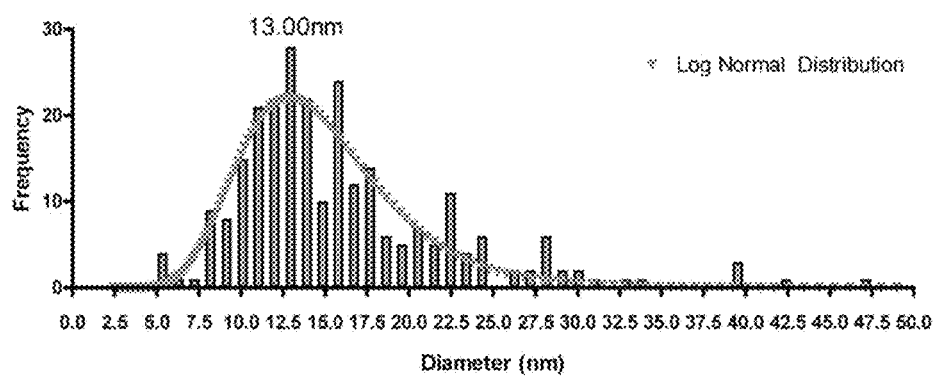
FIG. 42b shows a particle size distribution histogram from TEM measurements for the nanocrystals made according to GB-166.

FIG. 42a shows a representative TEM Photomicrograph of gold nanocrystals, dried from suspension GB-166; and FIG. 42b shows the particle size distribution histogram based on TEM measurements of the dried gold nanocrystals from suspension GB-166.

Figure 43A:
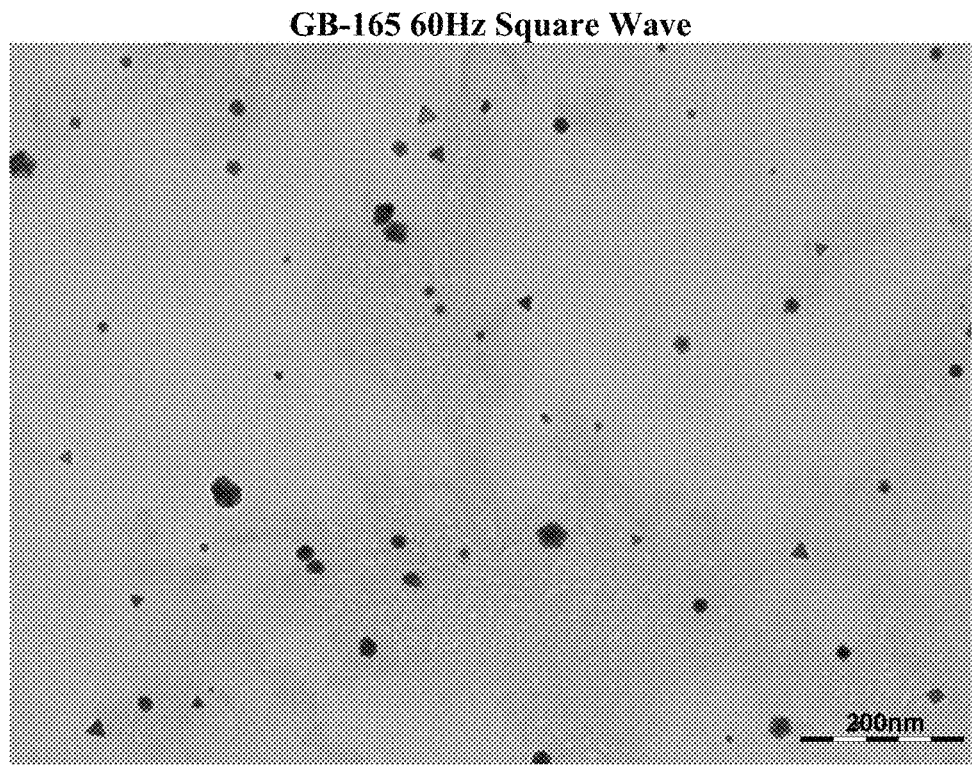
FIG. 43*a* is a representative TEM photomicrograph of gold nanocrystals from dried solution GB-165 (60 Hz square wave) made according to Example 14.
Figure 43B:
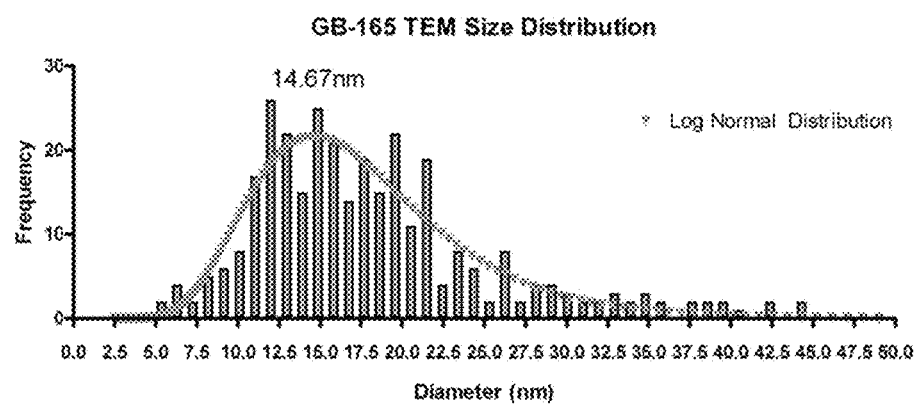
FIG. 43*b* shows a particle size distribution histogram from TEM measurements for the nanocrystals made according to GB-165.

FIG. 43a shows a representative TEM Photomicrograph of gold nanocrystals, dried from suspension GB-165; and FIG. 43b shows the particle size distribution histogram based on TEM measurements of the dried gold nanocrystals from suspension GB-165.

Figure 44A:
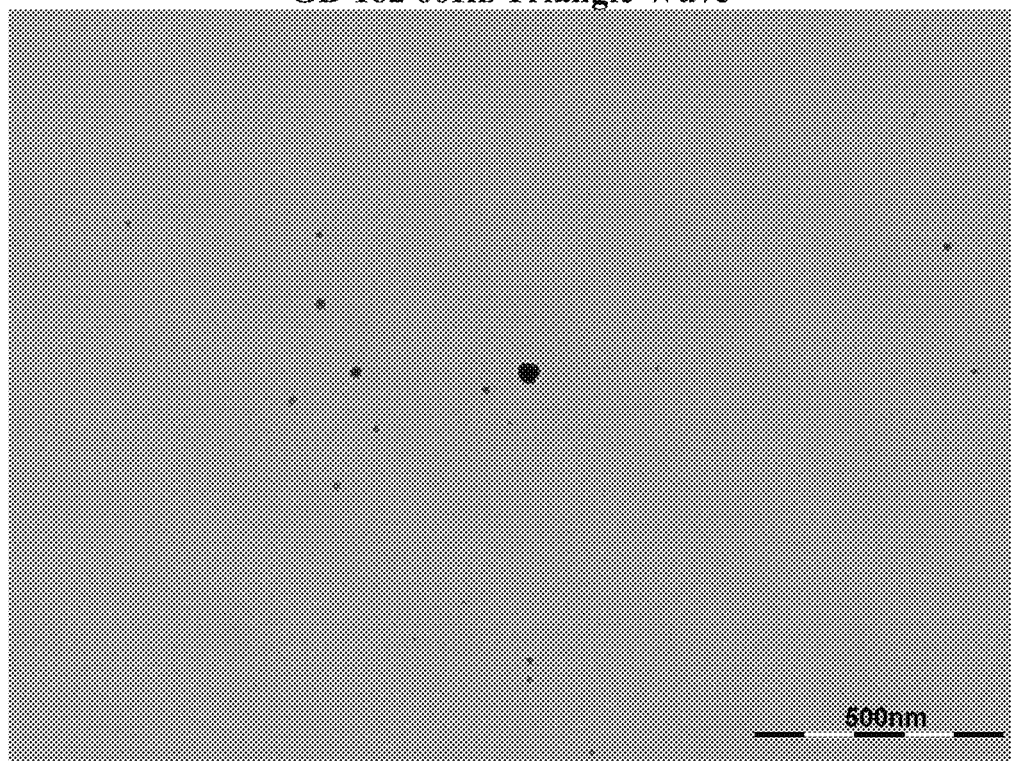
FIG. 44*a* is a representative TEM photomicrograph of gold nanocrystals from dried solution GB-162 (60 Hz triangle wave) made according to Example 14.
Figure 44B:
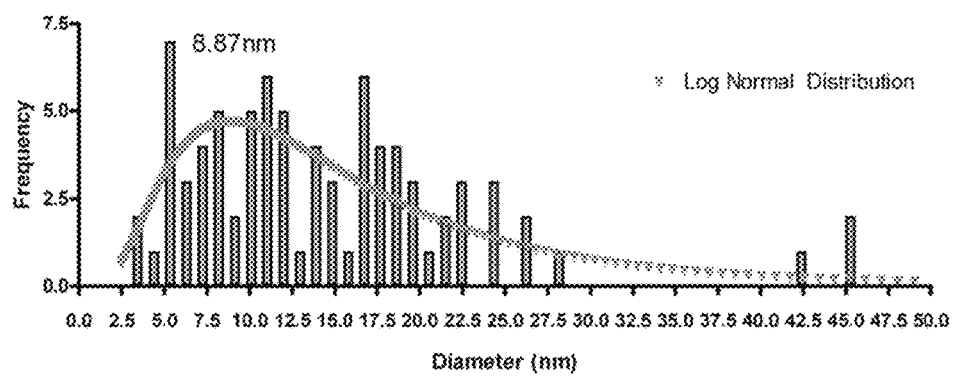
FIG. 44*b* shows a particle size distribution histogram from TEM measurements for the nanocrystals made according to GB-162.

FIG. 44a shows a representative TEM Photomicrograph of gold nanocrystals, dried from suspension GB-162; and FIG. 44b shows the particle size distribution histogram based on TEM measurements of the dried gold nanocrystals from suspension GB-162.

Example 15

Manufacturing Gold-Based
Nanoparticles/Nanoparticle Suspensions (GB-163
and GB-164)

Figure 45:
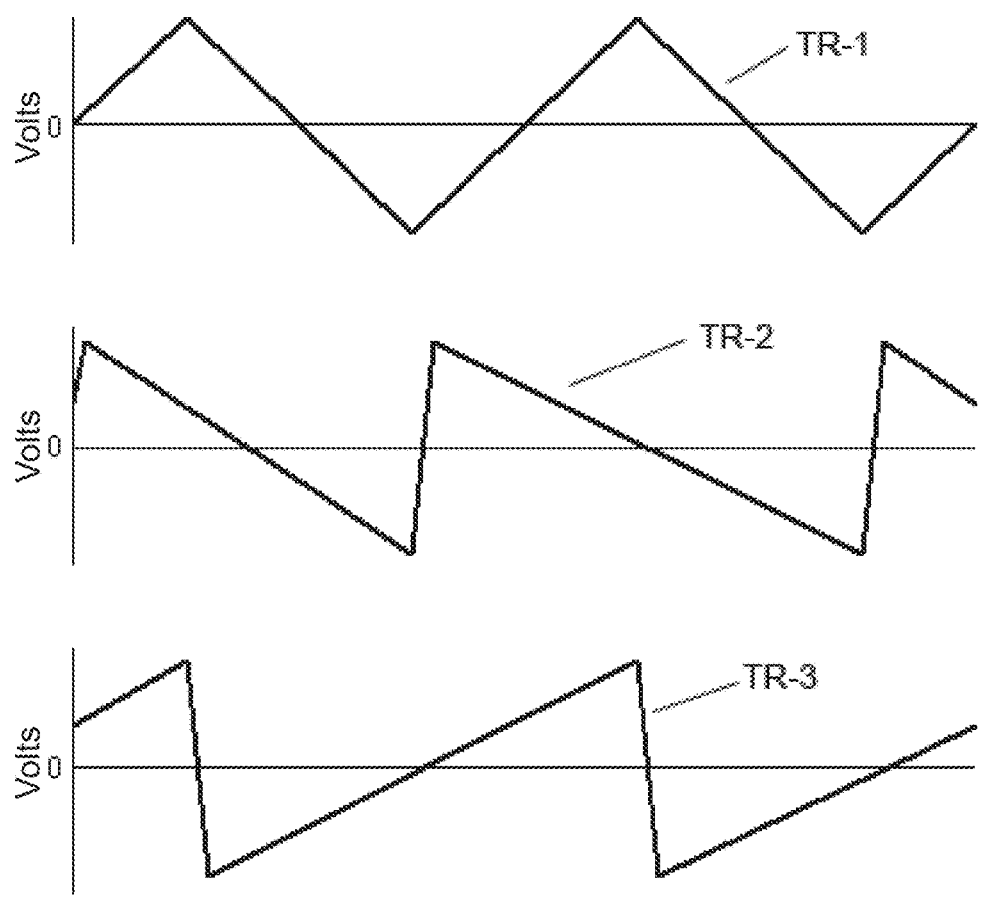
FIG. 45 is a schematic of the triangular-shaped electrical wave forms utilized to generate samples in accordance with GB-163 and GB-164.

In general, this Example used the same manufacturing set-up used for making GB-134 in Example 16, and for the sake of brevity, the specifics of the trough apparatus used are discussed in detail in that Example. The primary difference in making the suspensions or colloids in this Example was that two different duty cycles for the triangular waveforms from the signal wave generator 501FG and programmable AC power source 501AC (i.e., discusses in Example 14) were used. The applied voltage for each triangular waveform was 250 volts. Specifically, each of GB-166 and GB-164 utilized the triangular-shaped waveforms TR-1, TR-2 and TR-3 shown in FIG. 45 as electrical inputs to the electrodes 5a/5b. Waveform TR-2 was the maximum duty cycle, while TR-3 was the minimum duty cycle.

Figure 46A:
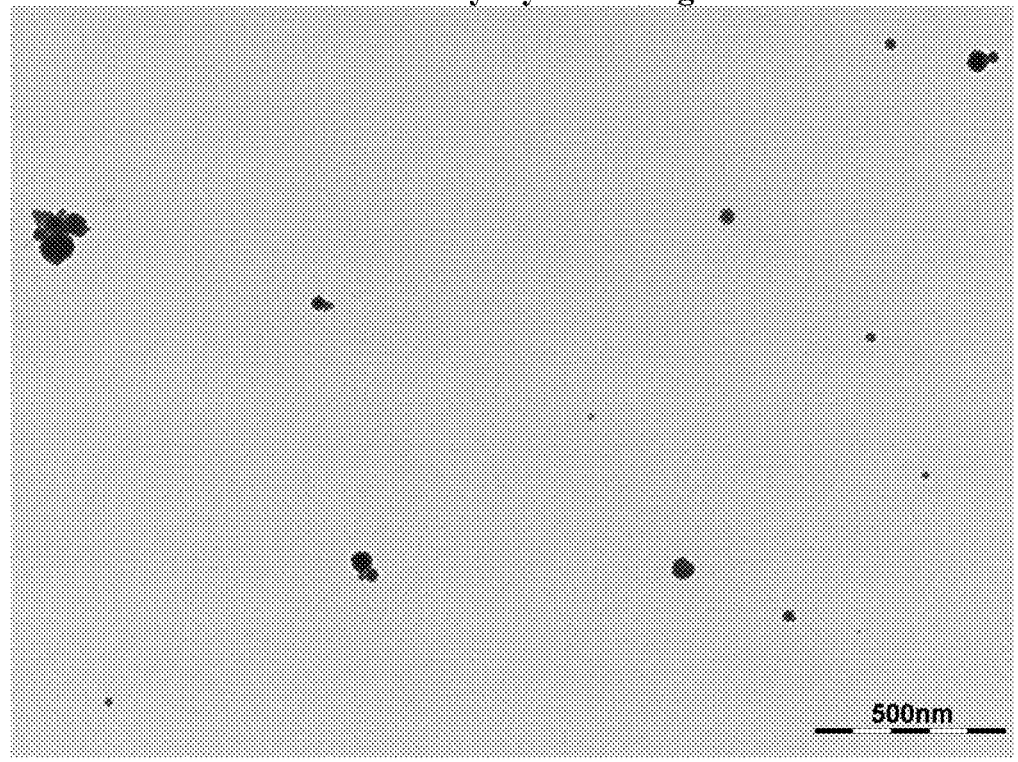
FIG. 46*a* is a representative TEM photomicrograph of gold nanocrystals from dried solution GB-163 (max duty cycle triangle wave) made according to Example 15.
Figure 46B:
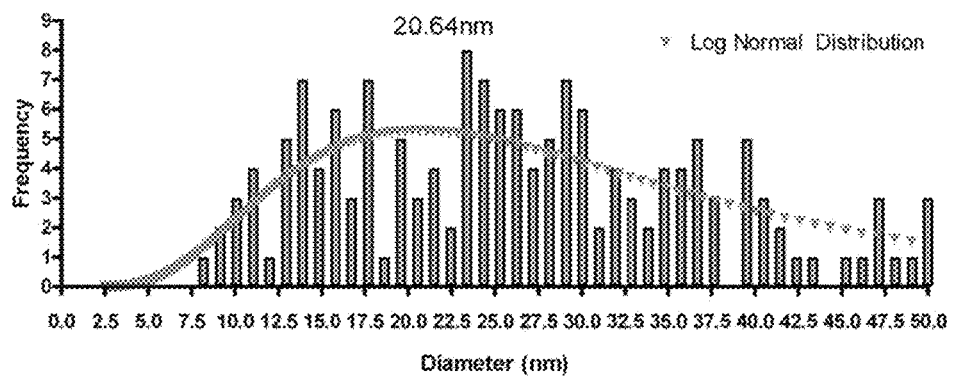
FIG. 46*b* shows a particle size distribution histogram from TEM measurements for the nanocrystals made according to GB-163.

FIG. 46a shows a representative TEM Photomicrograph of gold nanocrystals, dried from suspension GB-163; and FIG. 46b shows the particle size distribution histogram based on TEM measurements of the dried gold nanocrystals from suspension GB-163.

Figure 47A:
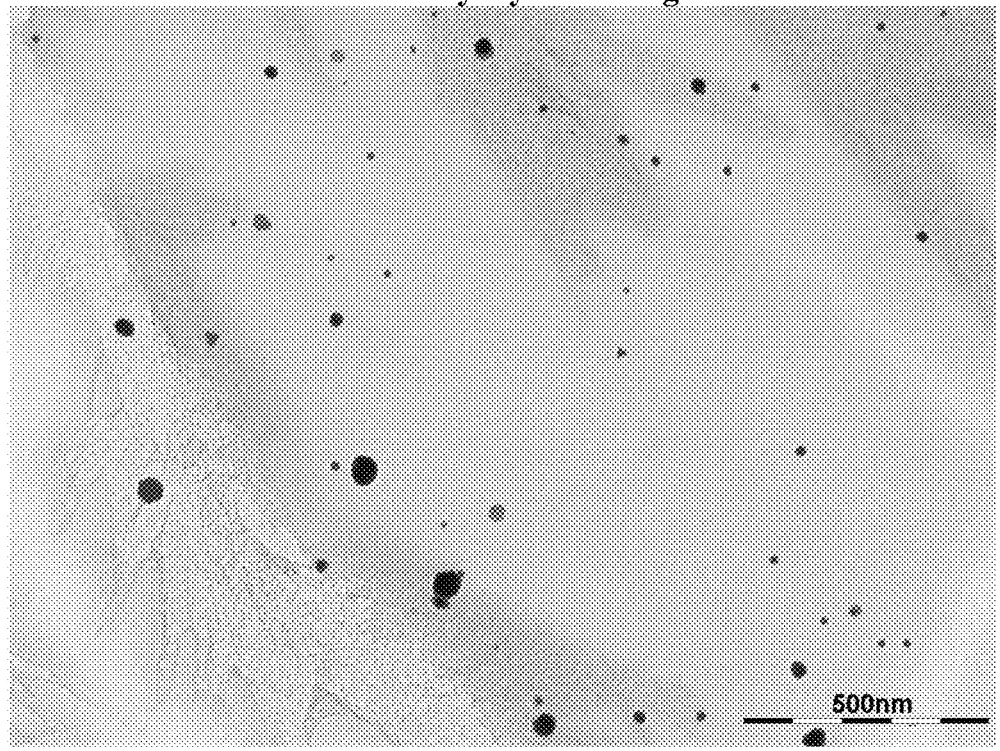
FIG. 47*a* is a representative TEM photomicrograph of gold nanocrystals from dried solution GB-164 (min duty cycle triangle wave) made according to Example 15.
Figure 47B:
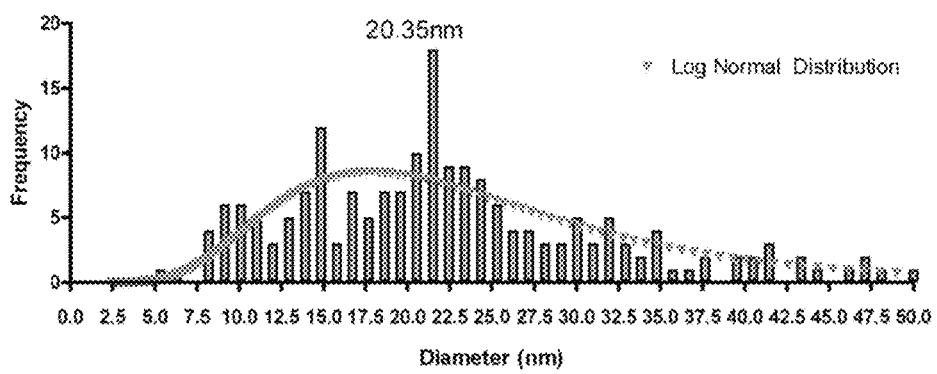
FIG. 47*b* shows a particle size distribution histogram from TEM measurements for the nanocrystals made according to GB-164.
Figure 48B:
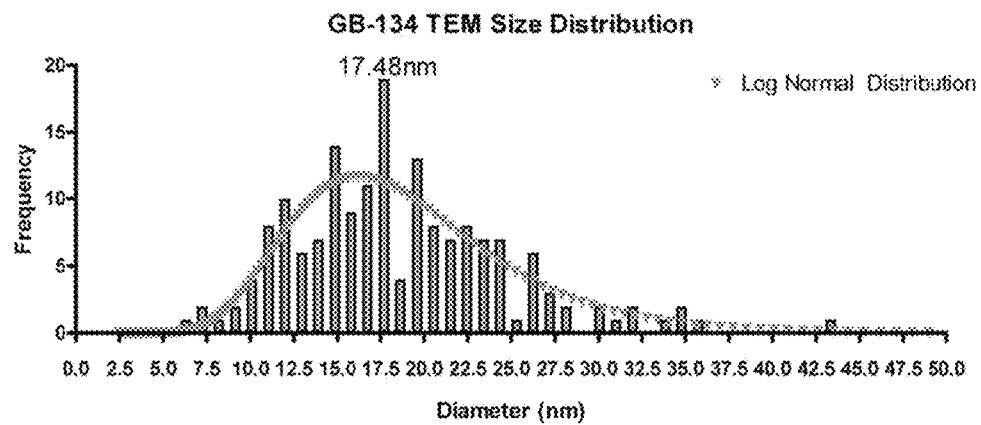
FIG. 48*b* shows a particle size distribution histogram from TEM measurements for the nanocrystals made according to Example 16.
Figure 48C:
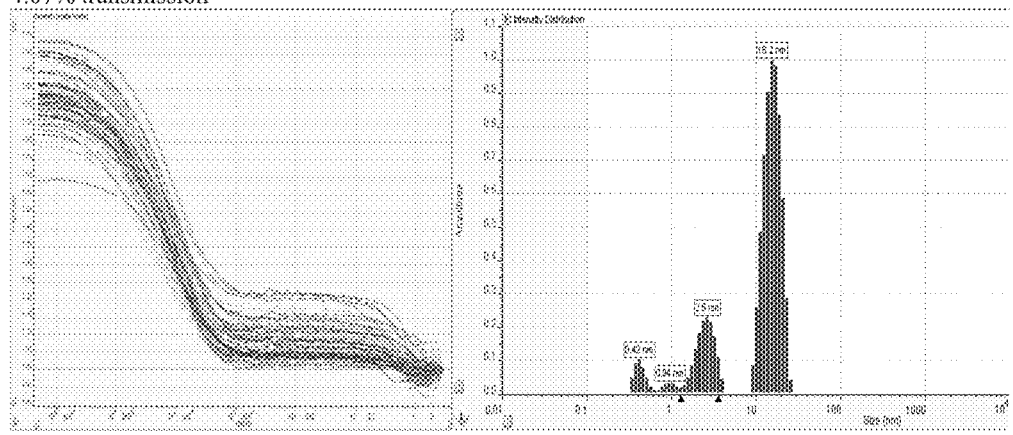
FIG. 48*c* shows dynamic light scattering data (i.e., hydrodynamic radii) for gold nanocrystals made according to Example 16.
Figure 49B:
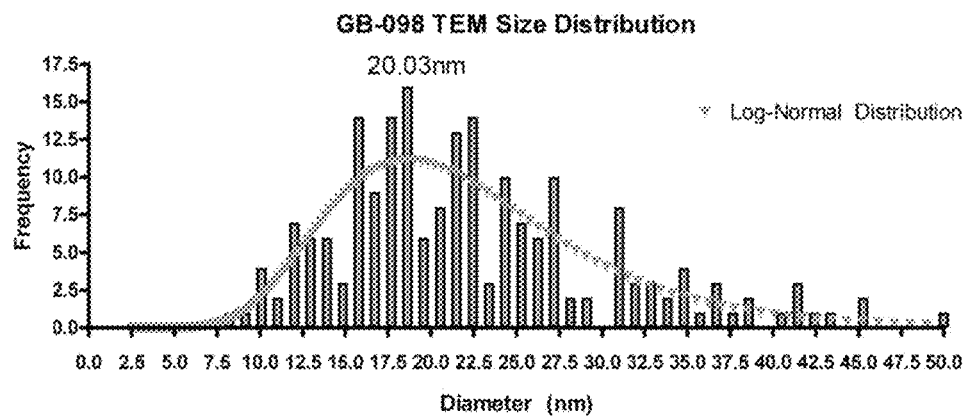
Figure 49C:
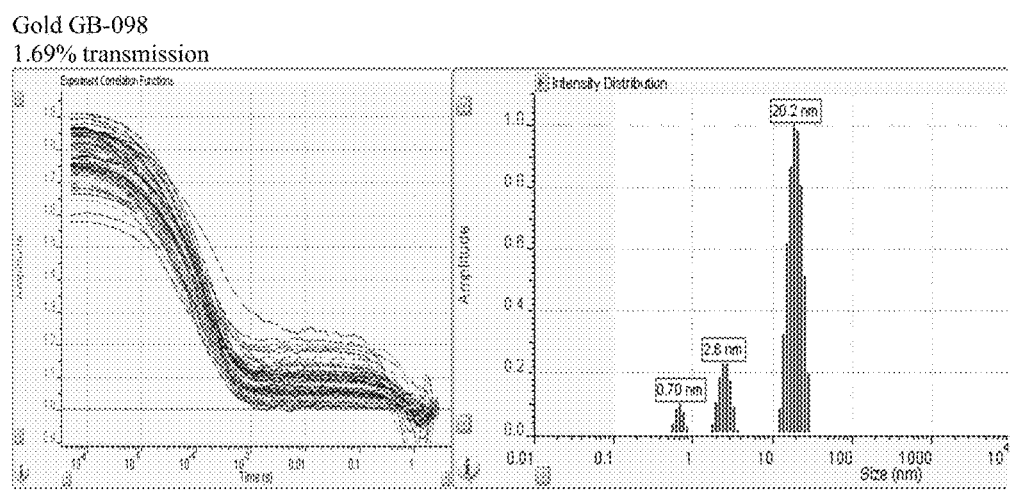
Figure 50B:
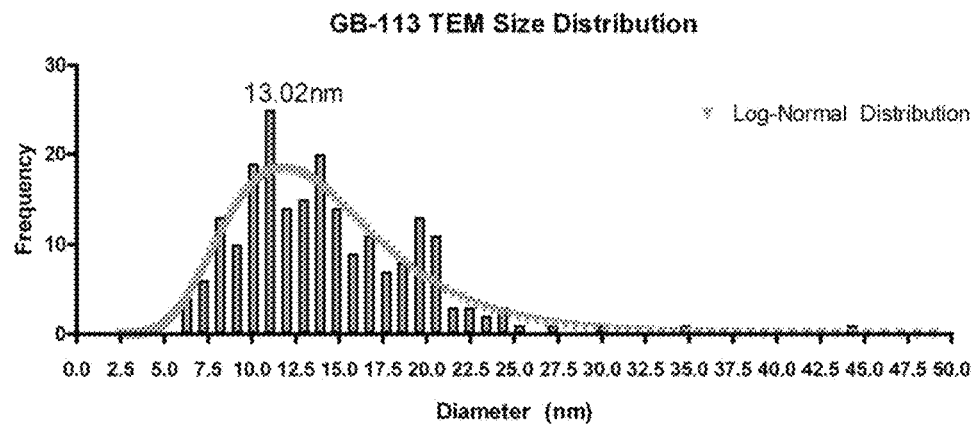
Figure 50C:
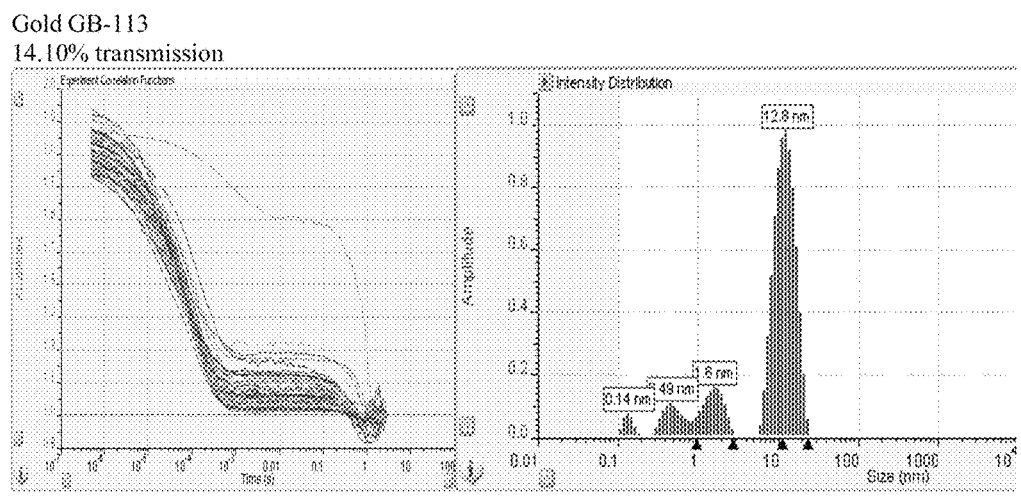
Figure 51B:
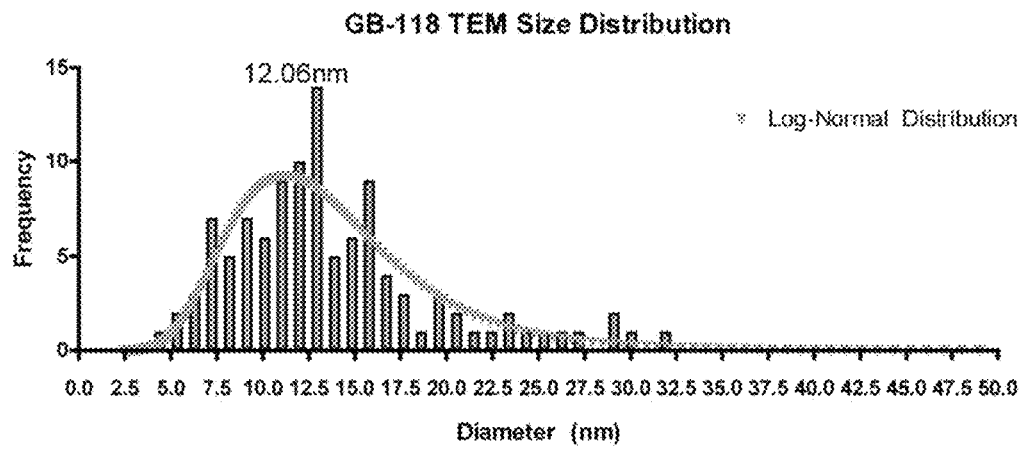
Figure 51C:
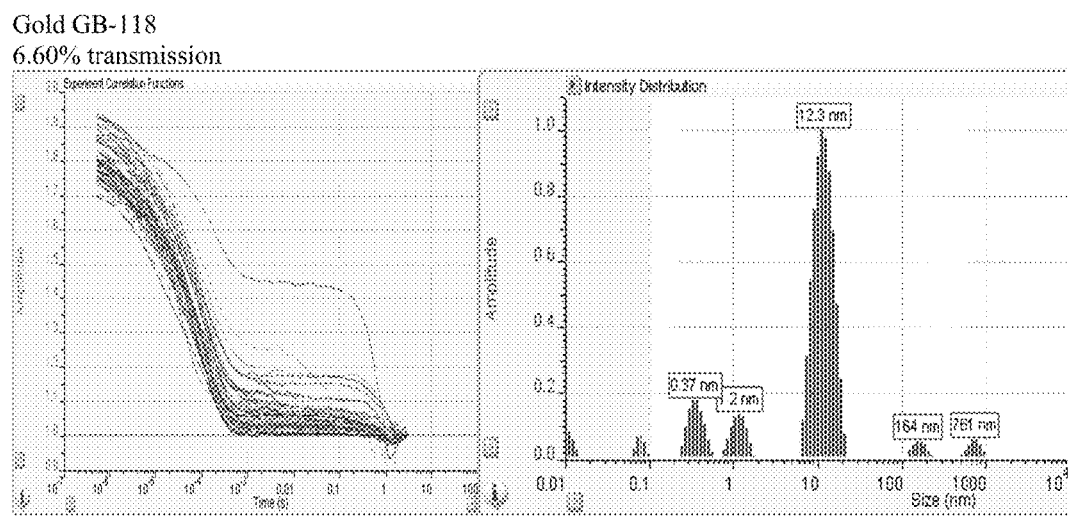
Figure 52B:
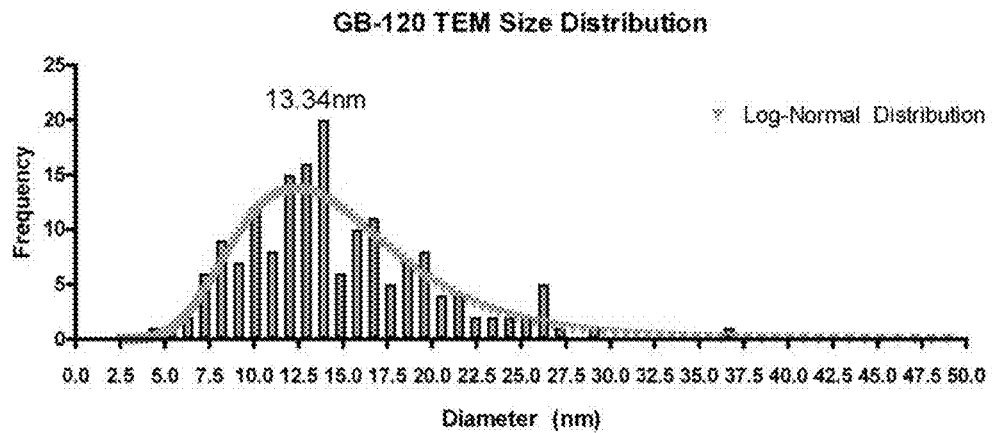
Figure 52C:
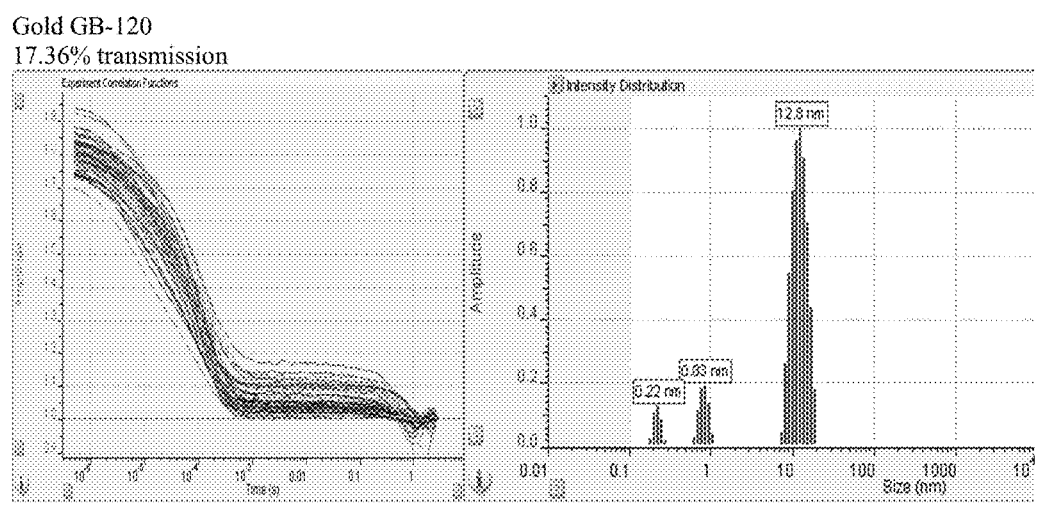
Figure 53B:
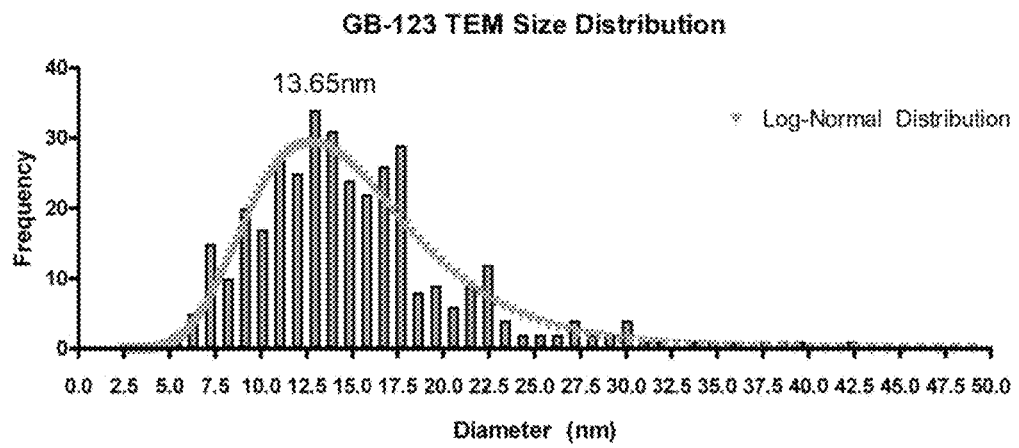
Figure 53C:
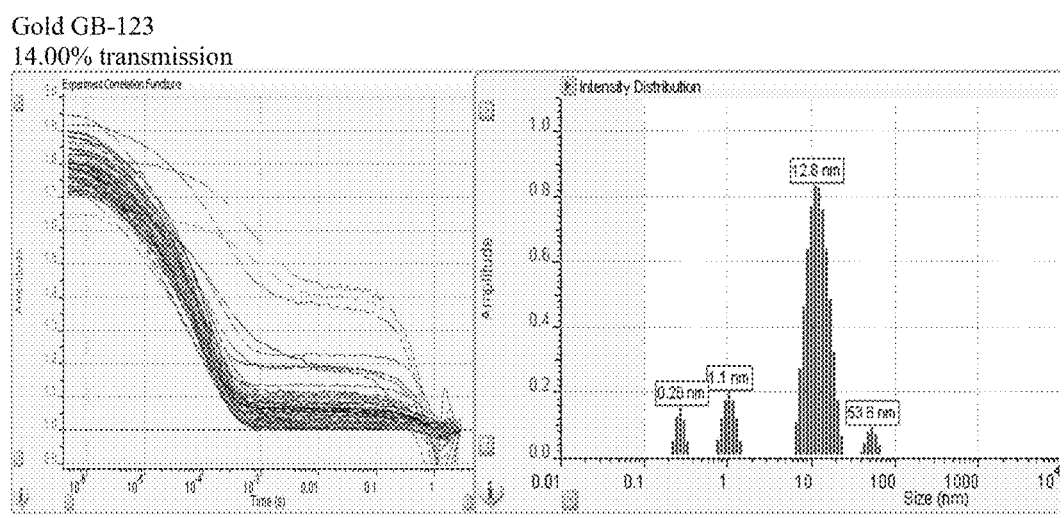

FIG. 47a shows a representative TEM Photomicrograph of gold nanocrystals, dried from suspension GB-164; and FIG. 47b shows the particle size distribution histogram based on TEM measurements of the dried gold nanocrystals from suspension GB-164.

Example 16

Manufacturing Gold-Based Nanocrystals/Nanocrystal Suspensions (GB-134); (GB-098, GB-113 and GB-118); (GB-120 and GB-123); (GB-139); (GB-141 and GB-144); (GB-079, GB-089 and GB-062); and (GB-076 and GB-077)

In general, this Example 16 utilizes certain embodiments of the invention associated with the apparatuses generally shown in FIGS. 20c-h, 21b-g and 22b. Additionally, Table 5 summarizes key processing parameters used in conjunction with FIGS. 20c-h, 21b-g and 22b. Also, Table 5 discloses: 1) resultant "ppm" (i.e., gold nanoparticle concentrations), 2) a single number for "Hydrodynamic Radii" taken from the average of the three highest amplitude peaks shown in each of FIGS. 49c-61 (discussed later herein) and 3) "TEM Average Diameter" which is the mode, corresponding to the particle diameter that occurs most frequently, determined by TEM histogram graphs shown in FIGS. 49b-61b. These physical characterizations were performed as discussed elsewhere herein.

TABLE 5

| Run ID: | | GB-134 | GB-098 | GB-113 | GB-118 | GB-120 | GB-123 | GB-139 |
|---|---|---|---|---|---|---|---|---|
| Flow Rate: | In (ml/min) | 150 | 150 | 150 | 150 | 150 | 150 | 150 |
| | Out (ml/min) | 110 | 110 | 110 | 110 | 110 | 110 | 110 |
| Volts: | Set # 1 | 750 | 750 | 750 | 750 | 750 | 750 | 750 |
| | Set # 2 | 300 | 297 | 300 | 300 | 300 | 300 | 300 |
| | Set #'s 3-9 | 300 | 297 | 300 | 300 | 300 | 300 | 300 |
| PE: NaHCO3 (mg/ml) | | 0.53 | 0.40 | 0.53 | 0.53 | 0.53 | 0.53 | 0.53 |
| Wire Diameter (mm) | | 1.0 | 1.0 | 1.0 | 1.0 | 1.0 | 1.0 | 1.0 |
| Contact "$W_L$" (in/mm) | | .75/19 | 1/25 | 0.5/13 | 0.5/13 | 0.5/13 | 0.5/13 | 0.75/19 |
| Electrode Config. Figure | | 17b | 17b | 17b | 17c | 17b | 17b | 17d |
| Produced Au PPM | | 8.9 | 8.0 | 10.3 | 9.3 | 10.4 | 10.1 | 10.0 |
| Output Temp ° C. at 32 | | 85 | 93 | 88 | 86 | 84 | 93 | 87 |
| Dimensions | Plasma 4 Figs. | 18a | 18a | 18a | 18a | 18a | 18a | 18a |
| | Process Figures | 20h, 21e | 20f, 21b | 20f, 21b | 20f, 21b | 20g, 21d | 20g, 21d | 20c, 20h 21e, 21f, 21g |
| | M1 (in/mm) | 2/51 | 1/25 | 2/51 | 2/51 | 3.5/89 | 2/51 | 2/51 |
| | M2 (in/mm) | n/a | n/a | n/a | n/a | n/a | n/a | n/a |
| | $L_T$ (in/mm) | 36/914 | 48/1219 | 36/914 | 36/914 | 36/914 | 36/914 | 36/914 |
| | d (in/mm) | .75/19 | 1/25 | 0.5/13 | 0.5/13 | 0.5/13 | 0.5/13 | 0.75/19 |
| | S (in/mm) | 1.5/38.1 | 3/76.2 | 2.5/63.5 | 2.5/63.5 | 2.5/63.5 | 2.5/63.5 | 1.5/38.1 |
| Electrode Curr. (A) | | 0.56 | 0.53 | 0.53 | 0.52 | 0.51 | 0.48 | FIG. 54d |
| Total Curr. Draw (A) | | n/a | n/a | n/a | n/a | n/a | n/a | n/a |
| Hydrodynamic r (nm) | | 16.2 | 20.02 | 12.8 | 12.3 | 12.8 | 12.8 | 15.9 |
| TEM Avg. Dia. (nm) | | 17.48 | 20.03 | 13.02 | 12.06 | 13.34 | 13.65 | 13.97 |
| | "c-c" (mm) | 76 | 83 | 83 | 83 | 83 | 83 | 83 |
| Set 1 | electrode # | 1a | 1a | 1a | 1a | 1a | 1a | 1a |
| | "x" (in/mm) | 0.25/6.4 | 0.25/6.4 | 0.25/6.4 | 0.25/6.4 | 0.25/6.4 | 0.25/6.4 | 0.25/6.4 |
| | electrode # | 5a | 5a | 5a | 5a | 5a | 5a | 5a |
| | "c-c" (mm) | 89 | 83 | 89 | 89 | 89 | 89 | 83 |
| Set 2 | electrode # | 5b | 5b | 5b | 5b | 5b | 5b | 5b |
| | "x" (in/mm) | n/a | n/a | n/a | n/a | n/a | n/a | n/a |
| | electrode # | 5b' | 5b' | 5b' | 5b' | 5b' | 5b' | 5b' |
| | "c-c" (mm) | 38 | 76 | 59 | 56 | 57 | 38 | 76 |
| Set 3 | electrode # | 5c | 5c | 5c | 5c | 5c | 5c | 5c |
| | electrode # | 5c' | 5c' | 5c' | 5c' | 5c' | 5c' | 5c' |
| | "c-c" (mm) | 38 | 105 | 60 | 59 | 64 | 38 | 76 |
| Set 4 | electrode # | 5d | 5d | 5d | 5d | 5d | 5d | 5d |
| | electrode # | 5d' | 5d' | 5d' | 5d' | 5d' | 5d' | 5d' |
| | "c-c" (mm) | 89 | 143 | 70 | 68 | 70 | 44 | 127 |
| Set 5 | electrode # | 5e | 5e | 5e | 5e | 5e | 5e | 5e |
| | electrode # | 5e' | 5e' | 5e' | 5e' | 5e' | 5e' | 5e' |
| | "c-c" (mm) | 89 | 165 | 84 | 103 | 70 | 51 | 127 |
| Set 6 | electrode # | 5f | 5f | 5f | 5f | 5f | 5f | 5f |
| | electrode # | 5f' | 5f' | 5f' | 5f' | 5f' | 5f' | 5f' |
| | "c-c" (mm) | 89 | 178 | 108 | 102 | 64 | 54 | 127 |
| Set 7 | electrode # | 5g | 5g | 5g | 5g | 5g | 5g | 5g |
| | electrode # | 5g' | 5g' | 5g' | 5g' | 5g' | 5g' | 5g' |
| | "c-c" (mm) | 178 | 178 | 100 | 100 | 76 | 54 | 216 |
| Set 8 | electrode # | 5h | 5h | 5h | 5h | 5h | 5h | 5h |
| | electrode # | 5h' | 5h' | 5h' | 5h' | 5h' | 5h' | 5h' |
| | "c-c" (mm) | 89 | 216 | 127 | 135 | 76 | 57 | 83 |
| Set 9 | electrode # | n/a | 5i | 5i | 5i | 5i | 5i | n/a |
| | electrode # | n/a | 5i' | 5i' | 5i' | 5i' | 5i' | n/a |
| | "c-c" (mm) | n/a | 76 | 191 | 178 | 324 | 464 | n/a |

| Run ID: | | GB-141 | GB-144 | GB-079 | GB-089 | GB-062 | GB-076 | GB-077 |
|---|---|---|---|---|---|---|---|---|
| Flow Rate: | In (ml/min) | 150 | 110 | 150 | 150 | 150 | 150 | 150 |
| | Out (ml/min) | 110 | 62 | 110 | 110 | 110 | 110 | 110 |
| Volts: | Set # 1 | 750 | 750 | 750 | 750 | 750 | 750 | 750 |
| | Set # 2 | 299 | 299 | 255 | 255 | 750 | 750 | 750 |
| | Set #'s 3-9 | 299 | 299 | 255 | 255 | 249 | 306 | 313 |
| PE: NaHCO3 (mg/ml) | | 0.53 | 0.53 | 0.40 | 0.40 | 0.40 | 0.53 | 0.40 |
| Wire Diameter (mm) | | 1.0 | 1.0 | 0.5 | 0.5 | 0.5 | 0.5 | 0.5 |
| Contact "$W_L$" (in/mm) | | 0.5/13 | 0.5/13 | 2/51 | 2/51 | 2/51 | 1/25 | 1/25 |
| Electrode Config. Figure | | 17d | 17d | 17b | 17b | 17b | 17b | 17b |
| Produced Au PPM | | 10.1 | 20.2 | 10.8 | 12.4 | 16.7 | 7.8 | 7.5 |
| Output Temp ° C. at 32 | | 86 | 89 | 94 | 99 | 95 | 98 | 97 |
| Dimensions | Plasma 4 Figs. | 18a | 18a | 18a | 18a | 18b | 18b | 18b |
| | Process Figures | 20c, 20h 21e, 21f, 21g | 20c, 20h 21e, 21f, 21g | 20d, 21c | 20d, 21c | 20e, 21c | 20e, 22b | 20e, 22b |
| | M1 (in/mm) | 2/51 | 2/51 | 1/25 | 0.75/19 | 1/25 | 2.7/68.6 | 2.7/68.6 |
| | M2 (in/mm) | n/a | n/a | n/a | n/a | n/a | 0.5/13 | 0.5/13 |
| | $L_T$ (in/mm) | 36/914 | 36/914 | 24/610 | 24/610 | 24/610 | 24/610 | 24/610 |
| | d (in/mm) | 0.5/13 | 0.5/13 | 2/51 | 2/51 | 2/51 | 1/25 | 1/25 |
| | S (in/mm) | 1.5/38.1 | 1.5/38.1 | 3.3/83.8 | 3.3/83.8 | 3.3/83.8 | 3.5/88.9 | 3.5/88.9 |

TABLE 5-continued

Figure 55B:
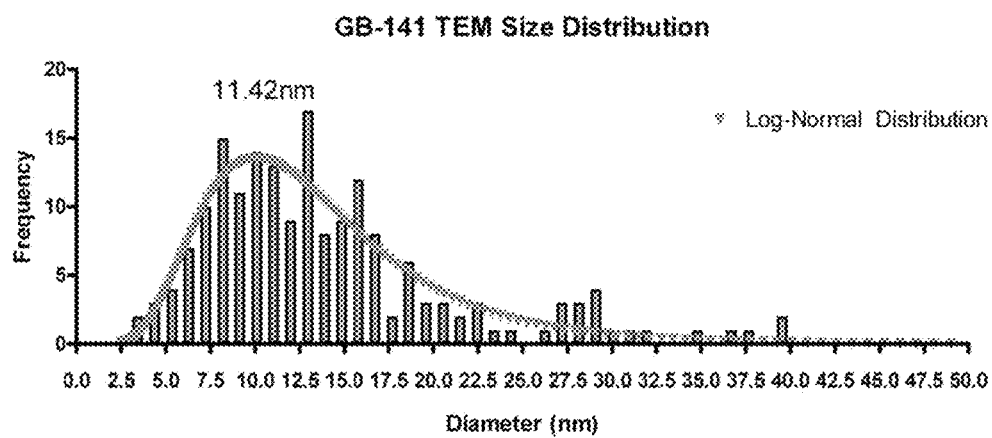
Figure 55C:
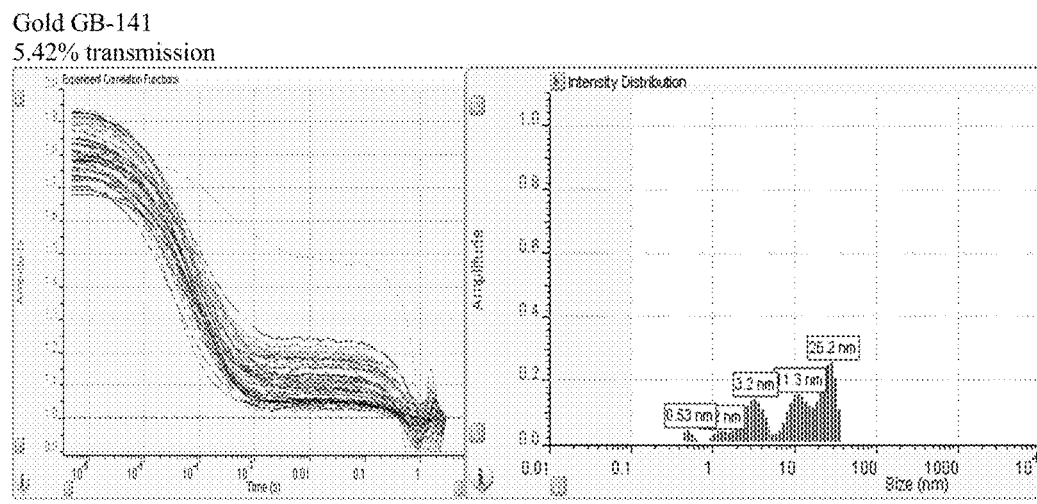
Figure 56B:
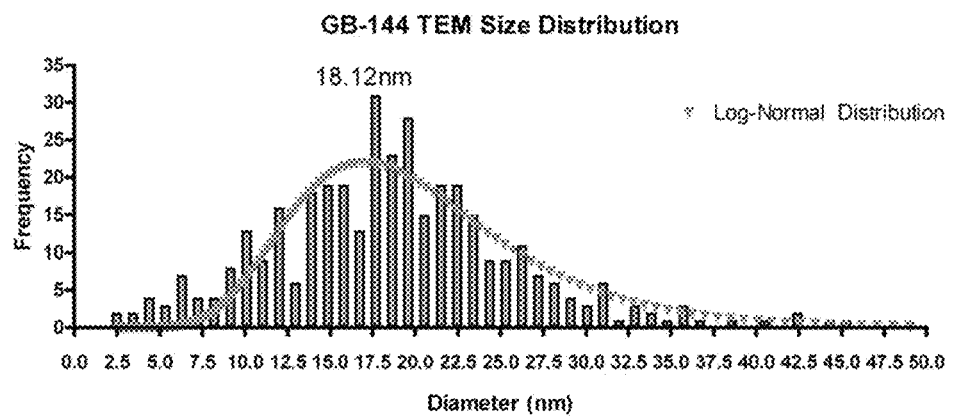
Figure 56C:
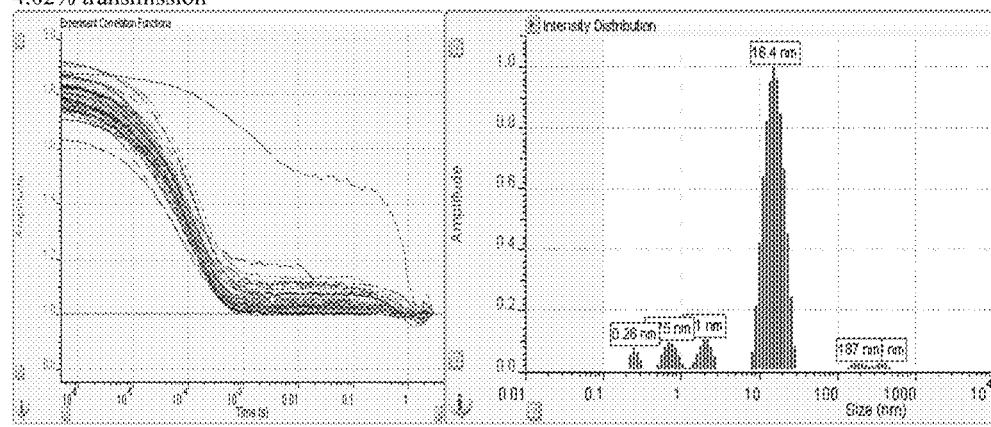
Figure 57B:
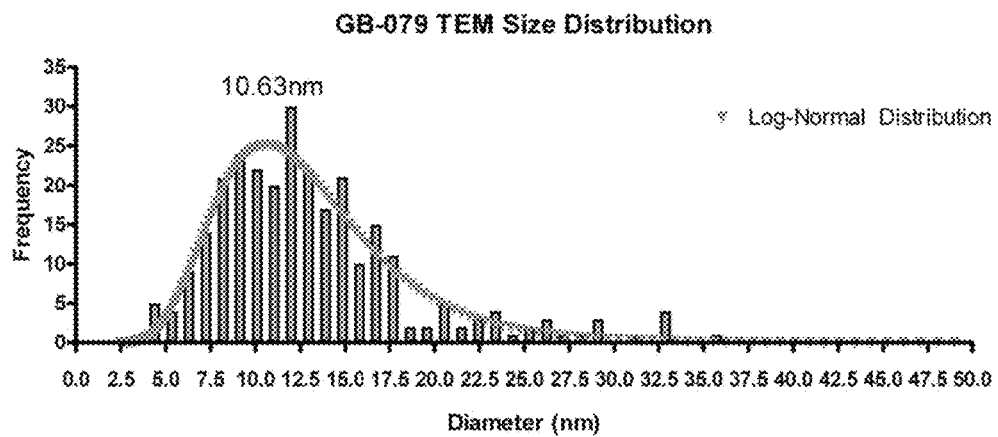
Figure 57C:
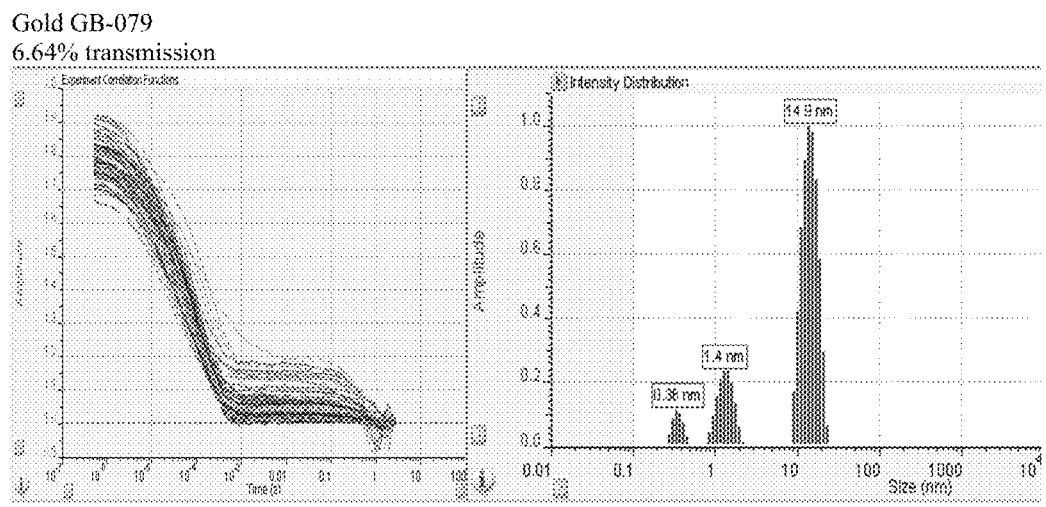
Figure 58B:
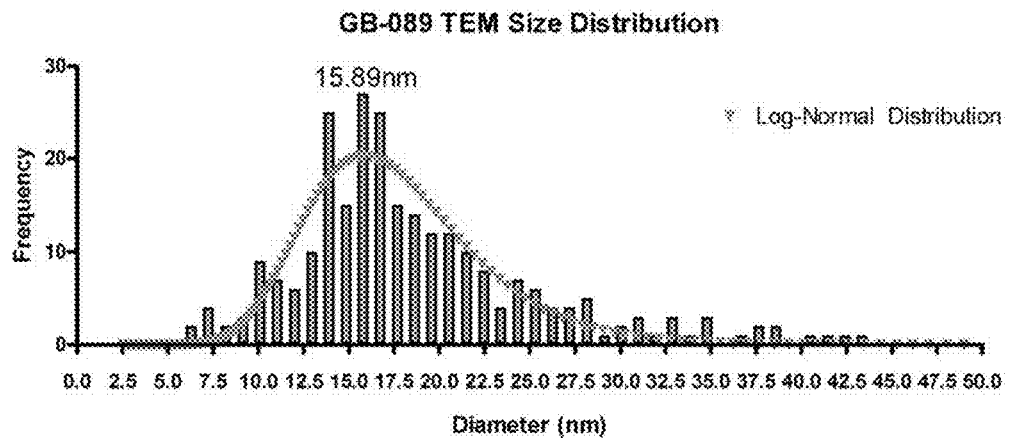
Figure 58C:
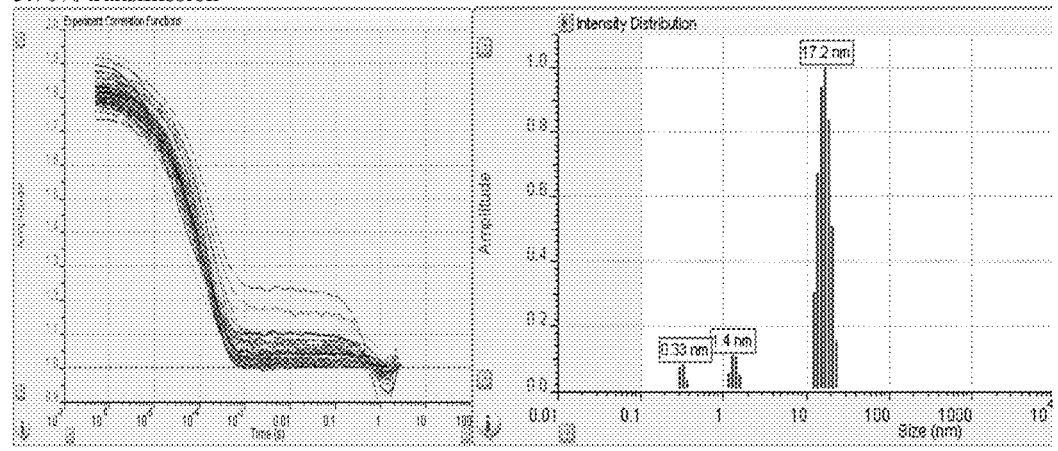
Figure 59B:
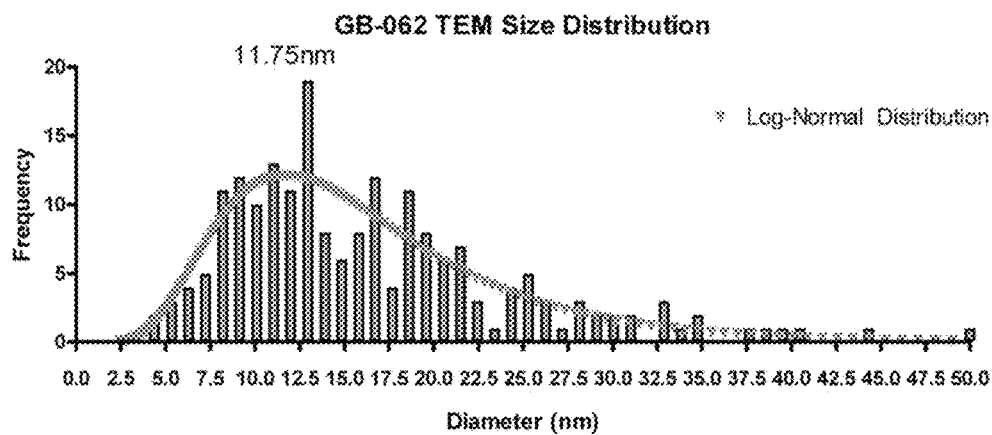
Figure 59C:
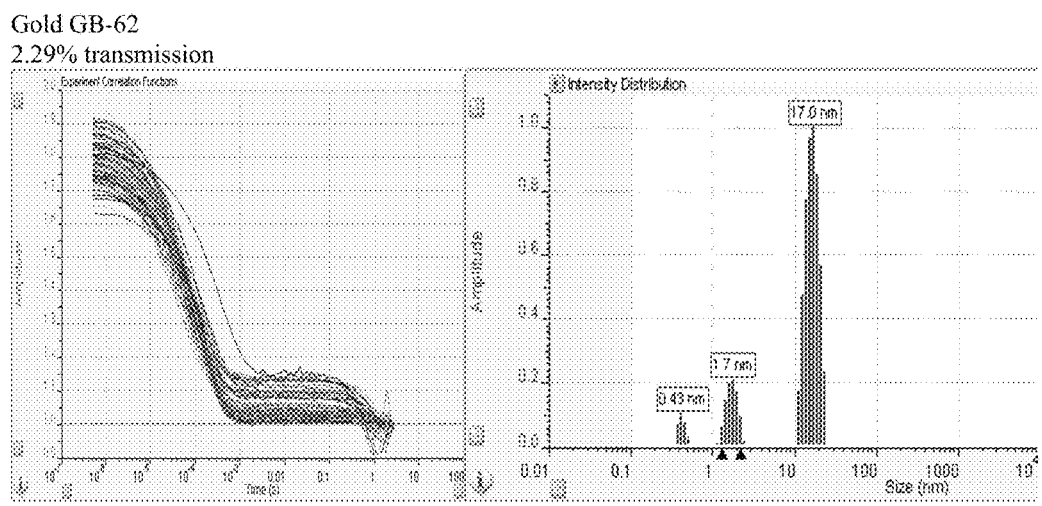
Figure 60B:
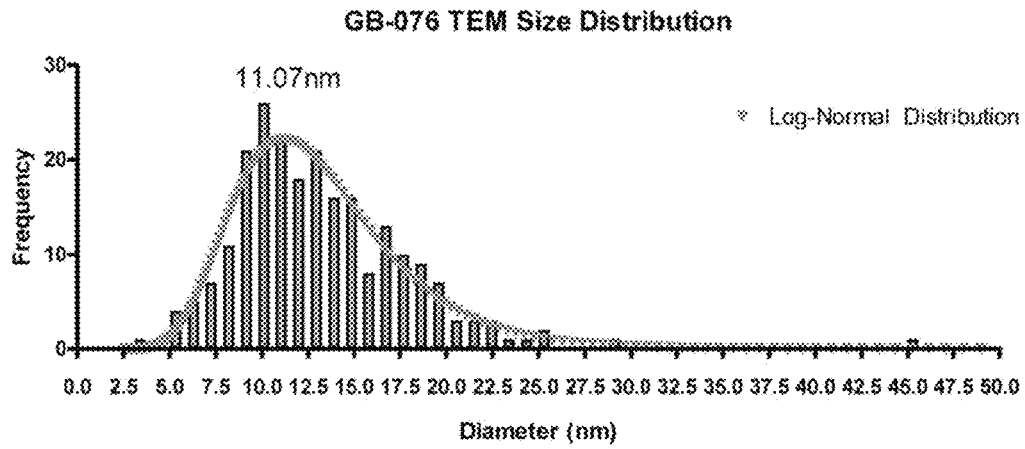
Figure 60C:
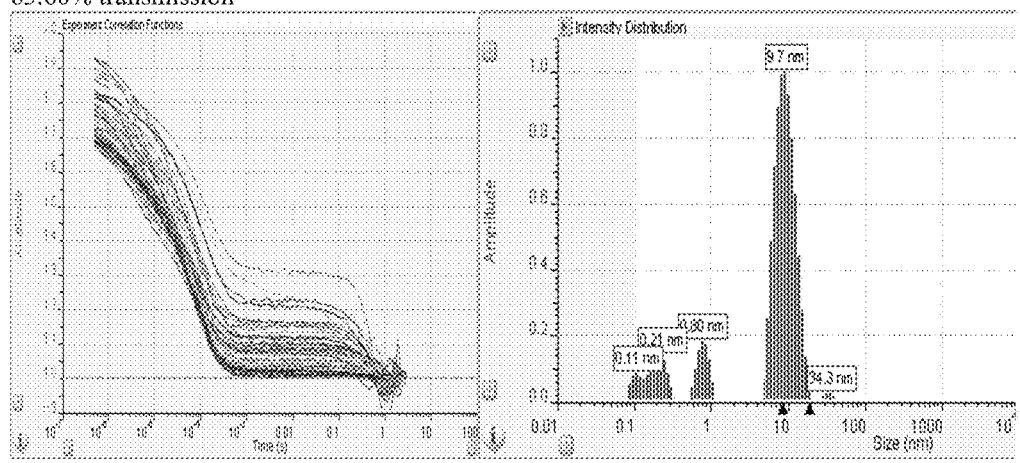

| | | FIG. 55d | FIG. 56d | | | | | |
|---|---|---|---|---|---|---|---|---|
| Electrode Curr. (A) | | FIG. 55d | FIG. 56d | 0.66 | n/a | 0.7 | 0.51 | 0.48 |
| Total Curr. Draw (A) | | n/a | n/a | 11.94 | 8.98 | 12.48 | 13.62 | 12.47 |
| Hydrodynamic r (nm) | | 26.2 | 16.4 | 14.9 | 17.2 | 17.0 | 9.7 | 11.5 |
| TEM Avg. Dia. (nm) | | 11.42 | 18.12 | 10.63 | 15.89 | 11.75 | 11.07 | 8.69 |
| | "c-c" (mm) | n/a | 83 | n/m | n/m | n/m | n/m | n/m |
| Set 1 | electrode # | n/a | 1a | 1a | 1a | 1a | 1a | 1a |
| | "x" (in/mm) | n/a | 0.25/6.4 | 0.25/6.4 | 0.25/6.4 | 0.25/6.4 | 0.25/6.4 | 0.25/6.4 |
| | electrode # | n/a | 5a | 5a | 5a | 5a | 5a | 5a |
| | "c-c" (mm) | 83 | 83 | n/m | n/m | n/m | n/m | n/m |
| Set 2 | electrode # | 5b | 5b | 5b | 5b | 1b | 1b | 1b |
| | "x" (in/mm) | n/a | n/a | n/a | n/a | 0.25/6.4 | 0.25/6.4 | 0.25/6.4 |
| | electrode # | 5b' | 5b' | 5b' | 5b' | 5b | 5b | 5b |
| | "c-c" (mm) | 76 | 76 | n/m | n/m | n/m | n/m | n/m |
| Set 3 | electrode # | 5c | 5c | 5c | 5c | 5c | 5c | 5c |
| | electrode # | 5c' | 5c' | 5c' | 5c' | 5c' | 5c' | 5c' |
| | "c-c" (mm) | 76 | 76 | n/m | n/m | n/m | n/m | n/m |
| Set 4 | electrode # | 5d | 5d | 5d | 5d | 5d | 5d | 5d |
| | electrode # | 5d' | 5d' | 5d' | 5d' | 5d' | 5d' | 5d' |
| | "c-c" (mm) | 127 | 127 | n/m | n/m | n/m | n/m | n/m |
| Set 5 | electrode # | 5e | 5e | 5e | 5e | 5e | 5e | 5e |
| | electrode # | 5e' | 5e' | 5e' | 5e' | 5e' | 5e' | 5e' |
| | "c-c" (mm) | 127 | 127 | n/m | n/m | n/m | n/m | n/m |
| Set 6 | electrode # | 5f | 5f | 5f | 5f | 5f | 5f | 5f |
| | electrode # | 5f' | 5f' | 5f' | 5f' | 5f' | 5f' | 5f' |
| | "c-c" (mm) | 127 | 127 | n/m | n/m | n/m | n/m | n/m |
| Set 7 | electrode # | 5g | 5g | 5g | 5g | 5g | 5g | 5g |
| | electrode # | 5g' | 5g' | 5g' | 5g' | 5g' | 5g' | 5g' |
| | "c-c" (mm) | 216 | 216 | n/m | n/m | n/m | n/m | n/m |
| Set 8 | electrode # | 5h | 5h | 5h | 5h | 5h | 5h | 5h |
| | electrode # | 5h' | 5h' | 5h' | 5h' | 5h' | 5h' | 5h' |
| | "c-c" (mm) | 83 | 83 | n/m | n/m | n/m | n/m | n/m |
| Set 9 | electrode # | n/a | n/a | n/a | n/a | 5i | 5i | 5i |
| | electrode # | n/a | n/a | n/a | n/a | 5i' | 5i' | 5i' |
| | "c-c" (mm) | n/a | n/a | n/a | n/a | n/m | n/m | n/m |

All trough members 30a' and 30b' in the aforementioned Figures were made from 1/8" (about 3 mm) thick plexiglass, and 1/4" (about 6 mm) thick polycarbonate, respectively. The support structure 34 (not shown in many of the Figures but discussed elsewhere herein) was also made from plexiglass which was about 1/4" thick (about 6-7 mm thick). In contrast to the embodiments shown in FIGS. 19a and 19b, each trough member 30a was integral with trough member 30b' and was thus designated 30a' (e.g., no separate pumping means was provided after trough member 30a, as in certain previous examples). The cross-sectional shape of each trough member 30a' used in this Example corresponded to that shape shown in FIG. 10b (i.e., was a trapezoidal-shaped cross-section). Relevant dimensions for each trough member portion 30b' are reported in Table 5 as "M1" (i.e., inside width of the trough at the entrance portion of the trough member 30b'), "M2" (i.e., inside width of the trough at the exit portion of the trough member 30b'), "$L_T$" (i.e., transverse length or flow length of the trough member 30b'), "S" (i.e., the height of the trough member 30b'), and "d" (i.e., depth of the liquid 3" within the trough member 30b'). In some embodiments, the distance "M" separating the side portions "S", "S'" (refer to FIG. 10a) of the trough member 30b' were the same. In these cases, Table 5 represents a value dimension for only "M1" and the entry for "M2" is represented as "N/A". In other words, some trough members 30b' were tapered along their longitudinal length and in other cases, the trough members 30b' were substantially straight along their longitudinal length. The thickness of each sidewall portion also measured about 1/4" (about 6 mm) thick. Three different longitudinal lengths "$L_T$" are reported for the trough members 30b' (i.e., either 610 mm, 914 mm or 1219 mm) however, other lengths $L_T$ should be considered to be within the metes and bounds of the inventive trough.

Table 5 shows that the processing enhancer NaHCO$_3$ was added to purified water (discussed elsewhere herein) in amounts of either about 0.4 mg/ml or 0.53 mg/ml. It should be understood that other amounts of this processing enhancer also function within the metes and bounds of the invention. The purified water/NaHCO$_3$ mixture was used as the liquid 3 input into trough member 30a'. The depth "d" of the liquid 3' in the trough member 30a' (i.e., where the plasma(s) 4 is/are formed) was about 7/16" to about 1/2" (about 11 mm to about 13 mm) at various points along the trough member 30a'. The depth "d" was partially controlled through use of the dam 80 (shown in FIGS. 18a and 18b). Specifically, the dam 80 was provided near the output end 32 of the trough member 30a' and assisted in creating the depth "d" (shown in FIG. 10b as "d") to be about 7/16"-1/2" (about 11-13 mm) in depth. The height "j" of the dam 80 measured about 1/4" (about 6 mm) and the longitudinal length "k" measured about 1/2" (about 13 mm). The width (not shown) was completely across the bottom dimension "R" of the trough member 30a'. Accordingly, the total volume of liquid 3' in the trough member 30a' during operation thereof was about 2.14 in$^3$ (about 35 ml) to about 0.89 in$^3$ (about 14.58 ml).

The rate of flow of the liquid 3' into the trough member 30a' as well as into trough member 30b', was about 150 ml/minute for all but one of the formed samples (i.e., GB-144 which was about 110 ml/minute) and the rate of flow out of the trough member 30b' at the point 32 was about 110 ml/minute (i.e., due to evaporation) for all samples except GB-144, which was about 62 ml/minute. The amount of evaporation that occurred in GB-144 was a greater percent than the other samples because the dwell time of the liquid 3" in the trough member 30b' was longer relative to the other samples made according to this embodiment. Other acceptable flow rates should be considered to be within the metes and bounds of the invention.

Such flow of liquid 3' was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute for all samples except GB-144 which was, for example, 110 ml/minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30'a by a flow diffusion means located therein. The flow diffusion means tended to minimize disturbance and bubbles in water 3 introduced into the trough member 30a' as well as any pulsing condition generated by the peristaltic pump 40. In this regard, a small reservoir served as the diffusion means and was provided at a point vertically above the end 31 of the trough member 30a' such that when the reservoir overflowed, a relatively steady flow of liquid 3' into the end 31 of the V-shaped trough member 30a' occurred.

Table 5 shows that there was a single electrode set 1a/5a, or two electrode sets 1a/5a, utilized in this Example 18. The plasma(s) 4 was/were created with an electrode 1 similar in shape to that shown in FIG. 5e, and weighed about 9.2 grams. This electrode was 99.95% pure gold. The other electrode 5a comprised a right-triangular shaped platinum plate measuring about 14 mm×23 mm×27 mm and about 1 mm thick and having about 9 mm submerged in the liquid 3'. All other pertinent run conditions are shown in Table 5.

As shown in FIGS. 20c-h, the output from the trough member 30a' was the conditioned liquid 3' and this conditioned liquid 3' flowed directly into a second trough member 30b'. The second trough member 30b', shown in FIGS. 21b-g and 22b had measurements as reported in Table 5. This trough member 30b' contained from about 600 ml of liquid 3" therein to about 1100 ml depending on the dimensions of the trough and the depth "d"" of the liquid 3" therein. Table 5, in connection with FIGS. 20c-h, 21b-g and 22b, show a variety of different electrode configurations. For example, previous examples herein disclosed the use of four sets of electrodes 5/5, with one electrode set 1/5. In this Example, either eight or nine electrode sets were used (e.g., one 1/5 set with seven or eight 5/5' sets; or two 1/5 sets with seven 5/5' sets). Each of the electrode sets 5/5' comprised 99.99% pure gold wire measuring either about 0.5 mm in diameter or 1.0 mm in diameter, as reported in Table 5. The length of each wire electrode 5 that was in contact with the liquid 3" (reported as "WL" in Table 5) measured from about 0.5 inches (about 13 mm) long to about 2.0 inches (about 51 mm) long. Two different electrode set configurations 5/5' were utilized. FIGS. 21b, 21c, 21e, 21f, 21g and 22b all show electrode sets 5/5' oriented along a plane (e.g., arranged in line form along the flow direction of the liquid 3"). Whereas FIG. 21d shows that the electrode sets 5/5' were rotated about 90° relative to the aforementioned electrode sets 5/5'. Further, the embodiments shown in FIGS. 20a-20h show the electrode sets 1/5 and 5/5' were all located along the same plane. However, it should be understood that the imaginary plane created between the electrodes in each electrode set 1/5 and/or 5/5' can be parallel to the flow direction of the liquid 3" or perpendicular to the flow direction of the liquid 3" or at an angle relative to the flow direction of the liquid 3."

With regard to FIGS. 20c-h, 21b-g and 22b, each separate electrode set 5/5' (e.g., Set 2, Set 3-Set 8 or Set 9) were electrically connected to the transformer devices, 50 and 50a, as shown therein. Specifically, transformers 50 and 50a were electrically connected to each electrode set, according to the wiring diagram show in FIGS. 20c-h. The exact wiring varied between examples and reference should be made to the FIGS. 20c-20g for specific electrical connection information. In most cases, each transformer device 50, 50a was connected to a separate AC input line that was 120° out of phase relative to each other. The transformers 50 and 50a were electrically connected in a manner so as not to overload a single electrical circuit and cause, for example, an upstream circuit breaker to disengage (e.g., when utilized under these conditions, a single transformer 50/50a could draw sufficient current to cause upstream electrical problems). Each transformer 50/50a was a variable AC transformer constructed of a single coil/winding of wire. This winding acts as part of both the primary and secondary winding. The input voltage is applied across a fixed portion of the winding. The output voltage is taken between one end of the winding and another connection along the winding. By exposing part of the winding and making the secondary connection using a sliding brush, a continuously variable ratio can be obtained. The ratio of output to input voltages is equal to the ratio of the number of turns of the winding they connect to. Specifically, each transformer was a Mastech TDGC2-5 kVA, 10A Voltage Regulator, Output 0-250V.

Table 5 refers to each of the electrode sets by "Set #" (e.g., "Set 1" through "Set 9"). Each electrode of the 1/5 or 5/5 electrode sets was set to operate within a specific voltage range. The voltages listed in Table 5 are the voltages used for each electrode set. The distance "c-c" (with reference to FIG. 14) from the centerline of each electrode set to the adjacent electrode set is also reported. Further, the distance "x" associated with each electrode 1 utilized is also reported. For the electrode 5, no distance "x" is reported. Sample GB-118 had a slightly different electrode 5a/5b arrangement from the other examples herein. Specifically, tips or ends 5t and 5f of the electrodes 5a/5b, respectively, were located closer to each other than other portions of the electrodes 5a/5b. The distance "dt" between the tips 5t and 5f varied between about 7/16 inches (about 1.2 cm) and about 2 inches (about 5 cm). Other relevant parameters are also reported in Table 5.

All materials for the electrodes 1/5 were obtained from ESPI, having an address of 1050 Benson Way, Ashland, Oreg. 97520. All materials for the electrodes 5/5 in runs GB-139, GB-141, GB-144, GB-076, GB-077, GB-079, GB-089, GB-098, GB-113, GB-118, GB-120 and GB-123 were obtained from Alfa Aesar, having an address of 26 Parkridgei Road, Ward Hill, Mass. 01835. All materials for the electrodes 5/5 in run GB-062 were obtained from ESPI, 1050 Benson Way, Ashland, Oreg. 97520.

FIGS. 49a-61a show two representative TEM photomicrographs for each of the gold nanocrystals, dried from each suspension or colloid referenced in Table 5, and formed according to Example 16.

FIGS. 49b-61b show the measured size distribution of the gold nanocrystals measured by using the TEM instrument/software discussed earlier in Examples 5-7 for each dried solution or colloid referenced in Table 5 and formed according to Example 16.

FIGS. 49c-61c show graphically dynamic light scattering data measurement sets for the nanocrystals (i.e., the hydrodynamic radii) made according to each suspension or colloid referenced in Table 5 and formed according to Example 16. It should be noted that the dynamic light scattering particle size information is different from the TEM measured histograms because dynamic light scattering uses algorithms that assume the particles are all spheres (which they are not) as well as measures the hydrodynamic radius (e.g., the particle's influence on the water is also detected and reported in addition to the actual physical radii of the particles). Accordingly, it is not surprising that there is a difference in the reported particle sizes between those reported in the TEM histogram data of those reported in the dynamic light scattering data just as in the other Examples included herein.

Reference is now made to FIGS. 20c, 20h, 21e, 21f and 20g which are representative of structures that were used to make samples GB-139, GB-141 and GB-144. The trough member 30b' used to make these samples was different from the other trough members 30b' used this Example 16 because: 1) the eight electrode sets 1/5 and 5/5 were all connected to control devices 20 and 20a-20g (i.e., see FIG. 20h) which automatically adjusted the height of, for example, each electrode 1/5 or 5/5 in each electrode set 1/5; and 2) female receiver tubes o5a/o5a'-o5g/o5g' which were connected to a bottom portion of the trough member 30b' such that the electrodes in each electrode set 5/5 could be removably inserted into each female receiver tube o5 when, and if, desired. Each female receiver tube o5 was made of polycarbonate and had an inside diameter of about ⅛ inch (about 3.2 mm) and was fixed in place by a solvent adhesive to the bottom portion of the trough member 30b'. Holes in the bottom of the trough member 30b' permitted the outside diameter of each tube o5 to be fixed therein such that one end of the tube o5 was flush with the surface of the bottom portion of the trough 30b'. The inside diameters of the tubes o5 effectively prevented any significant quantities of liquid 3" from entering into the female receiver tube o5. However, some liquid may flow into the inside of one or more of the female receiver tubes o5. The length or vertical height of each female receiver tube o5 used in this Example was about 6 inches (about 15.24 cm) however, shorter or longer lengths fall within the metes and bounds of this disclosure. Further, while the female receiver tubes o5 are shown as being subsequently straight, such tubes could be curved in a J-shaped or U-shaped manner such that their openings away from the trough member 30b' could be above the top surface of the liquid 3," if desired.

Figure 21D:
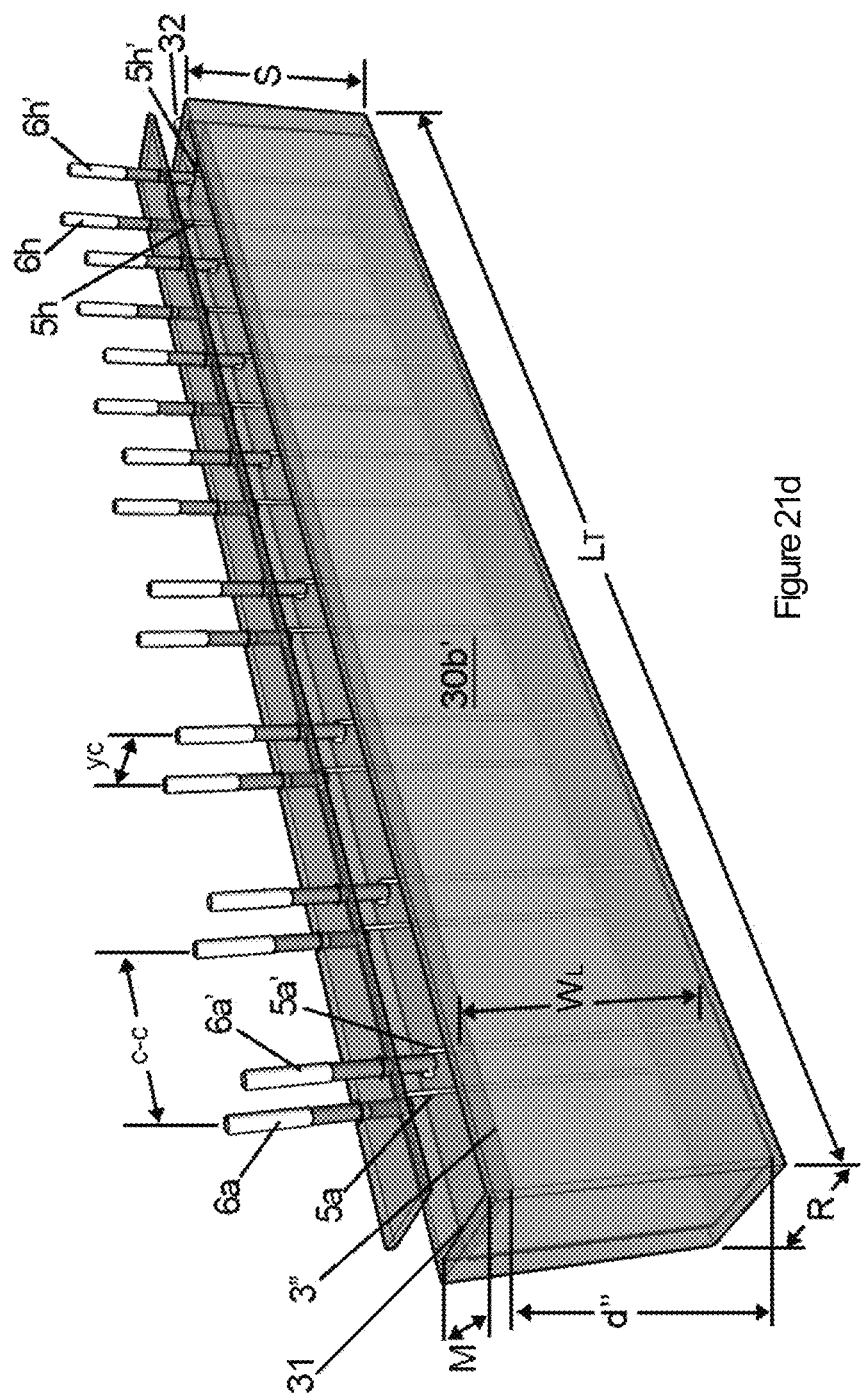
Figure 21E:
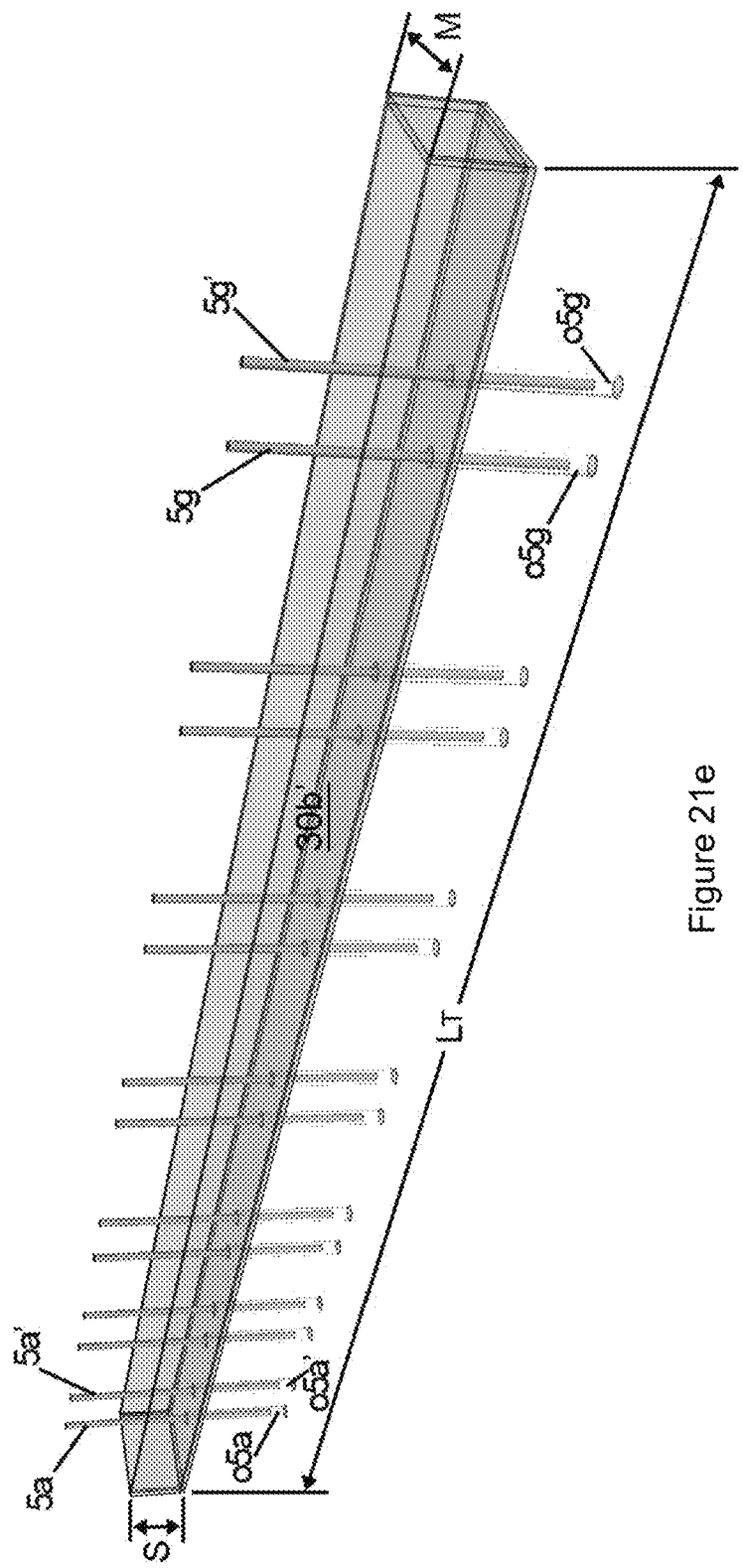
Figure 21F:
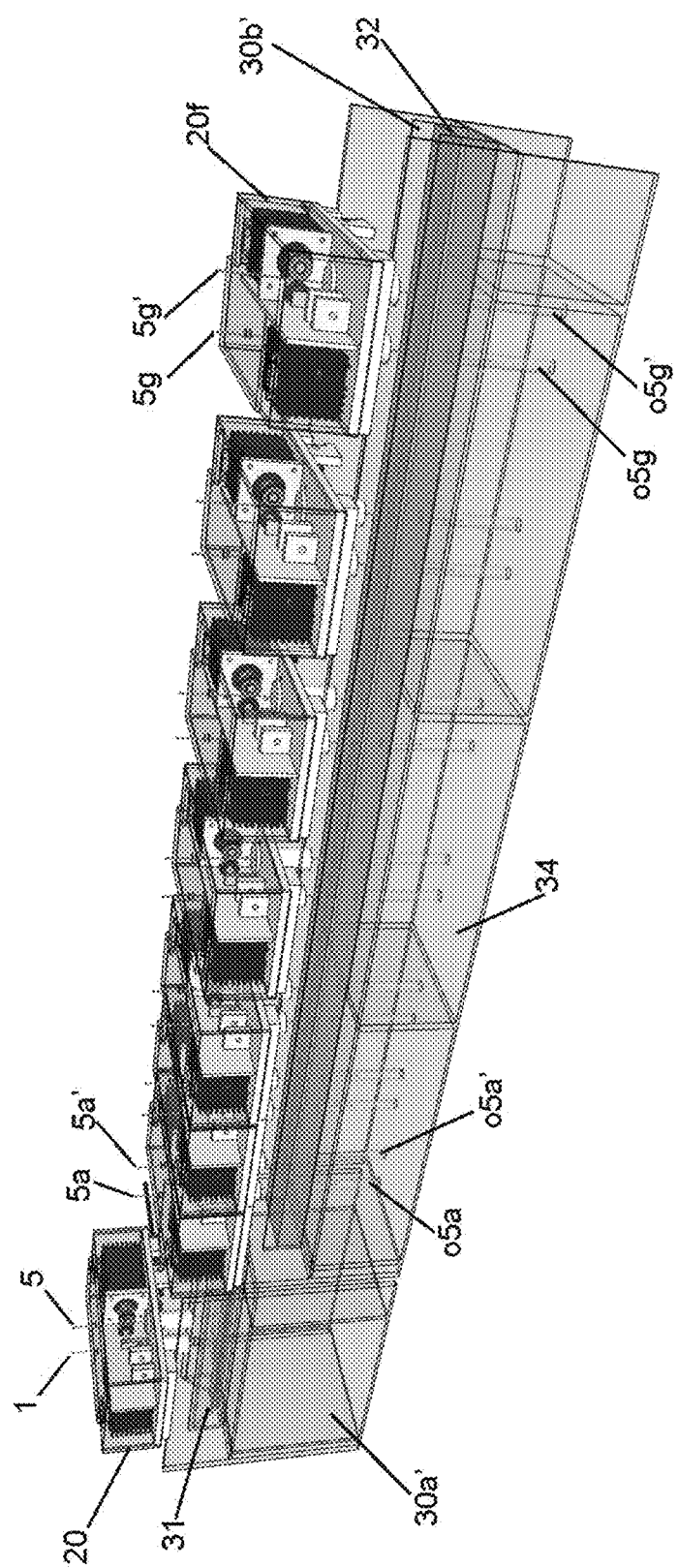
Figure 21G:
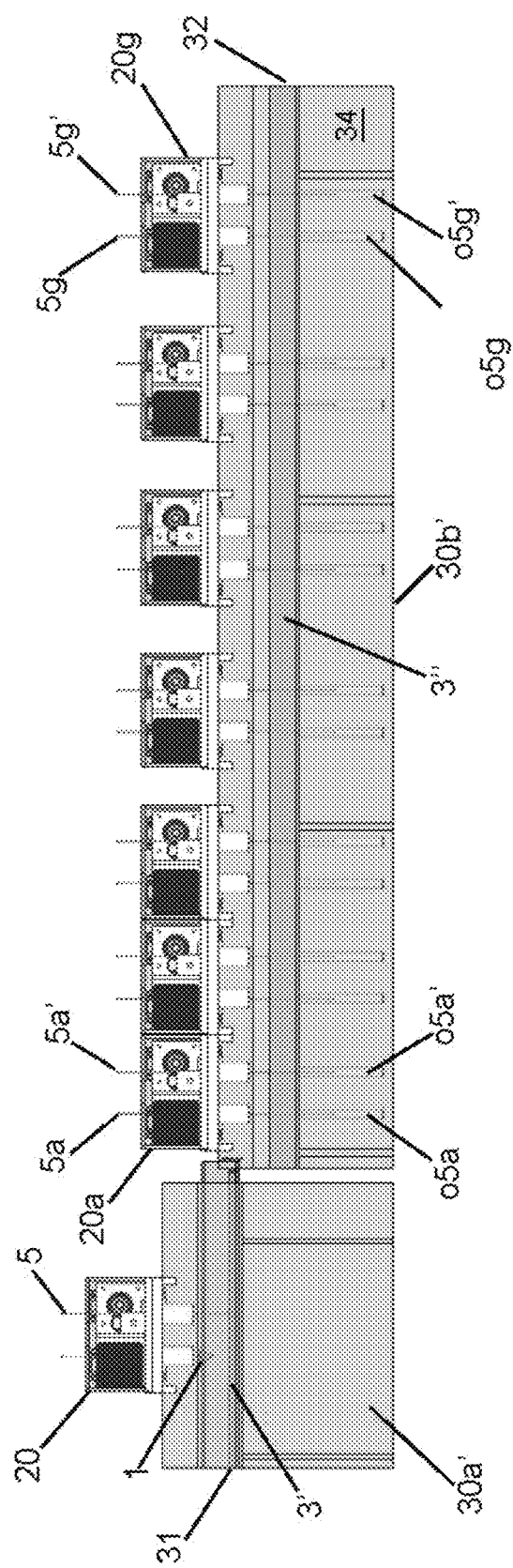

With reference to FIGS. 21e, f and g, each electrode 5/5' was first placed into contact with the liquid 3" such that it just entered the female receiver tube o5. After a certain amount of process time, gold metal was removed from each wire electrode 5 which caused the electrode 5 to thin (i.e., become smaller in diameter) which changed, for example, current density and/or the rate at which gold nanoparticles were formed. Accordingly, the electrodes 5 were moved toward the female receiver tubes o5 resulting in fresh and thicker electrodes 5 entering the liquid 3" at a top surface portion thereof. In essence, an erosion profile or tapering effect was formed on the electrodes 5 after some amount of processing time has passed (i.e., portions of the wire near the surface of the liquid 3" were typically thicker than portions near the female receiver tubes o5), and such wire electrode profile or tapering can remain essentially constant throughout a production process, if desired, resulting in essentially identical product being produced at any point in time after an initial pre-equilibrium phase during a production run allowing, for example, the process to be cGMP under current FDA guidelines and/or be ISO 9000 compliant as well.

Figure 54B:
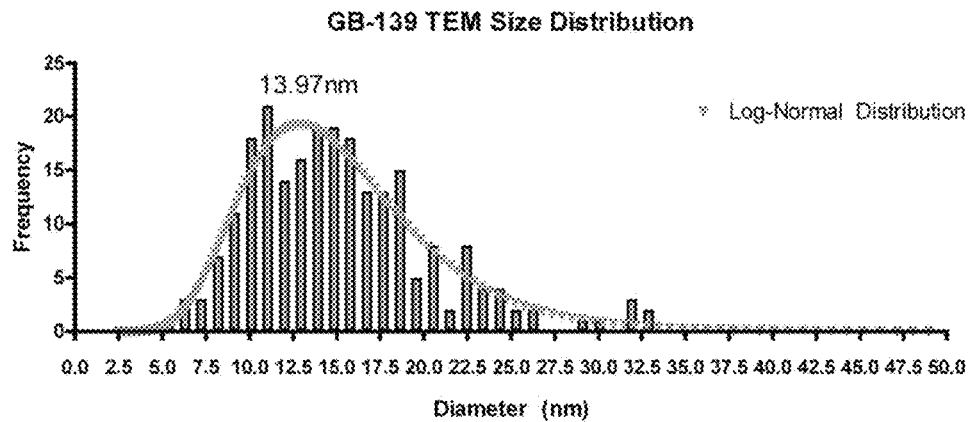
Figure 54C:
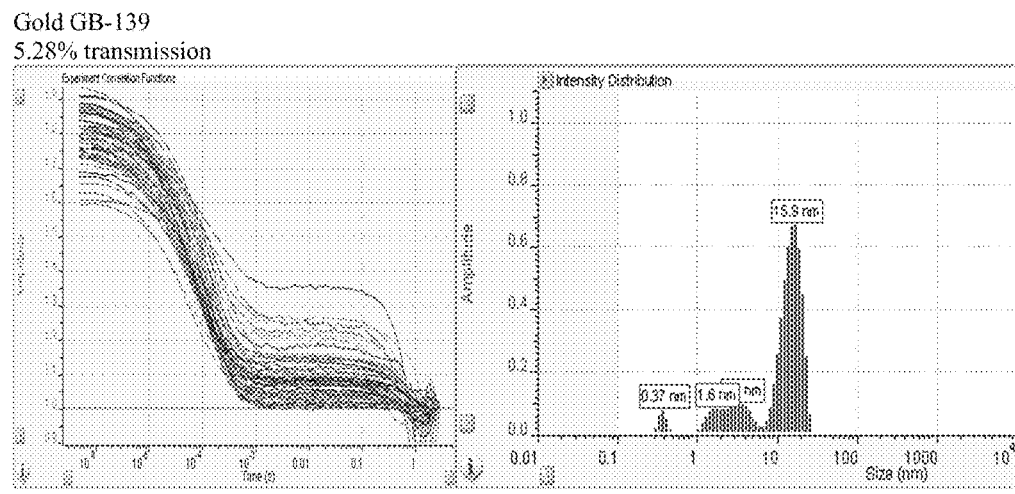

The movement of the electrodes 5 into the female receiver tubes o5 can occur by monitoring a variety of specific process parameters which change as a function of time (e.g., current, amps, nanocrystals concentration, optical density or color, conductivity, pH, etc.) or can be moved a predetermined amount at various time intervals to result in a fixed movement rate, whichever may be more convenient under the totality of the processing circumstances. In this regard, FIGS. 54d, 55d and 56d show that current was monitored/controlled as a function of time for each of the 16 electrodes used to make samples GB-139, GB-141 and GB-144, respectively, causing a vertical movement of the electrodes 5 into the female receiver tubes o5. Under these processing conditions, each electrode 5 was moved at a rate of about ¾ inch every 8 hours (about 2.4 mm/hour) to maintain the currents reported in FIGS. 54d, 55d and 56d. FIGS. 55d and 56d show a typical ramp-up or pre-equilibrium phase where the current starts around 0.2-0.4 amps and increases to about 0.4-0.75 after about 20-30 minutes. Samples were collected only from the equilibrium phase. The pre-equilibrium phase occurs because, for example, the concentration of nanocrystals produced in the liquid 3" increases as a function of time until the concentration reaches equilibrium conditions (e.g., substantially constant nucleation and growth conditions within the apparatus), which equilibrium conditions remain substantially constant through the remainder of the processing due to the control processes disclosed herein.

Energy absorption spectra were obtained for the samples in Example 16 by using UV-VIS spectroscopy. This information was acquired using a dual beam scanning monochrometer system capable of scanning the wavelength range of 190 nm to 1100 nm. The Jasco V-530 UV-Vis spectrometer was used to collect absorption spectroscopy. Instrumentation was setup to support measurement of low-concentration liquid samples using one of a number of fuzed-quartz sample holders or "cuvettes". The various cuvettes allow data to be collected at 10 mm, 1 mm or 0.1 mm optic path of sample. Data was acquired over the wavelength range using between 250-900 nm detector with the following parameters; bandwidth of 2 nm, with data pitch of 0.5 nm, a silicon photodiode with a water baseline background. Both deuterium (D2) and halogen (WI) scan speed of 400 nm/mm sources were used as the primary energy sources. Optical paths of these spectrometers were setup to allow the energy beam to pass through the center of the sample cuvette. Sample preparation was limited to filling and capping the cuvettes and then physically placing the samples into the cuvette holder, within the fully enclosed sample compartment. Optical absorption of energy by the materials of interest was determined. Data output was measured and displayed as Absorbance Units (per Beer-Lambert's Law) versus wavelength.

Spectral patterns in a UV-Visible range were obtained for each of the solutions/colloids produced in Example 16.

Figure 61B:
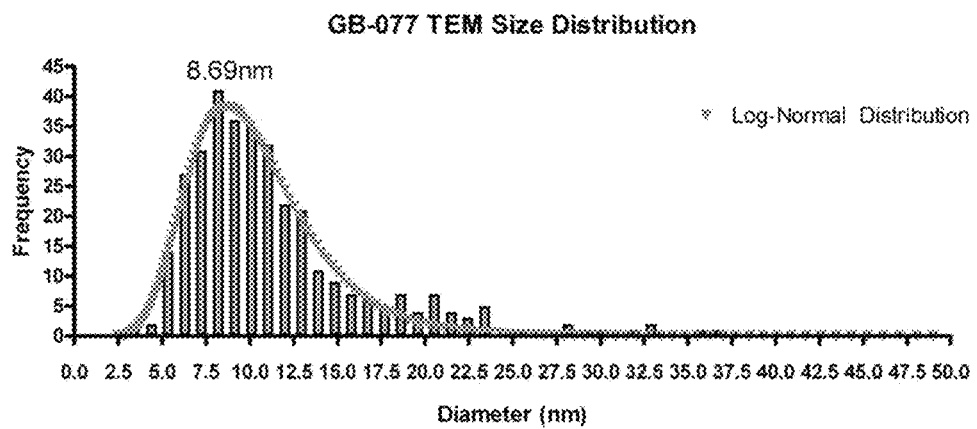
Figure 61C:
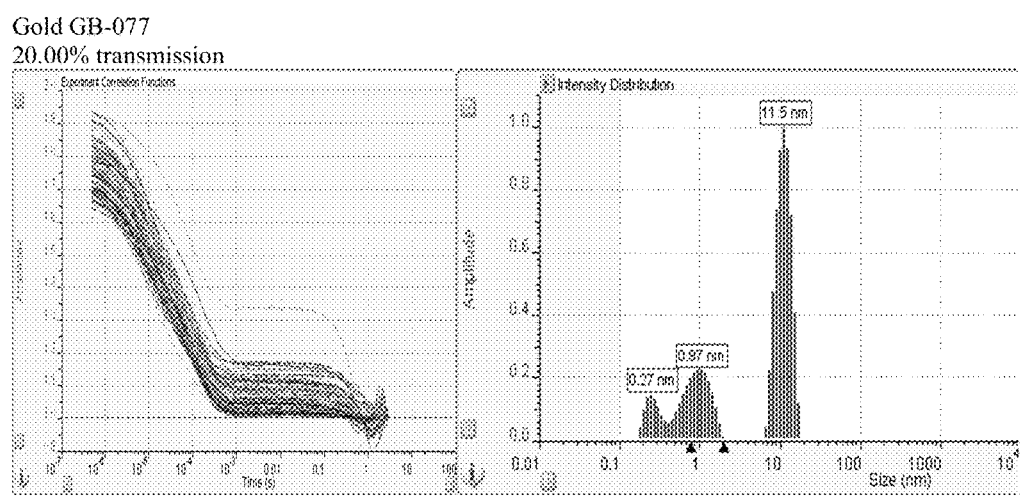
Figure 61D:
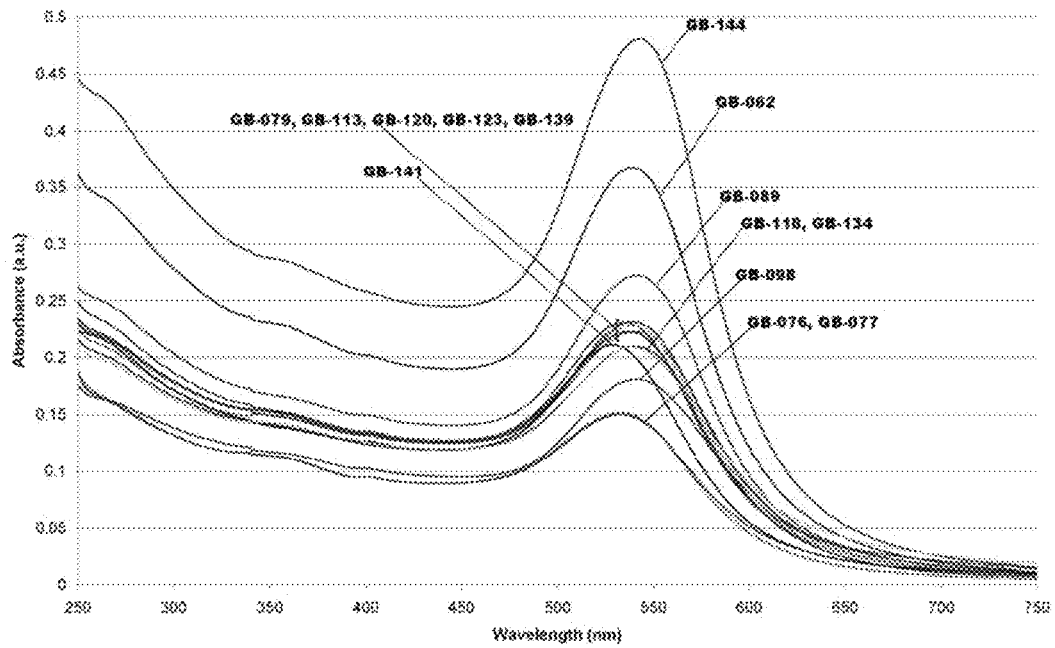
FIG. 61*d* shows the UV-Vis spectral patterns of each of the 14 suspensions/colloids made according to Example 16 (i.e., GB-098, GB-113 and GB-118); (GB-120 and GB-123); (GB-139); GB-141 and GB-144); (GB-079, GB-089 and GB-062); and (GB-076 and GB-077) over an interrogating wavelength range of about 250 nm-750 nm.

Specifically, FIG. 61d shows UV-Vis spectral patterns of each of the 14 suspensions/colloids, (GB-134) (GB-098, GB-113 and GB-118); (GB-120 and GB-123); (GB-139); (GB-141 and GB-144); (GB-079, GB-089 and GB-062); and (GB-076 and GB-077) within a wavelength range of about 250 nm-750 nm.

Figure 61E:
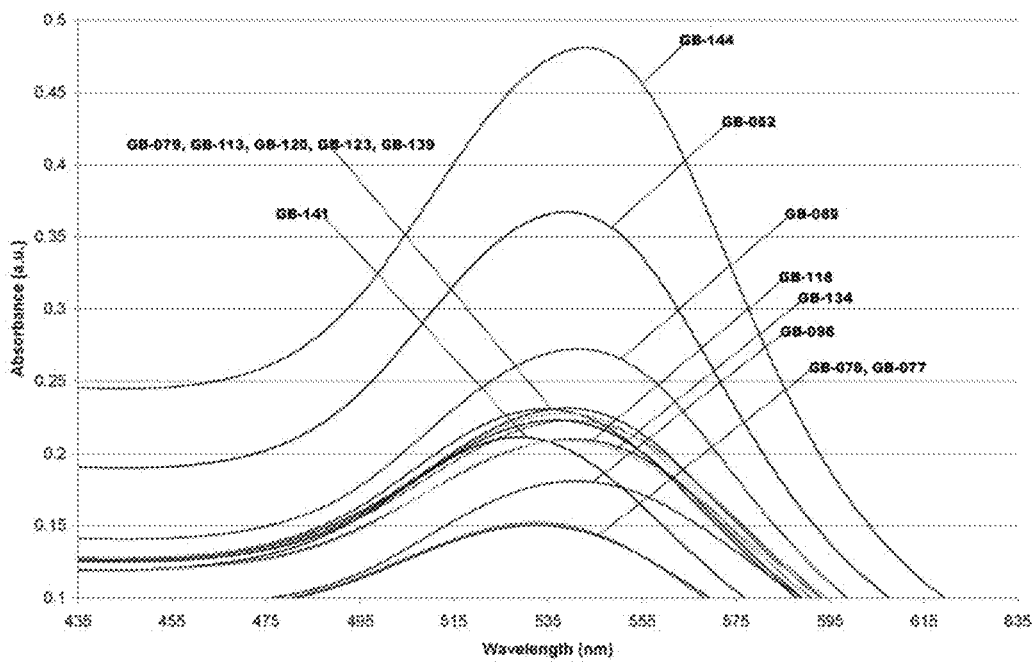
FIG. 61*e* shows the UV-Vis spectral patterns for each of the 14 suspensions over an interrogating wavelength range of about 435 nm-635 nm.
Figure 62A:
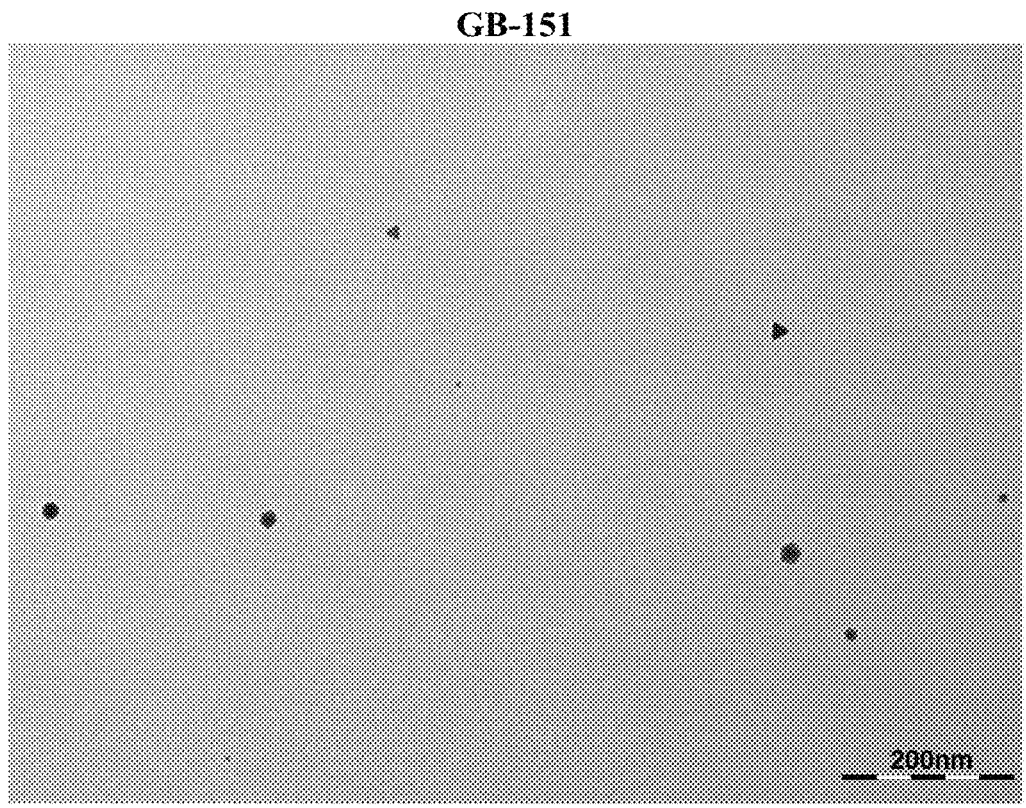
FIG. 62*a* is a representative TEM photomicrograph of gold nanocrystals from dried solution GB-151 made according to Example 18.
Figure 62B:
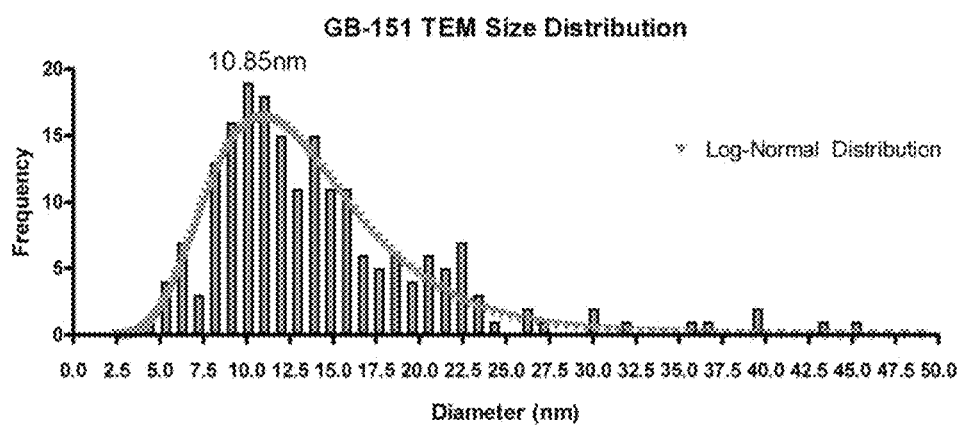
FIG. 62*b* shows a particle size distribution histogram from TEM measurements for the nanocrystals made according to GB-151.
Figure 63A:
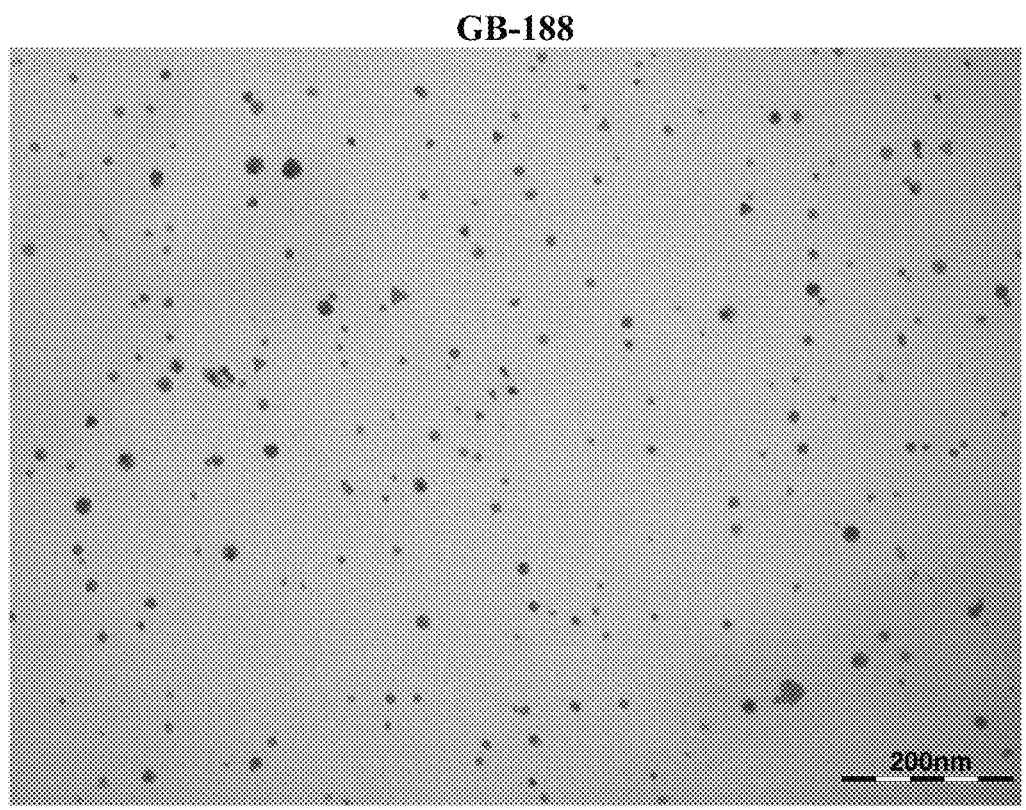
FIG. 63*a* is a representative TEM photomicrograph of gold nanocrystals from dried solution GB-188 made according to Example 18.
Figure 63B:
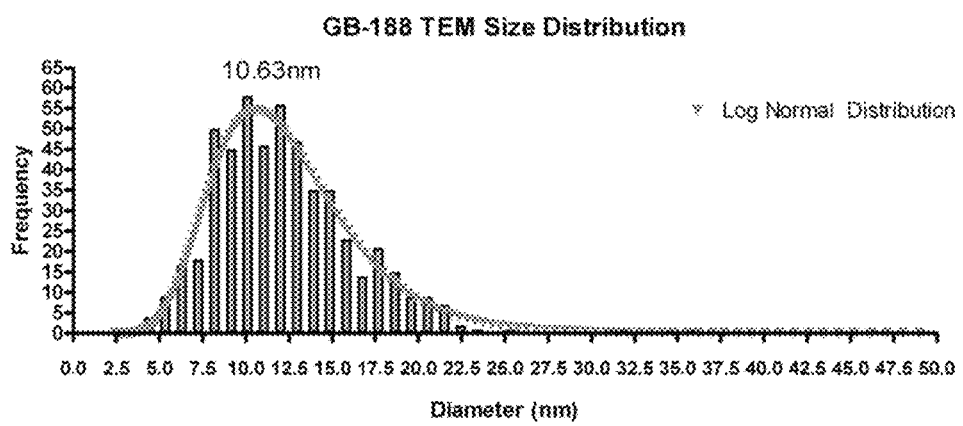
FIG. 63*b* shows a particle size distribution histogram from TEM measurements for the nanocrystals made according to GB-188.
Figure 64A:
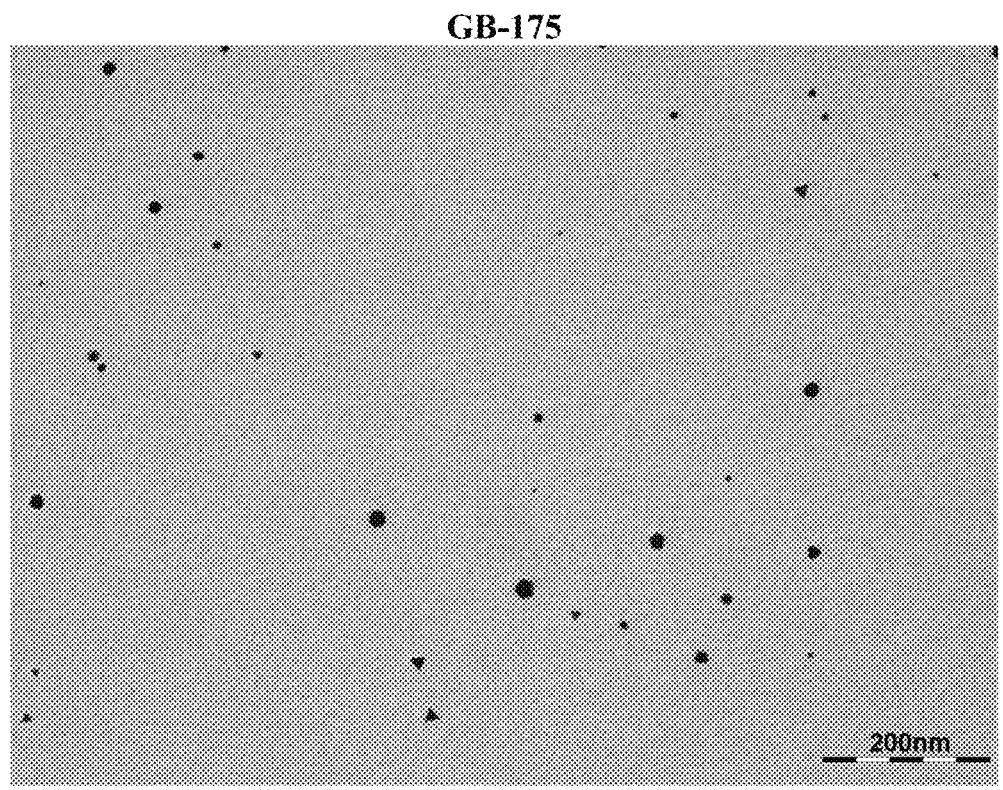
FIG. 64*a* is a representative TEM photomicrograph of gold nanocrystals from dried solution GB-175 made according to Example 18.
Figure 64B:
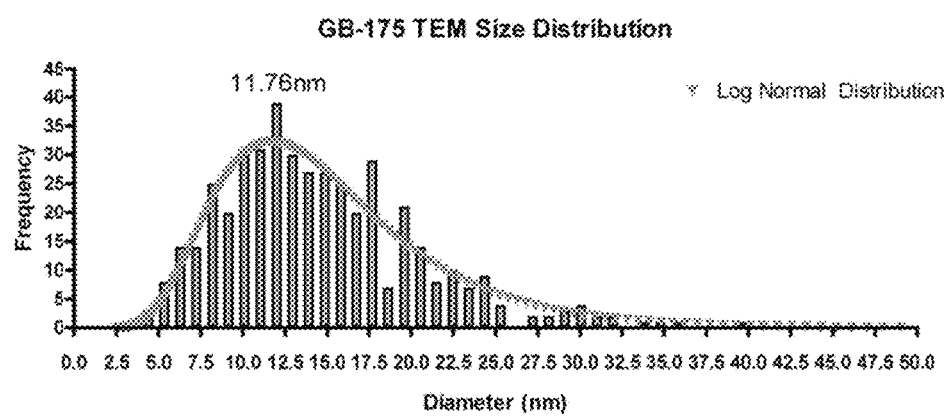
FIG. 64*b* shows a particle size distribution histogram from TEM measurements for the nanocrystals made according to GB-175.
Figure 65A:
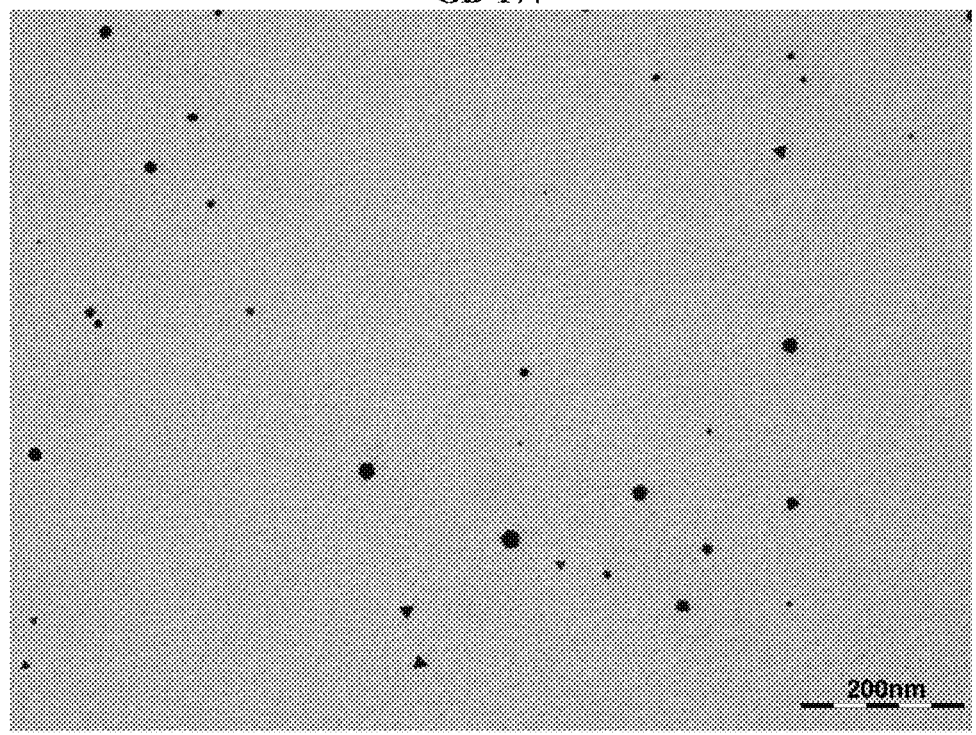
FIG. 65*a* is a representative TEM photomicrograph of gold nanocrystals from dried solution GB-177 made according to Example 18.
Figure 65B:
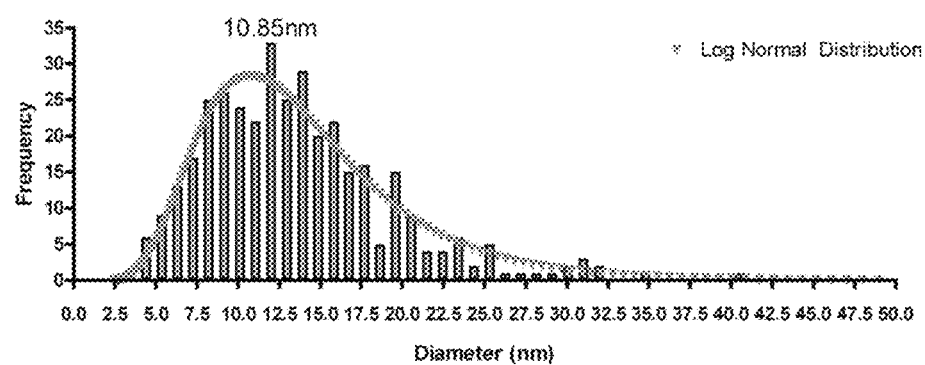
FIG. 65*b* shows a particle size distribution histogram from TEM measurements for the nanocrystals made according to GB-177.
Figure 66A:
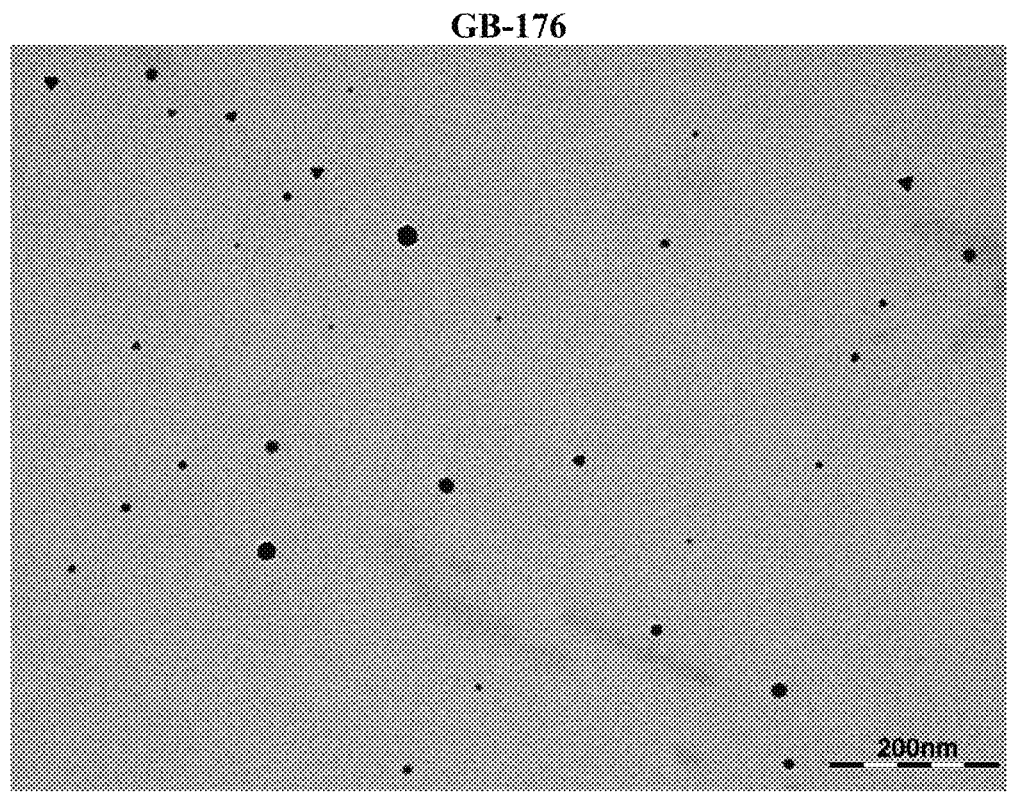
FIG. 66*a* is a representative TEM photomicrograph of gold nanocrystals from dried solution GB-176 made according to Example 18.
Figure 66B:
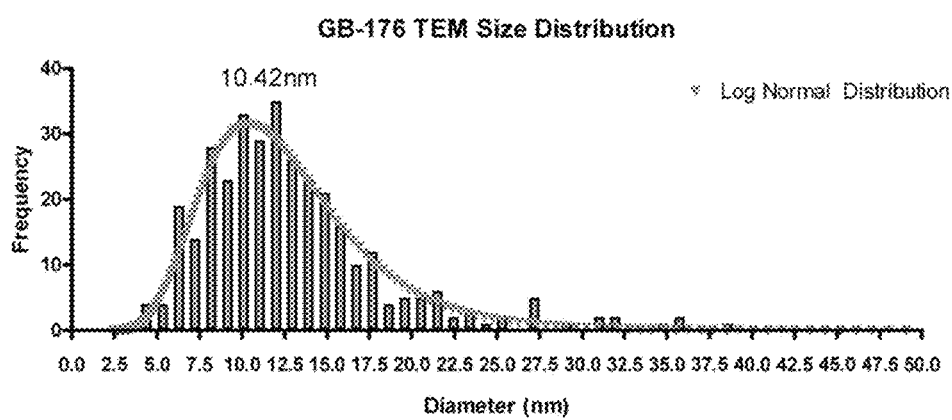
FIG. 66*b* shows a particle size distribution histogram from TEM measurements for the nanocrystals made according to GB-176.
Figure 67A:
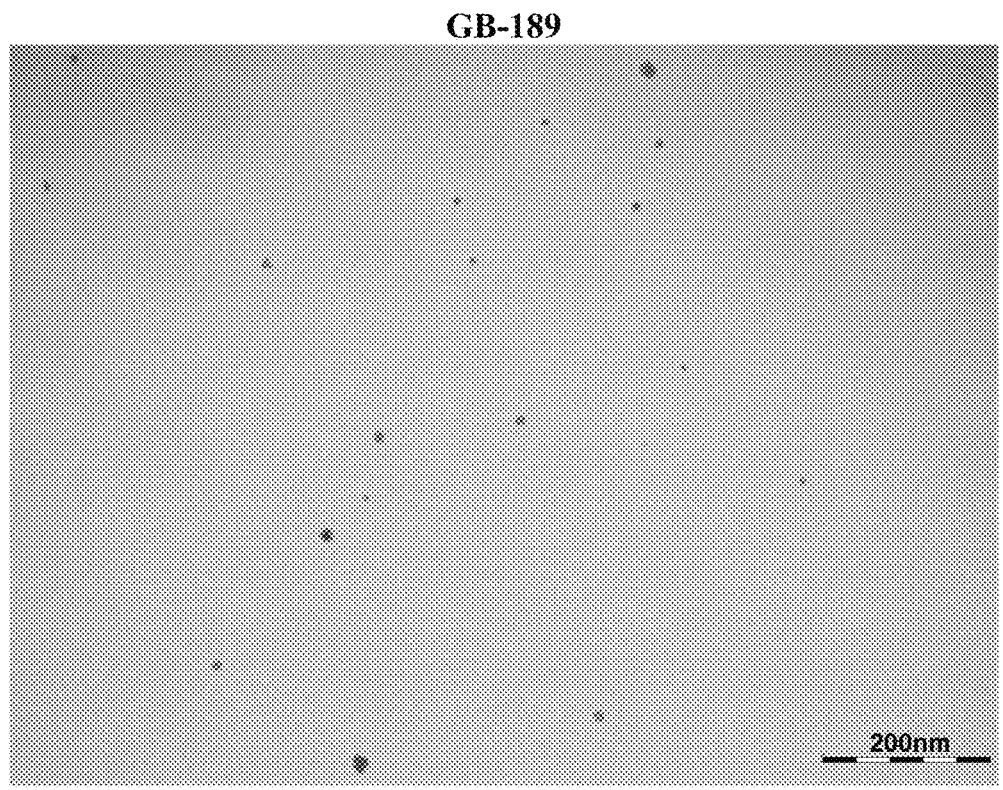
FIG. 67*a* is a representative TEM photomicrograph of gold nanocrystals from dried solution GB-189 made according to Example 18.
Figure 67B:
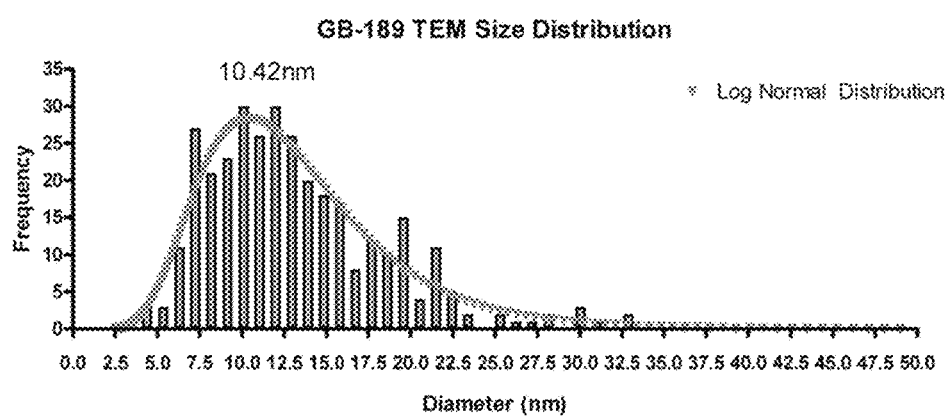
FIG. 67*b* shows a particle size distribution histogram from TEM measurements for the nanocrystals made according to GB-189.
Figure 68A:
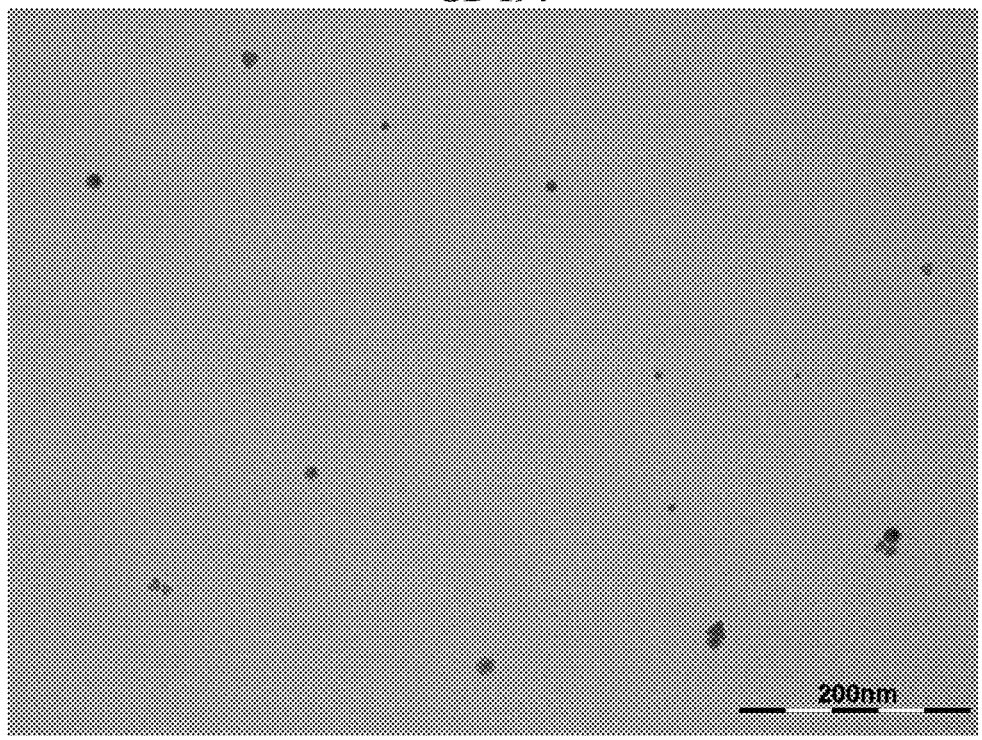
FIG. 68*a* is a representative TEM photomicrograph of gold nanocrystals from dried solution GB-194 made according to Example 18.
Figure 68B:
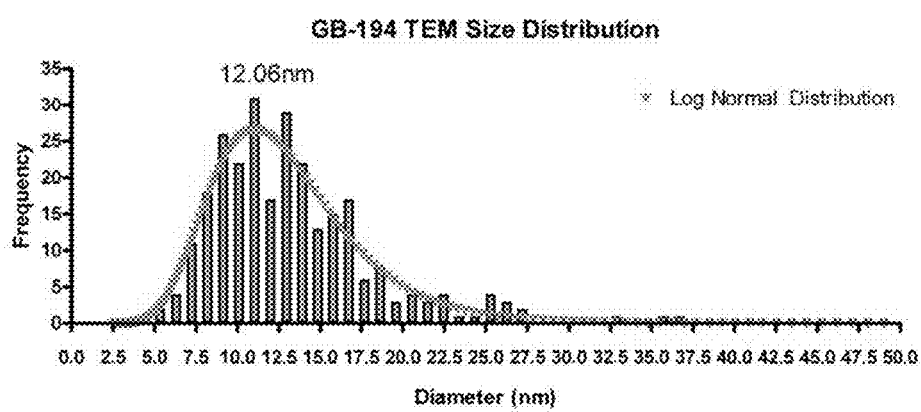
FIG. 68*b* shows a particle size distribution histogram from TEM measurements for the nanocrystals made according to GB-194.
Figure 69A:
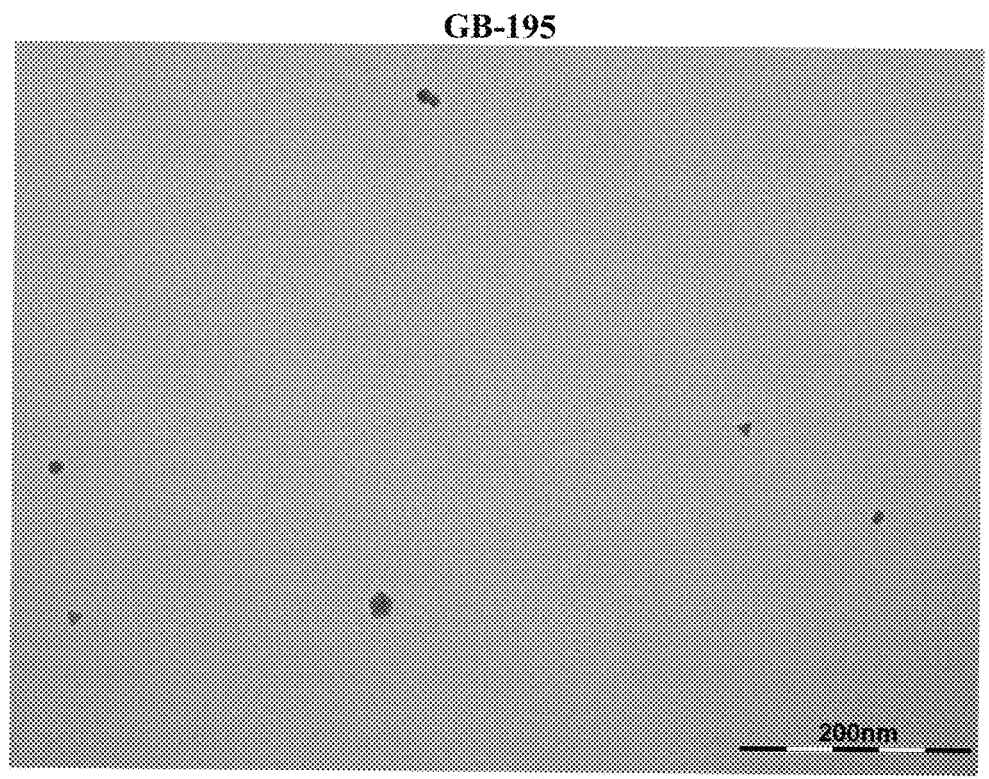
FIG. 69*a* is a representative TEM photomicrograph of gold nanocrystals from dried solution GB-195 made according to Example 18.
Figure 69B:
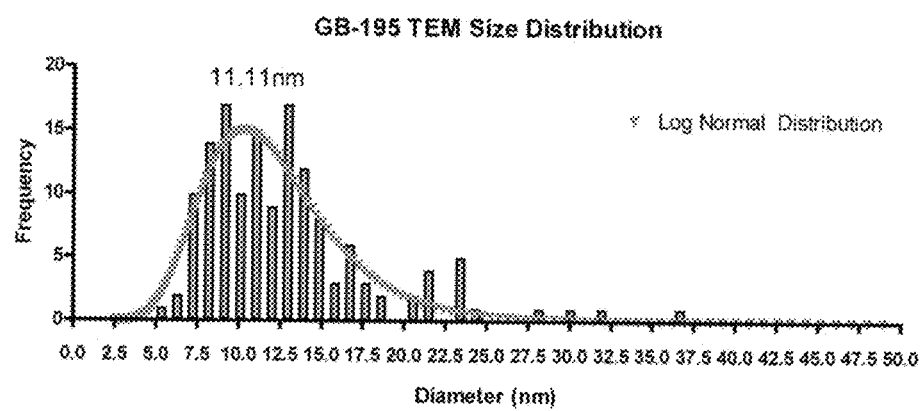
FIG. 69*b* shows a particle size distribution histogram from TEM measurements for the nanocrystals made according to GB-195.
Figure 70A:
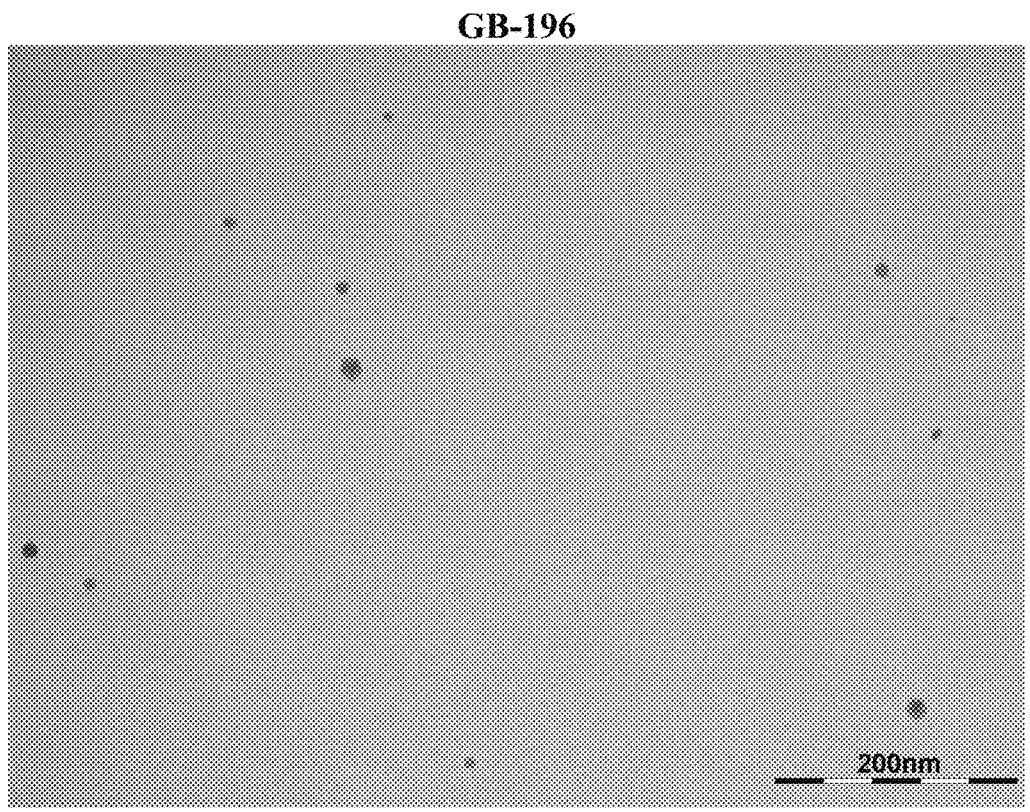
FIG. 70*a* is a representative TEM photomicrograph of gold nanocrystals from dried solution GB-196 made according to Example 18.
Figure 70B:
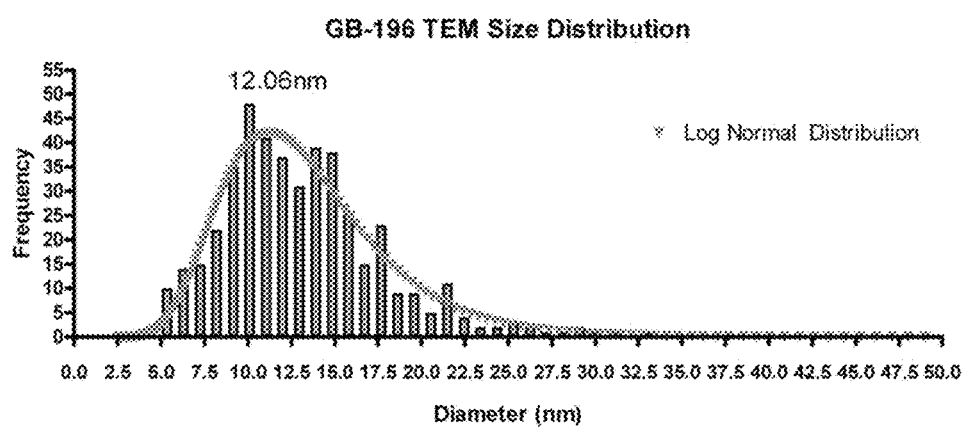
FIG. 70*b* shows a particle size distribution histogram from TEM measurements for the nanocrystals made according to GB-196.

FIG. 61e shows the UV-Vis spectral pattern for each of the 14 suspensions/colloids over a wavelength range of about 435 nm-635 nm.

In general, UV-Vis spectroscopy is the measurement of the wavelength and intensity of absorption of near-ultraviolet and visible light by a sample. Ultraviolet and visible light are energetic enough to promote outer electrons to higher energy levels. UV-Vis spectroscopy can be applied to molecules and inorganic ions or complexes in solution or suspension.

The UV-Vis spectra have broad features that can be used for sample identification but are also useful for quantitative measurements. The concentration of an analyte in solution can be determined by measuring the absorbance at some wavelength and applying the Beer-Lambert Law.

Example 17

Manufacturing Gold-Based Nanocrystals/Nanocrystal Suspension GB-056

Figure 18A:
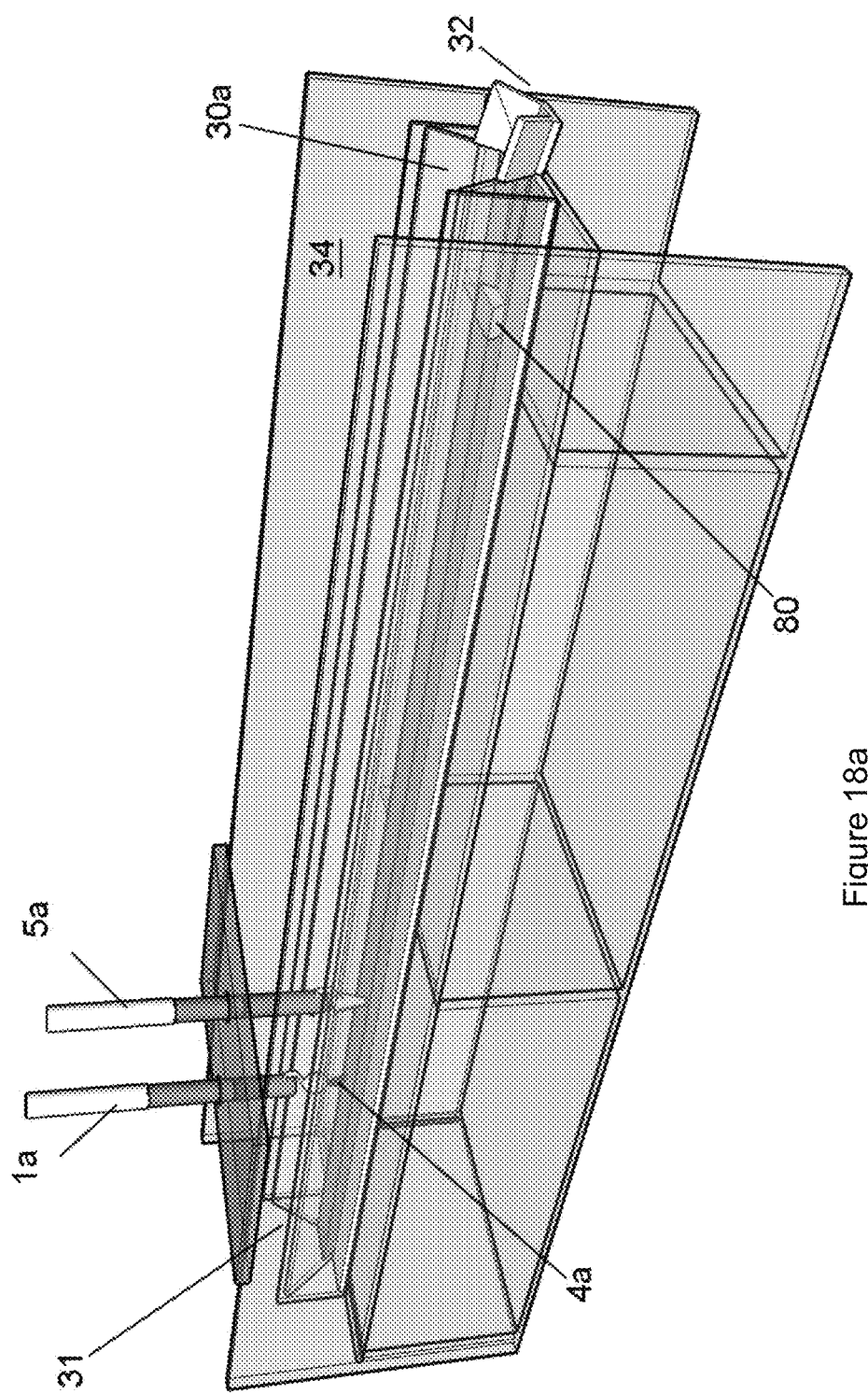
FIGS. 18a and 18b show a first trough member 30a wherein one or more plasma(s) 4 is/are created. The output of this first trough member 30a flows into a second trough member 30b, as shown in FIGS. 19a and 19b.
Figure 18B:
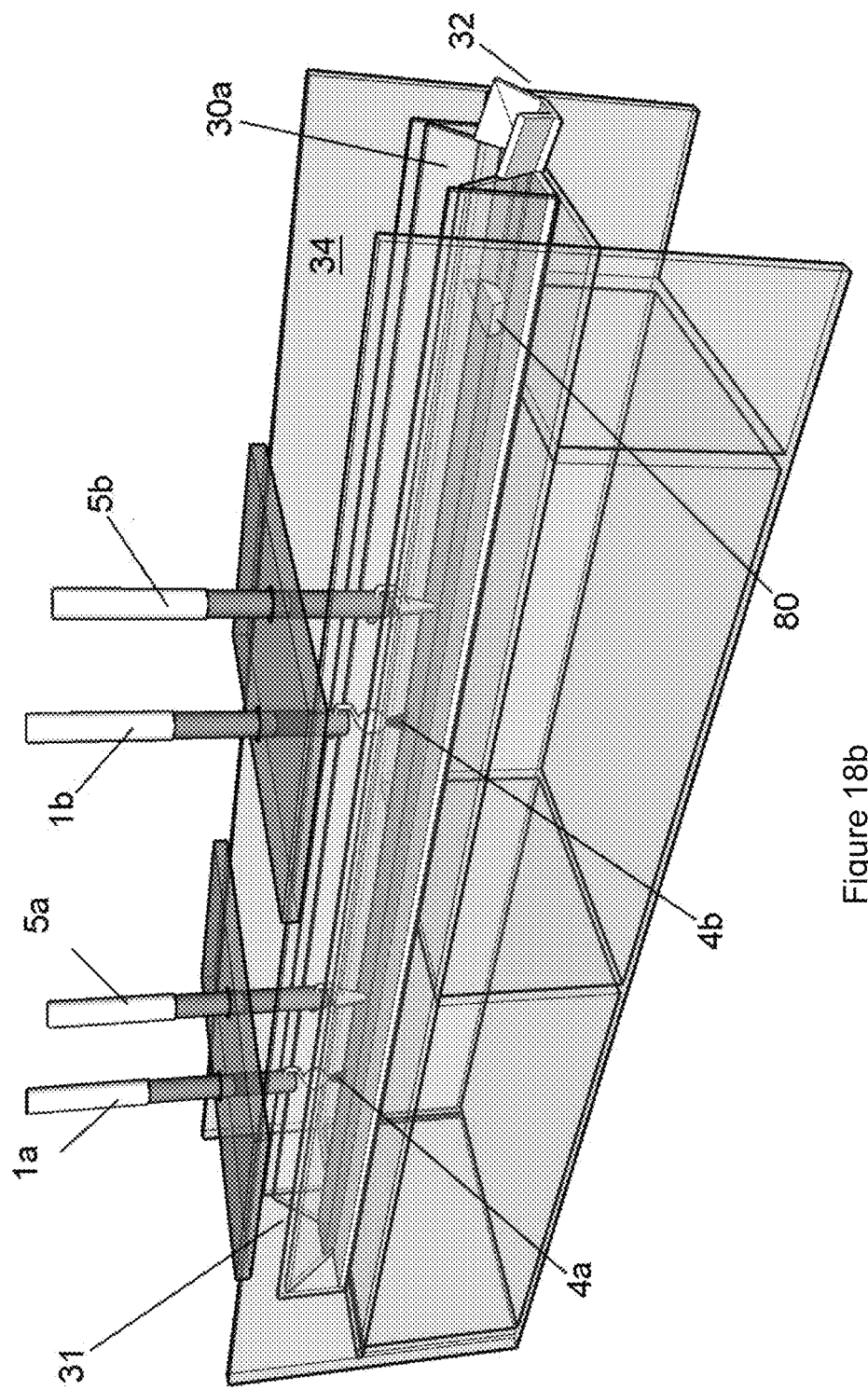
Figure 20A:
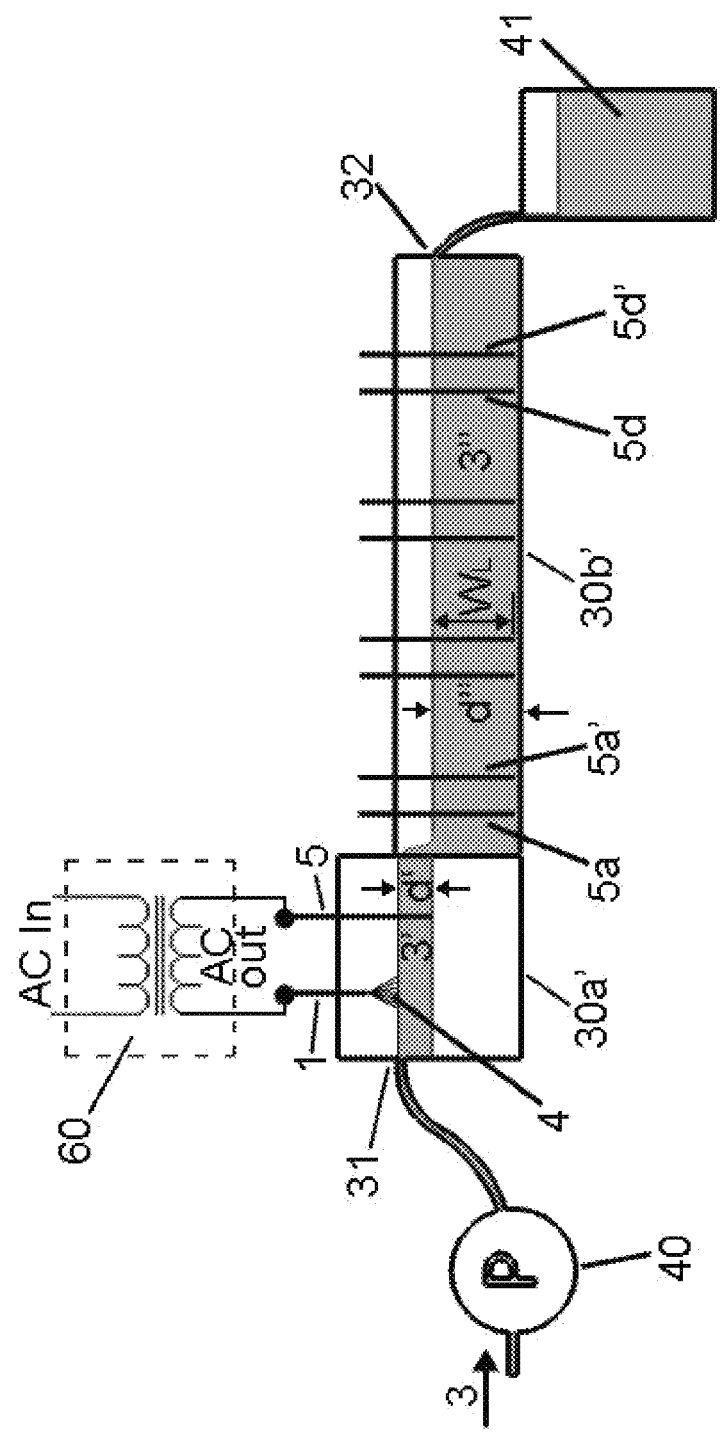
FIGS. 20a-20h are alternatives of the apparatus shown in FIGS. 19a and 19b (again having different electrode 5 wiring arrangements and/or different numbers of electrodes), wherein the trough members 30a' and 30b' are contiguous.
Figure 20B:
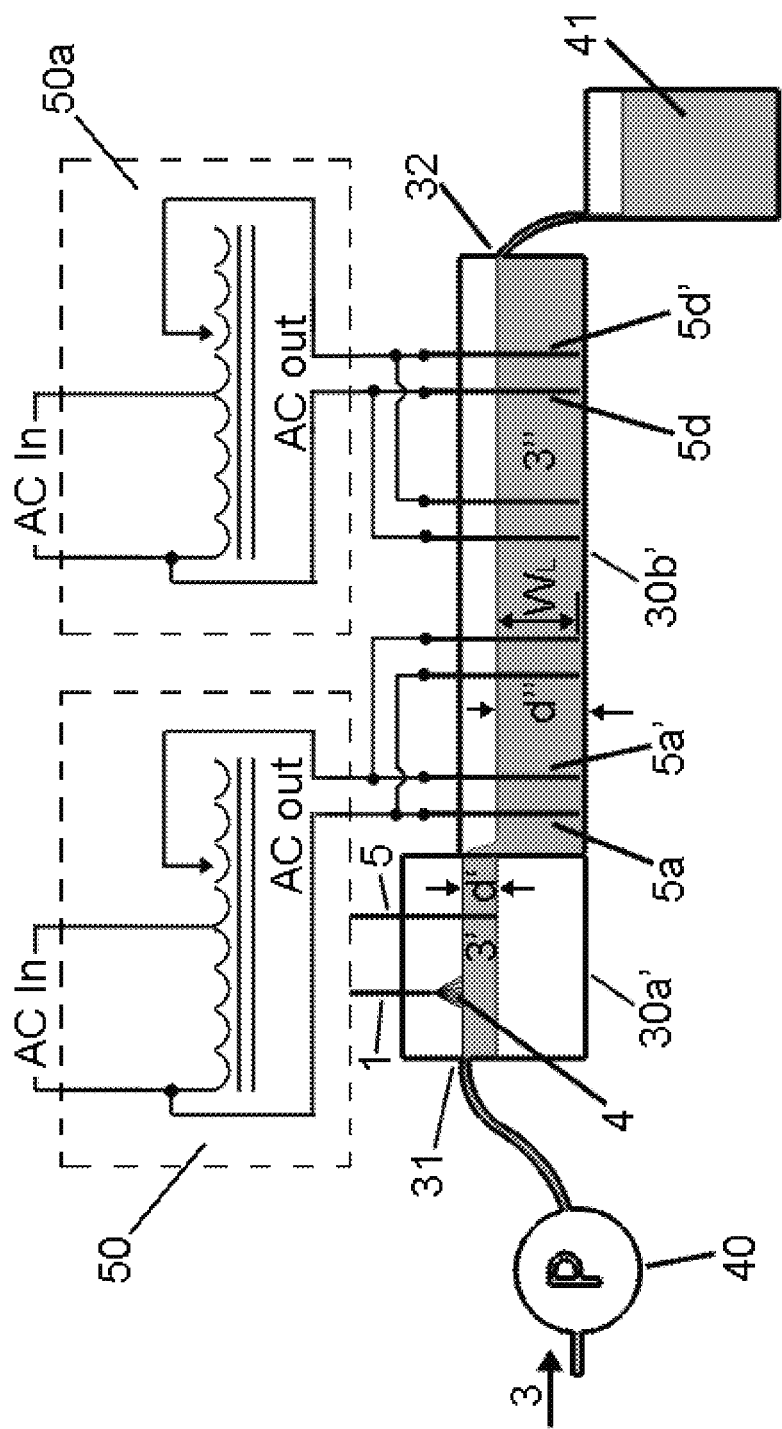
Figure 20C:
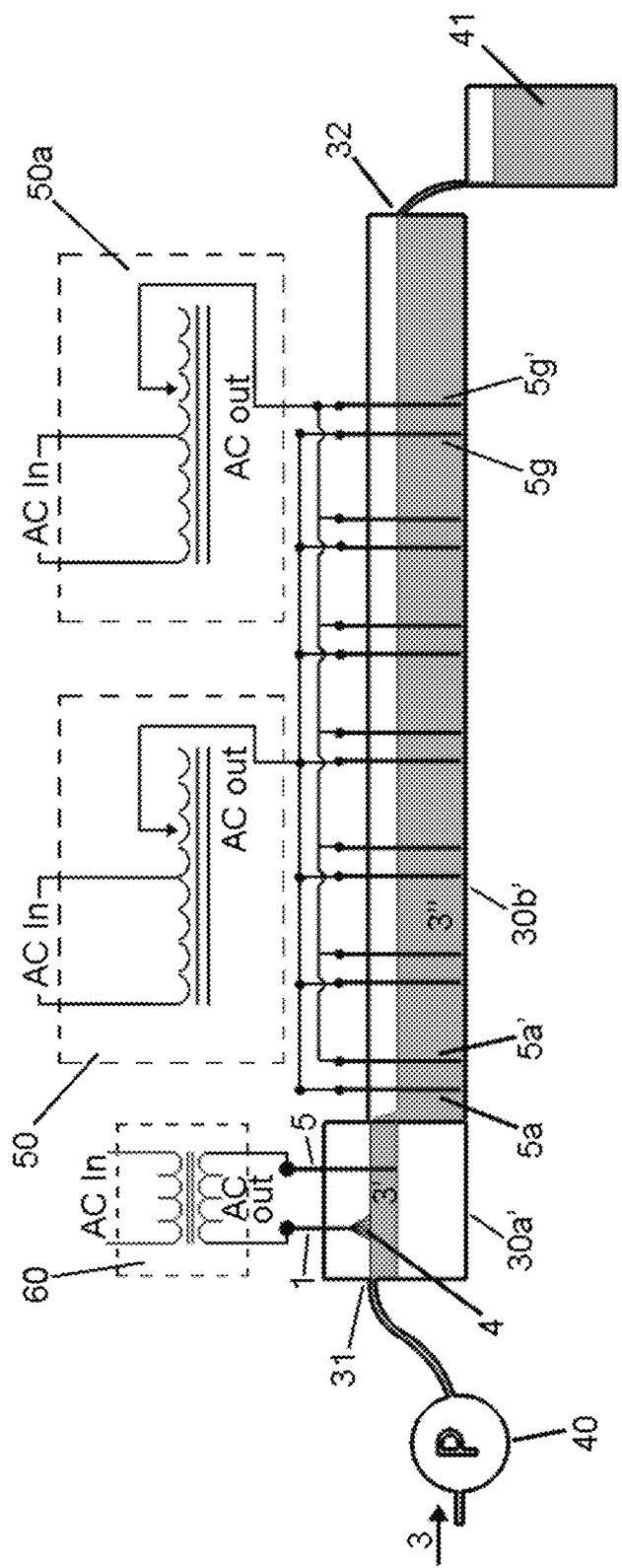
Figure 20D:
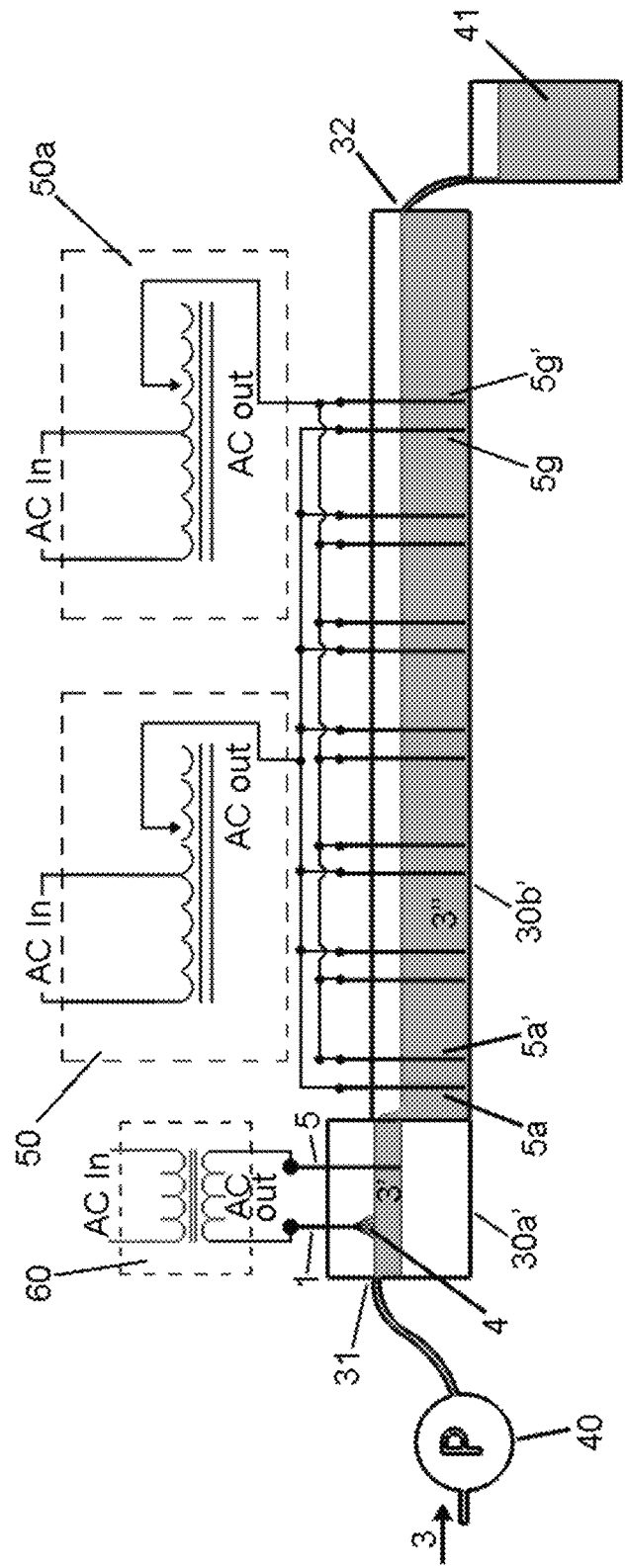
Figure 20E:
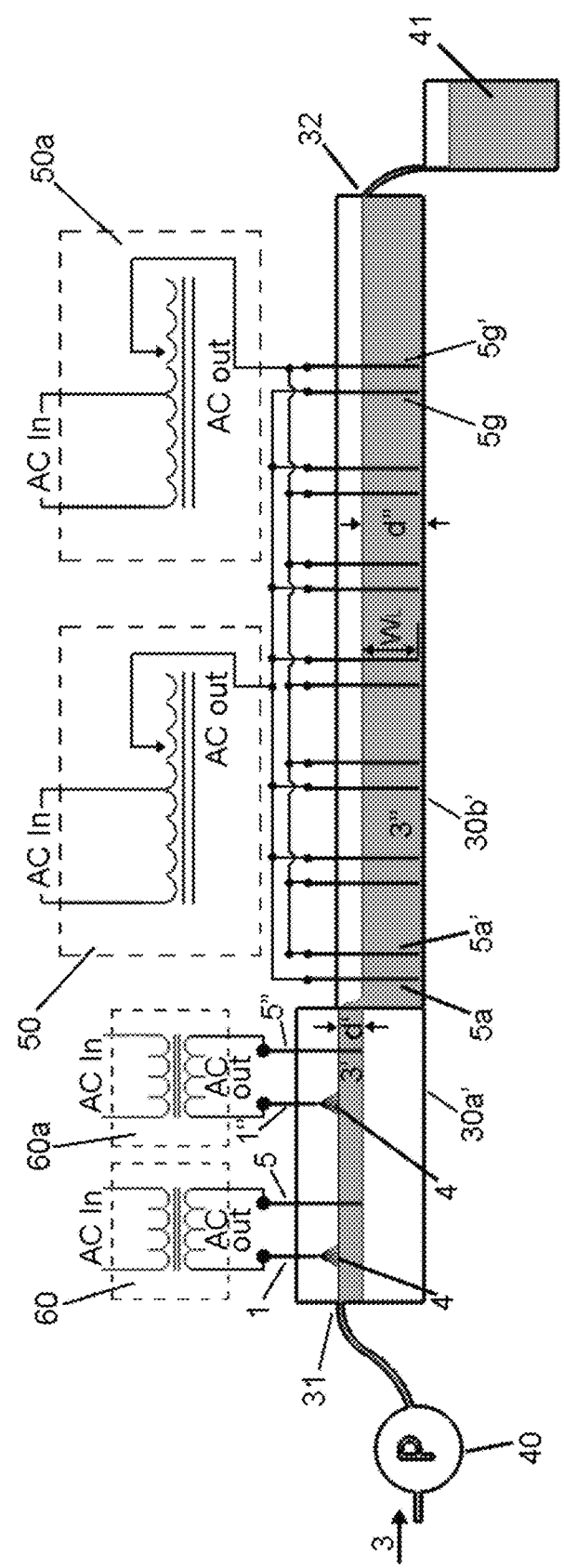
Figure 20F:
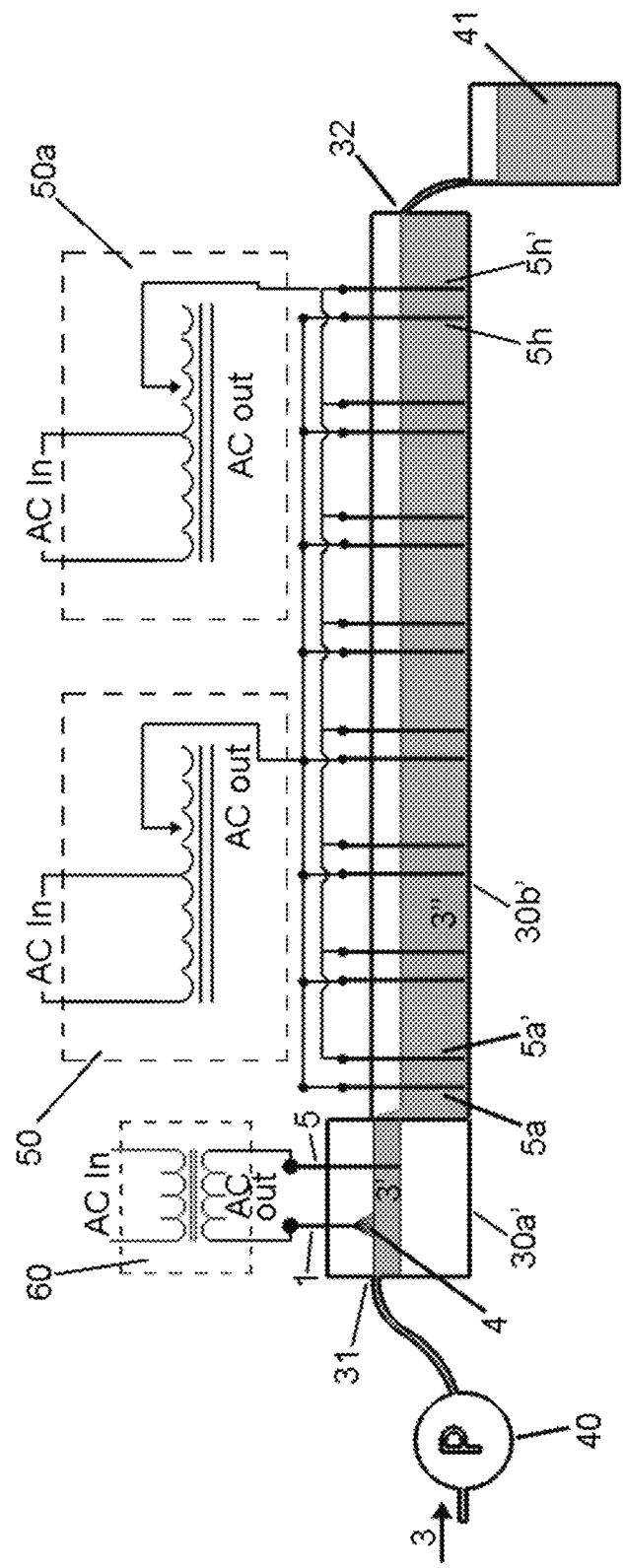
Figure 20G:
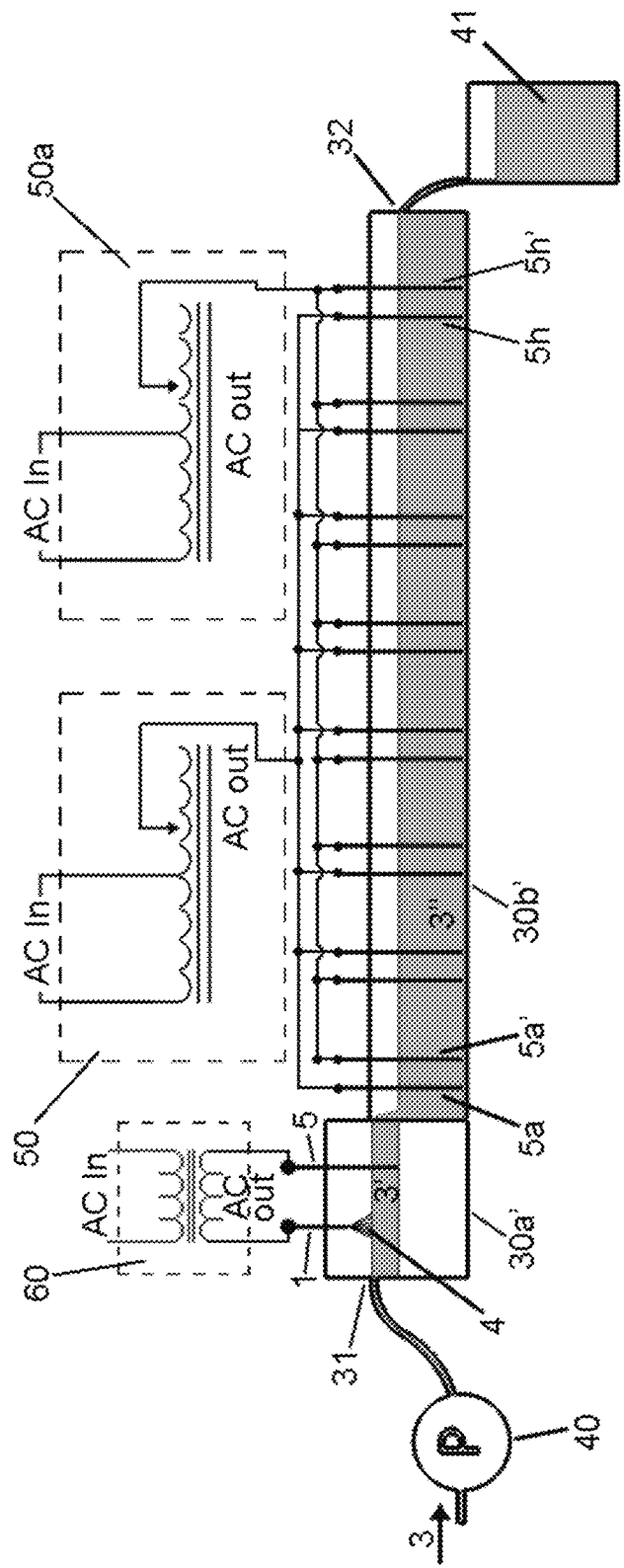
Figure 20H:
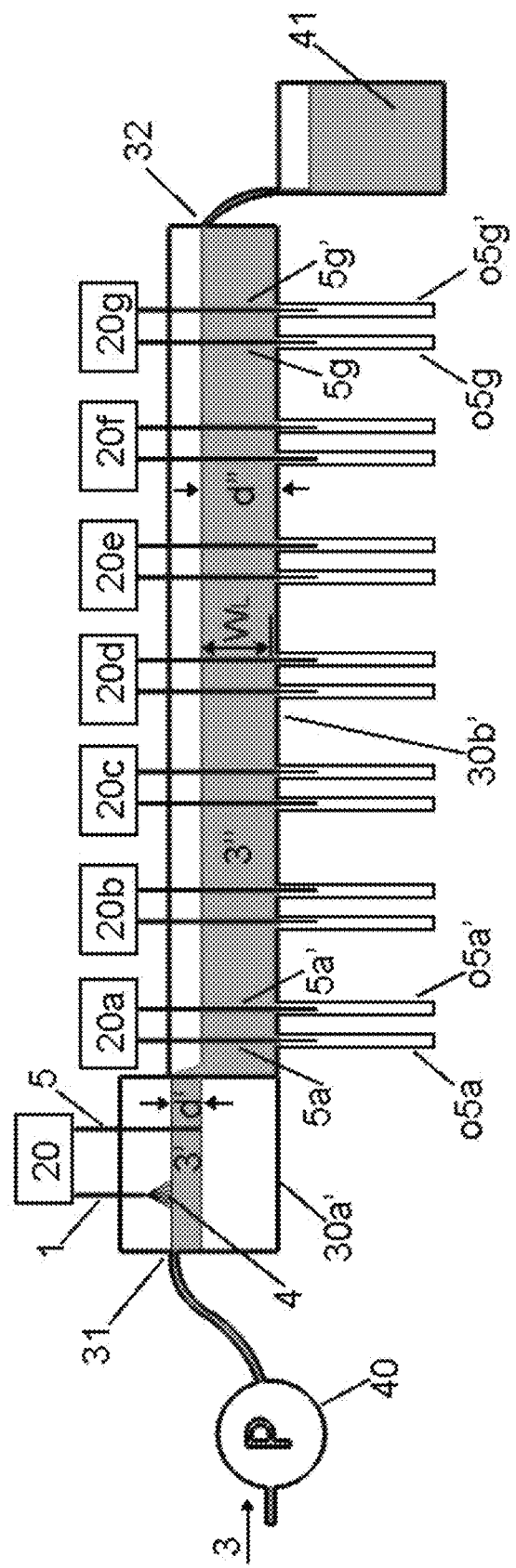

In general, Example 17 utilizes certain embodiments of the invention associated with the apparatuses generally shown in FIGS. 17a, 18a, 20b and 22a. The trough members 30a (30a') and 30b were made from ¼" (about 6 mm) thick plexiglass, and ⅛" (about 3 mm) thick polycarbonate, respectively. The support structure 34 was also made from plexiglass which was about ¼" thick (about 6-7 mm thick). As shown in FIG. 20b, the trough member 30a was integrated with trough member 30b' and was designated 30a' (e.g., no separate pumping means was provided after trough member 30a, as in certain previous examples). The cross-sectional shape of the trough member 30a' as shown in FIGS. 18a and 20b corresponds to that shape shown in FIG. 10b (i.e., a truncated "V"). The base portion "R" of the truncated "V" measured about 0.5" (about 1 cm), and each side portion "S", "S'" measured about 1.5" (about 3.75 cm). The distance "M" separating the side portions "S", "S'" of the V-shaped trough member 30a was about 2¼"-2⅚" (about 5.9 cm) (measured from inside to inside). The thickness of each sidewall portion also measured about ⅛" (about 3 mm) thick. The longitudinal length "$L_T$" (refer to FIG. 11a) of the V-shaped trough member 30a' measured about 1 foot (about 30 cm) long from point 31 to point 32.

Purified water (discussed elsewhere herein) was mixed with about 0.396 g/L of $NaHCO_3$ and was used as the liquid 3 input into trough member 30a'. The depth "d" (refer to FIG. 10b) of the liquid 3' in the V-shaped trough member 30a' was about 7/16" to about ½" (about 11 mm to about 13 mm) at various points along the trough member 30a'. The depth "d" was partially controlled through use of the dam 80 (shown in FIG. 18a). Specifically, the dam 80 was provided near the end 32 and assisted in creating the depth "d" (shown in FIG. 10b) to be about ⅞"-½" (about 11-13 mm) in depth. The height "j" of the dam 80 measured about ¼" (about 6 mm) and the longitudinal length "k" measured about ½" (about 13 mm). The width (not shown) was completely across the bottom dimension "R" of the trough member 30a'. Accordingly, the total volume of liquid 3' in the V-shaped trough member 30a' during operation thereof was about 2.14 in³ (about 35 ml).

The rate of flow of the liquid 3' into the trough member 30a' was about 150 ml/minute and the rate of flow out of the trough member 30b' at the point 32 was about 110 ml/minute (i.e., due to evaporation). Such flow of liquid 3' was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30'a by a flow diffusion means located therein. The flow diffusion means tended to minimize disturbance and bubbles in water 3 introduced into the trough member 30a' as well as any pulsing condition generated by the peristaltic pump 40. In this regard, a small reservoir served as the diffusion means and was provided at a point vertically above the end 31 of the trough member 30a' such that when the reservoir overflowed, a relatively steady flow of liquid 3' into the end 31 of the V-shaped trough member 30a' occurred.

There was a single electrode set 1a/5a utilized in this Example 17. The plasma 4 was created with an electrode 1 similar in shape to that shown in FIG. 5e, and weighed about 9.2 grams. This electrode was 99.95% pure gold. The other electrode 5a comprised a right-triangular shaped platinum plate measuring about 14 mm×23 mm×27 mm and about 1 mm thick and having about 9 mm submerged in the liquid 3'. All other pertinent run conditions are shown in Table 10.

As shown in FIG. 20b, the output from the trough member 30a' was the conditioned liquid 3' and this conditioned liquid 3' flowed directly into a second trough member 30b'. The second trough member 30b', shown in FIG. 22a measured about 3.75 inches high, about 3.75 inches wide at the end 32 thereof, and about 1 inch wide at the end 31 thereof. This trough member 30b' contained about 1450 ml of liquid 3" therein which was about 2.5 inches deep. In this Example, each of four electrode sets 5a, 5a'-5d, 5d' comprised 99.95% pure gold wire measuring about 0.5 mm in diameter. The length of each wire 5 measured about 5 inches (about 12 cm) long. The liquid 3" was about 2.5 inches deep (about 6 cm) with about 4.25 inches (about 11 cm) of the j-shaped wire being submerged therein. Each electrode set 5b, 5b'-5e, 5e' was shaped like a "J", as shown in FIG. 17a. The distance "g" shown in FIG. 17a measured about 1-8 mm.

With regard to FIGS. 20b and 22a, 4 separate electrode sets (Set 2, Set 3, Set 4 and Set 5) were attached to 2 separate transformer devices, 50 and 50a as shown in FIG. 20b. Specifically, transformers 50 and 50a were electrically connected to each electrode set, according to the wiring diagram show in FIG. 19a. Each transformer device 50, 50a was connected to a separate AC input line that was 120° out of phase relative to each other. The transformers 50 and 50a were electrically connected in a manner so as not to overload a single electrical circuit and cause, for example, an upstream circuit breaker to disengage (e.g., when utilized under these conditions, a single transformer 50/50a could draw sufficient current to cause upstream electrical problems). Each transformer 50/50a was a variable AC transformer constructed of a single coil/winding of wire. This winding acts as part of both the primary and secondary winding. The input voltage was applied across a fixed portion of the winding. The output voltage was taken between one end of the winding and another connection along the winding. By exposing part of the winding and making the secondary connection using a sliding brush, a continuously variable ratio was obtained. The ratio of output to input voltages is equal to the ratio of the number of turns of the winding they connect to. Specifically, each transformer was a Mastech TDGC2-5 kVA, 10A Voltage Regulator, Output 0-250V.

Table 6 refers to each of the 4 electrode sets by "Set #". Each electrode of the 4 electrode sets was set to operate within a specific voltage range. The actual voltages, listed in Table 10, were about 255 volts. The distance "c-c" (with reference to FIG. 14) from the centerline of each electrode set to the adjacent electrode set is also represented. Further, the distance "x" associated with the electrode 1 utilized is also reported. For the electrode 5, no distance "x" is reported. Other relevant parameters are reported in Table 6.

All materials for the electrodes 1/5 were obtained from ESPI having an address of 1050 Benson Way, Ashland, Oreg. 97520.

TABLE 6

0.396 mg/ml of NaHCO$_3$ (Au)

| Run ID: | GB-056 |
| --- | --- |
| Flow Rate: | 150 ml/min |
| Voltage: | 255 V |
| NaHCO$_3$: | 0.396 mg/ml |
| Wire Dia.: | .5 mm |
| Configuration: | J/J |
| PPM: | 12 |

| Set# | Electrode # | Distance "c-c" in/mm | Distance "x" in/mm | Voltage | cross section |
| --- | --- | --- | --- | --- | --- |
| 1 | 1a | 4.5/114.3* | 0.25/6.35 | 750 | V |
|   | 5a |  | N/A | 750 |   |
|   |    | 23/584.2** |   |   |   |
| 2 | 5b | 2.5/63.5* | N/A | 255 |   |
|   | 5b' |  | N/A |   |   |
|   |    | 3.5/88.9 |   |   |   |
| 3 | 5c |  | N/A | 255 |   |
|   | 5c' |  | N/A |   |   |
|   |    | 3.5/88.9 |   |   | Tapered 3" Deep |
| 4 | 5d |  | N/A | 255 |   |
|   | 5d' |  | N/A |   |   |
|   |    | 3.5/88.9 |   |   |   |
| 5 | 5e |  | N/A | 255 |   |
|   | 5e' |  | N/A |   |   |
|   |    | 376.2** |   |   |   |
|   |    |   |   |   | Output Water Temperature 98 C. |

*Distance from water inlet to center of first electrode set
**Distance from center of last electrode set to water outlet FIGS. 100a-e show five representative TEM photomicrographs of the gold nanocrystals, dried from the solution/colloid GB-056, formed according to Example 16.

FIG. 101a shows the measured size distribution of the gold nanocrystals dried from the suspension/colloid measured by using the TEM instrument/software discussed earlier in Examples 5-7.

FIG. 101b shows graphically three dynamic light scattering data measurement sets for the nanocrystals (i.e., the hydrodynamic radii) made according to this Example 17. It should be noted that the dynamic light scattering particle size information is different from the TEM measured histograms because dynamic light scattering uses algorithms that assume the nanocrystals are all spheres (which they are not) as well as measures the hydrodynamic radius (e.g., the nanocrystal's influence on the water is also detected and reported in addition to the actual physical radii of the nanocrystals). Accordingly, it is not surprising that there is a difference in the reported nanocrystal sizes between those reported in the TEM histogram data of those reported in the dynamic light scattering data just as in the other Examples included herein.

FIGS. 102a-102d show additional representative TEM photomicrographs of the same suspension/colloid GB-056 made according to Example 17, however, this suspension/colloid was exposed to the mice via their water bottles in Treatment Group B discussed in Example 26. It should be noted that these representative TEM nanocrystal images are of the dried solution GB-056 so certain drying conditions can affect the images. It is clear that some clustering together of the gold nanocrystals occurred, for example, during drying. However, FIG. 103a shows nanocrystal size distributions which are substantially similar to those that are shown in FIG. 101a. In this regard, the data shown in FIGS. 102 and 103 correspond to suspensions that were in the mouse drinking bottles for a 24-hour time period between day 2 and day 3 of the Example 26 EAE study. Of interest, is the comparison of FIG. 103b to FIG. 101b. In this regard, the dynamic light scattering data has changed. Specifically, the largest hydrodynamic radius shown in FIG. 101b is about 16.8 nm, whereas in FIG. 103b, it is about 20.2 nm. Clearly, the dynamic light scattering data is recognizing some type of the clustering of nanocrystals in suspension which is also represented by the dried suspension/gold nanocrystal TEM photomicrographs shown in FIGS. 102a-102d.

Likewise, FIGS. 104a-104c; FIG. 105a; and FIG. 105c all correspond to suspension/colloid GB-056 that was in the drinking bottles for a 24-hour time period between day 4 and day 5 of the EAE study discussed in Example 26. Once again, it is evident that some type of clumping together of the nanocrystals was occurring.

While FIGS. 101a, 103a and 105a are all substantially similar for TEM measured nanocrystal sizes, it is clear that the dynamic light scattering radii (e.g., the hydrodynamic radii) of the nanocrystals has enlarged, as shown in FIG. 105b, just as it enlarged in FIG. 103b, both relative to the smaller hydrodynamic radii reported in FIG. 101b.

Taken together, these data suggest that exposure of the inventive compositions disclosed herein to certain constituents in, for example, mouse saliva, can cause a clustering or clumping together of the nanocrystals suspended in the liquid. Accordingly, prolonged exposure to certain proteins may have a "denaturing" effect on these inventive compositions. This "denaturing" effect is manageable, and without wishing to be bound by any particular theory or explanation, may be very desirable in that such reactivity due to very "clean" surfaces may support desirable in vivo activity (e.g., certain protein-binding mechanisms).

Example 18

Manufacturing Gold-Based Nanocrystals/Nanocrystal Suspensions (GB-151, GB-188, GB-175, GB-177, GB-176, GB-189, GB-194, GB-195, GB-196, GB-198 and GB-199)

In general, this Example utilizes certain embodiments of the invention associated with the apparatuses generally shown in FIGS. 18a and 21d. Control devices 20 (not shown in FIG. 21d) were connected to the electrodes 1/5 and 5/5, however, due to the short run times in each "Run ID," there was no need to actuate the control devices 20. Accordingly, in reference to FIGS. 3c and 9c, the ends 9' of the electrodes 5a and 5b were juxtaposed with the bottom of the trough member 30b'. Additionally, Table 7 summarizes key processing parameters used in conjunction with FIGS. 18a and 21d. Also, Table 7 discloses: 1) resultant "ppm" (i.e., gold nanocrystal concentrations) and 2) "TEM Average Diameter" which is the mode, corresponding to the crystal diameter that occurs most frequently, determined by the TEM histograms shown in FIGS. 62b-72b. These physical characterizations were performed as discussed elsewhere herein.

TABLE 7

| Run ID: | | GB-151 | GB-188 | GB-175 | GB-177 | GB-176 |
|---|---|---|---|---|---|---|
| Flow | In (ml/min) | 220 | 230 | 230 | 230 | 230 |
| Rate: | Out (ml/min) | 175 | 184 | 184 | 184 | 184 |
| Volts: | Set # 1 | 750 | 750 | 750 | 750 | n/a |
| | Set #'s 2-8 | 230 | 198 | 210 | 208 | 210 |
| PE: NaHCO3 (mg/ml) | | 0.53 | 0.53 | 0.53 | 0.53 | 0.53 |
| Wire Diameter (mm) | | 1.0 | 1.0 | 2.0 | 1.1 | 3.0 |
| Contact "$W_L$" (in/mm) | | 1/25 | 1/25 | 1/25 | 1/25 | 1/25 |
| Electrode Separation "y" (in/mm) | | .25/6.4 | .25/6.4 | .25/6.4 | .25/6.4 | .25/6.4 |
| Electrode Config. Figure | | 17b | 17b | 17b | 17b | 17b |
| Produced Au PPM | | 8.3 | 8.4 | 10.5 | 9.5 | 10.1 |
| Output Temp ° C. at 32 | | 89 | 84 | 89 | 88 | 86 |
| Dimensions | Plasma 4 Figs. | 18a | 18a | 18a | 18a | n/a |
| | Process Figures | 21d | 21d | 21d | 21d | 21d |
| | M1 (in/mm) | 2/51 | 1.5/38 | 1.5/38 | 1.5/38 | 1.5/38 |
| | $L_T$ (in/mm) | 30/762 | 36/914 | 36/914 | 36/914 | 36/914 |
| | d (in/mm) | 1/25 | 1/25 | 1/25 | 1/25 | 1/25 |
| | S (in/mm) | 1.5/38 | 1.5/38 | 2/51 | 2/51 | 2/51 |
| Electrode Curr. (A) | | 0.89 | .85 | .93 | .80 | .88 |
| Total Curr. Draw (A) | | n/m | 6.06 | 7.02 | 6.84 | 6.82 |
| Hydrodynamic r (nm) | | 11.6 | 12 | 14 | 13.1 | 13.2 |
| TEM Avg. Dia. (nm) | | 10.85 | 10.63 | 11.76 | 10.85 | 10.42 |
| | "c-c" (mm) | 152 | 76 | 76 | 76 | n/a |
| Set 1 | electrode # | 1a | 1a | 1a | 1a | n/a |
| | "x" (in/mm) | 0.25/6.4 | 0.25/6.4 | 0.25/6.4 | 0.25/6.4 | n/a |
| | electrode # | 5a | 5a | 5a | 5a | n/a |
| | "c-c" (mm) | 63 | 102 | 102 | 102 | 102 |
| Set 2 | electrode # | 5b | 5b | 5b | 5b | 5b |
| | "x" (in/mm) | n/a | n/a | n/a | n/a | n/a |
| | electrode # | 5b' | 5b' | 5b' | 5b' | 5b' |
| | "c-c" (mm) | 76 | 76 | 76 | 76 | 76 |
| Set 3 | electrode # | 5c | 5c | 5c | 5c | 5c |
| | electrode # | 5c' | 5c' | 5c' | 5c' | 5c' |
| | "c-c" (mm) | 76 | 76 | 76 | 76 | 76 |
| Set 4 | electrode # | 5d | 5d | 5d | 5d | 5d |
| | electrode # | 5d' | 5d' | 5d' | 5d' | 5d' |
| | "c-c" (mm) | 114 | 127 | 127 | 127 | 127 |
| Set 5 | electrode # | 5e | 5e | 5e | 5e | 5e |
| | electrode # | 5e' | 5e' | 5e' | 5e' | 5e' |
| | "c-c" (mm) | 114 | 127 | 127 | 127 | 127 |
| Set 6 | electrode # | 5f | 5f | 5f | 5f | 5f |
| | electrode # | 5f' | 5f' | 5f' | 5f' | 5f' |
| | "c-c" (mm) | 114 | 152 | 152 | 152 | 152 |
| Set 7 | electrode # | 5g | 5g | 5g | 5g | 5g |
| | electrode # | 5g' | 5g' | 5g' | 5g' | 5g' |
| | "c-c" (mm) | 127 | 178 | 178 | 178 | 178 |
| Set 8 | electrode # | 5h | 5h | 5h | 5h | 5h |
| | electrode # | 5h' | 5h' | 5h' | 5h' | 5h' |
| | "c-c" (mm) | 76 | 76 | 76 | 76 | 76 |

| Run ID: | | GB-189 | GB-194 | GB-195 | GB-196 | GB-198 | GB-199 |
|---|---|---|---|---|---|---|---|
| Flow | In (ml/min) | 230 | 250 | 250 | 250 | 150 | 150 |
| Rate: | Out (ml/min) | 184 | 200 | 200 | 200 | 120 | 120 |
| Volts: | Set # 1 | 750 | 750 | 750 | 750 | n/a | 750 |
| | Set #'s 2-8 | 208 | 210 | 210 | 210 | 205 | 205 |
| PE: NaHCO3 (mg/ml) | | 0.53 | 0.53 | 0.53 | 0.53 | 0.26 | 0.26 |
| Wire Diameter (mm) | | 1.2 | 4.0 | 1.3 | 5.0 | 1.4 | 6.0 |
| Contact "$W_L$" (in/mm) | | 1/25 | 1/25 | 1/25 | 1/25 | 1/25 | 1/25 |
| Electrode Separation "y" (in/mm) | | .25/6.4 | .25/6.4 | .25/6.4 | .25/6.4 | .125/3.18 | .125/3.18 |
| Electrode Config. Figure | | 17b | 17b | 17b | 17b | 17b | 17b |
| Produced Au PPM | | 8.4 | 8.7 | 7.7 | 8.7 | 9.9 | 12.4 |
| Output Temp ° C. at 32 | | 85 | 93 | 96 | 89 | 74 | 80 |
| Dimensions | Plasma 4 Figs. | 18a | 18a | 18a | 18a | n/a | 18a |
| | Process Figures | 21d | 21d | 21d | 21d | 21d | 21d |
| | M1 (in/mm) | 1.5/38 | .75/19 | .5/13 | 1/25 | 1.5/38 | 1.5/38 |
| | $L_T$ (in/mm) | 36/914 | 36/914 | 36/914 | 36/914 | 36/914 | 36/914 |
| | d (in/mm) | 1/25 | 1/25 | 1/25 | 1/25 | .75/19 | .75/19 |
| | S (in/mm) | 2/51 | 2/51 | 2/51 | 1.5/38 | 2/51 | 2/51 |
| Electrode Curr. (A) | | .91 | n/m | n/m | n/m | n/m | n/m |
| Total Curr. Draw (A) | | 6.36 | 6.25 | 5.59 | 5.93 | 3.57 | 3.71 |
| Hydrodynamic r (nm) | | 12 | 16 | 16 | 12.5 | 13.9 | 14.2 |
| TEM Avg. Dia. (nm) | | 10.42 | 12.06 | 11.11 | 12.06 | 11.74 | 13.02 |
| | "c-c" (mm) | 76 | 76 | 76 | 76 | n/a | 76 |

TABLE 7-continued

| Set | | | | | | | |
|---|---|---|---|---|---|---|---|
| Set 1 | electrode # | 1a | 1a | 1a | 1a | n/a | 1a |
| | "x" (in/mm) | 0.25/6.4 | 0.25/6.4 | 0.25/6.4 | 0.25/6.4 | n/a | 0.25/6.4 |
| | electrode # | 5a | 5a | 5a | 5a | n/a | 5a |
| | "c-c" (mm) | 102 | 102 | 102 | 102 | 102 | 102 |
| Set 2 | electrode # | 5b | 5b | 5b | 5b | 5b | 5b |
| | "x" (in/mm) | n/a | n/a | n/a | n/a | n/a | n/a |
| | electrode # | 5b' | 5b' | 5b' | 5b' | 5b' | 5b' |
| | "c-c" (mm) | 76 | 76 | 76 | 76 | 76 | 76 |
| Set 3 | electrode # | 5c | 5c | 5c | 5c | 5c | 5c |
| | electrode # | 5c' | 5c' | 5c' | 5c' | 5c' | 5c' |
| | "c-c" (mm) | 76 | 76 | 76 | 76 | 76 | 76 |
| Set 4 | electrode # | 5d | 5d | 5d | 5d | 5d | 5d |
| | electrode # | 5d' | 5d' | 5d' | 5d' | 5d' | 5d' |
| | "c-c" (mm) | 127 | 127 | 127 | 127 | 127 | 127 |
| Set 5 | electrode # | 5e | 5e | 5e | 5e | 5e | 5e |
| | electrode # | 5e' | 5e' | 5e' | 5e' | 5e' | 5e' |
| | "c-c" (mm) | 127 | 127 | 127 | 127 | 127 | 127 |
| Set 6 | electrode # | 5f | 5f | 5f | 5f | 5f | 5f |
| | electrode # | 5f' | 5f' | 5f' | 5f' | 5f' | 5f' |
| | "c-c" (mm) | 152 | 152 | 152 | 152 | 152 | 152 |
| Set 7 | electrode # | 5g | 5g | 5g | 5g | 5g | 5g |
| | electrode # | 5g' | 5g' | 5g' | 5g' | 5g' | 5g' |
| | "c-c" (mm) | 178 | 178 | 178 | 178 | 178 | 178 |
| Set 8 | electrode # | 5h | 5h | 5h | 5h | 5h | 5h |
| | electrode # | 5h' | 5h' | 5h' | 5h' | 5h' | 5h' |
| | "c-c" (mm) | 76 | 76 | 76 | 76 | 76 | 76 |

All trough members 30a' and 30b' in the aforementioned FIGS. 18a and 21d were made from ⅛" (about 3 mm) thick plexiglass, and ¼" (about 6 mm) thick polycarbonate, respectively. The support structure 34 (not shown in the Figures but discussed elsewhere herein) was also made from plexiglass which was about ¼" thick (about 6-7 mm thick). In contrast to the embodiments shown in FIGS. 19a and 19b, each trough member 30a was integral with trough member 30b' and was thus designated 30a' (e.g., no separate pumping means was provided after trough member 30a, as in certain previous examples). The cross-sectional shape of each trough member 30a' used in this Example corresponded to that shape shown in FIG. 10b (i.e., was a trapezoidal-shaped cross-section). Relevant dimensions for each trough member portion 30b' are reported in Table 7 as "M1" (i.e., the inside width of the trough at the entrance portion of the trough member 30b') was the same as the inside width of the trough at the exit portion of the trough member 30b'), "$L_T$" (i.e., transverse length or flow length of the trough member 30b'), "S" (i.e., the height of the trough member 30b'), and "d" (i.e., depth of the liquid 3" within the trough member 30b'). The thickness of each sidewall portion also measured about ¼" (about 6 mm) thick. Two different longitudinal lengths "$L_T$" are reported for the trough members 30b' (i.e., either 762 mm or 914 mm) however, other lengths $L_T$ should be considered to be within the metes and bounds of the inventive trough.

Table 7 shows that the processing enhancer NaHCO₃ was added to purified water (discussed elsewhere herein) in amounts of either about 0.26 mg/ml or 0.53 mg/ml. It should be understood that other amounts of this processing enhancer (and other processing enhancers) also function within the metes and bounds of the invention. The purified water/NaHCO₃ mixture was used as the liquid 3 input into trough member 30a'. The depth "d" of the liquid 3' in the trough member 30a' (i.e., where the plasma(s) 4 is/are formed) was about ⁷⁄₁₆" to about ½" (about 11 mm to about 13 mm) at various points along the trough member 30a'. The depth "d" was partially controlled through use of the dam 80 (shown in FIGS. 18a and 18b). Specifically, the dam 80 was provided near the output end 32 of the trough member 30a' and assisted in creating the depth "d" (shown in FIG. 10b as "d") to be about ⅞"-½" (about 11-13 mm) in depth. The height "j" of the dam 80 measured about ¼" (about 6 mm) and the longitudinal length "k" measured about ½" (about 13 mm). The width (not shown) was completely across the bottom dimension "R" of the trough member 30a'. Accordingly, the total volume of liquid 3' in the trough member 30a' during operation thereof was about 2.14 in³ (about 35 ml) to about 0.89 in³ (about 14.58 ml).

The rate of flow of the liquid 3' into the trough member 30a' as well as into trough member 30b', varied (as shown in Table 7) and the rate of flow out of the trough member 30b' at the point 32 also varied due to different flow rate inputs and evaporation. Other acceptable flow rates should be considered to be within the metes and bounds of the invention.

Such flow of liquid 3' was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute for all samples except GB-144 which was, for example, 110 ml/minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30'a by a flow diffusion means located therein. The flow diffusion means tended to minimize disturbance and bubbles in water 3 introduced into the trough member 30a' as well as any pulsing condition generated by the peristaltic pump 40. In this regard, a small reservoir served as the diffusion means and was provided at a point vertically above the end 31 of the trough member 30a' such that when the reservoir overflowed, a relatively steady flow of liquid 3' into the end 31 of the V-shaped trough member 30a' occurred.

Table 7 shows that there was a single electrode set 1a/5a, utilized in this Example 18. The plasma(s) 4 was/were created with an electrode 1 similar in shape to that shown in FIG. 5e, and weighed about 9.2 grams. This electrode was 99.95% pure gold. The other electrode 5a comprised a 99.95% 1 mm gold wire submerged in the liquid 3'. All other pertinent run conditions are shown in Table 7.

Figure 5A:
FIGS. 5a-5e show five different representative embodiments of configurations for the electrode 1.
Figure 5B:
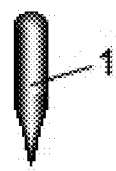
Figure 5C:
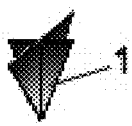
Figure 5D:
Figure 5E:
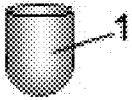

The output from the trough member 30a' was the conditioned liquid 3' and this conditioned liquid 3' flowed directly into a second trough member 30b'. The second trough member 30b', shown in FIG. 21d had measurements as reported in Table 7. This trough member 30b' contained from about 260 ml of liquid 3" therein to about 980 ml depending on the dimensions of the trough and the depth "d"" of the liquid 3" therein. Table 7, in connection with FIG. 21d the electrode configurations used. For example, previous examples herein disclosed the use of four sets of electrodes 5/5, with one electrode set 1/5. In this Example, eight electrode sets were used (e.g., one 1/5 set with seven or eight 5/5' sets). Each of the electrode sets 5/5' comprised 99.99% pure gold wire measuring either about 0.5 mm in diameter or 1.0 mm in diameter, as reported in Table 7. The length of each wire electrode 5 that was in contact with the liquid 3" (reported as "WL" in Table 7) measured from about 0.75 inches (about 19 mm) long to about 1 inch (about 25 mm) long. FIG. 21d shows that the electrode sets 5/5' were arranged as shown in FIG. 5c.

Each electrode set 5a/5b was connected to a Chroma 61604 programmed AC power source (not shown and as discussed elsewhere herein). The applied voltages are reported in Table 7. Specifically, Table 7 refers to each of the electrode sets by "Set #" (e.g., "Set 1" through "Set 8"). Each electrode of the 1/5 or 5/5 electrode sets was set to operate within a specific voltage range. The voltages listed in Table 7 are the voltages used for each electrode set. The distance "c-c" (with reference to FIG. 14) from the centerline of each electrode set to the adjacent electrode set is also reported. Further, the distance "x" (e.g., see FIG. 2a) associated with each electrode 1 utilized is also reported. Other relevant parameters are also reported in Table 7.

All materials for the electrodes 1/5 were obtained from Hi-Rel Alloys having an address of 23 Lewis Street, Fort Erie, Ontario L2A2P6, Canada.

FIGS. 62a-72a show two representative TEM photomicrographs for each of the gold nanoparticles, dried from each solution or colloid referenced in Table 7, and formed according to Example 18.

FIGS. 62b-72b show the measured size distribution of the gold particles measured by using the TEM instrument/software discussed earlier in Examples 5-7 for each dried solution or colloid referenced in Table 7 and formed according to Example 18.

Energy absorption spectra were obtained for the samples in Example 18 by using UV-VIS spectroscopy. This information was acquired using a dual beam scanning monochromater system capable of scanning the wavelength range of 190 nm to 1100 nm. The Jasco V-530 UV-Vis spectrometer was used to collect absorption spectroscopy. Instrumentation was setup to support measurement of low-concentration liquid samples using one of a number of fuzed-quartz sample holders or "cuvettes." The various cuvettes allow data to be collected at 10 mm, 1 mm or 0.1 mm optic path of sample. Data was acquired over the wavelength range using between 250-900 nm detector with the following parameters; bandwidth of 2 nm, with data pitch of 0.5 nm, a silicon photodiode with a water baseline background. Both deuterium (D2) and halogen (WI) scan speed of 400 nm/mm sources were used as the primary energy sources. Optical paths of these spectrometers were setup to allow the energy beam to pass through the center of the sample cuvette. Sample preparation was limited to filling and capping the cuvettes and then physically placing the samples into the cuvette holder, within the fully enclosed sample compartment. Optical absorption of energy by the materials of interest was determined. Data output was measured and displayed as Absorbance Units (per Beer-Lambert's Law) versus wavelength.

Spectral patterns in a UV-Visible range were obtained for each of the solutions/colloids produced in Example 18.

Specifically, FIG. 72c shows UV-Vis spectral patterns of each of the 11 suspensions/colloids, (GB-151, GB-188, GB-175, GB-177, GB-176, GB-189, GB-194, GB-195, GB-196, GB-198 and GB-199) within a wavelength range of about 250 nm-750 nm.

FIG. 72d shows the UV-Vis spectral pattern for each of the 11 suspensions/colloids over a wavelength range of about 435 nm-635 nm.

In general, UV-Vis spectroscopy is the measurement of the wavelength and intensity of absorption of near-ultraviolet and visible light by a sample. Ultraviolet and visible light are energetic enough to promote outer electrons to higher energy levels. UV-Vis spectroscopy can be applied to molecules and inorganic ions or complexes in solution.

The UV-Vis spectra have broad features that can be used for sample identification but are also useful for quantitative measurements. The concentration of an analyte in solution can be determined by measuring the absorbance at some wavelength and applying the Beer-Lambert Law.

Example 19

Manufacturing Gold-Based Nanoparticles/Nanoparticle Suspensions or Colloids Aurora-002, Aurora-004, Aurora-006, Aurora-007, Aurora-009, Aurora-011, Aurora-012, Aurora-013, Aurora-014, Aurora-016, Aurora-017, Aurora-019, Aurora-020, Aurora-021, Aurora-022, Aurora-023, Aurora-024, Aurora-025, Aurora-026, Aurora-027, Aurora-028, Aurora-029 and Aurora-030

In general, Example 19 utilizes a trough member 30 and electrode 1/5 combination different from any of the other Examples disclosed herein. Specifically, this Example utilizes a first set of four electrodes 1 and a single electrode 5a in a trough member 30a' which create a plurality of plasmas 4, resulting in conditioned liquid 3'. The conditioned liquid 3' flows into and through a longitudinal trough member 30b', wherein parallelly located electrodes 5b/5b' are positioned along substantially the entire longitudinal or flow length of the trough member 30b'. Specific reference is made to FIGS. 23a, 23b, 23c and 23d which show various schematic and perspective views of this embodiment of the invention. Additionally, Table 8 contains relevant processing parameters associated with this embodiment of the invention.

TABLE 8

| Run ID: | Aurora-002 | Aurora-004 | Aurora-006 | Aurora-007 | Aurora-009 | Aurora-011 | Aurora-012 | Aurora-013 | Aurora-014 |
|---|---|---|---|---|---|---|---|---|---|
| Flow Rate: In (ml/min) | 300 | 300 | 150 | 150 | 150 | 300 | 450 | 60 | 60 |
| Volts: Set # 1 | 1000 | 1000 | 1000 | 1000 | 1000 | 1000 | 1000 | 1000 | 1000 |
| Electrodes 5b | 100 | 120 | 100 | 50 | 100 | 90 | 110 | 50 | 40 |
| # of Electrodes 1 | 4 | 4 | 4 | 4 | 4 | 4 | 4 | 4 | 4 |
| PE: NaHCO3 (mg/ml) | 0.396 | 0.396 | 0.396 | 0.396 | 0.396 | 0.396 | 0.396 | 0.396 | 0.396 |
| Wire Diameter (mm) | 0.5 | 0.5 | 0.5 | 0.5 | 0.5 | 0.5 | 0.5 | 0.5 | 0.5 |
| Electrode Config. Figure | 23a | 23a | 23a | 23a | 23a | 23a | 23a | 23a | 23a |
| Produced Au PPM | 12.3 | 15.9 | 39.6 | 4.1 | 17.8 | 17.4 | 12.7 | 46.5 | 65.7 |
| Dimensions Plasma 4 Figs. | 23a | 23a | 23a | 23a | 23a | 23a | 23a | 23a | 23a |
| Process Figures | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d |
| Wire Length (in) "$W_L$" | 54 | 54 | 54 | 54 | 54 | 54 | 54 | 54 | 54 |
| $L_T$ (in/mm) | 59/1500 | 59/1500 | 59/1500 | 59/1500 | 59/1500 | 59/1500 | 59/1500 | 59/1500 | 59/1500 |
| wire apart (in/mm) "b" | 0.125/3.2 | 0.125/3.2 | 0.125/3.2 | 0.125/3.2 | 0.125/3.2 | 0.063/1.6 | 0.063/1.6 | 0.063/1.6 | 0.063/1.6 |
| Electrode Curr. (A) | 10.03 | 14.2 | 15.3 | 5.2 | 11.9 | 15.9 | 19.5 | 10 | 7.87 |
| Hydrodynamic r (nm) | 23.2 | 19.4 | 23.2 | 26.2 | 19.6 | 16.3 | 13.1 | 26.2 | 22.0 |
| TEM Avg. Dia. (nm) | n/a | n/a | n/a | n/a | n/a | n/a | n/a | n/a | n/a |

| Run ID: | Aurora-016 | Aurora-017 | Aurora-019 | Aurora-020 | Aurora-021 | Aurora-022 | Aurora-023 | Aurora-024 | Aurora-025 |
|---|---|---|---|---|---|---|---|---|---|
| Flow Rate: In (ml/min) | 60 | 30 | 30 | 30 | 30 | 60 | 60 | 60 | 60 |
| Volts: Set # 1 | 1000 | 1000 | 1000 | 1000 | 1000 | 1000 | 1000 | 1000 | 1000 |
| Electrodes 5b | 30 | 30 | 30 | 50 | 50 | 50 | 80 | 30 | 30 |
| # of Electrodes 1 | 4 | 4 | 1 | 1 | 4 | 4 | 4 | 4 | 4 |
| PE: NaHCO3 (mg/ml) | 0.396 | 0.396 | 0.396 | 0.396 | 0.396 | 0.396 | 0.396 | 3.963 | 3.963 |
| Wire Diameter (mm) | 0.5 | 0.5 | 0.5 | 0.5 | 0.5 | 0.5 | 0.5 | 0.5 | 0.5 |
| Electrode Config. Figure | 23a | 23a | 23a | 23a | 23a | 23a | 23a | 23a | 23a |
| Produced Au PPM | 35.5 | 24.8 | 22.5 | 128.2 | 67.1 | 64.2 | 73.8 | 0.8 | 0.5 |
| Dimensions Plasma 4 Figs. | 23a | 23a | 23a | 23a | 23a | 23a | 23a | 23a | 23a |
| Process Figures | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d | 23a, 23b, 23c, 23d |
| Wire Length (in) "$W_L$" | 54 | 54 | 54 | 54 | 54 | 54 | 50 | 50 | 50 |
| $L_T$ (in/mm) | 59/1500 | 59/1500 | 59/1500 | 59/1500 | 59/1500 | 59/1500 | 59/1500 | 59/1500 | 59/1500 |
| wire apart (in/mm) "b" | 0.063/1.6 | 0.063/1.6 | 0.063/1.6 | 0.063/1.6 | 0.063/1.6 | 0.063/1.6 | 0.063/1.6 | 0.063/1.6 | 0.063/1.6 |
| Electrode Curr. (A) | 5.18 | 4.95 | 4.65 | 10.7 | 10 | 9.8 | 18 | 17 | 14.96 |
| Hydrodynamic r (nm) | 26.6 | 27.4 | 26.0 | 31.0 | 27.1 | 28.3 | 27.0 | n/a | n/a |
| TEM Avg. Dia. (nm) | n/a | n/a | n/a | 16-40 | n/a | n/a | n/a | n/a | n/a |

| Run ID: | Aurora-026 | Aurora-027 | Aurora-028 | Aurora-029 | Aurora-030 |
|---|---|---|---|---|---|
| Flow Rate: In (ml/min) | 60 | 60 | 60 | 60 | 60 |
| Volts: Set # 1 | 1000 | 1000 | 1000 | 1000 | 1000 |
| Electrodes 5b | 30 | 30 | 100 | 130 | 150 |
| # of Electrodes 1 | 4 | 4 | 4 | 4 | 4 |
| PE: NaHCO3 (mg/ml) | 3.963 | 3.963 | 0.106 | 0.106 | 0.106 |
| Wire Diameter (mm) | 0.5 | 0.5 | 0.5 | 0.5 | 0.5 |
| Electrode Config. Figure | 23a | 23a | 23a | 23a | 23a |
| Produced Au PPM | 3.7 | 2.0 | 8.1 | 21.6 | 41.8 |
| Dimensions Plasma 4 Figs. | 23a | 23a | 23a | 23a | 23a |
| Process Figures | 23a, 23b, 23c, 23d | 23a, 23b, 23c, 23d | 23a, 23b, 23c, 23d | 23a, 23b, 23c, 23d | 23a, 23b, 23c, 23d |
| Wire Length (in) "$W_L$" | 50 | 50 | 50 | 50 | 50 |
| $L_T$ (in/mm) | 59/1500 | 59/1500 | 59/1500 | 59/1500 | 59/1500 |
| wire apart (in/mm) "b" | 0.063/1.6 | 0.063/1.6 | 0.063/1.6 | 0.063/1.6 | 0.063/1.6 |

TABLE 8-continued

| Electrode Curr. (A) | 13.4 | 16.32 | 6.48 | 10 | 12 |
|---|---|---|---|---|---|
| Hydrodynamic r (nm) | 33.7 and 77.5 | n/a | 26.1 | 21.9 | 25.2 |
| TEM Avg. Dia. (nm) | n/a | n/a | n/a | n/a | n/a |

Figure 23A:
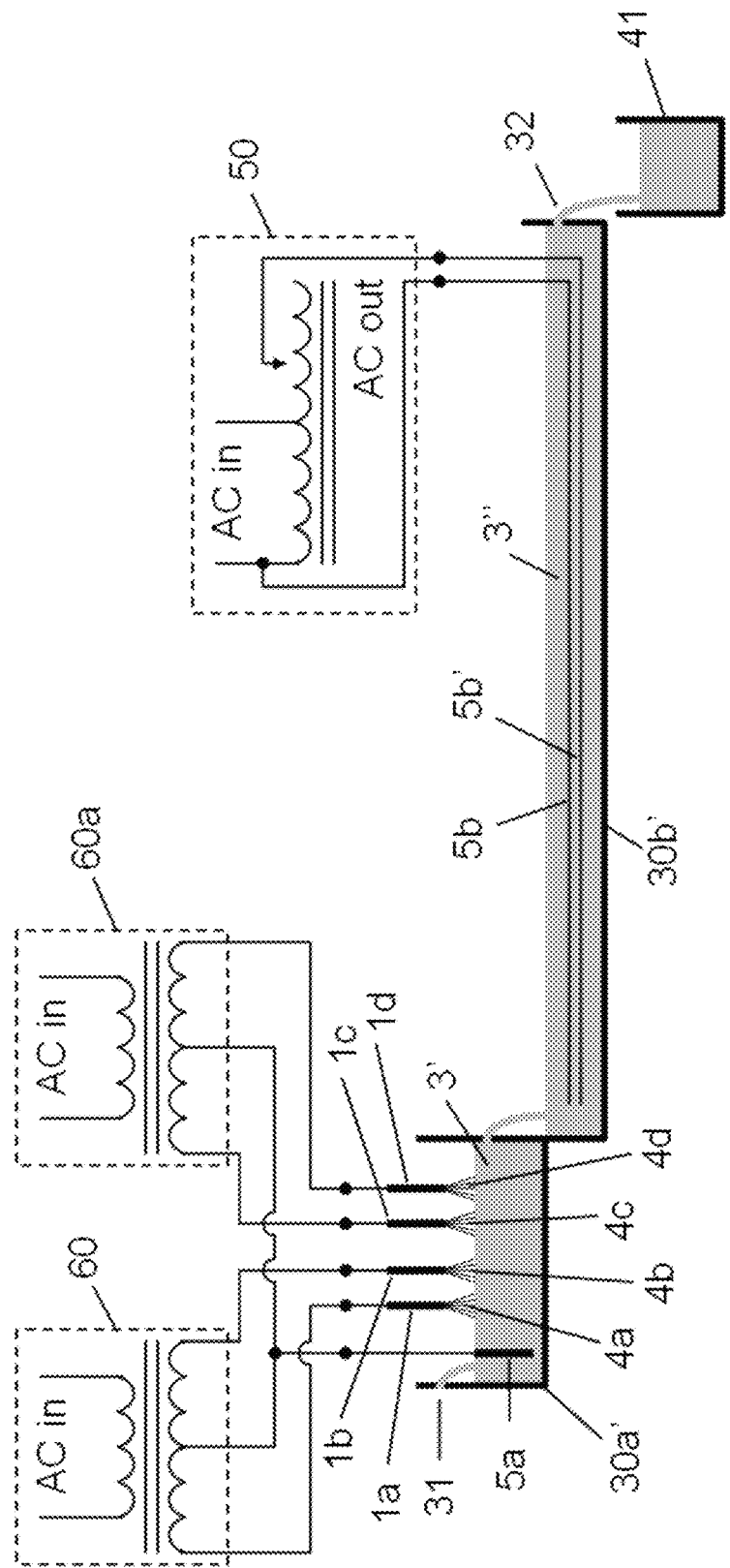
FIGS. 23a-23d show various schematic and perspective views of an alternative trough embodiment utilized in Example 19.
Figure 23B:
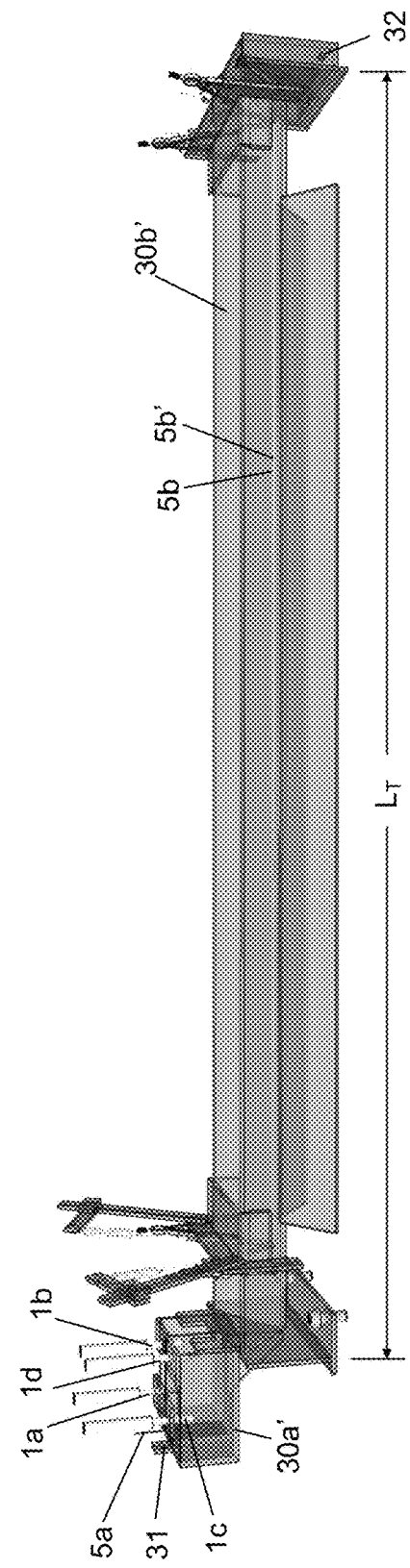
Figure 23C:
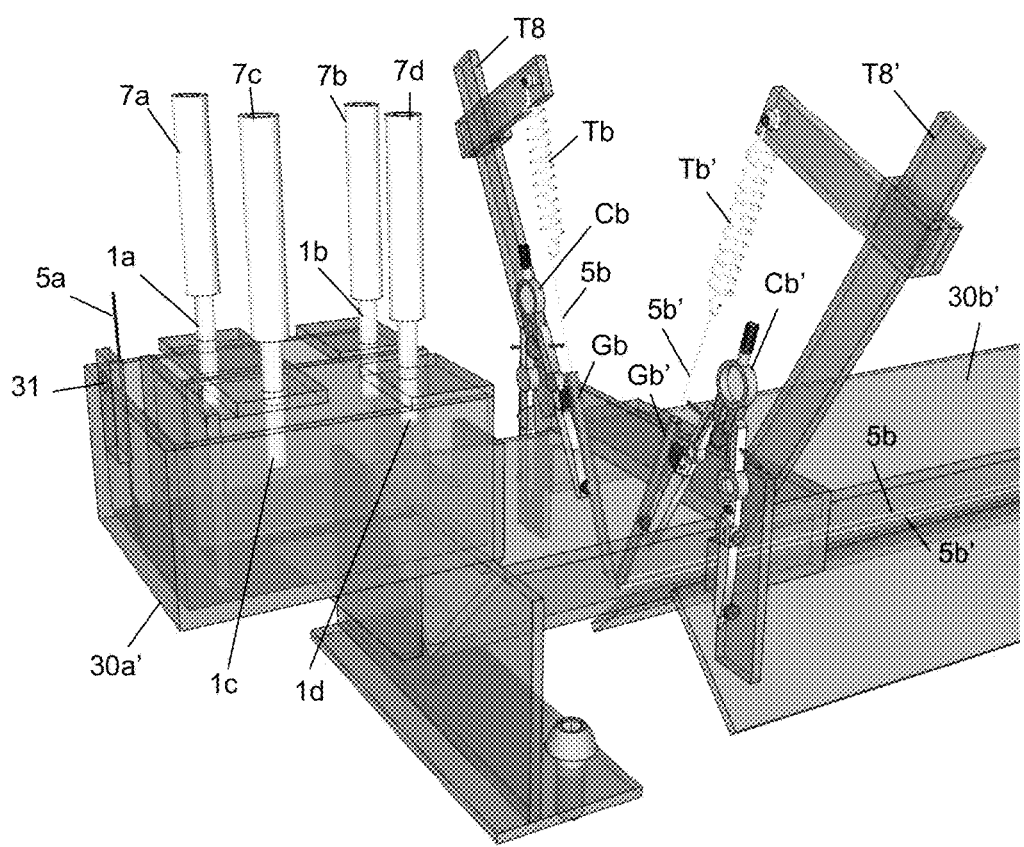
Figure 23D:
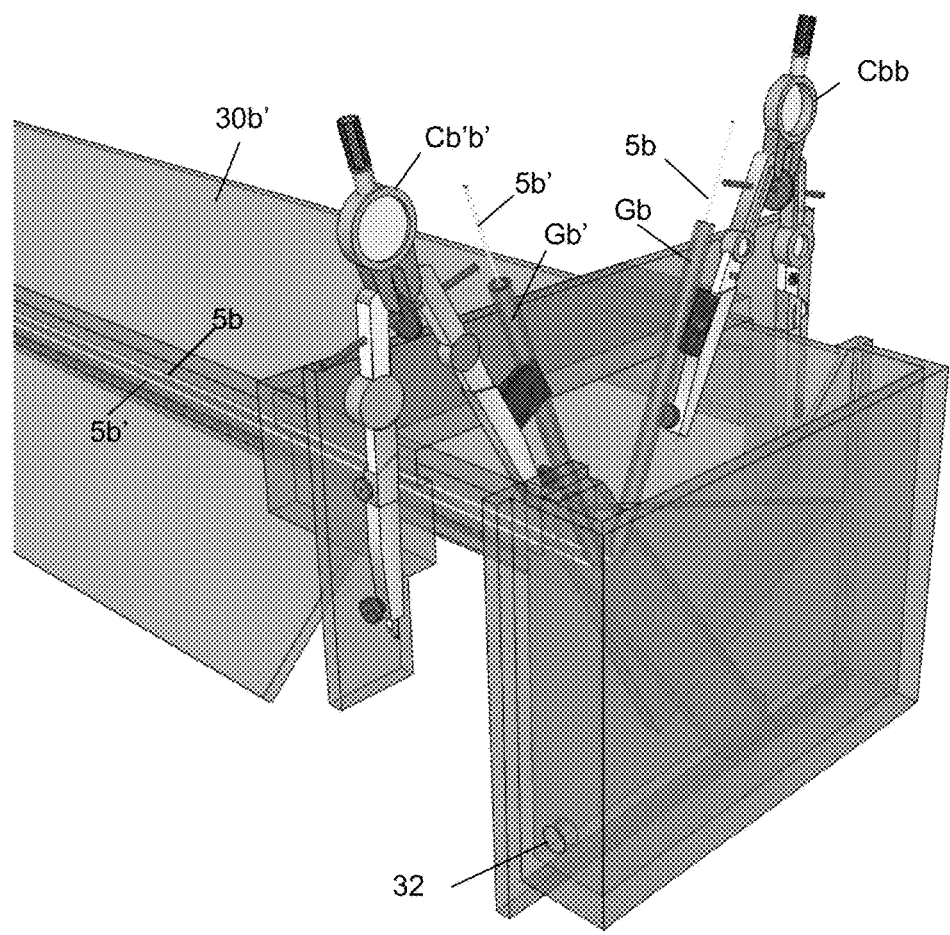

With regard to FIG. 23a, two AC power sources 60 and 60a are electrically connected as shown and create four separate plasmas 4a, 4b, 4c and 4d at four corresponding electrodes 1a, 1b, 1c and 1d, in a first trough member portion 30a'. As shown in FIG. 23a, only a single electrode 5a is electrically connected to all four electrodes 1. These power sources 60 and 60a are the same power sources reported in other Examples herein. Two different amounts of processing enhancer NaHCO$_3$ were added to the liquid 3 prior to the four plasmas 4a-4d conditioning the same as reported in Table 13. The amount and type of processing enhancer reported should not be construed as limiting the invention. The rate of flow of the liquid 3/3' into and out of the trough member 30a', as well as into the trough member 30b' is also reported in Table 8. The rate of flow out of the trough member 30b' was approximately 5% to 50% lower due to liquid loss in evaporation, with higher evaporation at higher power input at electrodes 5b/5b'. Varying flow rates for the liquid 3/3' can be utilized in accordance with the teachings herein.

Only one set of electrodes 5b/5b' was utilized in this particular embodiment. These electrodes 5b/5b' were connected to an AC power source 50, as described in the other Examples herein. The gold wire electrodes 5b/5b' used in this particular Example were the same gold wires, with dimensions as reported in Table 8, that were used in the other Examples reported herein. However, a relatively long length (i.e., relative to the other Examples herein) of gold wire electrodes was located along the longitudinal length $L_T$ of the trough member 30b'. The wire length for the electrodes 5b/5b' is reported in Table 8. Two different wire lengths either 50 inches (127 cm) or 54 inches (137 cm) were utilized. Further, different transverse distances between the wires 5b/5b' are also reported. Two separate transverse distances are reported herein, namely, 0.063 inches (1.6 mm) and 0.125 inches (3.2 mm). Different electrode 5b/5b' lengths are utilizable as well as a plurality of different transverse distances between the electrodes 5b/5b'.

The wire electrodes 5b/5b' were spatially located within the liquid 3" in the trough member 30b' by the devices Gb, Gb', T8, T8', Tb and Tb' near the input end 31 (refer to FIG. 23c) and corresponding devices Gb, Gb', Cb, Cb', Cbb and Cb'b' (refer to FIG. 23d) near the output end 32. It should be understood that a variety of devices could be utilized to cause the electrodes 5b/5b' to be contiguously located along the trough member 30b' and those reported herein are exemplary. Important requirements for locating the electrodes 5b/5b' include the ability to maintain desired transverse separation between the electrodes along their entire lengths which are in contact with the liquid 3" (e.g., contact of the electrodes with each other would cause an electrical short circuit). Specifically, the electrodes 5b/5b' are caused to be drawn through guide members Gb and Gb' made of polycarbonate near the input end 31 and the glass near output end 32. The members Gb and Gb' at each end of the trough member 30b' are adjusted in location by the compasses Cbb, Cb'b' near an output end 32 of the trough member 30b' and similar compasses Cb and Cb' at the opposite end of the trough 30b'. Electrical connection to the electrodes 5b/5b' was made at the output end 32 of the trough member 30b' near the top of the guide members Gb and Gb'. Tension springs Tb and Tb' are utilized to keep the electrode wires 5b/5b' taught so as to maintain the electrodes in a fixed spatial relationship to each other. In this regard, the electrodes 5b/5b' can be substantially parallel along their entire length, or they can be closer at one end thereof relative to the other (e.g., creating different transverse distances along their entire length). Controlling the transverse distance(s) between electrode 5b/5b' influences current, current density concentration, voltages, etc. Of course, other positioning means will occur to those of ordinary skill in the art and the same are within the metes and bounds of the present invention.

Table 8 shows a variety of relevant processing conditions, as well as certain results including, for example, "Hydrodynamic r" (i.e., hydrodynamic radii (reported in nanometers)) and the process current that was applied across the electrodes 5b/5b'. Additionally, resultant ppm levels are also reported for a variety of process conditions with a low of about 0.5 ppm and a high of about 128 ppm.

FIG. 73a shows two representative TEM photomicrographs of the gold nanoparticles, dried from the solution or colloid Aurora-020, which has a reported 128 ppm concentration of gold measured next day after synthesis. In two weeks the concentration of that sample reduced to 107 ppm, after another 5 weeks the concentration reduced to 72 ppm.

FIG. 73b shows the measured size distribution of the gold nanoparticles measured by the TEM instrument/software discussed earlier in Examples 5-7 corresponding to dried Aurora-020.

FIG. 73c shows graphically dynamic light scattering data measurement sets for the nanocrystals (i.e., the hydrodynamic radii) made according to Aurora-020 referenced in Table 8 and measured after 7 weeks from the synthesis. The main peak in intensity distribution graph is around 23 nm. Dynamic light scattering measurements on fresh Aurora-020 sample (not shown) resulted in main peak at 31 nm. It should be noted that the dynamic light scattering particle size information is different from the TEM measured histograms because dynamic light scattering uses algorithms that assume the particles are all spheres (which they are not) as well as measures the hydrodynamic radius (e.g., the particle's influence on the water is also detected and reported in addition to the actual physical radii of the particles). Accordingly, it is not surprising that there is a difference in the reported particle sizes between those reported in the TEM histogram data of those reported in the dynamic light scattering data just as in the other Examples included herein.

Accordingly, it is clear from this continuous processing method that a variety of process parameters can influence the resultant product produced.

Example 20

Manufacturing Gold-Based Nanoparticles/Nanoparticle Suspensions or Colloids GA-002, GA-003, GA-004, GA-005, GA-009, GA-011 and GA-013 by a Batch Process This Example utilizes a batch process according to the present invention. FIG. 24a shows the apparatus used to condition the liquid 3 in this Example. Once conditioned, the liquid 3' was processed in the apparatus shown in FIG. 24c. A primary goal in this Example was to show a variety of different processing enhancers (listed as "PE" in Table 9). Specifically, Table 9 sets forth voltages used for each of the electrodes 1 and 5, the dwell time for the liquid 3 being exposed to plasma 4 in the apparatus of FIG. 24a; the volume of liquid utilized in each of FIGS. 24a and 24c; the voltages used to create the plasma 4 in FIG. 24a and the voltages used for the electrodes 5a/5b in FIG. 24c.

the average of the three highest amplitude peaks shown in each of FIGS. 74c-80c and "TEM Average Diameter" which corresponds to the average measured gold nanocrystal size calculated from the TEM histogram graphs shown in FIGS. 74b-80b).

FIGS. 74a1,a2-80a1,a2 show two representative TEM photomicrographs each of the gold nanocrystals, dried from each solution or colloid referenced in Table 9 formed according to this Example.

TABLE 9

| Run ID: | | GA-002 | GA-003 | GA-004 | GA-005 | GA-009 | GA-011 | GA-013 |
|---|---|---|---|---|---|---|---|---|
| Dwell Times (min) | Plasma 4 | 25 | 25 | 25 | 25 | 25 | 25 | 25 |
| | Electrodes 5a/5b | 42 | 42 | 42 | 42 | 42 | 42 | 42 |
| Volume $H_2O$ & PE (mL) | Plasma 4 | 3790 | 3790 | 3790 | 3790 | 3790 | 3790 | 3790 |
| | Electrodes 5a/5b | 900 | 900 | 900 | 900 | 900 | 900 | 900 |
| Volts: | Plasma 4 | 750 | 750 | 750 | 750 | 750 | 750 | 750 |
| | Electrodes 5a/5b | 300 | 300 | 300 | 300 | 298 | 205.6 | 148 |
| PE* | Type: | $Na_2CO_3$ | $K_2CO_3$ | $KHCO_3$ | $NaHCO_3$ | $NaHCO_3$ | $NaHCO_3$ | $NaHCO_3$ |
| | mg/ml: | 0.22 | 0.29 | 0.44 | 0.47 | 0.52 | 0.51 | 0.51 |
| Wire Diameter (mm) | | 1.0 | 1.0 | 1.0 | 1.0 | 1.0 | 1.0 | 1.0 |
| Wire Configuration Figure | | 17b | 17b | 17b | 17b | 17b | 17b | 17b |
| PPM: | | 7.8 | 10.0 | 10.0 | 11.3 | 9.7 | 10.0 | 7.7 |
| Final Liquid Temp ° C. | | 96 | 93.5 | 90.5 | 89 | 90.5 | 74.5 | 57 |
| Dimensions & Configuration | Plasma 4 Figure | 24a | 24a | 24a | 24a | 24a | 24a | 24a |
| | Electrodes 5a/5b Figure | 24c | 24c | 24c | 24c | 24c | 24c | 24c |
| | Contact "$W_L$" (in/mm) | 0.75/19 | 0.75/19 | 0.75/19 | 0.75/19 | 0.75/19 | 0.75/19 | 0.75/19 |
| | Separation (in/mm) | 1.5/38 | 1.5/38 | 1.5/38 | 1.5/38 | 1.5/38 | 0.25/6 | 0.063/1.6 |
| Electrode Current (A) | | 0.69 | 0.65 | 0.64 | 0.66 | 0.76 | 0.78 | 0.60 |
| Hydrodynamic r (nm) | | 11.1 | 12.0 | 13.9 | 11.9 | 17.6 | 17.1 | 10.3 |
| TEM Avg. Diameter (nm) | | 12.24 | 12.74 | 14.09 | 14.38 | 11.99 | 11.99 | 11.76 |
| "c-c" (in/mm) | | n/m | n/m | n/m | n/m | n/m | n/m | n/m |
| Plasma 4 | electrode # | 1a | 1a | 1a | 1a | 1a | 1a | 1a |
| | "x" (in/mm) | 0.25/6.4 | 0.25/6.4 | 0.25/6.4 | 0.25/6.4 | 0.25/6.4 | 0.25/6.4 | 0.25/6.4 |
| | electrode # | 5a | 5a | 5a | 5a | 5a | 5a | 5a |
| "c-c" (in/mm) | | n/m | n/m | n/m | n/m | n/m | n/m | n/m |
| Electrodes | electrode # | 5a | 5a | 5a | 5a | 5a | 5a | 5a |
| | electrode # | 5b | 5b | 5b | 5b | 5b | 5b | 5b |

With regard to the reported processing enhancers (PE) utilized, different mg/ml amounts were utilized in an effort to have similar conductivity for each solution (e.g., also similar molar quantities of cations present in the liquid 3/3'). The electrode wire diameter used in each Example was the same, about 1.0 mm, and was obtained from ESPI, having an address of 1050 Benson Way, Ashland, Oreg. 97520, as reported elsewhere herein.

The amount of electrode contacting the liquid 3' in the apparatus shown in FIG. 24c was the same in each case, namely, 0.75 inches (19.05 mm).

Table 9 also shows the effects of transverse electrode separation (i.e., the distance "b" between substantially parallel electrodes 5a/5b shown in FIG. 24c) for the same processing enhancer, namely, $NaHCO_3$. It is clear that electrode current and corresponding final liquid temperature were less for closer electrode placement (i.e., smaller "b" values).

A voltage source 60 (discussed elsewhere herein) was used to create the plasma 4 shown in FIG. 24a. A voltage source 50 (discussed elsewhere herein) was used to create a voltage and current between the electrodes 5a/5b shown in FIG. 24c.

Table 9 also reports the measured hydrodynamic radius (i.e., a single number for "Hydrodynamic Radii" taken from FIGS. 74b-80b show the measured size distribution of the gold nanocrystals measured by using the TEM instrument/software discussed earlier in Examples 5-7 for each suspension or colloid referenced in Table 9 formed according to this Example.

FIGS. 74c-80c show graphically dynamic light scattering data measurement sets for the nanocrystals (i.e., the hydrodynamic radii) made according to each suspension or colloid referenced in Table 9 formed according to this Example. It should be noted that the dynamic light scattering particle size information is different from the TEM measured histograms because dynamic light scattering uses algorithms that assume the nanocrystals are all spheres (which they are not) as well as measures the hydrodynamic radius (e.g., the nanocrystal's influence on the water is also detected and reported in addition to the actual physical radii of the nanocrystals). Accordingly, it is not surprising that there is a difference in the reported nanocrystal sizes between those reported in the TEM histogram data of those reported in the dynamic light scattering data just as in the other Examples included herein.

Comparative Example 21

Manufacturing Gold-Based Nanoparticles/Nanoparticle Suspensions According to the Bredig/Svedberg Processes This Example utilizes an underwater AC plasma created between two gold electrodes in an attempt to make a gold nanoparticle suspension similar to those made by Bredig and Svedberg (discussed in the Background).

Specifically, FIG. 81a shows a perspective view of an apparatus designed to function like the AC plasma apparatus of Svedberg. FIG. 81b shows a cross-sectional view of the same apparatus. In each of these figures, gold electrodes e1 and e2, each having a 1 mm diameter, were submerged into the water 3. About 1 gallon of water 3 was contained in a glass vessel. Electrically insulating sleeve members s1 and s2 prevented electrical arcing where undesired. The electrodes e1 and e2 were energized with the same transformer 60 discussed elsewhere herein. The electrode e1 was brought into close proximity of the end of electrode e2 at an area designated "Sh". The end "ea" of electrode of e1 was pounded to make it approximately flat. The flat end ea was then brought into close proximity with the end of the electrode e2 near the portion Sh. When the electrode end ea approached the portion Sh, an underwater plasma 4w was created. Once stabilized, the underwater plasma 4w was allowed to run for about 2.5 hours to make about 1 gallon of colloid. The results of the 2.5-hour run are shown in FIGS. 82a and 82b.

FIG. 82a is a representative TEM photomicrograph of the gold nanoparticles made according to this Example. FIG. 82b is a particle size distribution histogram from TEM measurements of the gold nanoparticles made according to this Example. As is clear from the TEM photomicrograph, no nanocrystals similar to those of the present invention are present.

Comparative Example 22a

Colloidal-Based Nanoparticle Suspensions Commercially Available

For comparison purposes, eight commercially available colloidal gold solutions were obtained. The commercial names and sources are listed in Table 10 below:

TABLE 10

| Solution Name | Manufacturer | Description |
| --- | --- | --- |
| Utopia Gold | Utopia Silver Supplements | Colloidal Gold |
| SNG911219 | Source Naturals, Inc. | Ultra Colloidal Gold |
| Nanopartz | Nanopartz | Accurate Spherical Gold Nanoparticles |
| Nanocomposix 15 nm | NanoComposix | Tannic Acid NanoXact Gold |
| Nanocomposix 10 nm | NanoComposix | Tannic NanoXact Gold |
| Harmonic Gold | Harmonic Innerprizes | |
| ElectraClear | InSpiral Technologies | Colloidal Gold |
| MesoGold | Purest Colloids, Inc. | |

FIG. 90c shows the UV-Vis spectral patterns of each of the 7 of the 8 commercially available gold nanoparticle suspensions discussed in FIG. 22a (Utopia Gold, SNG911219, Nanopartz, Nanocomposix 15 nm, Nanocomposix 10 nm, Harmonic Gold and MesoGold) over an interrogating wavelength range of about 250 nm-750 nm.

FIG. 90d shows the UV-Vis spectral patterns for 7 of the 8 commercially available gold nanoparticle suspensions discussed in FIG. 22a (Utopia Gold, SNG911219, Nanopartz, Nanocomposix 15 nm, Nanocomposix 10 nm, Harmonic Gold and MesoGold) over an interrogating wavelength range of about 435 nm-635 nm.

Particle-Size and Particle-Shape Analysis

Transmission electron microscope (TEM) images were analyzed by visual observation with the aid of software referenced in Examples 5-7. Individual particles/crystals were assigned to one of five groups according to the two-dimensional projection shown in the photomicrographs. The five categories are: triangle, pentagon, hexagon, diamond and other. These categories correspond to three-dimensional morphologies elucidated in the literature and prior TEM studies which utilized a tilting sample holder. The 2D/3D correspondence of the particle/crystal shape categories is listed in Table 11.

TABLE 11

| Two-Dimensional Projection | Possible Three-Dimensional Nanoparticle Morphologies |
| --- | --- |
| Triangle | Tetrahedron |
| Pentagon | Pentagonal Bipyramid (i.e., Decahedron) |
| Hexagon | Hexagonal Bipyramid, Icosahedrons, Octahedron |
| Diamond | Octahedron, Various Elongated Bipyramids, Fused Tetrahedrons, Side View of Bipyramids |
| Other | Icosahedrons, Spheroids, Ellipsoids, Rods, Aggregated Particles, Platelets, Particles of Uncertain Form |

Certain nanocrystal forms can take on multiple two-dimensional projections. For example, an icosahedron, a possible shape for gold nanocrystals, can appear as a hexagon, an irregular heptagon or a spheroid in a TEM micrograph. While care was taken to discern the hexagonal, octagonal and other shapes when viewed in the two-dimension projection, conclusive information regarding the true form of such nanocrystals can not always be discerned in the two-dimensional projection. Therefore, only the tetrahedron and pentagonal bipyramid (i.e., decahedron) categories can be absolutely discerned. Hexagonal, Diamond and Other categories are grouped together.

A pentagonal bipyramid nanocrystal viewed on its side could be projected as a diamond. This is an unlikely occurrence given the planar nature of the sample substrate and taking into consideration the very low number of diamonds counted throughout the analysis. Those decahedrons counted via the pentagon two-dimensional projection are distinct from this former group, per se, and their count was taken as one figure of merit or method of distinguishing the inventive crystals from those of the art. Likewise, triangles or tetrahedrons are also readily distinguishable and can also be used for comparison purposes.

Aggregation and agglomeration of particles or nanocrystals can occur in a colloid or as an artifact of the drying process required for TEM sample preparation/analysis. Dense agglomerations and larger aggregations (greater than approximately 50 particles/nanocrystals) were not analyzed due to possible counting errors. The crystal/particle number and particle/crystal shapes of smaller aggregates and visually resolvable agglomerations were analyzed. Additionally, only well resolved images were used for this investigation.

regarding possible differences between commercially available colloids and nanocrystalline colloids made according to the invention.

It is clear from Table 12 that the presence of nanocrystals corresponding in shape to pentagonal bipyramids and/or tetrahedrons is/are quite different from the commercially available colloids and ARCG-05. Moreover, these nanocrystals have substantially "clean" surfaces, as discussed, shown and defined elsewhere herein.

TABLE 12

| Product | Example Number | Pentagonal Bipyramid | Tertrahedron | Octahedron | Hexagonal | Other Shapes | PPM | TEM Average Diameter (nm) | pH |
|---|---|---|---|---|---|---|---|---|---|
| GD-007 | 5 | 21% | 10% | 2% | 40% | 27% | 14 | 14.3 | 8.9 |
| GB-056 | 17 | 34% | 13% | 6% | 30% | 17% | 12 | 12.1 | 9.1 |
| GB-077 | 16 | 22% | 8% | 3% | 40% | 27% | 8 | 8.7 | 9.0 |
| GB-134 | 16 | 31% | 18% | 5% | 27% | 19% | 9 | 17.5 | 9.2 |
| GB-151 | 18 | 32% | 8% | 5% | 36% | 19% | 8 | 10.9 | 9.4 |
| GB-154 | 13 | 14% | 7% | 4% | 23% | 51% | 5 | 14.1 | 9.7 |
| GB-156 | 13 | 18% | 16% | 5% | 30% | 30% | 5 | 19.4 | 9.2 |
| GB-162 | 14 | 15% | 32% | 1% | 16% | 37% | 8 | 8.9 | 9.0 |
| GB-163 | 15 | 9% | 21% | 2% | 28% | 40% | 8 | 20.6 | 9.1 |
| GB-164 | 15 | 12% | 12% | 7% | 32% | 37% | 8 | 20.4 | 9.3 |
| GB-165 | 14 | 22% | 19% | 5% | 24% | 30% | 7 | 14.7 | 9.0 |
| GB-166 | 14 | 15% | 10% | 2% | 24% | 49% | 6 | 13.0 | 9.0 |
| GB-175 | 18 | 25% | 22% | 1% | 23% | 29% | 11 | 11.8 | 9.3 |
| GB-176 | 18 | 23% | 20% | 1% | 35% | 21% | 10 | 10.4 | 9.3 |
| GB-177 | 18 | 29% | 19% | 1% | 28% | 23% | 10 | 10.9 | 9.3 |
| GB-188 | 18 | 25% | 23% | 6% | 23% | 24% | 8 | 10.6 | 9.1 |
| GB-189 | 18 | 26% | 21% | 0% | 23% | 30% | 8 | 10.4 | 9.2 |
| GB-194 | 18 | 22% | 19% | 3% | 33% | 23% | 9 | 12.1 | 9.2 |
| GB-195 | 18 | 17% | 16% | 3% | 45% | 19% | 8 | 11.1 | 9.2 |
| GB-196 | 18 | 21% | 16% | 1% | 31% | 30% | 9 | 12.1 | 9.1 |
| GB-198 | 18 | 14% | 10% | 0% | 51% | 25% | 10 | 11.7 | 9.2 |
| GB-199 | 18 | 33% | 9% | 1% | 40% | 17% | 12 | 13.0 | 9.1 |
| GA-002 | 20 | 30% | 23% | 5% | 24% | 18% | 11 | 12.2 | 10.5 |
| GA-003 | 20 | 27% | 17% | 6% | 32% | 18% | 10 | 12.7 | 10.3 |
| GA-004 | 20 | 15% | 9% | 3% | 38% | 35% | 10 | 14.1 | 9.0 |
| GA-005 | 20 | 14% | 13% | 4% | 31% | 37% | 11 | 14.4 | 9.1 |
| GA-009 | 20 | 11% | 11% | 2% | 36% | 39% | 10 | 12.0 | 9.2 |
| GA-011 | 20 | 8% | 6% | 6% | 37% | 44% | 10 | 12.0 | 8.9 |
| GA-013 | 20 | 8% | 13% | 5% | 28% | 48% | 8 | 11.8 | 8.7 |
| GT-033 | 1-4 | 4% | 1% | 1% | 26% | 68% | 2 | 11.8 | 6.7 |
| 1AC-261-1 | 12 | 12% | 12% | 2% | 37% | 37% | 14 | 12.2 | |
| AURORA 020 | 19 | 15% | 14% | 1% | 31% | 39% | 128 | 20.6 | 9.0 |
| ARCG-05 | 21 | 3% | 0% | 2% | 6% | 89% | 5 | 13.7 | 6.3 |
| Utopia Gold | 22 | 5% | 2% | 1% | 5% | 89% | 9 | 4.7 | 5.1 |
| SNG911219 | 22 | 2% | 0% | 0% | 11% | 87% | 13 | 18.4 | 6.9 |
| Nanopartz | 22 | 2% | 0% | 0% | 21% | 77% | 39 | 21.9 | 7.6 |
| Nanocomposix 15 nm | 22 | 3% | 4% | 2% | 10% | 81% | 49 | 17.8 | 5.2 |
| Nanocomposix 10 nm | 22 | 2% | 1% | 1% | 22% | 73% | 51 | 13.7 | 5.1 |
| Harmonic Gold | 22 | 8% | 2% | 2% | 35% | 55% | 5 | 8.9 | 8.8 |
| ElectraClear | 22 | 6% | 2% | 2% | 20% | 71% | 3 | 5.7 | 6.3 |
| MesoGold | 22 | 5% | 1% | 2% | 15% | 78% | 20 | 8.5 | 5.7 |

In order to be very conservative, during the analysis of TEM micrographs of all suspensions or colloids produced according of the invention, any questionable crystals were assigned to the group labeled "Other". Questionable crystals were those that possibly belong to a well defined crystal categories, but some uncertainty exists (e.g., a small pentagon with one corner obscured by an adjacent particle). In contrast, when performing the analysis of the particles in the commercially available colloids, any particle of questionable shape was given "the benefit of the doubt" and was assigned to the "category "Hexagonal" despite the uncertainty of its actual crystal structure. Thus the crystal/particle shape comparisons are not biased and are very conservative Example 22b The Zeta Potential Example The nature and/or amount of the surface change (i.e., positive or negative) on formed nanoparticles can also have a large influence on the behavior and/or effects of the nanoparticle/suspension or colloid. For example, a protein corona can be influenced by surface change on a nanoparticle. Such surface changes are commonly referred to as "zeta potential". In general, it is well known that the larger the zeta potential (either positive or negative), the greater the stability of the nanoparticles in the solution (i.e., the suspension is more stable). However, by controlling the nature and/or amount of the surface charges of formed nanoparticles the performance of such nanoparticle solutions in a variety of systems can be controlled. It should be clear to an artisan of ordinary skill that slight adjustments of chemical composition, reactive atmospheres, power intensities, temperatures, etc., can cause a variety of different chemical compounds (both semi-permanent and transient) nanoparticles (and nanoparticle components) to be formed, as well as different nanoparticle/solutions (e.g., including modifying the structures of the liquid 3 (such as water) per se). Accordingly, this Example measures the zeta potential of several suspensions made according to the invention, as well as several commonly available colloidal gold suspensions.

"Zeta potential" is known as a measure of the electrokinetic potential in colloidal systems. Zeta potential is also referred to as surface charge on particles. Zeta potential is also known as the potential difference that exists between the stationary layer of fluid and the fluid within which the particle is dispersed. A zeta potential is often measured in millivolts (i.e., mV). The zeta potential value of approximately 25 mV is an arbitrary value that has been chosen to determine whether or not stability exists between a dispersed particle in a dispersion medium. Thus, when reference is made herein to "zeta potential", it should be understood that the zeta potential referred to is a description or quantification of the magnitude of the electrical charge present at the double layer.

The zeta potential is calculated from the electrophoretic mobility by the Henry equation:

$$U_E = \frac{2\varepsilon z f(ka)}{3\eta}$$

where z is the zeta potential, $U_E$ is the electrophoretic mobility, $\varepsilon$ is a dielectric constant, $\eta$ is a viscosity, $f(ka)$ is Henry's function. For Smoluchowski approximation $f(ka) = 1.5$.

Electrophoretic mobility is obtained by measuring the velocity of the particles in an applied electric field using Laser Doppler Velocimetry ("LDV"). In LDV the incident laser beam is focused on a particle suspension inside a folded capillary cell and the light scattered from the particles is combined with the reference beam. This produces a fluctuating intensity signal where the rate of fluctuation is proportional to the speed of the particles (i.e. electrophoretic mobility).

In this Example, a Zeta-Sizer "Nano-ZS" produced by Malvern Instruments was utilized to determine zeta potential. For each measurement a 1 ml sample was filled into clear disposable zeta cell DTS1060C. Dispersion Technology Software, version 5.10 was used to run the Zeta-Sizer and to calculate the zeta potential. The following settings were used: dispersant—water, temperature—25° C., viscosity—0.8872 cP, refraction index—1.330, dielectric constant—78.5, approximation model—Smoluchowski. One run of hundred repetitions was performed for each sample.

FIG. 91 shows the Zeta potential of two colloidal nanocrystal solutions (GB-134 and GB-151) as a function of pH. The pH was varied by titrating 1 wt % solution of acetic acid. The measurements were performed on a Malvern Instruments Zeta sizer Nano-ZS90 in folded capillary cell DTS 1060 at 25° C. 20 and 50 sub runs per measurements were used at low and high pHs, respectively.

FIG. 92 shows the conductivity measurements for the same colloidal solutions tested for Zeta potential. The conductivity measurements were obtained simultaneously on the Malvern Instruments Zeta Sizer NanoZS90 when the Zeta potential was determined.

Example 23a

This Example 13a utilized a set of processing conditions similar to those set forth in Examples 5-7. This Example utilized an apparatus similar to those shown in FIGS. 17b, 18a, 19 and 21. Table 8 sets forth the specific processing conditions of this Example which show the differences between the processing conditions set forth in Examples 5-7. The main differences in this Example includes more processing enhancer added to the liquid 3 and a more rapid liquid 3 input flow rate.

TABLE 13

| 0.528 mg/ml of $NaHCO_3$ (Au) | |
| --- | --- |
| Run ID: | GD-006 |
| Flow Rate: | 240 ml/min |
| Voltage: | 255 V |
| $NaHCO_3$: | 0.528 mg/ml |
| Wire Dia.: | .5 mm |
| Configuration: | Straight/Straight |
| PPM: | 8.7 |

| Set# | Electrode# | Distance "c-c" in/mm | Distance "x" in/mm | Voltage | cross section |
| --- | --- | --- | --- | --- | --- |
| 1 | 1a | 4.5/114.3* | 0.25 | 750 | |
|   | 5a |  | N/A | 750 | V |
|   |    | 23/584.2** |  |  |  |
| 2 | 5b | 2.5/63.5* | N/A | 255 | |
|   | 5b' |  | N/A |  | |
|   |    | 8.5/215.9 |  |  |  |
| 3 | 5c |  | N/A | 255 | |
|   | 5c' |  | N/A |  | Rectangle 5.25" |
|   |    | 8.5/215.9 |  |  | Deep |
| 4 | 5d |  | N/A | 255 | |
|   | 5d' |  | N/A |  | |
|   |    | 8/203.2 |  |  |  |
| 5 | 5e |  | N/A | 255 | |
|   | 5e' |  | N/A |  | |
|   |    | 2/50.8** |  |  |  |
|   |    |  |  | Output Water Temperature | 95 C. |

*Distance from water inlet to center of first electrode set
**Distance from center of last electrode set to water oulet FIG. 93 shows a representative Viscotek output for the suspension produced in accordance with Example 23a. The numbers reported correspond to hydrodynamic radii of the nanocrystals in the suspension.

Example 23b

This Example 23b utilized the suspension of Example 23a to manufacture a gel or cream product. Specifically, about 1,300 grams of the suspension made according to Example 13a was heated to about 60° C. over a period of about 30 minutes. The suspension was heated in a 1 liter Pyrex® beaker over a metal hotplate. About 9.5 grams of Carbopol® (ETD 2020, a carbomer manufactured by Noveon, Inc., Cleveland, Ohio) was added slowly to the heated suspension, while constantly stirring using a squirrel rotary plastic paint mixer. This mixing occurred for about 20 minutes until large clumps of the Carbopol were dissolved.

About 15 grams of high purity liquid lanolin (Now Personal Care, Bloomingdale, Ill.) was added to the suspension and mixed with the aforementioned stirrer.

About 16 grams of high purity jojoba oil were then added and mixed to the suspension.

About 16 grams of high purity cocoa butter chunks (Soap Making and Beauty Supplies, North Vancouver, B.C.) were heated in a separate 500 mL Pyrex® beaker and placed on a hotplate until the chunks became liquid and the liquid cocoa butter then was added and mixed to the aforementioned suspension.

About 16 grams of potassium hydroxide (18% solution) was then added and mixed together with the aforementioned ingredients to cause the suspension to gel. The entire suspension was thereafter continuously mixed with the plastic squirrel rotating mixer to result in a cream or gel being formed. During this final mixing of about 15 minutes, additional scent of "tropical island" (2 mL) was added. The result was a pinkish, creamy gel.

Example 23c

This Example 23c utilized the suspension made according to Example 7. Specifically, this Example utilized the product of Example 7 (i.e., GD-015) to manufacture a gel or cream product. Specifically, about 650 grams of the solution made according to Example 7 was heated to about 60° C. over a period of about 30 minutes. The suspension was heated in a 1 liter Pyrex® beaker over a metal hotplate. About 9.6 grams of Carbopol® (ETD 2020, a carbomer manufactured by Noveon, Inc., Cleveland, Ohio) was added slowly to the heated suspension, while constantly stirring using a squirrel rotary plastic paint mixer. This mixing occurred for about 20 minutes until large clumps of the carbopol were dissolved.

About 7 grams of high purity liquid lanolin (Now Personal Care, Bloomingdale, Ill.) was added to the solution and mixed with the aforementioned stirrer.

About 8 grams of high purity jojoba oil were then added and mixed to the suspension.

About 8 grams of high purity cocoa butter chunks (Soap Making and Beauty Supplies, North Vancouver, B.C.) were heated in a separate 500 mL Pyrex® beaker and placed on a hotplate until the chunks became liquid and the liquid cocoa butter then was added and mixed to the aforementioned suspension.

About 45 grams of the liquid contained in Advil® liquid gel caps (e.g., liquid ibuprofen and potassium) was added to, and thoroughly mixed with, the suspension.

About 8 grams of potassium hydroxide (18% solution) was then added and mixed in to cause the suspension to gel. The entire solution was thereafter continuously mixed with the plastic squirrel rotating mixer to result in a cream or gel being formed. During this final mixing of about 15 minutes, additional scent of "tropical island" (2 mL) was added. The result was a pinkish, creamy gel.

Example 23d

This Example 23d utilized suspension equivalent to GB-139 to manufacture a gel or cream product. Specifically, about 650 grams of the suspension was heated to about 60° C. over a period of about 30 minutes. The suspension was heated in a 1 liter Pyrex® beaker over a metal hotplate. About 6 grams of Carbopol® (ULTREZ10, a carbomer manufactured by Noveon, Inc., Cleveland, Ohio) was added slowly to the heated suspension, while constantly stirring using a squirrel rotary plastic paint mixer. This mixing occurred for about 20 minutes until large clumps of the Carbopol were dissolved.

About 7 grams of high purity liquid lanolin (Now Personal Care, Bloomingdale, Ill.) was added to the suspension and mixed with the aforementioned stirrer.

About 8 grams of high purity jojoba oil were then added and mixed to the suspension.

About 8 grams of high purity cocoa butter chunks (Soap Making and Beauty Supplies, North Vancouver, B.C.) were heated in a separate 500 mL Pyrex® beaker and placed on a hotplate until the chunks became liquid and the liquid cocoa butter then was added and mixed to the aforementioned suspension.

About 8 grams of potassium hydroxide (18% solution) was then added and mixed together with the aforementioned ingredients to cause the suspension to gel. The entire suspension was thereafter continuously mixed with the plastic squirrel rotating mixer to result in a cream or gel being formed. The result was a pinkish, creamy gel.

Example 23e

This Example 23e utilized a suspension substantially equivalent to 1AC-261 to manufacture a gel or cream product. Specifically, about 450 grams of the suspension was heated to about 60° C. over a period of about 30 minutes. The suspension was heated in a 1 liter Pyrex® beaker over a metal hotplate. About 4.5 grams of Carbopol® (ULTREZ10, a carbomer manufactured by Noveon, Inc., Cleveland, Ohio) was added slowly to the heated suspension, while constantly stirring using a squirrel rotary plastic paint mixer. This mixing occurred for about 20 minutes until large clumps of the Carbopol were dissolved.

About 6.5 grams of potassium hydroxide (18% solution) was then added and mixed together with the aforementioned ingredients to cause the suspension to gel. The entire suspension was thereafter continuously mixed with the plastic squirrel rotating mixer to result in a cream or gel being formed. The result was a pinkish, creamy gel.

Example 24

In Vitro Study of the Effects of Gold Nanocrystalline Formulation GB-079 on Monocyte Cytokine Production Summary This in vitro Example was designed to determine the effects of gold nanocrystalline suspension GB-079 on four different cytokines/chemokines. Specifically in this Example, human peripheral blood mononuclear cells ("hPBMC") were cultured in the presence or absence of each of four different concentration or ppm levels of gold nanocrystalline suspension GB-079 (i.e., a suspension or colloid made in accordance with the disclosure of one example herein) in the presence or absence of (as disclosed herein) bacterial lipopolysaccharide ("LPS").

It is known that lipopolysaccharide binds to TLR4, a receptor expressed on a number of different immune system cells, and such binding typically triggers activation and/or expression of a series of cytokines, typically in an NFkB-dependent (i.e., Nuclear Factor kB-dependent) manner. After about 24 hours of culture conditions at about 37° C. in about 5% $CO_2$ and a humidified atmosphere of about 95% relative humidity, supernatants were removed and assayed for the presence of a series of different cytokines/chemokines, including: MIF, TNFα, IL-6 and IL-10. The majority of, but not the only source of, these cytokines in the hPBMC population would be expected to be monocytes. Cultures in the absence of LPS indicate whether treatments induce the production of these cytokines/chemokines, while those cultures in the presence of LPS will indicate whether treatments are able to modulate the production of cytokines in response to an inflammatory stimulus. Cytokine assays were performed by the Luminex® Extracellular Assay Protocol. The Luminex system uses antibody coated microspheres that bind specifically to the cytokine being assayed. When excited by laser light the microspheres that have bound the antigen are measured and this is a direct assessment of the amount of the cytokine being produced and data were provided as raw data and absolute quantities of each cytokine/chemokine measured.

Preparation of hPBMC
Materials Used for Cell Preparation:

|  | Supplier | Cat. No. |
|---|---|---|
| PBMC Isolation | | |
| Histopaque 1077 | Sigma | H8889 |
| RPMI 1640 x10 | Sigma | R1145 |
| Endotoxin-free water (EFW) | Gibco | 15230-170 |
| 50 ml falcon tubes | Corning | 430829 |
| Citrate ACD | Sigma | C3821-50 ml |
| AB serum | National Blood Service | |
| Plastic 24 well plates | Costar/Corning | 3524 |
| LPS | Sigma | |
| Media supplements | | |
| Penicillin/streptomycin | Sigma | P0871 |
| HEPES | Sigma | H0887 |
| Glutamine | Gibco | 25030-024 |
| Sodium Bicarbonate (7.5%) | Gibco | 25080 |
| Equipment | | |

NucleoCounter (i.e., cell number and viability counter made by Chemometec)
Benchtop centrifuge
Tissue culture hood Collection of Human Blood
Blood from a healthy volunteer was drawn into a syringe and placed into a 50 ml falcon tube.
3.3 ml citrate anticoagulant (ACD, Sigma) was added to the 50 ml falcon tubes in a sterile manner.
Tubes were inverted to mix.

Cell Preparation Method
1. 10×RPMI+supplements (25 ml 10×RPMI+2.5 ml Penstrep+2.5 ml L-glutamine+5 ml HEPES+6.7 ml sodium bicarbonate solution (7.5%)) were mixed together in a falcon tube, herein referenced to as the "culture media".
2. Blood was resuspended in an equal volume of 1×RPMI 1640 (diluted from 10×RPMI in EFW-200 ml prepared [20 ml in 180 ml]) and mixed by inversion in a falcon tube.
3. The histopaque was prewarmed to room temperature (RT) and 20 ml was added to a 50 ml falcon tube.
4. The histopaque was gently overlayed with 30 ml blood/medium then mixed in.
5. The histopaque blood mix sample was spun at 1600 rpm in a benchtop centrifuge for about 25 min at RT (no brake).
6. PBMCs were separated into the interface layer between the medium and the histopaque, cells were removed by aspiration into a 50 ml falcon tube and 10 ml of the culture media was added thereto.
7. The cell sample was spun at 1800 rpm for about 10 minutes at RT.
8. The cell sample was washed twice with 30 ml RPMI and resuspended in culture medium (RPMI, supplemented as described above=RPMI/no serum).
9. During the spin, RPMI supplemented with 5% AB serum was prepared.
10. The cell sample was resuspended in 2 ml RPMI+supplements+serum.
11. Cell counts were completed and viability assessment was performed using the Nucleocounter (i.e., a cell viability counter).
12. Cells were resuspended in 1×RPMI to give a final concentration of $2.5 \times 10^6$ cells/ml.
13. 500 µl of cells were transferred into a 24-well plate.
14. 10×RPMI+supplements (500 µl PenStrep, 500 µl L-Glutamine, 1 ml HEPES, 2.5 ml AB serum) was prepared by mixing together in a falcon tube, thereby forming the "test media".
15. The inventive GB-079 gold nanocrystal suspension was added to the wells in the 24 well plate (900 µl total volume)
16. 100 µl 10×RPMI+supplements were added to each well of a costar 24 well plate.
17. The 24 well plates were placed into a humidified incubator set at 37° C./5% $CO_2$ for 1 hour.
18. LPS was prepared at 4× final concentration in 1×RPMI
19. 500 µl of LPS was added per well, or 500 µl media to wells not receiving LPS, bringing the total well volume of material to each well to 2 ml.
20. Plates were placed into a humidified incubator set at 37° C./5% $CO_2$ for about 24 hours.
21. 1800 µl (3×600 µl aliquots) of supernatant were removed for ELISA analysis and Luminex analysis.
22. Supernatants were stored at −80° C. until assayed in the Luminex® system.

Luminex® Assay System
The supernatants were assayed in accordance with the Luminex® Extracellular Assay Protocol, accessed on Jan. 11, 2010.

TABLE 14

| Sample | Compound | EFW | 10x RPMI | Cells | LPS | 1x RPMI |
|---|---|---|---|---|---|---|
| Cells + Vehicle | | 900 µl | 100 µl | 500 µl | | 500 µl |
| Cells + Vehicle + LPS | | 900 µl | 100 µl | 500 µl | 500 µl | |
| Cells + [Test]$_{1:5}$ | 400 µl | 500 µl | 100 µl | 500 µl | | 500 µl |
| Cells + [Test]$_{1:10}$ | 200 µl | 700 µl | 100 µl | 500 µl | | 500 µl |
| Cells + [Test]$_{1:20}$ | 100 µl | 800 µl | 100 µl | 500 µl | | 500 µl |
| Cells + [Test]$_{1:40}$ | 50 µl | 850 µl | 100 µl | 500 µl | | 500 µl |
| Cells + [Test]$_{1:100}$ | 20 µl | 880 µl | 100 µl | 500 µl | | 500 µl |
| Cells + [Test]$_{1:5}$ + LPS | 400 µl | 500 µl | 100 µl | 500 µl | 500 µl | |
| Cells + [Test]$_{1:10}$ + LPS | 200 µl | 700 µl | 100 µl | 500 µl | 500 µl | |
| Cells + [Test]$_{1:20}$ + LPS | 100 µl | 800 µl | 100 µl | 500 µl | 500 µl | |
| Cells + [Test]$_{1:40}$ + LPS | 50 µl | 850 µl | 100 µl | 500 µl | 500 µl | |
| Cells + [Test]$_{1:100}$ + LPS | 20 µl | 880 µl | 100 µl | 500 µl | 500 µl | |

Cells were stimulated with LPS (a high dose of 1 mg/ml and a low dose of 10 ng/ml), the supernatants were then collected after 24 hours and analyzed for the amounts present of the 4 cytokines discussed herein. Control wells contained cells and the inventive test compound GB-079 but no LPS. Results obtained for each of the other cytokines/chemokines are shown in FIGS. 94a-94d.

Figure 94A:
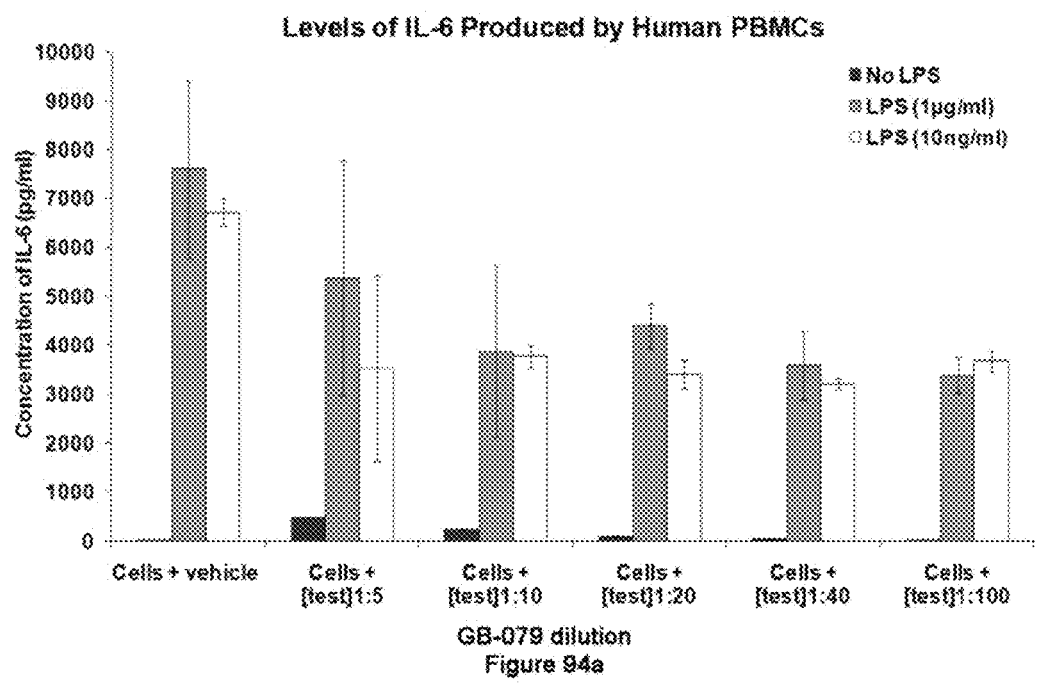

FIG. 94a shows the effects of GB-079 on IL-6 production by human peripheral blood mononuclear cells (hPBMCs). It is clear from FIG. 94a that IL-6 levels were reduced by GB-079 in LPS stimulated PBMC. Some IL-6 production was also observed with the highest concentrations of GB-079 in the absence of LPS stimulation at five different concentration levels.

Figure 94B:
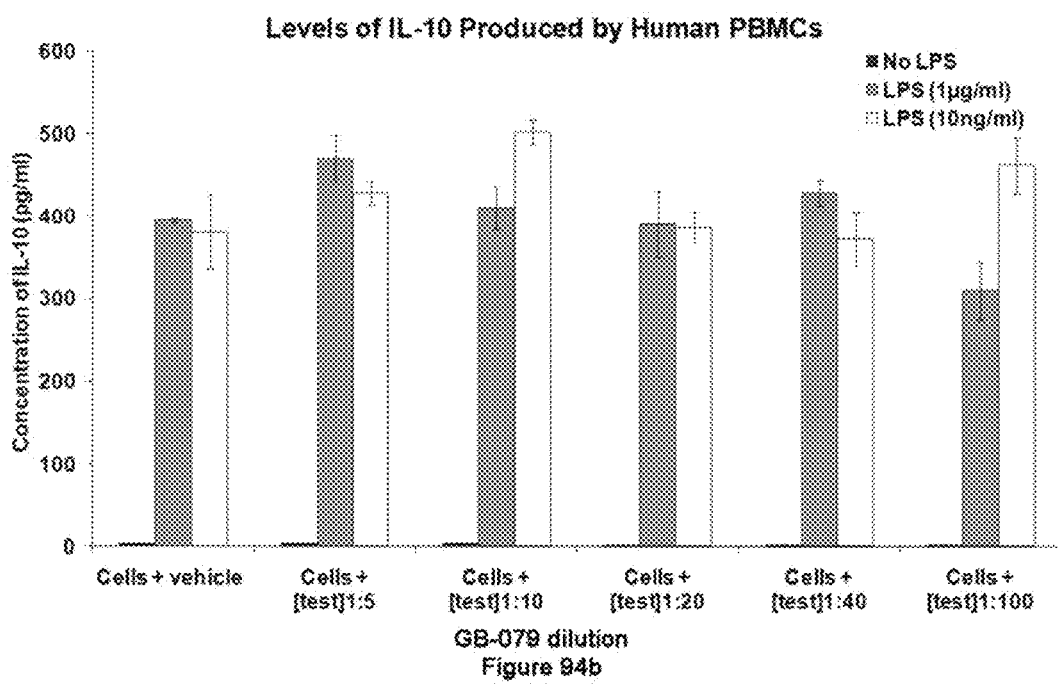

FIG. 94b shows the effects of GB-079 on IL-10 production by hPBMCs. It is clear from FIG. 94b that the levels of IL-10 observed were unaffected by the addition of GB-079 at all concentration levels.

Figure 94C:
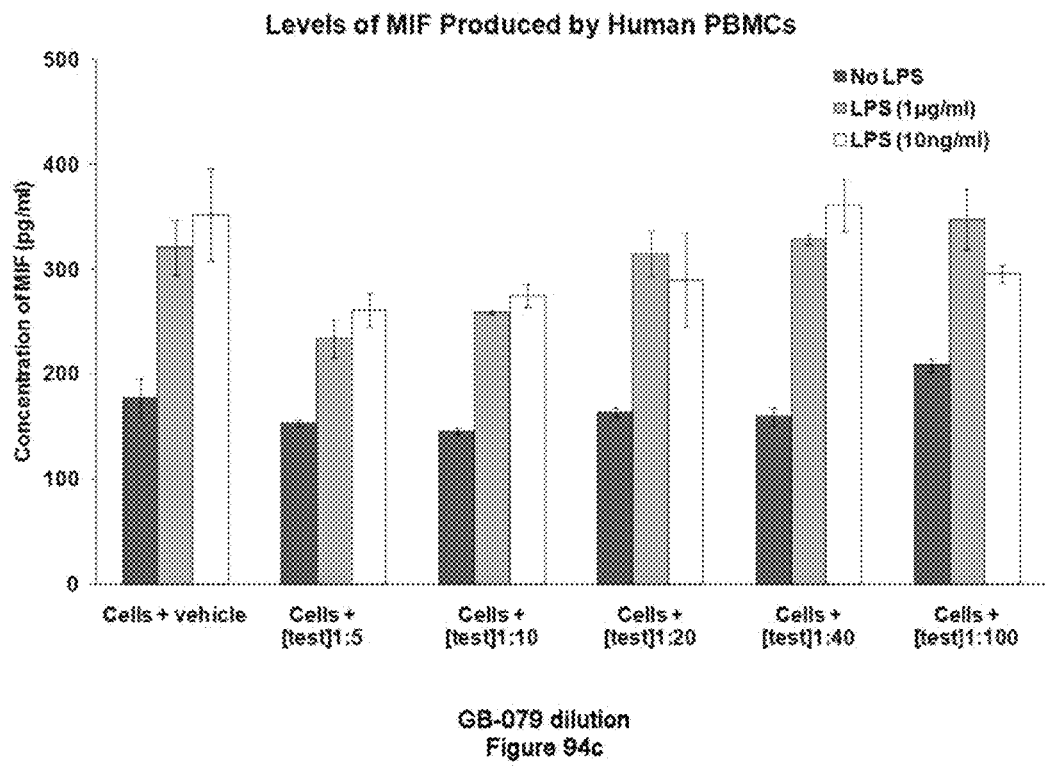

FIG. 94c shows the effects of GB-079 on MIF production by hPBMCs. Specifically, FIG. 94c shows that following LPS stimulation, the levels of MIF were reduced in a dose dependent manner. This reduction was observed at dilution levels of 1:5 and 1:10, while MIF levels returned to that of control samples by the 1:20 concentration of GB-079.

Figure 94D:
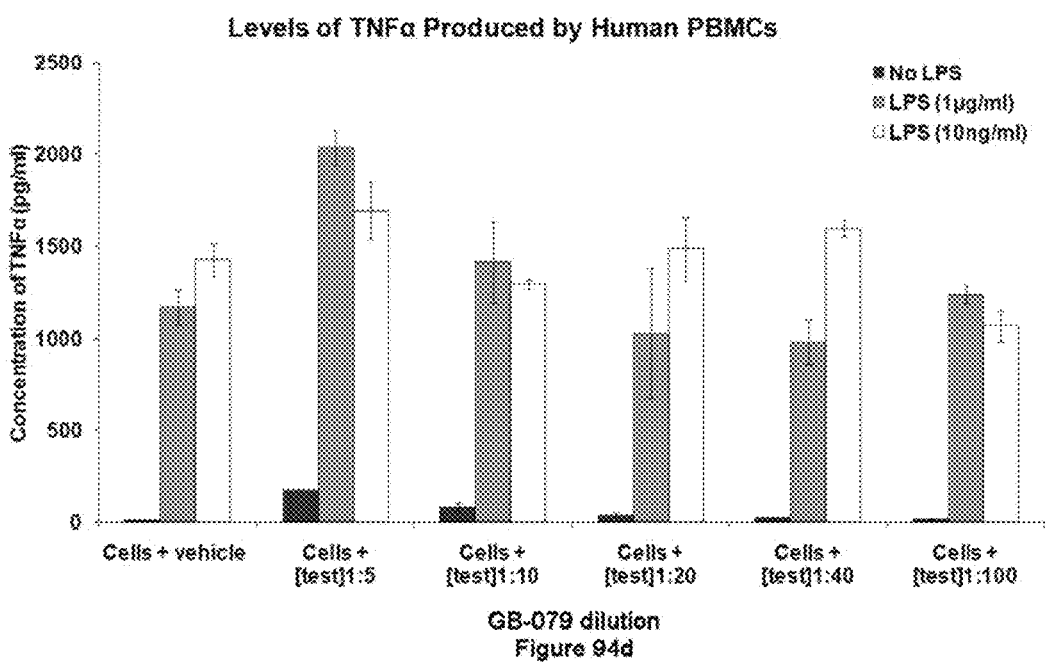

Further, FIG. 94d shows that GB-079 at the highest concentrations caused an increase in TNFα levels (with both tested doses of LPS) above that of vehicle control stimulated samples. Some TNFα production was also observed with the highest doses of GB-079 in the absence of LPS stimulation.

Example 25

Collagen Induced Arthritis (CIA) Study in Mice

Summary

This Example demonstrates the efficacy of two of the inventive gold nanocrystalline compositions (i.e., GT033 and GD-007) in a mouse CIA model. Specifically, male DBA/1 mice (12 weeks old) were given 100 μg Chicken Type II collagen emulsified into complete Freund's adjuvant ("CII/CFA") on day 0 of the study by injection at the base of the tail. Clinical joint swelling was scored three times weekly from day 14 until termination at day 42. Those results are summarized in FIG. 95. Treatments were given according to the protocol below. Bleeds were taken on day 0 and day 42. At termination animals were bled, hind legs were removed and ankle joints were prepared for histopathology examination. Histopathology results are set forth in Table 6 and Table 7.

Methodology

Animals
　Species: Mice
　Strain: DBA/1
　Source: Harlan
　Gender and number: Male, 30
　Age: About 12 weeks old at the start of the study.
　Identification: Each mouse was given a unique identity number.
　Animal husbandry: On receipt, all animals were examined for external signs of ill-health and all unhealthy animals were excluded from further evaluation. Animals were housed in groups of five under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.
　Housing Animals were housed in groups of 10 per cage in a controlled room, to ensure correct temperature, humidity and 12 hour light/dark cycle for the duration of the study.
　Diet: Irradiated pellet diet and water was available ad libitum throughout the holding, acclimatisation and post-dose periods.

Compound and Reagents
Chicken Collagen Type II (Sigma, C9301).
Incomplete Freund's Adjuvant ("IFA") (Sigma, FF5506)
*Mycobacterium tuberculosis* H37Ra (BD Biosciences, 231141)
Phosphate buffered saline ("PBS")
Test compounds gold nanocrystal formulations GT033 and GD-007.
Vehicle: Water.

Treatment Groups and Dosages
　Control Group 1, First Treatment "Group 2" and Second Treatment "Group 3" each had 10 animals per group.
Group 1: Day 0 CII/CFA, given normal drinking water from day 0-42.
Group 2: Day 0 CII/CFA, gold nanocrystal formulation (GT033; Example 4/Table 1d; gold ppm 2.0) as drinking water from day 0-42.
Group 3: Day 0 CII/CFA, gold nanocrystal formulation (GD-007; Example 5/Table 2a; gold ppm 14.8) as the only liquid for drinking from day 0-42.

Protocol

1. On arrival of animals, the health of all animals was checked and after passing the health test, each was numbered with a unique ear tag.
2. The animals were allowed to acclimate for at least 72 hours.
3. Chicken Type II collagen was prepared so as to achieve a suspension with a concentration of about 16 mg/ml in 0.1M acetic acid. After dissolution overnight at 4° C., the solution was diluted with cold PBS to achieve a suspension with a concentration of about 8 mg/ml.
4. Fresh mycobacterium was prepared by grinding it finely with a mortar and pestle and adding about 7 ml of IFA, drop-by-drop, to create an emulsion or suspension of CFA with a final concentration of about 5 mg/ml.
5. An emulsion of Chicken Type II collagen and CFA was prepared using approximately equal volumes of each to result in the injectable suspension of collagen in CFA (i.e., "CII/CFA").
6. On Day 0, the animals were injected with 50 μl of the CII/CFA solution at the base of the tail.
7. Treatments using gold nanocrystal formulation GT033 (i.e., Group 2) and gold nanocrystal formulation GD-007 (i.e., Group 3) were given according to the schedule above until Day 42. Specifically, each water bottle containing either normal drinking water, GT033 or GD-007 was topped-off as needed either every other day or every third day. The bottles were not specifically cleaned or specifically emptied during the 42 day trial.
8. The limb scores were determined three times per week from Day 14 to the end of the study. Each of the four limbs was given a score according to the following;
0=Normal.
1=Slight swelling of whole joint or individual digit inflammation.
2=Intermediate swelling of whole joint with redness and/or inflammation in more than one digit.

3=severe joint inflammation and redness spreading to multiple digits.

4=severe joint inflammation and redness spreading to multiple digits; overt signs of bone remodeling.

9. All animals were bled on days 0 and day 42 and the retrieved serum was stored for optional analysis.
10. The animals were sacrificed on Day 42 and the ankle joints were removed and placed in neutral-buffered formalin in preparation for histopathology.
11. These sections were processed and stained with hematoxylin and eosin stain ("H & E") and were scored by a qualified (and experimentally blinded) histopathologist using a semi-quantitative measurement of the degree of infiltration and damage.

FIG. 95 shows graphically the results of the limb scoring CIA-test. Clearly the gold nanocrystal formulation GD-007 (Group 3), having a measured gold concentration of about 14.8 ppm, performed the best, on par (or better), perhaps with a typical steroid treatment, the results of which have also been placed onto FIG. 95 (even though not actually measured). The gold nanocrystal formulation GT033 (Group 2) performed better than Control Group 1 at a concentration of about 2.0 ppm of gold nanocrystals suspended in water.

Histopathology was performed on the left and right paws from each of the 10 mice in Group 1 (control) and Group 3 (GD-007). No histopathology was performed on Group 2 mice.

Each pair of paws was assigned a Pathology numerical code (e.g., R0248-09 for one mouse in Group 1) and the limbs distinguished as left ("L") or right ("R") from each numbered animal.

Histopathology/Methodology:

The skin was dissected from the paw.

The dissected samples were decalcified to permit sectioning.

The decalcified samples were routinely processed, sectioned and one H & E-stained section was prepared for examination. This included both halves of each specimen being hemi-sectioned.

Each histopath paw was scored as described below. Samples were scored in blinded fashion, without knowledge of the experimental protocol or identity of groups.

Multiple phalangeal and tarsal joints were generally present on each section. Scoring related to the most severely affected of these joints in each case.

TABLE 15

Figure 97A:
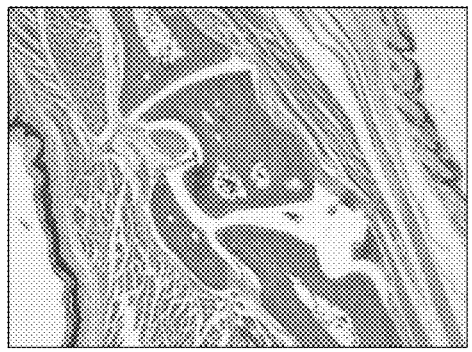
Figure 97B:
Figure 97C:
Figure 97D:
Figure 97E:
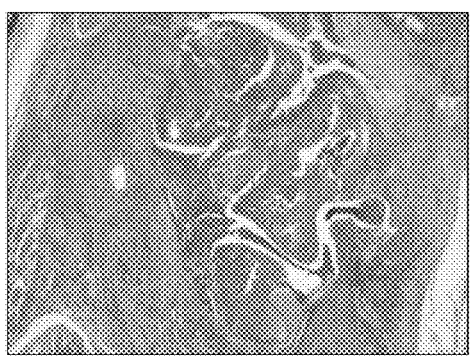

Scoring System
In this instance, three aspects of the joint pathology were scored individually to contribute to a composite score (i.e., maximum possible score = 9). Thus, the higher the number, the greater the damage. Representative photomicrographs of joints corresponding to the aforementioned grades 0-3 are shown in FIGS. 96a-96d, respectively. Representative compilations of these grades 0-3 are shown in FIGS. 97a (i.e., Grade 0) through FIG. 97e (i.e., Grade 9).

| Aspect | Grade 0 | Grade 1 | Grade 2 | Grade 3 |
| --- | --- | --- | --- | --- |
| Inflammation | Normal joint | Mild synovial hyperplasia with inflammation dominated by neutrophils. Low numbers of neutrophils and macrophages in joint space. | Synovial hyperplasia with moderate to marked inflammation involving both neutrophils and macrophages. Neutrophils and macrophages in joint space; may be some necrotic tissue debris. | Synovial hyperplasia with marked inflammation involving both neutrophils and macrophages. Loss of synoviocyte lining. Inflammation may extend from synovium to surrounding tissue including muscle. Numerous neutrophils and macrophages in joint space, together with significant necrotic tissue debris. |
| Articular cartilage damage | Normal joint | Articular cartilage shows only mild degenerative change. Early pannus formation may be present peripherally. | Articular cartilage shows moderate degenerative change and focal loss. Pannus formation is present focally. | Significant disruption and loss of articular cartilage with extensive pannus formation. |
| Damage to underlying metaphyseal bone | Normal joint | No change to underlying metaphyseal bone. | May be focal necrosis or fibrosis of metaphyseal bone. | Disruption or collapse of metaphyseal bone. Extensive inflammation, necrosis or fibrosis extending to medullary space of the metaphysis. |

TABLE 16

Paw Histopathology Scoring

|  | Pathology Number | Mouse Number and Limb | In-flammation | Cartilage | Bone | Total score | Comments |
|---|---|---|---|---|---|---|---|
| Control | R0248-09 | 1.1 L | 1 | 0 | 0 | 1 | Few neutrophils in mildly thickened synovium focally. |
|  |  | 1.1 R | 2 | 2 | 2 | 6 |  |
|  | R0249-09 | 1.2 L | 3 | 2 | 2 | 7 |  |
|  |  | 1.2 R | 1 | 0 | 0 | 1 |  |
|  | R0250-09 | 1.3 L | 3 | 2 | 2 | 7 |  |
|  |  | 1.3 R | 0 | 0 | 0 | 0 |  |
|  | R0251-09 | 1.4 L | 3 | 2 | 2 | 7 |  |
|  |  | 1.4 R | 3 | 1 | 1 | 5 | Reaction localized to P1-metatarsal |
|  | R0252-09 | 1.5 L | 3 | 2 | 2 | 7 |  |
|  |  | 1.5 R | 3 | 2 | 2 | 7 |  |
|  | R0253-09 | 1.6 L | 0 | 0 | 0 | 0 |  |
|  |  | 1.6 R | 3 | 1 | 2 | 6 |  |
|  | R0254-09 | 1.7 L | 3 | 2 | 2 | 7 |  |
|  |  | 1.7 R | 3 | 2 | 2 | 7 |  |
|  | R0255-09 | 1.8 L | 0 | 0 | 0 | 0 |  |
|  |  | 1.8 R | 3 | 1 | 1 | 5 |  |
|  | R0256-09 | 1.9 L | 0 | 0 | 0 | 0 |  |
|  |  | 1.9 R | 0 | 0 | 0 | 0 |  |
|  | R0257-09 | 1.10 L | 0 | 0 | 0 | 0 |  |
|  |  | 1.10 R | 0 | 0 | 0 | 0 |  |
| Treatment Group3 | R0258-09 | 2.1 L | 0 | 0 | 0 | 0 |  |
|  |  | 2.1 R | 0 | 0 | 0 | 0 |  |
|  | R0259-09 | 2.2 L | 0 | 0 | 0 | 0 |  |
|  |  | 2.2 R | 0 | 0 | 0 | 0 |  |
|  | R0260-09 | 2.3 L | 0 | 0 | 0 | 0 |  |
|  |  | 2.3 R | 0 | 0 | 0 | 0 |  |
|  | R0261-09 | 2.4 L | 0 | 0 | 0 | 0 |  |
|  |  | 2.4 R | 0 | 0 | 0 | 0 |  |
|  | R0262-09 | 2.5 L | 0 | 0 | 0 | 0 |  |
|  |  | 2.5 R | 0 | 0 | 0 | 0 | Has localized subcutaneous inflammatory response; joints normal. |
|  | R0263-09 | 2.6 L | 0 | 0 | 0 | 0 |  |
|  |  | 2.6 R | 0 | 0 | 0 | 0 |  |
|  | R0264-09 | 2.7 L | 0 | 0 | 0 | 0 |  |
|  |  | 2.7 R | 0 | 0 | 0 | 0 |  |
|  | R0265-09 | 2.8 L | 0 | 0 | 0 | 0 |  |
|  |  | 2.8 R | 0 | 0 | 0 | 0 |  |
|  | R0266-09 | 2.9 L | 3 | 1 | 0 | 4 |  |
|  |  | 2.9 R | 0 | 0 | 0 | 0 |  |
|  | R0267-09 | 2.10 L | 3 | 1 | 2 | 6 | Localized metatarsal-P1 reaction with marked periosteal new bone and cartilage formation-probably localized fracture repair rather than joint disease. |
|  |  | 2.10 R | 3 | 2 | 2 | 7 |  |

TABLE 17

Mean Group Scores

| Group | Paws (n=) | Mean Score | Number [%] of Joints affected |
|---|---|---|---|
| 1-Control | 20 | 3.65 | 14/20 [70%] |
| 2-GD-007 | 20 | 0.85 | 3/20 [15%] |

As is typical for this type of murine CIA model, one animal in Treatment "Group 3," GD-007, (i.e., R0266-09) exhibited a lack of correlation between its right and left joints in terms of the presence/absence of arthritis. Similar discrepancies occur in some of the control mice, as well as differences in the severity of the arthritis between different joints in the same mouse (e.g., R0250-09).

It is clear, however, that the most severe pathology occurred in Control Group 1 (i.e., drinking water) and the least severe pathology occurred in First "Treatment Group 2" (i.e., gold nanocrystal formulation GD-007).

One animal in Treatment Group 3 (i.e., R0267-09) suffered a broken bone which probably accounted for its higher scores. Exclusion of this animal resulted in a mean score of 0.22. Further, the histopathology data suggests no resulting damage at all in 8 of the 10 mice (i.e., 16 total paw joints examined). Clearly the gold nanocrystal formulation GD-007 had a significant positive effect in this CIA test.

It is clear that the gold nanocrystal formulations produced according to the invention significantly reduced the negative induced arthritis effects in the CIA model, relative to the control. It is known that reduction of excessive IL-6 and/or reduction of excessive MIF both reduce the negative effects of arthritic conditions. Accordingly, without wishing to be bound by any particular theory or explanation, by reducing excessive MIF, and/or one or more signaling pathways associated with MIF, arthritic conditions can be reduced. The gold nanocrystalline formulation GD-007 showed significantly improved results, relative to the control. These results, along with the results shown in the in vitro example and the EAE mouse model Example herein, suggest that the inventive gold nanocrystal compositions may be altering MIF and/or more signaling pathways associated with MIF, as well as IL-6.

Example: Doses Comparison

As stated above, in the gold nanocrystal trial, each mouse had access to GD-007 solution as the only source of drinking fluid. To calculate the dose of gold consumed by a mouse per day, following equation was used:

$$\text{Dose} = \frac{\text{Volume consumed (ml)} \times \text{Concentration (mg/L)}}{\text{Animal weight (kg)}}$$

where
Dose is the nanocrystal gold consumed per mouse per day in mg/kg/day,
Volume is an average amount of GB-134 solution drunk by a mouse per day in mL/day,
Concentration is the amount of nanocrystal gold in the GD-007 solution in mg/mL,
Weight is a mouse body weight in kg.

The following assumptions were used to calculate the nanocrystal gold dose:
Volume=4 mL
Concentration=0.0148 mg/mL
Weight=0.025 kg This results in a nanocrystal gold dose of 2.4 mg/kg/day.

Below is the comparison of the gold content in doses typically used for Auranofin treatment in the type II collagen-induced arthritis mouse model. Typical Auranofin dose is 40 mg/kg/day (Agata et al., 2000). Since the gold content in Auranofin is 29%, this results in gold dose of approximately 12 mg/kg/day.

In the only known human study (Abraham et al. 1997, 2008) using gold nanoparticles, a 30 mg/day gold nanoparticle dose was used for patients weighing from 108 to 280 lb. This corresponds to approximately 0.24 to 0.61 mg/kg/day gold nanoparticle dose.

A comparison between dose levels of gold content in Auranofin, gold in gold nanoparticles, and the novel gold nanocrystals, used in these different efficacy studies, is shown below in Table 17a, demonstrating that the present novel gold nanocrystals are fundamentally different from, and perform very differently and at a much higher level of potency than, conventional gold, whether in molecular form in Auranofin, or in nanoparticle form as in Abraham, et. al.

TABLE 17a

| Study | Type of Gold Product | Gold mg/kg/day |
|---|---|---|
| Mouse RA CIA | Novel Gold Nanocrystals | 2.4 |
| Agata/Mouse RA CIA | Auranofin | 12 (5X) |
| Estimated Human dose* | Novel gold Nanocrystals | 0.005 |
| Abraham/human | Colloidal gold | 0.24 to 0.61 (47X to 122X) |

*Using mouse/mouse Auranofin/Nanocrystals potency factor applied to Auranofin human dose Example 26

Acute Murine Model of Experimental Auto-Immune Encephalitis ("EAE")

Summary

This Example demonstrates the efficacy of the inventive gold nanocrystalline composition GB-056 in a mouse EAE model. Female Biozzi mice 7-8 weeks old were challenged in the flank with mouse spinal cord homogenate in CFA on day 0 of the study by injection at the base of the tail. Ten treatment group mice were orally administered the gold nanoparticle suspension treatment GB-056 (i.e., as discussed in Example 17) as their only liquid for drinking by using standard water bottles. Fresh gold nanocrystalline formulation GB-056 was provided daily along with clean water bottles. Control group mice were provided ordinary tap drinking water. Clinical scoring in this EAE test was completed by a standard scoring system of 0-5.0 scored from day 1 until termination at day 28. Those results are presented in Tables 9a and 9b, as well as in FIGS. 98-99. Treatments were given according to the protocol below.

Methodology
Animals
  Species: Mice
  Strain: BIOZZI
  Source: Harlan
  Gender and number: Female, 20
  Age: About 7-8 weeks old at the start of the study.
  Identification: Each mouse was given a unique identity number.
  Animal husbandry: On receipt, all animals were examined for external signs of ill-health and all unhealthy animals were excluded from further evaluation. Animals were housed in groups of five under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.
  Housing Animals were housed in groups of 10 per cage in a controlled room, to ensure correct temperature, humidity and 12 hour light/dark cycle for the duration of the study.
  Diet: Irradiated pellet diet and water was available ad libitum throughout the holding, acclimatisation and post-dose periods.
Compound and Reagents
Mouse and Spinal Cord Homeogenate ("MSCH") produced in-house.
Incomplete Freund's Adjuvant ("IFA") (Sigma, FF5506)
Mycobacterium tuberculosis H37Ra (BD Biosciences, 231141)
Phosphate buffered saline ("PBS") in-house.
Test compound gold nanocrystalline suspension GB-056 (discussed elsewhere herein)
Vehicle: Water.
Treatment Groups and Dosages
  Control Group 1 and the Treatment Group 2 each had 10 animals per group.
  Group 1: Day 0 a mixture of MSCH/IFA/tuberculosis (see Protocol below) was injected into each mouse at base of tail and each was given normal drinking water dispensed from a water bottle, from day 0 to day 28.
  Group 2: Day 0 a mixture of MSCH/CFA/tuberculosis was injected into each mouse at base of tail and each was given gold nanocrystal formulation (GB-056) dispensed from a daily-cleaned water bottle with fresh GB-056 provided daily, as the only liquid for drinking, from day 0 to day 28.
Protocol
  On arrival of animals, the health of all animals was checked and after passing the health test, each was numbered with a unique ear tag.

1. The animals were allowed to acclimate for at least 72 hours.
2. The spinal cord was reconstituted in PBS containing mycobacterium tuberculosis H37RA. This resulted in 6.6 mg/ml of MSCH and 400 ug/ml of H37RA. An equal volume of Freund's incomplete adjuvant was added to this mixture to make the final immunogen (3.3 mg/ml SCH and 200 ug/ml H37RA). This mixture could not be considered complete Freund's because amount of *mycobacterium* was much lower.
3. On Day 0, the animals were injected with 50 μl of the solution discussed in step 3 at the base of the tail.
4. Treatment using gold nanocrystal formulation GB-056 was given according to the schedule above until Day 28. Fresh GB-056 was provided daily (i.e., replaced approximately every 24 hours).
5. The scores were determined daily from Day 1 to the end of the study. Scoring of each mouse occurred according to the following;

0: Normal
0.5: Paretic tail
1.0: Flaccid tail
1.5: Slow and/or absent righting reflex
2.0: One hind limb paralysis
2.5: One hind limb paralysis and unusual gait
3.0: Two hind limbs paralysis
3.5: Two hind limbs paralysis+one front limb paresis
4.0: Two hind limbs paralysis+one or two front limb paralysis
5.0: Moribund 6. The animals were sacrificed on Day 28 and the brain and spinal cord were removed and placed in neutral-buffered formalin in preparation for histopathology.
7. These sections were processed and stained with hematoxylin and eosin stain ("H & E"). Tables 9a and 9b show the raw scoring for each of the 20 mice in this EAE study.

TABLE 18a

| Animal # | Day 10 | Day 11 | Day 12 | Day 13 | Day 14 | Day 15 | Day 16 | Day 17 | Day 18 | Day 19 | Day 20 | Day 21 | Day 22 | Day 23 | Day 24 | Day 25 | Day 26 | Day 27 | Day 28 |
|---|---|---|---|---|---|---|---|---|---|---|---|---|---|---|---|---|---|---|---|
| Water Control ||||||||||||||||||||
| 1 | 0 | 0 | 0 | 0 | 0 | 0 | 0 | 0 | 0 | 0 | 1.5 | 2 | 2.5 | 5 | 5 | 5 | 5 | 5 | 5 |
| 2 | 0 | 0 | 0 | 0 | 0 | 0 | 0 | 1.5 | 1.5 | 1.5 | 2.5 | 2.5 | 5 | 5 | 5 | 5 | 5 | 5 | 5 |
| 3 | 0 | 0 | 0 | 0 | 0 | 0 | 0 | 0 | 0 | 0 | 0 | 0 | 0 | 0 | 0 | 1.5 | 1.5 | 1.5 | 0 |
| 4 | 0 | 0 | 0 | 0 | 0 | 0 | 0 | 1 | 1 | 2.5 | 1.5 | 1.5 | 1.5 | 1.5 | 1.5 | 1.5 | 1.5 | 1.5 | 0 |
| 5 | 0 | 0 | 0 | 0 | 0 | 0 | 0 | 0 | 0 | 0 | 0 | 0 | 0 | 0 | 0 | 0 | 0 | 0 | 1.5 |
| 6 | 0 | 0 | 0 | 0 | 0 | 0 | 0 | 0 | 1.5 | 1.5 | 1.5 | 5 | 5 | 5 | 5 | 5 | 5 | 5 | 5 |
| 7 | 0 | 0 | 0 | 0 | 0 | 0 | 0 | 0 | 0 | 1.5 | 2 | 2.5 | 1.5 | 1.5 | 1.5 | 1.5 | 1.5 | 1.5 | 0 |
| 8* | 0 | 0 | 0 | 0 | 0 | 0 | 0 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 1 | 1.5 | 2 | 2 | 2 | 2 | 2 | 1.5 | 1.5 | 0 |
| 10 | 0 | 0 | 0 | 0 | 0 | 0 | 0 | 0 | 0 | 0 | 0 | 1.5 | 1.5 | 3 | 3 | 3 | 3 | 3 | 3 |
| GR-056 ||||||||||||||||||||
| 1 | 0 | 0 | 0 | 0 | 0 | 0 | 0 | 0 | 0 | 0 | 0 | 0 | 0 | 1.5 | 1.5 | 2.5 | 3 | 3 | 3 |
| 2 | 0 | 0 | 0 | 0 | 0 | 0 | 0 | 0 | 0 | 0 | 1.5 | 2 | 2.5 | 3 | 3 | 2.5 | 1.5 | 1.5 | 1.5 |
| 3* | 0 | 0 | 0 | 0 | 0 | 0 | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 1.5 | 1.5 | 2 | 5 | 5 | 5 | 5 | 5 | 5 | 5 |
| 5* | 0 | 0 | 0 | 0 | 0 | 0 | 0 | 0 | 0 | 0 | 0 | 0 | 0 | 0 | 0 | 0 | 0 | 0 | 0 |
| 6* | 0 | 0 | 0 | 0 | 0 | 0 | 0 | 0 | 0 | 0 | 0 | 0 | 0 | 0 | 0 | 0 | 0 | 0 | 0 |
| 7* | 0 | 0 | 0 | 0 | 0 | 0 | 0 | 0 | 0 | 0 | 0 | 0 | 0 | 0 | 0 | 0 | 0 | 0 | 0 |
| 8* | 0 | 0 | 0 | 0 | 0 | 0 | 0 | 0 | 0 | 0 | 0 | 0 | 0 | 0 | 0 | 0 | 0 | 0 | 0 |
| 9* | 0 | 0 | 0 | 0 | 0 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 1 | 1.5 | 1.5 | 1.5 | 1.5 | 1.5 | 2.5 | 3 | 3 | 1.5 |

*= Disease Free

TABLE 18b

|  | Day 10 | Day 11 | Day 12 | Day 13 | Day 14 | Day 15 | Day 16 | Day 17 | Day 18 | Day 19 |
|---|---|---|---|---|---|---|---|---|---|---|
| MEAN ||||||||||||
| Water Control | 0.00 | 0.00 | 0.00 | 0.00 | 0.00 | 0.00 | 0.00 | 0.25 | 0.40 | 0.65 |
| GR-056 | 0.00 | 0.00 | 0.00 | 0.00 | 0.00 | 0.00 | 0.00 | 0.00 | 0.00 | 0.25 |
| SEM ||||||||||||
| Water Control | 0.00 | 0.00 | 0.00 | 0.00 | 0.00 | 0.00 | 0.00 | 0.17 | 0.21 | 0.29 |
| GR-056 | 0.00 | 0.00 | 0.00 | 0.00 | 0.00 | 0.00 | 0.00 | 0.00 | 0.00 | 0.17 |
| INCIDENCE ||||||||||||
| Water Control | 0 | 0 | 0 | 0 | 0 | 0 | 0 | 20 | 30 | 40 |
| GR-056 | 0 | 0 | 0 | 0 | 0 | 0 | 0 | 0 | 0 | 20 |
| CUM. INCIDENCE ||||||||||||
| Water Control | 0 | 0 | 0 | 0 | 0 | 0 | 0 | 20 | 30 | 40 |
| GR-056 | 0 | 0 | 0 | 0 | 0 | 0 | 0 | 0 | 0 | 20 |

TABLE 18b-continued

| CUM. DISEASE FREE | | | | | | | | | | |
|---|---|---|---|---|---|---|---|---|---|---|
| Water Control | 100 | 100 | 100 | 100 | 100 | 100 | 100 | 80 | 70 | 60 |
| GR-056 | 100 | 100 | 100 | 100 | 100 | 100 | 100 | 100 | 100 | 80 |

| | Day 20 | Day 21 | Day 22 | Day 23 | Day 24 | Day 25 | Day 26 | Day 27 | Day 28 |
|---|---|---|---|---|---|---|---|---|---|
| MEAN | | | | | | | | | |
| Water Control | 1.00 | 1.65 | 2.00 | 2.30 | 2.30 | 2.45 | 2.40 | 2.40 | 1.95 |
| GR-056 | 0.30 | 0.50 | 0.85 | 0.90 | 1.10 | 1.20 | 1.30 | 1.25 | 1.10 |
| SEM | | | | | | | | | |
| Water Control | 0.29 | 0.48 | 0.59 | 0.66 | 0.66 | 0.62 | 0.63 | 0.63 | 0.73 |
| GR-056 | 0.20 | 0.26 | 0.52 | 0.53 | 0.54 | 0.56 | 0.57 | 0.57 | 0.54 |
| INCIDENCE | | | | | | | | | |
| Water Control | 60 | 70 | 70 | 70 | 70 | 80 | 80 | 80 | 50 |
| GR-056 | 20 | 30 | 30 | 30 | 40 | 40 | 40 | 40 | 40 |
| CUM. INCIDENCE | | | | | | | | | |
| Water Control | 60 | 70 | 70 | 70 | 70 | 80 | 80 | 80 | 90 |
| GR-056 | 20 | 30 | 30 | 30 | 40 | 40 | 40 | 40 | 40 |
| CUM. DISEASE FREE | | | | | | | | | |
| Water Control | 40 | 30 | 30 | 30 | 30 | 20 | 20 | 20 | 10 |
| GR-056 | 80 | 70 | 70 | 70 | 60 | 60 | 60 | 60 | 60 |

FIG. 98 shows graphically the percent of animals developing any symptoms of disease in each of the Control Group 1 and the gold nanocrystal Treatment Group 2 (i.e., GB-056). Control Group 1 showed that 90% of the mice developed at least some symptoms, whereas only 40% of the mice in Treatment Group 2 developed some level of symptoms.

FIG. 99 shows the EAE scoring averages for each group. Of note, the onset of any symptoms was delayed by two days in gold nanocrystal Treatment Group 2 and the overall scoring for Treatment Group 2 was significantly less than the reported averages in Control Group 1. Clearly the gold nanocrystal formulation GB-056, having a measured gold concentration of about 12 ppm, significantly outperformed the Control Group 1 in this EAE test.

As is typical for this EAE model, one animal in Treatment Group 2 (i.e., animal 4) died; whereas 3 animals in Control Group 1 died.

The most severe pathology occurred in Control Group 1 and the least severe in Treatment Group 2.

The one animal in Treatment Group 2 that died (i.e., animal 4) caused the group to have a much higher score. Clearly the inventive gold nanocrystal suspension GB-056 had a significant positive effect in this EAE test. Without wishing to be bound by any particular theory or explanation, the results of this Example, in combination with the results of the murine CIA model and the in vitro MIF cytokine analysis, strongly suggest that MIF, and/or MIF signaling pathways, are being favorably influenced by the inventive gold nanocrystalline compositions of the present invention.

Example 27

Long Term Exposure of Gold Nanocrystal Suspension GD-013 in Mice

The purpose of this Example was to observe if any negative toxicology effects occurred in mice when the mice drank, ad libitum, gold nanocrystal suspension GD-013 as their only source of liquid for an extended period of time.

A total of 25 female mice were used in this Example, five (5) in the control group; and ten (10) in each of two treatment groups. The control group received regular bottled water in their drinking bottles. The two treatment groups received two different concentrations of GD-013 as their only drinking liquid. A first treatment group received a 50% GD-013 crystal suspension (with the other 50% being purified DI/RO water) while the second treatment group received 100% GD-013 crystal suspension. All groups were permitted to drink as much, or as little, as desired; food was provided ad libitum as well. The weight of each animal and the average amount of liquid consumed were recorded weekly. At week 23 of the study, 6 mice were sacrificed (3 mice from each of the GD-013 crystal suspension treatment groups) for necropsy and pathology. The remaining mice continued to consume the two treatment suspensions through 46 weeks.

Materials and Methods:

In this type of exposure study it is acceptable to use only one sex, females, for the purposes of testing for toxicity. Data from other studies have shown that there is generally no difference between the sexes, but when one sex does react more strongly it is typically the females. Males are only used when there is some form of evidence indicating that they may have a stronger reaction. Since, there is no such information indicating that males would be affected in this way, only females were used. The females used were adult, nulliparous and non-pregnant. The Swiss Webster strain of outbred mice was used in this example. This strain was chosen because of its widespread use in general purpose and toxicology research. It also is known to not have any detrimental genetic deficits that could potentially interfere with data collection.

TABLE 19

Study Information

| Species | Strain | Group | Mode of Administration | Doses | Duration |
|---|---|---|---|---|---|
| Mus musculus | Swiss Webster | Control - 5/F 50% GD-013 - 10/F 100% GD-013 - 10/F | Via Water Bottle | Ad libitum | 23 weeks and 46 weeks |

Dose Preparation

All treatment groups involved in this study received the referenced GD-013 nanocrystalline suspensions in their water bottles. The mice were allowed to drink free choice. The control group received purified, bottled water.

TABLE 20

GD-013 Treatment Information

| Treatment Group | Lot Numbers | Au Content |
|---|---|---|
| Control | Bottled Water | 0.0 ppm Au |
| 50% GD-013 Au 50% RO H$_2$O | 50/50 GD-013/RO H$_2$O | 7.6 ppm Au |
| 100% GD-013 Au | GD-013 | 15.2 ppm Au |

Housing and Feeding

All study personnel entering the mouse study area wore personal protection clothing (i.e. gloves, face mask, and shoe covers). Mice were purchased from Harlan Laboratories. Upon receipt of the mice, the mice were given permanent identification in the form of a tail tattoo (Harvard Apparatus Tattoo). The mice were then randomly assigned and housed by groups of 5 mice per cage. The cages were large enough to allow adequate room for 5 individuals and were not so small as to hinder clear observations of each animal. The mice were acclimated to the lab environment for a period of one week. The housing area was maintained at a constant temperature of 22° C. (±3° C.), and the relative humidity was maintained at 30%-50%. Artificial, full spectrum lighting was used (PureLite 60 w, 120 v bulbs). Timers were used to achieve a 12 hour light 12 hour dark cycle. Food was provided ad libitum (Purina Certified Rodent Diet 5002). Standard corncob bedding was provided in the cages. Cage changes were carried out once weekly. When an animal was found dead the cage that it was housed in was changed immediately after the dead animal was removed.

Procedure and Observation

After the acclimation period, both treatment groups began receiving the noted GD-013 nanocrystalline suspensions in their water bottles. The control group continued to receive purified drinking water. On the first day of treatment each mouse was weighed and their weights were recorded. At the start of each week, all of the mice were again weighed and their weights recorded. Also, the approximate amount of water and GD-013 crystal suspension consumed, was recorded each week. Throughout the study the mice were observed for any abnormalities or signs of distress.

Weight Gain

When the study began, all of the mice were approximately the same weight. Each week, each animal was weighed and its weight was recorded. The individual weights of each animal in the groups were then averaged and plotted graphically in FIG. 106 to show the average weight gain of all the groups over the course of the study. A vertical line at week 23 is present in FIG. 106 and denotes the time when histopathology was performed.

Average Daily Consumption

Every week the amount of: (1) water, (2) 50% GD-013, and (3) 100% GD-013 that each group consumed was measured. Once the amount of liquid, 50% purified water, that had been consumed during the previous week had been determined, calculations were made to find an approximate daily intake per animal over the course of the week. The liquid consumption data for 46 weeks is shown in FIG. 107.

Results/Conclusions:

Weight Gain

Statistical analysis of the average weights of the groups was performed to determine if there was any difference in weight gain and/or loss between the groups. Each treatment group was compared to the control group; and the two treatment groups were also compared to each other. Overall there was a statistically significant weight loss between the 100% GD-013 Treatment Group and the Control Group (P<0.05). There was no statistically significant weight gain/loss between the two Treatment Groups or between the 50% GD-013 Treatment Group and the Control Group.

Average Weekly Consumption

All three of the groups consumed what is considered to be normal amounts of liquid daily, so dehydration was not an issue. Again, statistical analyses of the consumption values for each group was performed to determine if there was a significant difference in consumption. Both Treatment Groups were compared to the Control Group and both Treatment Groups were compared to each other. The Control Group consumed significantly less than both Treatment Groups (P<0.05). There was no statistical difference between the amounts consumed by the Treatment Groups (P>0.05). There were no observable differences in health, behavior, or issues related to dehydration.

Mortality

There were two recorded deaths in the study, one from each Treatment Group. The first death occurred in the 50% GD-013 group at week 20. The second death occurred at week 22 in the 100% GD-013 group. The mouse from the 50% GD-013 treatment group had always been much smaller than the rest and had not been gaining weight; the cause of this is unknown. The other mouse had not shown any indicators of distress or poor health. No pathology was possible for these two mice.

Pathology

Three mice from each treatment group were submitted for pathology at week 23. The following organs were submitted for histopathological evaluation: heart, thymus, lung, liver, kidney, spleen, stomach, duodenum, jejunum, ileum, cecum, colon, urinary bladder, ovary, striated muscle, haired skin, bone marrow (femur/tibia), pituitary and brain. The pathology findings concluded that despite some of the abnormalities that were noted, all were considered incidental findings that were associated with normal variation between individuals and normal wear and tear. None of the findings in the pathology report indicated any degree of toxicity to target organs. The pathologist was completely blind to what treatment the mice in the study received, nor did the pathologist have any knowledge of treatment in control mice in order to eliminate possible bias in the pathology findings.

All tissues referenced above were grossly examined and only the spleen and liver were found to have minimal to mild variations in color. The only specific histopathological findings are reported in Table 21. The numbers "2-3," "2-5" and "4-7" in the 50% GD-013 row refer to three different mice, to which the "Comments" are directed. Likewise, the histopathology "Comments" regarding the spleen are directed to three mice, "3-3," "5-9" and "5-10;" whereas the "Comments" regarding the liver apply to only one mouse (i.e., "5-10"). All gross examinations were consistent with congestion from euthanasia and/or fat storage and were considered to be within normal limits. No gross lesions were noted.

TABLE 21

Pathology Findings

| Group | Histopathological Findings | Comments |
|---|---|---|
| 50% GD-013 | Spleen: Hematopoiesis, extramedullary, multifocal, minimal red pulp (2-3, 2-5, 4-7) | EMH: normally observed in minimal to moderate degrees; is considered a common, incidental finding not indicative of toxic change or infection |
| 100% GD-013 | Spleen: Hematopoiesis, extramedullary, multifocal, minimal to moderate, red pulp (3-3, 5-9, 5-10) | EMH: normally observed in minimal to moderate degrees; is considered a common, incidental finding not indicative of toxic change or infection |
| | Liver: Microgranuloma, focal, minimal, hepatocytes (5-10) | Liver: Condition considered to be from bacterial showering from the hepatic portal system; not indicative of infection or toxic change |

Example 28

35-Day Uptake and Distribution Acute Toxicity Study

The purpose of this 35 day study was to determine the uptake and distribution and acute toxicity (if any) of two crystal suspensions (GB-134 and GB-151) and compare the results to a commercially available Mesogold product. Thirteen mice were involved in this study. Concentrations of gold were determined in the urine and the feces, as well as in certain vital organs and blood of the test animals. Additionally, a selection of organs from some individuals were examined histologically to determine if there were any abnormalities. Further, all mice were permitted to drink up to the point that they were sacrificed for this study. This procedure was followed to insure, for example, that accurate gold concentrations in the blood could be determined.

Materials and Methods:

TABLE 22

Study Information

| Species | Strain | Group | Mode of Administration | Doses | Duration |
|---|---|---|---|---|---|
| Mus musculus | Swiss Webster | Mesogold - 3/F GB-134 - 10/F GB-151 - 10/F | Free Choice | Mesogold, GB-134, GB-151 | 35 days |

Dose Preparation

All treatment groups involved in this study received their solutions in their water bottles. The mice were allowed to drink free choice. Each group received either: (1) Mesogold, (2) GB-134, or (3) GB-151 (all of which were not diluted) in their drinking bottles.

TABLE 23

Au Solution Treatment Information

| Treatment Group | Lot Numbers | Au Content |
|---|---|---|
| Mesogold | Mesogold | 19.8 ppm Au |
| GB-134 | GB-134 | 8.9 ppm Au |
| GB-151 | GB-151 | 8.3 ppm Au |

Procedure and Observation

After the animals received their respective treatments for one day, metabolic cage collections of urine and feces were initiated. A total of nine animals per week were housed in the metabolic cages and had their urine and feces collected. While in the metabolic cages the subject mice continued to receive in their water bottles the liquid they had been assigned to drink. The amount of liquid consumed during the 24 hour period was also measured and recorded. The urine and feces samples were then collected and tested for Au concentration. The volume of urine excreted and the weight of feces collected were also measured and recorded.

At the end of the study, all 13 animals were sent to Taconic Laboratories (Rockville, Md.) for the performance of a gross necropsy and pathology report or to have organ and blood samples collected and returned for further analysis (discussed later herein). Microscopic evaluations were performed on the following tissues: heart, lung, liver, spleen, kidney, brain, stomach, duodenum, jejunum, ileum, cecum and colon. Additionally, certain heart, lung (left and right), liver, spleen, kidney (left and right), and brain were collected and returned in an empty, sterile glass vial for further concentration analysis.

Procedure for the Digestion of Feces and Urine Samples

Specific methods were developed to determine the amount of gold in the feces and the urine. PTFE sample cups and microwave digestion bombs were ordered from Fisher Scientific and obtained from Parr Instrument Company (www.parrinst.com). 23 mL PTFE sample cup (Fisher Cat No. 0102322A) and Parr 4781 microwave digestion bomb (Fisher Cat No. 0473155) were used for digestion.

The microwave used was a Panasonic 1300 Watt. Model No. NN-SN667 W, Serial No. 6B78090247.

Urine 1.5 grams of urine was weighed in a PTFE sample cup. When urine exceeded that mass, another digestion was prepared. When the urine sample mass was below 1.5 grams the appropriate amount of D.I. water was added to bring the mass up to approximately 1.5 grams. 0.24 mL of 50% v/v $HNO_3$ was added to the sample cup, followed by 0.48 mL of 36% v/v HCl. The sample cup was sealed and placed inside a microwave bomb. The microwave bomb was sealed and placed in the center of a microwave. The sample was irradiated until the Teflon indicator screw raised up 1 mm from the top of the bomb. The time the bomb spent in the microwave ranged between 30 to 60 seconds depending on the urine sample. The microwave digestion bomb was removed from the microwave and cooled for 20-30 minutes, until the Teflon indicator screw was lowered to its original position. The sample cup was removed from the microwave digestion bomb, and the liquid sample was transferred to a vial for testing.

Feces (1 pellet sample):

A singe fecal pellet was weighed in a PTFE sample cup. 5 mL of D.I. water was added to the sample cup. 0.8 mL of 50% v/v $HNO_3$ was added to the sample cup, followed by 1.6 mL of 36% v/v HCl. The sample cup was sealed and placed inside a microwave bomb. The microwave bomb was sealed and placed in the center of the microwave. The sample was irradiated until the Teflon indicator screw raised up 1 mm from the top of the bomb. The time the bomb spent in the microwave ranged between 20 to 30 seconds depending on the mass of the 1 pellet fecal sample. The microwave digestion bomb was removed from the microwave and cooled for 20-30 minutes, until the Teflon indicator screw was lowered to its original position. The sample cup was removed from the microwave digestion bomb, and the liquid sample was transferred to a vial for testing.

Bulk Feces Sample

About 0.300 grams of feces was weighed in a PTFE sample cup. 5 mL of D.I. water was added to the sample cup. 0.8 mL of 50% v/v $HNO_3$ was added to the sample cup, followed by 1.6 mL of 36% v/v HCl. The sample cup was sealed and placed inside a microwave bomb. The microwave bomb was sealed and placed in the center of a microwave. The sample was irradiated until the Teflon indicator screw raised up 1 mm from the top of the bomb. The time the bomb spent in the microwave ranged between 20 to 40 seconds depending on the mass of the bulk feces sample. The microwave digestion bomb was removed from the microwave and cooled for 20-30 minutes, until the Teflon indicator screw was lowered to its original position. The sample cup was removed from the microwave digestion bomb, and the liquid sample was transferred to a vial for testing. Bulk feces samples may require several digestions to digest all the feces present in the original sample.

Note: If the sample didn't appear to be fully digested (i.e. solids still present/discoloration on the PTFE sample cup's side walls) a second digestion was performed. This required a second addition of the volumes of D.I. water, 50% v/v $HNO_3$ and 36% v/v HCl specified for the appropriate sample. (See above procedures for correct volumes) The sample was then microwaved again, and allowed to cool for 20-30 minutes before transferring to a sample vial for testing.

*D.I. water=Deionized water.
*PTFE=polytetrafluoroethylene

One digested, all samples were analyzed using the atomic absorption spectroscopy techniques discussed above herein.

The pathology findings for the 35-day study are shown in Table 24. All tissues were grossly examined and only the spleen and liver were found to have minimal to mild variations in color. All gross examinations were consistent with congestion from euthanasia and/or fat storage and were considered to be within normal limits. No gross lesions were noted. The comments were directed to specific mice and are noted in Table 24. The designation "M-3" refers to one mouse in the Mesogold group; whereas "GB-134-7" refers to one mouse in the "GB-134" group; and "G151-9" refers to one mouse in the "GB-151" group.

TABLE 24

| Group | Histopathological Findings | Comments |
| --- | --- | --- |
| Mesogold | Spleen: Hematopoiesis, extramedullary, multifocal, minimal to moderate, red pulp (M-3) Liver: Microgranuloma, focal, minimal, hepatocytes (M-3) | EMH: normally observed in minimal to moderate degrees; is considered a common, incidental finding not indicative of toxic change or infection Liver: Condition considered to be from bacterial showering from the hepatic portal system; not indicative of infection or toxic change |

TABLE 24-continued

| Group | Histopathological Findings | Comments |
| --- | --- | --- |
| GB-134 | Spleen: Hematopoiesis, extramedullary, multifocal, minimal red pulp (GB-134-7, GB-134-8) Liver: Microgranuloma, focal, minimal, hepatocytes (GB-134-8) | EMH: normally observed in minimal to moderate degrees; is considered a common, incidental finding not indicative of toxic change or infection Liver: Condition considered to be from bacterial showering from the hepatic portal system; not indicative of infection or toxic change |
| GB-151 | Spleen: Hematopoiesis, extramedullary, multifocal, minimal to moderate, red pulp (GB-151-9, GB-151-10) | EMH: normally observed in minimal to moderate degrees; is considered a common, incidental finding not indicative of toxic change or infection |

FIG. 108 shows the there were no significant difference in weight gain found between any of the groups (all P>0.05)

FIG. 109 shows that there were no significant difference in consumption of fluids found between any of the groups (all P>0.05)

FIG. 110 shows that there was a significant difference in the amount of Au found in the feces between the MesoGold group and both GB-134 and GB-151 groups (P<0.01). There was no significant difference found between the GB-134 and GB-151 groups (P>0.05). Table 25 shows the actual recorded results.

TABLE 25

Average Weekly Amount of Au Found in Feces

| | Treatment Groups | | |
| --- | --- | --- | --- |
| Week | Meso (ppm) | GB-134 (ppm) | GB-151 (ppm) |
| 0 | 1.7286 | 0.5343 | 0.6871 |
| 1 | 58.8611 | 24.3989 | 24.8668 |
| 2 | 59.0330 | 19.1658 | 27.4792 |
| 3 | 91.3662 | 15.9090 | 19.6045 |
| 4 | 86.5076 | 18.4982 | 18.1742 |
| 5 | 65.3942 | 20.3575 | 24.9802 |

FIG. 111 shows that there was no significant difference in the average amount of Gold found in the urine between any of the groups (all P>0.05)

TABLE 26

Average Weekly Amount of Au Found in Urine

| | Treatment Groups | | |
| --- | --- | --- | --- |
| Week | Meso (ppm) | GB-134 (ppm) | GB-151 (ppm) |
| 0 | 0.0090 | 0.0240 | 0.0330 |
| 1 | 0.1318 | 0.0821 | 0.0263 |
| 2 | 0.1004 | 0.3453 | 0.0727 |
| 3 | 0.4471 | 0.1518 | 0.1264 |
| 4 | 0.1457 | 0.0920 | 0.0360 |
| 5 | 0.1953 | 0.0261 | 0.0380 |

Procedure for Neutron Activation Analysis Measurements of Tissue Samples and Blood Certain samples of heart, liver, spleen, kidney, brain and blood were analyzed for gold content. Specifically, neutron activation analysis was utilized. Instrumental neutron activation analysis (NAA) is especially powerful in its sensitivity and its ability to determine accurately many elements in a single sample. NAA does not require any chemical treatments or special chemical preparation of samples, thus minimizing the possibilities of losses, contamination and any incomplete tissue sample dissolution, for example.

The NAA method involves weighing the tissue sample in polyethylene vials. An inert material is added to each vial to prevent evaporative loss. Each vial is uniquely identified with a bar code and a neutron flux monitor affixed to the base of each vial. These vials are stacked into one-foot long bundles for irradiation with neutrons from a nuclear reactor. The bundles contain randomly selected duplicate samples and gold standards (or known concentrations of gold) are inserted at random positions in the bundles.

All bundles are treated in a similar manner. The bundles are submitted for exposure to a flux of neutrons at a nuclear reactor. Specifically, the bundles are inserted into the core of a nuclear reactor for about 45 minutes. The bundles are rotated during irradiation so that there is no horizontal flux variation. (The vertical flux variation is monitored with the individual flux monitors.) This irradiation causes any gold present in the sample to become radioactive and gold then begins to emit radiation in the form of penetrating gamma rays whose energies (or wavelengths) are characteristic of gold (e.g., Au 198, 411.8 keV).

After a decay period of about six days, the irradiated samples are loaded onto a counting system. Specifically, each radiated and partially decayed sample is placed adjacent to a gamma-ray spectrometer with a high resolution, coaxial germanium detector. Gamma rays radiate continuously from each sample (so long as gold is present) and the interaction of the radiated gamma rays with the detector leads to discrete voltage pulses proportional in height to the incident gamma-ray energies. A specially developed multi-channel analyser sorts out the voltage pulses from the detector according to their size and digitally constructs a spectrum of gamma-ray energies versus intensities. The counting time is about 45 minutes per sample. By comparing spectral peak positions and areas with library standards, gold is both qualitatively and quantitatively identified. The results of the analysis are set forth below.

In conjunction with Table 27 below, FIG. 112 shows a bar chart, by mouse organ type and the colloid that was orally consumed by the identified mice. The numbers at the end of each colloid identification refer to a specific mouse. Specifically, organs from two mice, GB-151-4 and GB-151-5 were examined. GB-151-4 means that mouse #4 consumed GB-151. Organs from another mouse, GB-134-3 (i.e., mouse #3 that consumed suspension GB-134) were examined as well. Organs from another mouse, Mouse #2, (Meso-2) consumed a commercially available colloidal gold. While the sample size was relatively small, differences are apparent.

Gold was not detected in two brain samples, GB-151-6 and GB-134-3, with the detection limit of 0.35 ppb and 0.25 ppb, respectively. Blood samples GB-151-5 and GB-134-3 were not analyzed because of insufficient amount available for analysis.

TABLE 27

Gold concentration in different tissue samples and blood measured by NAA.

| Sample ID | Sample mass, g | Gold wt %, ppb |
|---|---|---|
| GB-151-4, -5 Heart* | 0.356 | 0.89 ± 0.187 |
| GB-151-5 Liver | 1.536 | 1.76 ± 0.107 |
| GB-151-4, -5 Spleen* | 0.213 | 1.74 ± 0.244 |
| GB-151-4, -5, -5 Kidney* | 0.661 | 2.54 ± 0.170 |
| GB-151-4, -5 Brain* | 0.889 | 0.73 ± 0.102 |
| GB-151-6 Heart | 0.129 | 0.94 ± 0.329 |
| GB-151-6 Liver | 0.899 | 2.34 ± 0.140 |
| GB-151-6 Spleen | 0.093 | 4.00 ± 0.480 |
| GB-151-6 Blood | 0.386 | 1.06 ± 0.212 |
| GB-151-6 R& L Kidney | 0.476 | 2.16 ± 0.203 |
| GB-151-6 Brain | 0.432 | <0.35 |
| GB-134-3 Heart | 0.158 | 1.10 ± 0.275 |
| GB-134-3 Liver | 0.523 | 0.91 ± 0.146 |
| GB-134-3 Spleen | 0.118 | 1.14 ± 0.342 |
| GB-134-3 R&L Kidney | 0.406 | 1.59 ± 0.191 |
| GB-134-3 Brain | 0.455 | <0.25 |
| Meso-2 Heart | 0.145 | 1.67 ± 0.301 |
| Meso-2 Liver | 0.935 | 6.67 ± 0.254 |
| Meso-2 Spleen | 0.080 | 3.01 ± 0.572 |
| Meso-2 R&L Kidney | 0.415 | 7.63 ± 0.351 |
| Meso-2 Brain | 0.400 | 0.74 ± 0.148 |
| Meso-2 Blood | 0.268 | 2.05 ± 0.287 |

*organs from two mice were combined to make one sample

The invention claimed is:

1. A suspension comprising:
   a.) water;
   b.) at least one processing enhancer comprising at least one material selected from the group consisting of sodium bicarbonate, sodium carbonate, potassium bicarbonate, potassium carbonate, trisodium phosphate, disodium phosphate, monosodium phosphate, and potassium phosphates;
   c.) gold nanocrystals suspended in said water forming a suspension, wherein said gold nanocrystals:
      i.) having surfaces that do not have organic chemical constituents adhered or attached to said surfaces;
      ii.) having a mode particle size of less than about 50 nm;
      iii.) are present in said suspension at a concentration of at least 2 ppm by weight per volume; and
   d.) said suspension having a pH of between about 5 to about 9.5, said gold nanocrystals having a zeta potential of about −20 mV or lower at a temperature of about 25° C., said zeta potential being determined by measuring the electrophoretic mobility of the gold nanocrystals in the suspension, and the suspension does not contain chloride ions.

2. The suspension of claim 1, wherein said gold nanocrystals have a zeta potential of about −30 mV or lower.

3. The suspension of claim 1, wherein said gold nanocrystals have a zeta potential of about −40 mV or lower.

4. The suspension of claim 1, wherein said gold nanocrystals have a zeta potential of about −50 mV or lower.

5. The suspension of claim 1, wherein said gold nanocrystals have shapes comprising faces with spatially extended low index crystal planes, said shapes appearing as triangles and pentagons.

6. The suspension of claim 5, wherein said shaped gold nanocrystals further comprise shapes which appear as hexagons and diamond shapes.

7. The suspension of claim 1, wherein said gold nanocrystals are present at a concentration of about 2-200 ppm by weight per volume.

8. A composition comprising:
   a.) a suspension medium comprising water and at least one processing enhancer comprising sodium bicarbonate dissolved therein, said suspension medium having a pH of between about 5 to about 9.5; and
   b.) shaped gold nanocrystals in said suspension medium forming a suspension, said shaped gold nanocrystals having a zeta potential of about −20 mV or lower at a temperature of about 25° C., said zeta potential being determined by measuring the electrophoretic mobility of the shaped gold nanocrystals in the suspension; wherein said shaped gold nanocrystals:
      i.) having surfaces that do not have organic chemical constituents adhered or attached to said surfaces;
      ii.) having a mode particle size of less than about 50 nm;
      iii.) are present in said suspension at a concentration of at least about 2 ppm by weight per volume; and
      iv.) having shapes comprising low Miller index crystal planes.

9. The suspension of claim 8, wherein said shaped gold nanocrystals having a zeta potential of about −40 mV or lower.

10. The suspension of claim 8, wherein said mode particle size is within a range of about 8-18 nm and said pH is between 8 to about 9.5.

11. The suspension of claim 10, wherein said shaped gold nanocrystals having said low Miller index crystal planes comprising triangle and pentagon shapes.

12. The suspension of claim 11, wherein said shaped gold nanocrystals having said low Miller index crystal planes further comprise hexagon and diamond shapes.

13. A suspension comprising:
   a.) a suspension medium comprising water and sodium bicarbonate dissolved therein, said suspension medium having a pH of between about 5 to about 9.5;
   b.) shaped gold nanocrystals in said suspension medium forming a suspension, said shaped gold nanocrystals having a zeta potential of about −30 mV or lower at a temperature of about 25° C., said zeta potential being determined by measuring the electrophoretic mobility of the shaped gold nanocrystals in the pharmaceutical suspension; and wherein said shaped gold nanocrystals:
      i.) having surfaces that do not have organic chemical constituents adhered or attached to said surfaces;
      ii.) having a mode particle size of less than about 30 nm;
      iii.) are present in said suspension at a concentration of at least about 2 ppm by weight per volume; and
      iv.) comprise triangle and pentagon shapes.

14. The suspension of claim 13, wherein said shaped gold nanocrystals have a zeta potential of about −40 mV or lower.

15. The suspension of claim 13, wherein said shaped gold nanocrystals having a mode particle size within a range of about 8-18 nm.

16. The suspension of claim 13, wherein said shaped gold nanocrystals having a mode particle size of less than about 21 nm and having a zeta potential of about −40 mV or lower.

17. The suspension of claim 13, wherein said shaped gold nanocrystals further comprising hexagon and diamond shapes.

18. The suspension of claim 13, wherein said suspension does not contain chloride ions.

19. The suspension of claim 13, wherein said shaped gold nanocrystals are present in said suspension at a concentration of about 2-200 ppm.

20. The suspension of claim 13, wherein said shaped gold nanocrystals having a mode particle size within a range of about 8-18 nm and the suspension has a pH of between about 8 to about 9.5.

21. The suspension of claim 13, wherein said pH is between about 8 and about 9.5, said mode particle size is within a range of about 8-18 nm, and said zeta potential is about −40 mV or lower.

22. The suspension of claim 1, wherein said pH is between about 8 and about 9.5, said mode particle size is within a range of about 8-18 nm, and said zeta potential is about −40 mV or lower.

23. The suspension of claim 6, wherein said pH is between about 8 and about 9.5, said mode particle size is within a range of about 8-18 nm, and said zeta potential is about −40 mV or lower.

24. The suspension of claim 7, wherein said pH is between about 8 and about 9.5, said mode particle size is within a range of about 8-18 nm, and said zeta potential is about −40 mV or lower.

25. The suspension of claim 4, wherein said gold nanocrystals comprise shapes comprising low Miller index crystal planes, said shapes appearing as triangles and pentagons.

26. The suspension of claim 7, wherein said pH is between about 8 and about 9.5, said mode particle size is within a range of about 8-18 nm, and said zeta potential is about −40 mV or lower.

27. The suspension of claim 3, wherein said gold nanocrystals are shaped and comprising at least one low Miller index {111} crystal plane.

28. The suspension of claim 1, wherein said gold nanocrystals are shaped and include least one low Miller index crystal plane selected from the group of crystal planes consisting of {111}, {110} and {100}.

29. The suspension of claim 1, wherein said gold nanocrystals are shaped and comprising at least one low Miller index {111} crystal plane.

30. The suspension of claim 1, wherein said gold nanocrystals have a mode particle size of less than about 30 nm.

31. The suspension of claim 1, wherein said gold nanocrystals have a mode particle size within a range of about 8-18 nm.

32. A composition comprising:
   a.) water and $NaHCO_3$ dissolved therein,
   b.) gold nanocrystals suspended in said water forming a suspension, wherein said gold nanocrystals:
      i.) having surfaces that do not have organic chemical constituents adhered or attached to said surfaces;
      ii.) having a mode particle size of less than about 50 nm;
      iii.) are present in said suspension at a concentration of at least 2 ppm (w/v);
      iv.) are shaped and comprising at least one low Miller index crystal plane selected from the group of crystal planes consisting of {111}, {110} and {100}; and
   c.) said suspension having a pH of between about 8 to about 9.5, said gold nanocrystals have a zeta potential of about −30 mV or lower at a temperature of about 25° C., said zeta potential being determined by measuring the electrophoretic mobility of the gold nanocrystals in the suspension, and the suspension does not contain chloride ions.

33. The suspension of claim 32, wherein said gold nanocrystals have shapes comprising faces with spatially extended low index crystal planes, said shapes appearing as triangles and pentagons when dried from suspension on a surface.

34. The suspension of claim 33, wherein said shaped gold nanocrystals further comprise hexagon and diamond shapes.

35. The suspension of claim 32, wherein said at least one low Miller index crystal plane comprises a crystal plane {111}.

36. [Newly Added] A suspension comprising:
   a.) water;
   b.) at least one processing enhancer comprising potassium bicarbonate;
   c.) gold nanocrystals suspended in said water forming a suspension, wherein said gold nanocrystals:
      i.) having surfaces that do not have organic chemical constituents adhered or attached to said surfaces;
      ii.) having a mode particle size of less than about 50 nm;
      iii.) are present in said suspension at a concentration of at least 2 ppm by weight per volume; and
   d.) said suspension having a pH of between about 5 to about 9.5, said gold nanocrystals having a zeta potential of about −20 mV or lower at a temperature of about 25° C., said zeta potential being determined by measuring the electrophoretic mobility of the gold nanocrystals in the suspension, and the suspension does not contain chloride ions.

\* \* \* \* \*